United States Patent
Hansen et al.

(10) Patent No.: US 6,939,880 B2
(45) Date of Patent: Sep. 6, 2005

(54) COMPOUNDS WITH GROWTH HORMONE RELEASING PROPERTIES

(75) Inventors: Thomas Kruse Hansen, Herlev (DK); Bernd Peschke, Maaloev (DK); Jesper Lau, Farum (DK); Behrend Friedrich Lundt, Kokkedal (DK); Michael Ankersen, Frederiksberg (DK); Brett Watson, Vaerloese (DK); Kjeld Madsen, Vaerloese (DK)

(73) Assignee: Novo Nordisk A/S, Bagsvaerd (DK)

(*) Notice: Subject to any disclaimer, the term of this patent is extended or adjusted under 35 U.S.C. 154(b) by 0 days.

(21) Appl. No.: 10/067,895

(22) Filed: Feb. 5, 2002

(65) Prior Publication Data

US 2003/0055261 A1 Mar. 20, 2003

Related U.S. Application Data

(60) Continuation of application No. 09/534,135, filed on Mar. 23, 2000, now Pat. No. 6,555,570, which is a division of application No. 09/218,686, filed on Dec. 21, 1998, now Pat. No. 6,127,391, which is a division of application No. 08/769,020, filed on Dec. 18, 1996, now Pat. No. 5,977,178.
(60) Provisional application No. 60/022,062, filed on Jul. 22, 1996.

(30) Foreign Application Priority Data

Dec. 22, 1995 (DK) .............................. 1462/95
Jun. 25, 1996 (DK) .............................. 0698/96
Jul. 24, 1996 (DK) .............................. 0812/96
Nov. 6, 1996 (DK) .............................. 1248/96

(51) Int. Cl.[7] .................. A61K 31/445; C07D 211/06; C07D 401/00
(52) U.S. Cl. .................. 514/326; 514/317; 514/319; 546/205; 546/210

(58) Field of Search .................. 514/326, 319, 514/317; 546/210, 205

(56) References Cited

FOREIGN PATENT DOCUMENTS

WO    WO 96/15148    * 5/1996

OTHER PUBLICATIONS

McDowell, Proc. Natl. Acad. Sci, USA, vol 92, PP11165–11169, Nov. 1995.□□□□.*
CA 124:21930, 1995.*
CA 124:251268, 1996.*
CA 124:9462, 1995.*

* cited by examiner

*Primary Examiner*—D. Margaret Seaman
(74) *Attorney, Agent, or Firm*—Rosemarie R. Wilk-Orescan; Reza Green; Richard W. Bork

(57) ABSTRACT

Compounds of peptide mimetic nature having the general formula I

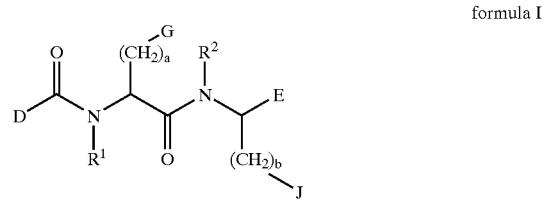

formula I wherein a and b are independently 1 or 2, $R^1$ and $R^2$ are independently H or $C_{1-6}$alkyl, G and J are independently, inter alia, aromats, and D and E are independently several different groups are growth hormone secretagogous with improved bioavailability.

14 Claims, No Drawings

COMPOUNDS WITH GROWTH HORMONE RELEASING PROPERTIES

CROSS REFERENCE TO RELATED APPLICATIONS

This application is a continuation of Ser. No. 09/534,135 filed on Mar. 23, 2000 now U.S. Pat. No. 6,555,570 which is divisional of U.S. application Ser. No. 09/218,686 filed Dec. 21, 1998, now U.S. Pat. No. 6,127,391 which is a divisional of U.S. application Ser. No. 08/769,020 filed Dec. 18, 1996 now U.S. Pat. No. 5,979,178 and claims priority under 35 U.S.C. 119 of Danish application nos: 1462/95, 0698/96, 0812/96 and 1248/96 filed Dec. 22, 1995, Jun. 25, 1996, Jul. 24, 1996 and Nov. 6, 1996, respectively, and of U.S. provisional application no. 60/022,062 filed Jul. 22, 1996, the contents of which are fully incorporated herein by reference.

FIELD OF INVENTION

The present invention relates to novel compounds, compositions containing them, and their use for treating medical disorders resulting from a deficiency in growth hormone.

BACKGROUND OF THE INVENTION

Growth hormone is a hormone which stimulates growth of all tissues capable of growing. In addition, growth hormone is known to have a number of effects on metabolic processes, e.g., stimulation of protein synthesis and free fatty acid mobilisation and to cause a switch in energy metabolism from carbohydrate to fatty acid metabolism. Deficiency in growth hormone can result in a number of severe medical disorders, e.g., dwarfism.

Growth hormone is released from the pituitary. The release is under tight control of a number of hormones and neurotransmifters either directly or indirectly. Growth hormone release can be stimulated by growth hormone releasing hormone (GHRH) and inhibited by somatostatin. In both cases the hormones are released from the hypothalamus but their action is mediated primarily via specific receptors located in the pituitary. Other compounds which stimulate the release of growth hormone from the pituitary have also been described. For example arginine, L-3,4-dihydroxyphenylalanine (1-Dopa), glucagon, vasopressin, PACAP (pituitary adenylyl cyclase activating peptide), muscarinic receptor agonists and a synthethic hexapeptide, GHRP (growth hormone releasing peptide) release endogenous growth hormone either by a direct effect on the pituitary or by affecting the release of GHRH and/or somatostatin from the hypothalamus.

In disorders or conditions where increased levels of growth hormone is desired, the protein nature of growth hormone makes anything but parenteral administration non-viable. Furthermore, other directly acting natural secretagogues, e.g., GHRH and PACAP, are longer polypeptides for which reason parenteral administration is preferred.

The use of certain compounds for increasing the levels of growth hormone in mammals has previously been proposed, e.g. in EP 18 072, EP 83 864, WO 89/07110, WO 89/01711, WO 89/10933, WO 88/9780, WO 83/02272, WO 91/18016, WO 92/01711, WO 93/04081, WO 9517422, WO 9517423 and WO 9514666.

The composition of growth hormone releasing compounds is important for their growth hormone releasing potency as well as their bioavailability. It is therefore the object of the present invention to provide compounds of peptide mimetic nature with growth hormone releasing properties which have improved properties relative to known compounds of this type.

SUMMARY OF THE INVENTION

In accordance with the present invention there is provided compounds which act directly on the pituitary cells under normal experimental conditions in vitro to release growth hormone therefrom.

These growth hormone releasing compounds can be utilized in vitro as unique research tools for understanding, inter alia, how growth hormone secretion is regulated at the pituitary level.

Moreover, the growth hormone releasing compounds of the present invention can also be administered in vivo to increase growth hormone release.

Accordingly, the present invention relates to a compound of the general formula I

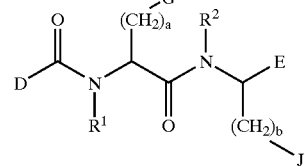

formula I wherein $R^1$ and $R^2$ are independently hydrogen, or $C_{1-6}$alkyl optionally substituted with aryl;
a and b are independently 1 or 2;
G is hydrogen, $-O-(CH_2)_k-R^{27}$,

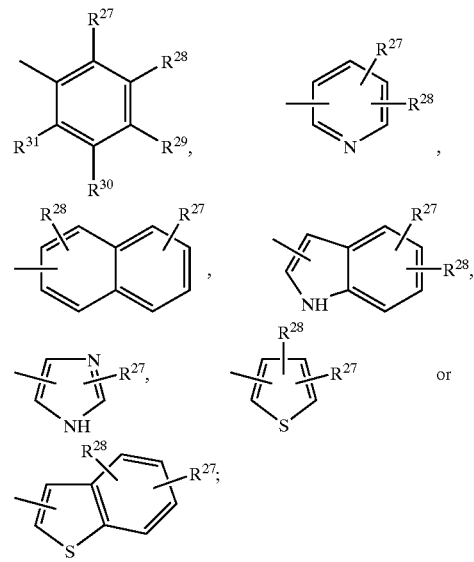

J is hydrogen, —O—(CH$_2$)$_l$R$^{32}$,

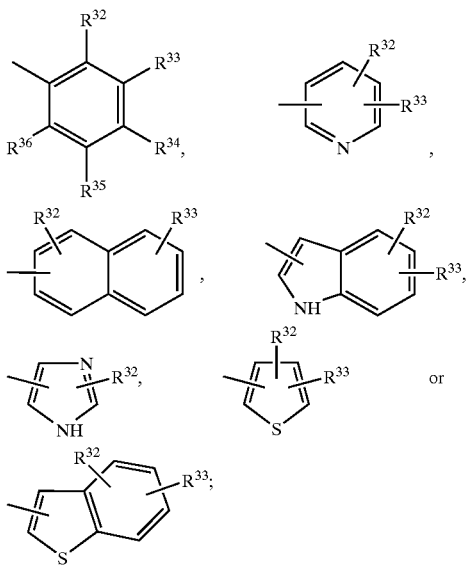

wherein R$^{27}$, R$^{28}$, R$^{29}$, R$^{30}$, R$^{31}$, R$^{32}$, R$^{33}$, R$^{34}$, R$^{35}$ and R$^{36}$ independently are hydrogen, halogen, aryl, C$_{1-6}$-alkyl or C$_{1-6}$-alkoxy;
k and l are independently 0, 1 or 2;
D is

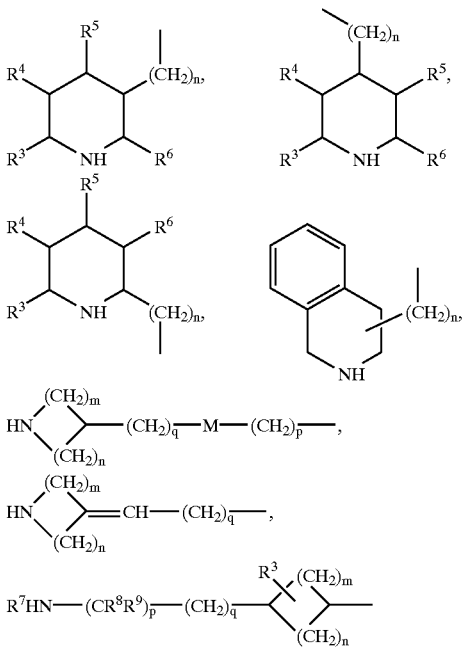

wherein R$^3$, R$^4$, R$^5$, R$^6$, R$^7$, R$^8$ and R$^9$ are independently hydrogen or C$_{1-6}$-alkyl optionally substituted with halogen, amino, hydroxyl or aryl;
n, m and q are independently 0, 1, 2, or 3;
p is 0 or 1;
M is —CR$^{11}$=CR$^{11a}$—, aryl, —O—, or —S—;
R$^{11}$ and R$^{11a}$ are independently hydrogen, or C$_{1-6}$-alkyl optionally substituted with aryl;
with the proviso that at least one of R$^3$, R$^4$, R$^5$ and R$^6$ is different from hydrogen, when E is
—CONR$^{12}$R$^{13}$, —(CH$_2$)$_v$—NR$^{12}$SO$_2$R$^{14}$, —(CH$_2$)$_v$—NR$^{12}$COR$^{13}$, —(CH$_2$)$_v$—OR$^{13a}$, —CH$_2$)$_v$—OCOR$^{13}$, —CH(R$^{12}$)R$^{13}$, —(CH$_2$)$_v$—NR$^{12}$—CS—NR$^{13}$R$^{14}$, —(CH$_2$)$_v$-NR$^{12}$—CO—NR$^{13}$R$^{14}$,

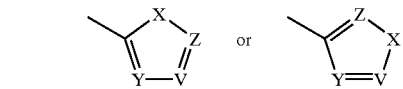

wherein
X is —N(R$^{15}$)—, —O— or —S—,
V is —C(R$^{16}$)= or —N=,
Y is —C(R$^{17}$)= or —N=,
Z is —C(R$^{18}$)= or —N=,
R$^{15}$ is hydrogen or C$_{1-6}$-alkyl optionally substituted with aryl,
R$^{16}$, R$^{17}$ and R$^{18}$ independently are hydrogen, —COOR$^{19}$, —CONR$^{20}$R$^{21}$, —(CH$_2$)$_w$NR$^{20}$R$^{21}$, —(CH$_2$)$_w$OR$^{19}$, —(CH$_2$)$_w$R$^{19}$ or halogen;
R$^{12}$, R$^{13}$, R$^{19}$, R$^{20}$ and R$^{21}$ independently are hydrogen or C$_{1-6}$-alkyl optionally substituted with halogen, —CONR$^{22}$R$^{23}$, —N(R$^{22}$)R$^{23}$, —CF$_3$, hydroxyl, C$_{1-6}$-alkoxy, C$_{1-6}$-alkoxycarbonyl, C$_{1-6}$-alkylcarbonyloxy or aryl,
or R$^{13}$ is

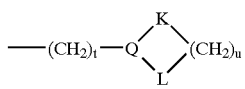

wherein
Q is —CH< or —N<,
K and L are independently —CH$_2$—, —CO—, —O—, —S—, —NR$^{26}$— or a valence bond, where R$^{26}$ is hydrogen or C$_{1-6}$-alkyl;
t and u are independently 0, 1, 2, 3 or 4;
R$^{13a}$ is C$_{1-6}$ alkyl substituted with aryl;
R$^{14}$ is C$_{1-6}$ alkyl;
R$^{22}$ and R$^{23}$ are independently hydrogen or C$_{1-6}$-alkyl;
v and w are independently 0, 1, 2 or 3;
D is

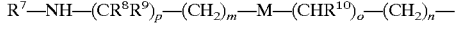

wherein R$^7$, R$^8$, R$^9$ and R$^{10}$ are independently hydrogen or C$_{1-6}$ alkyl optionally substituted with halogen, amino, hydroxyl or aryl;
R$^7$ and R$^8$ or R$^7$ and R$^9$ or R$^8$ and R$^9$ optionally forming —(CH$_2$)$_i$—U—(CH$_2$)$_j$—, wherein i and j are independently are 1 or 2 and U is —O—, —S— or a valence bond;
n and m are independently 0, 1, 2, or 3;
o and p are independently 0 or 1;
M is —CR$^{11}$=CR$^{11a}$—, aryl, —O—, or —S—;
R$^{11}$ and R$^{11a}$ are independently hydrogen, or C$_{1-6}$-alkyl optionally substituted with aryl,
when E is
—CONR$^{12}$R$^{13}$, —(CH$_2$)$_v$—NR$^{12}$SO$_2$R$^{14}$, —(CH$_2$)$_v$—NR$^{12}$COR$^{13}$, —(CH$_2$)$_v$—OR$^{13a}$, —CH$_2$)$_v$—OCOR$^{13}$, —CH(R$^{12}$)R$^{13}$, —(CH$_2$)$_v$—NR$^{12}$—CS—NR$^{13}$R$^{14}$ or —(CH$_2$)$_v$—NR$^{12}$—CO—NR$^{13}$R$^{14}$,
wherein
R$^{12}$ and R$^{13}$ independently are hydrogen or C$_{1-6}$-alkyl optionally substituted with halogen, —CONR$^{22}$R$^{23}$, —N(R$^{22}$)R$^{23}$, —CF$_3$, hydroxyl, C$_{1-6}$-alkoxy, C$_{1-6}$-alkoxycarbonyl, C$_{1-6}$-alkylcarbonyloxy or aryl;

or R[13] is

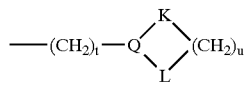

wherein
Q is —CH< or —N<,
K and L are independently —CH$_2$—, —CO—, —O—, —S—, —NR[26]— or a valence bond, where R[26] is hydrogen or C$_{1-6}$ alkyl;
t and u are independently 0, 1, 2, 3 or 4;
R[13a] is C$_{1-6}$ alkyl substituted with aryl;
R[14] is C$_{1-6}$ alkyl;
R[22] and R[23] are independently hydrogen or C$_{1-6}$ alkyl;
v and w are independently 0, 1, 2 or 3;
or a pharmaceutically acceptable salt thereof, and the compounds of formula I comprise any optical isomers thereof, in the form of separated, pure or partially purified optical isomers or racemic mixtures thereof.

In the compound of the above formula I D is preferably 3-(1-aminoethyl)phenyl, 4-amino-4-ethylhex-1-enyl, (1E)-2-(azetidin-3-yl)ethenyl, piperidin-4-ylidenyl, 2-methylpiperidin-4-yl, 2-methylpiperidin-3-yl, 2-methylpiperidin-5-yl, (1,2,3,4-tetrahydroisoquinolin-1-yl) methyl, 4-aminocyclohexyl, 2-piperidylmethoxymethyl, 4-piperidyloxymethyl, 2-(2-amino-2-methylpropyl) cyclopropyl, (((2R)-pyrrolidin-2-yl)methoxy)methyl, (1E)-4-amino-1-benzyl-4-methylpent-1-enyl, (1E)-4-amino-4-methylpent-1-enyl, (2-amino-2-methylpropoxy)methyl, (2S)-(2-pyrrolidinyl)methoxymethyl, (2R)-(2-pyrrolidinyl) methoxymethyl, (1E)-4-amino-2,4-dimethylpent-1-enyl, (1E)-4-methyl-4-(methylamino)pent-1-enyl, (1Z)-4-amino-4-methylpent-1-enyl, (1E)-4-((2R)-2-hydroxypropylamino)-4-methylpent-1-enyl, (2-aminobutoxy)methyl, 3-(1-aminoethyl)phenyl, 3-aminomethylphenyl, 3-(1-amino-1-methylethyl)phenyl, 2-(1-amino cyclopropyl)ethenyl, 3-(1-aminocyclobutyl)-1-propenyl, 3-(1-aminocyclopropyl)-1-propenyl or 2-(1-amino cyclobutyl)ethenyl.

In the compound of the above formula I E is preferably methylcarbamoyl, ethylcarbamoyl, N,N-dimethylcarbamoyl, 2-methoxyethylcarbamoyl, (2S)-2-hydroxypropylcarbamoyl, (2R)-2-hydroxypropylcarbamoyl, (cyclopropylmethyl)carbamoyl, (2-(acetoxy)-2-methylpropyl)carbamoyl, phenylethylcarbamoyl, 4-pyridylcarbamoyl, (3-acetoxypropyl)carbamoyl, (3-hydroxypropyl)carbamoyl, methylsulfonylaminomethyl, ((tetrahydrofuran-2-yl)methyl)carbamoyl, 3-cyclopropylthioureido, N-methyl-N-(methylsulfonylamino)methyl, (2,2,2-trifluoroethyl)carbamoyl, cyclopropylcarbamoyl, ((3-methyl-1,2,4-oxadiazol-5-yl)methoxy)methyl, 3-methyl-1,2,4-oxadiazol-5-yl, methylsulfonylaminomethyl, 2,2-dimethyl-3-hydroxypropylcarbamoyl, 2-(1-methylpyrrolidine-2-yl) ethylcarbamoyl, N-methyl-N-(3-(dimethylamino)propyl) carbamoyl, N-(N, N-dimethylcarbamoyl)-N-methylcarbamoyl, N-(carbamoylmethyl)carbamoyl or 3-cyclopropylthioureido.

In the compound of the above formula I G is preferably 2-naphthyl, 1-naphthyl, 2-benzyloxy, biphenyl-4-yl or 3-benzo[b]thiophenyl, 4-methoxyphenyl, 2,3,4,5,6-pentafluorophenyl.

In the compound of the above formula I J is preferably phenyl, 2-fluorophenyl, 4-fluorophenyl, 4-iodophenyl, 3,4-difluorophenyl 2-thienyl, 4-methoxyphenyl, 2,3,4,5,6-pentafluorophenyl, 2-naphthyl or 1-naphthyl.

In the compound of the above formula I R[1] is preferably hydrogen, methyl or ethyl.

More preferably R[1] is hydrogen, or methyl.

In the compound of the above formula I R[2] is preferably hydrogen, methyl or ethyl.

In the compound of the above formula I a is preferably 1.

In the compound of the above formula I b is preferably 1.

Preferred compounds of the invention are:

(2E)-5-Amino-5-methylhex-2-enoic acid N-methyl-N-((1R)-1-(N-methyl-N-((1R)-1-(methylcarbamoyl)-2-phenylethyl)carbamoyl)-2-(2-naphthyl)ethyl)amide:

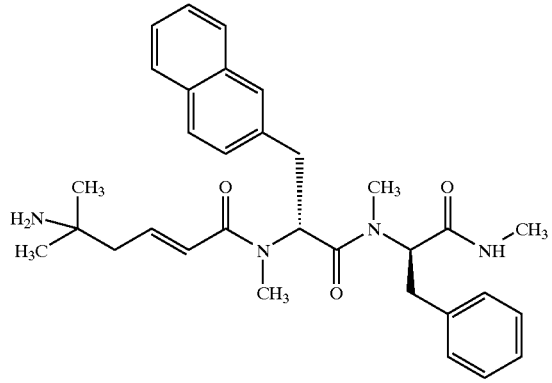

(2E)-3-(3-Azetidinyl)acrylic acid N-methyl-N-((1R)-1-(N-methyl-N-((1R)-1-(methyl-carbamoyl)-2-phenylethyl) carbamoyl)-2-(2-naphthyl)ethyl)amide:

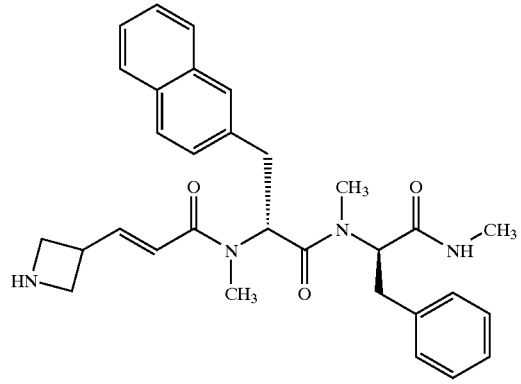

2-(Piperidin-4-ylidene)acetic acid N-methyl-N-((1R)-1-(N-methyl-N-((1R)-1-(methylcarbamoyl)-2-phenylethyl) carbamoyl)-2-(2-naphthyl)ethyl)amide:

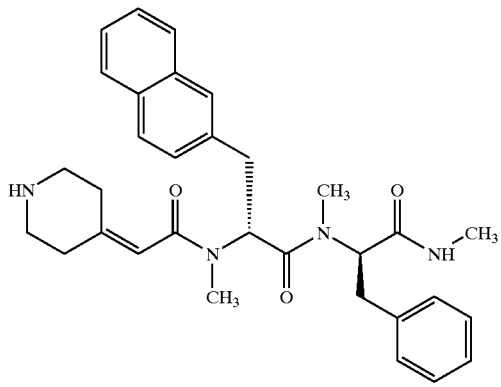

2-(2-Amino-2methylpropyl)cyclopropanecarboxylic acid N-methyl-N-((1R)-1-(N-methyl-N-((1R)-1-(methylcarbamoyl)-2-phenylethyl)carbamoyl)-2(2-naphthyl)ethyl)amide:

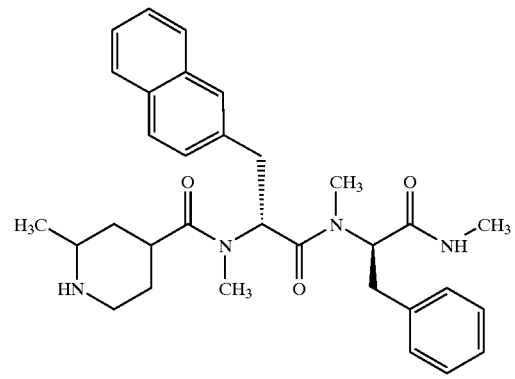

2-Methylpiperidine-3-carboxylic acid N-methyl-N-((1R)-1-(N-methyl-N-((1R)-1-(methylcarbamoyl)-2-phenylethyl)carbamoyl)-2-(2-naphthyl)ethyl)amide:

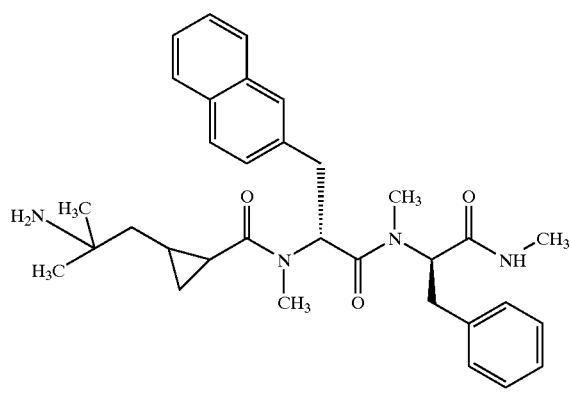

2-(2-Amino-2-methylpropoxy)acetic acid N-methyl-N-((1R)-1-(N-methyl-N-((1R)-1-(methylcarbamoyl)-2-phenylethyl)carbamoyl)-2-(2-naphthyl)ethyl)amide:

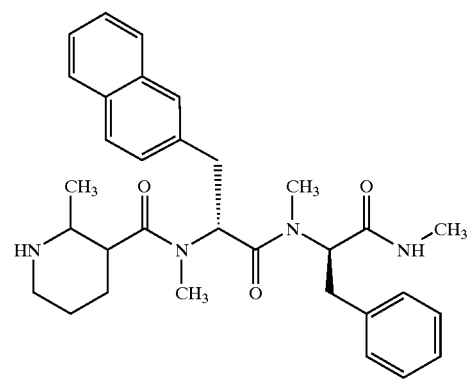

2-Methylpiperidine-5-carboxylic acid N-methyl-N-((1R)-1-(N-methyl-N-((1R)-1-(methylcarbamoyl)-2-phenylethyl)carbamoyl)-2-(2naphthyl)ethyl)amide:

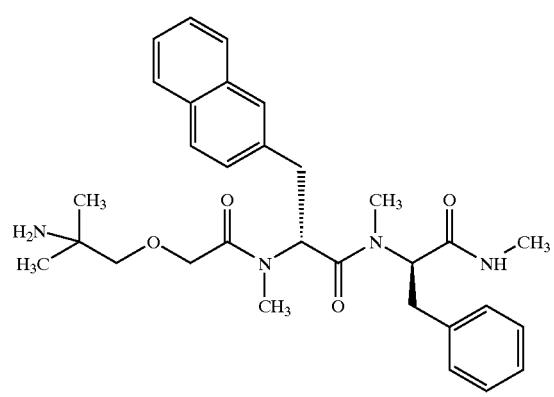

2-Methylpiperidine-4-carboxylic acid N-methyl-N-((1R)-1-(N-methyl-N-((1R)-1-(methylcarbamoyl)-2-phenylethyl)carbamoyl)-2-(2-naphthyl)ethyl)amide:

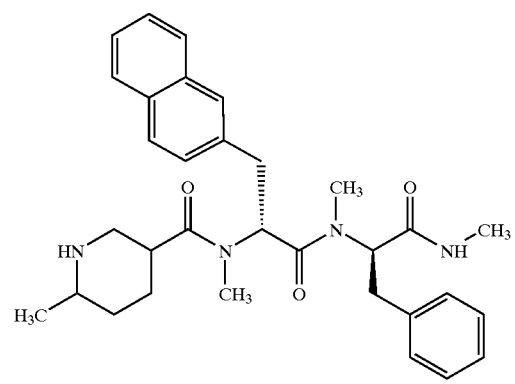

2-(1,2,3,4-Tetrahydroisoquinolin-1-yl)acetic acid N-methyl-N-((1R)-1-(N-methyl-N-((1R)-1-(methylcarbamoyl)-2-phenylethyl)carbamoyl)-2-(2-naphthyl)ethyl)amide:

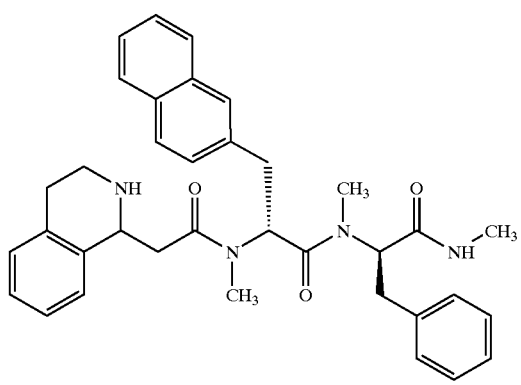

4-Aminocyclohexanecarboxylic acid N-methyl-N-((1R)-1-(N-methyl-N-((1R)-1-(methylcarbamoyl)-2-phenylethyl)carbamoyl)-2-(2-naphthyl)ethyl)amide:

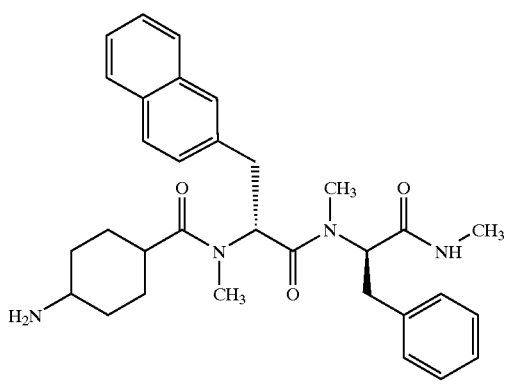

(2E)-5-Amino-5-methylhex-2-enoic acid N-((1R)-1-(N-((1R)-1-(benzylcarbamoyl)-2-phenylethyl)-N-methylcarbamoyl)-2-(2-naphthyl)ethyl)-N-methylamide:

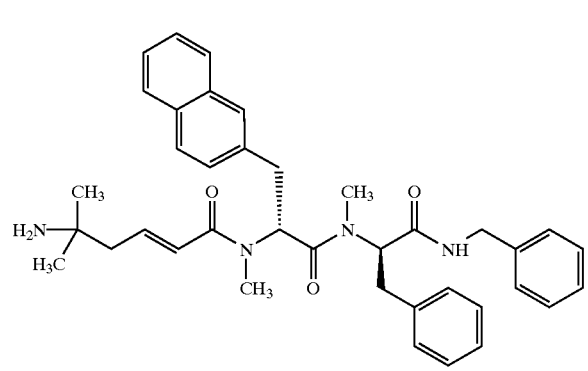

(2E)-5-Amino-5-methylhex-2-enoic acid N-methyl-N-((1R)-1-(N-methyl-N-((1R)-1-(phenethylcarbamoyl)-2-phenylethyl)carbamoyl)-2-(2-naphthyl)ethyl)amide:

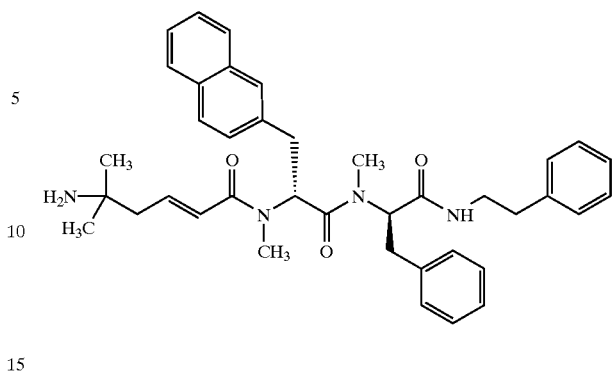

(2E)-5-Amino-5-methylhex-2-enoic acid N-((1R)-1-{N-[(1R)-1-(acetylaminomethyl)-2-phenylethyl]-N-methylcarbamoyl}-2-(2-naphthyl)ethyl)-N-methylamide:

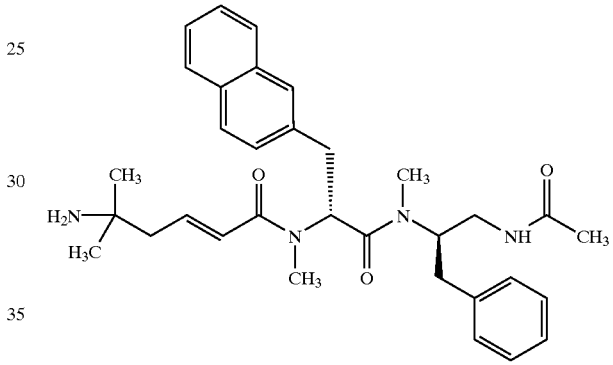

(2E)-5-Amino-5-methylhex-2-enoic acid N-methyl-N-((1R)-1-{N-methyl-N-[(1R)-1-(methylsulfonylaminomethyl)-2-phenylethyl]carbamoyl}-2-(2-naphthyl)ethyl)amide:

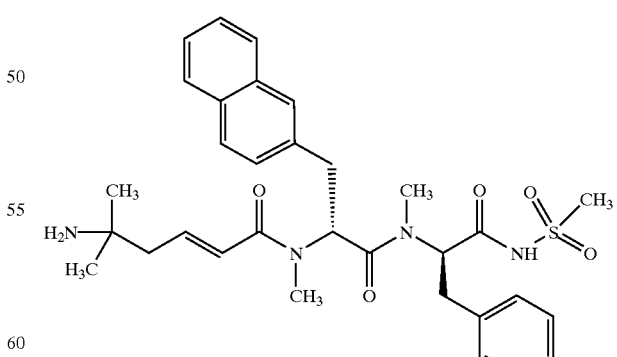

(2E)-5-Amino-5-methylhex-2-enoic acid N-((1R)-1-(N-((1R)-1-((cyclopropyl-methyl)carbamoyl)-2-phenylethyl)-N-methylcarbamoyl)-2-(2-naphthyl)ethyl)-N-methylamide:

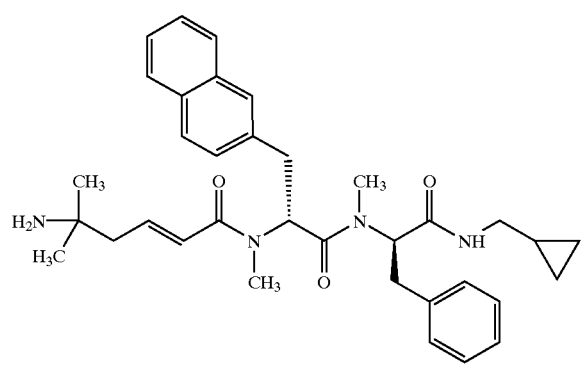

(2E)-5-Amino-5-methylhex-2-enoic acid N-((1R)-1-(N-((1R)-1-(N-(2-methoxy-ethyl)carbamoyl)-2-phenylethyl)-N-methylcarbamoyl)-2-(2-naphthyl)ethyl)-N-methylamide:

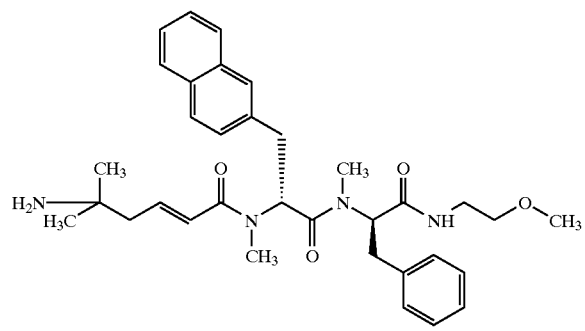

(2E)-5-Amino-5-methylhex-2-enoic acid N-methyl-N-((1R)-1-(N-methyl-N-((1R)-2-phenyl-1-((N-tetrahydrofuran-2-yl)methyl)carbamoyl)ethyl)carbamoyl)-2-(2-naphthyl)ethyl)amide:

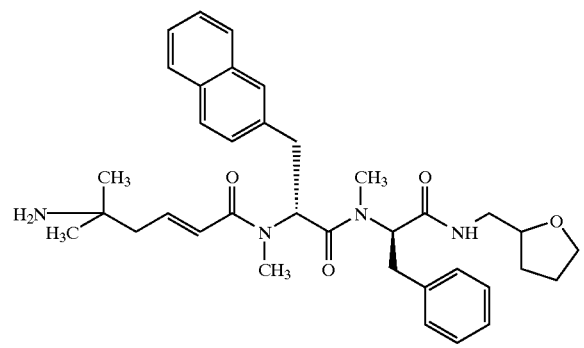

(2E)-5-Amino-5-methylhex-2-enoic acid N-((1R)-1-(N-((1R)-1-(N-(2S)-2hydroxy-methylamide:

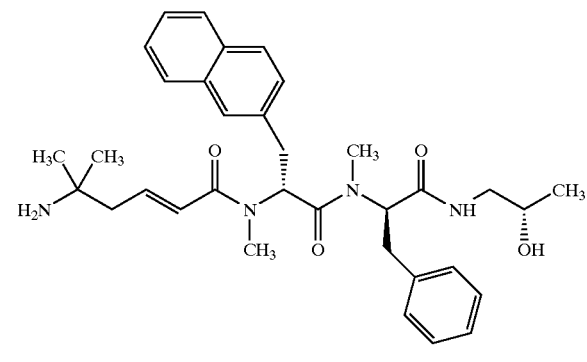

(2E)-5-Amino-5-methylhex-2-enoic acid N-methyl-N-((1R)-1-(N-methyl-N-((1R)-1-(N-(3-(2-oxopyrrolidin-1-yl)propyl)carbamoyl)-2-phenylethyl)carbamoyl)-2-(2-naphthyl)ethyl)amide:

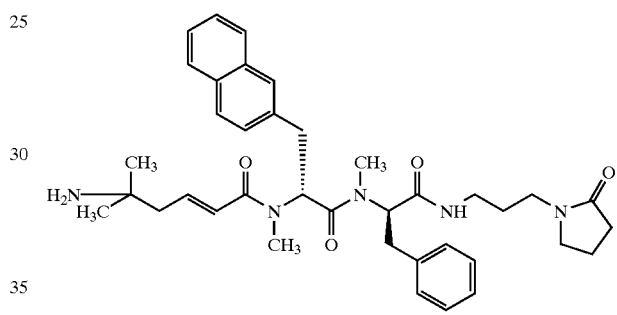

(2E)-5-Amino-5-methylhex-2-enoic acid N-((1R)-1-{N-[(1R)-1-((2,5-dioxopyrrolidine-1-yl)methyl)-2-phenylethyl]-N-methylcarbamoyl}-2-(2-naphthyl)ethyl)-N-methylamide:

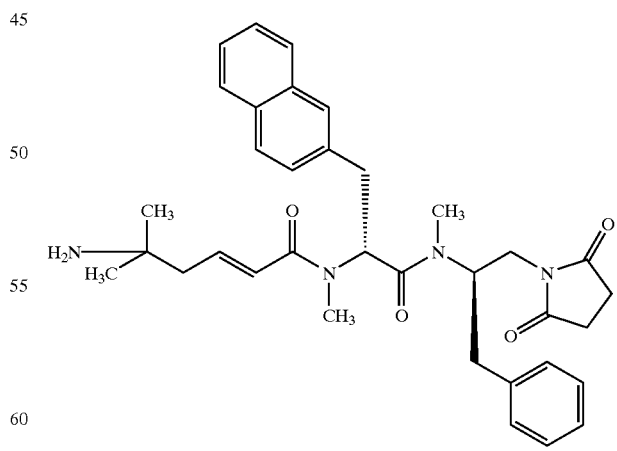

(2R)-2-(N-((2-Amino-2-methylpropoxy)acetyl)-N-methyl-amino-N-methyl-3(2-naphthyl)-N-((1R)-2-phenyl-1-(((tetrahydrofuran-2-yl)methyl)carbamoyl)ethyl)-propionamide:

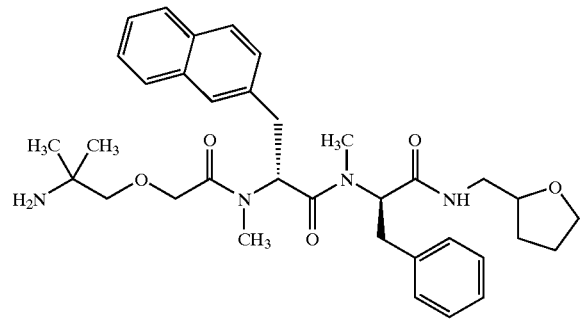

(2E)-5-Amino-3,5-dimethylhex-2-enoic acid N-methyl-N-((1R)-1-(N-methyl-N-((1R)-2-phenyl-1-(((2-tetrahydrofuranyl)methyl)carbamoyl)ethyl)carbamoyl)-2-(2-naphthyl)ethyl)amide:

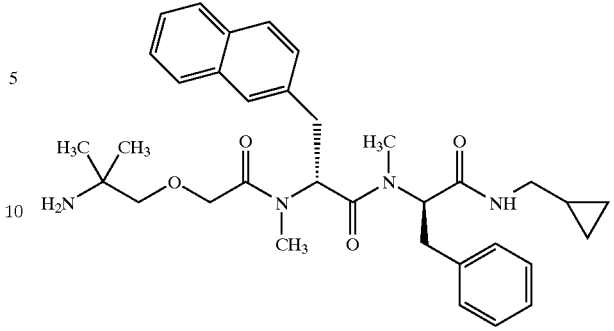

(2R)-2-(N-((2-Amino-2-methylpropoxy)acetyl)methylamino)-N-((1R)-2-(2-fluorophenyl)-1-(methylcarbamoyl)ethyl)-N-methyl-3-(2-naphthyl)propionamide:

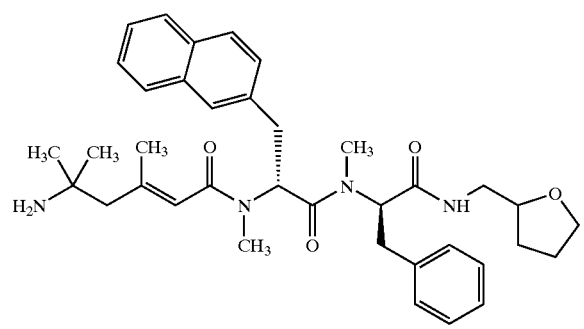

(2E)-5-Amino-5-methylhex-2-enoic acid N-((1R)-2-benzyloxy-1-(N-methyl-N-((1R)-1-methylcarbamoyl-2-phenylethyl)carbamoyl)ethyl)-N-methylamide:

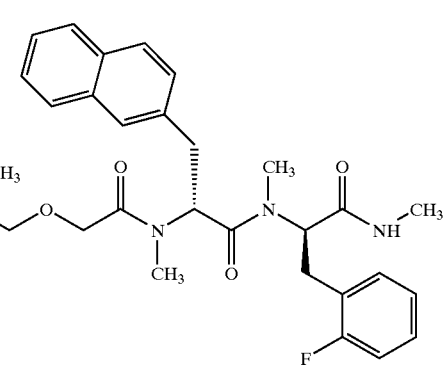

(2E)-5-Amino-5-methylhex-2-enoic acid N-(1R)-1-(N-((1R)-2-(4-fluorophenyl)-1-(methylcarbamoyl)ethyl)-N-methylcarbamoyl)-2-(2-naphthyl)ethyl)-N-methylamide:

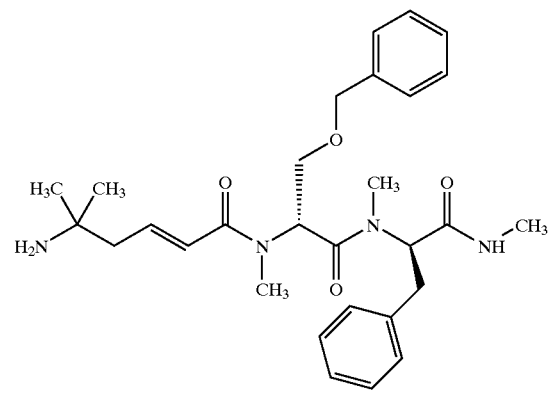

(2R)-2-(N-((2-Amino-2-methylpropoxy)acetyl)-N-methylamino)-N-((R)-1-(cyclopropylmethyl)carbamoyl)-2-phenylethyl)-N-methyl-3-(2-naphthyl)-propionamide:

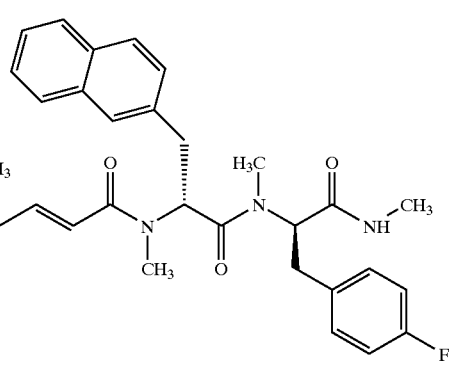

(2R)-2-(N-((2-Amino-2methylpropoxy)acetyl)N-methylamino)-N-((1R)-2-(4-fluorophenyl)-1-(methylcarbamoyl)ethyl)-N-methyl-3-(2-naphthyl)propionamide:

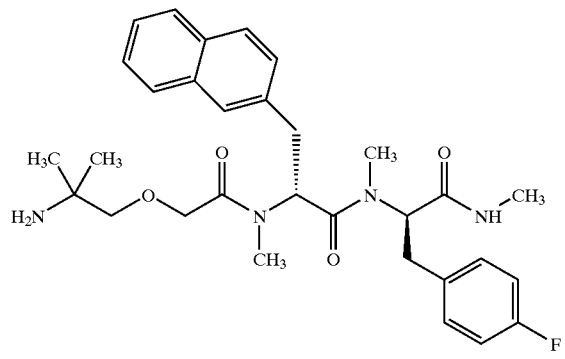

(2E)-5-Amino-5-methylhex-2-enoic acid ((1R)-2-(biphenyl-4-yl)-1-(N-methyl-N-((1R)-1-(methylcarbamoyl)-2-phenylethyl)carbamoyl)ethyl)-N-methylamide:

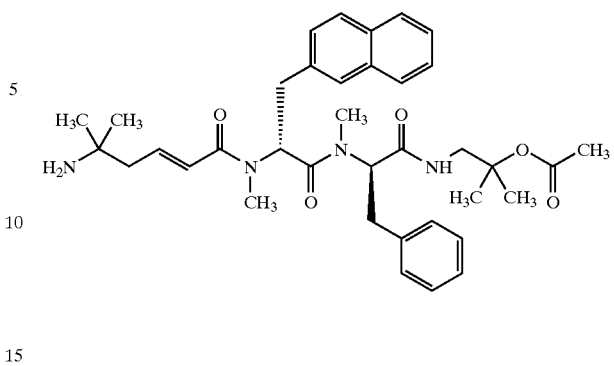

(2E)-5-Amino-2-benzyl-5-methylhex-2-enoic acid N-methyl-N-((1R)-1-(N-methyl-N-((1R)-1-(methylcarbamoyl)-2-phenylethyl)carbamoyl)-2-(2-naphthyl)ethyl)amide:

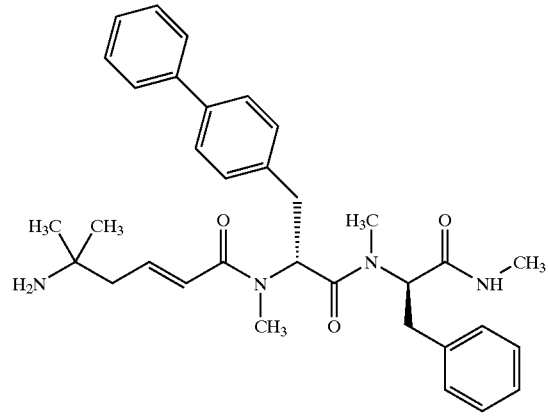

(2E)-5-Amino-3, 5-dimethylhex-2-enoic acid N-methyl-N-((1R)-1-(N-methyl-N-((1R)-1-(methylcarbamoyl)-2-phenylethyl)carbamoyl)-2-(2-naphthyl)ethyl)amide:

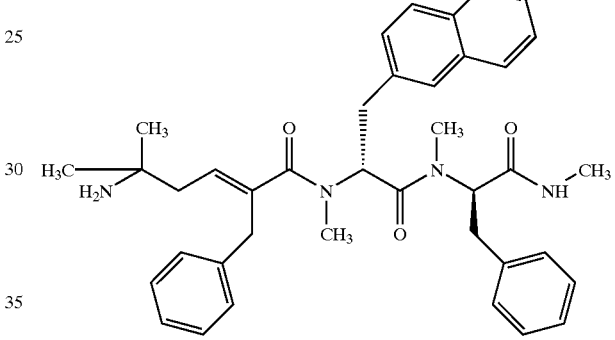

(2E)-5-Amino-5-methylhex-2-enoic acid N-methyl-N-((1R)-1-(N-methyl-N-((1R)-1-(methylcarbamoyl)-2-phenylethyl)-carbamoyl)-2-(1-naphthyl)ethyl)amide:

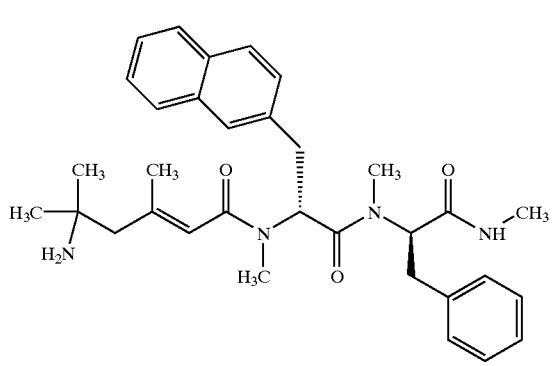

2-((2R)-2-(N-((2R)-2-(N-((2E)-5-Amino-5-methylhex-2-enoyl)-N-methylamino)-3-(2-naphthyl)propionyl)-N-methylamino)-3-phenylpropionylamino)-1,1-dimethylethyl acetate:

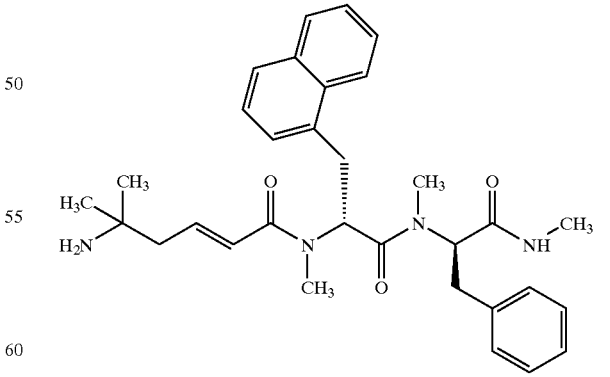

(2R)-2-(N-((2-Amino-2-methylpropoxy)acetyl)-N-methylamino)-N-methyl-N-((1R)-1-methylcarbamoyl-2-phenylethyl)-3-(1-naphthyl)propionamide:

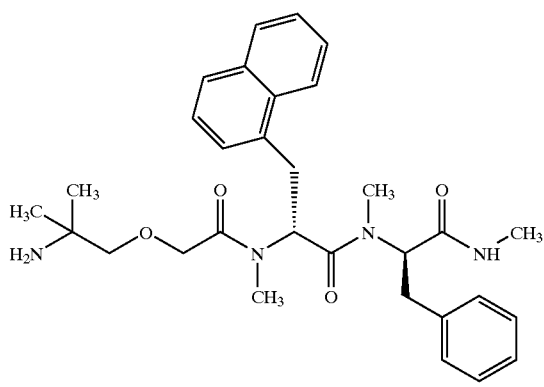

(2E)-5-Amino-5-methylhex-2-enoic acid N-((1R)-2-(benzo[b]thiophen-3-yl)-1-(N-methyl-N-((1R)-1-(methylcarbamoyl)-2-phenylethyl)carbamoyl)ethyl)N-methylamide:

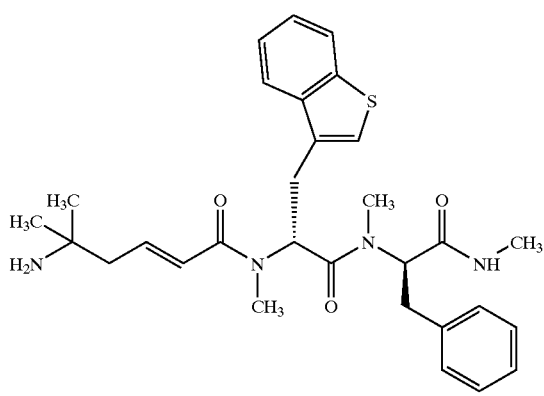

(2R)-2-(N-((2-Amino-2-methylpropoxy)acetyl)-N-methylamino)-3-(benzo[b]thio-phen-3-yl)-N-methyl-N-((1R)-1-(methylcarbamoyl)-2-phenylethyl)propionamide:

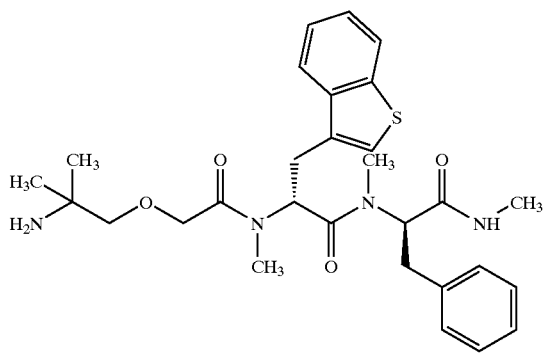

(2E)-5Amino-5-methylhex-2-enoic acid N-methyl-N-((1R)-1-(N-methyl-N-((1R)-2-phenyl-1 (((tetrahydrofuran-2-yl)methyl)carbamoyl)ethyl)carbamoyl)-2-(1-naphthyl)ethyl)amide:

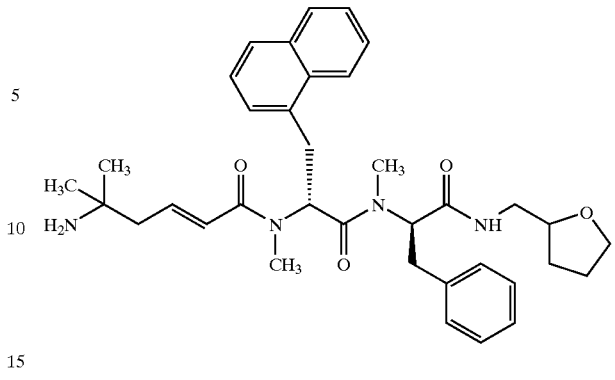

3-((2R)-2-(N-((2R)-2-(N-((2E)-5-Amino-5-methylhex-2-enoyl)-N-methylamino)-3-(2-naphthyl)propionyl)-N-methylamino)-3-phenylpropionylamino)propyl acetate:

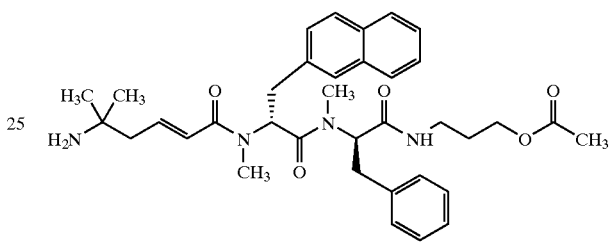

(2E)-5-Amino-5-methylhex-2-enoic acid N-((1R)-1-(N-((1R)-1-(3-hydroxypropyl-carbamoyl)-2-phenylethyl)-N-methylcarbamoyl)-2-(2-naphthyl)ethyl)-N-methyl-amide:

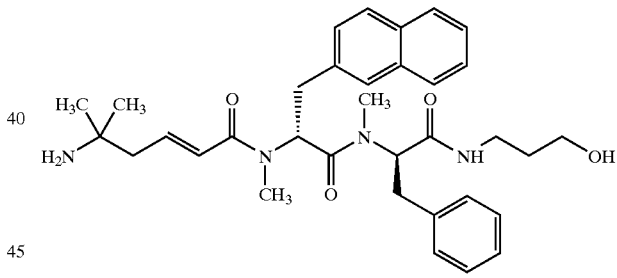

(2E)-5-Amino-5-methylhex-2-enoic acid N-methyl-N-((1R)-1-(N-methyl-N-((1R)-1-(((3-methyl-1,2,4-oxadiazol-5-yl)methoxy)methyl)-2-phenylethyl)carbamoyl)-2-(2-naphthyl)ethyl)amide:

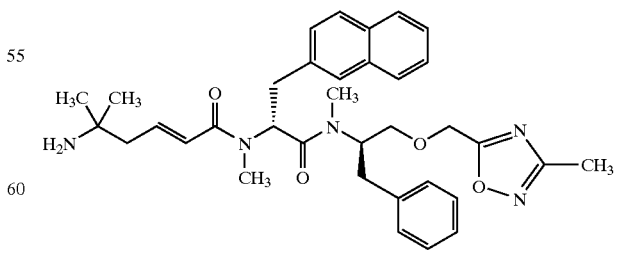

N-Methyl-N-((1R)-1-(methylcarbamoyl)-2-phenylethyl)-2-(N-methyl-N-{[(2-piperidinyl)methoxy]acetyl}amino)-3-(2-naphthyl)propionamide:

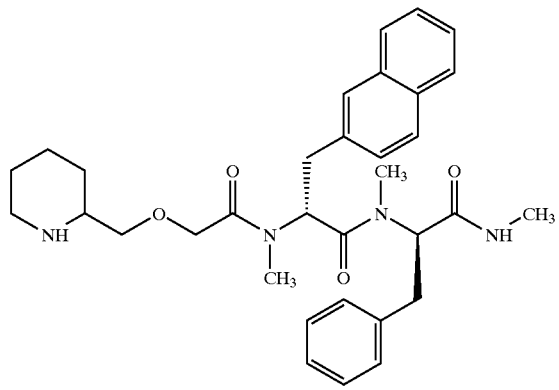

4-Aminocyclohexanecarboxylic acid N-methyl-N-((1R)-1-[N-methyl-N-{(1R)-1-(methylcarbamoyl)-2-phenylethyl}carbamoyl]-2-(2-naphthyl)ethyl)amide:

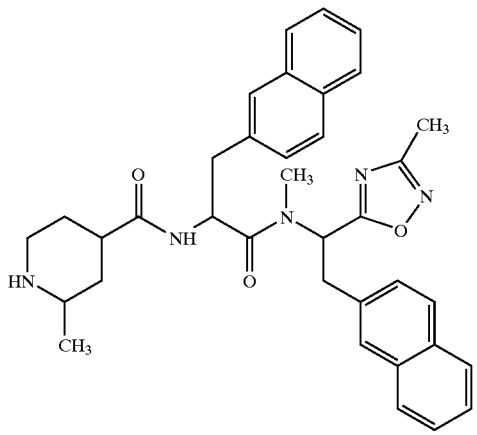

(2R)-2-(N-((2R)-2-(N-((2E)-5((2R)-2-Hydroxypropylamino)-5-methylhex-2-enoyl)-N-methylamino)-3-(2-naphthyl)propionyl)-N-methylamino)-N-methyl-3-phenylpropionamide;

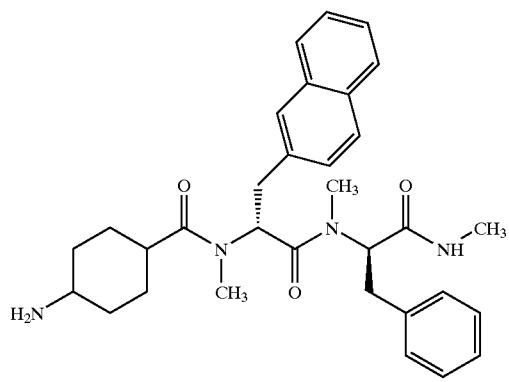

(2R)-N-Methyl-N-((1R)-1-(methylcarbamoyl)-2-phenylethyl)-2-(N-methyl-N´[{piperidin-4-yloxy}acetyl]amino)-3-(2naphthyl)propionamide:

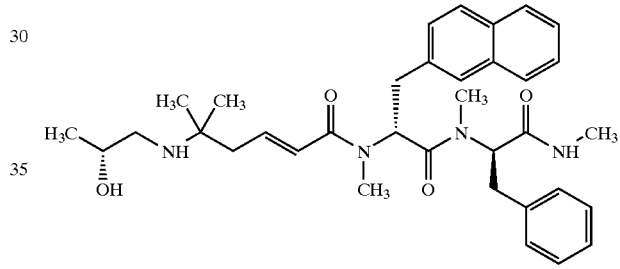

(2E)-5-Amino-N-((1R)-1-(N-((1R)-1-benzyl-2-((methylsulfonyl)amino)ethyl)-N´-methylcarbamoyl)-2-(2-naphthyl)ethyl)-5-methyl-N-methylhex-2-enamide;

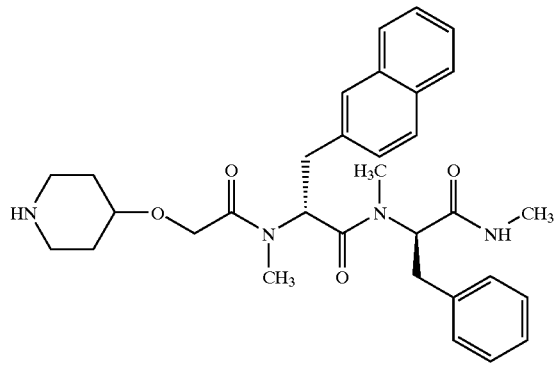

2-Methyl-piperidine-carboxylic acid N{1-[N-methyl-N-(1-(3-methyl-1,2,4-oxadiazol-5-yl)-2-(2-naphthyl)ethyl)carbamoyl]-2-(2-naphthyl)ethyl}amide:

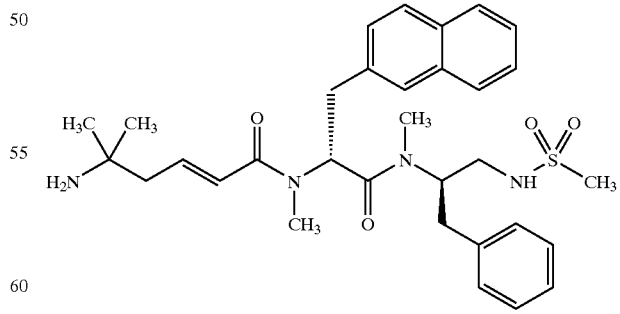

3-(1-Aminoethyl)benzoic acid N-methyl-N-((1R)-1-(N-methyl-N-((1R)-1-(methylcarbamoyl)-2-phenylethyl)carbamoyl)-2-(2-naphthyl)ethyl)amide:

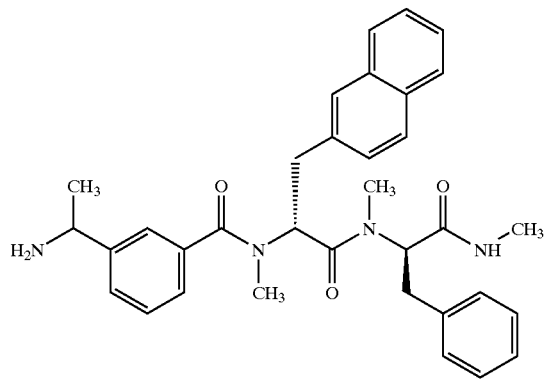

5-Amino-5-methyl-hex-2-enoic acid ((1R)-1-(((1R)-1-((2R)-2-hydroxypropylcarbamoyl)-2-phenylethyl)methylcarbamoyl)-2-(2-naphthyl)ethyl) methylamide:

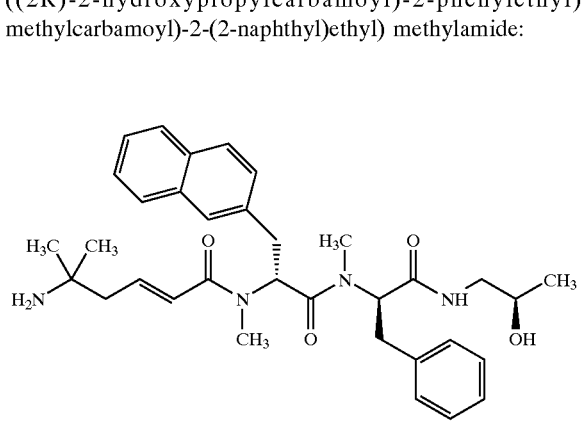

(4-(1-Aminocyclobutyl)but-2-enoic acid ((1R)-1-(((1R)-1-(1-methylcarbamoyl-2-phenylethyl)methylcarbamoyl)-2-(2-naphthyl)ethyl)methylamide:

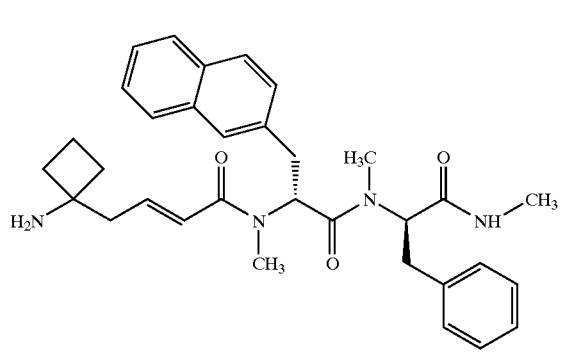

5-Amino-5-methyl-hex-2-enoic acid ((1R)-1-(((1R)-1-((2S)-2-hydroxypropylcarbamoyl)-2-(2-thienyl)ethyl)methylcarbamoyl)-2-(2-naphthyl)ethyl)methylamide.

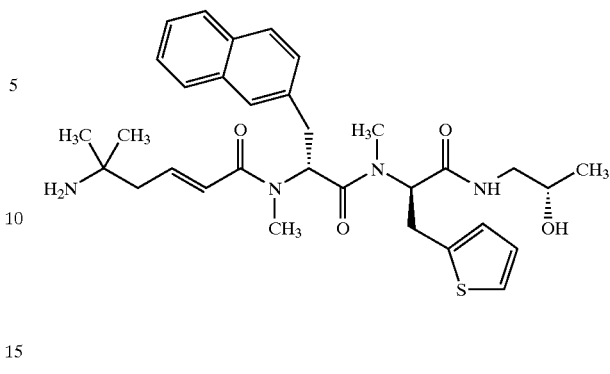

(2R)-2-(N-[(2R)-2-(N-[(2-Aminobutoxy)acetyl]-N-methylamino)-3-(2-naphthyl)propionyl]-N-methylamino)-N-methyl-3-phenylpropionamide:

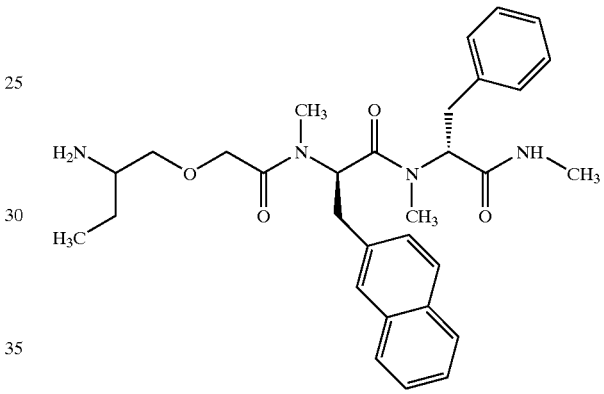

(2R)-N-Methyl-2-(N-methyl-N-((2R)-2-(N-methyl-N-((((2S)-pyrrolidin-2-yl)methoxy)acetyl)amino)-3-(2-naphthyl)propionyl)amino)-3-phenylpropionamide

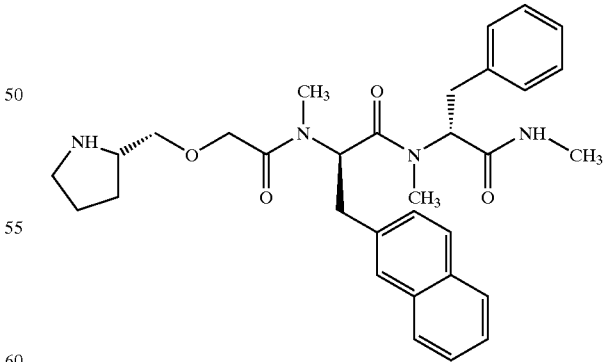

3-((2R)-2-(N-((2R)-2-(N-((2-Amino-2-methylpropoxy)acetyl)-N-methylamino)-3-(2-naphthyl)propionyl)-N-methylamino)-3-phenylpropionylamino)propyl acetate

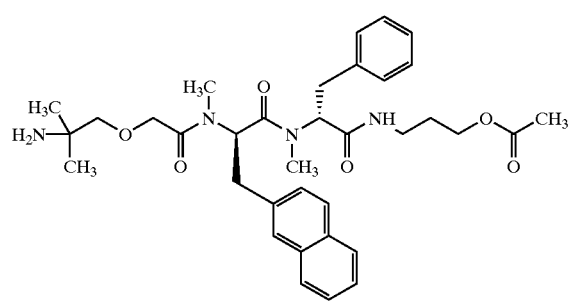

(2E)-5-Amino-5-methylhex-2-enoic acid N-((1R)-1-(N-((1R)-1-(dimethylcarbamoyl)-2-phenylethyl)-N-methylcarbamoyl) 2-(2-naphthyl)ethyl)-N-methylamide:

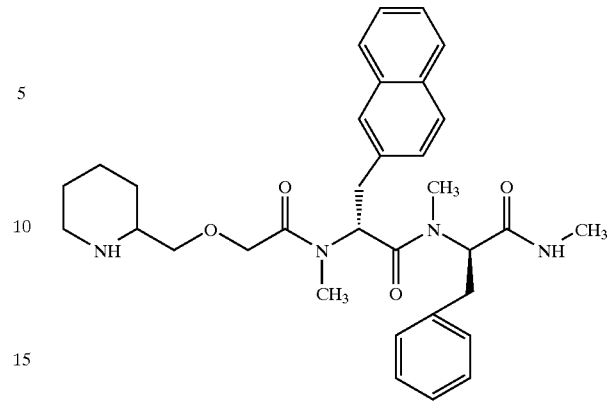

(2E)-5-Amino-5-methylhex-2-enoic acid N-methyl-N-((1R)-1-{N-[(1R)-2-(1-naphthyl)-1-(methylcarbamoyl)ethyl]-N-methylcarbamoyl}-2-(2-naphthyl)ethyl)amide:

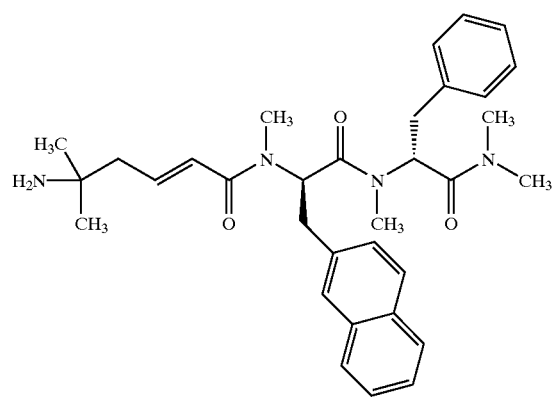

(2R)-N-Methyl-N-((1R)-1-(methyl carbamoyl)-2-phenylethyl)-2-(N-methyl-N-[{piperidine-4yloxy}acetyl]amino)-3-(2-naphthyl) propionamide (2E)-5-Amino-5-methylhex-2-enoic acid N-methyl-N-((1R)-1-{N-[(1R)-2-(1-naphthyl)-1-(methylcarbamoyl)ethyl]N-methylcarbamoyl}-2-(4-methoxyphenyl)ethyl)amide:

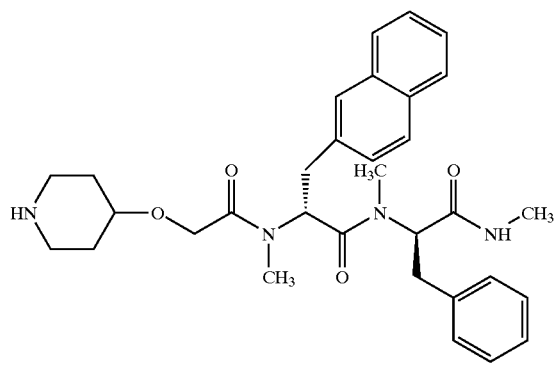

N-Methyl-N-((1R)-1-methylcarbamoyl)-2-phenylethyl)-2-(N-methyl-N-{[(2-piperidinyl)methoxy]acetyl}amino)-3-(2-naphthyl)propinamide

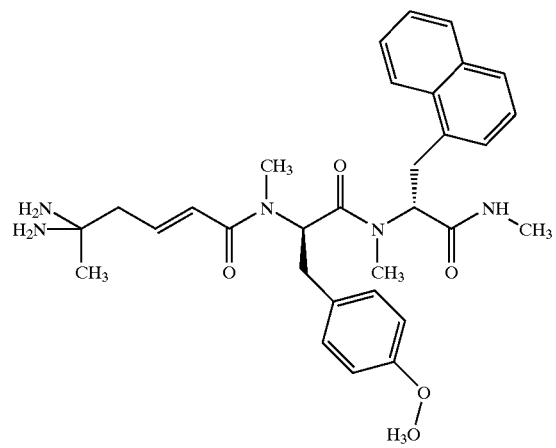

(2E)-5-Amino-5-methylhex-2-enoic acid N-methyl-N-((1R)-1-{N-[(1R)-2-(1-naphthyl)-1-(methylcarbamoyl)ethyl]-N-methylcarbamoyl}-2-phenylethyl) amide:

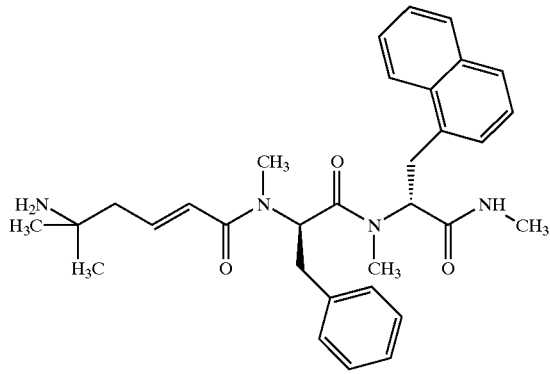

(2E)-5-Amino-5-methylhex-2-enoic acid N-methyl-N-((1R)-1-{N-[(1R)-2-(2-naphthyl)-1-(methylcarbamoyl)ethyl]-N-methylcarbamoyl)-2-(1-naphthyl)ethyl)amide:

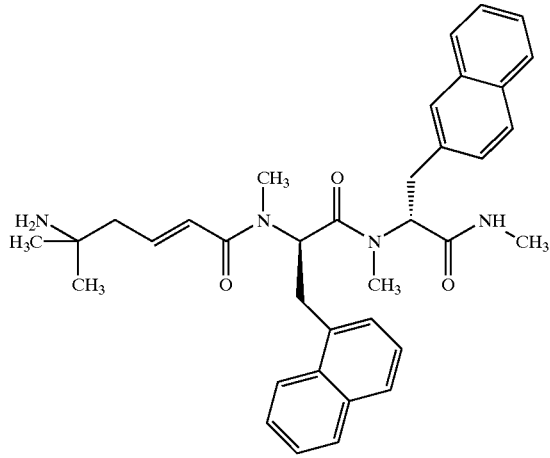

(2E)-5-Amino-5-methylhex-2-enoic acid N-methyl-N-((1R)-1-{N-[(1R)-2-(2-naphthyl)-1-(methylcarbamoyl)ethyl]-N-methylcarbamoyl)-2-phenylethyl)amide:

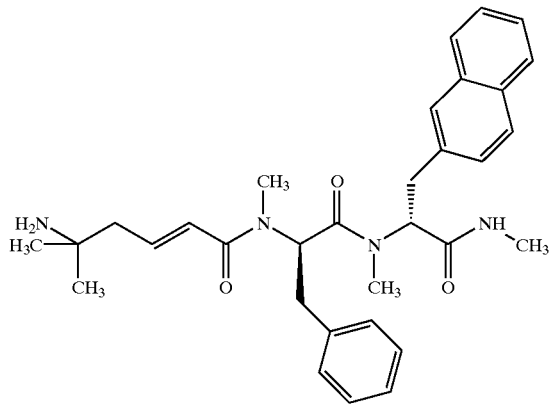

(2E)-5-Amino-5-methylhex-2-enoic acid N-methyl-N-((1R)-1-{N-[(1R)-2-(4-methoxyphenyl)-1-(methylcarbamoyl)ethyl]-N-methylcarbamoyl}2-(1-naphthyl)ethyl)amide:

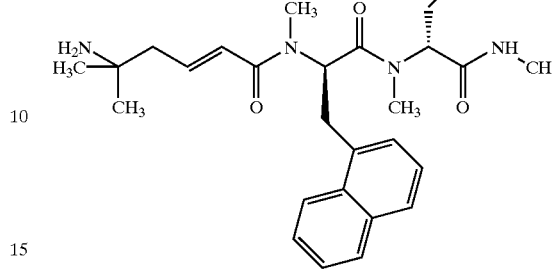

(2E)-5-Amino-5methylhex-2-enoic acid N-methyl-N-((1R)-1-{N-[(1R)-2-(4-methoxyphenyl)-1-(methylcarbamoyl)ethyl]-N-methylcarbamoyl}-2-(4-methoxyphenyl)ethyl) amide:

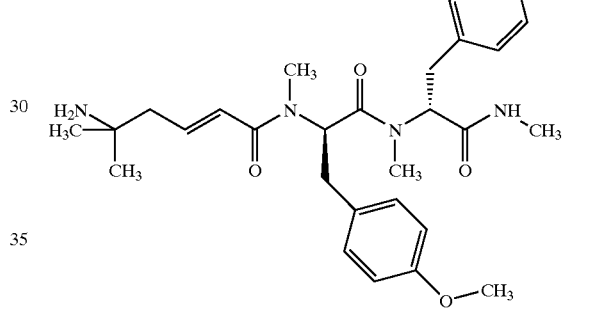

(2E)-5-Amino-5-methylhex-2-enoic acid N-methyl-N-((1R)-1-{N-[(1R)-2-(4-methoxyphenyl)-1-(methylcarbamoyl)ethyl]-N-methylcarbamoyl}-2-(2,3,4,5,6-pentafluorophenyl)ethyl)amide:

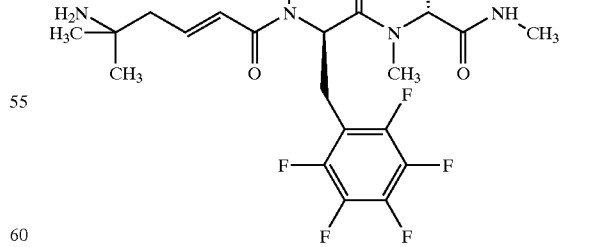

(2E)-5-Amino-5-methylhex-2-enoic acid N-methyl-N-((1R)-1-{N-[(1R)-2-(4-methoxyphenyl)-1-(methylcarbamoyl)ethyl]-N-methylcarbamoyl}-2-phenylethyl)amide:

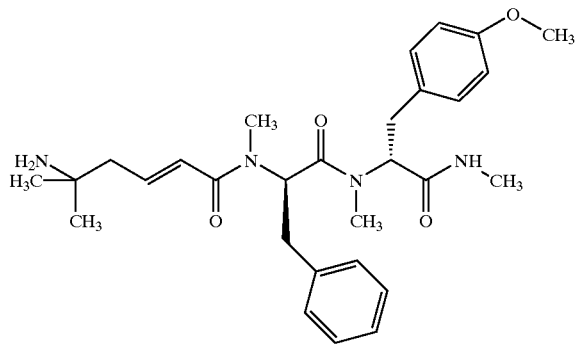

(2E)-5-Amino-5-methylhex-2-enoic acid N-methyl-N-((1R)-1-{N-[(1R)-2-(2,3,4,5,6-pentafluorophenyl)-1-(methylcarbamoyl)ethyl]-N-methylcarbamoyl}2-(1-naphthyl)ethyl)amide:

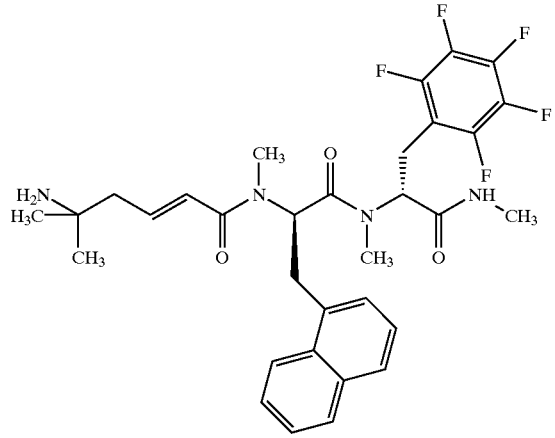

(2E)-5-Amino-5-methylhex-2-enoic acid N-methyl-N-((1R)-1-{N-[(1R)-2-(2,3,4,5,6-pentafluorophenyl)-1-(methylcarbamoyl)ethyl]-N-methylcarbamoyl}2-(4-methoxyphenyl)ethyl)amide:

(2E)-5-Amino-5-methylhex-2-enoic acid N-methyl-N-((1R)-1-{N-[(1R)-2-(2,3,4,5,6-pentafluorophenyl)-1-(methylcarbamoyl)ethyl]-N-methylcarbamoyl}-2-phenylethyl)amide:

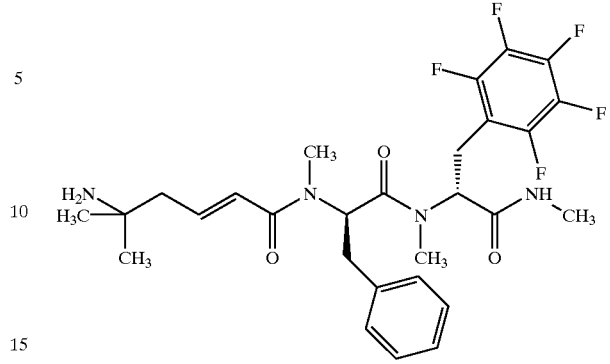

(2E)-5-Amino-5-methylhex-2-enoic acid N-methyl-N-((1R)-1-{N-[(1R)-2-phenyl-1-(methylcarbamoyl)ethyl]-N-methylcarbamoyl}-2-(4-methoxyphenyl)ethyl)amide:

(2E)-5-Amino-5-methylhex-2-enoic acid N-methyl-N-((1R)-1-{N-[(1R)-2-phenyl-1-(methylcarbamoyl)ethyl]-N-methylcarbamoyl}-2-(2,3,4,5,6-pentafluorophenyl)ethyl)amide:

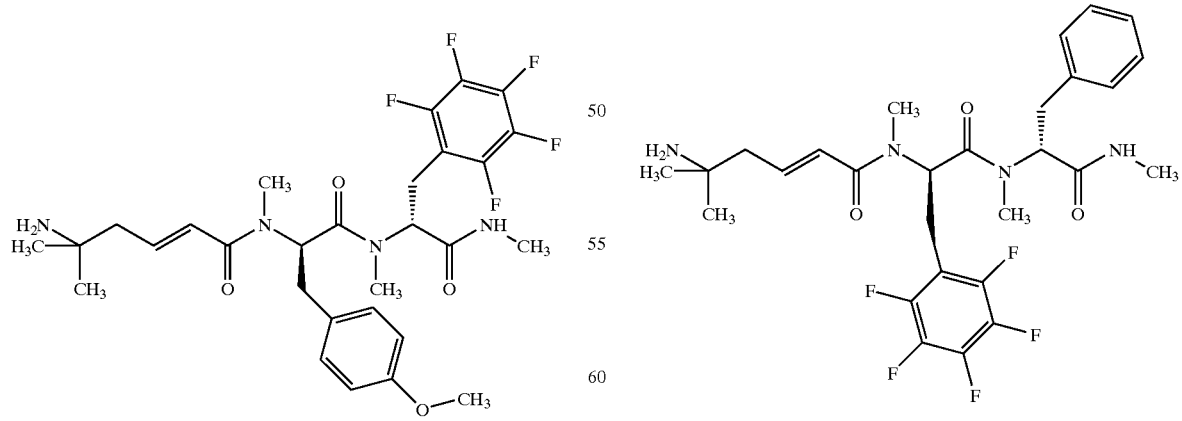

(2E)-5-Amino-5-methylhex-2-enoic acid N-methyl-N-((1R)-1-{N-[(1R)-2-phenyl-1-(methylcarbamoyl)ethyl]-N-methylcarbamoyl}-2-phenylethyl)amide:

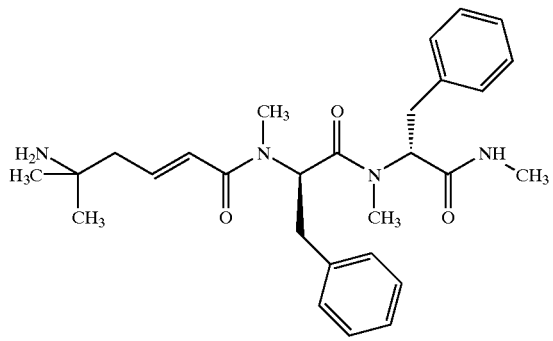

(2E)-5-Amino-5-methylhex-2-enoic acid N-methyl-N-((1R)-1-(N-methyl-N-((1R)-1-(methylcarbamoyl)-2-(thiophen-2-yl) ethyl)carbamoyl)-2-(2-naphthyl)ethyl) amide

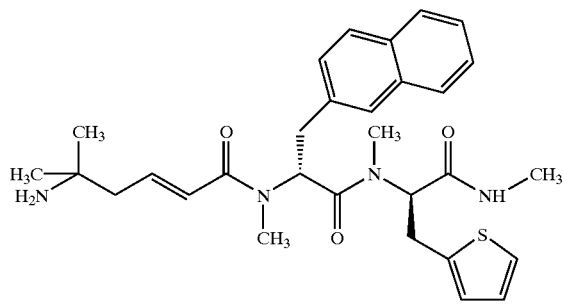

(2E)-5-Methyl-5-methylaminohex-2-enoic acid N-methyl-N-((1R)-1-(N-methyl-N-((1R)-1-(methylcarbamoyl)-2-phenyl ethyl)carbamoyl)-2-(2-naphthyl)ethyl)amide

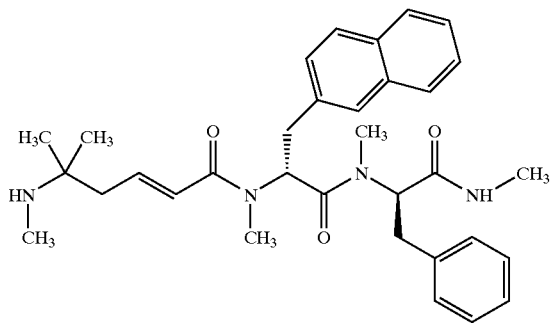

(2E)-5-Amino-3,5-dimethylhex-2-enoic acid N-methyl-N-((1R)-1-(N-methyl-N-((1R)-1-(methylcarbamoyl)-2-(thiophen-2-yl)ethyl)carbamoyl)-2-(2-naphthyl)ethyl) amide.

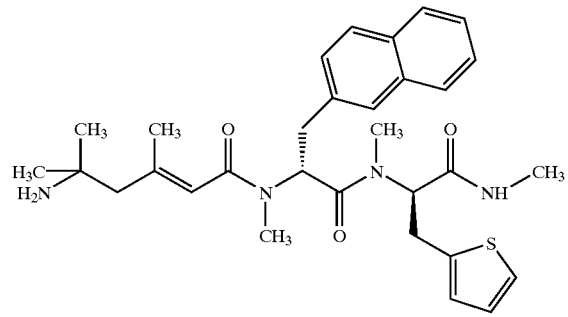

(2E)-5-Amino-5-methylhex-2-enoic acid N-methyl-N-((1R)-1-(N-methyl-N-(2-phenyl-1-(((tetrahydrofuran-2-yl)methyl)carbamoyl)ethyl)carbamoyl)-2-(1-naphthyl)ethyl) amide

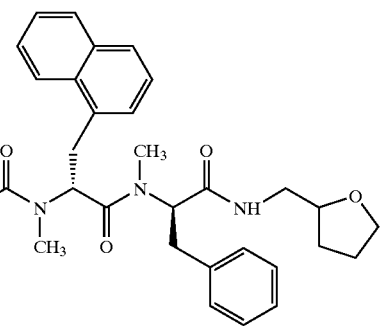

5-Amino-3,5-dimethylhex-2-enoic acid N-((1R)-2-(biphenyl-4-yl)-1-(N-methyl-N-((1R)-1-(methylcarbamoyl)-2-phenylethyl) carbamoyl)ethyl)-N-methylamide.

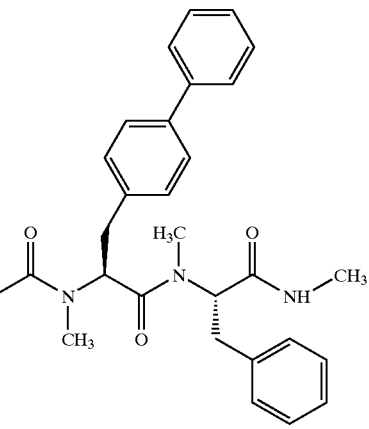

(2E)-5-Amino-5-methylhex-2-enoic acid N-((1R)-1-(N-((1R)-2-(4-iodophenyl)-1-(methyl carbamoyl)ethyl)-N-methylcarbamoyl)-2-(2-naphthyl)ethyl)-N-methylamide

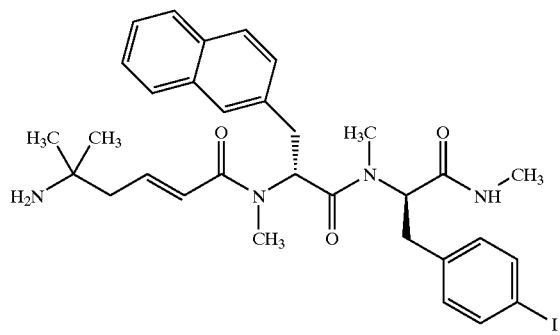

(2E)-5-Methyl-5-methylaminohex-2-enoic acid N-((1R)-1-(N-((1R)-2-(4-iodophenyl)-1-(methylcarbamoyl)ethyl)-N-methylcarbamoyl)-2-(2-naphthyl)ethyl)-N-methylamide

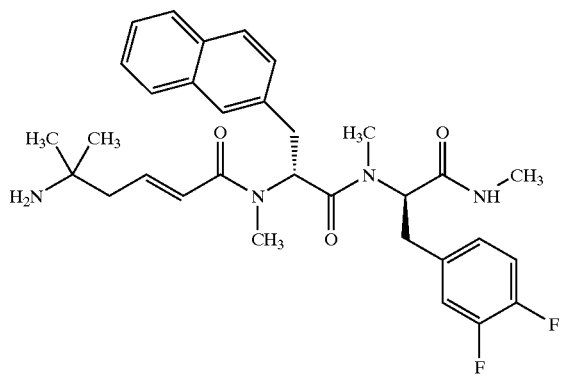

5-methylamino-hex-2-enoic acid ((1R)-1-(((1R)-2-phenyl-1-ethylcarbamoylethyl)methylcarbamoyl) -2-(2-naphthyl)ethyl)methylamide

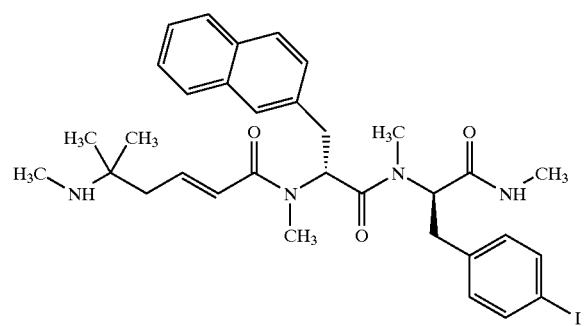

(2E) 5-Methyl-5-amino-5-methylhex-2-enoic acid-N-methyl-N-((1R)-2-(N-methyl-N-((1R)-(methylcarbamoyl)-2-(thien-2-yl)ethyl)carbamoyl)-2-(2-naphthyl)ethyl)amide.

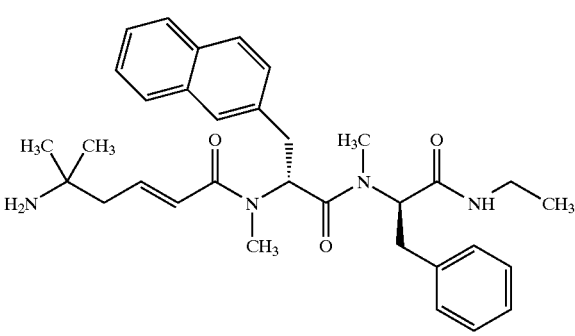

5-Amino-5-methyl-hex-2-enoic acid ((1R)-1-(((1R)-1-((2S)-2-hydroxypropylcarbamoyl)-2-(3,4-difluorophenyl)ethyl)methylcarbamoyl)-2-(2-naphthyl)ethyl)methylamine.

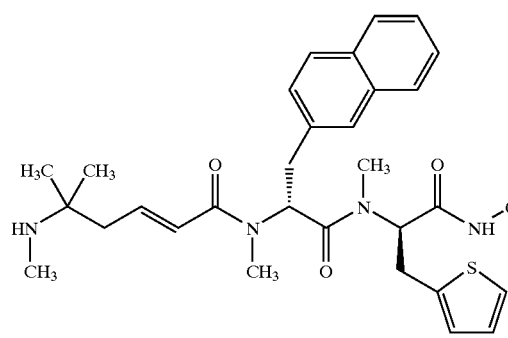

5-methylamino-hex-2-enoic acid ((1R)-1-(((1R)-2-(3,4-difluorophenyl)-1-methylcarbamoylethyl)methylcarbamoyl)-2-(2-naphthyl)ethyl)methylamide

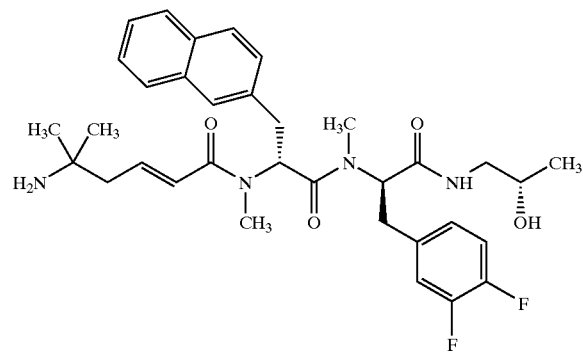

5-Amino-5-methyl-hex-2-enoic acid (1-{[2-(2fluorophenyl)-1-methylcarbamoylethyl]methylcarbamoyl}-2-(2-naphthyl)ethyl)methylamide.

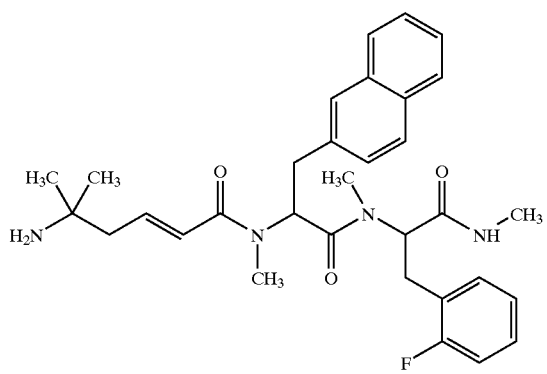

(2Z)-5-Amino-3,5-dimethylhex-2-enoic acid N-methyl-N-((1R)-1-(N-methyl-N-((1R)-1-methylcarbamoyl-2-phenylethyl)carbamoyl)-2-(2-naphthyl)ethyl)amide.

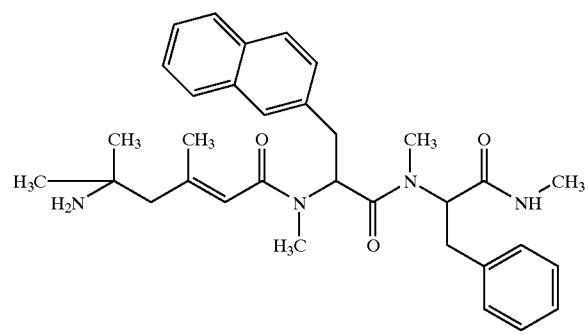

(2R)-2-(N-((2E)-5-Amino-5-methylhex-2-enoyl)-N-methylamino)-N-((1R)-1-benzyl-2-(3-cyclopropylthioureido)ethyl)-N-methyl-3-(2-naphthyl)propionamide

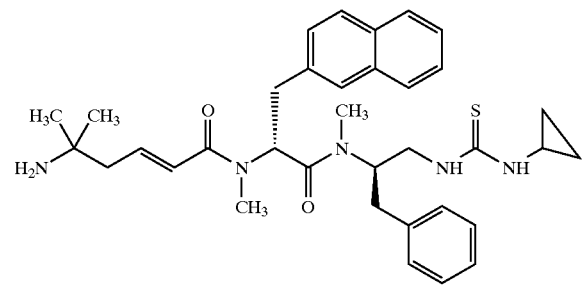

(2R)-2-(N-[}2-Amino-2-methylpropoxy}acetyl]-N-methylamino)-N-((1R)-1-(dimethylcarbamoyl)-2-phenylethyl)-N-methyl-3-(2-naphthyl)propionamide:

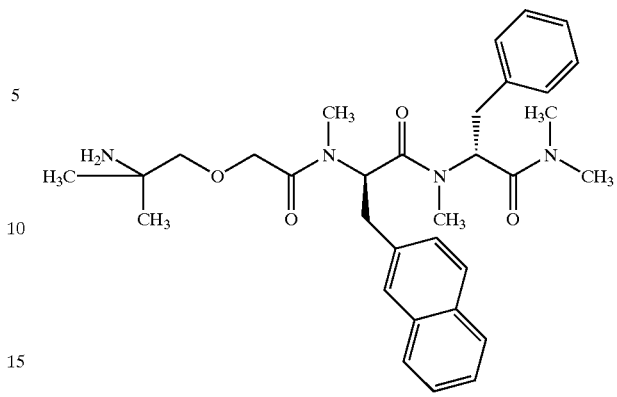

(2E)-5-Amino-5-methyl-N-methyl-N((1R)-1-(N-methyl-N-((1R)-2-phenyl-1-((2,2,2-trifluroethyl)carbamoyl)ethyl)carbamoyl)-2-(2-naphthyl)ethyl)hex-2-enamide, and its acetate salt;

(2E)-5-Amino-5-methylhex-2-enoic acid N-((1R)-1-(N-((1R)-1-(cyclopropylcarbamoyl)-2-phenylethyl)-N-methylcarbamoyl)-2-(2-naphthyl)ethyl)-N-methylamide;

(2E)-4-(1-Aminocyclobutyl)but-2-enoic acid N-((1R)-1-(N-((1R)-2-(3,4-difluorophenyl)-1-(methylcarbamoyl)ethyl)-N-methylcarbamoyl)-2-(2-naphthyl)ethyl)-N-methylamide;

(2E)-4-(1-Aminocyclobutyl)but-2-enoic acid N-((1R)-1-(N-((1R)-1-(cyclopropylcarbamoyl)-2-phenylethyl)-N-methylcarbamoyl)-2-(2-naphthyl)ethyl) N-methylamide;

(2E)-4-(1-Aminocyclobutyl)-but-2-enoic acid N-((1R)-2-(biphenyl-4-yl)-1-(N-methyl-N-((1R)-1-(methylcarbamoyl)-2-phenylethyl)carbamoyl)ethyl)-N-methylamide;

3-(1-Aminoethyl)-N-methyl-N-((1R)-1-(N-methyl-N-((1R)-1-(methylcarbamoyl)-2(2thienyl)ethyl)-carbamoyl)-2-(2-naphthyl)ethyl)benzamide;

3-Aminomethyl-N-methyl-N-((1R)-1-(N-methyl-N-((1R)-1-(methylcarbamoyl)-2-(2-thienyl)ethyl)carbamoyl)-2-(2-naphthyl)ethyl)benzamide;

(2R)-2-(N-((2-Aminobutoxy)acetyl)-N-methylamino)-N-methyl-N-((1R)-1-(methylcarbamoyl)-2-(2-thienyl)ethyl)-3-(2-naphthyl)propionamide;

(2R)-2-(N-((((2S)-2-Pyrrolidinyl)methoxy)acetyl)-N-methylamino)-N-methyl-N-((1R)-1-(methylcarbamoyl)-2-(2-thienyl)ethyl)-3-(2-naphthyl)propionamide;

(2R)-2-(N-((2-Amino-2-methylpropoxy)acetyl)-N-methylamino)-N-methyl-N-((1R)-1-(methylcarbamoyl)-2-(2-thienyl)ethyl)-3-(2-naphthyl)propionamide;

3-(1-Aminoethyl)-N-methyl-N-((1R)-1-(N-methyl-N-((1R)-1-(methylcarbamoyl)-2-(2-thienyl)ethyl)-carbamoyl)-2-(benzo[b]thiophen-3-yl)ethyl)-benzamide;

3-(1-Aminomethyl)-N-methyl-N-((1R)-1-(N-methyl-N-((1R)-1-(methylcarbamoyl)-2-(2-thienyl)ethyl)-carbamoyl)-2-(benzo[b]thiophen-3-yl)ethyl)benzamide;

(2R)-2-(N-((2-Aminobutoxy)acetyl)-N-methylamino)-N-methyl-N-((1R)-1-(methylcarbamoyl)-2-(2-thienyl)ethyl)-3-(benzo[b]thiophen-3-yl)propionamide;

(2R)-2-(N-((((2S)-2-Pyrrolidinyl)methoxy)acetyl)-N-methylamino)-N-methyl-N-((1R)-1-(methylcarbamoyl)-2-(2-thienyl)ethyl)-3-(benzo[b]thiophen-3-yl)propionamide;

(2R)-2-(N-((2-Amino-2-methylpropoxy)acetyl)-N-methylamino)-N-methyl-N-((1R)-1-(methylcarbamoyl)-2-(2-thienyl)ethyl)-3-(benzo[b]thiophen-3-yl)propionamide;

(2E)-5-Amino-5-methylhex-2-enoic acid N-methyl-N-((1R)-1-(N-methyl-N-((1R)-1-(methylcarbamoyl)-2-(2-thienyl)ethyl)carbamoyl)-2-(benzo[b]thiophen-3-yl)ethyl)amide;

3-(1-Aminoethyl)-N-methyl-N-((1R)-1-(N-methyl-N-((1R)-1-(methylcarbamoyl)-2-(2-thienyl)ethyl)carbamoyl)-2-(benzyloxy)ethyl)benzamide;

3-Aminomethyl-N-methyl-N-((1R)-1-(N-methyl-N-((1R)-1-(methylcarbamoyl)-2-(2-thienyl)ethyl)carbamoyl)-2-(benzyloxy)ethyl)benzamide;

(2R)-2-(N-((2-Aminobutoxy)acetyl)-N-methylamino)-N-methyl-N-((1R)-1-(methylcarbamoyl)-2-(2-thienyl)ethyl)-3-(benzyloxy)propionamide;

(2R)-2-(N-((((2S)-2-Pyrrolidinyl)methoxy)acetyl)-N-methylamino)-N-methyl-N-((1R)-1-(methylcarbamoyl)-2-(2-thienyl)ethyl)-3-(benzyloxy)propionamide;

(2R)-2-(N-((2-Amino-2-methylpropoxy)acetyl)-N-methylamino)-N-methyl-N-((1R)-1-(methylcarbamoyl)-2-(2-thienyl)ethyl)-3-(benzyloxy)propionamide;

(2E)-5-Amino-5-methylhex-2-enoic acid N-methyl-N-((1R)-1-(N-methyl-N-((1R)-1-(methylcarbamoyl)-2-(2-thienyl)ethyl)carbamoyl)-2-(benzyloxy)ethyl)amide;

3-(1-Aminoethyl)-N-methyl-N-((1R)-1-(N-methyl-N-((1R)-1-(methylcarbamoyl)-2-(2-thienyl)ethyl)carbamoyl)-2-(biphenyl-4-yl)ethyl)benzamide;

3-Aminomethyl-N-methyl-N-((1R)-1-(N-methyl-N-((1R)-1-(methylcarbamoyl)-2-(2-thienyl)ethyl)carbamoyl)-2-(biphenyl-4-yl)ethyl)benzamide;

(2R)-2-(N-((2-Aminobutoxy)acetyl)-N-methylamino)-N-methyl-N-((1R)-1-(methylcarbamoyl)-2-(2-thienyl)ethyl)-3-(biphenyl-4-yl)propionamide;

(2R)-2-(N-((((2S)-2-Pyrrolidinyl)methoxy)acetyl)-N-methylamino)-N-methyl-N-((1R)-1-(methylcarbamoyl)-2-(2-thienyl)ethyl)-3-(biphenyl-4-yl)propionamide;

(2R)-2-(N-((2-Amino-2-methylpropoxy)acetyl)-N-methylamino)-N-methyl-N-((1R)-1-(methylcarbamoyl)-2-(2-thienyl)ethyl)-3-(biphenyl-4-yl)propionamide;

(2E)-5-Amino-5-methylhex-2-enoic acid N-methyl-N-((1R)-1-(N-methyl-N-((1R)-1-(methylcarbamoyl)-2-(2-thienyl)ethyl)carbamoyl)-2-(biphenyl-4-yl)ethyl)amide;

3-(1-Aminoethyl)-N-methyl-N-((1R)-1-(N-methyl-N-((1R)-1-(methylcarbamoyl)-2-(2-fluorophenyl)-ethyl)carbamoyl)-2-(2-naphthyl)ethyl)benzamide;

3-Aminomethyl-N-methyl-N-((1R)-1-(N-methyl-N-((1R)-1-(methylcarbamoyl)-2-(2-fluorophenyl)ethyl)carbamoyl)-2-(2-naphthyl)ethyl)benzamide;

(2R)-2-(N-((2-Aminobutoxy)acetyl)-N-methylamino)-N-methyl-N-((1R)-1-(methylcarbamoyl)-2-(2-fluorophenyl)ethyl)-3-(2-naphthyl)propionamide;

(2R)-2-(N-((((2S)-2-Pyrrolidinyl)methoxy)acetyl)-N-methylamino)-N-methyl-N-((1R)-1-(methylcarbamoyl)-2-(2-fluorophenyl)ethyl)-3-(2-naphthyl)propionamide;

(2R)-2-(N-((2-Amino-2-methylpropoxy)acetyl)-N-methylamino)-N-methyl-N-((1R)-1-(methylcarbamoyl)-2-(2-fluorophenyl)ethyl)-3-(2-naphthyl)propionamide;

3-(1-Aminoethyl)-N-methyl-N-((1R)-1-(N-methyl-N-((1R)-1-(methylcarbamoyl)-2-(2-fluorophenyl)-ethyl)carbamoyl)-2-(benzo[b]thiophen-3-yl)ethyl)-benzamide;

3-Aminomethyl-N-methyl-N-((1R)-1-(N-methyl-N-((1R)-1-(methylcarbamoyl)-2-(2-fluorophenyl)ethyl)carbamoyl)-2-(benzo[b]thiophen-3-yl)ethyl)benzamide;

(2R)-2-(N-((2-Aminobutoxy)acetyl)-N-methylamino)-N-methyl-N-((1R)-1-(methylcarbamoyl)-2-(2-fluorophenyl)ethyl)-3-(benzo[b]thiophen-3-yl)propionamide;

(2R)-2-(N-((((2S)-2-Pyrrolidinyl)methoxy)acetyl)-N-methylamino)-N-methyl-N-((1R)-1-(methylcarbamoyl)-2-(2-fluorophenyl)ethyl)-3-(benzo[b]thiophen-3-yl)propionamide;

(2R)-2-(N-((2-Amino-2-methylpropoxy)acetyl)-N-methylamino)-N-methyl-N-((1R)-1-(methylcarbamoyl)-2-(2-fluorophenyl)ethyl)-3-(benzo[b]thiophen-3-yl)propionamide;

3-(1-Aminoethyl)-N-methyl-N-((1R)-1-(N-methyl-N-((1R)-1-(methylcarbamoyl)-2-(2-fluorophenyl)ethyl)carbamoyl)-2-(benzyloxy)ethyl)benzamide;

3-Aminomethyl-N-methyl-N-((1R)-1-(N-methyl-N-((1R)-1-(methylcarbamoyl)-2-(2-fluorophenyl)-ethyl)carbamoyl)-2-(benzyloxy)ethyl)benzamide;

(2R)-2-(N-((2-Aminobutoxy)acetyl)-N-methylamino)-N-methyl-N-((1R)-1-(methylcarbamoyl)-2-(2-fluorophenyl)ethyl)-3-(benzyloxy)propionamide;

(2R)-2-(N-((((2S)-2-Pyrrolidinyl)methoxy)acetyl)-N-methylamino)-N-methyl-N-((1R)-1-(methylcarbamoyl)-2-(2-fluorophenyl)ethyl)-3-(benzyloxy)propionamide;

(2R)-2-(N-((2-Amino-2-methylpropoxy)acetyl)-N-methylamino)-N-methyl-N-((1R)-1-(methylcarbamoyl)-2-(2-fluorophenyl)ethyl)-3-(benzyloxy)propionamide;

3-(1-Aminoethyl)-N-methyl-N-((1R)-1-(N-methyl-N-((1R)-1-(methylcarbamoyl)-2-(2-fluorophenyl)ethyl)carbamoyl)-2-(biphenyl-4-yl)ethyl)benzamide;

3-Aminomethyl-N-methyl-N-((1R)-1-(N-methyl-N-((1R)-1-(methylcarbamoyl)-2-(2-fluorophenyl)ethyl)carbamoyl)-2-(biphenyl-4-yl)ethyl)benzamide;

(2R)-2-(N-((2-Aminobutoxy)acetyl)-N-methylamino)-N-methyl-N-((1R)-1-(methylcarbamoyl)-2-(2-fluorophenyl)ethyl)-3-(biphenyl-4-yl)propionamide;

(2R)-2-(N-((((2S)-2-Pyrrolidinyl)methoxy)acetyl)-N-methylamino)-N-methyl-N-((1R)-1-(methylcarbamoyl)-2-(2-fluorophenyl)ethyl)-3-(biphenyl-4-yl)propionamide;

(2R)-2-(N-((2-Amino-2-methylpropoxy)acetyl)-N-methylamino)-N-methyl-N-((1R)-1-(methylcarbamoyl)-2-(2-fluorophenyl)ethyl)-3-(biphenyl-4-yl)propionamide;

(2E)-5-Amino-5-methylhex-2-enoic acid N-methyl-N-((1R)-1-(N-methyl-N-((1R)-1-(methylcarbamoyl)-2-(2-fluorophenyl)ethyl)carbamoyl)-2-(biphenyl-4-yl)ethyl)amide;

3-(1-Aminoethyl)-N-methyl-N-((1R)-1-(N-methyl-N-((1R)-1-(methylcarbamoyl)-2-phenylethyl)carbamoyl)-2-(benzo[b]thiophen-3-yl)ethyl)benzamide;

3-Aminomethyl-N-methyl-N-((1R)-1-(N-methyl-N-((1R)-1-(methylcarbamoyl)-2-phenylethyl)carbamoyl)-2-(benzo[b]thiophen-3-yl)ethyl)benzamide;

(2R)-2-(N-((2-Aminobutoxy)acetyl)-N-methylamino)-N-methyl-N-((1R)-1-(methylcarbamoyl)-2-phenylethyl)-3-(benzo[b]thiophen-3-yl)propionamide;

(2R)-2-(N-((((2S)-2-Pyrrolidinyl)methoxy)acetyl)-N-methylamino)-N-methyl-N-((1R)-1-(methylcarbamoyl)-2-phenylethyl)-3-(benzo[b]thiophen-3-yl)propionamide;

(2R)-2-(N-((2-Amino-2-methylpropoxy)acetyl)-N-methylamino)-N-methyl-N-((1R)-1-(methylcarbamoyl)-2-phenylethyl)-3-(benzo[b]thiophen-3-yl)propionamide;

(2E)-5-Amino-5-methylhex-2-enoic acid N-methyl-N-((1R)-1-(N-methyl-N-((1R)-1-(methylcarbamoyl)-2-phenylethyl)carbamoyl)-2-(benzo[b]thiophen-3-yl)ethyl)amide;

3-(1-Aminoethyl)-N-methyl-N-((1R)-1-(N-methyl-N-((1R)-1-(methylcarbamoyl)-2-phenylethyl)carbamoyl)-2-(benzyloxy)ethyl)benzamide;

3-Aminomethyl-N-methyl-N-((1R)-1-(N-methyl-N-((1R)-1-(methylcarbamoyl)-2-phenylethyl)carbamoyl)-2-(benzyloxy)ethyl)benzamide;

(2R)-2-(N-((2-Aminobutoxy)acetyl)-N-methylamino)-N-methyl-N-((1R)-1-(methylcarbamoyl)-2-phenylethyl)-3-(benzyloxy)propionamide;

(2R)-2-(N-((((2S)-2-Pyrrolidinyl)methoxy)acetyl)-N-methylamino)-N-methyl-N-((1R)-1-(methylcarbamoyl)-2-phenylethyl)-3-(benzyloxy)propionamide;

(2R)-2-(N-((2-Amino-2-methylpropoxy)acetyl)-N-methylamino)-N-methyl-N-((1R)-1-(methylcarbamoyl)-2-phenylethyl)-3-(benzyloxy)propionamide;

3-(1-Aminoethyl)-N-methyl-N-((1R)-1-(N-methyl-N-((1R)-1-(methylcarbamoyl)-2-phenylethyl)carbamoyl)-2-(biphenyl-4-yl)ethyl)benzamide;

3-Aminomethyl-N-methyl-N-((1R)-1-(N-methyl-N-((1R)-1-(methylcarbamoyl)-2-phenylethyl)carbamoyl)-2-(biphenyl-4-yl)ethyl)benzamide;

(2R)-2-(N-((2-Aminobutoxy)acetyl)-N-methylamino)-N-methyl-N-((1R)-1-(methylcarbamoyl)-2-phenylethyl)-3-(biphenyl-4-yl)propionamide;

(2R)-2-(N-((((2S)-2-Pyrrolidinyl)methoxy)acetyl)-N-methylamino)-N-methyl-N-((1R)-1-(methylcarbamoyl)-2-phenylethyl)-3-(biphenyl-4-yl)propionamide;

(2R)-2-(N-((2-Amino-2-methylpropoxy)acetyl)-N-methylamino)-N-methyl-N-((1R)-1-(methylcarbamoyl)-2-phenylethyl)-3-(biphenyl-4-yl)propionamide;

3-(1-Aminoethyl)-N-methyl-N-((1R)-1-(N-methyl-N-((1R)-1-(methylcarbamoyl)-2-(4-methoxyphenyl)-ethyl)carbamoyl)-2-(2-naphthyl)ethyl)benzamide;

3-Aminomethyl-N-methyl-N-((1R)-1-(N-methyl-N-((1R)-1-(methylcarbamoyl)-2-(4-methoxyphenyl)ethyl)carbamoyl)-2-(2-naphthyl)ethyl)benzamide;

(2R)-2-(N-((2-Aminobutoxy)acetyl)-N-methylamino)-N-methyl-N-((1R)-1-(methylcarbamoyl)-2-(4-methoxyphenyl)ethyl)-3-(2-naphthyl)propionamide;

(2R)-2-(N-((((2S)-2-Pyrrolidinyl)methoxy)acetyl)-N-methylamino)-N-methyl-N-((1R)-1-(methylcarbamoyl)-2-(4-methoxyphenyl)ethyl)-3-(2-naphthyl)-propionamide;

(2R)-2-(N-((2-Amino-2-methylpropoxy)acetyl)-N-methylamino)-N-methyl-N-((1R)-1-(methylcarbamoyl)-2-(4-methoxyphenyl)ethyl)-3-(2-naphthyl)propionamide;

(2E)-5-Amino-5-methylhex-2-enoic acid N-methyl-N-((1R)-1-(N-methyl-N-((1R)-1-(methylcarbamoyl)-2-(4-methoxyphenyl)ethyl)carbamoyl)-2-(2-naphthyl)-ethyl) amide;

3-(1-Aminoethyl)-N-methyl-N-((1R)-1-(N-methyl-N-((1R)-1-(methylcarbamoyl)-2-(4-methoxyphenyl)-ethyl)carbamoyl)-2-(benzo[b]thiophen-3-yl)ethyl)-benzamide;

3-Aminomethyl-N-methyl-N-((1R)-1-(N-methyl-N-((1R)-1-(methylcarbamoyl)-2-(4-methoxyphenyl)ethyl)carbamoyl)-2-(benzo[b]thiophen-3-yl)ethyl)-benzamide;

(2R)-2-(N-((2-Aminobutoxy)acetyl)-N-methylamino)-N-methyl-N-((1R)-1-(methylcarbamoyl)-2-(4-methoxyphenyl)ethyl)-3-(benzo[b]thiophen-3-yl) propionamide; (2R)-2-(N-((((2S)-2-Pyrrolidinyl) methoxy)acetyl)-N-methylamino)-N-methyl-N-((1R)-1-(methylcarbamoyl)-2-(4-methoxyphenyl)ethyl)-3-(benzo[b]thiophen-3-yl)propionamide;

(2R)-2-(N-((2-Amino-2-methylpropoxy)acetyl)-N-methylamino)-N-methyl-N-((1R)-1-(methylcarbamoyl)-2-(4-methoxyphenyl)ethyl)-3-(benzo[b]thiophen-3-yl) propionamide;

(2E)-5-Amino-5-methylhex-2-enoic acid N-methyl-N-((1R)-1-(N-methyl-N-((1R)-1-(methylcarbamoyl)-2-(4-methoxyphenyl)ethyl)carbamoyl)-2-(benzo[b]thiophen-3-yl)ethyl)amide;

3-(1-Aminoethyl)-N-methyl-N-((1R)-1-(N-methyl-N-((1R)-1-(methylcarbamoyl)-2-(4-methoxyphenyl)-ethyl)carbamoyl)-2-(benzyloxy)ethyl)benzamide;

3-Aminomethyl-N-methyl-N-((1R)-1-(N-methyl-N-((1R)-1-(methylcarbamoyl)-2-(4-methoxyphenyl)-ethyl)carbamoyl)-2-(benzyloxy)ethyl)benzamide;

(2R)-2-(N-((2-Aminobutoxy)acetyl)-N-methylamino)-N-methyl-N-((1R)-1-(methylcarbamoyl)-2-(4-methoxyphenyl)ethyl)-3-(benzyloxy)propionamide;

(2R)-2-(N-((((2S)-2-Pyrrolidinyl)methoxy)acetyl)-N-methylamino)-N-methyl-N-((1R)-1-(methylcarbamoyl)-2-(4-methoxyphenyl)ethyl)-3-(benzyloxy)propionamide;

(2R)-2-(N-((2-Amino-2-methylpropoxy)acetyl)-N-methylamino)-N-methyl-N-((1R)-1-(methylcarbamoyl)-2-(4-methoxyphenyl)ethyl)-3-(benzyloxy)propionamide;

(2E)-5-Amino-5-methylhex-2-enoic acid N-methyl-N-((1R)-1-(N-methyl-N-((1R)-1-(methylcarbamoyl)-2-(4-methoxyphenyl)ethyl)carbamoyl)-2-(benzyloxy)ethyl) amide;

3-(1-Aminoethyl)-N-methyl-N-((1R)-1-(N-methyl-N-((1R)-1-(methylcarbamoyl)-2-(4-methoxyphenyl)-ethyl)carbamoyl)-2-(biphen-4-yl)ethyl)benzamide;

3-Aminomethyl-N-methyl-N-((1R)-1-(N-methyl-N-((1R)-1-(methylcarbamoyl)-2-(4-methoxyphenyl)ethyl)-carbamoyl)-2-(biphenyl-4-yl)ethyl)benzamide;

(2R)-2-(N-((2-Aminobutoxy)acetyl)-N-methylamino)-N-methyl-N-((1R)-1-(methylcarbamoyl)-2-(4-methoxyphenyl)ethyl)-3-(biphenyl-4-yl)propionamide;

(2R)-2-(N-((((2S)-2-Pyrrolidinyl)methoxy)acetyl)-N-methylamino)-N-methyl-N-((1R)-1-(methylcarbamoyl)-2-(4-methoxyphenyl)ethyl)-3-(biphenyl-4-yl) propionamide; or (2E)-5-Amino-5-methyl-N-methyl-N-((1R)-1-(N-methyl-N-((1R)-1-((N-methyl-N-(methylsulfonyl)amino)methyl)-2-(2-thienyl)ethyl)carbamoyl)-2-(2-naphthyl)ethyl)hex-2-enamide.

It is believed that compounds of formula I exhibit an improved resistance to proteolytic degradation by enzymes because they are non-natural, in particular because the natural amide bonds are replaced by non-natural amide bond mimetics. The increased resistance to proteolytic degradation combined with the reduced size of the compounds of the invention in comparison with known hormone releasing peptides is expected to improve their bioavailability compared to that of the peptides suggested in the prior literature.

In the above structural formulas and throughout the present specification, the following terms have the indicated meaning:

The $C_{1-6}$-alkyl groups specified above are intended to include those alkyl groups of the designated length in either a linear or branched or cyclic configuration, Examples of linear alkyl groups are methyl, ethyl, propyl, butyl, pentyl and hexyl. Examples of branched alkyl groups are isopropyl, sec-butyl, tert-butyl, isopentyl, and isohexyl. Examples of cyclic alkyl are cyclopropyl, cyclobutyl, cyclopentyl and cyclohexyl.

Especially preferred $C_{1-6}$-alkyl groups are the $C_{1-3}$-alkyl groups. Preferred $C_{1-3}$-alkyl groups are methyl, ethyl, isopropyl and cyclopropyl.

The $C_{1-6}$-alkoxy groups specified above are intended to include those alkoxy groups of the designated length in either a linear or branched or cyclic configuration. Examples of linear alkoxy groups are methoxy, ethoxy, propoxy, butoxy, pentoxy and hexoxy. Examples of branched alkoxy are isopropoxy, sec-butoxy, tert-butoxy, isopentoxy and isohexoxy. Example of cyclic alkoxy are cyclopropyloxy, cyclobutyloxy, cyclopentyloxy and cyclohexyloxy.

Especially preferred $C_{1-6}$-alkoxy groups are the $C_{1-3}$-alkoxy groups. Preferred $C_{1-3}$-alkoxy groups are methoxy, ethoxy, isopropoxy and cyclopropoxy.

In the present context, the term $C_{1-6}$-alkoxycarbonyl is intended to include the above defined $C_{1-6}$-alkoxy groups attached to a carbonyl moiety.

In the present context, the term $C_{1-6}$-alkoxycarbonyloxy is intended to include the above defined $C_{1-6}$-alkoxy groups attached to a carbonyloxy moiety.

In the present context, the term "aryl" is intended to include aromatic rings, such as carboxyclic and heterocyclic aromatic rings selected from the group consisting of phenyl, naphthyl, pyridyl, tetrazolyl, thiazolyl, imidazolyl, indolyl, quinolinyl, pyrimidinyl, thiadiazolyl, pyrazolyl, oxazolyl, isoxazolyl, thienyl, furanyl or oxadiazolyl optionally substituted with halogen, amino, hydroxy, $C_{1-6}$-alkyl or $C_{1-6}$-alkoxy. Aryl is preferably phenyl, thienyl, imidazolyl, pyridyl, indolyl, oxadiazole or naphthyl optionally substituted with halogen, amino, hydroxy, $C_{1-6}$-alkyl or $C_{1-6}$-alkoxy.

The term "halogen" includes Cl, F, Br and I.

The compounds of the present invention may have one or more asymmetric centres and it is intended that stereoisomers, as separated, pure or partially purified stereoisomers or racemic mixtures thereof are included in the scope of the invention.

Pharmaceutically acceptable acid addition salts of compounds of formula I include those prepared by allowing the compound to react with an inorganic or organic acid such as hydrochloric, hydrobromic, sulfuric, acetic, phosphoric, lactic, maleic, phthalic, citric, glutaric, gluconic, methanesulfonic, salicylic, succinic, tartaric, toluenesulfonic, trifluoroacetic, sulfamic or fumaric acid.

In another aspect, the present invention relates to a pharmaceutical composition comprising, as an active ingredient, a compound of the general formula I or a pharmaceutically acceptable salt thereof together with a pharmaceutically acceptable carrier or diluent.

Pharmaceutical compositions containing a compound of the present invention may be prepared by conventional techniques, e.g. as described in *Remington's Pharmaceutical Sciences*, 1985. The compositions may appear in conventional forms, for example capsules, tablets, aerosols, solutions, suspensions or topical applications.

The pharmaceutical carrier or diluent employed may be a conventional solid or liquid carrier. Examples of solid carriers are lactose, terra alba, sucrose, cyclodextrin, talc, gelatin, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene or water.

Similarly, the carrier or diluent may include any sustained release material known in the art, such as glyceryl monostearate or glyceryl distearate, alone or mixed with a wax.

If a solid carrier is used for oral administration, the preparation may be tabletted, placed in a hard gelatin capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatin capsule or sterile injectable liquid such as an aqueous or non-aqueous liquid suspension or solution.

A typical tablet which may be prepared by conventional tabletting techniques may contain:

| Core: | |
|---|---|
| Active compound (as free compound or salt thereof) | 100 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | |

| -continued | |
|---|---|
| Coating: | |
| HPMC approx. | 9 mg |
| *Mywacett 9-40 T approx. | 0.9 mg |

*Acylated monoglyceride used as plasticizer for film coating.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

Generally, the compounds of the present invention are dispensed in unit dosage form comprising 50–200 mg of active ingredient together with a pharmaceutically acceptable carrier per unit dosage.

The dosage of the compounds according to this invention is suitably 0.1–500 mg/day, e.g. from about 5 to about 50 mg, such as about 10 mg per dose, when administered to patients, e.g. humans, as a drug.

The compounds of the invention possess interesting pharmacological properties, and it has been demonstrated that compounds of the general formula I possess the ability to release endogenous growth hormone in vivo. The compounds may therefore be used in the treatment of conditions which require increased plasma growth hormone levels such as in growth hormone deficient humans or in elderly patients or livestock.

Thus, in a particular aspect, the present invention relates to a pharmaceutical composition for stimulating the release of growth hormone from the pituitary, the composition comprising, as an active ingredient, a compound of the general formula I or a pharmaceutically acceptable salt thereof together with a pharmaceutically acceptable carrier or diluent.

In a further aspect, the present invention relates to a method of stimulating the release of growth hormone from the pituitary, the method comprising administering to a subject in need thereof an effective amount of a compound of the general formula I or a pharmaceutically acceptable salt thereof.

In a still further aspect, the present invention relates to the use of a compound of the general formula I or a pharmaceutically acceptable salt thereof for the preparation of a medicament for stimulating the release of growth hormone from the pituitary.

To those skilled in the art, it is well known that the current and potential uses of growth hormone in humans are varied and multitudinous. Thus, compounds of formula I can be administered for purposes stimulating release of growth hormone from the pituitary and would then have similar effects or uses as growth hormone itself. The uses of growth hormone may be summarized as follows: stimulation of growth hormone release in the elderly; prevention of catabolic side effects of glucocorticoids, prevention and treatment of osteoporosis, stimulation of the immune system, acceleration of wound healing, accelerating borte fracture repair, treatment of growth retardation, treating renal failure or insufficiency resulting from growth retardation, treatment of physiological short stature including growth hormone deficient children and short stature associated with chronic illness, treatment of obesity and growth retardation associated with obesity, treating growth retardation associated with the Prader-Willi syndrome and Tumer's syndrome;

accelerating the recovery and reducing hospitalization of burn patients; treatment of intrauterine growth retardation, skeletal dysplasia, hypercortisolism and Cushing's syndrome; induction of pulsatile growth hormone release; replacement of growth hormone in stressed patients, treatment of osteochondrodysplasias, Noonan's syndrome, schizophrenia, depressions, Alzheimer's disease, delayed wound healing and psychosocial deprivation, treatment of pulmonary dysfunction and ventilator dependency, attenuation of protein catabolic responses after major surgery, reducing cachexia and protein loss due to chronic illness such as cancer or AIDS; treatment of hyperinsulinemia including nesidioblastosis, adjuvant treatment for ovulation induction; to stimulate thymic development and prevent the age-related decline of thymic function, treatment of immunosuppressed patients, improvement in muscle strength, mobility, maintenance of skin thickness, metabolic homeostasis, renal homeostasis in the frail elderly, stimulation of osteoblasts, bone remodelling and cartilage growth, stimulation of the immune system in companion animals and treatment of disorder of aging in companion animals, growth promoter in livestock and stimulation of wool growth in sheep.

For the above indications the dosage will vary depending on the compound of formula I employed, on the mode of administration and on the therapy desired. However, generally dosage levels between 0.0001 and 100 mg/kg body weight daily are administered to patients and animals to obtain effective release of endogenous growth hormone. Usually, dosage forms suitable for oral, nasal, pulmonal or transdermal administration comprise from about 0.0001 mg to about 100 mg, preferably from about 0.001 mg to about 50 mg of the compounds of formula I admixed with a pharmaceutically acceptable carrier or diluent.

The compounds of formula I may be administered in pharmaceutically acceptable acid addition salt form or, where appropriate, as a alkali metal or alkaline earth metal or lower alkylammonium salt. Such salt forms are believed to exhibit approximately the same order of activity as the free base forms.

Optionally, the pharmaceutical composition of the invention may comprise a compound of formula I combined with one or more compounds exhibiting a different activity, e.g., an antibiotic or other pharmacologically active material.

The route of administration may be any route which effectively transports the active compound to the appropriate or desired site of action, such as oral, nasal, pulmonary, transdermal or parenteral, the oral route being preferred.

Apart from the pharmaceutical use of the compounds of formula I, they may be useful in vitro tools for investigating the regulation of growth hormone release.

Compounds of formula I may also be useful in vivo tools for evaluating the growth hormone releasing capability of the pituitary. For example, serum samples taken before and after administration of these compounds to humans can be assayed for growth hormone. Comparison of the growth hormone in each serum sample would directly determine the ability of the patients pituitary to release growth hormone.

Compounds of formula I may be administered to commercially important animals to increase their rate and extent of growth, and to increase milk production.

A further use of growth hormone secretagogue compounds of formula I is in combination with other secretagogues such as GHRP (2 or 6), GHRH and its analogues, growth hormone and its analogues or somatomedins including IGF-1 and IGF-2.

Pharmacological Methods

Compounds of formula I may be evaluated in vitro for their efficacy and potency to is release growth hormone in rat pituitary primary cultures.

The isolation of rat pituitary cells is a modification of O. Sartor et al., *Endocrinology* 116, 1985, pp. 952–957. Male albino Sprague-Dawley rats (250+/−25 grams) were purchased from Møllegaard, Lille Skensved, Denmark. The rats were housed in group cages (four animals/cage) and placed in rooms with 12 hour light cycle. The room temperature varied from 19–24° C. and the humidity from 30–60%.

The rats were decapitated and the pituitaries dissected. The neurointermediate lobes were removed and the remaining tissue was immediately placed in icecold isolation buffer (Gey's medium (Gibco 041-04030) supplemented with 0.25% D-glucose, 2% non-essential amino acids (Gibco 043-01140) and 1% bovine serum albumine (BSA) (Sigma AA503)). The tissue was cut into small pieces and transferred to isolation buffer supplemented with 3.8 mg/ml of trypsin (Worthington #3707 TRL-3) and 330 mg/ml of DNase, (Sigma D4527). This mixture was incubated at 70 rotations/min for 35 min at 37° C. in a 95/5% atmosphere of $O_2/CO_2$. The tissue was then washed three times in the above buffer. Using a standard pasteur pipet, the tissue was then aspirated into single cells. After dispersion, cells were filtered through a nylon filter (160 mm) to remove undigested tissue. The cell suspension was washed 3 times with isolation buffer supplemented with trypsin inhibitor (0.75 mg/ml, Worthington #2829) and finally resuspended in culture medium; DMEM (Gibco 041-01965) supplemented with 25 mM HEPES (Sigma H-3375),4 mM glutamine (Gibco 043-05030H), 0.075% sodium bicarbonate (Sigma S-8875), 0.1% non-essential amino acid, 2.5% fetal calf serum (FCS, Gibco 011-06290), 3% horse'serum (Gibco 034-06050), 10% fresh rat serum, 1 nM $T_3$ (Sigma T-2752) and 40 mg/L dexamethasone (Sigma D4902) pH 7.3, to a density of $2\times10^5$ cells/ml. The cells were seeded into microtiter plates (Nunc, Denmark), 200-ml/well, and cultured for 3 days at 37° C. and 8% $CO_2$.

Compound Testing

After culturing, the cells were washed twice with stimulation buffer (Hanks Balanced Salt Solution (Gibco 041-04020) supplemented with 1% BSA (Sigma AA503), 0.25% D-glucose (Sigma G-5250) and 25 mM HEPES (Sigma H-3375) pH 7.3) and preincubated for 1 hour at 37° C. The buffer was exchanged with 90 ml stimulation buffer (37° C.). Ten ml test compound solution was added and the plates were incubated for 15 min at 37° C. and 5% $CO_2$. The medium was decanted and analyzed for GH content in an rGH SPA test system.

All compounds were tested in doses ranging from 10 pM to 100 mM. A dose-response relation was constructed using the Hill equation (Fig P, Biosoft). The efficacy (maximal GH released, $E_{maz}$) was expressed in % of the $E_{max}$ of GHRP-6. The potency ($EC_{50}$) was determined as the concentration inducing half maximal stimulation of the GH release.

Compounds of formula I may be evaluated for their metabolic stability.

Compounds were dissolved at a concentration of 1 mg/ml in water. 25 ml of this solution is added to 175 ml of the respective enzyme-solution (resulting in an enzyme:substrate ratio (w/w) of approximately 1:5). The solution is left at 37° C. overnight. 10 ml of the various degradation solutions is analyzed against a corresponding zero-sample using flow injection electrospray mass spectrometry (ESMS) with selected ion monitoring of the molecular ion. If the signal has decreased more than 20% compared to the zero-sample, the remainder of the solution is analyzed by HPLC and mass spectrometry in order to identify the extent and site(s) of degradation precisely.

Several standard peptides (ACTH 4–10, Angiotensin 1–14 and Glucagon) have been included in the stability tests in order to verify the ability of the various solutions to degrade peptides.

Standard peptides (angiotensin 1–14, ACTH 4–10 and glucagon) were purchased from Sigma, Mo., USA)

Enzymes (trypsin, chymotrypsin, elastase aminopeptidase M and carboxypeptidase Y and B) were all purchased from Boehringer Mannheim GmbH (Mannheim, Germany)

Pancreatic enzyme mix: trypsin, chymotrypsin and elastase in 100 mM ammoniumbicarbonate pH 8.0 (all concentrations 0.025 mg/ml).

Carboxypeptidase mix: carboxypeptidase Y and B in 50 mM ammoniumacetate pH 4.5 (all concentrations 0.025 mg/ml).

Aminopeptidase M solution: aminopeptidase M (0.025 mg/ml) in 100 mM ammoniumbicarbonate pH 8.0.

Mass spectrometric analysis was performed using two different mass spectrometers. A Sciex API III triple quadrupole LC-MS instrument (Sciex instruments, Thornhill, Ontario) equipped with an electrospray ion-source and a Bio-Ion 20 time-of-flight Plasma Desorption instrument (Bio-Ion Nordic AB, Uppsala, Sweden).

Quantification of the compounds (before and after degradation) was done on the API III instrument using single ion monitoring of the molecular ion in question with flow injection of the analyte. The liquid flow (MeOH:water 1:1) of 100 ml/min was controlled by an ABI 140B HPLC unit (Perkin-Elmer Applied Biosystems Divisions, Foster City, Calif.). The instrument parameters were set to standard operation conditions, and SIM monitoring was performed using the most intense molecular ion (in most cases this corresponded to the doubly charged molecular ion).

Identification of degradation products furthermore involved the use of plasma desorption mass spectrometry (PDMS) with sample application on nitrocellulose coated targets and standard instrumental settings. The accuracy of the hereby determined masses is generally better than 0.1%.

Separation and isolation of degradation products was done using a HY-TACH C-18 reverse phase 4.6×105 mm HPLC column (Hewlett-Packard Company, Palo Alto, Calif.) with a standard acetonitril:TFA separation gradient. The HPLC system used was HP1090M (Hewlett-Packard Company, Palo (Alto, Calif.).

| Peptide derivative | MW/SIM ion (amu) | Carboxy- peptidase mix | Pan. enzyme mix |
|---|---|---|---|
| Standards | | | |
| ACTH 4-10 | 1124.5/562.8 | + | – |
| Glucagon | 3483/871.8 | – | – |
| Insulin (B23-29) | 859.1/430.6 | | |
| Angiotensin 1-14 | 1760.1/881.0 | – | – |
| GHRP-2 | 817.4/409.6 | – | – |
| GHRP-6 | 872.6/437.4 | – | – |

+: Stable (less than 20% decrease in SIM signal after 24 h in degradation solution)
–: Unstable (more than 20% decrease in SIM signal after 24 h in degradation solution)

Any novel feature or combination of features described herein is considered essential to this invention.

EXAMPLES

The process for preparing compounds of formula I and preparations containing them is further illustrated in the following examples, which however, are not to be construed as limiting.

The structures of the compounds are confirmed by either elemental analysis (MA) nuclear magnetic resonance (NMR) or mass spectrometry (MS). NMR shifts (d) are given in parts per million (ppm) and only selected peaks are given. mp is melting point and is given in ° C. Column chromatography was carried out using the technique described by W.C. Still et al, J. Org. Chem. 1978, 43, 2923–2925 on Merck silica gel 60 (Art 9385). Compounds used as starting materials are either known compounds or compounds which can readily be prepared by methods known per se.

| Abbrevations: | |
|---|---|
| TLC: | thin layer chromatography |
| DMSO: | dimethylsulfoxide |
| CDCl$_3$: | deutorated chloroform |
| DMF: | N,N-dimethylformamide |
| min: | minutes |
| h: | hours |

HPLC-Analysis:

Method B1.

The RP-HPLC analysis was performed using UV detection at 214 nm and a Vydac 218TP54 4.6 mm×250 mm 5 m C-18 silica column (The Seperations Group, Hesperia), which was eluted at 1 ml/minute. Two solvent systems were used: Solvent system I: 0.1% Trifluoroacetic acid in acetonitrile. Solvent system II: 0.1% rifluoroacetic acid in water.

The column was equilibrated with a mixture composed of 5% of solvent system I and 95% of solvent system II. After injection of the sample a gradient of 5% to 60% of solvent system I in solvent system II was run over 50 minutes. The gradient was then extended to 100% of solvent system I over 15 minutes followed by isocratic elution with 100% of this system for 5 minutes.

Method A1.

The RP-analysis was performed using UV detections at 214, 254, 276, and 301 nm on a Vydac 218TP54 4.6 mm×250 mm 5 m C-18 silica column (The Seperations Group, Hesperia), which was eluted at 1 mumin at 42° C. The column was equilibrated with 5% acetonitrile in a buffer consisting of 0.1 M ammonium sulfate, which was adjusted to pH 2.5 with 4M sulfuric acid. after injection the sample was eluted by a gradient of 5% to 60% acetonitrile in the same buffer during 50 min.

Example 1

(2E) 5-Amino-5-methylhex-2-enoic acid N-methyl-N-((1R)-1-(N-methyl-N-((1R)-1-(methylcarbamoyl)-2-phenylethyl)carbamoyl)-2-(2-naphthyl)ethyl)amide hydrochloride:

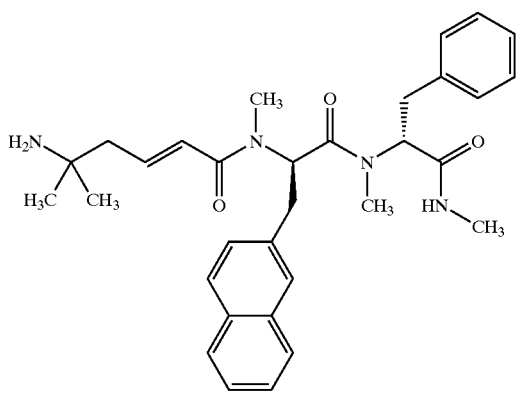

3-Hydroxy-1,1-dimethylpropylcarbamic acid tert-butyl ester:

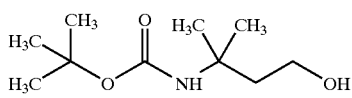

Step A:
At 0° C., ethyl chloroformate (1.10 mL, 11.5 mmol) was given dropwise to a solution of 3-tert-butoxycarbonylamino-3-methylbutanoic acid (2.50 g, 11.5 mmol) and triethylamine (1.92 mL, 13.8 mmol) in tetrahydrofuran (10 mL). The solution was stirred for 40 min at 0° C. The formed precipitate was filtered off and washed with tetrahydrofuran (20 mL). The liquid was immediately cooled to 0° C. A 2M solution of lithium boronhydride in tetrahydrofuran (14.4 mL, 28.8 mmol) was added dropwise. The solution was stirred at 0° C. for 2 h, and then warmed to room temperature. over a period of 4 h. It was cooled to 0° C. Methanol (5 mL) was added carefully. 1 N Hydrochloric acid (100 mL) was added. The solution was extracted with ethyl acetate (2×100 mL, 3×50 mL). The combined organic layers were washed with saturated sodium hydrogen carbonate solution (100 mL) and dried over magnesium sulfate. The solvent was removed in vacuo. The crude product was chromatographed on silica (110 g) with ethyl acetatelheptane 1:2 to give 1.84 g of 3-hydroxy-1,1-dimethylpropylcarbamic acid tert-butyl ester.
$^1$H-NMR (CDCl$_3$): d 1.33 (s, 6H); 1.44 (s, 9H); 1.88 (t, 2H); 1.94 (br, 1H); 3.75 (q, 2H); 4.98 (br, 1H).

3-(tert-Butoxycarbonylamino)-3-methylbutanal:

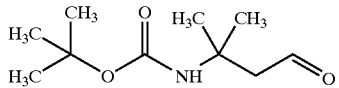

Step B:
DMSO (1.22 mL, 17.2 mmol) was added to a solution of oxalyl chloride (1.1 mL, 12.9 mmol) at −78° C. in dichloromethane (15 mL). The mixture was stirred for 15 min at −78° C. A solution of 3-hydroxy-1,$_1$-dimethylpropylcarbamic acid tert-butyl ester (1.75 g, 8.6 mmol) in dichloromethane (10 mL) was added dropwise over a period of 15 min. The solution was stirred at -78° C. for another 15 min.
Triethylamine (6.0 mL, 43 mmol) was added. The solution was stirred at −78° C. for 5 min and then warmed to room temperature. The solution was diluted with dichloromethane (100 mL) and extracted with 1N hydrochloric acid (100 mL). The aqueous phase was extracted with dichloromethane (50 mL). The combined organic layers were washed with saturated sodium hydrogen carbonate solution (100 mL) and dried over magnesium sulfate. The solvent was removed in vacuo. The crude product was purified by column chromatography on silica (140 g) with ethyl acetate/heptane (1:3) to give 1.10 g of 3-(tert-butoxycarbonylamino)-3-methylbutanal.
MHz-$^1$H-NMR (CDCl$_3$): d 1.39 (s, 6H); 1.45 (s, 9H); 2.85 (d, 2H); 4.73 (br. 1H); 9.80 (t, 1H).

Ethyl (2E)-5-(tert-Butoxycarbonylamino)-5-methylhex-2-enoate:

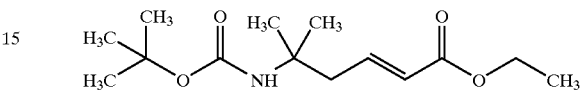

Step C:
Triethylphoshonoacetate (1.96 mL, 9.8 mmol) was dissolved in tetrahydrofuran (30 mL). Potassium tert-butoxide (1.10 g, 9.8 mmol) was added. The solution was stirred for 40 min at room temperature. A solution of 3-(tert-butoxycarbonylamino)-3-methylbutanal (1.10 g, 5.5 mmol) in Tetrahydrofuran (6 mL) was added. The solution was stirred at room temperature. for 75 min. It was diluted with ethyl acetate (100 mL) and 1N hydrochloric acid (100 mL). The phases were separated. The aqueous phase was extracted with ethyl acetate (2×50 mL). The combined organic phases were washed with saturated sodium hydrogen carbonate solution (60 mL) and dried over magnesium sulfate. The solvent was removed in vacuo. The crude product was purified by column chromatography on silica (90 g) with ethyl acetate/hepatane (1:4) to give 1.27 g of ethyl (2E)-5-(tert-butoxycarbonylamino)-5-methylhex-2-enoate.
$^1$H-NMR (CDCl$_3$): d 1.30 (s, 6H); 1.30 (t, 3H); 1.46 (s, 9H); 2.62 (d, 2H); 4.27 (q, 2H); 4.42 (br, 1H); 5.88 (d, 1H); 6.94 (td, 1H).

(2E)-5-(tert-Butoxycarbonylamino)-5-methylhex-2-enoic acid:

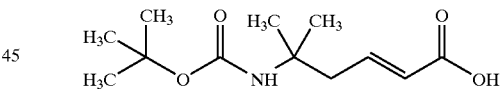

Step D:
Ethyl (2E)-5-(tert-butoxycarbonylamino)-5-methylhex-2-enoate (1.233 g, 4.54 mmol) was dissolved in dioxane (20 mL). Lithium hydroxide (0.120 g, 5.00 mmol) was added as a solid. Water (10 mL) was added, until a clear solution was reached. The solution was stirred 16 h at room temperature. The solution was diluted with water (70 mL) and was extracted with tert-butyl methyl ether (2×100 mL). The aqueous phase was acidified with 1 N sodium hydrogensulfate solution is (pH=1) and was extracted with tert-butylmethylether (3×70 mL). The organic phases were combined and dried over magnesium sulfate. The solvent was removed in vacuo to give 1.05 g of (2E)-5-(tert-butoxycarbonylamino)-5-methylhex-2-enoic acid. The crude product was used for further syntheses.
$^1$H-NMR (DMSO d,): d 1.15 (s, 6H); 1.35 (s, 9H); 2.53 (d, 2H); 5.75 (d, 1H); 6.57 (br, 1H); 6.75 (td, 1H); 12.15 (s, 1H).

N-Methyl-N-((R)-1-(methylcarbamoyl)-2-phenylethyl) carbamic acid tert-butyl ester:

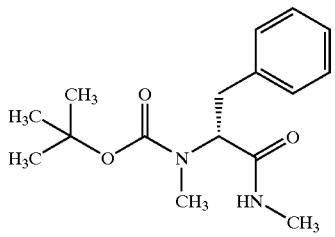

Step E:

N-Tert-butoxycarbonyl-N-methyl-D-phenylalanine (1.22 g, 4.4 mmol), 1-hydroxybenzotriazole hydrate(0.59 g, 4.4 mmol) and 1-ethyl-3-(3-dimethyl-aminopropyl)carbodiimid hydrochloride (0.88 g, 4.6 mmol) were dissolved in N,N-dimethylformamide (25 mL) and stirred for 30 min. Methylamine (0.51 g of a 40% solution in methanol, 6.6 mmol) was added and the mixture was stirred overnight. Methylene chloride (80 mL) and water (100 mL) were added and the phases were separated. The organic phase was washed with sodium hydroxide (20 mL, 1N), sodium hydrogensulfate (50 mL, 10%) and water (50 mL). The organic phase was dried (magnesium sulfate) and the solvent removed in vacuo to afford 1.39 g of N-methyl-N-((R)1-(methylcarbamoyl)-2-phenylethyl)carbamic acid tert-butyl ester.

$^1$H-NMR (CDCl$_3$): d 1.25, 1.35 (two s (br), 9H); 2.73–2.94 (m, 7H); 3.30–3.50 (m, 1 H); 4.68, 4.90 (two m, 1H); 5.90, 6.12 (two s (br); 1H); 7.12–7.25 (m, 5H).

(R)-N-Methyl-2-methylamino-3-phenylpropionamide:

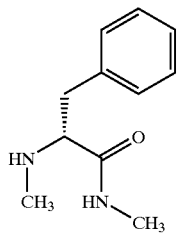

Step F:

N-Methyl-N-((R)-1-(methylcarbamoyl)-2-phenylethyl) carbamic acid tert-butyl ester (1.39 g, 7.23 mmol) was dissolved in a mixture of trifluoroacetic acid (5 mL) and methylene chloride (10 mL) and stirred for 45 min. The volatiles were removed in vacuo and the residue was stirred with a mixture of ethyl acetate (100 mL) and water (100 mL). Sodium hydrogen carbonate (50 mL, saturated) was added and the phases were separated. The organic phase was dried (magnesium sulfate) and the solvent removed in vacuo to afford 330 mg of (R)-N-methyl-2-methylamino-3-phenylpropionamide.

$^1$H-NMR (CDCl$_3$): d 2.1 (s(br), 3H); 2.32 (s, 3H); 2.77 (dd, 1H); 2.81 (two s, 3H); 3.21 (dd, 1H); 3.32 (dd, 1H); 7.12 (s(br), 1H); 7.20–7.34 (m, 5H).

N-Methyl-N{(1R)-1-(N-methyl-N-((1R)-1-(methylcarbamoyl)-2-phenylethyl)-carbamoyl)-2-(2-naphthyl)ethyl}carbamic acid tert-butyl ester:

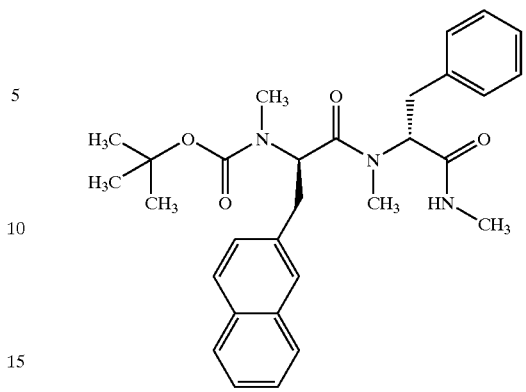

Step G:

(R)-Tert-butoxycarbonyl-N-methylamino-3-(2-naphthyl) propionic acid (548 mg, 1.66 mmol) was dissolved in methylene chloride (5 mL); 1-hydroxy-7-azabenzotriazole (227 mg, 1,66 mmol) was added along with N,N-dimethylformamide (2 mL). 1-Ethyl-3-(3-dimethylaminopropyl)carbodiimide hydrochloride (351 mg, 1.83 mmol) was added and the solution was stirred for 15 10 min. (R)-N-Methyl-2-methylamino-3-phenylpropionamide (320 mg, 1.66 mmol) dissolved in methylene chloride (4 mL) and diisopropylethylamine (0.28 mL, 1.66 mmol) were added and the mixture was stirred overnight. Methylene chloride (50 mL) was added and the organic phase was washed with water (100 mL), sodium hydrogensulfate (50 mL, 5%) and sodium hydrogen carbonate (50 mL, saturated). The organic phase was dried (magnesium sulfate) and the solvent removed in vacuo. The residue was chromatographed (silica, 2×45 cm) using ethylacetate/methylene chloride (1:1) to afford 604 mg of N-methyl-N-{(1R)-1-(N-methyl-N-((1R)-1-(methylcarbamoyl)-2-phenylethyl) carbamoyl)-2-(2-naphthyl)-ethyl}carbamic acid tert-butyl ester.

$^1$H-NMR (CDCl$_3$): d 1.05, 1.31, 1.56 (three s, 9H); 2.28–3.37 (several m, 13H); 5.04, 5.17, 5.29, 5.48 (four dd, 2H); 7.05–7.79 (m, 12H).

(2R)-N-Methyl-2-methylamino-N-((1R)-1-(methylcarbamoyl)-2-phenylethyl)-3-(2-naphthyl) propionamide:

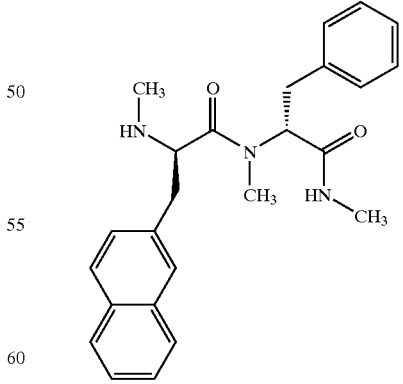

Step H:

N-Methyl-N{(1R)-1-(N-methyl-N-((1R)-1-(methylcarbamoyl)-2-phenyl-ethyl)carbamoyl))-2-(2-naphthyl)ethyl)carbamic acid tert-butyl ester (600 mg, 1.19 mmol) was stirred in trifluoroacetic acid/methylene chloride (1:1, 5 mL) for 10 min and the volatiles were removed in vacuo. The residue was stripped with diethylether (2×5 mL) and dissolved in methanol (2 mL) and mixed with sodium hydrogen carbonate (10 mL) and ethylacetate (15 mL). The organic phase was separated and dried (magnesium sulfate) to afford 420 mg of (2R)-N-methyl-2-methylamino-N-((1R)-1-(methylcarbamoyl)-2-phenylethyl)-3-(2-naphthyl) propionamide.

$^1$H-NMR (CDCl$_3$): (selected values) d 1.69 (s, 3H); 2.08 (d, 3H); 2.54 (s, 3H); 2.76 (dd, 1H); 2.92 (dd, 1H), 3.12 (dd, 1H), 3.31 (dd, 1H); 3.72 (dd, 1H), 4.95 (q (br), 1H); 5.50 (dd, 1H).

((3E)-1,1-Dimethyl-4-(N-methyl-N-((1R)-1-(N-methyl-N-((1R)-1-(methylcarbamoyl)-2-phenylethyl)carbamoyl)-2-(2-naphthyl)ethyl)carbamoyl)but-3-enyl)carbamic acid Tert-butyl ester:

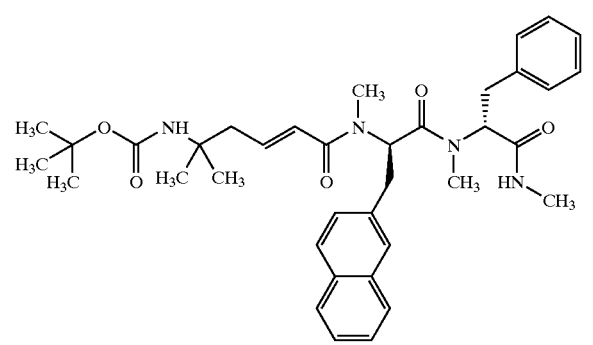

Step I:
(2E)-5-(tert-Butyloxycarbonylamino)-5-methylhex-2-enoic acid (200 mg, 0.82 mmol), 1-hydroxy-7-azabenzotriazole (112 mg, 0.82 mmol) and 1-ethyl-3-(3-s dimethylaminopropyl)-carbodiimide hydrochloride (173 mg, 0.90 mmol) were dissolved in a mixture of methylene chloride (10 mL) and N,N-dimethylformamide (1 mL) and strirred for 15 min. N-Methyl-2-methylamino-N-((1R)-1-(methylcarbamoyl)-2-phenylethyl)-3-(2-naphthyl) propionamide (332 mg, 0.82 mol) dissolved in methylene chloride (5 mL) and diisopropylethylamine (0.14 mL) were added and the mixture was stirred overnight under nitrogen atmosphere. The mixture was diluted with methylene chloride (50 mL), washed with water (50 mL), sodium hydrogen carbonate (30 mL, saturated), and sodium hydrogensulfate (30 mL, 5%). The phases were separated and the organic phase was dried with magnesium sulfate and evaporated in vacuo. The residue was chromatographed (silica, 2×40 cm) to afford 450 mg of ((3E)-1,1dimethyl-4-(N-methyl-N-((1R)-1-(N-methyl-N-((1R)-1-(methylcarbamoyl)-2-phenylethyl)carbamoyl)-2-(2-naphthyl)ethyl)carbamoyl) but-3-enyl)-carbamic acid tert-butyl ester.

$^1$H-NMR (CDCl$_3$): (selected values) d 1.20, 1.22, 1.24, 1.30, 1.41, 1.55 (six s, 15H), 4.30, 4.40 (two s (br), 1H); 5.08, 5.18, 5.32, 5.60, 5.87 (five dd, 2H); 6.05 (dd, 1H); 6.75 (m, 1H).

Step J:
((3E)-1,1-Dimethyl-4-(methyl-((1R)-1-(methyl-((1R)-1-(methylcarbamoyl)-2-phenylethyl)carbamoyl)-2-(2-naphthyl)ethyl)carbamoyl)but-3-enyl)carbamic acid tert-butyl ester (403 mg, 0.63 mmol) was stirred in a mixture of trifluroacetic acdi (4 mL) and methylene chloride (4 mL) for 10 min. The volatiles were removed in vacuo and the crude product was chromatographed on silica (400 g) using a mixture of methylene chloride, ethanol and ammonia (25% in water) (80/18/2) as eluent. The isolated product was dissolved in 3M hydrochloric acid in ethyl acetate and evaporated, then redissolved in methylene chloride and evaporated twice to afford 140 mg of the title compound.

$^1$H-NMR (CDCl$_3$): d 1.05, 1.10, 1.15, 1.16 (fours, 6H); 2.07 (s (br); 3H); 5.12, 5.32, 5.40, 5.60, 5.91 (five dd, 2H); 6.05, 6.14 (two d, 1H); 6.80 (m, 1H)

HPLC: R$_t$=29.02 min (Method A1)

ESMS: m/z=529 (100%)(M+H)$^+$

Example 2

(2E)-5-Amino-5-methylhex-2-enoic acid N-((1R)-1-(((1R)-1-((2-methoxyethyl)-carbamoyl)-2-phenylethyl)-methylcarbamoyl)-2-(2-naphthyl)ethyl)-N-methylamide:

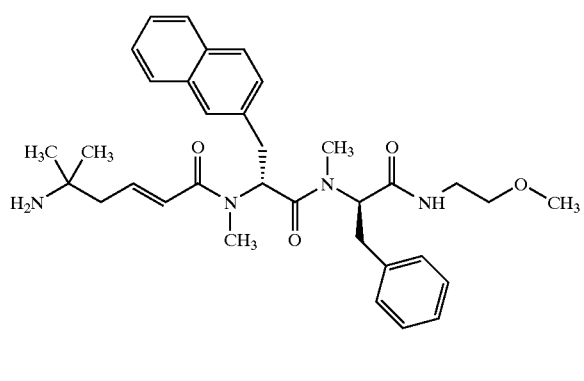

This compound was prepared analogously to example 1. 2-methoxyethylamine was substituted for methylamine in step E.

$^1$H-NMR (CDCl$_3$) (selected peaks, mixture of rotamers) d 1.05; 1.10 (two d, 6H), 3.34 (s, 3H), 6.02 (d, 1H)

HPLC: R$_t$=30.47 min (Method A1)

PDMS: m/z=573.3 (100%) (M+H)$^+$

Example 3

(2E)-5-Amino-5-methylhex-2-enoic acid N-((1R)-1-(((1R)-1-((2S)-2-hydroxy-propylcarbamoyl)-2-phenylethyl)-methylcarbamoyl)-2-(2-naphthyl)ethyl)-N-methylamide:

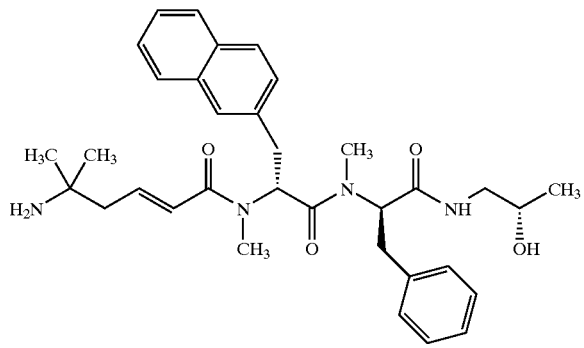

This compound was prepared analogously to example 1. (S)-2-hydroxypropylamine was substituted for methylamine in step E.

$^1$H-NMR (CDCl$_3$) (selected peaks, mixture of rotamers) d 3.90 (m, 1H); 5.55 (dd, 1H); 5.58 (d, 1H)

HPLC: F =29.03 min (Method A1)

PDMS: m/z =573.5 (100%)(M+H)$^+$

Example 4

(2E)-5-Amino-5-methylhex-2-enoic acid N-methyl-N-((1R)-1-(methyl-((1R)-2-phenyl-1-(((tetrahydrofuran-2-yl)methyl)-carbamoyl)-2-phenylethyl)carbamoyl)-2-(2-naphthyl)amide:

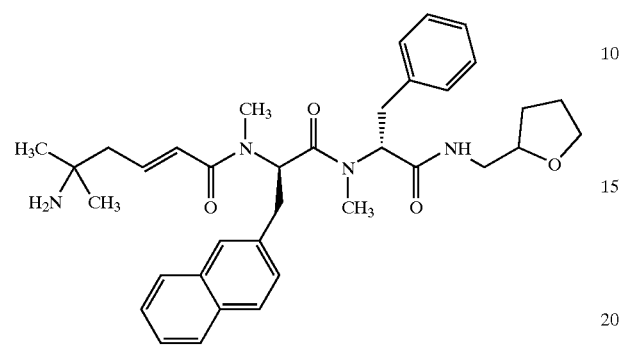

This compound was prepared analogously to example 1. 2-(methyl-amino)tetrahydrofuran was substituted for methylamine in step E.

$^1$H-NMR (CDCl$_3$) (selected peaks, mixture of rotamers) d 1.06, 1.09 (two d, 6H); 2.78 (d, 2H); 5.25–5.62 (m, 2H); 6.05 (m, 1H)

HPLC: R$_t$=33.65 min (method A1)

Example 5

(2E)-5-Amino-5-methylhex-2-enoic acid N-((1R)-1-(((1R)-1-((cyclopropylmethyl)-carbamoyl)-2-phenylethyl)methylcarbamoyl)-2-(2-naphthyl)ethyl)-N-methylamide:

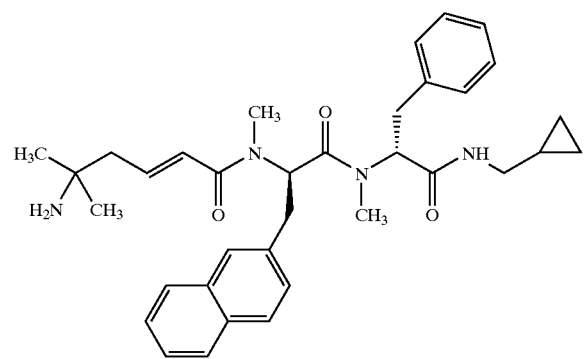

This compound was prepared analogously to example 1. Cyclopropylmethylamine was substituted for methylamine in step E.

$^1$H-NMR (CDCl$_3$) (selected peaks, mixture of rotamers) d 0.08–0.20 (m, 2H); 1.05; 1.15 (twos, 6H); 6.02, 6.05 (two d, 1H)

HPLC: R$_t$=35.7 m, (Method A1)

Example 6

(2E)-3-(Azetidin-3-yl)-N-methyl-N-((1R)-1-(N-methyl-N-((1R)-1-methylcarbamoyl-2-phenylethyl)carbamoyl)-2-(2-naphthyl)ethyl)acrylamide:

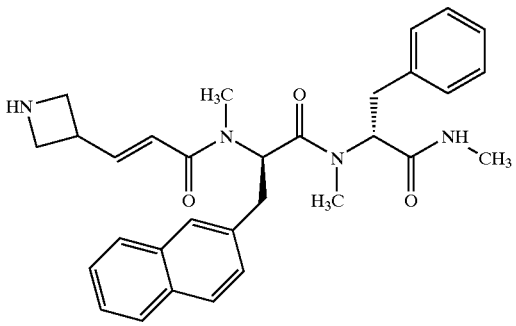

3-Carboxyazetidine-1-carboxylic acid tert-butyl ester.

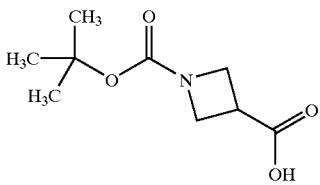

Azetidine-3-carboxylic acid (10.0 g; 98.9 mmol) was dissolved in tetrahydrofuran (1 20 mL) and water (20 mL). An aqueous solution of sodium hydroxide (10 mL; 1 N) was added. Ditert butyl dicarbonate (25.9 g; 118.7 mmol) was dissolved in tetrahydrofuran (80 mL) and added dropwise to the reaction mixture. The reaction mixture was stirred for 12 hours at room temperature and evaporated in vacuo. To the residue was added water (100 mL) and an aqueous solution of sodium hydroxide (100 mL; 1N) and the aqueous phase was extracted with diethyl ether (2×100 mL). The aqueous phase was acidified with an aqueous solution of sodium is hydrogensulfate (1 M) until pH 2. Diethyl ether (200 mL) was added and the organic phase was dried (magnesium sulfate) and evaporated in vacuo to afford 20 g of 3-carboxyazetidine-1-carboxylic acid tert-butyl ester.

$^1$H-NMR (CDCl$_3$) d 1.43 (s, 9H); 3.37 (p, 1H); 4.14 (d, 4H); 10.05 (s, 1H).

3-Hydroxymethylazetidine-1-carboxylic acid tert-butyl ester.

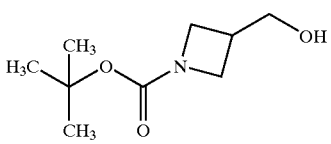

1-Carboxyazetidine-1-carboxylic acid tert-butyl ester (5.0 g; 24.8 mmol) was dissolved in dry tetrahydrofuran. Triethylamine (4.1 mL; 29.8 mmol) was added and the reaction mixture was cooled to 0° C. Ethyl chloroformate (2.4 mL; 24.8 mmol) was added and the reaction mixture was stirred for 40 min at 0° C. The reaction mixture was filtered and the filter cake was washed with dry tetrahydrofuran (30 mL). The combined filtrates were cooled to 0° C. and lithium borohydride (2.0 M in tetrahydrofuran; 31 mL; 62.1 mmol) was added dropwise to the reaction mixture and it was then heated to room temperature and stirred for 12 hours. The reaction mixture was cooled to 0° C. and methanol (10 mL)

was added dropwise. An aqueous solution of sodium hydrogen carbonate (100 mL; 10%) was added and the reaction mixture was extracted with ethyl acetate (4×100 mL). The combined organic phases were washed with a saturated solution of sodium hydrogen carbonate (100 mL), dried (magnesium sulfate) and evaporated in vacuo to afford 3.43 g of 3-hydroxymethylazetidine-1-carboxylic acid tert-butyl ester.

$^1$H-NMR (CDCl$_3$) d: 1.43 (s, 9H); 2.7 (p, 1H); 3.63–3.70 (m, 2H), 3.74 (d, 1H); 3.88 (d, 1H); 3.94.0 (m, 2H).
3-Formylazetidine-1-carboxylic acid tert-butyl ester.

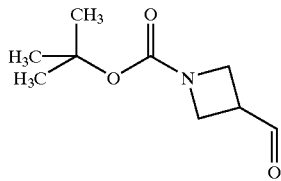

Oxalyl chloride (2.1 mL; 24.0 mmol) was dissolved in methylene chloride (30 mL) and cooled to −78° C. Dimethyl sulfoxide (2.3 mL; 32.0 mmol) was added. A solution of 3-hydroxymethylazetidine-1-carboxylic acid tert-butyl ester (3.0 g; 16.0 mmol) in methylene chloride (20 mL) was added dropwise to the reaction mixture. Triethyl amine (11.1 mL; 80.1 mmol) was added and the reaction mixture was heated to room temperature. Methylene chloride (200 mL) and hydrochloric acid (200 mL; 1 N) was added. The aqueous phase was extracted with methylene chloride (100 mL). The combined organic phases were washed with saturated sodium hydrogen carbonate (100 mL), dried (magnesium sulfate) and evaporated in vacuo. The residue was chromatographed on silica (3×30 cm) using ethyl acetatelheptane (4:1) as eluent to afford 1.11 g of 3-formylazetidine-1-carboxylic acid tert-butylester.

$^1$H-NMR (CDCl$_3$) d: 1.43 (s, 9H); 3.37 (p, 1H); 4.054.15 (m, 4H)>9.82 (s, 1H).
3-((E)-2-Ethoxycarbonylvinyl)azetidine-1-carboxylic acid tert-butylester:

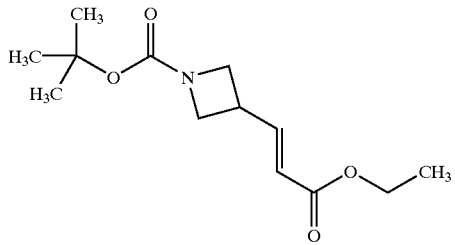

Triethyl phosphonoacetate (1.9 mL; 9.72 mmol) was dissolved in tetrahydrofuran (30 mL). Potassium tert-butoxide (1.1 g; 9.72 mmol) was added portionwise. 3-Formylazetidine-1-car-boxylic acid tert-butyl ester (1.0 g; 5.40 mmol) was dissolved in tetrahydrofuran (6 mL) and added to the reaction mixture. The reaction mixture was stirred for 1 hour at room temperature. Ethyl acetate (100 mL) and hydrochloric acid (100 mL; 1 N) were added and the phases were separated. The aqueous phase was extracted with ethyl acetate (2×50 mL) and the combined organic phases were washed with saturated sodium hydrogen carbonate (100 mL), dried (magnesium sulfate) and evaporated in vacuo. The residue was chromatographed on silica (3×30 cm) using ethyl acetate/heptane (1:1) as eluent to afford 1.0 g of 3-((E)-2-ethoxycarbonylvinyl)azetidine-1-carboxylic acid tert-butyl ester.

$^1$H-NMR (CDCl$_3$) d: 1.24 (t, 3H); 1.48 (s, 9H); 3.22–3.32 (m, 1H); 3.75 (dd, 2H); 4.08 (t, 2H); 4.15 (q, 2H); 5.8 (d, 1H); 7.02 (dd, 1H).
3-((E)-2-Carboxyvinyl)azetidine-1-carboxylic acid tert-butyl ester:

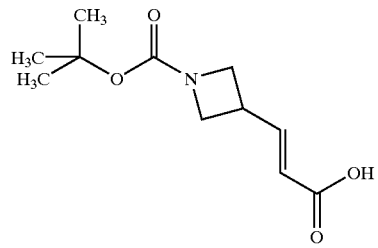

3-((E)-2-Ethoxycarbonylvinyl)azetidime-1-carboxylic acid tert-butyl ester (0.95 g; 3.72 mmol) was dissolved in 1,4dioxane (15 mL). Lithium hydroxide (0.098 g; 4.1 mmol) and water (10 mL) were added. The reaction mixture was stirred for 12 hours at room temperature. Water (70 mL) was added and the reaction mixture was washed with tert-butyl methyl ether (70 mL) and the phases were separated. The aqueous phase was adjusted to pH 2 with an aqueous solution of sodium hydrogensulfate (10%) and extracted with tert-butyl methylether (3×70 mL). The combined organic phases were dried (magnesium sulfate) and the solvent evaporated in vacuo to afford 0.76 g of 3-((E)-2-carboxyvinyl)azetidine-1-carboxylic acid tert-butyl ester.

$^1$H-NMR (CDCl$_3$) d :1.43 (s, 9H); 3.31–3.42 (m, 1H); 3.84 (dd, 2H); 4.16 (t, 2H); 5.88 (d, 1H); 7.1 8(dd, 1H).
3-(2-(Methyl-((1R)-1-(methyl-((1R)-1-(methylcarbamoyl)-2phenylethyl)carbamoyl)-2-(2-naphthyl)ethyl)carbamoyl) vinyl)azetidine-1-carboxylic acid tert-butyl ester:

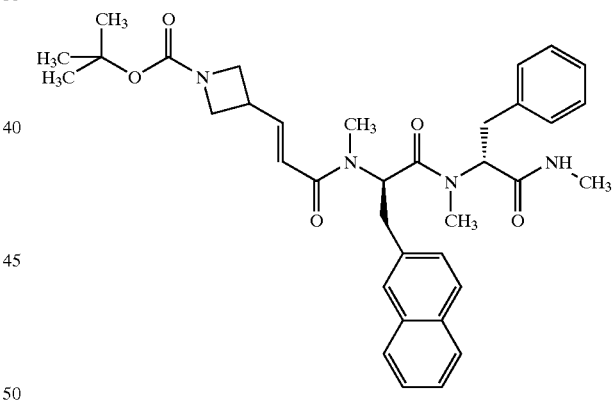

3-((E)-2-Carboxyvinyl)azetidine-1-carboxylic acid tert-butyl ester (0.28 g; 1.24 mmol) was dissolved in methylene chloride (3 mL). 1-Hydroxy-7-azabenzotriazole (0.17 g; 1.24 mmol) and N-(3dimethylaminopropyl)-N'-ethylcarbodiimide hydrochloride (0.26 g; 1.36 mmol) were added and the reaction mixture was stirred for 15 min at room temperature. N-Methyl-2-methylamino-N-(1-(methylcarbamoyl)-2-phenylethyl)-3-(2-naphthyl)propionamide (0.50 g; 1.24 mmol) (prepared as in example 1) was dissolved in methylene chloride (3 mL) and added to the reaction mixture. Ethyldiisopropylamine (0.21 mL; 1.24 mmol) was added and the reaction mixture was stirred for 12 hours at room temperature. Methylene chloride (20 mL) was added and the reaction mixture was washed with water (10 mL), an aqueous solution of sodium hydrogen sulfate (10 mL; 10%), an aqueous solution of sodium hydrogen carbonate (10 mL; sat.) and water (10 mL). The organic phase was dried (magnesium sulfate) and evaporated in vacuo. The residue was chromatographed on silica (2,5×20 cm) using 2.5%(7% ammonia in ethanol) in methylene chloride as eluent to afford 0.49 g of 3-((E)-2-(methyl((1R)-1-(methyl((1R)-1-(methylcarbamoyl)-2-phenylethyl)carbamoyl)-2-(2-naphthyl)ethyl)carbamoyl)vinyl)azetidine-1-carboxylic acid tert-butyl ester.

$^1$H-NMR (CDCl$_3$) d 1.41, 1.45 (two s, 9H); 1.55, 1.58 (two s, 3H); 2.21 (d, 1H); 2.54 (s, 1H); 2.72–2.81 (m, 3H); 2.83–2.96 (m, 1H); 3.0 (d, 3H); 3.02–3.42 (m, 3H); 3.68–3.82 (m, 2H); 4.06 (q, 1H); 4.14 (q, 1H); 5.11, 5.31 (two m, 1H); 5.58, 5.88 (two dd, 1H); 6.03 (d, 1H); 6.88, 6.91 (two dd, 1H); 7.0–7.23 (m, 5H); 7.3–7.58 (m, 3H); 7.65–7.81 (m, 3H).

3-((E)-2-(Methyl((1R)-1-(methyl-((1R)-1-(methylcarbamoyl)-2-phenylethyl)-carbamoyl)-2-(2-naphthyl)ethyl)carbamoyl)vinyl)azetidine-1-carboxylic acid tert-butyl ester (0.45 g; 0.73 mmol) was dissolved in methylene chloride (2 mL). Trifluoroacetic acid (2 mL) was added and the reaction mixture was stirred for 7 min. Methylene chloride (50 mL), an aqueous solution of sodium hydrogen carbonate/sodium carbonate (50 mL; pH 9) and sodium carbonate were added to the reaction mixture until pH 8. The organic phase was dried (magnesium sulfate) and evaporated in vacuo to afford 0.29 g of the title compound.

$^1$H-NMR (CDCl$_3$) d (selected peaks): 2.25, 2.26, 2.28 (three s, 3H); 5.12, 5.31, 5.59, 5.88 (four dd, 2H); 6.00 (dd, 1H; J$_1$=15 Hz; J$_2$=2.5 Hz); 6.91 (m, 1H).

ESMS: m/z 513.2 (M+H)$^+$

HPLC: r$_t$=29.40 min (A1)

Example 7

(2R)-N-Methyl-N-((1R)-1-(methylcarbamoyl)-2-phenylethyl)-2-(methyl((piperidin-4-ylidene)acetyl)amino)-3-(2-naphthyl)propionamide:

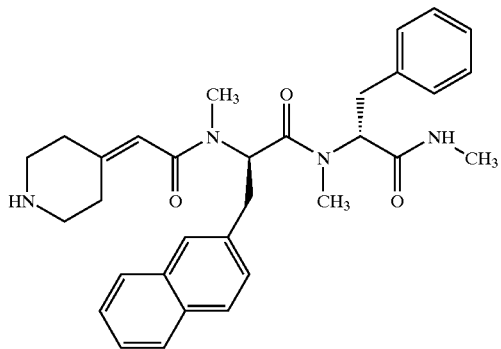

4-Oxopiperidine-1-carboxylic acid tert-butyl ester:

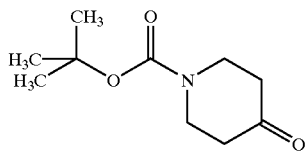

Piperidin-4-one hydrochloride (10.0 g; 74.3 mmol) was dissolved in tetrahydrofuran (100 mL) and an aqueous solution of sodium hydroxide (74 mL; 74.3 mmol; 1 N) was added. Di-tert-butyl dicarbonate (19.5 g; 89.2 mmol) was dissolved in tetrahydrofuran (50 mL) and added dropwise. The reaction mixture was stirred for 12 hours at room temperature and evaporated in vacuo. The residue was extracted with ethyl acetate (3×100 mL). The combined organic phases were washed with an aqueous solution of sodium hydrogen sulfate (100 mL; 10%), dried (magnesium sulfate) and evaporated. The residue was crystallised from heptane and dried in vacuo to afford 10.9 g of 4-oxopiperidine-1-carboxylic acid tert-butyl ester.

$^1$H-NMR (CDCl$_3$) d: 1.50 (s, 9H); 2.44 (t, 4H); 3.71 (t, 4H).

4-Carboxymethylenepiperidine-1-carboxylic acid tert-butyl ester:

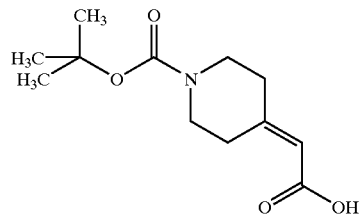

4-Oxopiperidine-1-carboxylic acid tert-butyl ester (8.0 g; 40.2 mmol) was dissolved in toluene (80 mL). Carboethoxymethylene triphenylphosphorane (17.5 g; 50.2 mmol) was added and the reaction mixture was heated 12 hours at reflux. The reaction mixture was evaporated in vacuo and the residue was chromatographed on silica (4.5×30 cm) using diethyl ether/heptane (1:1) as eluent to afford 9.5 g (35.7 mmol) of 4-Ethoxycarbonylmethylenepiperidine-1-carboxylic acid tert-butyl ester, which was dissolved in 1,4-dioxane and cooled to 0° C. Lithium hydroxide (2.73 g; 114 mmol) was dissolved in water (20 mL) and added. The reaction mixture was stirred for 12 hours at room temperature. Ethyl acetate (200 mL) and water (100 mL) was added. Sodium hydrogen sulfate (10%; aqueous solution) was added to pH 2. The organic phase was washed with water (100 mL), dried (magnesium sulfate) and evaporated in vacuo to afford 5.49 g of 4-carboxymethylenepiperidine-1-carboxylic acid tert-butyl ester.

$^1$H-NMR (CDCl$_3$) d: 1.47 (s, 9H); 2.31 (t, 2H), 2.94 (t, 2H); 3.50 (dt, 4H); 5.75 (s, 1H); 10.75 (s, 1H).

4-((N-Methyl-N-((1R)-1-(N-methyl-N-((1R)-1-methylcarbamoyl-2-phenylethyl)-carbamoyl)-2-(2-naphthyl)ethyl)carbamoyl)methylene)piperidine-1-carboxylic acid Tert-butyl ester:

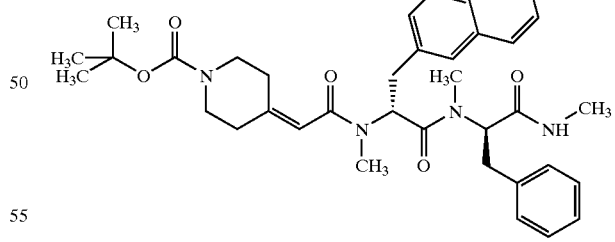

4-Carboxymethylenepiperidine-1-carboxylic acid tert-butyl ester (0.60 g; 2.45 mmol) was dissolved in methylene chloride (50 mL) and N-(3-dimethylaminopropyl)-N'-ethylcarbodiimide hydrochloride (0.26 g; 1.36 mmol) was added. The reaction mixture was stirred for 15 min at room temperature. (2R)-N-Methyl-2-methylamino-N-((1R)-1-(methyl-carbamoyl)-2-phenylethyl)-3-(2-naphthyl)propionamide (0.5 g; 1.24 mmol, prepared as in example 1) was added and the reaction mixture was stirred for 12 hours at room temperature. The reaction mixture was washed with water (50 mL), an aqueous solution of sodium hydrogen sulfate (50 mL; 10%), an aqueous solution of sodium hydrogen carbonate (50 mL; sat.), dried (magnesium sulfate) and evaporated in vacuo. The residue was chromatographed on silica (2×20 cm) using ethyl acetate as eluent to afford 0.270 g of 4-((N-Methyl-N-((1R)-1-(N-methyl-N-((1R)-1-(methyl-carbamoyl)-2-phenylethyl)carbamoyl)-2-(2-naphthyl)ethyl)carbamoyl)methylene)piperidine-1-carboxylic acid tert-butyl ester.

$^1$H-NMR (CDCl$_3$) d: 1.42 (s, 3H); 1.45 (s, 3H); 1.52, 1.55 (two s, 9H); 2.05–2.18 (m, 1H); 2.34–2.42 (m, 2H); 2.71–2.80 (m, 3H); 2.80–2.89 (m, 1H); 2.90–3.01 (m, 3H); 3.02–3.36 (m, 3H); 5.16, 5.36 (two m, 1H); 5.57, 5.90 (two t, 1H); 6.90–7.25 (m, 6H); 7.28–7.53 (m, 3H); 7.61–7.82 (m, 3H).

4-((N-Methyl-N-((1R)-1-(N-methyl-N-((1R)-1-(methylcarbamoyl)-2-phenylethyl)-carbamoyl)-2-(2tert-butyl ester (0.27 g; 0.43 mmol) was dissolved in methylene chloride (8 mL) and trifluoroacetic acid (8 mL) was added. The reaction mixture was stirred for 10 min. Methylene chloride (30 mL) and an aqueous solution of sodium hydrogen carbonate (10 mL; satturated) were added. Solid sodium hydrogen carbonate was added to pH 8. The organic phase was dried (magnesium sulfate) and evaporated in vacuo to afford 0.17 g of the title compound.

$^1$H-NMR (CDCl$_3$) d (rotamers, selected peaks): 5.18; 5.38; 5.58; 5.90 (four dd, 2H); 5.49, 5.52 (two s, 1H)

ESMS: m/z 527.4 (M+H)$^+$

HPLC: r$_t$=28.62 min (Method A1)

Example 8

(2R)-2-(N-((2-Amino-2-methylpropoxy)acetyl)-N-methylamino)-N-methyl-3-(2-naphthyl)-N-((1R)-2-phenyl-1-(((tetrahydrofuran-2-yl)methyl)carbamoyl)ethyl)-propionamide:

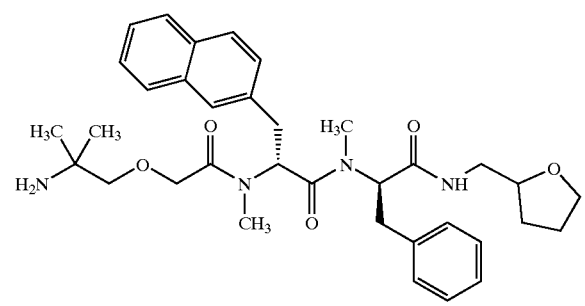

Methyl-((1R)-2-phenyl-1-((tetrahydrofuran-2-yl)methyl)-carbamoyl)ethyl)carbamic acid tert-butyl ester:

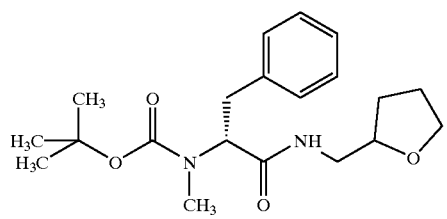

(2R)-2-(tert-Butoxycarbonylmethylamino)-3-phenylpropionic acid (5.0 g; 17.9 mmol) was dissolved in methylene chloride (50 mL). 1-Hydroxybenzotriazole (2.42 g; 17.9 mmol) and N-(3dimethylaminopropyl)-N'-ethylcarbodiimide hydrochloride (3.58 g; 18.8 mmol) were added. The reaction mixture was stirred for 15 min at room temperature. ((Tetrahydrofuran-2-yl)methyl)amine (1.72 g; 17.1 mmol) and diisopropyl-ethylamine (3.2 mL; 18.8 mmol) were added and the reaction mixture was stirred for 12 hours at room temperature. Methylene chloride (200 mL) was added and the reaction mixture was washed with water (100 mL), an aqueous solution of sodium hydrogen sulfate (10%, 100 mL), an aqueous solution of sodium hydrogen carbonate (saturated, 100 mL), water (100 mL) and dried (magnesium -sulfate). The solvent was removed in vacuo and the residue was chromatographed on silica (3×40 cm) using ethyl acetate/heptane (2:1) as eluent to afford 5.62 g of methyl-((1R)-2-phenyl-1-(((tetrahydrofuran-2-yl)methyl) carbamoyl)ethyl)carbamic acid tert-butyl ester.

$^1$H-NMR (CDCl$_3$) d: 1.28; 1.38 (two s, 9H); 1.40–1.57 (m, 1H); 1.76–2.01 (m, 3H); 2.70–2.80 (m, 3H); 2.86–2.96 (m, 1H); 3.15–3.61 (m, 3H); 3.67–3.75 (m, 1H); 3.76–3.85 (m, 1H); 3.86–3.99 (m, 1H); 4.72; 4.92 (two m, 1H); 6.26; 6.4 (two m, 1H); 7.14–7.29 (m, 5H).

(2R)-2-Methylamino-3-phenyl-N-((2-tetrahydrofuranyl)methyl)propionamide:

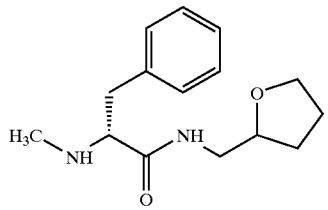

Methyl-((1R)-2-phenyl-1-((tetrahydrofuran-2-ylmethyl) carbamoyl)ethyl)carbamic acid tert-butyl ester (5.5 g; 15.2 mmol) was dissolved in methylene chloride (20 mL) and trifluoroacetic acid (20 mL) was added. The reaction mixture was stirred for 1 hour at room temperature. Methylene chloride (100 mL) and an aqueous solution of sodium hydrogen carbonate/sodium carbonate (pH 9, 50 mL) were added and solid sodium hydrogen carbonate was added until pH 8. The aquous phase was extracted with methylene chloride (100 mL) and the combined organic phases were dried (magnesium sulfate). The solvent was removed in vacuo to afford 3.62 g of (2R)-2-Methyl-amino-3-phenyl-N-((2-tetrahydrofuranyl)methyl)propionamide.

$^1$H-NMR (CDCl$_3$) d: 1.46–1.57 (m, 1H); 1.62 (s, 1);1.82–2.01 (m, 3H); 2.29 (d, 3H); 2.65–2.74 (m, 1H); 3.16–3.27 (m, 3H); 3.49–3.58 (m, 1H); 3.7–3.78 (m, 1H); 3.8–3.88 (m, 1H); 3.9–3.98 (m, 1H); 7.19–7.34 (m, 5H); 7.43 (s, 1H).

Methyl-((1R)-1-(methyl-((1R)-2-phenyl-1-(((tetrahydrofuran-2-yl)methyl)-carbamoyl)ethyl)carbamoyl)-2-(2-naphthyl)ethyl)carbamic acid tert-butyl ester:

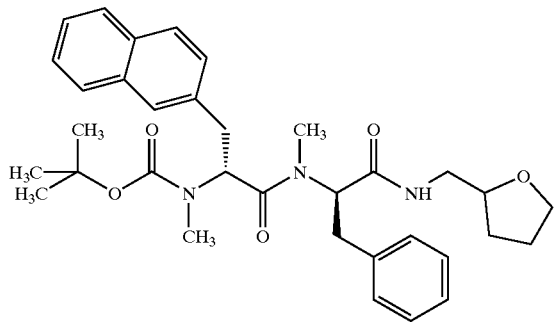

(2R)-2-(tert-Butoxycarbonylmethylamino)-3-(2-naphthyl)propionic acid (4.14 g; 12.58 mmol) was dissolved in methylene chloride (40 mL). 1-Hydroxy-7-azabenzotriazole (1.71 g; 12.6 mmol) and N-(3-dimethylaminopropyl)-N'-ethylcarbodiimide hydrochloride (2.52 g; 13.2 mmol) were added and the reaction mixture was stirred for 15 min at room temperature. (2R)-2-Methylamino-3-phenyl-N-((2-tetrahydrofuranyl)methyl)propionamide (3.0 g; 11.4 mmol) and diisopropylethylamine (2.15 mL; 12.6 mmol) were added. The reaction mixture was stirred for 12 hours at room temperature. Methylene chloride (200 mL) was added. The reaction mixture was washed with water (200 mL), an aqueous solution of sodium hydrogen carbonate/sodium carbonate (pH 9, 100 mL), an aqueous solution of sodium hydrogen sulfate (10%, 100 mL), water (100 mL) and dried (magnesium sulfate). The solvent was removed in vacuo and the residue was chromatographed on silica (4×40 cm) using ethyl acetate/heptane (1:1) as eluent to afford 4.27 g of methyl-((1R)-1-(methyl-((1R)-2-phenyl-1-(((tetrahydro-furan-2-yl)methyl)-carbamoyl)ethyl)carbamoyl)-2-(2-naphthyl)ethyl)carbamic acid tert-butyl ester.
$^1$H-NMR (CDCl$_3$) d: 1.01 (s, 2H); 1.24 and 1.27 (two s, 9H); 1.54–1.64 (m, 1H); 1.65–1.99 (m, 2H); 2.24 (t, 2H); 2.7–2.8 (m, 1H); 2.82; 2.88 (two d, 3H); 2.95 (s, 3H); 3.00–3.44 (m, 2H); 2.45–2.98 (m, 3H); 4.96–5.10 (m, 1H); 5.30–5.45 (m, 1H); 5.95; 6.17 (two m, 1H); 7.02–7.10 (m, 1H); 7.11–7.23 (m, 4H); 7.34–7.47 (m, 3H); 7.65 (s, 1H); 7.68–7.8 (m, 4H).
(2R)-N-Methyl-2-methylamino-3-(2-naphthyl)-N-((1R)-2-phenyl-1-(((tetrahydrofuran-2-yl)methyl)carbamoyl)ethyl)propionamide:

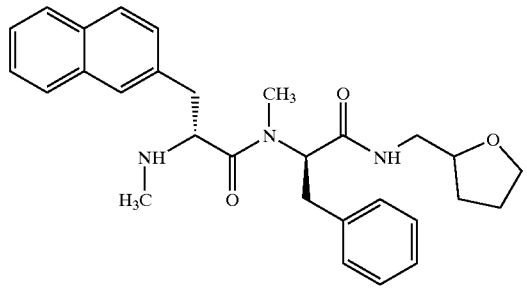

Methyl-((1R)-1-(methyl-((1R)-2-phenyl-1-(((tetrahydrofuran-2-yl)methyl)-carbamoyl)ethyl)carbamoyl)-2-(2-naphthyl)ethyl)carbamic acid tert-butyl ester. (4.2 g; 7.32 mmol) was dissolved in methylene chloride (20 mL) and trifluoroacetic acid (20 mL) was added. The reaction mixture was stirred for 15 min at room temperature. Methylene chloride (100 mL), an aqueous solution of sodium hydrogen carbonate/sodium carbonate (pH 9, 100 mL) and solid sodium hydrogen carbonate were added to the reaction mixture until pH 8. The organic phase was dried (magnesium sulfate) and evaporated in vacuo to afford 3.5 g of (2R)-N-methyl-2-methylamino-3-(2-naphthyl)-N-((1R)-2-phenyl-1-(((tetrahydrofuran-2-yl)methyl)carbamoyl)ethyl)propionamide.
(1,1-Dimethyl-2-((N-methyl-N-((1R)-1-(N-methyl-N-((1R)-2-phenyl-1-(((tetrahydrofuran-2-yl)methyl)carbamoyl)ethyl)carbamoyl)-2-(2-naphthyl)-ethyl)carbamoyl)methoxy)ethyl)carbamic acid tert-butyl ester:

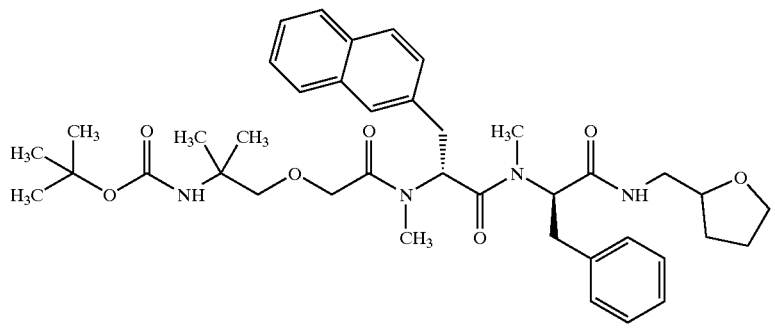

(2-tert Butoxycarbonylamino-2-methylpropoxy)acetic acid (0.5 g; 2.06 mmol) was dissolved in methylene chloride (10 mL). 1-Hydroxy-7-azabenzotriazole (0.2 g; 1.51 mmol) and N-(3-dimethylaminopropyl)-N'-ethylcarbodiimide hydrochloride (0.30 g; 1.58 mmol) were added. The reaction mixture was stirred for 15 min at room temperature. (2R)-N-Methyl-2-methylamino-3-(2-naphthyl)-N-((1R)-2-phenyl-1-(((tetrahydrofuran-2-yl)methyl)carbamoyl)ethyl)propionamide (0.65 g; 1.37 mmol) and diisopropylethylamine (0.26 mL; 1.51 mmol) were added and the reaction mixture was stirred for 12 hours at room temperature. Methylene chloride (100 mL) was added. The reaction mixture was washed with an aqueous solution of sodium hydrogen sulfate (10%; 50 mL), an aqueous solution of sodium hydrogen carbonate (sat; 50 mL) and dried (magnesium sulfate). The solvent was removed in vacuo and the residue was filtered through silica to afford 0.76 g of (1,1-dimethyl-2-((N-methyl-N-((1R)-1-(N-methyl-N-((1R)-2-phenyl-1-(((tetrahydrofuran-2-ylmethyl)carbamoyl)ethyl)-carbamoyl)-2-(2-naphthyl)ethyl)carbamoyl)methoxy)ethyl)carbamic acid tert-butyl ester.

¹H-NMR (CDCl₃) d: 0.89–0.95 (m, 3H); 1.1; 1.15 (two s, 3H); 1.41; 1.43 (two s, 9H); 1.68–2.0 (m, 4H); 2.22 (s, 1H); 2.26 (s, 1H); 2.82; 2.86 (two d, 3H); 2.88–2.97 (m, 2H); 2.99 (d, 3H); 3.06–3.36 (m, 3H); 3.45–3.95 (m, 5H); 5.05; 5.16 (two m, 1H); 5.33 (s, 1H); 5.37–5.5 (m, 1H); 5.81; 5.91 (two q, 1H); 6.89–7.1 (m, 2H); 7.13–7.24 (m, 4H); 7.34–7.47 (m, 3H); 7.63 (s, 1H); 7.69–7.79 (m, 3H).

(1 1-Dimethyl-2-((N-methyl-N-((1R)-1-(N-methyl-N-((1R)-2-phenyl-1-(((tetrahydrofuran-2-yl)methyl) carbamoyl)ethyl)carbamoyl)-2-(2-naphthyl)ethyl) carbamoyl)methoxy)ethyl)carbamic acid tert-butyl ester (0.76 g; 1.08 mmol) was dissolved in methylene chloride (5 mL) and trifluoroacetic acid (5 mL) was added. The reaction mixture was stirred for 10 min at room temperature. Methylene chloride (50 mL), an aqueous solution of sodium hydrogen carbonate/sodium carbonate (pH 9; 50 mL) and solid sodium hydrogen carbonate was added to the reaction mixture until pH 8. The aqueous phase was extracted with methylene chloride (2×50 mL) and the combined organic layers were dried (magnesium sulfate) and evaporated in vacuo to afford 0.6 g of the title compound.

¹H-NMR (CDCl₃) d (rotamers; selected peaks): 1.00; 1.02; 1.03; 1.09 (four s; 6H); 5.07; 5.15; 5.78; 5.97 (four dd, 1H); 5.42 (m; 1H).

ESMS: m/z 602.9 (M+H)⁺
HPLC: $R_t$=33.30 (Method A1)

Example 9
(2E)-5-Amino-3,5-dimethylhex-2-enoic acid N-methyl-N-((1R)-1-(N-methyl-N-((1R)-2-phenyl-1-(((2-tetra-hydrofuranyl)methyl)carbamoyl)ethyl)carbamoyl)-2-(2-naphthyl)ethyl)amide:

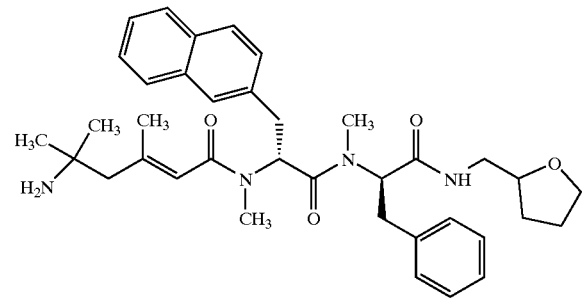

(1,1-Dimethyl-3-oxobutyl)carbamic acid tert-butylester:

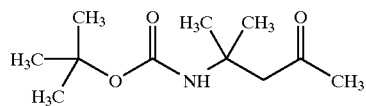

Diacetonamine hydrogen oxalate (30.0 g; 146 mmol) was suspended in tetrahydrofuran (400 mL). An aqueous solution of sodium hydroxide (1 N; 146 mL) was added. Di-tert-Butyl dicarbonate (38.3 g; 175 mmol) was dissolved in tetrahydrofuran (100 mL) and added dropwise to the reaction mixture. The reaction mixture was stirred for 2 hours at room temperature. Sodium hydroxide (1 N; 146 mL) was added and the reaction mixture was stirred for 12 hours at room temperature. Water (200 mL) and ethyl acetate (200 mL) were added. The aqueous phase was extracted with ethyl acetate (4×200 mL). The combined organic phases were dried (magnesium sulfate) and the solvent was removed in vacuo. The residue was chromatographed on silica (6×40 cm) using ethyl acetate/heptane (1:3) as eluent to afford 28.4 g of (1,1-dimethyl-3-oxobutyl)carbamic acid tert-butyl ester.

¹H-NMR (CDCl₃) d 1.34 (s, 6H); 1.42 (s, 9H); 2.14 (s, 3H); 2.86 (s, 2H); 4.85 (s, 1H).

(E)-5-tert-Butoxycarbonylamino-3,5-dimethylhex-2-enoic acid Ethylester:

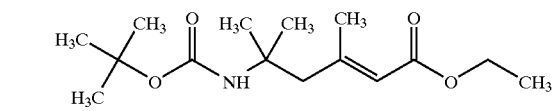

Triethyl phosphono acetate (4.7 g; 20.9 mmol) was dissolved in tetrahydrofuran (36 mL). Potassium tert-butoxide (2.3 g; 20.9 mmol) was added and the reaction mixture was stirred for 40 min at room temperature.

(1,1-dimethyl-3-oxobutyl)carbamic acid tert-butylester (2.5 g; 11.6 mmol) was dissolved in tetrahydrofuran (15 mL) and added dropwise to the reaction mixture which was heated to reflux for 12 h. Ethyl acetate (100 mL) and hydrochloric acid (1 N; 100 mL) were added and the phases were separated. The aqueous phase was extracted with ethyl acetate (3×50 mL). The combined organic phases were washed with an aqueous solution of sodium hydrogen carbonate (saturated; 100 mL), dried (magnesium sulfate) and evaporated in vacuo. The residue was chromatographed on silica (3×40 cm) using ethyl acetate/heptane (1:2) as eluent to afford 2.0 g of (E)-5-tert-Butoxycarbonylamino-3,5-dimethylhex-2-enoic acid ethylester.

¹H-NMR (CDCl₃) d 1.25 (t, 3H); 1.30 (s, 6H); 1.44 (s, 9H); 2.21 (s, 3H); 2.58 (s, 2H); 4.14 (q, 2H); 4.48 (s, 1H); 5.65 (s, 1H).

(2E)-5-tert-Butoxycarbonylamino-3,5-dimethylhex-2enoic acid:

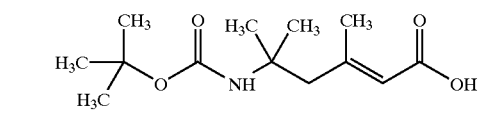

(E)-5-tert-Butoxycarbonylamino-3,5-dimethylhex-2-enoic acid ethylester (1.95 g; 6.83 mmol) was dissolved in 1,4-dioxane (25 mL) and water (15 mL). Lithium hydroxide (0.18 g; 7.52 mmol) was added and the reaction mixture was stirred for 12 hours at room temperature. Water (150 mL) and tert-butyl methyl ether (150 mL) was added. The aqueous phase was diluted with an aqueous solution of sodium hydrogensulfate (10%) until pH 2,5 and extracted with tert-butyl methylether (3×100 mL). The combined organic phases were dried (magnesium sulfate) and evaporated in vacuo. The residue was recrystallized from heptane (20 mL) to afford 0.6 g of (2E)-5-tert-Butoxycarbonylamino-3,5-dimethylhex-2-enoic acid.

¹H-NMR (CDCl₃) d 1.29 (s, 6H); 1.44 (s, 9H); 2.23 (s, 3H); 2.62 (s, 2H); 4.45 (s, 1H); 5.66 (s, 1H).

((3E)-1,1,3-Trimethyl-4-(N-methyl-N-((1R)-1-(N-methyl-N-((1R)-2-phenyl-1-(((tetrahydrofuran-2-yl)methyl) carbamoyl)ethyl)carbamoyl)-2-(2-naphthyl)-ethyl) carbamoyl)but-3-enyl)carbamic acid tert-butyl ester:

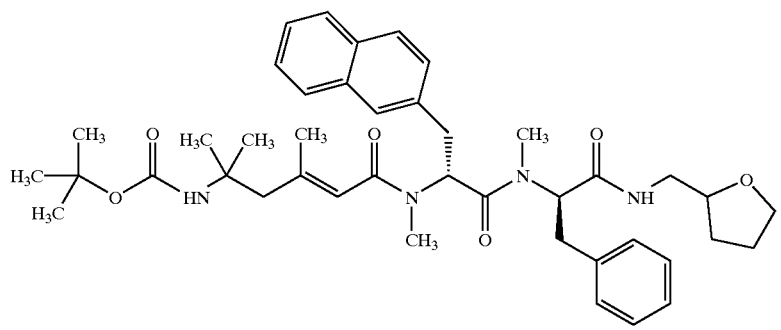

(2E)-5-tert-Butoxycarbonylamino-3,5-dimethylhex-2-enoic acid (0.3 g; 1.17 mmol) was dissolved in methylene chloride (10 mL). 1-Hydroxy-7-azabenzotriazole (0.12 g; 0.85 mmol) and N-(3dimethylaminopropyl)-N'-ethylcarbodiimide hydrochloride (0.17 g; 0.89 mmol) were added and the reaction mixture was stirred for 15 min at room temperature.

(2R)-N-Methyl-2-methylamino-3-(2-naphthyl)-N-((1R)-2-phenyl-1-(((tetrahydrofuran-2-yl)methyl)carbamoyl) ethyl)propionamide (0.37 g; 0.78 mmol) and diisopropyl-ethylamine (0.15 mL; 0.85 mmol) were added and the reaction mixture was stirred for 12 hours at room temperature. Methylene chloride (50 mL) was added and the reaction mixture was washed with water (50 mL), an aqueous solution of sodium hydrogen carbonate (saturated; 30 mL), an aqueous solution of sodium hydrogen sulfate (10%; 30 mL), water (30 mL), and dried (magnesium sulfate). The solvent was removed in vacuo and the residue was chromatographed on silica (2.5×30 cm) using ethyl acetate/heptane (2:1) as eluent to afford 0.21 g of ((3E)-1,1,3-trimethyl-4-(N-methyl-N-((1R)-1-(N-methyl-N-((1R)-2-phenyl-1-(((tetrahydrofuran-2-yl)methyl)carbamoyl)ethyl) carbamoyl)-2-(2-naphthyl)ethyl)carbamoyl)but-3-enyl) carbamic acid tert-butylester.

$^1$H-NMR (CDCl$_3$)(rotamers; selected peaks) d: 1.15; 1.21; (two s; 6H); 1.30; 1.41 (two s; 9H).

((3E)-1,1,3-Trimethyl-4-(N-methyl-N-((1R)-1-(N-methyl-N-((1R)-2-phenyl-1-(((tetrahydrofuran-2-yl)methyl) carbamoyl)ethyl)carbamoyl)-2-(2-naphthyl)ethyl)-carbamoyl)but-3-enyl)carbamic acid tert-butylester (0.20 g; 0.28 mmol) was dissolved in methylene chloride (3 mL). Trifluoroacetic acid (3 mL) was added and the reaction mixture was stirred for 6 min at room temperature. Methylene chloride (50 mL), an aqueous solution of sodium hydrogen carbonate/sodium carbonate (pH 9; 50 mL) and solid sodium hydrogen carbonate were added to the reaction mixture to pH 8. The organic phase was dried (magnesium sulfate) and evaporated in is vacuo to afford 0.155 g of the title compound.

$^1$H-NMR (CDCl$_3$)(rotamers; selected peaks) d: 1.36; 1.41 (two s; 6H); 4.38; 5.12; 5.31; 6.25 (four m; 2H).

ESMS: m/z : 613.7 (M+H)$^+$

HPLC: R$_t$=34.47 (Method A1)

Example 10

(2E)-5-Amino-5-methylhex-2-enoic acid N-((1R)-2-benzyloxy-1-(N-methyl-N-((1R)-1-(methylcarbamoyl)-2-phenylethyl)carbamoyl)ethyl)-N-methylamide:

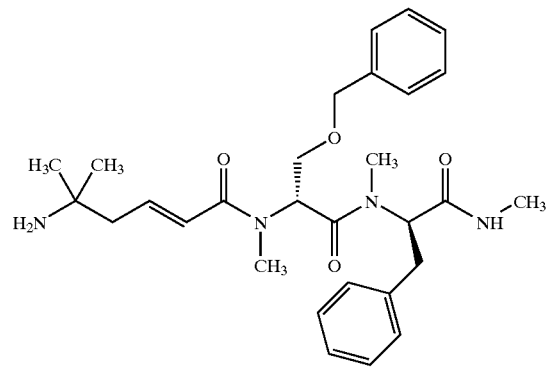

(2R)-3-Benzyloxy-2-(tert-butoxyarbonylmethylamino) propionic acid:

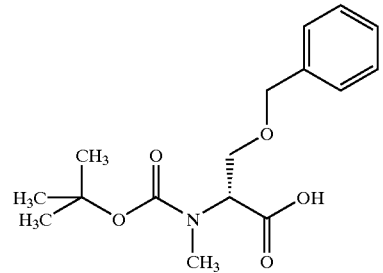

(2R)-3-Benzyloxy-2-tert-butoxycarbonylaminopropionic acid (7.0 g; 23.7 mmol) was dissolved in dry tetrahydrofuran and iodomethane (11.9 mL; 189 mmol) was added. The reaction mixture was cooled to OIC and sodium hydride (60% in mineral oil) (2.73 g; 71 mmol) was added. The reaction mixture was left 3 days without stirring at 0° C. Citric acid (5%) was added until pH 2.5. Tetrahydrofuran was removed in vacuo and the residue was extracted with methylene chloride (3×100 mL). The organic phase was dried (magnesium sulfate) and evaporated in vacuo. The residue was dissolved in diethyl ether (20 mL) and dicyclohexylamine (10 mL) and is heptane (100 mL) were added. The reaction mixture was left 3 days without stirring at 0° C. The reaction mixture was filtered to afford 5.78 g of (2R)-3-benzyloxy-2-(tert-butoxycarbonylmethylamino)propionic acid.

$^1$H-NMR (CDCl$_3$) d 1.40; 1.42 (two s, 9H); 2.91; 2.97 'two s, 3H); 3.90, 3.91 (two s, 2H); 4.55 (two d, 2H); 3.83; 4.90 (two t; 1H); 7.25–7.38 (arom. 5H).

N-((1R)-2-Benzyloxy-1-(N-methyl-N-((1R)-1-methylcarbamoyl-2-phenylethyl)carbamoyl)ethyl)N-methylcarbamic acid tert-butyl ester:

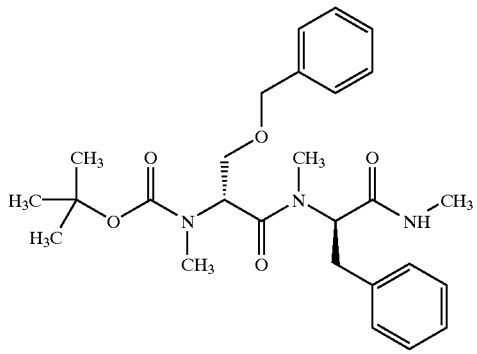

(2R)-3-Benzyloxy-2-(tert-butoxycarbonylmethylamino) propionic acid (0.39 g; 1.25 mmol) was dissolved in methylene chloride (10 mL). 1-Hydroxy-7-azabenzotriazole (0.16 g; 1.14 mmol) and N-(3-dimethylaminopropyl)-N'-ethylcarbodiimide hydrochloride (0.23 g; 1.20 mmol) were added and the reaction mixture was stirred for 15 min at room temperature.

N-methyl-2-methylamino-3-phenyl-propionamide (0.2 g; 1.04 mmol, prepared as in example 1) and diisopropylethylamine (0.2 mL; 1.14 mmol) were added and the is reaction mixture was stirred for 12 hours at room temperature. Methylene chloride (30 mL) was added. The reaction mixture was washed with water (50 mL), an aqueous solution of sodium hydrogen carbonate (saturated, 30 mL), an aqueous solution of sodium hydrogen sulfate (10%, 30 mL) and water (30 mL) and dried (magnesium sulfate). The solvent was removed in vacuo and the residue was chromatographed on silica (2.5×30 cm) using ethyl acetate/heptane (2:1) as eluent to afford 0.241 g of N-((1R)-2-benzyloxy-1-(N-methyl-N-((1R)-1-methylcarbamoyl-2-phenylethyl)carbamoyl)ethyl)-N-methylcarbamic acid tert-butyl ester.

$^1$H-NMR (CDCl$_3$) (selected peaks) d 1.42; 1.45 (two s; 9H); 2.71; 2.78 (two d, 3H); 2.84; 2.92 (twos; 3H); 4.11; 4.30 (two d; 1H); 4.43; 4.57 (two t; 1H)

(2R)-3-Benzyloxy-N-methyl-2-(methylamino)-N-((1R)-1-(methylcarbamoyl)-2-phenylethyl)propionamide:

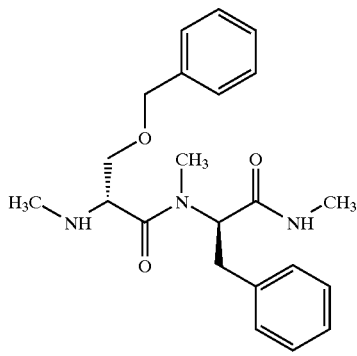

N-((1R)-2-Benzyloxy-1-(N-methyl-N-((1R)-1-methylcarbamoyl-2-phenylethyl)-carbamoyl)ethyl)N-methylcarbamic acid tert-butyl ester (0.23 g; 0.476 mmol) was dissolved in methylene chloride (3 mL) and trifluoroacetic acid (3 mL) was added. The reaction mixture was stirred for 10 min at room temperature. Methylene chloride (50 mL), an aqueous solution of sodium hydrogen carbonate/sodium carbonate (pH 9) and sodium hydrogen carbonate (solid) were added to the reaction mixture until pH 9. The organic phase was dried (magnesium sulfate) and evaporated in vacuo to afford 0.182 g of (2R)-3-Benzyloxy-N-methyl-2-(methylamino)-N-((1R)-1-(methylcarbamoyl)-2-phenylethyl)propionamide.

$^1$H-NMR (CDCl$_3$) (selected data for major rotamer) d 2.18 (d, 3H); 2.92–2.95 (d and s, 6H); 3.31–3.45 (m, 4H); 3.65 (t, 1H); 4.45 (d, 1H); 4.48 (d, 1H); 4.65 (dd; 1H).

((3E)-4-(N-((1R)-2-Benzyloxy-1-(N-methyl-N-((1R)-1-(methylcarbamoyl)-2-phenylethyl)carbamoyl)ethyl)-N-methylcarbamoyl)-1,1-dimethylbut-3-enyl)carbamic acid tert-butyl ester:

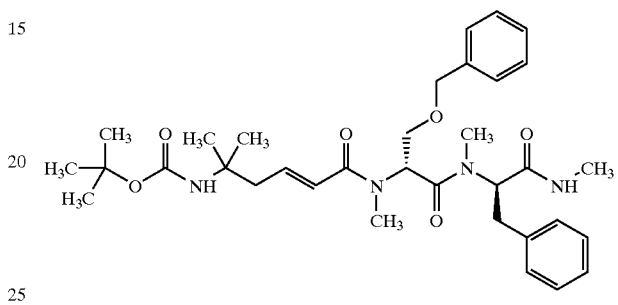

(2E)-5-(tert-Butyloxycarbonylamino)-5-methylhex-2-enoic acid (0.12 g; 0.49 mmol) was dissolved in methylene chloride (10 mL). 1-Hydroxy-7-azabenzotriazole (0.07 g; 0.49 mmol) and N-(3-dimethylaminopropyl)-N'-ethylcarbodiimide hydrochloride (0.1 g; 0.51 mmol) were added and the reaction mixture was stirred for 15 min at room temperature. (2R)-3-Benzyloxy-N-methyl-2-(methylamino)-N-((1R)-1-(methylcarbamoyl)-2-phenylethyl)-propionamide (0.17 g; 0.44 mmol) and diisopropylethylamine (0.084 mL; 0.49 mmol) were added and the reaction mixture was stirred for 12 hours at room temperature. The reaction mixture was extracted with an aqueous solution of sodium hydrogen carbonate (saturated; 30 mL) and an aqueous solution of sodium hydrogen sulfate (10%; 30 mL) and dried (magnesium sulfate). The solvent was removed in vacuo and the residue was chromatographed on silica (2.5×30 cm) using methylene chloride/ethyl acetate (1:1) as eluent to afford 0.275 g of ((3E)-4-(N-((1R)-2-benzyloxy-1-(N-methyl-N-((1R)-1-(methylcarbamoyl)-2-phenylethyl)carbamoyl)ethyl)-N-methylcarbamoyl)-1,1-dimethylbut-3-enyl)carbamic acid tert-butyl ester.

$^1$H-NMR (CDCl$_3$) (selected data for major rotamer) d 1.25 (s, 3H); 1.27 (s, 3H); 1.41 (s, 9H); 2.05 (s, 3H); 2.78 (d, 3H); 3.07 (s, 3H); 4.32 (d, 1H); 4.41 (d, 1H); 5.05 (dd, 1H); 5.51 (dd, 1H); 6.30 (d; J=17 Hz; 1H); 6.79 (m, 1H).

((3E)-4-(N-((1R)-2-Benzyloxy-1-(N-methyl-N-((1R)-1-(methylcarbamoyl)-2-phenylethyl)carbamoyl)ethyl)-N-methylcarbamoyl)-1,1-dimethylbut-3-enyl)carbamic acid tert-butyl ester (0.275 g; 0.452 mmol) was dissolved in methylene chloride (3 mL) and trifluoroacetic acid (3 mL) was added and the reaction mixture was stirred for 7 min at room temperature. Methylene chloride (30 mL), an aqueous solution of sodium hydrogen carbonate/sodium carbonate (pH 9; 30 mL) and sodium hydrogen carbonate (solid) were added to the reaction mixture until pH 8. The organic phase was dried (magnesium sulfate) and evaporated in vacuo to afford 0.13 g of the title compound.

$^1$H-NMR (CDCl$_3$) (selected data for major rotamer) d 1.27 (s, 3H); 1.28 (s; 3H); 2.84 (d, 3H); 2.95 (s, 3H); 3.08 (s, 3H); 4.32 (d; 1H); 4.40 (d, 1H); 5.12 (dd, 1H); 6.34 (d, J=18 Hz, 1H).

ESMS: m/z 509.7 (M+H)+
HPLC: $R_t$=23.45 min (Method A1)

Example 11

(2R)-2-(N-((2-Amino-2-methylpropoxy)acetyl)-N-methylamino)-N-((1R)-1-((cyclopropylmethyl)carbamoyl)-2-phenylethyl)-N-methyl-3-(2-naphthyl)-propionamide:

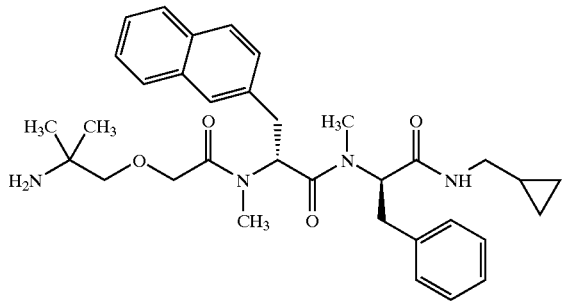

(2-((N-((1R)-1-(N-((1R)-1-(Cyclopropylmethylcarbamoyl)-2-phenylethyl)-N-methylcarbamoyl)-2-(2-naphthyl)ethyl)-N-methylcarbamoyl)methoxy)-1,1-dimethylethyl)carbamic acid tert-butylester:

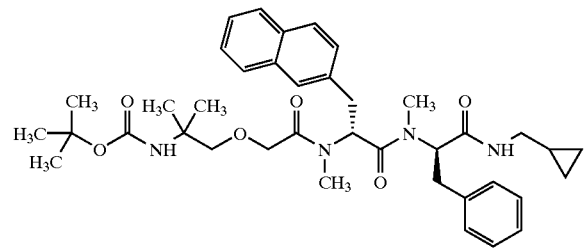

(2-tert-Butoxycarbonylamino-2-methylpropoxy) acetic acid (0.36 g; 1.49 mmol) was dissolved in methylene chloride (5 mL). 1-Hydroxy-7-azabenzotriazole (0.2 g; 1.49 mmol) and N-(3-dimethylaminopropyl)-N'-ethylcarbodiimide hydrochloride (0.3 g; 1.56 mmol) were added and the reaction mixture was stirred for 15 min at room temperature.

(2R)-N-((1R)-1-((Cyclopropylmethyl)carbamoyl)-2-phenylethyl)-N-methyl-2-methylamino-3-(2-naphthyl) propionamide (0.60 g; 1.35 mmol) and diisopropylethylamine (0.26 mL; 1.49 mmol) were added and the reaction mixture was stirred for 12 hours at room temperature. Methylene chloride (30 mL) was added. The reaction mixture was washed with an aqueous solution of sodium hydrogen carbonate (saturated; 30 mL) and an aqueous solution of sodium hydrogen sulfate (10%; 30 mL) and dried (magnesium sulfate). The solvent was removed in vacuo and the residue was chromatographed on silica (3.5×40 cm) using ethyl acetate/heptane (1:1) as eluent to afford 0.64 g of (2-((N-((1R)-1-(N-((1R)-1-((cyclopropylmethyl) carbamoyl)-2-phenylethyl)-N-methylcarbamoyl)-2-(2-naphthyl)ethyl)-N-methylcarbamoyl)methoxy)-1,1-dimethylethyl)carbamic acid tert-butyl ester.

$^1$H-NMR (CDCl$_3$) (rotamers, selected peaks) d : −0.11 (m 1H); 0.19 (m, 1H); 0.45 (m, 1H); 0.95; 1.17; 1.25; 1.27; 1.40; 1.43; 1.58 (seven s, 15H); 2.29; 2.81; 2.91; 3.03 (four s, 6H).

(2-((N-((1R)-1-(N-((1R)-1-((Cyclopropylmethyl) carbamoyl)-2-phenylethyl)-N-methylcarbamoyl)-2-(2-naphthyl)ethyl)-N-methylcarbamoyl)methoxy)-1,1-dimethylethyl)carbamic acid tert-butylester (0.64 g; 0.951 mmol) was dissolved in methylene chloride (3 mL) and trifluoroacetic acid (3 mL) was added. The reaction mixture was stirred for 5 min. Methylene chloride (25 mL), an aqueous solution of sodium hydrogen carbonate/sodium carbonate (pH 9; 25 mL) and sodium hydrogen carbonate (solid) were added to the reaction mixture to pH 8. The organic phase was dried (magnesium sulfate) and evaporated in vacuo to afford 0.48 g of the title compound.

$^1$H-NMR (CDCl$_3$) (rotamers, selected peaks) d: 0.55; 0.57; 0.80; 0.82 (four s, 6H); 2.09; 2.62; 2.75; 2.84 (four s; 6H); 3.68; 3.82 (two d, 2H together with a singlet at 3.69); 4.92; 5.22; 5.30; 5.38; 5.65 (five dd, 3H);
ESMS: m/z 572.0 (M+H)+
HPLC: $R_t$=35.52 min (Method A1)

Example 12

(2R)-2-(((2-Amino-2-methylpropoxy)acetyl)methylamino)-N-((1R)-2-(2-fluorophenyl)-1-(methylcarbamoyl)ethyl)-N-methyl-3-(2-naphthyl)propionamide:

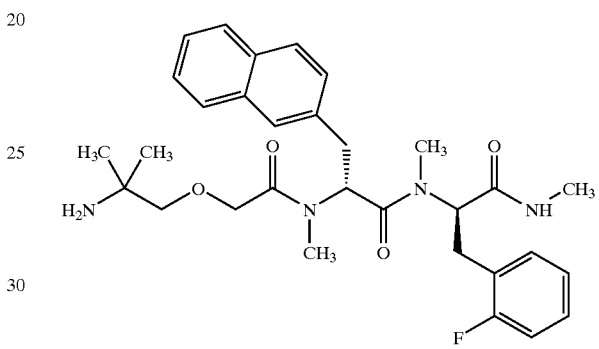

(2R)-2-(N-tert-Butoxycarbonyl-N-methylamino)-3-(2-fluorophenyl)propionic acid:

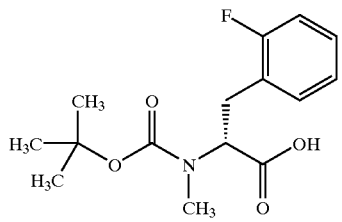

(The N-methylation in this and other examples in this invention may be performed as in Can. J. Chem. 1977, 55, 906).

(2R)-2-tert-Butoxycarbonylamino-3-(2-fluorophenyl) propionic acid (5.0 g; 17.5 mmol) was dissolved in dry tetrahydrofuran. Iodomethane (7.2 mL; 1 15 mmol) was added and the reaction mixture was cooled to 0° C. Sodium hydride (60% susp. in oil; 1.41 g; 42.0 mmol) was added and the reaction mixture was stirred for 12 hours is at room temperature. Ethyl acetate (50 mL) was added and water (20 mL) was added dropwise. The ethyl acetate was removed in vacuo and the residue was diluted with ether (30 mL) and water (100 mL). The organic phase was extracted with an aqueous solution of sodium hydrogen carbonate (aqueous; 50 mL). To the combined aqueous layers was added citric acid (5%) until pH 3 and ethyl acetate (3×50mL) was added and the phases were separated. The combined organic layers were washed with water (2×50 mL), an aqueous solution of sodium thiosulfate (5%; 2×50 mL) and water (50 mL) and dried (magnesium sulfate). The solvent was removed in vacuo and the residue was dissolved in diethyl ether (10 mL). Dicyclohexylamine (9.0 mL) was added. The reaction mixture was filtered to afford 5.57 g of (2R)-2-(N-tert-butoxycarbonyl-N-methylamino)-3–2-fluorophenyl) propionic acid as a dicyclohexylammonium salt.

¹H-NMR (CDCl₃) d 1.27; 1.35 (two s, 9H); 2.21; 2.25 (two s, 3H); 3.03 (m, 2H); 4.26; 4.37 (two dd, 1H); 6.9–7.3 (arom 4H).

N-((1R)-2-(2-Fluorophenyl)-1-(methylcarbamoyl)ethyl)-N-methylcarbamic acid tert-butylester:

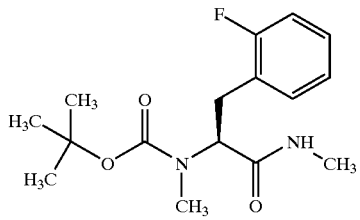

(2R)-2-(N-tert-Butoxycarbonyl-N-methylamino)-3-(2-fluorophenyl)propionic acid as a dicyclohexylammonium salt (5.57 9; 18.73 mmol) was dissolved in methylene chloride (30 mL) and washed with an aqueous solution of sodium hydrogen sulfate (10%; 30 mL). The organic phase was dried (magnesium sulfate) and filtered. 1-Hydroxybenzotriazole hydrate (2.53 g; 18.73 mmol) and N-(3-dimethylaminopropyl)-N'-ethylcarbodiimide hydrochloride (3.75 g; 19.6 mmol) were added to the filtrate and the mixture was stirred for 15 min at room temperature. Methylamine (40% in methanol; 0.53 g; 17.0 mmol) and diisopropylethylamine (3.2 mL; 18.7 mmol) were added and the reaction mixture was stirred for 12 hours at room temperature. The reaction mixture was washed with an aqueous solution of sodium hydrogen carbonate (50 mL) and an aqueous solution of sodium hydrogen sulfate (10%; 50 mL) and dried (magnesium sulfate). The solvent was removed in vacuo and the residue was chromatographed on silica (3.5×40 cm) using ethyl acetate/heptane (2:1) as eluent to afford 2.4 g of N-((1R)-2-(2-Fluorophenyl)-1-(methylcarbamoyl)ethyl)-N-methylcarbamic acid tert-butyl ester.

¹H-NMR (CDCl₃) d: 1.25; 1.35; 1.38 (three s, 9H); 2.74 (s, 3H); 2.75 (d, 3H); 2.80–3.55 (m, 2H); 4.35; 4.82; 5.00; 5.12 (four dd; 6.9–7.3 (arom, 4H).

(2R)-3-(2-Fluorophenyl)-N-methyl-2-(methylamino)-propionamide:

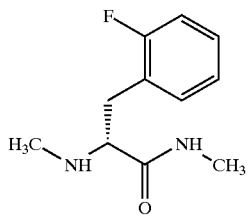

N-((1R)-2-(2-Fluorophenyl)-1-(methylcarbamoyl)ethyl)-N-methylcarbamic acid tert-butylester (2.4 g; 7.73 mmol) was dissolved in methylene chloride. Trifluoroacetic acid (1 0 mL) was added and the reaction mixture was stirred for 30 min at room temperature. Methylene chloride (30 mL), an aqueous solution of sodium hydrogen carbonate/sodium carbonate (pH 9; 30 mL) and sodium hydrogen carbonate (solid) were added to the reaction mixture until pH 8. The organic phase was dried (magnesium sulfate) and evaporated in vacuo to afford 1.1 g of (2R)-3-(2-fluorophenyl)-N-methyl-2-(methylamino)-propionamide.

H-NMR (CDCl₃) d 2.31 (s, 3H); 2.80 (d, 3H); 2.86 (dd, 1H); 3.17 (dd, 1H); 3.28 (dd, 1H); 7.0–7.30 (arom. 4H).

N-((1R)-1-(N-((1R)-2-(2-Fluorophenyl)-1-(methylcarbamoyl)ethyl)-N-methylcarbamoyl)-2-(2-naphthyl)-ethyl)-N-methylcarbamic acid tert-butyl ester.

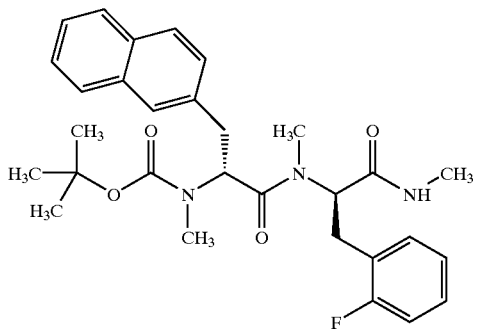

Tert-Butoxycarbonylaminoacetic acid (0.18 g; 2.39 mmol) was dissolved in methylene chloride (20 mL). 1-Hydroxybenzotriazole (0.32 g; 2.39 mmol) and N-(3-dimethylaminopropyl)-N'-ethylcarbodiimide hydrochloride (0.55 g; 2.87 mmol) were added and the reaction mixture was stirred for 15 min at room temperature. (2R)-3-(2-Fluorophenyl)-N-methyl-2-(methylamino)propionamide (1.0 g; 4.78 mmol) and diisopropylethylamine (0.9 mL; 5.26 mmol) was added and the reaction mixture was stirred for 12 hours at room temperature. A mixture of 2-(tert-butoxycarbonylmethylamino)-3-(2-naphthyl)propionic acid (0.78 g; 2.39 mmol), 1-hydroxy-7-azabenzotriazole (0.33 g; 2.39 mmol) and N-(3-dimethylaminopropyl)-N'-ethylcarbodiimide hydrochloride (0.55 g; 2.87 mmol) were dissolved in methylene chloride (20 mL) and added to the reaction mixture. The reaction mixture was stirred for 12 hours at room temperature. Methylene chloride (50 mL) was added and the reaction mixture was washed with water (30 mL), an aqueous solution of sodium hydrogen sulfate (10%; 30 mL), an aqueous solution of sodium hydrogen carbonate/sodium carbonate (pH 9; 30 mL) and water (30 mL) and dried (magnesium sulfate). The solvent was removed in vacuo and the residue was chromatographed on silica (2.5× 30 cm) using ethyl acetate/heptane (2:1) as eluent to afford 0.86 g of N-((1R)-1-(N-((1R)-2-(2-fluorophenyl)-1-(methylcarbamoyl)ethyl)-N-methylcarbamoyl)-2-(2-naphthyl)ethyl)-N-methyl-carbamic acid tert-butylester.

H-NMR (CDCl₃) (selected peaks, rotamers) d: 1.34 (s, 9H); 2.35 (s, 3H); 2.78 (s, 3H); 5.03–5.45 (four m, 2H).

(2R)-N-((1R)-2-(2-Fluorophenyl)-1-methylcarbamoylethyl)-N-methyl-2-methylamino-3-(2-naphthyl)propionamide:

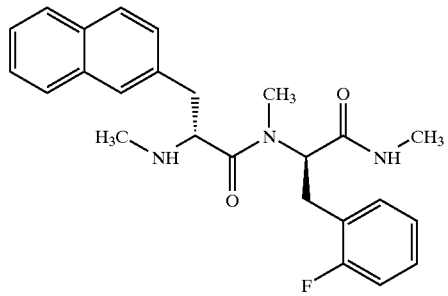

N-((1R)-1-(N-((1R)-2-(2-Fluorophenyl)-1-(methylcarbamoyl)ethyl)-N-methyl-carbamoyl)-2-(2- naphthyl)ethyl)-N-methylcarbamic acid tert-butylester (0.85 g; 1.63 mmol) was dissolved in methylene chloride (5 mL). Trifluoroacetic acid (5 mL) was added and the reaction mixture was stirred for 15 min at room temperature. Methylene chloride (25 mL), an aqueous solution of sodium hydrogen carbonate/sodium carbonate (pH 9; 25 mL) and sodium hydrogen carbonate (solid) were added to the reaction mixture until pH 8. The organic phase was dried (magnesium sulfate) and evaporated in vacuo to afford 0.669 g of (2R)-N-((1R)-2-(2-fluorophenyl)-1-(methylcarbamoyl) ethyl)-N-methyl-2-methylamino-3-(2-naphthyl) propionamide.

H-NMR (CDCl$_3$) (selected peaks, rotamers) d : 2.02 (d, 3H); 2.57 (s, 3H); 3.78 (dd, 1H); 5.55 (dd, 1H) (2-((((1R)-1-(((1R)-2-(2-Fluorophenyl)-1-(methylcarbamoyl)ethyl)methylcarbamoyl)-2-(2-naphthyl) ethyl)-methylcarbamoyl)methoxy)-1,1-dimethylethyl) carbamic acid Tert-butyl ester:

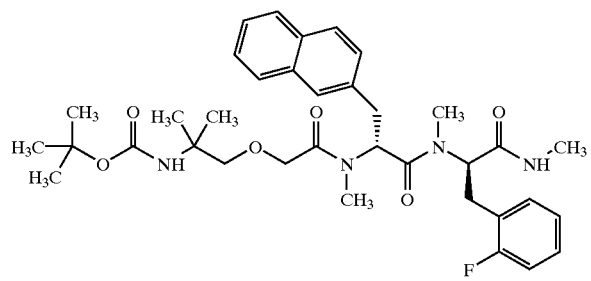

(2-tert-Butoxycarbonylamino-2-methylpropoxy) acetic acid (0.19 g; 0.78 mmol) was dissolved in methylene chloride (10 mL). 1-Hydroxy-7-azabenzotriazole (0.12 g; 0.86 mmol) and N-(3-dimethylaminopropyl)-N'-ethylcarbodiimide hydrochloride (0.17 g; 0.90 mmol) were added and the reaction mixture was stirred for 15 min at room temperature. (2R)-N-((1R)-2-(2-Fluorophenyl)-1-(methylcarbamoyl)ethyl)-N-methyl-2-methylamino-3-(2-naphthyl)propionamide (0.33 g; 0.78 mmol) and diisopropylethylamine (0.17 mL; 0.86 mmol) were added and the reaction mixture was stirred for 12 hours at room temperature. Methylene chloride (50 mL) was added and the reaction mixture was washed with water (50 mL), an aqueous solution of sodium hydrogen sulfate (10%; 50 mL), an aqueous solution of sodium hydrogen carbonate (saturated; 50 mL), water (50 mL) and dried (magnesium sulfate). The solvent was removed in vacuo to afford 0.47 g of (2-((((1R)-1-(((1R)-2-(2-fluorophenyl)-1-methylcarbamoyl-ethyl)-methylcarbamoyl)-2-(2-naphthyl) ethyl)methyl-carbamoyl)methoxy)-1,1-dimethylethyl) carbamic acid tert-butyl ester.

H-NMR (CDCl$_3$) (rotamers, selected peaks for major isomer) d 1.03 (s, 3H); 1.06 (s, 3H); 2.78 (s, 3H); 2.80 (d, 3H); 3.98 (s, 3H); 4.95 (d, 1H); 5.00 (d, 1H); 5.70 (dd, 1H), 5.85 (dd, 1H).

(2-((((1R)-1-(((1R)-2-(2-Fluorophenyl)-1 (methylcarbamoyl)-ethyl)methylcarbamoyl)-2-(2-naphthyl) ethyl)-methylcarbamoyl)methoxy)-1,1-dimethylethyl) carbamic acid tert-butyl ester (0.46 g; 0.707 mmol) was dissolved in methylene chloride (3 mL). Trifluoroacetic acid (3 mL) was added and the reaction mixture was stirred for 5 min at room temperature. Methylene chloride (25 mL), an aqueous solution of sodium hydrogen carbonate/sodium carbonate (pH 9; 25 mL) and sodium hydrogen carbonate (solid) were added to the reaction mixture until pH 8. The organic phase was dried (magnesium sulfate) and evaporated in vacuo to afford 0.275 g of the title compound.

H-NMR (CDCl$_3$) (selected peaks, rotamers) d: 0.76; 0.99 (two d, 6H); 2.30; 2.80 (two d, 3H); 2.47; 2.78; 2.94; 2.97 (four s, 6H); (3.90 (d), 3.94(s), 4.05 (d), 2H); 5.27; 5.37; 5.67; 5.86 (four dd, 2H); 6.96–7.82 (arom. 12H).

PDMS: m/z 550.7 (M+H)$^+$

HPLC: R$_t$=31.28 min (Method A1)

Example 13

(2E)-5-Amino-5-methylhex-2-enoic acid ((1R)-1-(((1R)-2-(4-fluorophenyl)-1-(methylcarbamoyl)ethyl) methylcarbamoyl)-2-(2-naphthyl)ethyl)methylamide:

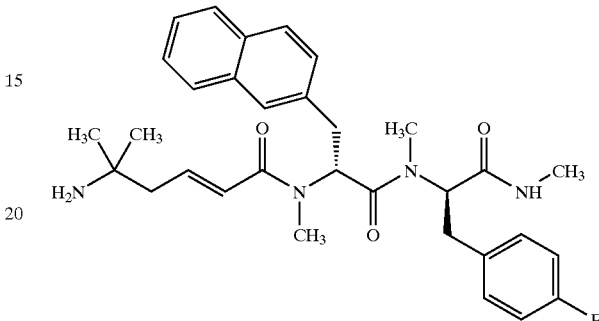

(R)-2-(N-tert-Butoxycarbonyl-N-methylamino)-3-(4-fluorophenyl)propionic acid:

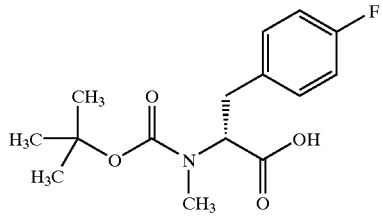

2-tert-Butoxycarbonylamino-3-(4-fluorophenyl) propionic acid (5.0 g; 17.7 mmol) was dissolved in dry tetrahydrofuran. Iodomethane (8.8 mL; 141 mmol) was added and the reaction mixture was cooled to 0° C. Sodium hydride (2.1 g; 53.0 mmol) was slowly added and the reaction mixture was stirred for 12 hours at room temperature. Ethyl acetate (50 mL) was added and water (20 mL) was added dropwise to the reaction mixture. The ethyl acetate was removed in vacuo and the residue was diluted with diethyl ether (30 mL) and water (100 mL). The organic phase was extracted with a saturated aqueous solution of sodium hydrogen carbonate (50 mL). Citric acid (5%) was added to the combined aqueous phases until pH 3, which were then extracted with ethyl acetate (2×50 mL) and the phases were separated. The organic phase was washed with water (2×50 mL), an aqueous solution of sodium thiosulfate (5%; 2×50 mL) and water (50 mL) and dried (magnesium sulfate). The solvent was removed in vacuo and the residue was dissolved in diethyl ether (10 mL). Dicyclohexylamine (10 mL) was added. Methylene chloride (30 mL) was added and the mixture was heated until the precipitate was dissolved. Diethyl ether (20 mL) and heptane (20 mL) were added and the reaction mixture was left 12 hours without stirring. The reaction mixture was filtered to afford 5.7 g of (R)-2-(N-tert-butoxycarbonyl-N-methylamino)-3-(4-fluorophenyl)propionic acid as a dicyclohexylammonium salt.

$^1$H-NMR (CDCl$_3$) (mixture of rotamers) d: 1.21; 1.31 (two s, 9H); 2.75; 2.84 (two s, 3H); 2.86–3.02 (m, 1H);

3.28–3.42 (m, 1H); 4.65; 4.85 (two dd, 1H); 6.85–7.00 (m, 2H); 7.10–7.25 (m, 2H).

((1R)-2-(4-Fluorophenyl)-1-(methylcarbamoyl)ethyl)-methylcarbamic acid tert-butylester:

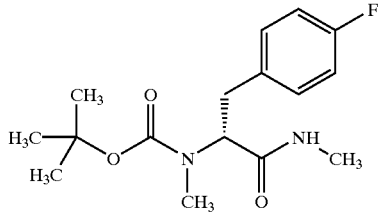

The dicyclohexylammoniumsalt of (R)-2-(N-tert-butoxycarbonyl-N-methylamino)-3-(4-fluorophenyl)propionic acid (3.00 g; 10.1 mmol) was dissolved in methylene chloride (30 mL) and washed with an aqueous solution of sodium hydrogen sulfate (10%; 30 mL). The organic phase was dried (magnesium sulfate) and filtered. 1-Hydroxybenzotriazole (1.40 g; 10.1 mmol) and N-(3-dimethylaminopropyl)-N'-ethylcarbodiimide hydrochloride (2.0 g; 10.6 mmol) were added to the filtrate and the reaction mixture was stirred for 15 min at room temperature. Methylamine (40% in methanol; 0.75 g; 9.17 mmol) and diisopropylethylamine (1.7 mL; 10.1 mmol) were added and the reaction mixture was stirred for 12 hours at room temperature. The reaction mixture was washed with an aqueous solution of sodium hydrogen carbonate (sat; 50 mL) and an aqueous solution of sodium hydrogen sulfate (10%; 50 mL) and dried (magnesium sulfate). The solvent was removed in vacuo and the residue was chromatographed on silica (3×40 cm) using ethyl acetate/heptane (2:1) as eluent to afford 1.06 g of ((1R)-2-(4-fluorophenyl)-1-(methylcarbamoyl)ethyl)-methylcarbamic acid tert-butylester.

$^1$H-NMR (CDCl$_3$) d: 1.29; 1.37 (two s, 9H); 2.74 (s, 3H); 2.8 (s, 3H); 2.82–2.95 (m, 1H); 3.36–3.48 (m, 1H); 4.63; 4.86 (m, 1H); 5.89; 6.14 (two s, 1H); 6.9–7.0 (m, 2H); 7.1–7.21 (m, 2H).

(2R)-3-(4-Fluorophenyl)-N-methyl-2-(methylamino)propion-amide:

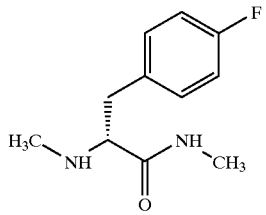

((1R)-2-(4-Fluorophenyl)-1-(methylcarbamoyl)ethyl)-methylcarbamic acid tert-butylester (1.0 g; 3.22 mmol) was dissolved in methylene chloride (5 mL). Trifluoroacetic acid (5 mL) was added and the reaction mixture was stirred for 30 min at room temperature. Methylene chloride (30 mL), an aqueous solution of sodium hydrogen carbonate/sodium carbonate (pH 9; 30 mL) and sodium hydrogen carbonate (solid), were added to the reaction mixture, until pH 9. The organic phase was dried (magnesium sulfate) and evaporated in vacuo to afford 0.62 g of (2R)-3-(4-fluorophenyl)-N-methyl-2-methylaminopropionamide.

$^1$H-NMR (CDCl$_3$) d: 1.31 (s, 1H); 2.29 (s, 3H); 2.65–2.73 (m, 1H); 2.82 (d, 3H); 3.12–3.20 (m, 2H); 6.96–7.02 (m, 2H); 7.11 (s, 1H); 7.14–7.20 (m, 2H).

((1R)-1-(((1R)-2-(4-Fluorophenyl)-1-(methylcarbamoyl)ethyl)methylcarbamoyl)-2-(2-naphthyl)-ethyl)methylcarbamic acid tert-butylester:

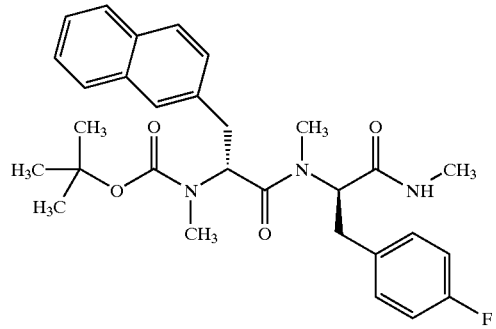

(2R)-2-(tert-Butoxycarbonylmethylamino)-3-(2-naphthyl)propionic acid (1.0 g; 3.1 mmol) was dissolved in methylene chloride (20 mL). 1-Hydroxy-7-azabenzotriazole (0.43 g; 3.1 mmol) and N-(3-dimethylaminopropyl)-N'-ethylcarbodiimide hydrochloride (0.63 g; 3.3 mmol) were added and the reaction mixture was stirred for 15 min at room temperature.

(2R)-3-(4-Fluorophenyl)-N-methyl-2-(methylamino)propionamide (0.6 g; 2.9 mmol) and diisopropylethylamine (0.54 mL; 3.1 mmol) was added and the reaction mixture was stirred for 12 hours at room temperature. Methylene chloride (30 mL) was added and the reaction mixture was washed with water (30 mL), an aqueous solution of sodium hydrogen sulfate (10%; 30 mL), an aqueous solution of sodium hydrogen carbonate/sodium carbonate (pH 9; 30 mL) and water (30 mL) and dried (magnesium sulfate). The solvent was removed in vacuo and the residue was chromatographed on silica (4.0×30 cm) using ethyl acetatelheptane (2:1) as eluent to afford 1.07 g of ((1R)-1-(((1R)-2-(4-fluorophenyl)-1-(methylcarbamoyl)-ethyl)methylcarbamoyl)-2-(2-naphthyl)ethyl)methylcarbamic acid tert-butylester.

$^1$H-NMR (CDCl$_3$) (selected peaks for major rotamer) d: 1.34 (s, 9H); 2.23 (d, 3H); 2.76 (s, 3H); 2.87 (s, 3H); 5.70 (dd, 1H); 5.95 (dd, 1H).

(2R)-N-((1R)-2-(4-Fluorophenyl)-1-(methylcarbamoyl)-ethyl)-N-methyl-2-methyl-amino-3-(2-naphthyl)propionamide:

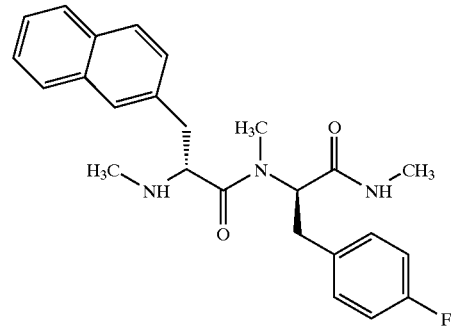

((1R)-1-(((1R)-2-(4-Fluorophenyl)-1-(methylcarbamoyl)-ethyl)methylcarbamoyl)-2-(2-naphthyl)ethyl)methylcarbamic acid tert-butylester. (1.0 g; 1.92 mmol) was dissolved in methylene chloride (5 mL). Trifluoroacetic acid (5 mL) was added and the reaction mixture was stirred for 15 min at room temperature. Methylene chloride (25 mL), an aqueous solution of sodium hydrogen carbonate/sodium carbonate (pH 9; 25 mL) and sodium hydrogen carbonate (solid) was added to the reaction mixture until pH 8. The organic phase was dried (magnesium sulfate) and evaporated in vacuo to afford 0.75 g of (2R)-N-((1R)-2-(4-fluorophenyl)-1-methylcarbamoylethyl)-N-methyl-2-methylamino-3-(2-naphthyl)propionamide.

¹H-NMR (CDCl₃) d: 1.81 (s, 3H); 2.07 (d, 3H); 2.54 (s, 3H); 2.68-2.77 (m, 1H); 2.88-2.97 (m, 1H); 3.18 (dd, 1H); 3.27 (dd, 1H); 3.8 (dd, 1H); 4.95 (s, 1H); 5.43 (dd, 1H); 6.72 (t, 1H); 6.90 (t, 2H); 7.12 (dd, 2H); 7.32 (d, 1H); 7.42–7.50 (m, 2H); 7.62 (s, 1H); 7.70–7.83 (m, 2H).

(4(((1R)-1(((1R)-2(4-Fluorophenyl)-1-(methylcarbamoyl)-ethyl)methylcarbamoyl)-2-(2-naphthyl)ethyl)methylcarbamoyl)-1,1-dimethylbut-3-enyl)carbamic acid tert-butylester:

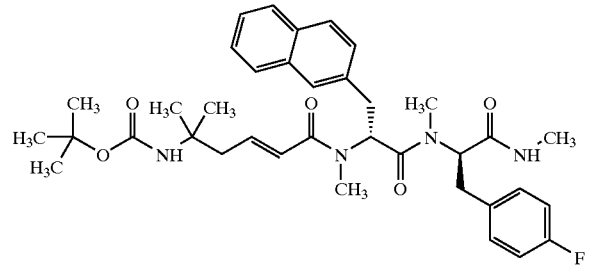

(2E)-5-(tert-Butyloxycarbonylamino)-5-methylhex-2-enoic acid (0.22 g; 0.89 mmol, prepared as in example 1) was dissolved in methylene chloride (10 mL). 1-Hydroxy-7-azabenzotriazole (0.13 g; 0.98 mmol) and N-(3-dimethylaminopropyl)-N'-ethylcarbodiimide hydrochloride (0.2 g; 1.02 mmol) were added and the reaction mixture was stirred for 15 min at room temperature.

(2R)-N-((1R)-2-(4-Fluorophenyl)-1-(methylcarbamoyl)ethyl)-N-methyl-2-methyl-amino-3-(2-naphthyl)propionamide (0.38 g; 0.89 mmol) and diisopropylethylamine (0.17 mL; 0.98 mmol) were added and the reaction mixture was stirred for 12 hours at room temperature.

Methylene chloride (50 mL) was added and the reaction mixture was washed with water (50 mL), an aqueous solution of sodium hydrogen sulfate (10%; 50 mL), an aqueous solution of sodium hydrogen carbonate/sodium carbonate (pH 9; 50 mL) and water (50 mL) and dried (magnesium sulfate). The solvent was removed in vacuo and the residue was chromatographed on silica (4×30 cm) using ethyl acetate/heptane (2:1) as eluent to afford 0.34 g of (4-(((1R)-1-(((1R)-2-(4-fluorophenyl)-1-methylcarbamoylethyl)methylcarbamoyl)-2-(2-naphthyl)-ethyl)methylcarbamoyl)-1,1-dimethylbut-3-enyl)carbamic acid tert-butyl ester.

¹H-NMR (CDCl₃) (selected peaks for major rotamer) d: 0.85 (s, 3H); 0.87 (s, 3H); 1.42 (s, 9H); 2.12 (d, 3H); 2.72 (s, 3H); 2.96 (s, 3H); 5.75 (dd, 1H); 5,92 (dd, 1H); 6.12 (dd, 1H).

(4-(((1R)-1-(((1R)-2-(4-Fluorophenyl)-1-methylcarbamoyl-ethyl)methylcarbamoyl)-2-is (2-naphthyl)ethyl)methyl-carbamoyl)-1,1-:dimethylbut-3-enyl)carbamic acid tert-butylester (0.33 g; 0.51 mmol) was dissolved in methylene chloride (3 mL). Trifluoroacetic acid (3 mL) was added and the reaction mixture was stirred for 5 min at room temperature. Methylene chloride (25 mL), an aqueous solution of sodium hydrogen carbonate/sodium carbonate (pH 9; 25 mL) and sodium hydrogen carbonate (solid) were added to the reaction mixture until pH 9. The organic phase was dried (magnesium sulfate) and evaporated in vacuo to afford 0.18 g of the title compound.

¹H-NMR (CDCl₃) (selected peaks for major rotamer) d: 1.15 (s, 6H); 2.14 (d, 3H); 2.73 (s, 3H); 3.09 (s, 3H); 5.23 (dd, 1H); 5.90 (dd, 1H); 6.12 (dd, 1H).

PDMS: m/z 547.4 (M+H)⁺
HPLC: R$_t$=32.05 min (Method A1)

Example 14

(2R)-2-(((2-Amino-2-methylpropoxy)acetyl)methylamino)-N-((1R)-2-(4-fluorophenyl)-1-(methylcarbamoyl)ethyl)-N-methyl-3-(2-naphthyl)propionamide:

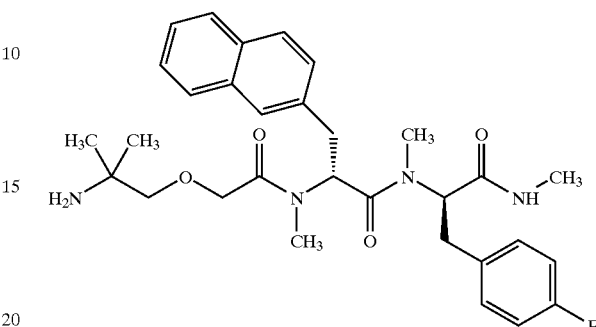

(2-((((1R)-1-(((1R)-2-(4-Fluorophenyl)-1-methyl-carbamoylethyl)-methylcarbamoyl)-2-(2-naphthyl)ethyl)-methylcarbamoyl)methoxy)-1,1-dimethylethyl)carbamic acid Tert-butylester:

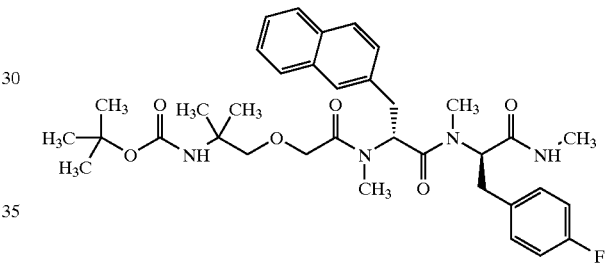

(2-tert-Butoxycarbonylamino-2-methylpropoxy)acetic acid (0.22 g; 0.89 mmol) was dissolved in methylene chloride (10 mL). 1-Hydroxy-7-azabenzotriazole (0.13 g; 0.98 mmol) and N-(3-dimethylaminopropyl)-N'-ethylcarbodiimide hydrochloride (0.20 g; 1.02 mmol) were added and the reaction mixture was stirred for 15 min at room temperature. (2R)-N-((1R)-2-(4-Fluorophenyl)-1-(methylcarbamoyl)ethyl)-N-methyl-2-methylamino-3-(2-naphthyl)propionamide (0.38 g; 0.89 mmol) and diisopropylethylamine (0.17 mL; 0.98 mmol) were added and the reaction mixture was stirred for 12 hours at room temperature. Methylene chloride (50 mL) was added and the reaction mixture was washed with water (50 mL), an aqueous solution of sodium hydrogen carbonate/sodium carbonate (pH 9; 50 mL), an aqueous solution of sodium hydrogen sulfate (10%; 50 mL) and water (50 mL) and dried (magnesium sulfate). The solvent was removed in vacuo to afford 0.53 g of (2-((((1R)-1-(((1R)-2-(4-fluorophenyl)-1-methylcarbamoylethyl)-methylcarbamoyl)-2-(2-naphthyl)ethyl)methylcarbamoyl)-methoxy)-1,1-dimethylethyl) carbamic acid tert-butylester.

¹H-NMR (CDCl₃) (selected peaks for major rotamer) d: 1.20 (s, 3H); 1.25 (s, 3H); 1.44 (s, 9H); 2.18 (d, 2H); 2.59 (s, 3H); 2.74 (s, 3H); 2.77 (d, 3H); 4.02 (s), 2H); 5.25 (dd, 1H); 5.82 (dd, 1H).

(2-((((1R)-2-(4-Fluorophenyl)-1-(methylcarbamoyl)-ethyl)methylcarbamoyl)-2-(2-naphthyl)ethyl)-methylcarbamoyl)-methoxy)-1,1-dimethylethyl) carbamic acid tert-butylester (0.53 g; 0.81 mmol) was dissolved in methylene chloride (3 mL). Trifluoroacetic acid (3 mL) was added and the reaction mixture was stirred for 5 min at room temperature. Methylene chloride (25 mL), an aqueous solution of sodium hydrogen carbonate/sodium carbonate (pH 9; 25 mL) and sodium hydrogen carbonate (solid) were added to the reaction mixture until pH 9. The organic phase was dried (magnesium sulfate) and evaporated in vacuo to afford 0.26 g of the title compound.

$^1$H-NMR (CDCl$_3$) (selected peaks for major rotamer) d 0.99 (s, 3H); 1.09 (s, 3H); 2.25 (d, 3H); 2.28 (s, 3H); 2.95 (s, 3H); 3.90 (s, 2H); 5.31 (dd, 1H); 5.83 (dd, 1H).

PDMS: m/z 550.6 (M+H)$^+$

HPLC: r$_t$=31.83 min (A1)

Example 15

(2E)-5-Amino-5-methylhex-2-enoic acid ((1R)-2-(biphenyl-4-yl)-1-(methyl-((1R)-1-(methylcarbamoyl)-2-phenylethyl)carbamoyl)ethyl)methylamide:

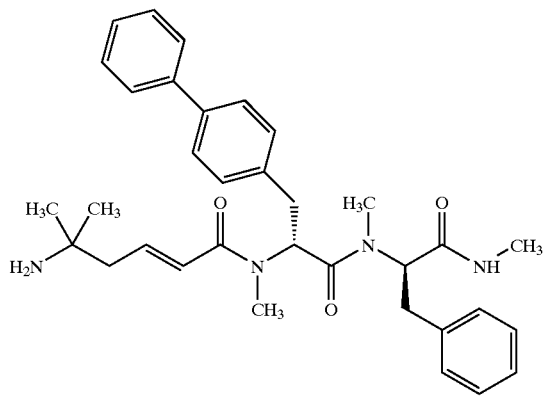

(2R)-3-(1,1'-Biphenyl-4-yl)-2-(N-tert-butoxycarbonyl-N-methylamino)propionic acid:

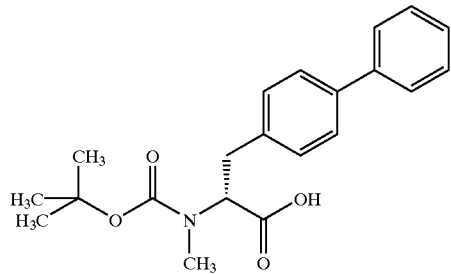

3-(1,1'-Biphenyl-4-yl)-2-tert-butoxycarbonylaminopropionic acid (5.0 g; 14.66 mmol) was dissolved in dry tetrahydrofuran (45 mL). Iodomethane (7.3 mL; 117.3 mmol) was added and the reaction mixture was cooled to 00 C. Sodium hydride (1.75 g; 44.0 mmol) was added and the reaction mixture was stirred for 5 days at room temperature. Ethyl acetate (50 mL) was added and water (20 mL) was added dropwise. The solvent was removed in vacuo and the residue was dissolved in an aqueous solution of sodium hydrogen carbonate (saturated; 50 mL) and washed with diethyl ether (30 mL). The aqueous phase was acidified to pH 3 using citric acid (5%) and extracted with ethyl acetate (3×50 mL). The organic phase was washed with an aqueous solution of sodium thiosulfate (5%; 75 mL) and dried (magnesium sulfate). The solvent was removed in vacuo to afford 3.85 g of (2R)-3-(1,1'-biphenyl-4-yl)-2-(N-tert-butoxycarbonyl-N-methylamino) propionic acid.

$^1$H NMR (200 MHz, CDCl$_3$) d (mixture of rotamers) 1.47 (s, 4.5H), 1.49 (s, 4.5H), 2.54 (s, 1.5H), 2.56 (s, 1.5H), 3.00–3.40 (bm, 1H), 3.45–3.91 (bm, 1H), 4.53–4.55 (m, 0.5H), 4.55–4.58 (m, 0.5H), 7.3–7.6 (m, 9H).

((1R)-2-(1,1'-Biphenyl-4-yl)-1-(methyl-((1R)-1-methylcarbamoyl-2-phenylethyl)-carbamoyl)ethyl)methylcarbamic acid tert-butylester:

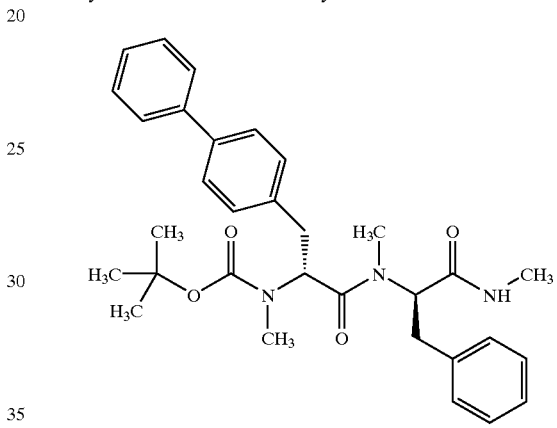

(2R)-3-(1,1'-Biphenyl-4-yl)-2-(N-tert-butoxycarbonyl-N-methylamino)propionic acid is (1.50 g; 4.23 mmol) was dissolved in methylene chloride (20 mL). 1-Hydroxy-7-azabenzotriazole (0.57 g; 4.23 mmol) and N-(3dimethylaminopropyl)-N'-ethylcarbodiimide hydrochloride (0.89 g; 4.65 mmol) were added and the reaction mixture was stirred for 15 min at room temperature. N-Methyl-2-methylamino-3-phenylpropionamide (0.81 g; 4.23 mmol) and diisopropylethylamine (0.73 mL; 4.23 mmol) were added and the reaction mixture was stirred for 12 hours at room temperature. Methylene chloride (50 mL) was added and the reaction mixture was washed with water (50 mL), an aqueous solution of sodium hydrogen carbonate (sat; 50 mL), an aqueous solution of sodium hydrogen sulfate (10%; 50 mL) and water (50 mL) and dried (magnesium sulfate). The solvent was removed in vacuo and the residue was chromatographed on silica (4×25 cm) using ethyl acetatelheptane (2:1) as eluent to afford 1.02 g of ((1R)-2-(1,1'-biphenyl-4-yl)-1-(methyl-((1R)-1-methylcarbamoyl-2-phenylethyl)carbamoyl)ethyl)methylcarbamic acid tert-butyl ester.

$^1$H-NMR (CDCl$_3$) (selected peaks for major rotamer) d: 1.15 (s, 6H); 1.31 and 1.34 (two s; 9H); 2.24 (d, 3H); 2.80 (s, 3H); 2.98 (s, 3H); 4.98 (m, 1H); 5.38 (m, 1H).

3-(11'-Biphenyl-4-yl)-N-methyl-2-methylamino-N-((1R)-1-methylcarbamoyl-2-phenylethyl)propionamide:

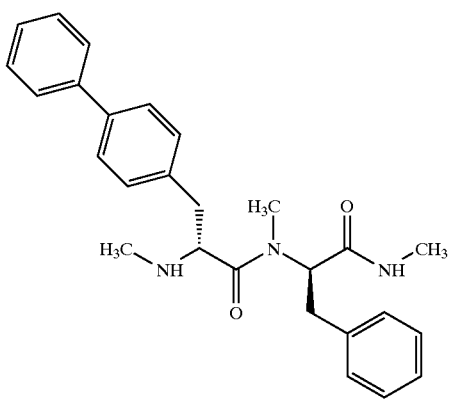

((1R)-2-(1,1'-Biphenyl-4-yl)-1-(methyl-((1R)-1-(methylcarbamoyl)-2-phenylethyl)-carbamoyl)ethyl) methyl-carbamic acid tert-butylester (1.0 g; 1.8 mmol) was dissolved in methylene chloride (4 mL). Trifluoroacetic acid (4 mL) was added and the reaction mixture was stirred for 15 min at room temperature. Methylene chloride (40 mL), an aqueous solution of sodium hydrogen carbonate/sodium carbonate (pH 9; 40 mL) and sodium hydrogen carbonate (solid) were added to the reaction mixture until pH 9. The organic phase was dried (magnesium sulfate) and the solvent was removed in vacuo to afford 0.76 g of (2R)-3-(1,1'-biphenyl-4-yl)-N-methyl-2-methylamino-N-((1R)-1-methylcarbamoyl-2-phenylethyl)propionamide.

$^1$H-NMR (CDCl$_3$) (selected peaks for major rotamer) d: 1.71 (s, 3H); 2.58 (s, 3H);
2.69 (d, 3H); 5.52 (dd, 2H).

(3E)-4-(((1R)-2-(1,1'-Biphenyl-4-yl)-1-(methyl-((1R)-1-methylcarbamoyl-2-phenylethyl)carbamoyl)ethyl)methyl-carbamoyl)-1,1-dimethylbut-3-enyl)carbamic acid tert-butylester:

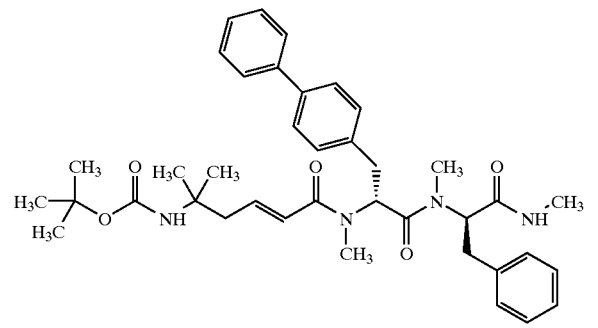

(2E)-5-(tert-Butyloxycarbonylamino)-5-methylhex-2-enoic acid (0.24 g; 0.98 mmol) was dissolved in methylene chloride (10 mL). 1-Hydroxy-7-azabenzotriazole (0.13 g; 0.98 mmol) and N-(3-dimethylaminopropyl)-N'-ethylcarbodiimide hydrochloride (0.2 g; 1.02 mmol) were added and the reaction mixture was stirred for 15 min at room temperature. (2R)-3-(1,1'-Biphenyl-4-yl)-N-methyl-2-methylamino-N-((1R)-1-methylcarbamoyl-2-phenylethyl) propionamide (0.38 g; 0.89 mmol) and diisopropylethylamine (0.17 mL; 0.98 mmol) were added and the reaction mixture was stirred for 12 hours at room temperature. Methylene chloride (50 mL) was added and the reaction mixture was washed with water (50 mL), an aqueous solution of sodium hydrogen sulfate (10%; 50 mL), an aqueous solution of sodium hydrogen carbonate/sodium carbonate (pH 9; 50 mL) and water (50 mL) and dried (magnesium sulfate). The solvent was removed in vacuo and the residue was chromatographed on silica (4×20 cm) using ethyl acetate/heptane (2:1) as eluent to afford 0.46 g of ((3E)-4-(((1R)-2-(1,1'-biphenyl-4-yl)-1-(methyl-((1R)-1-methylcarbamoyl-2-phenylethyl)-carbamoyl)ethyl) methylcarbamoyl)-1,1-dimethylbut-3-enyl)-carbamic acid tert-butylester.

$^1$H-NMR (CDCl$_3$) (selected peaks for major rotamer) d: 1.22 (s, 3H); 1.23 (s, 3H); 1.42 (s, 9H); 2.75 (d, 3H); 2.82 (s, 3H); 2.98 (s, 3H); 5.54 (dd, 1H); 5.82 (dd, 1H); 6.12 (d, J=17 Hz, 1H).

((3E)-4-(((1R)-2-(1, '-Biphenyl-4-yl)-1-(methyl-((1R)-1-methylcarbamoyl-2-phenylethyl)carbamoyl)ethyl)methyl-carbamoyl)-1,1-dimethylbut-3-enyl)carbamic acid tert-butylester (0.45 g; 0.69 mmol) was dissolved in methylene chloride (10 mL). Trifluoroacetic acid (10 mL) was added and the reaction mixture was stirrred for 5 min at room temperature. Methylene chloride (50 mL), an aqueous solution of sodium hydrogen carbonate/sodium carbonate (pH 9; 50 mL) and sodium hydrogen carbonate (solid) were added to the reaction mixture until pH 9. The organic phase was dried (magnesium sulfate) and evaporated in vacuo to afford 0.22 g of the title compound.

$^1$H-NMR (CDCl$_3$) (selected peaks for major rotamer) d: 1.18 (s, 6H); 2.75 (d, 3H); 3.5 2.78 (s, 3H); 2.97 (s, 3H); 5.45 (dd, 1H); 5.75 (dd, 1H); 6.08 (d, J=17 Hz, 1H).

ESMS: m/z 555.8 (M+H)$^+$

HPLC: $R_t$=34.45 min (Method A1).

Example 16
(2E)-5-Amino-3,5-dimethylhex-2-enoic acid N-methyl-N-((1R)-1-(N-methyl-N-((1R)-1-(methylcarbamoyl)-2-phenylethyl)carbamoyl)-2-(2-naphthyl)ethyl)amide:

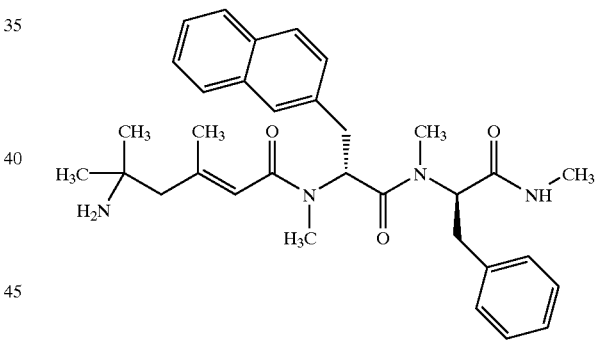

((3E)-1,1,3-Trimethyl-4-(methyl-((1R)-1-(methyl-((1R)-1-methyl carbamoyl-2-phenylethyl)carbamoyl)-2-(2-naphthyl) ethyl)carbamoyl)but-3-enyl)carbamic acid Tert butylester:

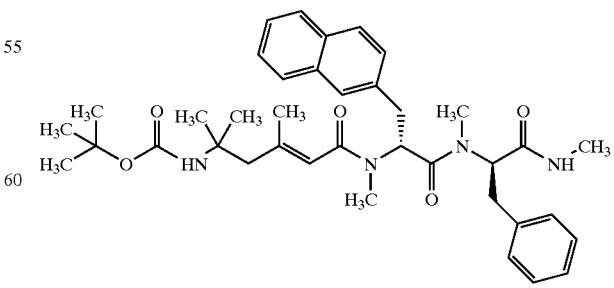

(2E)-5-tert-Butoxycarbonylamino-3,5-dimethylhex-2enoic acid (0.30 g; 1.17 mmol.) was dissolved in methylene chloride (10 mL). 1-Hydroxy-7-azabenzotriazol (0.16 g; 1.17 mmol) and N-(3-dimethylaminopropyl)-N'-ethylcarbodiimide hydrochloride (0.26 g; 1.28 mmol) were added and the reaction mixture was stirred for 15 min at room temperature.

N-Methyl-2-methylamino-N-((2R)-1t-(methylcarbamoyl)-2-phenylethyl)-3-(2-naphthyl) propionamide (0.47 g; 1.67 mmol) was dissolved in methylene chloride (10 mL) and added. Diisopropylethylamine (0.20 mL; 1.66 mmol ) was added and the reaction was stirred for 12 hours at room temperature. Methylene chloride (10 mL) was added and the reaction was washed with water (10 mL), an aqueous solution of sodium hydrogen sulfate (10%; 10 mL) and an aqueous solution of sodium hydrogen carbonate (pH 8; 10 mL) and dried (magnesium sulfate). The solvent was removed in vacuo and the residue was chromatographed on silica (3×30 cm) using ethyl acetate/methylene chloride (1:1) as eluent to afford 0.37 g of ((3E)-1,1,3-trimethyl-4-(methyl-((1R)-1-(methyl-((1R)-1-methylcarbamoyl-2-phenylethyl)carbamoyl)-2-(2-naphthyl)ethyl)carbamoyl)but-3-enyl)carbamic acid tert butylester.

$^1$H-NMR (CDCl$_3$) (selected peaks for major rotamer) d 1.16 (s, 3H); 1.17 (s; 3H); 1.42 (s, 9H); 1.68 (s, 3H); 2.75 (d, 3H); 2.76 (s, 3H); 2.95 (s, 3H); 5.21 (dd, 1H); 5.51 (s, 1H); 5.59 (dd, 1H).

((3E)-1,1,3-Trimethyl-4-(methyl-((1R)-1-(methyl-((1R)-1-methylcarbamoyl-2-phenylethyl)carbamoyl)-2-(2-naphthyl) ethyl)carbamoyl)but-3-enyl)carbamic acid tert butylester (0.37 g ; 0.56 mmol ) was dissolved in methylene chloride (2 mL) and trifluoroacetic acid (2 mL) was added. The reaction mixture was stirred for 5 min at room temperature. Methylene chloride (2 mL), water (5mL) and sodium hydrogen carbonate (solid) were added to the reaction until pH=9. The aqueous phase was extracted with methylene chloride (3×10 mL) and the combined organic phases were dried (magnesium sulfate). The solvent was removed in vacuo to afford 0.17 g of the title compound.

$^1$H-NMR (CDCl$_3$) (selected peaks for major rotamer) d: 1.18 (s, 3H); 1.19 (s, 3H); 1.67 (s, 3H); 2.75 (d, 3H); 2.76 (s, 3H); 2.95 (s, 3H); 5.52 (dd, 1H); 5.62 (s, 1H); 5.86 (dd, 1H).

HPLC: R$_t$=31.78 min (Method A1)

PDMS: m/z 542.8 (M+H)$^+$

Example 17

2-((2R)-2-(N-((2R)-2-(N-((2E)-5-Amino-5-methylhex-2-enoyl)-N-methylamino)-3-(2-naphthyl)propionyl)-N-methylamino)-3-phenylpropionylamino)-1,1-dimethylethyl acetate:

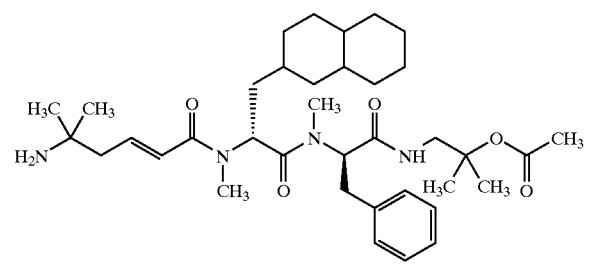

Ethyl 2-(tert-butoxycarbonylamino)acetate

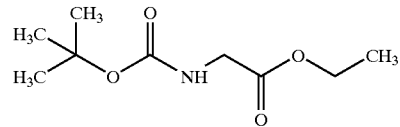

(tert-Butoxycarbonylamino)acetic acid (4.00 g, 22.8 mmol) was dissolved in dichloromethane (8 ml). Ethanol (1.60 ml, 27.40 mmol) and 4-dimethylaminopyridine (0.31 g, 25.1 mmol) were added. The solution was cooled to 0° C. N-(3-Dimethylaminopropyl)-N'-ethylcarbodiimide hydrochloride (4.81 g, 25.11 mmol) was added. The solution was stirred for 16 h, while warming up to room temperature. It was diluted with ethyl acetate (150 ml) and 10% aqueous sodium hydrogen sulfate solution (100 ml). The phases were separated. The aqueous phase was extracted with ethyl acetate (4×50 ml). The combined organic layers were washed with saturated sodium hydrogen carbonate solution (150 ml) and dried over magnesium sulfate. The solvent was removed in vacuo. The crude product was purified by flash chromatography on silica (100 g), using ethyl acetate/heptane (1:4) as eluent, to give 4.25 g of ethyl 2-(tert-butoxycarbonylamino)acetate.

$^1$H-NMR (CDCl$_3$): d 1.30 (t, 3H); 1.47 (s, 9H); 3.90 (d, 2H); 4.21 (q, 2H); 5.06 (br, H).

2-Hydroxy-2-methylpropylcarbamic acid tert-butyl ester

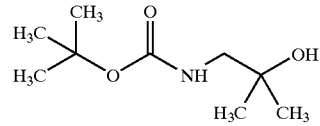

Ethyl 2-(tert-butoxycarbonylamino)acetate (4.17 g, 20.52 mmol) was dissolved in tetrahydrofuran (60 ml). The solution was cooled to −78° C. A 22% solution of methyl magnesium chloride in toluene/tetrahydrofuran (purchased from Chemmetallgesellschaft, 27.1 ml, 67.72 mmol) was added dropwise. The reaction mixture was stirred for 1.5 h at −78° C. and then warmed to room temperature. A 10% aqueous solution of ammonium chloride (200 ml) was added dropwise. The phases were separated. The aqueous phase was extracted with ethyl acetate (3×100 ml). The combined organic layers were washed with saturated sodium hydrogen carbonate solution (200 ml) and dried over magnesium sulfate. The solvent was removed in vacuo. The crude product was purified by flash chromatography on silica (110 g), using ethyl acetate/heptane (1:1) as eluent, to give 1.31 g of 2-hydroxy-2-methylpropylcarbamic acid tert-butyl ester.

$^1$H-NMR (CDCl$_3$): d 1.21 (s, 6H); 1.45 (s, 9H); 1.34 (d, 2H); 5.00 (br, 1H).

2-(tert-Butoxycarbonylamino)-1,1-dimethylethyl acetate

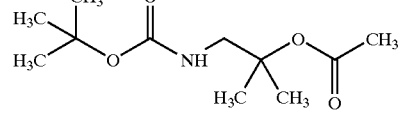

2-Hydroxy-2-methylpropylcarbamic acid tert-butylester (510 mg, 2.69 mmol) was dissolved in dichloromethane (7 ml). The solution was cooled to 0° C. Ethyldiisopropylamine (0.70 ml, 4.04 mmol), 4-dimethylaminopyridine (33 mg, 0.27 mmol), and acetic acid anhydride (0.33 ml, 3.50 mmol) were added successively. The reaction mixture was stirred for 16 h, while slowly warming up to room temperature. It was diluted with ethyl acetate (30 ml) and extracted with 1N hydrochloric acid (30 ml). The aqueous phase was extracted with ethyl acetate (2×20 ml). The combined organic layers were washed with saturated sodium hydrogen carbonate solution (50 ml) and dried over magnesium sulfate. The solvent was removed in vacuo. The crude product was purified by flash chromatography on silica (100 g), using ethyl acetatelheptane (1:2) as eluent, to give 550 mg of 2-(tert-butoxycarbonylamino)-1,1-dimethylethyl acetate.

$^1$H-NMR (CDCl$_3$): d 1.45 (s, 9H); 1.46 (s, 6H); 2.00 (s, 3H); 3.35 (d, 2H); 4.96 (br, 1H).

2-Amino-1,1-dimethylethyl acetate hydrochloride

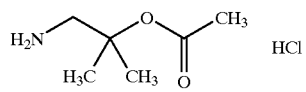

2-(tert-Butoxycarbonylamino)-1,1-dimethylethyl acetate (508 mg, 2.2 mmol) was dissolved in ethyl acetate (6 ml). 3 M hydrogen chloride in ethyl acetate (4 ml, 12 mmol) was added. The reaction mixture was stirred for 20 h at room temperature. The precipitation was filltered off and washed with diethyl ether (50 ml). It was dried in vacuo to give 246 mg of 2-amino-1,1-dimethylethyl acetate hydrochloride.

$^1$H-NMR (DMSO d$_6$): d 1.45 (s, 6H); 2.00 (s, 3H); 3.09 (s, 2H); 8.25 (br, 3H).

2-((2R)-2-(N-(tert-Butoxycarbonyl)-N-methylamino)-3-phenylpropionylamino)-1,1-dimethylethyl acetate

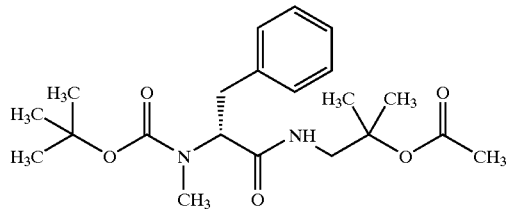

(2R)-2-(N-(tert-Butoxycarbonyl)-N-methylamino)-3-phenylpropionic acid (391 mg, 1.4 mmol) was dissolved in N,N-dimethylformamide (6 ml). 1-Hydroxybenzotriazole hydrate (189 mg, 1.4 mmol) and N-(3-dimethylaminopropyl)-N'-ethylcarbodiimide hydrochloride were added. The reaction mixture was stirred for 10 min at room temperature. 2-Amino-1,1-dimethylethyl acetate hydrochloride (237 mg, 1.4 mmol) was added as a solid. Ethyldiisopropylamine (0.53 ml, 3.1 mmol) was added. The reaction mixture was stirred for 20 h at room temperature. It was diluted with ethyl acetate (200 ml) and washed with i N hydrochloric acid. The aqueous phase was extracted with ethyl acetate (2×50 ml). The combined organic layers were washed with saturated sodium hydrogen carbonate solution (100 ml) and dried over magnesium sulfate. The solvent was removed in vacuo. The crude product was purified by flash chromatography on silica (80 g), using ethyl acetate/heptane (1:1) as eluent, to give 442 mg of 2-((2R)-2-(N-(tert-butoxycarbonyl)-N-methylamino)-3-phenylpropionylamino)-1,1-dimethylethyl acetate.

$^1$H-NMR (CDCl$_3$): d 1.30 and 1.35 (both s, together 6H); 1.41 (s, 9H); 1.98 (s, 3H); 2.70–3.05 (m, 4H); 3.30–3.65 (m, 3H); 4.75–4.95 (m, 1H); 6.65 (br, 1H); 7.15–7.35 (m, 5H). 1,1-Dimethyl-2-((2R)-2-methylamino-3-phenylpropionylamino)-ethyl acetate:

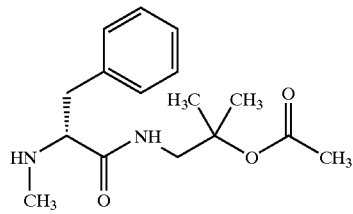

2-((2R)-2-(N-(tert-butoxycarbonyl)-N-methylamino)-3-phenylpropionylamino)-1,1-dimethylethyl acetate (426 mg, 1.1 mmol) was dissolved in dichloromethane (2 ml) and cooled to 0° C. Trifluoroacetic acid (2 ml) was added and the reaction mixture was stirred for 15 min at 0° C. The solvent was removed in vacuo at 20° C. The residue was dissolved in dichloromethane (50 ml) and the solvent was removed in vacuo. This latter procedure was repeated two times. The crude product was purified by flash chromatography on silica (45 g), using dichloromethanelmethanol/25% aqueous ammonia (100:10:1) as eluent, to give 312 mg of 1,1-dimethyl-2((2R)-2-methylamino-3-phenylpropionylamino) ethyl acetate.

$^1$H-NMR (CDCl$_3$): d 1.43 (s, 6H); 2.00 (s, 3H); 2.30 (s, 3H); 2.67 (dd, 1H); 3.24 (m, 2H); 3.53 (ABX, 2H); 7.15–7.45 (m, 5H); 7.61 (br, 1H).

2-((2R)-2-(N-((2R)-2-(N-tert-Butoxycarbonyl-N-methylamino)-3-(2-naphthyl)-propionyl)-N-methylamino)-3-phenylpropionylamino)-1,1-dimethylethyl acetate:

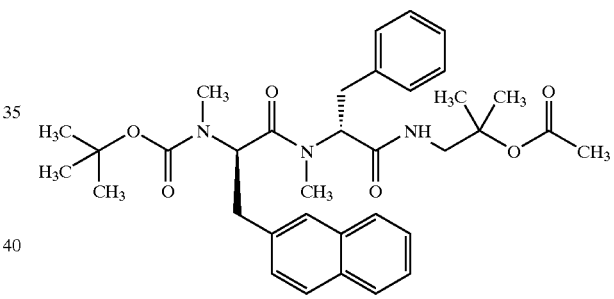

(2R)-2-(N-(tert-Butoxycarbonyl)-N-methylamino)-3-(2-naphthyl)propionic acid (373 mg, 1.13 mmol) was dissolved in N,N-dimethylformamide (2 ml) and dichloromethane (2 ml). 1-Hydroxy-7-azabenzotriazole (153 mg, 1.13 mmol) was added. The solution was cooled to 0° C. N-(3-Dimethylaminopropyl)-N'-ethyl-carbodiimide hydrochloride (217 mg, 1.13 mmol) was added. The reaction mixture was stirred for 10 min at 0° C. 1,1-Dimethyl-2-((2R)-2-methylamino-3-phenylpropionylamino)-ethyl acetate (301 mg, 1.03 mmol) was dissolved in is dichloromethane (2 ml) and added. Ethyldiisopropylamine (0.18 ml, 1.03 mmol) was added. The reaction mixture was stirred for 20 h, while it was warming up to room temperature. It was diluted with ethyl acetate (100 ml) and washed with 1 N hydrochloric acid. The aqueous phase was extracted with ethyl acetate (3×30 ml). The combined organic layers were washed with saturated sodium hydrogen carbonate solution (100 ml) and dried over magnesium sulfate. The solvent was removed in vacuo. The crude product was purified by flash chromatography on silica (85 g), using ethyl acetatelheptane (1:1) as eluent, to give 547 mg of 2-((2R)-2-(N-((2R)-2(N-tert-butoxycarbonyl-N-methylamino)-3-(2-naphthyl)propionyl)-N-methylamino)-3-phenylpropionylamino)-1,1-dimethyl ethyl acetate.

¹H-NMR (CDCl₃, selected values): d 0.98 and 1.23 (both s, together 9H); 1.95 and 2.03 (both s, together 3H); 2.18 and 2.25 (both s, together 3H); 5.05 and 5.35–5.55 (both m, together 2H).

1,1-Dimethyl-2-((2R)-2-(N-methyl-N-((2R)-2-methylamino-3-(2-naphthyl)propion-yl)amino)-3-phenylpropionylamino)ethyl acetate:

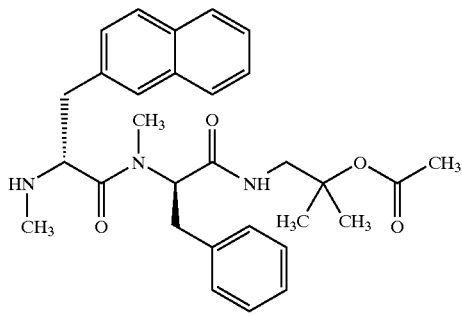

2-((2R)-2-(N-((2R)-2-(N-tert-Butoxycarbonyl-N-methylamino)-3-(2-naphthyl)-propionyl)-N-methylamino)-3-phenylpropionylamino)-1,1-dimethylethyl acetate (511 mg, 0.85 mmol) was dissolved in dichloromethane (2 ml) and cooled to 0° C. Trifluoroacetic acid (2 ml) was added, and the solution was stirred for 15 min at 0° C. The solvents were removed in vacuo without warming. The residue was dissolved in dichloromethane (50 ml), and the solvent was removed in vacuo. The latter procedure was repeated two times. The crude product was purified by flash chromatogrpahy on silica (30 g), using dichloromethane/methanol/25% aqueous ammonia (100:10:1) as eluent, to give 160 mg of 1,1dimethyl-2-((2R)-2-(N-methyl-N-((2R)-2-methylamino-3-(2-naphthyl)propionyl)amino)-3-phenylpropionylamino)ethyl acetate.

¹H-NMR (CDCl₃, selected values): d 0.82 and 0.90 (s and m, together 6H); 1.86 and 1.91 (both s, together 3H); 2.01 and 2.35 (both s, together 3H); 2.75 and 2.95 (both s, together 3H); 4.60 and 5.50 (both dd, together 1H).

2-((2R)-2-(N-((2R)-2-(N-((2E)-5-(tert-Butoxycarbonylamino)-5-methylhex-2-enoyl)-N-methylamino)-3-(2-naphthyl)propionyl)-N-methylamino)-3-phenylpropionylamino)-1,1-dimethylethyl acetate:

2-((2R)-2-(N-methyl-N-((2R)-2-methylamino-3-(2-naphthyl)propionyl)amino)-3-phenylpropionylamino)ethyl acetate (152 mg, 0.30 mmol) in dichloromethane (2 ml) and ethyldiisopropylamine (0.05 ml, 0.30 mmol) were added successively. The solution was stirred for 16 h, while warming up to room temperature. It was diluted with ethyl acetate (150 ml), washed with 1N hydrochloric acid (100 ml) and saturated sodium hydrogen carbonate solution, and dried over magnesium sulfate. The solvent was removed in vacuo. The crude product was purified by flash chromatography on silica (40 g), using ethyl acetate/heptane (first 1:1 (250 ml), then 2:1) to give 221 mg of 2-((2R)-2-(N-((2R)-2-(N-((2E)-5-(tert-butoxycarbonylamino)-5-methylhex-2-enoyl)-N-methylamino)-3-(2-naphthyl)propionyl)-N-methylamino)-3-phenylpropionylamino)-1,1-dimethylethyl acetate.

¹H-NMR (CDCl₃, selected values): d 5.25, 5.45, 5.60, and 5.90 (all dd, together 2 H); 5.92–6.07 (m, 1H); 6.60–6.85 (m, 1H).

2-((2R)-2-(N-((2R)-2-(N-((2E)-5-(tert-Butoxycarbonylamino)-5-methylhex-2-enoyl)-N-methylamino)-3-(2-naphthyl)propionyl)-N-methylamino)-3-phenylpropionylamino)-1,1-dimethylethyl acetate (199 mg, 0.27 mmol) was dissolved in dichloromethane (2 ml). The solution was cooled to 0° C. Trifluoroacetic acid (2 ml) was added. The solution was stirred for 15 min at 0° C. The solvent was removed in vacuo at 20° C. The residue was dissolved in dichloromethane (50 ml) and the solvent was removed in vacuo. The latter procedure was repeated two times. The crude product was purified by flash chromatography on silica (25 g), using dichloromethane/methanol/25% aqueous ammonia (100:10:1) as eluent, to give 75 mg of the title compound.

¹H-NMR (CDCl₃, selected values): d 0.95, 0.96, 0.98, 0.99, 1.16, 1.20, 1.35, and 1.40 (all s, together 12H); 1.90 and 1.95 (both s, together 3H); 2.83 and 2.84 (both s, together 3H); 2.98 and 3.03 (both s, together 3H); 5.25, 5.45, 5.57, and 5.90 (all dd, together 2H); 6.95–6.10 (m, 1H); 6.65–6.90 (m, 1H).

HPLC: (A1) R$_t$=36.15 min.

MS: 630±1 [M+1]⁺

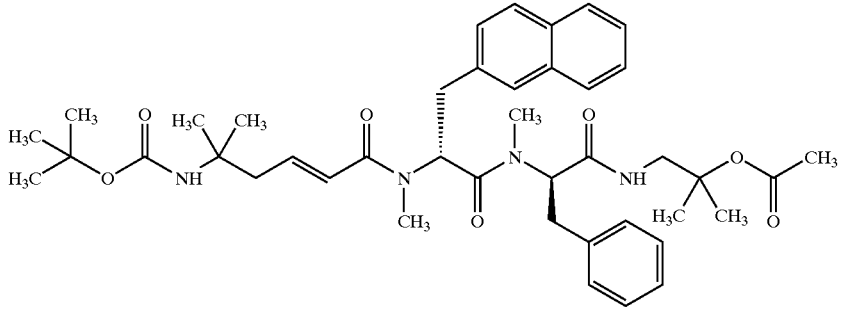

(2E)-5-(tert-Butoxycarbonylamino)-5-methylhex-2-enoic acid (81 mg, 0.33 mmol) was dissolved in N,N-dimethylformamide (2 ml) and dichloromethane (2 ml). 1-Hydroxy-7-azabenzotriazole (45 mg, 0.33 mmol) was added. The solution was cooled to 0° C. N-(3-Dimethylaminopropyl)-N'-ethylcarbodiimide hydrochloride (69 mg, 0.36 mmol) was added. A solution of 1,1-dimethyl-

Example 18
(2E)-5-Amino-2-benzyl-5-methylhex-2-enoic acid N-methyl-N-((1R)-1-(N-methyl-N-((1R)-1-methylcarbamoyl-2-phenylethyl)carbamoyl)-2-(2-naphthyl)ethyl)amide:

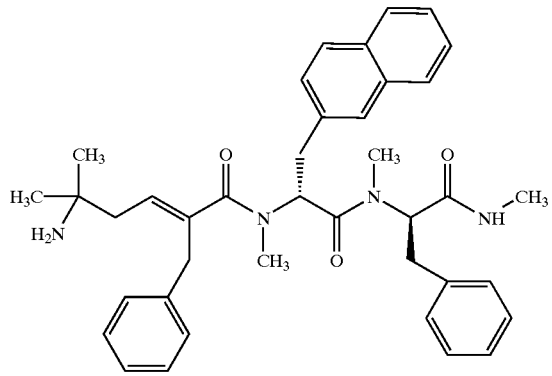

(2E)-2-Benzyl-5-(tert butoxycarbonylamino)-5-methylhex-2-enoic acid methyl-(1-(methyl-(1-methylcarbamoyl-2-phenylethyl)carbamoyl)-2-(2-naphthyl)ethyl amide:

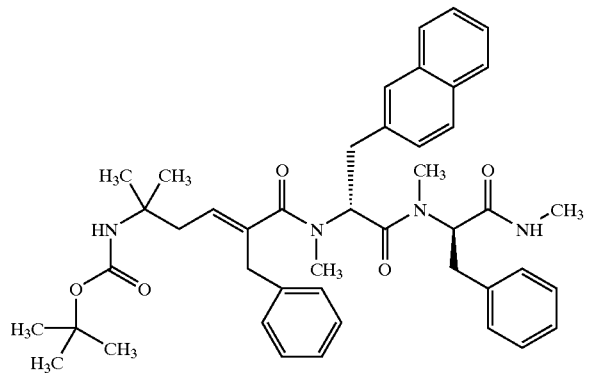

(2E)-2-Benzyl-5-tert-butoxycarbonylamino-5-methylhex-2-enoic acid (0.125 g 0.38 mmol) was dissolved in methylene chloride (10 mL). 1-Hydroxy-7-azabenzotriazole (0.05 g; 0.37 mmol) and N-(3-dimethylaminopropyl)-N'-ethylcarbodiimide hydrochloride (0.08 g; 0.41 mmol) were added and the reaction mixture was stirred for 15 min at room temperature. (2R)-N-Methyl-2-methylamino-N-((1R)-1-methylcarbamoyl-2-phenylethyl)-3-(2-naphthyl))propionamide (0.151 g; 0.37 mmol) is was dissolved in methylene chloride (5 mL) and added. Diisopropylethylamine (0.064 mL; 0.37 mmol) was added. The reaction mixture was stirred for 12 hours at room temperature. Methylene chloride (5 mL) was added. The reaction mixture was washed with water (10 mL), an aqueous solution of sodium hydrogen sulfate (10%; 10 mL), and an aqueous solution of sodium hydrogen carbonate (pH 8; 10 mL) and dried (magnesium sulfate). The solvent was removed in vacuo and the residue was chromatographed on silica (2×20 cm) using ethylacetat/methylene chloride 1:1 as eluent to afford 0.08 g of (2E)-2-Benzyl-5-(tert-butoxycarbonylamino)-5-methylhex-2-enoic acidmethyl-(1-(methyl-(1-methylcarbamoyl-2-phenylethyl)-carbamoyl)-2-(2-naphthyl)ethyl amide.

$^1$H-NMR: (CDCl$_3$)(selected peaks for major rotamer) d 0.96 (s, 3H); 1.11 (s, 3H); 1.38 (s, 9H); 2.65 (d, 3H); 2.71 (s, 3H); 2.99 (s, 3H); 4.80 (m, 1H); 5.30 (m, 3H); 5.80 (t, 1H).

(2E)-2-Benzyl-5-(tert butoxycarbonylamino)-5-methylhex-2-enoic acid methyl-(1-(methyl-(1-methylcarbamoyl-2-phenylethyl)carbamoyl)-2-(2-napthyl)ethyl amide (0.10 g; 0.14 mmol) was dissolved in methylene chloride (2 mL) and trifluoroacetic acid (1 mL) was added. The reaction mixture was stirred for 5 min at room temperature. Methylene chloride (3 mL) and sodium hydrogen carbonate (solid) were added until pH 8. The aqueous phase was extracted with methylene chloride (3×10 mL) and the combined organic phases were dried (magnesium sulfate). The solvent was removed in vacuo to afford 0.09 g of the title compound.

$^1$H-NMR: (CDCl$_3$) (selected peaks for major rotamer) d 0.89 (s, 3H); 0.92 (s, 3H); 2.38 (d, 3H); 2.45 (s, 3H); 2.95 (s, 3H); 5.21 (m, 1H); 5.45 (m, 1H).

ESMS : m/z 618.2 (M+H)$^+$

HPLC: R$_t$=37.53 min (Method A1)

Example 19
(2E)-5-Amino-5-methylhex-2-enoic acid N-methyl-N-((1R)-1-(N-methyl-N-((1R)-1-(methylcarbamoyl)-2-phenylethyl)-carbamoyl)-2-(1-naphthyl)ethyl)amide:

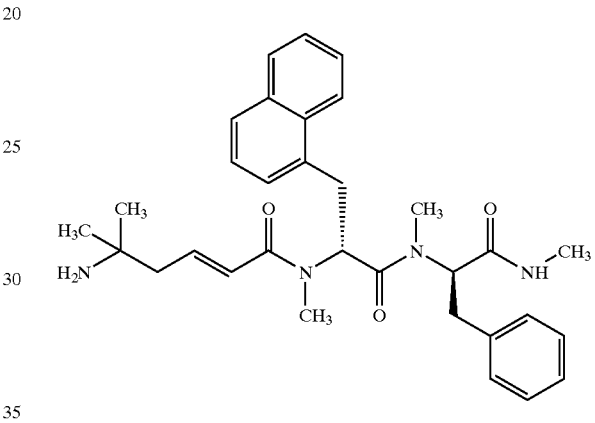

Methyl-((1R)-1-(methyl-((1R)-1-methylcarbamoyl-2-phenylethyl)carbamoyl)-2-(1-naphthyl)ethyl)carbamic acid tert-butylester:

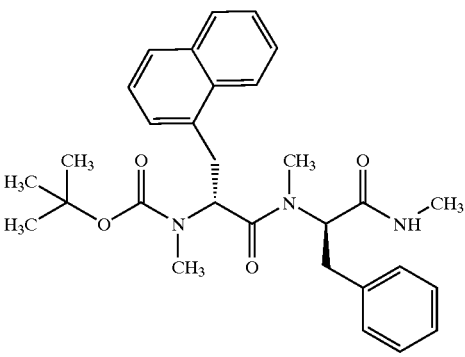

(2R)-2-(tert-Butoxycarbonylmethylamino)-3-(1-naphthyl)-propionic acid (2.00 g; 6.07 mmol) was dissolved in methylene chloride (10 mL). 1-Hydroxy-7-azabenzotriazole (0.83 g ; 6.07 mmol) and N-(3-dimethylaminopropyl)-N'-ethylcarbodiimide hydrochloride (1.28 g; 6.68 mmol) were added. The reaction mixture was stirred for 15 min at room temperature. (2R)N-Methyl-2-methylamino-3-phenyl-propionamide (1.17 g; 6.07 mmol) was dissolved in methylene chloride (10 mL) and added. Diisopropylethylamine (1.04 mL; 6.07 mmol) was added. The reaction mixture was stirred for 12 hours at room temperature. Methylene chloride (20 mL) was added. The reaction mixture was washed with water (20 mL), an aqueous solution of sodium hydrogen sulfate (10%; 20 mL), and an aqueous solution of sodium hydrogen carbonate (saturated 20 mL) and dried (magnesium sulfate). The solvent was removed in vacuo and the residue was chromatographed on silica (3×30 cm) using ethyl acetat/methylene chloride 1:1 as eluent to afford 0.77 g of methyl-((1R)-1-(methyl-((1R)-1-methylcarbamoyl-2-phenylethyl)carbamoyl)-2-(1-naphthyl)ethyl)carbamic acid tert-butylester.

$^1$H-NMR: (CDCl$_3$) (selected peaks for major rotamer) d 1.39 (s, 9H); 2.30 (s, 3H); 2.75 (s, 3H); 3.68 (dd, 1H); 5.35 (dd, 1H).

(2R)-N-Methyl-2-methylamino-N-((1R)-1-methylcarbamoyl-2-phenylethyl)-3-(1-naphthyl)propionamide:

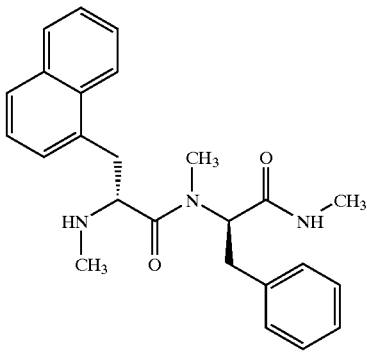

Methyl-((1R)-1-(methyl-((1R)-1-methylcarbamoyl-2-phenylethyl)carbamoyl)-2-(1-naphthyl)ethyl)carbamic acid tert butyl ester (0.77 g; 1.52 mmol) was dissolved in methylene chloride (4 mL) and trifluoroacetic acid (4 mL) was added. The reaction mixture was stirred for 30 min at room temperature. Water (5 mL) and methylene chloride (5 mL) were added. An aqueous solution of sodium hydrogen carbonate was added until pH 8. The organic phase was extracted with methylene chloride (3×10 mL) and dried (magnesium sulfate). The solvent was removed in vacuo to afford 0.64 g of (2R)-N-methyl-2-methylamino-N-((1R)-1-methylcarbamoyl-2-phenylethyl)-3-(1-naphthyl)propionamide.

$^1$H-NMR: (CDCl$_3$)(selected peaks for major rotamer) d 1.69 (s, 3H); 2.05 (s, 3H); 2.57 (d, 3H); 3.91 (dd, 1H); 5.45 (dd, 1H).

((3E)-1,1-Dimethyl-4-(N-methyl-N-((1R)-1-(N-methyl-N-((1R)-1-(methylcarbamoyl)-2-phenylethyl)carbamoyl)-2-(1-naphthyl)-ethyl)carbamoyl)but-3-enyl)carbamic acid tert butylester:

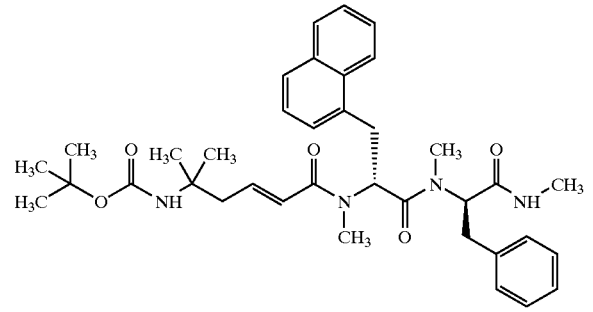

(2E)-5-(tert-Butoxycarbonylamino)-5-methylhex-2-enoic acid (0. 19 g ;0.80 mmol) was dissolved in methylene chloride (1 0 mL). 1-Hydroxy-7-azabenzotriazole (0.108 is g; 0.795 mmol) and N-(3-dimethylaminopropyl)-N'-ethylcarbodiimide hydrochloride (0.17 g; 0.87 mmol) were added. The reaction mixture was stirred for 15 min at room temperature. (2R)-N-Methyl-2-methylamino-N-((1R)-1-methylcarbamoyl-2-phenylethyl)-3(1-naphthyl)propionamide (0.32 g; 0.80 mmol) was dissolved in methylene chloride (10 mL) and added. Diisopropylethylamine (0.14 mL; 0.80 mmol) was added. The reaction mixture was stirred for 12 hours at room temperature. Methylene chloride (5 mL) was added. The reaction mixture was washed with water (30 mL), an aqueous solution of sodium hydrogen sulfate (10%; 30 mL), an aqueous solution of sodium hydrogen carbonate (saturated; 30 mL) and dried (magnesium sulfate). The solvent was removed in vacuo and the residue was chromatographed on silica (3×30 cm) using ethylacetat/methylene chloride 1:1 as eluent to afford 0.26 g of ((3E)-1,1-dimethyl-4-(N-methyl-N-((1R)-1-(N-methyl-N-((1R)-1-(methylcarbamoyl)-2-phenylethyl)carbamoyl)-2-(1-naphthyl)ethyl)carbamoyl)but-3-enyl)carbamic acid tert butylester.

$^1$H-NMR: (CDCl$_3$)(selected peaks for major rotamer) d 1.31 (s, 3H); 1.32 (s, 3H); 1.48 (s, 9H); 2.45 (d, 3H); 2.65 (s, 3H); 2.92 (s, 3H); 5.22 (dd, 1H); 6.03 (dd, 1H); 6.14(d, 1H).

((3E)-1,1-Dimethyl-4-(N-methyl-N-((1R)-1-(N-methyl-N-((1R)-1-(methylcarbamoyl)-2-phenylethyl)carbamoyl)-2-(1-naphthyl)ethyl)carbamoyl)but-3-enyl)carbamic acid tert butylester (0.25 g; 0.40 mmol) was dissolved in methylene chloride (3 mL) and trifluoroacetic acid (2 mL) was added. The reaction mixture was stirred for 5 min at room temperature. Methylene chloride (5 mL) and solid sodium hydrogen carbonate were added until pH 8. The reaction mixture was washed with methylene chloride (3×1 0 mL). The combined organic phases were dried (magnesium sulfate) and evaporated in vacuo to afford 0.21 g of the title compound.

$^1$H-NMR: (CCCl$_3$) (selected peaks for major rotamer) d 1.22 (s, 3H); 1.23 (s, 3H); 2.82 (d, 3H); 2.92 (s, 3H); 3.08 (s, 3H); 5.22 (dd, 1H); 5.92 (dd, 1H); 6.12 (d, 1H).

ESMS: m/z 529.2 (M+H)$^+$

HPLC: R$_t$=30.90 ml (Method A1)

Example 20

(2R)-2-(N-((2-Amino-2-methylpropoxy)acetyl)-N-methylamino)-N-methyl-N-((1R)-1-methylcarbamoyl-2-phenylethyl)-3-(1-naphthyl)propionamide:

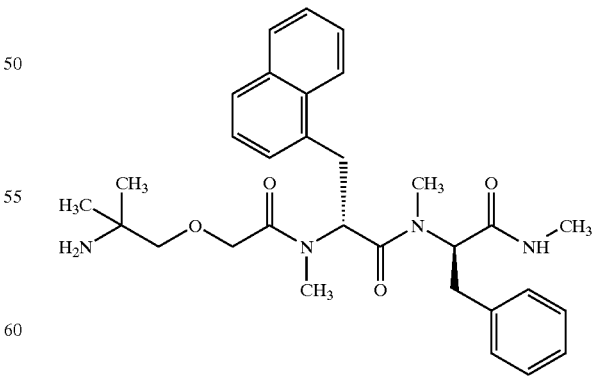

(1,1-Dimethyl-2-((N-methyl-N-((1R)-1-(N-methyl-N-((1R)-1-(methylcarbamoyl)-2-phenylethyl)carbamoyl)-2-(1-naphthyl)-ethyl)carbamoyl)methoxy)ethyl)carbamic acid tert butylester:

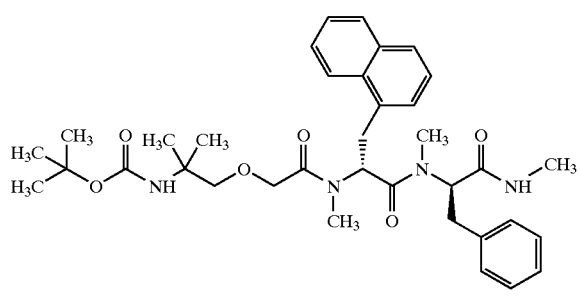

(2-tert-Butoxycarbonylamino-2-methylpropoxy)acetic acid (0.14 g; 0.54 mmol)(prepared as in example 33) was dissolved in methylene chloride (1 0 mL). 1-Hydroxy-7-azabenzotriazole (0.07 g; 0.54 mmol) and N-(3-dimethylaminopropyl)-N'-ethylcarbodiimide hydrochloride were added and the reaction mixture was stirred for 15 min at room temperature. (2R)-N-Methyl-2-methylamino-N-((1R)-1-methylcarbamoyl-2-phenylethyl)-3-(1-naphthyl) propionamide (0.21 ; 0.54 mmol) was dissolved in methylene chloride (10 mL) and added. The reaction mixture was stirred for 12 hours at room temperature. Methylene chloride (10 mL) was added. The reaction mixture was washed with water (30 mL), an aqueous solution of sodium hydrogen sulfate (10%; 20 mL) and an aqueous solution of sodium hydrogen carbonate (saturated; 20 mL) and dried (magnesium sulfate). The solvent was removed in vacuo and the residue was chromatographed on silica (2×20 cm) using methylene chloride/ethyl acetate (1:1) as eluent to afford 0.27 g of (1,1-dimethyl-2-((N-methyl-N-((1R)-1-(N-methyl-N-((1R)-1-(methylcarbamoyl)-2-phenylethyl)carbamoyl)-2-(1-naphthyl)ethyl)carbamoyl)methoxy)ethyl) carbamic acid tert butylester.

$^1$H-NMR: (CDCl$_3$) (selected peaks for major rotamer) d 1.39 (s, 3H); 1.40 (s, 3H); 1.45 (s, 9H); 2.52 (s, 3H); 2.71 (d, 3H); 2.98 (s, 3H); 5.27 (dd, 1H); 5.95 (dd, 1H).

(1,1-Dimethyl-2-((N-methyl-N-((1R)-1-(N-methyl-N-((1R)-1-(methylcarbamoyl)-2-phenylethyl)carbamoyl)-2-(1-naphthyl)-ethyl)carbamoyl)methoxy)ethyl)carbamic acid tert-butylester (0.26 g; 0.41 mmol) was dissolved in methylene chloride (3 mL) is and trifluoroacetic acid (2 mL) was added. The reaction mixture was stirred for 5 min at room temperature. Methylene chloride (5 mL), an aqueous solution of sodium hydrogen carbonate (saturated) and sodium hydrogen carbonate (solid) were added until pH 8. The aqueous phase was extrated with methylene chloride (3×15 mL) and the combined organic layers were dried (magnesium sulfate). The solvent was removed in vacuo to afford 0.25 g of the title compound.

$^1$H-NMR: (CDCl$_3$) (selected peaks for major rotamer) d 1.18 (s, 3H); 1.23 (s, 3H); 2.48 (s, 3H); 2.53 (s, 3H); 2.99 (s, 3H); 4.54 (dd, 1H); 5.25 (dd, 1H).

ESMS: m/z 533.2 (M+H)$^+$

HPLC: R$_t$=30.68 min (Method A1)

Example 21
(2E)-5-Amino-5-methylhex-2-enoic acid-((1R)-2-(benzo[b] thiophen-3-yl)-1-(methyl-((1R)-1-methylcarbamoyl-2-phenylethyl)carbamoyl)ethyl)-methylamide:

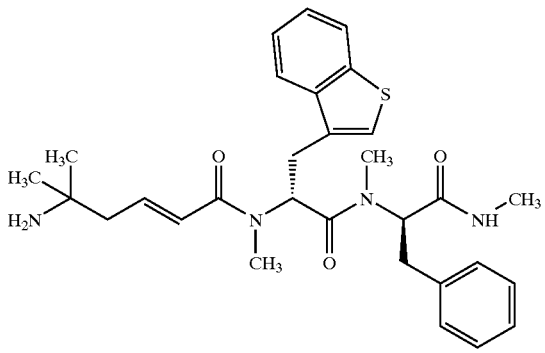

(2R)-3-(Benzo[b]thiophen-3-yl)-2-(tert-butoxycarbonylmethylamino)propionic acid

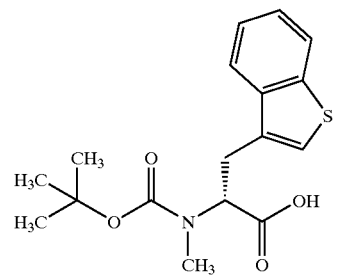

(2R)-3-(Benzo[b]thiophen-3-yl)-2-tert-butoxycarbonylamino-propionic acid (2.65 g; 8.25 mmol) was dissolved in dry tetrahydrofuran. Methyl iodide was added and the reaction mixture was cooled to 0° C. Sodium hydride (60% in mineral oil, 0.80 g, 24.8 mmol) was added. The reaction mixture was stirred for 48 hours at room temperature. Ethyl acetate (25 mL) and water (10 mL) were added dropwise. The solvent was removed in vacuo and the residue was dissolved in ether (15 mL) and water (15 mL). The organic phase was washed with an aqueous solution of sodium hydrogen carbonate (saturated; 20 mL). To the aqueous phase was added citric acid (5%) until pH 3 and extracted with ethyl acetate (4×20 mL). The combined is organic phases were washed with water (2×30 mL), an aqueous solution of sodium thiosulfate (5%; 30 mL) and water (30 mL) and dried (magnesium sulfate). The solvent was removed in vacuo and the residue was dissolved in ether (10 mL). Dicyclohexylamine (5 mL) was added. The precipitated crystals were filtered off, washed with ether (2×10 mL) and dissolved in water (30 mL). An aqueous solution of sodium hydrogen sulfate (10%; 20 mL) and ethyl acetate (40 mL) were added. The aqueous phase was extrated with ethylacetate (4×30 mL) and dried (magnesium sulfate). The solvent was removed in vacuo to afford 3.75 g of (2R)-3-(benzo[b]thiophen-3-yl)-2-(tert-butoxycarbonyl methylamino)propionic acid.

$^1$H-NMR: (CDCl$_3$) (selected peaks for major rotamer) d 1.45 (s, 9H); 2.81 (s, 3H); 3.21–3.61 (m, 2H); 4.88 (dd, 1H); 7.18 (s, 1H).

((1R)-2-(Benzo[b]thiophen-3-yl)-(methyl-((1R)-1-methylcarbamoyl-2-phenyl-ethyl)carbamoyl)ethyl) methylcarbamic acid tert butylester:

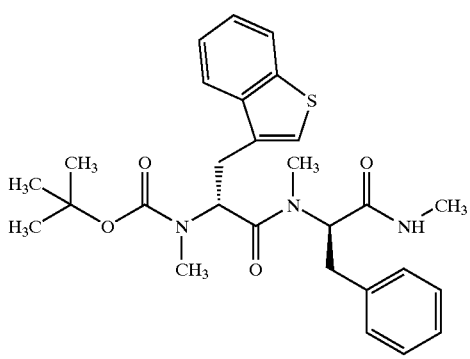

(2R)-3-(Benzo[b]thiophen-3-yl)-2-(tert-butoxycarbonyl methylamino)propionic acid (2.00 g ; 5.96 mmol) was dissolved in methylene chloride (1 0 mL). 1-Hydroxy-7-azabenzotriazole (0.81 g; 5.96 mmol) and N-(3-dimethylaminopropyl)-N ethylcarbodiimide hydrochloride (1.26 g ; 6.56 mmol) were added. The reaction mixture was stirred for 15 min at room temperature. (2R)-N-Methyl-2-methylamino-3-phenylpropionamide (1.15 g; 5.96 mmol) was dissolved in methylene chloride (10 mL) and added. Diisopropylethylamine (1.02 mL; 5.96 mmol) were added. The reaction mixture was stirred for 48 hours. Methylene chloride (10 mL) was added. The reaction was washed with water (30 mL), an aqueous solution of sodium hydrogen sulfate (10%; 30 mL), an aqueous solution of sodium hydrogen carbonate (saturated; 30 mL) and dried (magnesium sulfate). The solvent was removed in vacuo and the residue was chromatographed on silica (3×30 cm) using ethyl acetate/methylene chloride (1:1) as eluent to afford 0.89 g of ((1R)-2-(benzo[b]thiophen-3-yl)-1-(methyl-((1R)-1-methylcarbamoyl-2-phenylethyl)carbamoyl)ethyl)methyl carbamic acid tert-butylester.

$^1$H-NMR: (CDCl$_3$) (selected peaks for major rotamer) d 1.43 (s, 9H); 2.26 (d, 3H); 2.75 (s, 3H); 2.76 (s, 3H); 4.96 (dd, 1H); 5.05 (dd, 1H).

(2R)-3-(Benzo[b]thiophen-3-yl)-N-methyl-2-methylamino-N-((1R)-1-methylcarbamoyl-2-phenylethyl)propionamide:

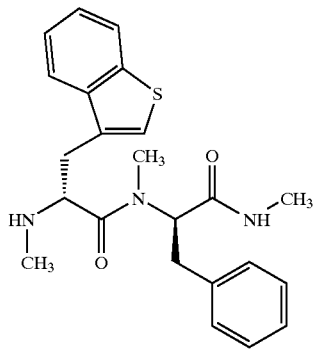

((1R)-2-(Benzo[b]thiophen-3-yl)-1-(methyl-((1R)-1-methylcarbamoyl-2-phenyl-ethyl)carbamoyl)ethyl)-methylcarbamic acid tert-butylester (0.89 g; 1.70 mmol) was dissolved in methylene chloride (3 mL) and trifluoroacetic acid (2 mL) was added. The reaction mixture was stirred for 45 min at room temperature. Water (5 mL) was added. Methylene chloride (5 mL), an aqueous solution of sodium hydrogen carbonate (saturated) and sodium hydrogen carbonate (solid) was added until pH 8. The aqueous phase was extracted with methylene chloride (3×10 mL). The combined organic phases were dried (magnesium sulfate) and evaporated in vacuo to afford 0.66 g of (2R)-3-(Benzo[b]thiophen-3-yl)-N-methyl-2-methylamino-N-((1R)-1-methylcarbamoyl-2-phenylethyl)propionamide.

$^1$H-NMR: (CDCl$_3$) (selected peaks for major rotamer) d 1.71 (s, 3H); 2.38 (s, 3H); 2.62 (d, 3H); 3.82 (dd, 1H); 5.47 (dd, 1H).

(3E)-4-(((1R)-2-(Benzo[b]thiophen-3-yl)-1-(methyl-(1-methylcarbamoyl-2-phenyl-ethyl)carbamoyl)ethyl)-methylcarbamoyl)-1,1-dimethylbut-3-enyl)carbamic acid tert-butylester:

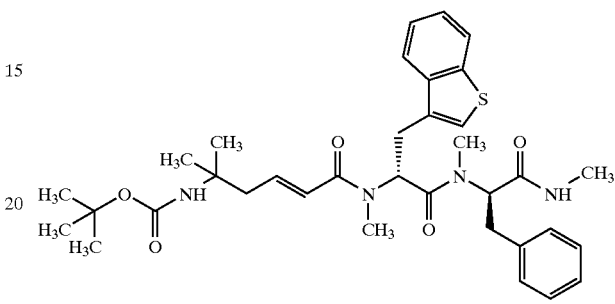

(2E)-5-(tert-Butyloxycarbonylamino)-5-methylhex-2-enoic acid (0;19 g; 0.78 mmol) was dissolved in methylene chloride (10 mL). 1-Hydroxy-7-azabenzotriazole (0.11 g; 0.78 mmol) and N-(3-dimethylaminopropyl)-N'-ethylcarbodiimide (0.16 g; 0.86 mmol) were added. The reaction mixture was stirred for 15 min at room temperature. 3-(Benzo[b]thiophen-3-yl)-N-methyl-2-methylamino-N-((1R)-1-methylcarbamoyl-2-phenylethyl)propionamide (0.32 g ; 0.78 mmol) was dissolved in methylene chloride (10 mL) and added. Diisopropylethylamine (0.13 mL; 0.78 mmol) was added. The reaction mixture was stirred for 12 hours at room temperature. Methylene chloride (10 mL) was added. The reaction was washed with water (20 mL), an aqueous solution of sodium hydrogen sulfate (10%; 20 mL), an aqueous solution of sodium hydrogen carbonate (saturated; 20 mL) and dried (magnesium sulfate). The solvent was removed in vacuo and the residue was chromatographed on silica (2×20 cm) using ethylacatate/methylene chloride (1:1) as eluent to afford 0.26 g of ((3E)-4-(((1R)-2-(benzo[b]thiophen-3-yl)-1-(methyl-(1-methylcarbamoyl-2-phenylethyl)carbamoyl)ethyl) methylcarbamoyl)-1,1-dimethylbut-3-enyl)carbamic acid tert-butylester.

$^1$H-NMR: (CDCl$_3$) (selected peaks for major rotamer) d 1.25 (s, 3H); 1.27 (s, 3H); 1.38 (s, 9H); 2.47 (s, 3H); 2.72 (d, 3H); 2.98 (s, 3H); 5.06 (dd, 1H); 5.67 (dd, 1H); 6.08 (d, 1H).

((3E)-4-(((1R)-2-(Benzo[b]thiophen-3-yl)-1-(methyl-(1-methylcarbamoyl-2-phenyl-ethyl)carbamoyl)ethyl)-methylcarbamoyl)-1,1-dimethylbut-3-enyl)carbamic acid tert-butylester was dissolved in methylene chloride (3 mL) and trifluoroacetic acid (2 mL) was added. The reaction mixture was stirred for 5 min at room temperature. Water (5 mL) was added. Methylene chloride (8 mL), an aqueous solution of sodium hydrogen carbonate (saturated), sodium hydrogen carbonate (solid) was added until pH 8. The aqueous phase was extracted with methylene chloride (3×10 mL) and the combined organic phases were dried (magnesium sulfate). The solvent was removed in vacuo to give 0.13 g of the title compound.

$^1$H-NMR: (CDCl$_3$) (selected peaks for major rotamer) d 1.25 (s, 6H); 2.47, (s, 3H); 2.75 (d, 3H); 2.96 (s, 3H); 4.98 (dd, 1H); 5.89 (dd, 1H); 6.10 (d, 1H).

PDMS: m/z 535.7 (M+H)+
HPLC: R$_t$=30.87 min (Method A1)

Example 22
(2R)-2-(((2-Amino-2-methylpropoxy)acetyl)methylamino)-3-(benzo[b]thiophen-3-yl)-N-methyl-N-((1R)-1-methylcarbamoyl-2-phenylethyl)propionamide:

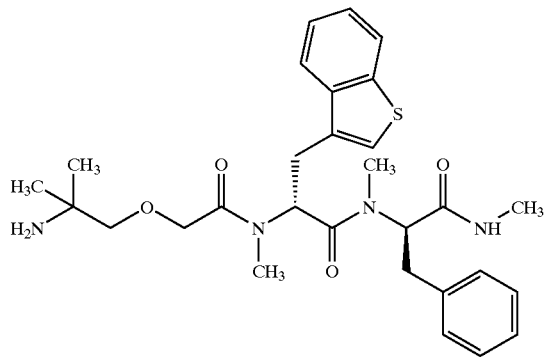

(2-((((1R)-2-(Benzo[b]thiophen-3-yl)-((methyl-((1R)-1-methylcarbamoyl-2-phenylethyl)carbamoyl)ethyl)methyl carbamoyl)methoxy)-1,1-dimethylethyl)-carbamic acid tert butyl ester:

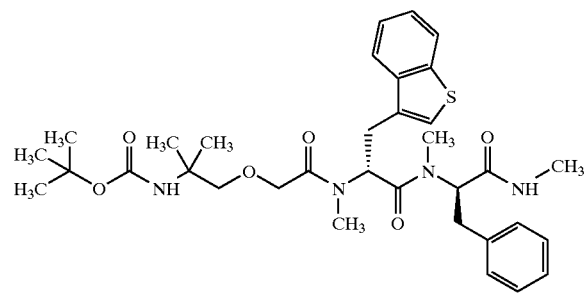

(2-tert-Butoxycarbonylamino-2-methylpropoxy)acetic acid (0.193 9g 0.78 mmol) was dissolved in methylene chloride (10 mL). 1-Hydroxy-7-azabenzotriazole (0.11 g; 0.78 mmol) and N-(3-dimethylaminopropyl)-N'-ethylcarbodiimide hydrochloride (0.16 g; 0.86 mmol) were added. The reaction mixture was stirred for 15 min at room temperature. (2R)-3-(Benzo[b]thiophen-3-yl)-N-methyl-2-methylamino-N-((1R)-1-methylcarbamoyl-2-phenylethyl) propionamide (0.32 g ; 0.78 mmol) was dissolved in methylene chloride (10 mL) and added. Diisopropylethylamine (0.13 mL; 0.78 mmol) was added. The reaction mixture was stirred for 12 hours at room temperature. Methylene chloride (10 mL) was added. The reaction was washed with water (30 mL), an aqueous solution of sodium hydrogen sulfate (10%; 20 mL) and an aqueous solution of sodium hydrogen carbonate (saturated; 20 mL) and dried (magnesium sulfate). The solvent was removed in vacuo and the residue was chromatographed on silica (3×30 cm) using ethyl acetate/methylene chloride (1:1) as eluent to afford 0.44 g of (2-((((1R)-2-(benzo[b]thiophen-3-yl)-1-((methyl-((1R)-1-methylcarbamoyl-2-phenylethyl)carbamoyl)-ethyl)methyl carbamoyl)methoxy)-1,1-dimethylethyl)carbamic acid tert butyl ester.

$^1$H-NMR: (CDCl$_3$) (selected peaks for major rotamer) d 1.25 (s, 3H); 1.28 (s, 3H); 1.42 (s, 9H); 2.70 (s, 3H); 2.78 (d, 3H); 2.97 (s, 3H); 4.99 (dd, 1H); 5.88 (dd, 1H).

(2-((((1R)-2-(Benzo[b]thiophen-3-yl)-1-((methyl-((1R)-1-methylcarbamoyl-2-phenylethyl)carbamoyl)ethyl) methyl-carbamoyl)methoxy)-1,1-dimethylethyl)-carbamic acid tert butyl ester (0.435 g; 0.68 mmol) was dissolved in methylene chloride (3 mL) and trifluoroacetic acid (2 mL) was added. The reaction mixture was stirred for 5 min at room temperature. Water (5 mL) was added. Methylene chloride (8 mL), an aqueous solution of sodium hydrogen carbonate (saturated) and solid sodium hydrogen carbonate was added until pH 8. The aqueous phase was washed with methylene chloride (3×10 mL). The combined organic phases were dried (magnesium sulfate) and evaporated in vacuo to afford 0.36 g of the title compound.

$^1$H-NMR: (CDCl$_3$) (selected peaks for major rotamer) d 1.25 (s, 6H); 2.65 (s, 3H); 2.75 (s, 3H); 2.98 (s, 3H); 4.68 (dd, 1H); 5.79 (dd, 1H).

HPLC: R$_t$=30.35 min (Method A1)
PDMS : m/z 538.1 (M+H)+

Example 23
(2E)-5-Amino-5-methylhex-2-enoic acid methyl-((1R)-1-(methyl-((1R)-2-phenyl-1-(((tetrahydrofuran-2-yl)-methyl) carbamoyl)ethyl)carbamoyl)-2-(1-naphthyl)ethyl)-amide:

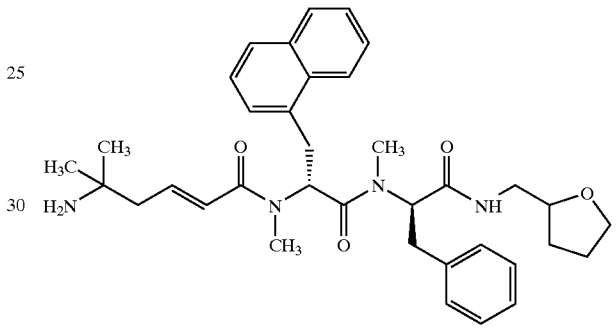

(2R)-2-(tert-Butoxycarbonylmethylamino)-3(1-naphthyl)-propionic acid:

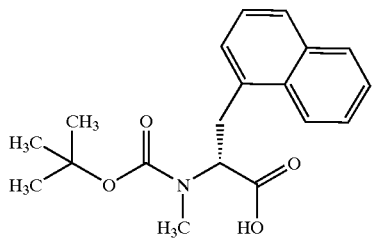

2-tert-Butoxycarbonylamino-3-(1-naphthyl)propionic acid (5.0 g; 0.015 mol) was dissolved in tetrahydrofuran (40 mL). Iodomethane (7.6 mL; 0.12 mol) was added. The reaction mixture was cooled to 0° C. and sodium hydride was added. The reaction mixture was stirred for 48 hours. Ethyl acetate (50 mL) and water (20 mL) were added dropwise. The solvent was removed in vacuo and ether (30 mL) and water (20 mL) were added. The organic phase was washed with an aqueous solution of sodium hydrogen carbonate (pH 8 ; 30 mL). To the aqueous phases was added citric acid (5%) to pH 3. The aqueous phase was extrated with ethylacetate (3×30 mL). The combined organic phases were washed with water (2×40 mL), an aqueous solution of sodiumthiosulfate (5%; 40 mL) and water (40 mL) and dried (magnesium sulfate). The solvent was removed in vacuo and ether (10 mL) and dicyclohexylamine (8.5 mL) were added. The precipitated crystals were filtered off and dissolved in water (20 mL). Hydrochloric acid was added to pH 2. The reaction mixture was extrated with ethyl acetate (4×40 mL), dried (magnesium sulfate) and evaporated in vacuo to afford 3.97 g of (2R)-2-(tert-butoxycarbonyl methylamino)-3-(1-naphthyl)propionic acid.

$^1$H-NMR: (CDCl$_3$) d 1.01 (s, 9H); 2.76 (s, 3H); 3.32 (dd, 1H); 3.93 (dd, 1H); 4.95 (dd, 1H); 7.30–8.10 (7 arom. H)

Methyl-((1R)-1-(methyl-((1R)-2-phenyl-1-(((tetrahydrofuran-2-yl)-methyl)-carbamoyl)ethyl)carbamoyl)-2-(1-naphthyl)ethyl)carbamic acid tert-butylester:

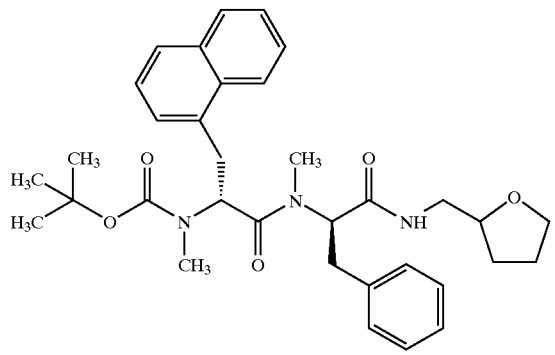

(2R)-2-(tert-Butoxycarbonylmethylamino)-3-(1-naphthyl)-propionic acid (0.68 g; 2.06 mmol) was dissolved in methylene chloride (10 mL). 1-Hydroxy-7-azabenzotriazol (0.28 g; 2.06 mmol) and N-(3-dimethylaminopropyl)-N'-ethylcarbodiimide hydrochloride (0.43 g; 2.26 mmol) were added. The reaction mixture was stirred for 15 min at room temperature.

(2R)-2-Methylamino-3-phenyl-N-((2-tetrahydrofuranyl)-methyl)propionamide (0.54 g; 2.058 mmol) was dissolved in methylene chloride (10 mL) and added. Diisopropylethylamine (0.35 mL; 2.06 mmol) was added and the reaction mixture was stirred for 12 hours at room temperature. Methylene chloride (10 mL) was added. The reaction mixture was washed with water (30 mL), an aqueous solution of sodium hydrogen sulfate (10%; 30 mL), an aqueous solution of sodium hydrogen carbonate (pH 8; 30 mL) and dried (magnesium sulfate). The solvent was removed in vacuo and the residue was chromatographed on silica (5×50 cm) using ethyl acetate/methylene chloride 1:1 as eluent to afford 1.08 g of methyl-((1R)-1-(methyl-((1R)-2-phenyl-1-(((tetrahydrofuran-2-yl)methyl)carbamoyl)ethyl)carbamoyl)-2-(1-naphthyl)ethyl)carbamic acid tert butylester.

$^1$H-NMR: (CDCl$_3$) (selected peaks for major rotamer) d 0.71 (s, 9H); 1.64 (s, 3H); 2.25 (s, 3H); 2.83 (d, 2H); 2.85 (s, 3H); 5.15 (dd, 1H); 5.44 (dd, 1H).

(2R)-N-Methyl-2-methylamino-3-(1-naphthyl)-N-((1R)-2-phenyl-1-(((tetrahydrofuran-2-yl)methyl)carbamoyl)ethyl)-propionamide:

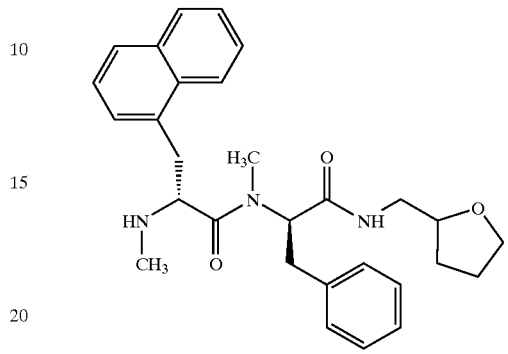

Methyl-((1R)-1-(methyl-((1R)-2-phenyl-1-(((tetrahydrofuran-2-yl)methyl)carbamoyl)ethyl)carbamoyl)-2-(1-naphtyl)ethyl)carbamic acid tert butylester (0.84 g; 1.46 mmol) was dissolved in methylene chloride (3 mL) and trifluoroacetic acid (2 mL) was added. The reaction mixture was stirred for 5 min at roomtemperature. Water (3 mL) and methylene chloride (5 mL) was added. Sodium hydrogen carbonate (solid) was added until pH 8. The reaction mixture was extracted with methylene chloride (3×10 mL). The combined organic layers were dried (magnesium sulfate) and evaporated in vacuo to afford 0.68 9 of (2R)-N-methyl-2-methylamino-3-(1-naphtyl)-N-((1R)-2-phenyl-1-((tetrahydrofuran-2-yl-methyl)-carbamoyl)ethyl)propionamide.

$^1$H-NMR: (CDCl$_3$) (selected peaks for major rotamer) d 1.75 (s, 3H); 2.08 (s, 3H); 2.40 (d, 2H); 2.95 (d, 3H); 4.45 (m, 1H); 5.45–5.50 (m, 2H).

((3E)-1,1-Dimethyl-4-(methyl-((1R)-1-(methyl-((1R)-2-phenyl-1-(((tetrahydrofuran-2-yl)methyl)carbamoyl)ethyl)-carbamoyl)-2(1-naphtyl)ethyl)carbamoyl)but-3-enyl) carbamic acid tert butylester:

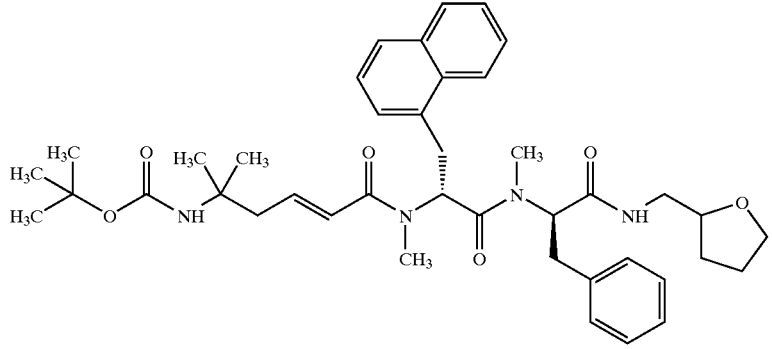

(2E)-5-(tert-Butoxycarbonylamino)-5-methylhex-2-enoic acid (0.344 g; 1.41 mmol) was dissolved in methylene chloride (10 mL). 1-Hydroxy-7-azabenzotriazole (0.19 g; 1.41 mmol) and N-(3-dimethylaminopropyl)-N'-ethylcarbodiimide hydrochloride (0.298 g; 1.56 mmol) were added. The reaction mixture was stirred for 15 min at room temperature. (2R)-N-Methyl-2-methylamino-3-(1-naphthyl)-N-((1R)-2-phenyl-1-(((tetrahydrofuran-2-yl)methyl)carbamoyl)ethyl)-propionamide (0.67 g; 1.42 mmol) was dissolved in methylene chloride (10 mL) and added. Diisopropyletylamine (0.242 mL; 1.41 mmol) was added. The reaction mixture was stirred for 12 hours at room temperature. Methylene chloride (20 mL) was added. The reaction mixture as washed with water (30 mL), an aqueous solution of sodium hydrogen sulfate (10%;30 mL), an aqueous solution of sodium hydrogen carbonate (pH 8; 30 mL) and dried (magnesium sulfate). The solvent was removed in vacuo and the residue was chromatographed on silica (3×30 cm) using methylene chloride/ethyl acetat (1:1) as eluent to afford 0.81 g of ((3E)-1,1-dimethyl-4-(methyl-((1R)-1-(methyl-((1R)-2-phenyl-1-(((tetrahydrofuran-2-yl)methyl)carbamoyl)ethyl)carbamoyl)-2(1-naphtyl)ethyl)-carbamoyl)but-3-enyl)carbamic acid tert butylester.

$^1$H-NMR: (CDCl$_3$) (selected peaks for major rotamer) d 1.28 (s, 9H); 1.47 (s, 6H); 2.90 (d, 3H); 6.06 (d, 1H).

((3E)-1,1-Dimethyl-4-(methyl-((1R)-1-(methyl-((1R)-2-phenyl-1-(((tetrahydrofuran-2-yl)methyl)carbamoyl)ethyl)-carbamoyl)-2(1-naphtyl)ethyl)carbamoyl)but-3-enyl) carbamic acid tert butylester (0.80 g; 1.15 mmol) was dissolved in methylene chloride (3 mL) and trifluoroacetic acid (2 mL) was added. The reaction mixture was stirred for 5 min at room temperature. Methylene chloride (5 mL) and sodium hydrogen carbonate were added until pH 8. The reaction mixture was extracted with methylene chloride (3×10 mL). The combind organic phases were dried (magnesium sulfate) and evaporated in vacuo to afford 0.50 g of the title compound.

$^1$H-NMR: (CDCl$_3$) (selected peaks for major rotamer) d 1.25 (s, 6H); 2.25 (d, 2H); 2.08 (s, 3H); 2.89 (d, 3H); 3.18 (s, 3H); 5.90 (dd, 1H); 6.65 (d, 1H).

PDMS: m/z 599.8 (M+H)$^+$

HPLC: R$_t$=33.50 (Method A1)

Example 24

3-((2R)-2-(N-((2R)-2-(N-((2E)-5-Amino-5-methylhex-2-enoyl)-N-methylamino)-3-(2-naphthyl)propionyl)-N-methylamino)-3-phenylpropionylamino)propyl acetate:

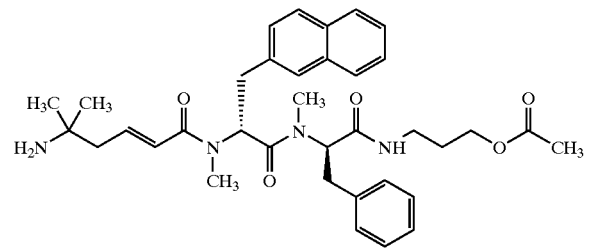

N-((1R)-1-(3-hydroxypropylcarbamoyl)-2-phenylethyl)-N-methylcarbamic acid tert-butylester:

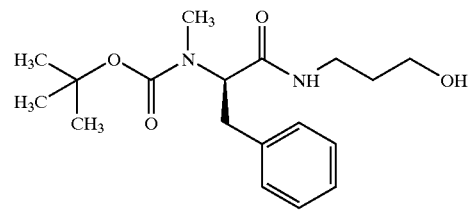

3-Aminopropan-1-ol (0.39 mL, 5.12 mmol) was added at room temperature to a solution of N-tert-butoxycarbonyl-N-methyl-D-phenylalanine (1.30 g, 4.65 mmol) in N,N-dimethylformamide (40 mL). 1-Hydroxybenzotriazole monohydrate (0.63 g, 4.65 mmol) and N-(3-dimethylaminopropyl)-N'-ethylcarbodiimide hydrochloride (0.89 g, 4.65 mmol) were added successively. The reaction mixture was stirred for 22 h at room temperature. It was diluted with 1 0% sodium hydrogensulfate solution (300 mL) and extracted with ethyl acetate (4×100 mL). The combined organic layers were dried over magnesium sulfate. The solvent was removed in vacuo and the crude product was purified by flash chromatography on silica (45 g) with dichloromethane/methanol (10:1) to give 1.01 g of N-((1R)-1-(3-hydroxypropylcarbamoyl)-2phenylethyl)-N-methylcarbamic acid tert-butylester.

$^1$H-NMR (CDCl$_3$): d 1.30 and 1.40 (both s, together 9H); 1.65 and 1.72 (both br, together 2H); 2.77 (s, 3H); 2.90–3.75 (m, 6H); 4.75 and 4.86 (both m, together 1H); 6.50 (m, 1H); 7.10–7.25 (m, 5H).

3-((2R)-2-(N-tert-Butoxycarbonyl-N-methylamino)-3-phenylpropionylamino)propyl acetate:

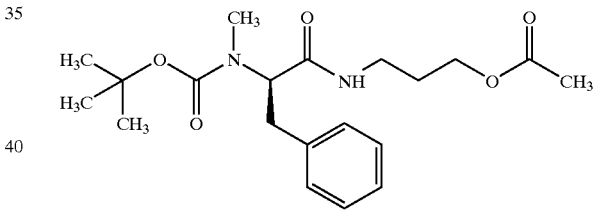

A solution of N-((1R)-1-(3-hydroxypropylcarbamoyl)-2-phenylethyl)-N-methyl-carbamic acid tert-butylester (965 mg, 2.86 mmol) in dichloromethane (10 mL) was cooled to 0° C. 4-(dimethylamino)pyridine (35 mg, 0.29 mmol), triethylamine (0.60 mL, 4.29 mmol), and acetic acid anhydride (0.32 mL, 3.43 mmol) were added. The reaction mixture was stirred for 5 hours, while it was warming slowly to room temperature. The reaction mixture was diluted with dichloromethane (100 mL) and washed with 10% sodium hydrogensulfate solution. The aqueous phase was extracted with dichloromethane (2×50 mL). The organic phases were combined and washed with saturated sodium hydrogen carbonate solution. They were dried over magnesium sulfate. The solvent was removed in vacuo, and the crude product was purified by flash chromatography on silica (90 9) with ethyl acetate/dichloromethane (1:3 to 1:1) to give 890 mg of 3-((2R)-2-(N-tert-butoxycarbonyl-N-methylamino)-3-phenylpropionylamino)propyl acetate.

$^1$H-NMR (CDCl$_3$) d 1.25 and 1.39 (both s, together 9H); 1.85 (m, 2H); 2.06 and 2.07 (both s, together 3H); 2.76 (s, 3H); 2.95 (m, 1H); 3.35 (m, 3H); 4.00–4.20 (m, 2H); 4.70–4.87 (both m, together 1H); 6.22 and 6.37 (both br, together 1H); 7.10–7.35 (m, 5H).

3-((2R)-2-(Methylamino)-3-phenylpropionylamino)propyl acetate:

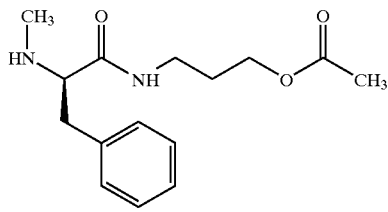

A solution of 3-((2R)-2-(N-tert-butoxycarbonyl-N-methylamino)-3-phenyl-propionylamino)propyl acetate (862 mg, 2.28 mmol) in dichloromethane (3 mL) was cooled to 0° C. Trifluoroacetic acid (3 mL) was added. The solution was stirred for 10 min. The solvents were removed in vacuo without warming. The residue was dissolved in dichloromethane (50 mL) and the solvent was removed in vacuo. The procedure was repeated twice. The crude product was purified by flash chromatography on silica (70 g) with dichloromethane/methanol/25% ammonia in water (100:10:1) to give 602 mg of 3-((2R)-2-(methylamino)-3-phenylpropionylamino)propyl acetate.

$^1$H-NMR (CDCl$_3$) d 1.85 (m, 2H); 2.07 (s, 3H); 2.80 (s, 3H); 2.72 (dd, 1H); 3.20 (m, 2H); 3.35 (m, 2H); 4.10 (t, 1H); 7.15–7.40 (m, 6H).

3-((2R)-2-(N-((2R)-2-(N-(tert-Butoxycarbonyl)-N-methylamino)-3-(2-naphthyl)propionyl)-N-methylamino)-3-phenylpropionylamino)propyl acetate:

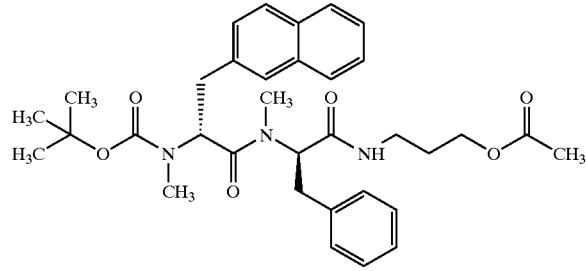

2R)-2-(N-(tert-Butoxycarbonyl)-N-methylamino)-3-(2-naphthyl)-propionic acid (659 mg, 2.0 mmol) was dissolved in N,N-dimethylformamide (3 mL) and dichloromethane (3 mL). The solution was cooled to 0° C. 1-Hydroxy-7-azabenzotriazole (272 mg, 2.0 mmol) was added. After 10 min N-(3-dimethylaminopropyl)-N'-ethylcarbodiimide hydrochloride (460 mg, 2.4 mmol) was added. The reaction mixture was stirred for 10 min. A solution of 3-((2R)-2-(methylamino)-3-phenylpropionylamino)propyl acetate (567 mg, 2.0 mmol) in dichloromethane (4 mL) was added. The solution was stirred for 16 hours, while the temperature rose to room temperature. The reaction mixture was diluted with ethyl acetate (150 mL). It was extracted with 10% sodium hydrogensulfate solution (150 mL). The aqueous phase was extracted with ethyl acetate (3×50 mL) and the organic phases were combined and dried over magnesium sulfate. The solvent was removed in vacuo. The crude product was purified by flash chromatography on silica (70 g) with ethyl acetate/heptane (2:1) to give 973 mg of 3-(2R)-2-(N-((2R)-2-(N-(tert-butoxycarbonyl)-N-methylamino)-3-(2-naphthyl)-propionyl)-N-methylamino)-3-phenylpropionylamino)propyl acetate.

$^1$H-NMR (CDCl$_3$): d 4.99, 5.11, 5.18, 5.35, and 5.42 (all dd, together 2H); 5.75 and 6.15 (both t, together 1H).

3-((2R)-2-(N-((2R)-2-Methylamino-3-(2-naphthyl)propionyl)-N-methylamino)-3-phenylpropionylamino)propyl acetate:

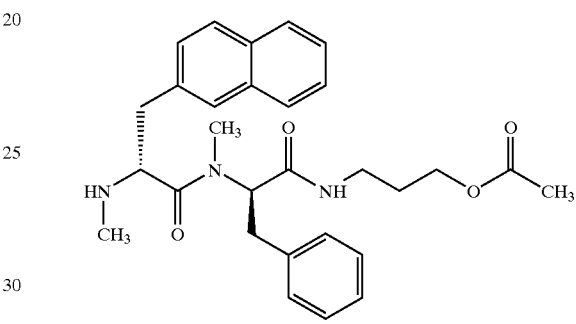

At 0° C., trifluoroacetic acid (3 mL) was added to a solution of 3-((2R)-2-(N-((2R)-2-(N-(tert-butoxycarbonyl)-N-methylamino)-3-(2-naphthyl)propionyl)-N-methylamino)-3-phenylpropionylamino)propyl acetate (885 mg, 1.50 mmol) in dichloromethane (3 mL). The reaction mixture was stirred for 5 min. The solvents were removed in vacuo at 20° C. The residue was dissolved in dichloromethane (40 mL). The S procedure was repeated twice. The crude product was purified by flash chromatography on silica (45 g) with dichloromethane/methanol/25% solution of ammonia in water (100:10:1) to give 497 mg of 3-((2R)-2-(N-((2R)-2-methylamino-3-(2-naphthyl)propionyl)-N-methylamino)-3-phenylpropionylamino)propyl acetate.

$^1$H-NMR (DMSO-d$_6$): d 1.65 (m, 2H); 2.01 and 2.02 (both s, together 3H); 4.67 and 5.35 (both dd, together 1H).

3-((2R)-2-(N-((2R)-2-(N-((2E)-5-tert-Butoxycarbonylamino)-5-methylhex-2-enoyl)-N-methylamino)-3-(2-naphthyl)propionyl)-N-methylamino)-3-phenyl-propionylamino)propyl acetate:

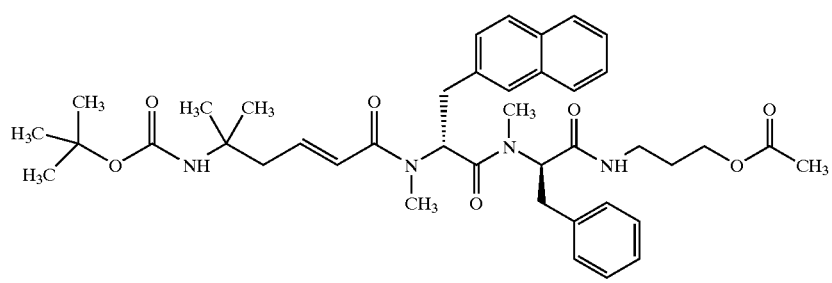

(2E)-5-tert-Butoxycarbonylamino-5-methylhex-2-enoic acid (277 mg, 1.14 mmol) and 1-hydroxy-7-azabenzotriazole (155 mg, 1,14 mmol) were dissolved in dichloromethane (3 mL) and N,N-dimethylformamide (3 mL). The solution was cooled to 0° C. N-(3-dimethylaminopropyl)-N'-ethylcarbodiimide hydrochloride (254 mg, 1.32 mmol) was added. The solution for stirred for 10 min at 0° C., before a solution of 3-((2R)-2-(N-((2R)-2-methylamino-3-(2-naphthyl)propionyl)-N-methylamino)-3-phenylpropionylamino)propyl acetate in dichloromethane (3 mL) was added. The solution was stirred for 18 hours, while it was warming up slowly to room temperature. It was diluted with ethyl acetate (100 mL) and extracted with 10% sodium hydrogensulfate solution. The aqueous phase was extracted with ethyl acetate (2×50 mL). The combined organic layers were washed with saturated sodium hydrogen carbonate solution (100 mL) and dried over magnesium sulfate. The solvent was removed in vacuo. The crude product was purified by flash chromatogrpahy on silica (45 g) with ethyl acetate/heptane (2:1) to give 427 mg of 3-((2R)-2-(N-((2R)-2-(N-((2E)-5-(tert-butoxycarbonylamino)-5-methylhex-2-enoyl)-N-methylamino)-3-(2-naphthyl)propionyl)-N-methylamino)-3-phenylpropionylamino)propyl acetate.

$^1$H-NMR (CDCl$_3$): d 1.80 (m, 2H); 4.10 (m, 2H); 6.05 (m, 1H); 6.75 (m, 1H). N-methylamino)-3-(2-naphthyl)propionyl)-N-methylamino)-3-phenyl-propionylamino) propyl acetate (412 mg, 0.58 mmol) was dissolved in dichloromethane (2 mL). The solution was cooled to 0° C. Trifluoroacetic acid (2 mL) was added. The solution was stirred for 8 min at 0° C., and the solvents were removed in vacuo with a water bath temperature of 20° C. The residue was dissolved in dichloromethane (30 mL) and the solvent was removed in vacuo. This latter procedure was repeated twice. The crude product was purified by flash chromatography on silica (35 g) with dichloromethanelmethanol/25% ammonia in water (100: 10:1). The product was dissolved in ethyl acetate (3 mL) and 3M hydrogen chloride in ethyl acetate (0.7 mL) was added. The solvent was removed in vacuo and the product was dried over night in vacuo to give 0.21 g of title compound as a hydrochloride.

$^1$H-NMR (DMSO-d$_6$) (selected values) d 1.70 (m, 2H); 4.00 (m, 2H).

MS: found: 616.3±1 [M+1]$^+$

HPLC: R$_T$=20.47 min (method A1)

Example 25

(2E)-5-Amino-5-methylhex-2-enoic acid N-((1R)-1-(N-((1R)-1-(3-hydroxypropyl-carbamoyl)-2-phenylethyl)-N-methylcarbamoyl)-2-(2-naphthyl)ethyl)-N-methyl-amide:

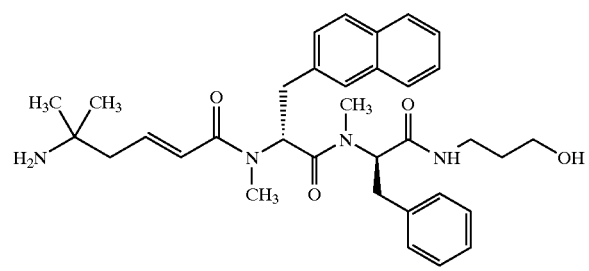

3-((2R)-2-(N-((2R)-2-(N-((2E)-5-Amino-5-methylhex-2-enoyl)-N-methylamino)-3-(2-anphthyl)propionyl)-N-methylamino)-3-phenylpropionylamino)propyl acetate hydrochloride (140 mg, 0.21 mmol) was dissolved in 1,4-dioxane (3 mL). A solution of lithium hydroxide (18 mg, 0.74 mmol) in water (1.5 mL) was added. Water was added until a clear solution was obtained. The reaction mixture was stirred for 16 h at room temp. It was diluted with water (30 mL) and extracted with tert-butylmethyl ether. The combined organic layers were dried over magnesium sulfate and the solvent was removed in vacuo. The residue was dissolved in water (15 mL) and acetic acid (0.8 mL) and the resulting solution was lyophilized to give 105 mg of the acetate salt of the title compound.

$^1$H-NMR (DMSO-d$_6$) (selected peaks): d 0.95 (s, 6H); 1.55 (m, 3H); 3.42 (m, 2H).

HPLC: R$_T$=30.97 min (method A1)

Example 26

(2E)-5-Amino-5-methylhex-2-enoic acid N-methyl-N-((1R)-1-(N-methyl-N-((1R)-1-(((3-methyl-1,2,4-oxadiazol-5-yl)methoxy)methyl)-2-phenylethyl)carbamoyl)-2-(2-naphthyl)ethyl)amide:

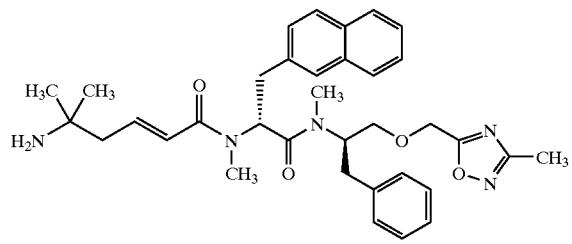

(2R)-2-(Methylamino)-3-phenylpropan-1-ol:

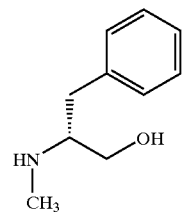

(2R)-2-(Methylamino)-3-phenylpropan-1-ol was prepared analogue to M. J. McKennon and A. I. Meyers J. Org. Chem. 1993 (58), 3568–3571. m.p. 69–69° C. (lit: A. I. Meyers, J. Org. Chem. 1993 (58), 3568–3571: 71–74° C.; A. Karim, A. Mortreux, F. Petit, G. Buono, G. Pfeiffer, C. Siv, J. Organomet. Chem. 1986, 317, 93: 68° C., for (2S)-2-(methylamino)-3-phenylpropan-1-ol)

N-((1R)-1-Hydroxymethyl-2-phenylethyl)-N-methyl carbamaic acid tert-butylester:

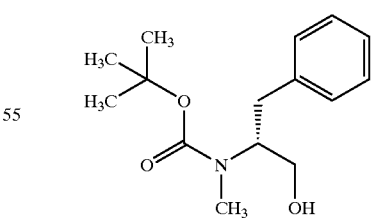

(2R)-2-(Methylamino)-3-phenylpropan-1-ol (6.00 g, 36.3 mmol) was dissolved in Tetrahydrofuran (80 mL). 1N sodium hydroxide solution (36.3 mL, 36.3 mmol) was added. A solution of di-tert.-butyl dicarbonate (9.50 g, 43.6 mmol) in tetrahydrofuran (60 mL) was slowly added at room temperature. The solution was stirred 16 h at room temperature. Water (200 mL) and ethyl acetate (200 mL) were added. The phases were separated. The aqueous phase was washed with ethyl acetate (2×100 mL). The combined organic phases were dried over magnesium sulfate. The solvent was removed in vacuum. The product was purified on silica (170 g) with ethyl aceate/heptane (1:1) to give 7.85 g (81%) of N-((1R)-1-hydroxymethyl-2-phenylethyl)-N-methyl carbamaic acid tert-butylester.

[1] H-NMR (CDCl$_3$): d =1.32–1.40 (br, 9H); 2.55–2.95 (m, 5H); 3.65–3.67 (br, 2H); 4.10–4.35 (br, 1H); 7.05–7.35 (m, 5H).

((2R)-2-(tert-Butoxycarbonylmethylamino)-3-phenylpropoxyl)acetic acid Ethyl Ester:

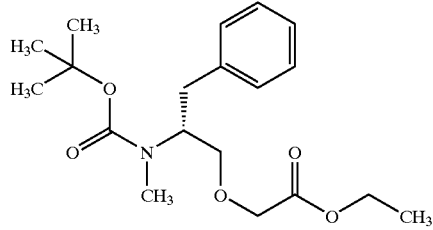

N-((1R)-1-Hydroxymethyl-2-phenylethyl)-N-methyl carbamaic acid (3.98 g, 15.0 mmol) was dissolved in 1,2-dichloroethane (150 mL). The solution was warmed to 75–80° C. Rhodium(II) acetate (0.1 g, 0.4 mmol) was added. During a period of 6 hours a solution of ethyl diazoacetate (2.4 mL, 22.5 mmol) in dichloromethane (100 mL) was added. After 3 h another portion of rhodium(II) acetate (0.1 g, 0.4 mmol) was added. After addition of ethyl diazoacetate, the solution was cooled to room temperature. It was filtered through a plug of celite. The solvent was removed in vacuum. The crude product was chromatographed on silica (100g) to give 1.53 g of ((2R)-2-(tert-butoxycarbonylmethylamino)-3-phenylpropoxyl)acetic acid ethyl ester.

1H-NMR (CDCl$_3$): d=1.28 (m, 3H); 1.39 and 1.48 (both s, together 9H); 2.65–2.95 (m, 9H); 3.58 (m, 1H); 3.67 (br, 1H); 3.98–4.27 (m, 4H); 4.35-4.55 (br, 1H); 7.10 -7.30 (m, 5H).

((2R)-2-(tert-Butoxycarbonylmethylamino)-3-phenylpropoxy)-acetic acid:

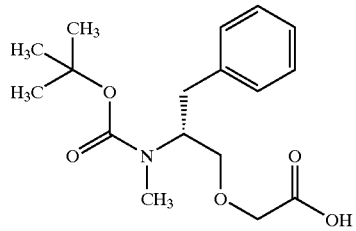

((2R)-2-(tert-butoxycarbonylmethylamino)-3-phenylpropoxyl)-acetic acid ethyl ester (0.60 g, 1.71 mmol) was dissolved in dioxane (5 mL). A solution of lithium hydroxide (0.05g, 2.20 mmol) in water (2 mL) was added. The solution was stirred at room temperature for 56 hours. Ethyl acetate (10 mL) and water (2 mL) were added. The phases were separated. The aqueous phase was extracted with ethyl acetate (10 mL). The combined organic layers were extracted with 1N sodium hydroxide solution (20 mL). The combined aqueous phases were acidified with a 1M sodium hydrogensulfate solution (pH 2) and extracted with ethyl acetate (2×20 mL). These ethyl acetate layers were combined and dried over magnesium sulfate. The solvent was removed in vacuum to give 0.38 g of crude ((2R)-2-(tert-butoxycarbonylmethylamino)-3-phenylpropoxy) acetic acid, which was used for the following steps.

1H-NMR (DMSO d$_6$): d=1.15 and 1.27 (both s, together 9H); 2.55–2.70 (m, 5H); 3.45–3.65 (m, 2H); 4.00–4.10 (m, 2H); 4.30–4.50 (m, 1H); 7.15-7.35 (m, 5H); 13.60 (br, 1H).

N-Methyl-N-((1R)-1-(((3-methyl-1,2,4-oxadiazol-5-yl)methoxy)methyl-2-phenyl-ethyl)carbamic acid tert-butylester:

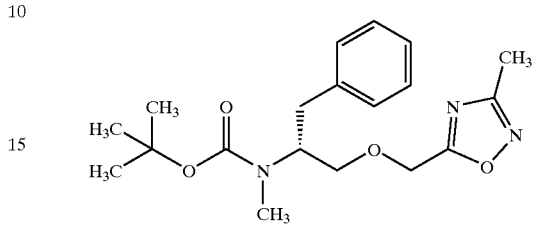

At −13° C., isobutyl chloroformate (0.80 mL, 6.19 mmol) was added slowly to a acid (2.0 g, 6.18 mmol) and N-methylmorpholine (0.68 mL, 6.18 mmol) in f tetrahydrofuran (25 mL). The solution was stirred for 15 min at this temperature. Acetamidoxim (0.92 g, 12.36 mmol) was added as a solid. Immediately after addition, N-methylmorpholine (0.68 mL, 6.18 mmol) was given to the reaction mixture. It was stirred for 45 min at −13° C., 3.5 h at room temperature and 16 hours at reflux. The reaction mixture was cooled to room temperature and diluted with ethyl acetate (100 mL). It was extracted with water and 10% sodium hydrogensulfate solution (10 mU 40 mL). The aqueous phase was extracted with ethyl acetate (2×50 mL). The combined organic phases were washed with saturated sodium hydrogen carbonate solution and dried over magnesium sulfate. The solvent was removed in vacuo. The crued product was purified on silica (90 g) with ethyl acetate/heptane (1:1) as eluent to give 1.17 g of N-methyl-N-((1R)-1-(((3-methyl-1,2,4-oxadiazol-5-yl)methoxy)methyl-2-phenylethyl) carbamcic acid tert-butylester.

$^1$H-NMR (CDCl$_3$) d 1.31 and 1.39 (both s, together 9H); 2.43 (s, 3H); 2.65–2.95 (m, 5H); 3.65 (m, 1H); 3.76 (m, 1H); 4.43 and 4.53 (both br, together 1H); 4.70–4.80 (m, 2H); 7.10–7.35 (m, 5H).

3-Methyl-5-(((2R)-2-(methylamino)-3-phenylpropoxy)methyl)-1,2,4-oxadiazole:

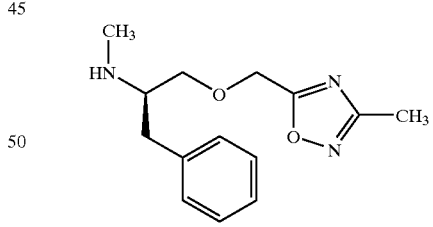

N-Methyl-N-((1R)-1-(((3-methyl-,2,4-oxadiazol-5-yl)methoxy)methyl-2-phenyl-ethyl)carbamcic acid tert-butylester (1.13 g; 3.13 mmol) was dissolved in dichloromethane (3 mL). The solution was cooled to 0° C. Trifluoroacetic acid (3 mL) was added. The solution was stirred at 0° C. for 5 min. The solvent was removed in vacuo without warming. The residue was dissolved in dichloromethane (100 mL) and the solvent was removed in vacuo. This procedure was repeated twice. The crude product was purified by flash chromatography on silica (70 g) with dichloromethane/methanol/25% aqueous ammonia (100:10:1) to give 0.75 g of 3-methyl-5-(((2R)-2-(methylamino)-3-phenylpropoxy)methyl)-1,2,4-oxadiazole.

¹H-NMR (CDCl₃) d 2.40 (s, 3H); 2.45 (s, 3H); 2.75 (dd, 1H); 2.85 (dd, 2H); 2.93 (m, 1H); 3.48 (dd, 1H); 3.56 (dd, 1H); 4.70 (AB, 2H); 7.15–7.35 (m, 5H)).
N-Methyl-N-((1R)-1-(N-methyl-N-((1R)-1-(((3-methyl-1,2,4-oxadiazol-5-yl)methoxy)methyl)-2-phenylethyl)carbamoyl)-2-(2-naphthyl)ethyl)carbamic acid tert-butylester:

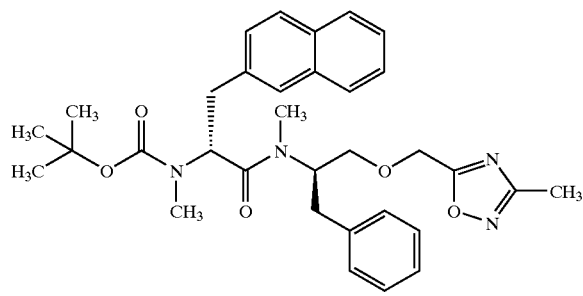

(2R)-2-(N-tert-Butoxycarbonyl-N-methylamino)-3-(2-naphthyl)propionic acid (701 mg, 2.68 mmol) was dissolved in dichloromethane (4 mL) and N,N-dimethylformamide (4 mL). The solution was cooled to 0° C. 1-Hydroxy-7-azabenzotriazole (365 mg, 2.68 mmol) and N-(3-dimethylaminopropyl)-N'-ethylcarbodiimide hydrochloride (617 mg, 3.22 mmol) were successively added. The solution was stirred for 15 min at 0° C. A solution of 3-methyl-5-(((2R)-2-(methylamino)-3-phenylpropoxy)methyl)-1,2,4-oxadiazole (701 mg, 2.68 mmol) in dichloromethane (4 mL) was added. The reaction mixture was stirred for 16 hours, while the temperature slowly rose to room temperature. It was diluted with ethyl acetate (100 mL) and extracted with a mixture of saturated sodium chloride solution (50 mL) and water (50 mL). The aqueous phase was extracted with ethyl acetate (3×50 mL). The combined organic layers were washed with saturated sodium hydrogen carbonate solution and dried over magensium sulfate. The solvent was removed in vacuo. The crude product was purified by flash chromatography on silica (90 g) with ethyl acetate/heptane (2:1) to give 1.23 g of N-methyl-N-((1R)-1-(N-methyl-N-((1R)-1-(((3-methyl-1,2,4-oxadiazol-5-yl)methoxy)methyl)-2-phenylethyl)-carbamoyl)-2-(2-naphthyl)ethyl)carbamic acid tert-butylester.

¹H-NMR (CDCl₃) d 0.95, 1.02, 1.13, and 1.26 (all s, together 9H); 2.35-2.45 (m, 3H); 7.00–7.80 (m, 12H).
(2R)-2-(Methylamino)-3-(2-naphthyl)propionic acid N-methyl-N-((1R)-1-(((3-methyl-1,2,4-oxadiazol-5-yl)methoxy)methyl)-2-phenylethyl)amide:

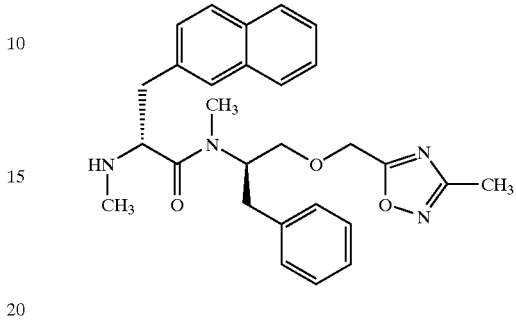

N-Methyl-N-((1R)-1-(N-methyl-N-((1R)-1-(((3-methyl-1,2,4-oxadiazol-5-yl)-methoxy)methyl)-2-phenylethyl)-carbamoyl)-2-(2-naphthyl)ethyl)carbamic acid tert-butylester (1.21 g, 2.12 mmol) was dissolved in dichloromethane (4 mL). The solution was cooled to 0° C. Trifluoroacetic acid (4 mL) was added. The solution was stirred for 12 min at 0° C. The solvent was removed in vacuo without warming. The residue was dissolved in dichloromethane (150 mL), and the solvent was removed in vacuo. This latter procedure was repeated twice. The crude product was purified by flash chromatogrpahy on silica (70 g) with dichloromethane/methanol/25% aqueous ammonia (200:10:1) to give 497 mg of (2R)-2-(methylamino)-3-(2-naphthyl)propionic acid N-methyl-N-((1R)-1-(((3-methyl-1,2,4-oxaidazol-5-yl)methoxy)methyl)-2-phenylethyl)amide.

¹H-NMR (DMSO d₆) d 1.67 and 1.92 (both s, together 3H); 2.32 and 2.34 (both s, together 3H); 2.71 and 2.86 (both s, together 3H); 4.60 and 4.79 (both s, together H); 7.05–7.90 (m, 12H).
(3E)-1,1-Dimethyl-4-(N-methyl-N-((1R)-1-(N-methyl-N-((1R)-1-(((3-methyl-1,2,4-oxadizol-5-yl)methoxy)methyl)-2-phenylethyl)carbamoyl)-2-(2-naphthyl)ethyl)-carbamoyl)but-3-enylcarbamic acid tert-butylester:

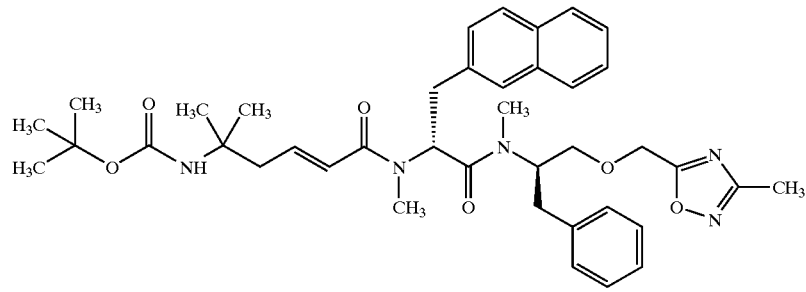

(2E)-5-(tert-Butoxycarbonylamino)-5-methylhex-2-enoic acid (258 mg, 1.06 mmol) was dissolved in dichloromethane (3 mL) and N,N-dimethylformamide (3 mL). 1-Hydroxy-7-azabenzotriazole (144 mg, 1.06 mmol) was added. The solution was cooled to 0° C. N-(3-dimethylaminopropyl)-N'-ethylcarbodiimide hydrochloride (260 mg, 1.36 mmol) was added. The solution was stirred for 15 min at 0° C. A solution of (2R)-2-(methylamino)-3-(2-naphthyl)propionic acid N-methyl-N-((1R)-1-(((3-methyl-1,2,4-oxaidazol-5-yl)methoxy)-methyl)-2-phenylethyl)amide (456 mg, 0.97 mmol) in dichloromethane (3 mL) was added. The reaction mixture was stirred for 16 h, at room temperature. The reaction mixture was diluted with ethyl acetate (150 mL). It was washed with saturated sodium chloride solution (150 mL). The aqueous phase was extracted with ethyl acetate (3×50 mL). The combined organic phases were washed with saturated sodium hydrogen carbonate solution and dried over magnesium sulfate. The solvent was removed in vacuo. The crude product was purified by flash chromatogrphy on silica (60 g) with ethyl acetate/heptane (2:1) to give 514 mg of (3E)-1,1-dimethyl-4-(N-methyl-N-((1R)-1-(N-methyl-N-((1R)-1-(((3-methyl-1,2,4-oxadizol-5-yl)methoxy)methyl)-2-phenylethyl)carbamoyl)-2-(2-naphthyl)ethyl)carbamoyl) but-3-enylcarbamic acid tert-butylester.

$^1$H-NMR (CDCl$_3$) d 1.05–1.50 (m, 15H); 6.05 (m, 1H); 6.55 and 6.74 (both m, together 1H); 7.05–7.85 (m, 12H).

(3E)-1,1-Dimethyl-4-(N-methyl-N-((1R)-1-(N-methyl-N-((1R)-1-(((3-methyl-1,2,4-oxadizol-5-y)methoxy)methyl)-2-phenylethyl)carbamoyl)-2-(2-naphthyl)ethyl)-carbamoyl) but-3-enylcarbamic acid tert-butylester (464 mg, 0.66 mmol) was dissolved in dichloromethane (2 mL). The reaction mixture was cooled to 0° C. Trifluoroacetic acid (2 mL) was added. The reaction mixture was stirred for 7 min at 0° C. The solvent was removed in vacuo. The residue was dissolved in dichloromethane (50 mL), and the solvent was removed in vacuo. This latter procedure was repeated two times. The crude product was purified by flash chromatography on silica (30 g) with dichloromethane/methanol/25% aqueous ammonia (100:10:1). The product was dissolved in ethyl acetate (3 mL) and 3 M hydrogen chloride in ethyl acetate (0.7 mL) was added. The solvent was removed in vacuo. The residue was dissolved in ethyl acetate (50 mL) and the solvent was removed in vacuo to give 285 mg of the title compound as a hydrochloride.

HPLC: R$_f$=35.40 min (Method A1)

$^1$H-NMR (DMSO-d$_6$) d 1.03, 1.04, and 1.15 (all s, together 6H);2.35 and 2.36 (both s, together 3H).

MS: 598.3 ([M+1]$^+$).

C$_{35}$H$_{44}$N$_5$ClO$_4$.2H$_2$O calc. C62.72; H7.22; N10.45 found C62.72; H7.04; N10.30

Example 27

2-Methyl-piperidine-4-carboxylic acid N-{1-[N-methyl-N-(1-(3-methyl-1,2,4-oxadiazol-5-yl)-2-(2-naphthyl)ethyl) carbamoyl]-2-(2-naphthyl)ethyl} amide:

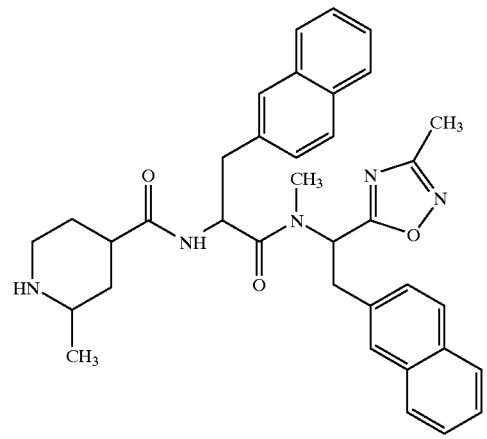

(R) N-Methyl-N-[1-(3-methyl-1,2,4-oxadiazol-5-yl)-2-(2-naphthyl)ethyl]carbamic acid tertbutyl ester:

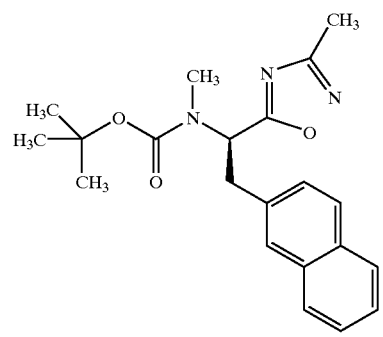

iso-Butylchloroformate (1.22 g, 9.0 mmol) was dropwise added to a solution of (R) N-methyl-N-tert-butoxycarbonyl-3-(2-naphthyl)alanine (3.0 g, 9 mmol) and N-methylmorpholine (0.91 g, 9.0 mmol) in dichloromethane (40 mL) at -20° C. After 15 min at -20° C. acetamidoxim (1.33 g, 18 mmol) was added followed by addition of N-methyl-morpholine (0.91 g, 9 mmol). After 30 min at –20° C. the reaction mixture was heated to 20° C. and diluted with N,N-dimethylformamide (40 mL). The dichloromethane was evaporated in vacuo and the reaction mixture was heated at 120° C. for 16 hours. The reaction mixture was poured into water (120 mL) and extracted with ethyl acetate (180 mL). The organic phases were collected, washed with water (40 mL) and dried (magnesium sulfate). The solution was concentrated in vacuo to give 3.5 g of crude (R) N-methyl-N-[1-(3-methyl-1,2,4-oxadiazol-5-yl)-2-(2-naphtyl)ethyl]carbamic acid tertbutyl ester that was used without further purification.

(R) N-Methyl-N-{1(3-methyl-1,2,4-oxadiazol-5-yl)-2-(2-naphthyl)ethyl}amine hydrochloride:

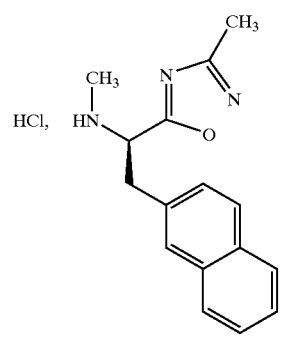

(R) N-Methyl-N-[1-(3-methyl-1,2,4-oxadiazol-5-yl)-2-(2-naphtyl)ethylcarbamic acid tertbutyl ester (3.3 g, 9.0 mmol) was dissolved in a saturated solution of hydrogen chloride in ethyl acetate (75 mL). After 3 hours at 20° C. the reaction mixture was filtered to give 1.52 g of (R) N-methyl-N{1-(3-methyl-1,2,4-oxadiazol-5-yl)-2-(2-naphthyl)ethyl}amine hydrochloride.

m.p. 198–202° C.
$^1$H-NMR (DMSO-$d_6$) d 2.35(s, 3H); 2.68(s, 3H); 3.43(dd, 1H); 3.80(dd, 1H); 5.29(dd, 1H); 7.30(d, 1H); 7.45–7.90(m, 7H).
HPLC: $R_t$=16.3 min (Method A1)

Calculated for $C_{16}H_{17}N_3O_1HCl$: C, 63.26; H, 5.97; N, 13.83%; found: C, 63,37; H, 6.11; N, 13.53%.

{(1R)-1-{N-Methyl-N-[(1R)-1-(3-methyl-1,2,4-oxadiazol-5-yl)-2-(2-naphthyl)ethyl]-carbamoyl)-2-(2-naphthyl)ethyl}carbamic acid tertbutyl ester:

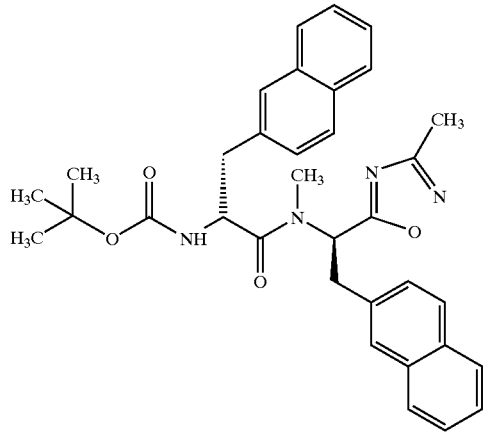

N-(3-Dimethylaminopropyl)-N'-ethylcarbodiimide hydrochloride (1.12 g, 5.85 mmol) and 1-hydroxy-7-azabenzotriazole (0.8 g, 5.85 mmol) were added to a solution of (R) N-tert-butoxycarbonyl-3-(2-naphthyl)alanine (1.84 g, 5.85 mmol) in N,N-dimethylformamide (45 mL). After 30 min at 20° C. a mixture of (R) N-methyl-N-{1-(3-methyl-1,2,4-oxadiazol-5-yl)-2-(2-naphthyl)ethyl}amine hydrochloride (1.27 g, 4.18 mmol) and triethylamine (0.42 g, 4.18 mmol) in N,N-dimethylformamide (15 mL) were added. After 18 hours at 20° C. the reaction mixture was poured on water (200 mL) and extracted several times with ethyl acetate (110 mL). The combined organic phases were washed with aqueous citric acid (10%, 40 mL), a saturated solution of sodium hydrogen carbonate (3×40 mL) and water (3×40 mL). After drying (magnesium sulfate) the solvent was concentrated in vacuo to give 2.4 g of crude {(1R)-1N-methyl-N-[(1R)-1-(3-methyl-1,2,4-oxadiazol-5-yl)-2-(2-naphthyl)ethyl]carbamoyl}2-(2-naphthyl)ethyl}carbamic acid tertbutyl ester which was used for the next step without further purification.

(2R)-2-Amino-N-methyl-N-[(1R)-1-(3-methyl-1,2,4-oxadiazol-5-yl)-2-(2-naphthyl)-ethyl]-3-(2-naphthyl)propionamide (as a Trifluoroacetate):

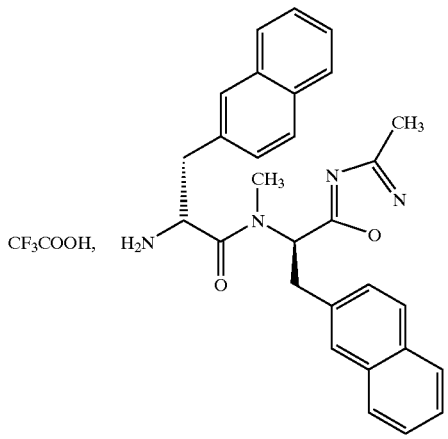

{(1R)-1-{N-Methyl-N-[(1R)-1-(3-methyl-1,2,4-oxadiazol-5-yl)-2-(2-naphthyl)ethyl]-carbamoyl}2-(2-naphthyl)ethyl}carbamic acid tertbutyl ester (2.4 g, 4.2 mmol) was dissolved in a mixture of trifluoroacetic acid (40 mL) and dichloromethane (40 mL) at 20° C. After 10 min the reaction mixture was concentrated in vacuo and coevaporated from dichloromethane (80 mL). The residue was crystallised from ethyl acetate to give 1. 19 g of (2R)-2-amino-N-methyl-N-[(1R)-1-(3-methyl-1,2,4-oxadiazol-5-yl)-2-(2-naphthyl)-ethyl]-3-(2-naphthyl)propionamide, trifluoroacetic acid.

mp 190–191° C.
$^1$H-NMR (DMSO-$d_6$) d 2.33(s, 3H); 2.88(s, 3H); 3.00–3.15(m, 2H); 3.45(dd, 1H); 3.65(dd, 1H); 4.71 (t, 1H); 7.25–7.95(m, 14H).
HPLC: $R_t$=24.3 min (Method A1)
Calculated for $C_{29}H_{28}N_4O_2$, $CF_3COOH$: C, 64.35; H, 5.05; N, 9.68%; found: C, 64,30; H, 5.13; N, 9.44%.
—2-Methylpiperidine-1,4-dicarboxylic acid 1-tert-butyl ester:

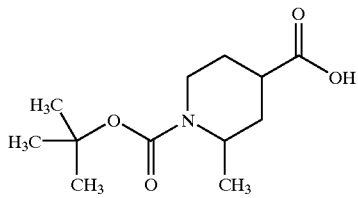

A suspension of 2-chloro-4-carboxy-6-methylpyridine (5.1 g, 3.0 mmol) in hydrochloric acid (1N, 50 mL) was hydrogenated over palladium on charcoal (20%, 0.95 g) at 150psi of hydrogen at 60° C. for 18 hours. The reaction mixture was filtered and concentrated in vacuo. The crude product was dissolved in aqueous sodium hydroxide (1N, 53 mL) and a solution of di-tert-butyloxocarbonyl (6.35 g, 29.1 mmol) in tetrahydrofuran (30 mL) was added. After 3 days at room temperature the reaction mixture was extracted with diethyl ether (50 mL) at pH 10. The aqueous phase was adjusted to pH 2 with sulfuric acid (1N, 30 mL) and extracted with ethyl acetate (30 mL). The organic phase was washed with water (4×15 mL), dried (magnesium sulfate) and concentrated in vacuo. The residue was chromatographed on silica (105 g) using ethyl acetate and heptane (1:1) as eluent to give 1.8 g of 2-methylpiperidine-1,4-dicarboxylic acid 1-tert-butyl ester.
M.p. 109–112° C.
$^1$H-NMR (DMSO-$d_6$) d 1.13(d, 3H); 1.42(s, 9H); 1.70(m, 1H); 1.95(m, 2H); 2.60(m, 1H); 3.12(m, 1H); 3.31(s, 1H); 3.77(m, 1H); 4.15(m, 1H); 12.25 (s, 1H).

Calculated for C$_{12}$H$_{21}$N$_1$O$_4$: C, 59.24; H, 8.70; N, 5.76%; found: C, 59.39; H, 9.13; N, 5.58%.

4-(1-{Methyl-[1-(3-methyl-1,2,4-oxadiazol-5-yl)-2-(2-naphthyl)ethyl]carbamoyl}-2-(2-naphthyl)ethyl)carbamoyl)-2-methylpiperidine-1-carboxylic acid tert-butyl ester:

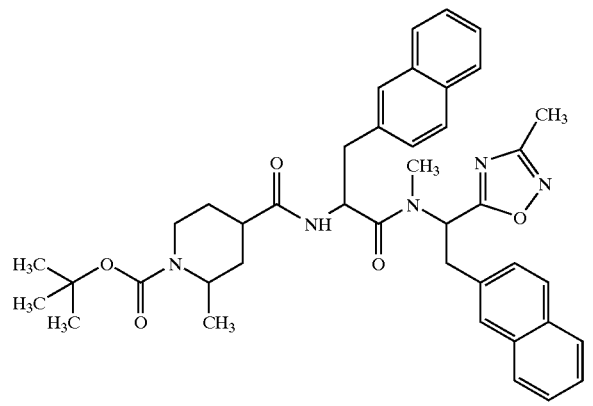

N-(3-Dimethylaminopropyl)-N'-ethylcarbodiimide hydrochloride (0.46 g, 2.42 mmol) and 1-hydroxybenzotriazole monohydrate(0.37 g, 2.41 mmol) were added to a solution of 2-methylpiperidine-1,4-dicarboxylic acid-1-tert-butylester (0.59 g, 2.42 mmol) in N,N-dimethylformamide (8 mL). After 30 min at 20° C. a solution of (2R)-2-amino-N-methyl-N-[(1R)-1-(3-methyl-1,2,4-oxadiazol-5-yl)-2-(2-naphthyl)ethyl]-3-(2-naphthyl) propionamide (as a trifluoroacetate) (1.0 g, 1.73 mmol) and diisopropylethylamine (0.22 g, 1.73 mmol) in N,N-dimethylformamide (4 mL) was added. After 18 h at 20° C. the reaction mixture was poured on water (100 mL) and extracted several times with ethyl acetate (total 60 mL). The collected organic phases were washed with aqueous citric acid (10%, 20 mL), a saturated solution of sodium hydrogen carbonate (20 mL) and water (3×20 mL). After drying (magnesium sulfate) the solution was concentrated in vacuo to give 1.25g of crude 4-(1-{methyl-[1-(3-methyl-1,2,4-oxadiazol-5-yl)-2-(2-naphthyl)ethyl]carbamoyl}2-(2-naphthyl)ethyl)-carbamoyl)-2-methylpiperidine-1-carboxylic acid tert-butyl ester that was used for the next step without further purification.

HPLC: R$_t$=35.8min (Method A1)

4-(1-{Methyl-[1-(3-methyl-1,2,4-oxadiazol-5-yl)-2-(2-naphthyl)ethyl]carbamoyl}-2-(2-naphthyl)ethyl)carbamoyl)-2-methylpiperidine-1-carboxylic acid tert-butyl ester (1.25 g, 1.81 mmol) was dissolved in a mixture of trifluoroacetic acid (5 mL) and dichloromethane (5 mL). After 10 min at 20° C. the reaction mixture was quenched with a saturated solution of sodium hydrogen carbonate (45 mL) and extracted with dichloromethane (60 mL). The organic phases were collected, dried (magnesium sulfate) and concentrated in vacuo. The residue was chromatographed on silica gel (105 g) using a 10% mixture of ammonia in ethanol and dichloromethane (1:9) as eluent to give 0.90 g of the title compound, which was finally lyophilysed in 10% acetic acid.

HPLC: R$_t$=24.3min (Method A1)

PDMS: calculated: 589.7 [M] found: 589.5±1 [M+1]

Example 28
4-Amino-cyclohexanecarboxylic acid N-methyl-N-((1R)-1-[N-methyl-N{(R)-1-methylcarbamoyl-2-phenylethyl}carbamoyl]-2-(2-naphtyl)ethyl)amide:

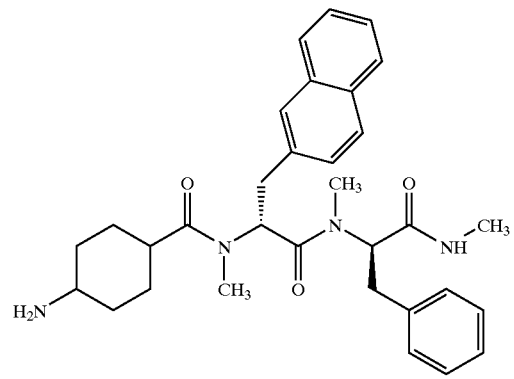

4-tert-Butoxycarbonylamino-cyclohexanecarboxylic acid:

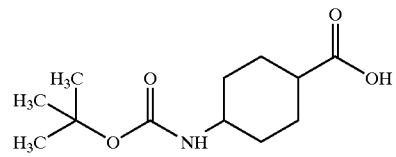

To a suspension of 4-aminocyclohexane carboxylic acid (3.0 g, 20.95 mmol) in dioxan (40 mL) and water (20 mL) was added 20 ml of a 1 M sodium hydroxide solution. Di-tert-butyl dicarbonate (5.0 g, 23.05 mmol) was added and the mixture was stirred overnight. The mixture was concentrated in vacuo to 30 ml of solvent and 60 ml of ethyl acetate was added and the mixture was cooled to OOC. The mixture was acidified to pH 2 with sodium bisulfate and the aqueous phase was extracted with ethyl acetate (2×100 ml). The combined organic phases were washed with water (100 ml) and dried over magnesium sulfate and concentrated in vacuo to give 4.13 g of 4-tert-butoxycarbonylamino cyclohexanecarboxylic acid. 1H-NMR (DMSO-d$_6$): dH 1.3 (s, 9H) 1.3–1.6 (m, 5H) 1.9 (m, 3H), 2.3 (m, 1H) 6.7 (m, 1H)

(4-[N-Methyl-N-{1R)-1-(N-methyl-[(1R)-1-(methylcarbamoyl)-2-phenylethyl]-carbamoyl)-2-(2-naphtyl)ethyl}carbamoyl]cyclohexyl)carbamic acid tert-butyl ester:

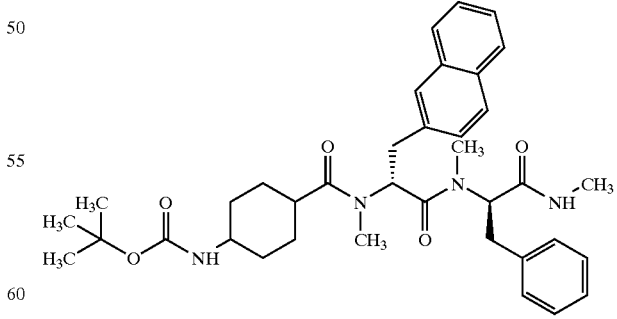

To a suspension of 4-tert-butoxycarbonylamino cyclohexanecarboxylic acid (115 mg, 0.47) in 5 ml of dichloromethane was added 1-hydroxy-7-azabenzotriazole (64 mg, 0.47 mmol) in 0.5 ml N,N-dimethylformamide. 1-Ethyl-3-(3-dimethylaminopropyl)carbodiimide hydrochloride (100 mg, 0.52) was added and the solution was stirred for 20 min. Diisopropylethylamine (120 mg, 0.94 mmol) and N-methyl-2-methylamino-N-(1-methylcarbamoyl-2-phenylethyl)-3-(2-naphthyl)propionamide (191 mg, 0.47 mmol) in 5 ml of dichloromethane was added and the mixture was allowed to stand overnight at room temperature. The mixture was washed with water (5 ml), sodium bicarbonate (5 ml) water (2×5 ml) and brine (5 ml), dried over magnesium sulfate and concentrated in vacuo. The crude product was chromatographed on silica (20 g) with ethyl acetate as eleuent to give 242 mg of (4-[N-Methyl-N{1R)-1-(N-methyl-[(1R)-1-(methylcarbamoyl)-2-phenylethyl]carbamoyl)-2-(2-naphtyl)ethyl}-carbamoyl]cyclohexyl)carbamic acid tert-butyl ester.

$^1$H-NMR (CDCl$_3$): d 1.0–1.8 (m, 8H) 1.5 (d, 9H) 2.4 (s, 3H) 2.7–3.3 (m, 4H) 2.9 (s, 3H) 3.0 (s, 3H) 3.7 (m, 1H) 4.6 (m, 1H) 5.2–5.8 (m, 2H) 7.0–7.8 (n), 12H)

4-Amino-cyclohexanecarboxylic acid N-methyl-N-((1R)-1-[N-methyl-N-{(1R)-1-methylcarbamoyl-2-phenylethyl}-carbamoyl]-2-(2-naphthyl)ethyl)amide:

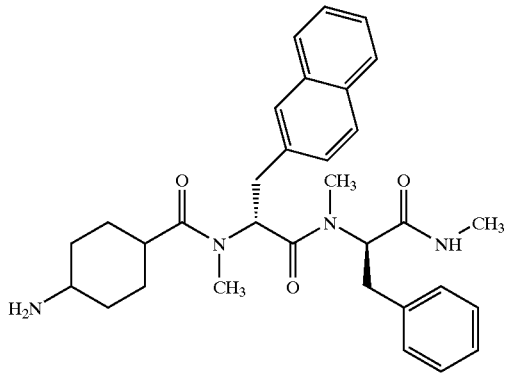

To a solution of (4-[N-Methyl-N-{(1R)-1-(N-methyl-[(1R)-1-(methylcarbamoyl)-2-phenylethy]carbamoyl)-2-(2-naphthyl)-ethyl}carbamoyl]cyclohexyl)carbamic acid tert-butyl ester (240 mg, 0.38 mmol) in 1 ml dichloromethane was added 0.5 ml trifluoroacetic acid and the mixture was stirred for 5 min. Sodium bicarbonate was added until gas evolution has ceased, and the mixture was extracted with dichloromethane (3×15 ml). The combined organic phases were washed with brine (5 ml), dried over magnesium sulfate and concentrated in vacuo. The crude product was chromatographed on silica (16 g) with dichloromethane/methanol (4:1). The obtained product was dissolved in 3 ml of methanol and added 40 ml of water and 0.5 ml of acetic acid and lyophilized to give 99 mg of the title compound.

$^1$H-NMR (DMSO-d$_6$), (free base): d 1.2–1.5 (m, 8H) 2.05 (s, 3H) 2.65 (d, 3H) 2.7 (s, 3H) 2.5–3.3 (m, 6H) 5.4 (m, 1H) 5.6 (m, 1H) 7.1–7.8 (m, 12H)

HPLC: R$_t$=30.2 min (method A1)

Example 29

N-Methyl-N-((1R)-1-methylcarbamoyl-2-phenylethyl)-2-(N-methyl-N-{[(2-piperidinyl)methoxy]acetyl}amino)-3-(2-naphthyl)propinamide:

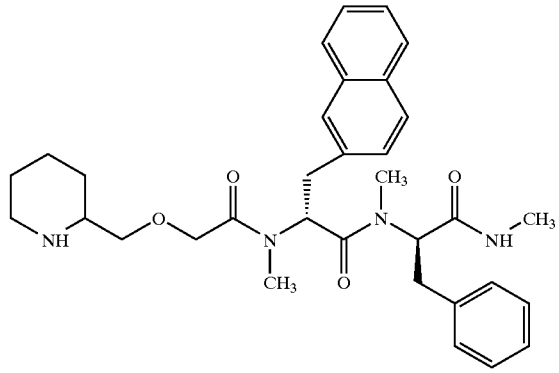

2-(Carboxymethoxymethyl)piperidine-1-carboxylic acid tert-butylester:

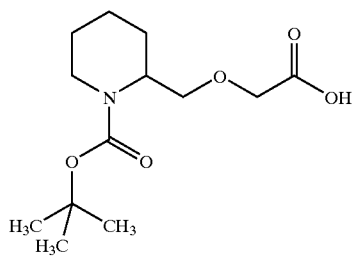

To a solution of N-(tert-butoxycarbonyl)-2-hydroxymethylpiperidine in 500 ml of dichloroethane was added 180 mg of rhodium(II) acetate and the mixture was heated to 80° C. Ethyldiazoacetate (3.7 ml, 35 mmol) in 180 ml dichloroethane was added (during approx. 1 hour) and stirred at 80° C. for 6 hours. Another portion of ethyldiazoacetate (1.25 ml, 12 mmol) in 40 ml of dichloroethane was added (over 20 min) and the mixture was refluxed at 80° C. for 7 h. The mixture was cooled to room temperature and washed with sodium bicarbonate (150 ml) and brine (100 ml), dried over magnesium sulfate and concentrated in vacuo. The crude product was chromatographed on silica (100 g) with pentane:ethyl acetate (4:1) as eluent to give 2.64 g of 2-(((ethoxycarbonyl)methoxy)methyl)piperidine-1-carboxyl acid tert-butylester. The obtaining product was taken up in 40 ml of 1 M LiOH in water:methanol (1:3) and stirred at room temperature for 30 min. The mixture was concentrated in vacuo and water (20 mL) was added and the solution was washed with ether (20 mL). The aqueous phase was acidified to pH 4 with 1 M aqueous hydrogen chloride and extracted with ethyl acetate (50 ml), dried over magnesium sulfate and concentrated in vacuo to give 2.41 g of 2-(carboxymethoxymethyl)piperidine-1-carboxylic acid tert-butylester.

MHz-$^1$H-NMR (CDCl$_3$): d 1.45 (s, 9H) 1.55 (m, 2H) 1.85 (m, 2H) 3.1 (m, 2H) 3.6 (m, 1H) 3.8 (m, 2H) 4.15 (s, 2H) 2-([N-Methyl-N-{1R)-1-(N-methyl-N-[(1R)-1-(methylcarbamoyl)-2-phenylethyl]-carbamoyl)-2-(2-naphthyl)ethyl}carbamoyl]methoxymethyl)piperidin-1-carboxylic acid tert-butyl ester:

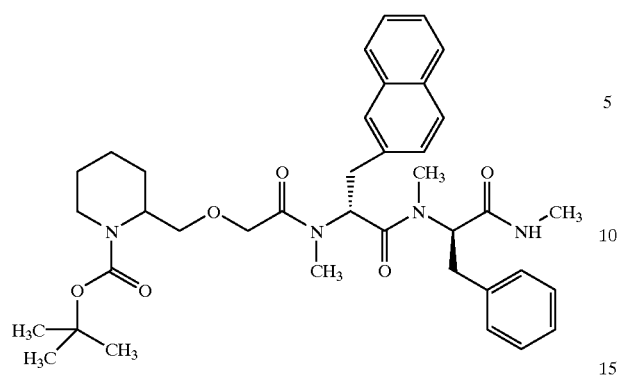

To a solution of 2-(carboxymethoxymethyl)piperidine-1-carboxylic acid tert-butylester (225 mg, 0.82 mmol) in 5 ml of dichloromethane was added 1-hydroxy-7-azabenzotriazole (112 mg, 0.82 mmol) and 1-ethyl-3-(3-dimethylamino-propyl)carbodiimide hydrochloride (173 mg, 0.90 mmol) and the mixture was to stirred for 30 min. N-Methyl-2-methylamino-N-(1-methylcarbamoyl-2-phenylethyl)-3-(2-naphthyl)propionamide (332 mg, 0.82 mmol) in dichloromethane (5mL) was added followed by diisopropylethylamine (0.14 ml, 0.82 mmol) and the mixture was stirred overnight at room temperature. The mixture was washed with water (5 ml) aqueous sodium bicarbonate (5 ml), water (2×5 ml), brine (5 ml), dried over magnesium sulfate and concentrated in vacuo. The crude product was chromatographed on silica (20 g) with ethyl acetate to give 416 mg of 2-([N-methyl-N-{(1R)-1-(N-methyl-N-[(1R)-1-(methylcarbamoyl)-2-phenylethyl]carbamoyl)-2-(2-naphthyl)ethyl}carbamoyl]methoxymethyl)piperidin-1-carboxylic acid tert-butyl ester.

$^1$H-NMR (CDCl$_3$) (selected peaks): d 1.45 (s, 9H) 2.45 (d, 3H) 2.75 (d, 3H) 2.90 (d, 3H) 3.0 (s, 2H)

To a solution of 2-([N-methyl-N-{(1R)-1-(N-methyl-N-[(1R)-1-(methylcarbamoyl)-2-phenylethyl]carbamoyl)-2-(2-naphthyl)ethyl}carbamoyl]methoxymethyl)piperidin-1-carboxylic acid tert-butyl ester (388 mg, 0.60 mmol) in dichloromethane (1 mL) was added trifluoroacetic acid (1 mL) and the mixture was stirred for 10 min at room temperature. Then saturated sodium bicarbonate was added until pH 8 and the organic phase was separated. The aqueous phase was extracted with dichloromethane (2×10 ml) and the combined organic phases were washed with brine (5 ml), dried over magnesium sulfate and concentrated in vacuo. The crude product was chromatographed on silica (15 g) with dichloromethane:methanol (9:1) to give 273 mg of the title compound.

$^1$H-NMR (CDCl$_3$) (selected peaks): d 5.3 (m, 1H) 5.75 (t, 1H) 7.0–7.8 (m, 12H)

EI/SPMS: 559.5 (M+)

HPLC: R$_t$=32.0 (Method A1)

Example 30
(2R)-N-Methyl-N-((1R)-1-(methylcarbamoyl)-2-phenylethyl)-2-(methyl[{piperidin-4-yloxy}acetyl]amino)-3-(2-naphthyl)propionamide:

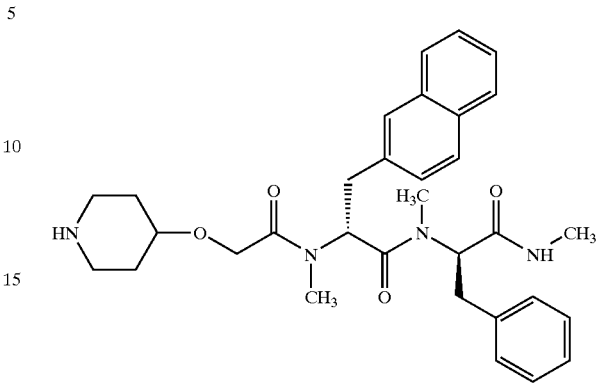

4-(Carboxymethoxy)piperidine-1-carboxylic acid tert-butyl ester:

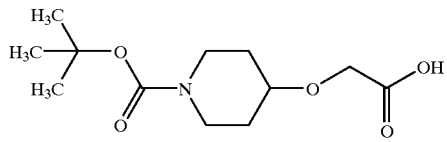

To a solution of 4-hydroxy-piperidine-1-carboxylic acid tert-butyl ester (5.0 g, 25 mmol) and rhodium(II) acetate (180 mg) in 500 ml dichloroethane at 80° C. was added (over 90 min) ethyl diazoacetate (4.2 ml, 50 mmol) in 220 ml dichloroethane. The mixture was stirred for 7 h and quenched with aqueous sodium bicarbonate (2×100 ml). The organic phase was isolated and washed with brine (2×100 ml), dried over magnesium sulfate and concentrated in vacuo. The crude product was chromatographed on silica (80g) in petroleum ether:ethyl acetate (4:1) to give 3.4 g of 4-(ethoxycarbonylmethoxy)piperidine-1-carboxylic acid tert-butylester. The product was taken up in 40 ml of a 1 M lithium hydroxide solution in water:methanol (1:3) and stirred for 60 min. The mixture was concentrated in vacuo and dissolved in 20 ml of water, acidified to pH 4 with 1 M aqueous hydrogen chloride and extracted with ethyl acetate (3×30 ml). The combined organic layers were washed with brine (10 ml), dried over magnesium sulfate and concentrated in vacuo to give 1.79 g of 4-(carboxymethoxy)piperidine-1-carboxylic acid tert-butyl ester.

$^1$H-NMR (CDCl$_3$): d 1.45 (s, 9H) 1.55 (m, 2H) 1.9 (m, 2H) 3.1 (m, 2H) 3.6 (m, 1H) 3.8 (m, 2H) 4.2 (s, 2H)

A solution of 4-(carboxymethoxy)piperidine-1-carboxylic acid tert-butyl ester (228 mg, 0.88 mmol), 1-hydroxy-7-azabenzotriazole (120 mg, 0.88 mmol) and 1-ethyl-3-(3-dimethylaminopropyl)carbodiimide hydrochloride (186 mg, 0.97 mmol) was stirred for 30 min at room temperature. N-Methyl-2-methylamino-N-(1-methylcarbamoyl-2-phenylethyl)-3-(naphthalen-2-yl)propionamide (355 mg, 0.88 mmol) in 5 ml of dichloromethane was added followed by diisopropylethylamine (0.2 ml, 1.14 mmol) and the mixture was stirred for 2 days at room temperature. The mixture was washed with water (5 ml) aqueous sodium bicarbonate (5 ml), water (2×5 ml), brine (5 ml), dried over magnesium sulfate and concentrated in vacuo. The crude product was chromatographed on silica (30 g) with ethyl acetate as eluent to give 391 mg of 4-([N-methyl-N-{(1R)-1-(N-methyl-N-[(1R)-1-(methyl carbamoyl)-2-phenylethyl]

carbamoyl)-2-(2-naphthyl)ethyl}carbamoyl]methoxy] piperidin-1-carboxylic acid tert-butylester. The product was taken up in 50% trifluoromethane/dichloromethane and allowed to stand for 10 min. Then saturated sodium bicarbonate was added until pH was about 8 and the organic layer was separated. The aqueous phase was extracted with dichloromethane (2×10 ml) and the combined organic phases were washed with brine (5 ml), dried over magnesium sulfate and concentrated in vacuo. The crude product was chromatographed on silica (15 g) with dichloromethane:methanol (9:1) to give 327 mg of the title compound.

$^1$H-NMR (CDCl$_3$) (selected peaks): d 3.75 (q, 2H) 5.5 (m, 1H) 5.8 (t, 1H) 7.0–7.8 (m, 12H)

EI/SPMS: 544.5 (M+)

HPLC: R$_t$=28.9 (Method A1)

Example 31

2-[1-Methyl-2-(2-amino-(2-methylpropoxy))acetylamino]-N-(1-methyl-1-((1-methylcarbamoyl)-2-(2-phenylethyl)-3-(2-naphthyl))propionamide:

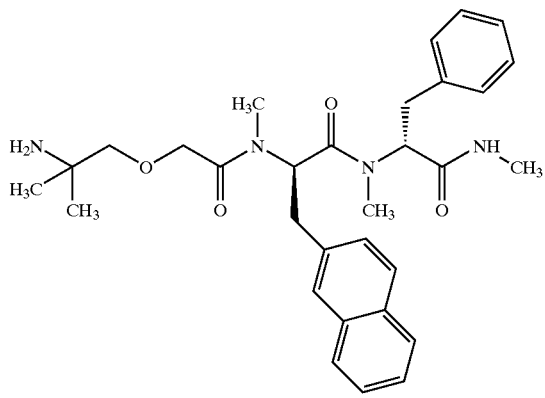

A solution of 2-butoxycarbonylamino-2-methylpropanol (5.0 g, 26.46 mmol) and rhodium(II)acetate (90 mg) in dichloroethane (500 mL) was heated to 80° C. Ethyldiazoacetate (4.0 g, 34.78 mmol) was slowly added over a period of 1 hr., and the mixture was stirred at reflux for 3 hr. Another 90 mg of rhodium(II)acetate was added and the mixture was refluxed for another 5 hr. The mixture was cooled overnight and 500 ml of saturated sodium bicarbonate was added, the yellow organic layer was separated and washed twice with saturated sodium bicarbonate (2×200 ml). The organic layer was dried over magnesium sulfate and concentrated in vacuo. The yellow oil was taken up in 200 ml of 1 M Lithium hydroxide in methanol:water (3:1) and stirred overnight. The solvent was removed in vacuo to a minimum and water was added (pH>9) and the mixture was washed with ether. Then 1 M hydrogen chloride was added until pH<4 and the mixture was extracted with ethyl acetate, dried over magnesium sulfate and concentrated in vacuo to give 2.5 g (38%) of (2-t-butoxycarbonylamino-2-methylpropoxy) acetic acid as a clear oil.

H$^1$-NMR (CDCl$_3$, 400 MHz) d 1.3 (s, 6H); 1.45 (s, 9H); 3.5 (s, 2H); 4.15 (s, 2H); 9.9 (b, 1H).

A solution of (2-tert-butoxycarbonylamino-2-methylpropoxy) acetic acid (184 mg, 0.74 mmol), 1-hydroxy-7-azobenzotriazole (101 mg, 0.74 mmol) and 1-ethyl-3-dimethylaminopropyl carbodiimide hydrocloric acid (157 mg, 0.82 mmol) in 9 ml of methylene chloride and 1 ml of DMF was stirred for 15 min. Tert N-methyl-2-methylamino-N-(1-methylcarbamoyl-2-phenylethyl)-3-(naphthalen-2-yl)propionamide (300 mg, 0.74 mmol) and diisopropylethylamine (96 mg, 0.74 mmol) in 1 ml of methylene chloride were added and allowed to stir overnight. The mixture was washed with saturated sodium bicarbonate, dried over magnesium sulfate and concentrated in vacuo. The mixture was chromatographed on 100 ml of silica gel with ethyl acetate to give 360 mg (76%) of 2-[1-methyl-2-(2-(t-butoxycarbonyl) amino-(2-methylpropoxy))acetylamino]-N-(1-methyl-1-((1-methylcarbamoyl)-2-(2-phenylethyl)-3-(2-naphthyl)) propionamide. The obtained mixture was taken up in 1 ml of TFA and 1 ml of methylene chloride and stirred at 0° C. for 5 min. Then saturated sodium bicarbonate was slowly added to the cooled solution and the organic layer was separated, washed with sodium bicarbonate, dried over magnesium sulfate and concentrated in vacuo to give 185 mg (47% from (2-t-butoxycarbonylamino-2-methylpropoxy) acetic acid) of 2-[1-methyl-2-(2-amino-(2-methylpropoxy))acetylamino]-N-(1-methyl-1-((1-methylcarbamoyl)-2-(2-phenylethyl)-3-(2-naphthyl))propionamide as an oil. The obtained oil was dissolved in dissolved in 0.1 N acetic acid (50 ml) and lyophilized to give an amorph white powder.

H$^1$-NMR (CDCl$_3$, 400 MHz, free amine) d 0.9 (d, 3H); 1.05 (d, 3H); 2.35 (s, 3H); 2.75 (s, 3H); 2.8 (s, 3H); 2.9 (s, 2H); 3.0 (s, 2H); 3.0–2.7 (m, 2H); 3.25 (m, 2H); 3.7 (t, 1H); 5.1 (dd, J=20 Hz, 1H); 5.8 (t, 1H, amine); 7.8–6.9 (m, 12H).

HPLC: Rt=30.65 min in (A1); 97% purity

Calculated for C$_{31}$H$_{40}$N$_4$O$_4$, CH$_3$COOH, H$_2$O: C, 64.9%; H, 7.6%; N, 9.1%; Found: C, 64.2%; H, 7.6%; N, 8.5%

Example 32

(2R)-2-(N-((2R)-2-(N-((2E)-5-((2R)-2-Hydroxypropylamino)-5-methylhex-2-enoyl)-N-methylamino)-3-(2-naphthyl)propionyl)-N-methylamino)-N-methyl-3-phenylpropionamide;

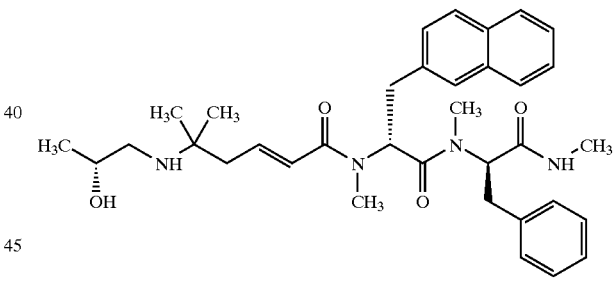

(2R)-2-(N-((2R)-2-(N-((2E)-5-((2R)-2-(tert-butyldimethylsilyloxy)propylamino)-5-methylhex-2-enoyl)-N-methylamino)-3-(2-naphthyl)propionyl)-N-methylamino)-N-methyl-3-phenylpropionamide;

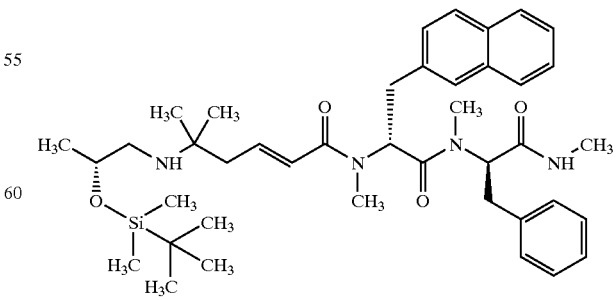

(2E)-5-Amino-5-methylhex-2-enoic acid N-methyl-N-((1R)-1-(N-methyl-N-((1R)-1-(methylcarbamoyl)-2- phenylethyl)carbamoyl)-2-(2-naphthyl)ethyl)amide (318 mg, 0.60 mmol) was dissolved in methanol (20 ml) and glacial acetic acid (0.48 ml, 8.4 mmol). 3 Å mol sieves (9 g) and a solution of (2R)-2-(tert-butyldimethylsilyloxy) propanal (1.33 g, 7.06 mmol) in methanol (10 ml) were added successively. Sodium cyanoborohydride (220 mg, 3.53 mmol) was added as a solid. The reaction mixture was stirred at room temperature for 45 min, before a second batch of sodium cyanoborohydride (220 mg, 3.53 mmol) was added. The reaction mixture was stirred for 16 h at room temperature. The mol sieves was filtered off through a plug of celite. The celite was washed with methanol (200 ml). The solvents of the combined filtrates were removed in vacuo. The residue was dissolved in 1 N sodium hydroxide solution (50 ml) and tert-butyl methyl ether (50 ml). The phases were separated. The aqueous phase was extracted with tert-butyl methyl ether (3×50 ml). The combined organic layers were dried over magnesium sulfate. The solvent was removed in vacuo. The crude product was purified by flash chromatography on silica (35 g), using ethyl acetate/heptane/triethylamine (20:10:1) as eluent, to give 99 mg of (2R)-2-(N-((2R)-2-(N-((2E)-5-((2R)-2-(tert-butyldimethylsilyloxy)propylamino)-5-methylhex-2-enoyl)-N-methylamino)-3-(2-naphthyl)propionyl)-N-methylamino)-N-methyl-3-phenylpropionamide.

$^1$H-NMR (CDCl$_3$, selected values): d 0.04, 0.05, and 0.10 (all s, together 6H); 0.85 and 0.91 (both s, together 9H); 3.86 (m, 1H); 6.04 and 6.08 (both d, together 1H); 6.89 (m, 1H).

MS: 701.2 [M+1].

HPLC: The RP-analysis was performed using UV detections at 214, 254, 276, and 301 nm on a 218TP54 4.6 mm×250 mm 5 m C-18 silica column (The Seperations Group, Hesperia), which was eluted at 1 m Lumin at 42° C. The column was equilibrated with 5% acetonitrile in a buffer consisting of 0.1% aqueous trifluoro acetic acid eluted by a gradient of 0% to 90% of 0.1% trifluoro acetic acid in acetonitrile during 50 min: R$_t$=37.25 min.

(2R)-2-(N-((2R)-2-(N-((2E)-5-((2R)-2-(tert-Butyldimethylsilyoxy)propylamino)-5-methylhex-2-enoyl)-N-methylamino)-3-(2-napthyl)prionyl)-N-methylamino-N-methyl-3-phenylpropionamide (99 mg, 0.14 mmol) was dissolved in tetrahydrofuran (2 ml). Tetra-n-butylammonium fluoride (0. 18 ml of a 1.1I M solution in tetrahydrofuran, 0.2 mmol) was added. The solution was stirred for 3 h, before another portion of tetra-n-butylammonium fluoride (0.23 ml of a 1.1 M solution in tetrahydorfuran, 0.25 mmol) was added. The reaction mixture was stirred for 2.5 h at room temperature and diluted with ethyl acetate (50 ml). It was extracted with 10% sodium carbonate solution (30 ml). The aqueous phase was extracted with ethyl acetate (20 ml). The organic layers were combined and dried over magnesium sulfate. The solvent was removed in vacuo. The crude product was purified by flash-chromatography on silica (30 g), using dichloromethanelmethanol/25% aqueous ammonia (100:10:1) as eluent, to give 28 mg of the title compound.

$^1$H-NMR (CDCl$_3$, selected values): d 3.65 and 3.72 (both m, together 1H); 5.15 and 5.30 (both dd, together I H); 5.60 and 5.90 (both dd, together 1H); 6.03 and 6.05 (both d, together 1H); 6.78 (m, 1H).

MS: 587.2 [M+1].

HPLC: R$_t$=27.47 (A1).

R$_t$=27.12 (B1).

For biological testing it was transferred into the acetate by liophilization from 0.5 M acetic acid (20 ml).

Example 33
(2E)-5-Amino-N-((1R)-1-(N-((1R)-1-benzyl-2-((methylsulfonyl)amino)ethyl)-N-methylcarbamoyl)-2-(2-naphthyl)ethyl)-5-methyl-N-methylhex-2-enamide;

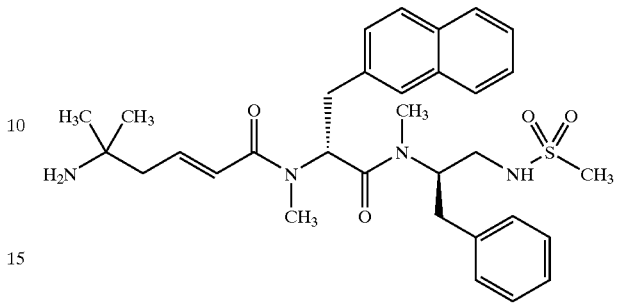

N-((1R)-1-Benzyl-2-(benzylamino)ethyl)-N-methylcarbamic acid tert-Butylester;

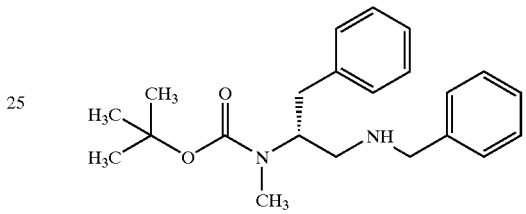

A solution of oxalyl chloride (3.16 ml, 36.17 mmol) in dichloromethane (50 ml) was coooled to −78° C. A solution of dimethylsulfoxide (3.42 ml, 48.22 mmol) in dichloromethane (50 ml) was added dropwise. The reaction mixture was stirred for 5 min at −78° C. A solution of N-((1R)-1-(hydroxymethyl)-2-phenylethyl)-N-methylcarbamic acid tert-butylester (6.40 g, 24.11 mmol) in dichloromethane (100 ml) was added dropwise over a period of 10 min. The solution was stirred for 25 min at −78° C. Ethyldiisopropylamine (16.68 ml, 96.44 mmol) was added dropwise at −78° C. The solution was warmed to −35° C., and immediately cooled to −78° C. Glacial acetic acid (6.07 ml, 106.08 mmol) was added. The reaction mixture was warmed to room temperature and diluted with dichloromethane (150 ml). It was washed with saturated sodium chloride solution (2×200 ml) and dried over magnesium sulfate. The solvent was removed in vacuo. The crude product was dissolved in methanol (200 ml). Benzylamine (2.6 ml, 24.1 mmol) was added. Glacial acetic acid (6.0 ml, 106 mmol) and 3 Å mol sieves (32 g) were added. Sodium cyanoborohydride (1.00 g, 15.9 mmol) was added as a solid. The reaction mixture was stirred for 1 h, before another portion of sodium cyanoborohydride (0.97 g, 15.4 mmol) was added. The mixture was first stirred for 16 h at room temperature and successively left 3 days without stirring. The mol sieves was filtered off through a plug of celite. The celite was washed with methanol (200 ml). The solvent was removed in vacuo. The residue was dissolved in 1 N sodium hydroxide solution/diethyl ether (250 ml/250 ml). The phases were separated. The aqueous phase was extracted with diethyl ether (2×100 ml). The combined organic layers were dried over magnesium sulfate. The solvent was removed in vacuo. The crude product was purified by flash chromatography on silica (230 g), using dichloromethane/methanol/25% aqueous ammonia (first 100:10:1, then 50:10:1) as eluent, to give 4.54 g of N-((1R)-1-benzyl-2-(benzylamino)ethyl)-N-methylcarbamic acid tert-butylester.

¹H-NMR (CDCl₃): d 1.28 and 1.36 (both br, together 9H); 2.50–2.90 (m, 8H); 3.70 (d, 1H); 3.88 (d, 1H); 4.45 and 4.65 (both br, together 1H); 7.10–7.40 (m, 10H).

MS: 355.2 [M+H]⁺.

N-((1R)-1-Aminomethyl-2-phenylethyl)-N-methylcarbamic acid tert-butylester;

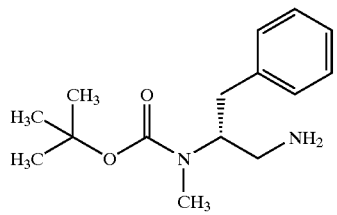

A suspension of 20% palladium hydroxide on charcoal (4.63 g) and N-((1R)-1-benzyl-2-(benzylamino)ethyl)-N-methylcarbamic acid tert-butylester (4.40 g, 12.4 mmol) was kept for 8 h under a hydrogen atmosphere at (pressure: 1 atm). The reaction mixture was flushed with nitrogen and filtered through a plug of celite. The solvent was removed. The crude product was purified by flash chromatography on silica (110 g), using dichloromethanelmethanol/25% aqueous ammonia as eluent, to give 830 mg of N-((1R)-1-aminomethyl-2-phenylethyl)-N-methylcarbamic acid tert-butylester.

¹H-NMR (CDCl₃): d 1.29 and 1.36 (both s, together 9H); 1.40 (s, 2H); 2.60–2.90 (m, 7H); 4.20 and 4.38 (both br, together 1H); 7.10–7.35 (m, 5H).

N-((1R)-1-Benzyl-2-((methylsulfonyl)amino)ethyl)-N-methylcarbamic acid tert-butylester;

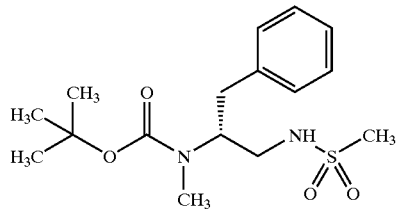

N-((1R)-1-Aminomethyl-2-phenylethyl)-N-methylcarbamic acid tert-butylester (830 mg, 3.14 mmol) was dissolved in dichloromethane (15 ml). Triethylamine (0.44 ml, 3.14 mmol) was added. The solution was cooled to −78° C. A solution of methanesulfonyl chloride (0.24 ml, 3.14 mmol) in dichloromethane (2 ml) was added dropwise. The reaction mixture was stirred for 16 h, while it was warming up to room temperature. It was diluted with dichloromethane (100 ml) and washed with saturated sodium chloride solution (100 ml). It was dried over magnesium sulfate. The solvent was removed in vacuo. The crude product was purified by flash chromatography on silica (65 g), using ethyl acetatelheptane (2:1) as eluent, to give 990 mg of N-((1R)-1-Benzyl-2-((methylsulfonyl)amino)ethyl)-N-methylcarbamic acid tert-butylester.

¹H-NMR (CDCl₃): d 1.30 and 1.40 (both br, together 9H); 2.60–3.00 (m, 5H); 2.93 (br, 3H); 3.15–3.50 (m, 2H); 4.40 (br, 1H); 4.50 and 4.70 (both br, together 1H); 7.05–7.35 (m, 5H).

N-((2R)-2-Methylamino-3-phenylpropyl)methansulfonamide;

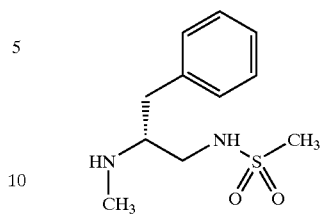

At 0° C., trifluoroacetic acid (5 ml) was added to a solution of N-((1R)-1-benzyl-2-((methylsulfonyl)amino) ethyl)-N-methylcarbamic acid tert-butylester (913 mg, 2.67 mmol) in dichloromethane (5 ml). The reaction mixture was stirred for 15 min at 0° C. The solvent was removed in vacuo without warming. The residue was dissolved in dichloromethane (50 ml) and the solvent was removed in vacuo. The latter procedure was repeated two times. The crude product was purified by flash chromatography on silica (20 g), using dichloromethane/methanol/25% aqueous ammonia as eluent, to give 658 mg of N-((2R)-2-methylamino-3-phenylpropyl)methansulfonamide.

¹H-NMR (CDCl₃, selected values): d 2.39 (s, 3H); 2.70–3.00 (m, 4H); 2.95 (s, 3H); 3.22 (dd, 1H), 7.15–7.35 (m, 5H).

N-((1R)-1-(N-((1R)-1-Benzyl-2-((methylsulfonyl)amino) ethyl)-N-methylcarbamoyl)-2-(2-naphthyl)ethyl)-N-methylcarbamic acid tert-butylester;

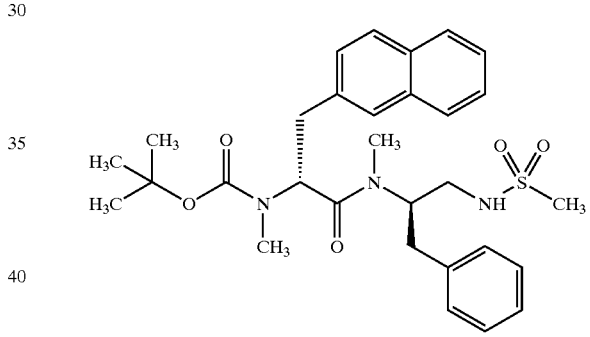

(2R)-2-(N-(tert-Butoxycarbonyl)-N-methylamino)-3-(2-naphthyl)propionic acid (1.05 g, 3.2 mmol) was dissolved in N,N-dimethylformamide (2 ml) and dichloromethane (2 ml). Hydroxy-7-azabenzotriazole (434 mg, 3.2 mmol) was added as a solid. The solution was cooled to 0° C. N-(3-dimethylaminopropyl)-N'-ethylcarbodiimide hydrochloride (612 mg, 3.2 mmol) was added. The solution was stirred for 5 min at 0° C. A solution of N-((2R)-2-methylamino-3-phenylpropyl)methansulfonamide (703 mg, 2.9 mmol) in dichloromethane (2 ml) was added. Ethyldiisopropylamine (0.50 ml, 2.90 mmol) was added. The solution was stirred for 27 h, while it was warming up to room temperature. It was diluted with ethyl acetate (200 ml) and extracted with 1N hydrochloric acid (100 ml). The aqueous phase was extracted with ethyl acetate (50 ml). The combined organic layers were washed with saturated sodium hydrogen carbonate solution and dried over magnesium sulfate. The solvent was removed in vacuo. The crude product was purified by flash chromatography on silica (45 g), using ethyl acetate/heptane (2:1) as eluent, to give 1.037 g of N-((1R)-1-(N-((1R)-1-Benzyl-2-((methylsulfonyl)amino) ethyl)-N-methylcarbamoyl)-2-(2-naphthyl)ethyl)-N-methylcarbamic acid tert-butylester.

¹H-NMR (CDCl₃, selected values): d 1.30 and 1.34 (both br, together 9H); 7.00-7.90 (m, 12H). N-((2R)-2-(N-Methyl- N-((2R)-2-methylamino-3-(2-naphthyl)propionyl)amino)-3-phenylpropyl)methanesulfonamide;

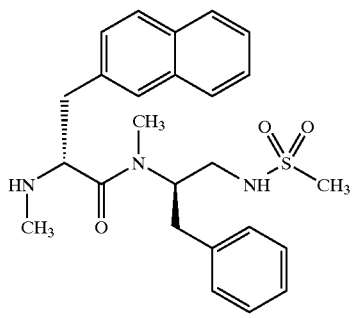

At 0° C., trifluoroacetic acid (4 ml) was added to a solution of N-((1R)-1-(N-((1R)-1-benzyl-2-((methylsulfonyl)amino)ethyl)-N-methylcarbamoyl)-2-(2-naphthyl)ethyl)-N-methylcarbamic acid tert-butylester (997 mg, 1.8 mmol) in dichloromethane (4 ml). The solution was stirred for 15 min at 0° C. The solvent was removed in vacuo at 20 ° C. The residue was dissolved in dichloromethane and the solvent was removed in vacuo. The latter procedure was repeated two times. The crude product was purified by flash chromatography on silica (45 g), using dichloromethane:methanol/25% aqueous ammonia as eluent, to give 646 mg of N-((2R)-2-(N-methyl-N-((2R)-2-methylamino-3-(2-naphthyl)propionyl)amino)-3-phenylpropyl)methanesulfonamide.

$^1$H-NMR (CDCl$_3$, selected values): d 1.87, 2,33, 2.38, 2,50, 2.62, 2.80, 2.82, 2.88, and 2,92 (all s, together 9H); 3.62 and 3.76 (both dd, together 1H); 4.56 and 4.72 (both br, together 1H); 4.84 and 5.02 (both br, together 1H); 6.90–7.95 (m, 12H).

MS: 454.2 [M+H]$^+$.

(3E)-4-(N-((1R)-1-(N-((1R)-1-Benzyl-2-(methylsulfonylamino)ethyl)-N-methylcarbamoyl)-2-(2-naphthyl)ethyl)-N-methylcarbamoyl)-1,1-dimethylbut-3-enylcarbamic acid tert-butyl ester;

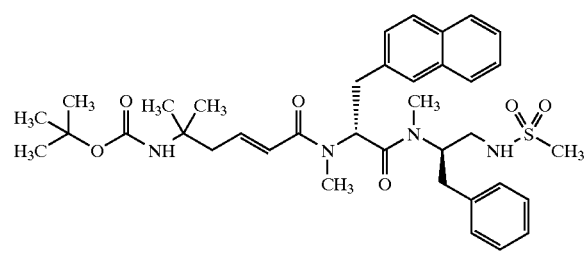

(2E)-5-tert-Butoxycarbonylamino-5-methylhex-2-enoic acid (352 mg, 1.45 mmol) was dissolved in N,N-dimethylformamide (2 ml) and dichloromethane (2 ml). Hydroxy-7-azabenzotriazole (197 mg, 1.45 mmol) was added as a solid. The solution was cooled to 0° C. N-(3-dimethylaminopropyl)-N'-ethylcarbodiimide hydrochloride (278 mg, 1.45 mmol) was added. The solution was stirred for 15 min at 0° C. A solution of N-((2R)-2-(N-methyl-N-((2R)-2-methylamino-3-(2-naphthyl)propionyl)amino)-3-phenylpropyl)methanesulfonamide (598 mg, 1.32 mmol) in dichloromethane (2 ml) and ethyldiisopropylamine (0.23 ml, 1.32 mmol) were added successively. The solution was stirred for 18 h, while it was warming up to room temperature. It was diluted with ethyl acetate (100 ml) and extracted with 1 is N hydrochloric acid. The aqueous phase was extracted with ethyl acetate (50 ml). The combined organic layers were washed with saturated sodium hydrogen carbonate solution (100 ml) and dried over magnesium sulfate. The solvent was removed in vacuo. The crude product was purified by flash chromatography on silica (60 g), using ethyl acetate/heptane (2:1) as eluent to give 740 mg of (3E)A-4-(N-((1R)-1-(N-((1R)-1 benzyl-2-(methylsulfonylamino)ethyl)-N-methylcarbamoyl)-2-(2-naphthyl)ethyl)-N-methylcarbamoyl)-1,1-dimethylbut-3-enylcarbamic acid tert-butyl ester.

$^1$H-NMR (CDCl$_3$, selected values): d 2.60, 2.80, 2.89, 2.92, 3.06, and 3.17 (all s, 259 together 9H); 6.06 and 6.25 (both d, together 1H); 6.82 and 6.96 (both m, together 1H); 7.00–7.85 (m, 12H).

(3E)-4-(N-((1R)-1-(N-((1R)-1-Benzyl-2-(methylsulfonylamino)ethyl)-N-methylcarbamoyl)-2-(2-naphthyl)ethyl)-N-methylcarbamoyl)-1,1-dimethylbut-3-enylcarbamic acid tert-butyl ester (729 mg, 1.07 mmol) was dissolved in dichloromethane (3 ml). The solution was cooled to 0° C. Trifluoroacetic acid (3 ml) was added. The reaction mixture was stirred for 15 min at 0° C. The solvents were removed in vacuo at 20° C. The residue was dissolved in dichloromethane (100 ml) and the solvent was removed in vacuo. The latter procedure was repeated two times. The crude product was purified by flash chromatography on silica (60 g), using dichloromethane:methanol/25% aqueous ammonia as eluent, to give 440 mg of the title compound as free base.

$^1$H-NMR (CDCl$_3$, selected values): d 1.10, 1.11, 1.1.14, and 1.15 (all s, together 6H); 2.64, 2.71, 2.88, 2.90, 3.06, 3.18 (all s, together 9H); 4.76 and 5.00 (both br, together 1H); 4.95 and 5.09 (both dd, together 1H); 6.08 and 6.28 (both d, together 1H); 6.83 and 7.00 (both m, together 1H).

MS: 579.0 [M+H]$^+$.

HPLC: R$_t$=31.98 min (A1).

R$_t$=27.53 min (B1).

For biological testing the title compound was transferred into its acetate by liophilization from 40 ml 0.5 M aqueous acetic acid.

Example 34

3-(1-Aminoethyl)benzoic acid N-methyl-N-((1R)-1-(N-methyl-N-((1R)-1-(methylcarbamoyl)-2-phenylethyl)carbamoyl)-2-(2-naphthyl)ethyl)amide:

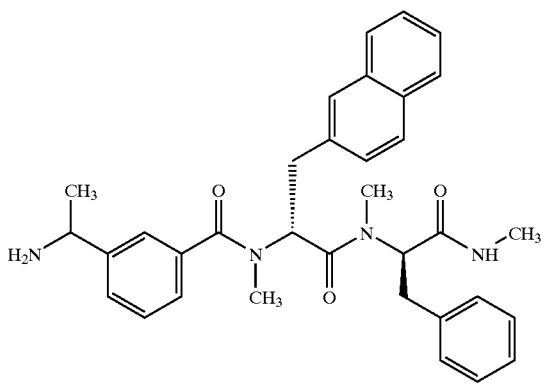

3-(1-(N-tertbutoxycarbonyl)aminoethyl) benzoic acid:

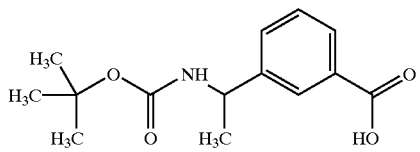

Ammonium acetate (10.6 g, 138 mmol) was evaporated from dry ethanol (100 mL), and redissolved in dry methanol (100 mL) over molecular sieves (3A, 3 g). 3Acetylbenzonitrile (2.0 g, 13.8 mmol) was added. After 30 minutes at room temperature sodium cyanoborohydride (0.87 g, 138 mmol) was added and the reaction mixture was stirred for 18 hours. The reaction mixture was concentrated in vacuo and redissolved in water (100 mL). Concentrated hydrochloric acid was added until pH 2, and the aqueous solution was extracted with ethyl acetate (2×100 mL). The aqueous phase was adjusted to pH 11 with solid potassium hydroxide, and extracted with dichloromethane (2×100 mL). The combined organic phases were dried (magnesium sulfate) and concentrated in vacuo. A concentrated solution of hydrogen chloride in ethyl acetate added (100 mL) was, and the solution was concentrated in vacuo. The residue was dissolved in ethanol (25 mL) and sulphuric acid (9N, 25 mL) was added. After 16 hours at room temperature and 2 hours at reflux temperature the ethanol was removed by evaporation in vacuo and the residual aqueous mixture was adjusted to pH >8 using solid potassium hydroxide. Ditertbutyldicarbonate (2.0 g) dissolved in tetrahydrofuran (100 mL) was added at 0° C. After 18 hours at room temperature the reaction mixture was concentrated in vacuo and redissolved in water (100 mL). Solid citric acid was added until pH 5. The reaction mixture was extracted with dichloromethane (2×100 mL), and the combined organic phases was dried (magnesium sulfate) and concentrated in vacuo. The residue was purified by column chromatography on silica gel (3×40 cm) using ethanol and dichloromethane (1:9) as eluent to give 1.1 g of 3-(1-(N-tertbutoxycarbonyl)aminoethyl) benzoic acid.

3-(1-(N-tert-Butyloxycarbonyl)aminoethyl)benzoic acid (132 mg, 0.50 mmol), 1-hydroxy-7-azabenzotriazole (68 mg, 0.50 mmol) and 1-ethyl-3(3-dimethylaminopropyl) carbodiimide hydrochloride (96 mg, 0.50 mmol) were dissolved in N,N-dimethylformamide(3 mL) and stirred for 15 min. (2R)-N-Methyl-N-((1R)-2-phenyl)-1-(methylcarbamoyl)ethyl)-2-methylamino-3-(2-naphtyl) propionamide (100 mg, 0.25 mmol) dissolved in dichloromethane (6 mL) was added followed by addition of diisopropylethylamine (0.085 mL, 0.50 mmol) and the mixture was stirred for 20 hours. The reaction mixture was evaporated in a stream of nitrogen and the residue was dissolved in ethyl acetate (25 mL). The mixture was washed with aqueous sodium hydrogen carbonate (2×25 mL, 5%) and aqueous potassium hydrogen sulfate (25 mL, 5%). The organic phase was dried (sodium sulfate) and evaporated in vacuo. The residue was dissolved in dichloromethane (2.5 mL), cooled to 0–4° C. and treated with trifluoroacetic acid (2.5 mL) for 10 minutes at 0–4° C. The volatiles were removed with a stream of nitrogen an the oily residue was dissolved in 0.1% triflouroacetic acid in acetonitrile and water (7:3, 10 mL) and diluted with water (290 mL). This solution was submitted to semipreperative HPLC purification using a 25×200 mm C18 column and using a linear gradient of 25–40% acetonitrile in water containing 0.1M ammonium sulfate (pH 2.5). The product was purified in three runs and after ion exchange on a Waters Seppak C18 the effluent was lyophilised to give the title compound.

PD-MS: Calculated 551.7 (M+1); Found 551.3 (M+1)

HPLC: Rt=31.8 min (Method A1)

Rt=33.93 min (Method B1)

Example 35

5-Amino-5-methyl-hex-2-enoic acid ((1R)-1-(((1R)-1-((2R)-2-hydroxypropylcarbamoyl)-2-phenylethyl) methylcarbamoyl)-2-t2-naphthyl)ethyl) methylamide:

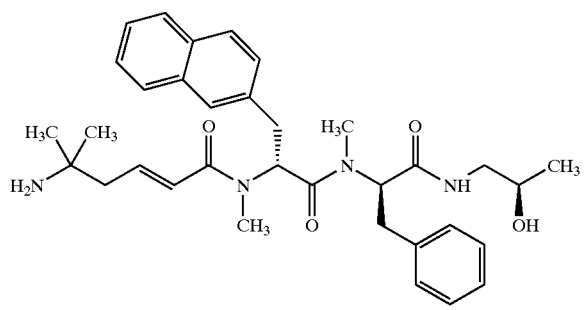

The title compound was prepared analogously to example 1.

$^1$H-NMR (CDCl$_3$): (selected peaks for major rotamer) d 1.09 (d, 3H); 1.19 (s, 6H); 2.97 (s, 3H); 2.99 (s, 3H); 5.15 (dd, 1H); 5.53 (dd, 1H); 6.12 (d, 1H)

HPLC: r$_t$=31.8 min. (A1)

PDMS: m/z 573.7 (M+H)$^+$

Example 36

(4-(1-Aminocyclobutyl)but-2-enoic acid ((1R)-1-(((1R)-1-(1-methylcarbamoyl-2-phenylethyl)methylcarbamoyl)-2-(2-naphthyl)ethyl)methylamide:

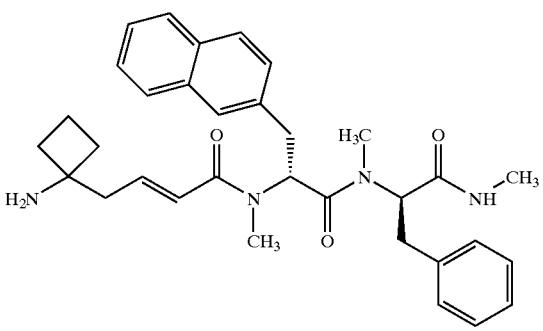

The title compound was prepared analogously to example 1. (4-(1-Aminocyclobutyl)but-2-enoic acid was prepared as in R. Graf, Org. Synth. 46, 51 (1966) and example 1.

$^1$H-NMR (CDCl$_3$): (selected peaks for major rotamer) d 2.26 (s, 3H); 2.98 (s, 3H); 3.00 (s, 3H); 5.15 (dd, 1H); 5.57 (dd, 1H); 6.11 (d, 1H).

HPLC: r$_t$=32.2 min. (A1)

Example 37

5-Amino-5-methyl-hex-2-enoic acid ((1R)-1-(((1R)-1-((2S)-2-hydroxypropylcarbamoyl)-2-(2-thienyl)ethyl)methylcarbamoyl)-2-(2-naphthyl)ethyl)methylamide.

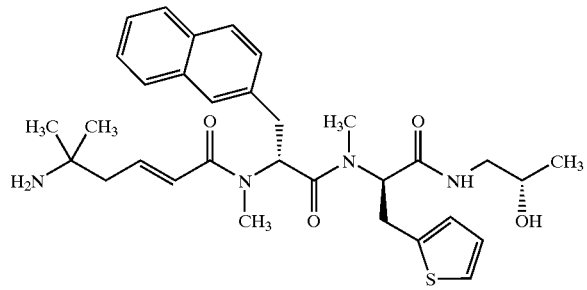

This compound was prepared analogously to example 1.

$^1$H-NMR (CDCl$_3$): (selected peaks for major rotamer) d 1.10 (d, 3H); 1.14 (s, 3H; 1.15 (s, 3H); 2.18 (d, 2H); 2.95 (s, 3H); 3.05 (s, 3H); 5.28 (dd, 1H); 5.72 (dd, 1H); 6.07 (d, 1H).

HPLC: r$_t$=30.4 min. (A1)

Example 38

(2R)-2-(N-[(2R)-2-(N-[(2-Aminobutoxy)acetyl]-N-methylamino)-3-(2-naphthyl)propionyl]-N-methylamino)-N-methyl-3-phenylpropionamide:

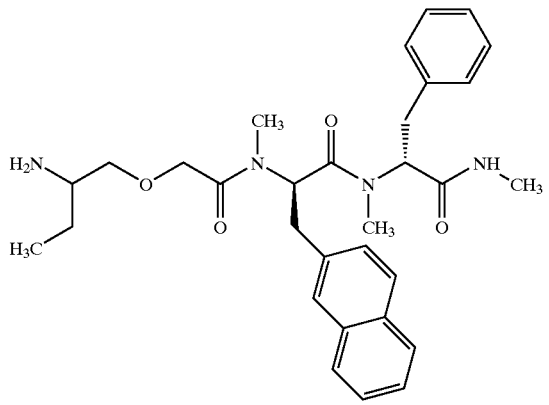

(2-(tert-Butoxycarbonylamino)butoxy)acetic acid:

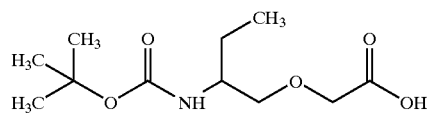

To a solution of (1-(hydroxymethyl)propyl)carbamic acid tert-butylester (7.2 g, 39 mmol) in 1,2-dichloroethane (500 ml) rhodium(II)acetate (180 mg) was added and the mixture was heated to 80° C. Ethyldiazoacetate (6.0 ml, 57 mmol) in 1,2-dichloroethane (1 80 ml) was added over a period of 60 min and the mixture was heated at 80° C. for 6 hours. Then another portion of ethyldiazoacetate (2.0 ml, 19 mmol) in 1,2-dichloroethane (40 ml) was added and the mixture was refluxed for 7 hours. The mixture was cooled to room temperature and washed with sodium bicarbonate (2×1 00 ml) and brine (100 ml), dried over magnesium sulfate and concentrated in vacuo. The crude product was chromatographed on silica (300 g) is with pentane/ethyl acetate 7:3 as eluent to give 4.3 of (2-(tert-butoxycarbonylamino)butoxy)acetic acid ethylester. The product was dissolved in of 1 M lithium hydroxide in water/methanol 1:3 (40 ml) and stirred at room temperature for 4 hours. The mixture was concentrated in vacuo and water (100 mL) was added and the solution was washed with ether (20 mL). The aqueous phase was acidified to pH 4 with 1 M aqueous hydrogen chloride and extracted with ethyl acetate (200 ml), dried over magnesium sulfate and concentrated in vacuo to give 2.46 g of (2-(tert butoxycarbonylamino)butoxy)acetic acid.

$^1$H-NMR (CDCl$_3$): d 0.95 (t, 3H) 1.45 (s, 9H) 1.60 (m, 3H) 3.55 (m, 2H) 4.10 (s, 2H)

To a solution of (2-(tert-butoxycarbonylamino)butoxy) acetic acid (1.1 g, 4.5 mmol) in dichloromethane (20 ml) were added 1-hydroxy-7-azabenzotriazole (612 mg, 4.5 mmol) and 1-ethyl-3-(3-dimethylaminopropyl)carbodiimide hydrochloride (9.5 mg, A5.0 mmol) and the mixture was stirred for 30 min. (2R)-N-methyl-2-methylamino-N-((1R)-1-methyl-carbamoyl-2-phenylethyl)-3-(2-naphthyl) propionamide (605 mg, 1.5 mmol) in dichloromethane (10 ml) was added followed by diisopropylethylamine (0.33 ml, 2.0 mmol) and the mixture was stirred for 2 hours at room temperature. The mixture was washed with water (10 ml), saturated aqueous sodium bicarbonate (10 ml), water (2×10 ml), brine (10 ml), dried over magnesium sulfate and concentrated in vacuo. The crude product was chromatographed on silica (40 g) with ethyl acetate/heptane 4:1 to give 766 mg of (1-[{N-methyl-N-((1R)-1-[N-methyl-N-{(1R)-1-(methylcarbamoyl)-2-phenylethyl}carbamoyl]-2-(2-naphthyl)ethyl)carbamoyl}methoxymethyl]-propyl) carbamic acid tert-butylester. The obtained product was taken up in 50% trifluoroacetic acid in dichloromethane (5 ml) and stirred for 10 min. Then saturated sodium bicarbonate was added until pH 8 and the phases were separated. The aqueous phase was extracted with dichloromethane (2×10 ml) and the combined organic phases were washed with brine (5 ml), dried over magnesium sulfate and concentrated in vacuo to give (2R)-2-(N-[(2R)-2-(N-[{2-aminobutoxy}acetyl]-N-methylamino)-3-(2-naphthyl) propionyl]-N-methylamino)-N-methyl-3-phenylpropionamide as an oil. The product was redissolved in water (30 ml) and acetic acid (2 ml) was added and the mixture was lyophilized to give 645 mg of the acetate salt of the title compound as an amorphous powder.

LC-MS: 533.0 (M+H)$^+$

HPLC: R$_t$=31.1 (Method A1)

$^1$H-NMR (DMSO) (selected peaks): d 0.6–0.8 (m, 3H) 2.65 (d, 3H) 2.75 (s, 3H) 5.35 (dd, 1H) 5.65 (dd, 1H) 7.1–7.9 (arom, 12H)

Example 39

(2R)-N-Methyl-2-(N-methyl-N-((2R)-2-(N-methyl-N-((((2S)-pyrrolidin-2-yl)methoxy)acetyl)amino)-3-(2-naphthyl)propionyl)amino)-3-phenylpropionamide

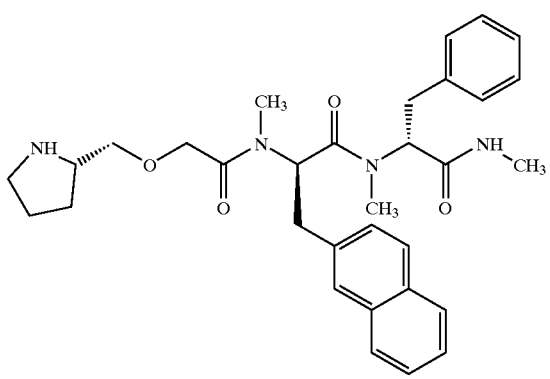

(2S)-2-(((Carboxy)methoxy)methyl)pyrrolidin-1-carboxylic acid tert-butylester

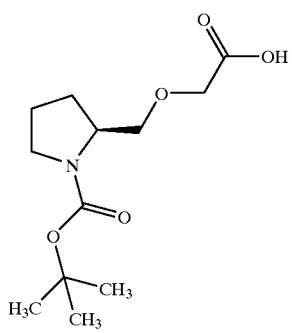

To a solution of N-t-butyloxycarbonyl-(S)-prolinol (5.0 g, 25 mmol) in 1,2-dichloroethane (500 ml) rhodium(II)acetate (180 mg) was added and the mixture was heated to 80° C. Ethyldiazoacetate (3.9 ml, 37 mmol) in 1,2-dichloroethane (180 ml) was added over a period of 90 min and the mixture was heated at 80° C. for 3 hours. Then another portion of ethyldiazoacetate (1.3 ml, 12 mmol) in 1,2-dichloroethane (40 ml) was added and the mixture was refluxed for 6 hours. The mixture was cooled to room temperature and washed with saturated sodium bicarbonate (2×100 ml) and brine (100 ml), dried over magnesium sulfate and concentrated in vacuo. The crude product was chromatographed on silica (300 g) with petrol ether/ethyl acetate 4:1 as eluent to give 4.7 g of (2S)-2-(((ethoxycarbonyl)methoxy)methyl) pyrrolidin-1-carboxylic acid tert-butylester. The obtained product was taken up in 50 ml of 1 M lithium hydroxide in water/methanol 1:3 and stirred at room temperature overnight. The mixture was concentrated in vacuo, water (20 mL) was added and washed with ether (20 mL). The aqueous phase was acidified to pH 4 with I M aqueous hydrogen chloride and extracted with ethyl acetate (200 ml), dried over magnesium sulfate and concentrated in vacuo to give 3.6 g of (2S)-2-(((carboxy)methoxy)methyl)pyrrolidin-1-carboxylic acid tert-butylester.

$^1$H-NMR (CDCl$_3$): d 1.45 (2, 9H) 1.90 (m, 4H) 3.55 (t, 2H) 3.60 (m, 3H) 4.10 (s, 2H) 10.6 (s, 1H)

To a solution of (2S)-2-(((carboxy)methoxy)methyl)-pyrrolidin-1-carboxylic acid tert-butylester (1.2 g, 4.5 mmol) in dichloromethane (20 ml) were added 1-hydroxy-7-azabenzotriazole (612 mg, 4.5 mmol) and 1-ethyl-3-(3-dimethylaminopropyl)carbodiimide hydrochloride (950 mg, 4.95 mmol) and the mixture was stirred for 30 min. (2R)-N-Methyl-2-methylamino-N-((1R)-1-(methylcarbamoyl)-2-phenylethyl)-3-(2-naphthyl)propionamide (605 mg, 1.5 mmol) in dichloromethane (10 mL) was added followed by diisopropylethylamine (0.33 ml, 2.0 mmol) and the mixture was stirred for 2 hours at room temperature. The mixture was washed with water (10 ml), aqueous sodium bicarbonate (10 ml), water (2×10 ml), brine (10 ml), dried over magnesium sulfate and concentrated in vacuo. The crude product was chromatographed on silica (40 g) with ethyl acetate/heptane 4:1 to give 760 mg of (2S)-2-([N-methyl-N (1R)-1-(N-methyl-N-[(1R)-1-(methylcarbamoyl)-2-phenylethyl]carbamoyl)-2-(2-naphthyl)ethyl}carbamoyl] methoxymethyl)pyrrolidine-1-carboxylic acid tert-butylester. The obtained product was taken up in 50% trifluoroacetic acid in methylene chloride (5 ml) and stirred for 10 min. Then saturated sodium bicarbonate was added until pH 8 and the phases were separated. The aqueous phase was extracted with dichloromethane (2×10 ml) and the combined organic phases were washed with brine (5 ml), dried over magnesium sulfate and concentrated in vacuo. The product was redissolved in water (30 ml) and acetic acid (2 ml) was added and the mixture was liophilized to give 720 mg of the acetate salt of the title compound as an amorphous powder.

$^1$H-NMR (DMSO) (selected peaks): d 0.75 (m, 1H) 1.35 (m, 1H) 1.6 (m, 1H) 1.7 (m, 1H) 2.65 (d, 3H) 2.75 (d, 3H) 3.95 (d, 2H) 5.35 (dd, 1H) 5.55 (dd, 1H)

LC-MS: 544.8 (M+H)$^+$

HPLC: R$_t$=31.1 (Method A1)

Example 40

3-((2R)-2-(N-((2R)-2-(N-((2-Amino-2-methylpropoxy) acetyl)-N-methylamino)-3-(2-naphthyl)propionyl)-N-methylamino)-3-phenylpropionylamino)propyl acetate

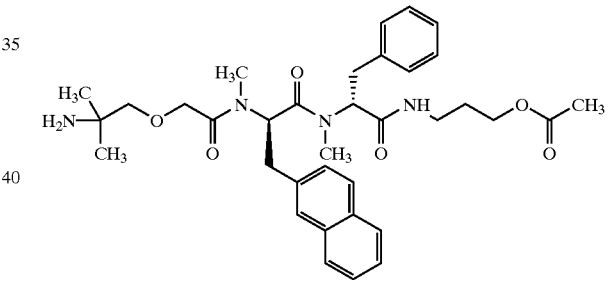

To a solution of (2-t-butoxycarbonylamino-2-methylpropoxy) acetic acid (504 mg, 2.0 mmol) in dichloromethane (10 ml) were added 1-hydroxy-7-azabenzotriazole (278 mg, 2.0 mmol) and 1-ethyl-3-(3-dimethylaminopropyl)carbodiimide hydrochloride (429 mg, 2.3 mmol) and the mixture was stirred for 30 min. 3-((2R)-2-(N-((2R)-2-methylamino-3-(2-naphthyl)propionyl)-N-methylamino)-3-phenylpropionylamino)-propyl acetate (500 mg, 1.0 mmol) in dichloromethane (10 mL) was added followed by diisopropylethylamine (0.23 ml, 1.32 mmol) and the mixture was stirred overnight at room temperature. The mixture was washed with water (10 ml), aqueous sodium bicarbonate (10 ml), water (2×10 ml), brine (10 ml), dried over magnesium sulfate and concentrated in vacuo. The crude product was chromatographed on silica (60 g) with ethyl acetate/heptane 4:1 to give 623 mg of 3-((2R)-2-(N-((2R)-2-(N-((2-(tert-butoxycarbonylamino)-2-methylpropoxy) acetyl)-N-methylamino)-3-(2-naphthy) propionyl)-N-methylamino)-3-phenylpropionylamino)-propyl acetate as an oil. The obtained product was taken up in 50% trifluoroacetic acid in dichloromethane (3 ml) and stirred for 10 min. Then saturated sodium bicarbonate was added until pH 8 and the organic phase was separated. The aqueous phase was extracted with dichloromethane (2×10 ml) and the combined organic phases were washed with brine (5 ml), dried over magnesium sulfate and concentrated in vacuo. The product was redissolved in water (30 ml) and the mixture was liophilized to give 434 mg of the title compound as an amorphous powder.

$^1$H-NMR (CDCl$_3$) (selected peaks): d 1.1 (s, 3H) 1.2 (s, 3H) 2.0 (s, 3H) 2.15 (s, 3H) 5.7 (m, 2H) 5.25 (m, 1H)

LC-MS : 619.6 (M+H)$^+$

HPLC: R$_t$=33.2 (Method A1)

Example 41

(2E)-5-Amino-5-methylhex-2-enoic acid N-((1R)-1-(N-((1R)-1-(dimethylcarbamoyl)-2-phenylethyl)-N-methylcarbamoyl)-2-(2-naphthyl)ethyl)-N-methylamide:

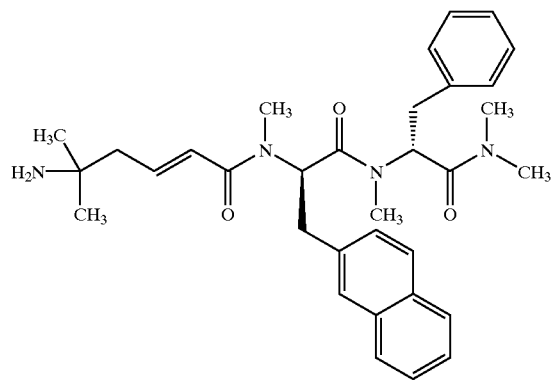

(2R)-N,N-Dimethyl-2-methylamino-3-phenylpropionamide

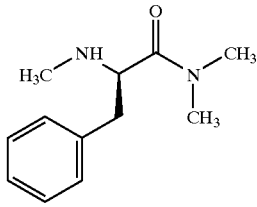

To a solution of (2R)-2-(tert-butoxycarbonylmethylamino)-3-phenylpropionic acid (10.0 g, 36.0 mmol) in dichloromethane (200 ml) was added 1-hydroxy-7-azabenzotriazole (6.8 g, 50.0 mmol) and I-ethyl-3-(3-3.0 dimethylaminopropyl)carbodiimide hydrochloride (1 0.0 g, 55.0 mmol) and the mixture was stirred for 30 min. Then dimethylamine hydrochloride (4.1 g, 50.0 mmol) in dichloromethane (100 ml) and diisopropylethylamine (19.0 ml, 110 mmol) were added and the mixture was stirred overnight at room temperature. The mixture was washed with water (100 ml) aqueous sodium bicarbonate (100 ml), water (2×100 ml), brine (100 ml), dried over magnesium sulfate and concentrated in vacuo. The crude product was chromatographed on silica (400 g) with dichloromethane/methanol 20:1 to give 6.3 g of (2R)-2-(N-(tert-butoxycarbonyl)-N-methylamino)-3phenylpropionic acid N,N-dimethylamide. The product was dissolved in 50% trifluoroacetic acid in dichloromethane (5 ml) and stirred for 10 min. Then saturated sodium bicarbonate was added until pH 8 and the phases were separated. The aqueous phase was extracted with dichloromethane (2×10 ml) and the combined organic phases were washed with brine (5 ml), dried over magnesium sulfate and concentrated in vacuo to give 4.58 mg of (2R)-N,N-dimethyl-2-methylamino-3-phenylpropionamide.

$^1$H-NMR (CDCl$_3$): d 2.3 (s, 3H) 2.7 (s, 3H) 2.9 (s, 3H) 2.8–3.4 (m, 2H) 4.45 (m, 1H) 7.1–7.3 (m, 5H)

N-((1R)-1-(N-((1R)-1-(dimethylcarbamoyl)-2-phenylethyl)-N-methylcarbamoyl)-2-(2-naphthyl)ethyl)-N-methylcarbamic acid tert-butylester

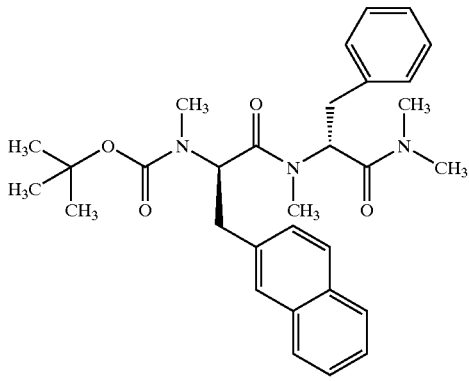

To a solution of (2R)-(N-tert-butoxycarbonyl-N-methylamino)-3-(2-naphthyl)propionic acid (8.78 g, 26.6 mmol) in dichloromethane (30 ml) were added 1-hydroxy-7-azabenzotriazole (3.62 g, 26.6 mmol) and 1-ethyl-3-(3-dimethylaminopropyl)carbodiimide hydrochloride (5.54 mg, 28.9 mmol) and the mixture was stirred for 30 min. Then (2R)-N,N-dimethyl-2-methylamino-3-phenylpropionamide (4.58 g, 22.2 mmol) in dichloromethane (15 ml) and diisopropylethylamine (4.94 ml, 28.9 mmol) were added and the mixture was stirred overnight at room temperature. The mixture was washed with water (20 ml), aqueous sodium bicarbonate (20 ml), water (2×20 ml), brine (20 ml), dried over magnesium sulfate and concentrated in vacuo. The crude product was chromatographed on silica (400 g) with ethyl acetatelheptane 1:4 to give 6.64 g of N-((1R)-1-(N-((1R)-1-(dimethylcarbamoyl)-2-phenylethyl)-N-methylcarbamoyl)-2-(2-naphthyl)ethyl)-N-methylcarbamic acid tert-butylester.

$^1$H-NMR (CDCl$_3$) (selected peaks for rotamers): d 1.1 and 1.4 (two s, 9H) 2.2, 2.3, 2.7 and 2.8 (four s, 6H) 2.35 and 2.6 (two s, 3H) 2.9 and 3.0 (two s, 3H)

A solution of N-((1R)-1-(N-((1R)-1-(dimethylcarbamoyl)-2-phenylethyl)-N-methylcarbamoyl)-2-(2-naphthyl)ethyl)-N-methylcarbamic acid tert-butylester (6.6 g, 12.8 mmol) in 50% trifluoroacetic acid/dichloromethane (15 ml) was stirred for 10 min. Then saturated sodium bicarbonate was added until pH 8 and the organic phase was separated. The aqueous phase was extracted with dichloromethane (2×20 ml) and the combined organic phases were washed with brine (10 ml), dried over magnesium sulfate and concentrated in vacuo to give 4.2 g of (2R)-N-((1R)-1-dimethylcarbamoyl-2-phenylethyl)-N-methyl-2-methylamino-3-(2-naphthyl)propionamide.

$^1$H-NMR (CDCl$_3$): d 2.7 (s, 3H) 2.75 (s, 3H) 2.85 (s, 3H) 2.9–3.15 (m, 4H) 3.7 (t, 1H) 5.8 (t, 1H) 7.1–7.8 (arom, 12H)

To a solution of (2E)-5-(tert-butyloxycarbonylamino)-5-methylhex-2-enoic acid (0.59, 2.1 mmol) in dichloromethane (5 ml) was added trifluoroacetic acid (5 ml) and stirred for 60 min and concentrated in vacuo. Then a 10% aqueous solution of sodium carbonate (30 ml) and dioxane (30 ml) were added followed by 9H-fluorenylmethyl-succinimidyl carbonate (0.67 g, 2.1 mmol) and stirred overnight. The mixture was washed with petrol ether (2×20 ml) and the aqueous layer was acidified with 4N sulphoric acid (pH~3) and extracted with ethyl acetate (3×50 ml). The combined organic layers were washed with 1N sulfuric acid, water (4×20 ml), brine (20 ml), dried (Magnesiumsulfate) and concentrated in vacuo. The obtained product was precipitated from dichloromethane/ether and filtered to give 280 mg of (2E)-5-(((9H-flouren-9-yl)methoxy)carbonylamino)-5-methyl-hex-2-enoic acid, which was used without further purification.

To a solution of (2E)-5-(((9H-flouren-9-yl)methoxy)-carbonylamino)-5-methylhex-2-enoic acid (280 mg, 0.77 mmol) in dichloromethane (5 ml) were added 1-hydroxy-7-azabenzotriazole (126 mg, 0.92 mmol) and 1-ethyl-3-(3-dimethylaminopropyl)carbodiimide hydrochloride (207 mg, 1.08 mmol) and the mixture was stirred for 30 min. Then 2R)-N-((1R)-1-dimethylcarbamoyl-2-phenylethyl)-N-methyl-2-methylamino-3-(2-naphthyl)propionamide (386 mg, 0.92 mmol) in dichloromethane (5 ml) and diisopropylethylamine (0.17 ml, 1.00 mmol) were added and the mixture was stirred overnight at room temperature. The mixture was washed with water (20 ml), saturated aqueous sodium bicarbonate (20 ml), water (2×20 ml), brine (20 ml), dried over magnesium sulfate and concentrated in vacuo. The crude product was chromatographed on silica (400 g) with ethyl acetate/heptan 1:1 to give 401 mg of ((3E)-4-(N-((1R)-1-(N-((1R)-1-dimethylcarbamoyl-2-phenylethyl)-N-methylcarbamoyl)-2-(2-naphthyl)ethyl)-N-methylcarbamoyl)-1,1-dimethylbut-3-enyl)carbamic acid 9H-flouren-9-ylmethyl ester. The obtained product was dissolved in 20% piperidine in dimethylformamide (10 ml) and stirred for 30 min. The mixture was chromatographed on silica (20 g) with dichloromethane/methanol/ammonia 89:10:1 to give 228 mg of (2E)-5-amino-5-methylhex-2-enoic acid N-((1R)-1-(N-((1R)-1-(dimethylcarbamoyl)-2-phenylethyl)-N-methylcarbamoyl)-2-(2-naphthyl)ethyl)-N-methylamide as an oil. The product was redissolved in water (30 ml) and acetic acid (2 ml) was added and the mixture was lyophilized to give 645 mg of the acetate salt of the title compound as an amorphous powder.

LC-MS: 543.0 (M+H)⁺

HPLC: R$_t$=32.9 (Method A1)

¹H-NMR (DMSO) (selected peaks): d 1.0 (s, 6H) 1.8 (s, 6H) 2.4 (s, 3H) 2,7 (s, 3H) 2.8 (s, 3H)

Example 42

5-Amino-5-methyl-hex-2-enoic acid (1-{[2-(2-fluorophenyl)-1-methylcarbamoylethyl]methylcarbamoyl}2-(2-naphthyl)ethyl)methylamide.

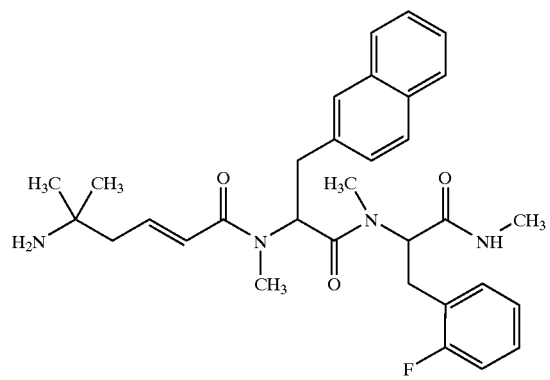

{4-[(1-{[2-(2-Fluorophenyl)-1-methylcarbamoylethyl]methylcarbamoyl}-2-(2naphthyl)ethyl)methylcarbamoyl]-1,1dimethyl-but-3-enyl}carbamic acid tert-butyl ester.

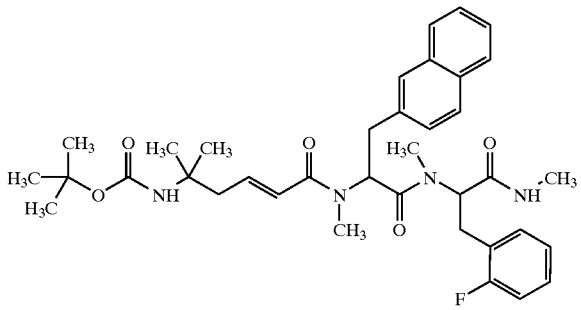

(2E)-5-(tert-Butyloxycarbonylamino)-5methylhex-2-enoic acid (0.19 g; 0.783 mmol was dissolved in methylene chloride (10 ml). 1Hydroxy-7azbenzotriazole (0.12 g; 0.861 mmol) and N-(3-dimethylaminopropyl)-N'-ethylcarbodiimide hydrochloride (0.17 g; 0.900 mmol) was added and the reaction mixture was stirred 15 min at room temperature. N-[2-(2-Fluorophenyl)-1-methylcarbamoylethyl]-N-methyl-2-methylamino-3-(2-naphthyl)propionamide (0.33 g; 0.783 mmol) and diisopropyl ethylamine (0.15 ml; 0.861 mmol) was added and the reaction mixture was stirred 12 hours at room temperature.

Methylene chloride (50 ml) was added and the reaction mixture was washed with water (50 ml), sodium hydrogen sulfate (10%; 50 ml), sodium hydrogen carbonate (sat; 50 ml), water (50 ml) and dried (magnesium sulfate). The solvent was removed in vacuo to afford 0.366 g of {4-[(1-{[2-(2-Fluorophenyl)-1-methylcarbamoylethyl]methylcarbamoyl}2-(2-naphthyl )ethyl)methylcarbamoyl]-1,1-dimethyl-but-3-enyl}carbamic acid tert-butyl ester.

{4-[(1-{[2-(2-Fluorophenyl)-1-methylcarbamoylethyl]methylcarbamoyl}2-(2-naphthyl)ethyl)methylcarbamoyl]-1,1-dimethyl-but-3-enyl}carbamic acid tert-butyl ester (0.36 g; 0.557 mmol) was dissolved in methylene chloride (3 ml). Trifluoro acetic acid (3 ml) was added and the reaction mixture was stirred 5 min at room temperature. Methylene chloride (25 ml), sodium hydrogen carbonate/sodium carbonate (3 ml) and sodium hydrogen carbonate (s) was added until pH=8. The organic phase was dried (magnesium sulfate) and the solvent was removed in vacuo. The residue was lyophylised to afford 0.237 g of the title compound.

Example 43

(2Z)-5-Amino-3,5-dimethylhex-2-enoic acid N-methyl-N-((1R)-1-(N-methyl-N-((1R)-1-methylcarbamoyl-2-phenylethyl)carbamoyl)-2-(2-naphthyl)ethyl)amide.

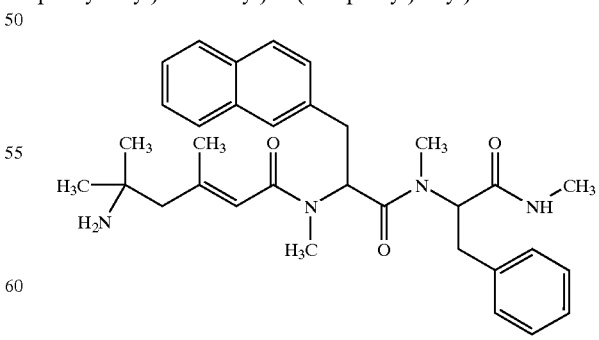

(Z)(1,1,3-Trimethyl-4-(methyl-(1-(methyl-(1-methyl carbamoyl-2-phenyl ethyl)carbamoyl)-2-(2-naphthyl) ethyl)carbamoyl)but-3-enyl)carbamic acid tert butylester (0.009 g; 0.014 mmol.) was dissolved in methylene chloride (0.12 mL) and trifluoro acetic acid (0.08 mL) was added. The reaction mixture was stirred 5 min at room temperature. Water (0.100 mL) was added. The solvent was removed in vacuo to afford 0.007 g (2Z)-5-Amino-3,5-dimethylhex-2-enoic acid N-methyl-N-((1R)-1-(N-methyl-N-((1R)-1-methylcarbamoyl-2-phenylethyl)carbamoyl)-2-(2-naphthyl)ethyl)amide ; trifluoro acetic acid salt.

ESMS: $M_w$=542.4

HPLC: $R_t$=34.82

Example 44

(2E)-5-Amino-5-methylhex-2-enoic acid N-methyl-N-((1R)-1-{N-[(1R)-2-(1-naphthyl)-1-(methylcarbamoyl)ethyl]-N-methylcarbamoyl}-2-(2-naphthyl)ethyl)amide:

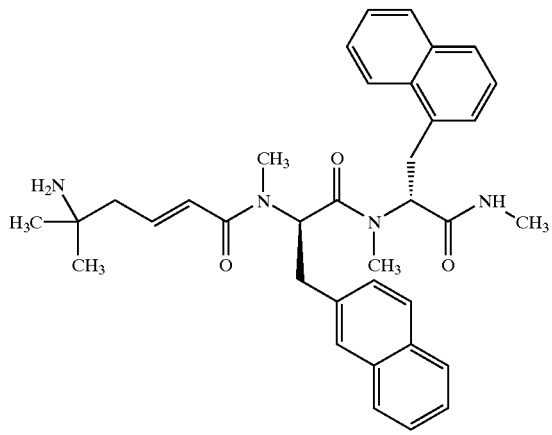

4-Formyl-3,5-dimethoxyphenol:

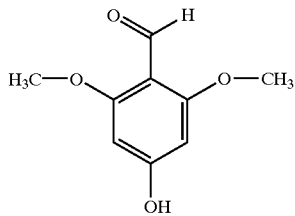

To a solution of 3,5-dimethoxyphenol (50 g, 320 mmol) in phosphorous oxychloride (60 mL, 650 mmol) at 0° C. was added dimethylformamide (37 mL, 490 mmol) over a period of 30 min and the mixture was warmed to room temperature and stirred overnight. The mixture was added to icewater (600 mL) and the mixture was washed with ether (3×200 mL). Then an 32% aqueous solution of sodium hydroxide was added until pH was 5.5 and the compound precipitated. The precipitate was separated and washed with water (100 mL) and ether (100 mL) and dried in vacuo. The precipitate was recrystallized from ethanol (600 mL) to give 22.6 g of 4-formyl-3,5-dimethoxyphenol.

bp. 224–226° C.

$^1$H-NMR (DMSO): d 3.75 (s, 6H) 6.1 (s, 2H) 10.1 (s, 1H)

Ethyl 5-(4-formyl-3,5-dimethoxyphenoxy)valerate:

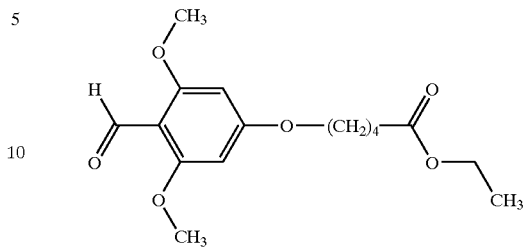

To a suspension of 4-formyl-3,5-dimethoxyphenol (22.6 g, 124 mmol) and potassium tert-butoxide (15.3 g, 136 mmol) in dimethylformamide (125 mL) was added ethyl 5-bromovalerate (28.5 g, 136 mmol) in dimethylformamide (125 mL) over a period of 20 min. The mixture was heated at 110° C. for 6 h and concentrated in vacuo. To the obtained product was added ethyl acetate (400 mL) and the mixture was filtered. The filtrate was washed with water (100 mL), 1 N sodium hydroxide (2×50 mL), and brine (3×100 mL), dried (magnesium sulfate), and concentrated in vacuo to 37 g of ethyl 5-(4-formyl-3,5-dimethoxyphenoxy)valerate.

$^1$H-NMR (CDCl$_3$): d 1.25 (t, 3H) 1.85 (m, 4H) 2.4 (m, 2H) 3.9 (s, 6H) 4.05 (t, 2H) 4.15 (q, 2H) 6.1 (s, 2H) 10.3 (1H)

5-(4-Formyl-3,5-dimethoxyphenoxy)valeric acid:

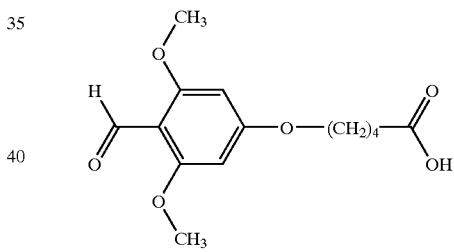

To a solution of ethyl 5-(4-formyl-3,5-dimethoxyphenoxy) valerate (37 g, 119 mmol) in methanol (200 mL) was added 4 N sodium hydroxide (200 mL) and the mixture was stirred for 2 h. The methanol was removed in vacuo, water (100 mL) was added and the mixture was washed with ethyl acetate (100 mL) and dichloromethane (2×100 mL). The aqueous layer was acidified with 12 N hydrochloric acid until pH-3 and extracted with ethyl acetate (2×200 mL). The combined organic layers were washed with brine (2×50 mL), dried (magnesium sulfate) and concentrated in vacuo. The obtained product was recrystallized from ethanol to give 26 g of 5-(4-formyl-3,5-dimethoxyphenoxy)valeric acid.

bp. 134–136° C.

$^1$H-NMR (CDCl$_3$): d 1.85 (m, 4H), 2.45 (m, 2H) 3.85 (s, 6H) 4.05 (m, 2H) 6.05 (s, 2H) 10.3 (s, 1H)

N-Methyl-PAL-Resin for Solid-Phase Synthesis (PAL Defined as in F. Albericio et al., J. Org. Chem., 55 (1990) pp. 3730–3743):

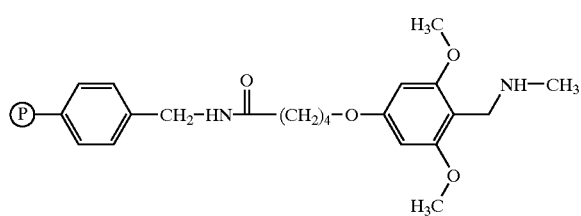

Aminomethylated polystyrene resin (10 g, 7.8 mmol, purchased from Bachem AG, # D-1005) and 1-hydroxybenzotriazole hydrate(1 g, 6.6 mmol) in dimethylformamide (100 mL) were shaken overnight. The resin was filtered and the resin was repeatedly swelled in dichloromethane and dimethylformamide until a homogeneous resin was obtained. The resin was washed with 5% diisopropylethylamine in dimethylformamide (2×100 mL) and dimethylformamide (100 mL), successively. A solution of 5-(4-formyl-3,5-dimethoxyphenoxy)valeric acid (6.6 g, 23 mmol), 1-hydroxybenzotriazole hydrate (3.5 g, 23 mmol) and diisopropylcarbodiimide (3.6 mL, 23 mmol) in dimethylformamide/dichloromethane 2:1 (50 mL) was added. After 5 h at room temperature the resin was filtered and washed with dimethylformamide (3×100 mL), dichloromethane (3×50 mL) and dichloromethane/methanol 1:1 (3×100 mL) and dried with a stream of nitrogen. To the resin in dimethylformamide (50 mL) were added 5% acetic acid in dimethylformamide (50 mL) and 40% methylamine in methanol (3.0 mL, 39 mmol) and the mixture was shaken for 20 min. Sodium triacetoxyborohydride (8.3 g, 39 mmol) was added and the mixture was shaken overnight. The mixture was filtered and the resin was washed with dimethylformamide (3×50 mL), dichloromethane (3×50 mL), dichloromethane/methanol 1:1 (3×50 mL), ether (3×50 mL) and dried with a stream of nitrogen to give 10 g of N-Methyl-PAL-Resin (loading: 0.35–0.45 mmol/g based on N-analysis).

Calc: N 1.82% Found: N 1.47%

The N-Methyl-PAL-Resin (450 mg) was washed with 5% diisopropylethylamine in dichloromethane (2×2 mL), dichloromethane (3×2 mL) and dimethylformamide (3×2 mL) and then swelled in dimethylformamide (7 mL). Then (2R)-2-(N-((9H-fluoren-9-yl)methoxycarbonyl)-N-methylamino)-3-(1-naphthyl)propionic acid (163 mg, 0.36 mmol) in dimethylformamide (1 mL), O-(7-azabenzotriazol-1-yl)-1,1,3,3-tetramethyluronium hexafluorophosphate (137 mg, 0.36 mmol) in dimethylformamide (1 mL), 1-hydroxy-7-azabenzotriazole (49 mg, 0.36 mmol) in dimethylformamide (1 ml) and diisopropylethylamine (123 mL, 0.72 mmol) in dimethylformamide (1 mL) were added and the mixture was shaken overnight. The resin was filtered and washed with dimethylformamide (3×2 mL), dichloromethane (3×2 mL) and dimethylformamide (2 mL). Then 20% piperidine in dimethylformamide (5 mL) was added and the mixture was shaken for 20 min, filtered and washed with dimethylformamide (3×2 mL), dichloromethane (3×2 mL) and dimethylformamide (2 mL). Then (2R)-2-(N-((9H-fluoren-9-yl)methoxycarbonyl)-N-methylamino)-3-(2-naphthyl)propionic acid (163 mg, 0.36 mmol) in dimethylformamide (1 mL), O-(7-azabenzotriazol-1-yl)-1,1,3,3-tetramethyluronium hexafluorophosphate (137 mg, 0.36 mmol) in dimethylformamide (1 mL), 1-hydroxy-7-azabenzotriazole (49 mg, 0.365 mmol) in dimethylformamide (1 mL) and diisopropylethylamine (123 ml, 0.72 mmol) in dimethylformamide (1 mL) were added and the mixture was shaken overnight. The resin was filtered and washed with dimethylformamide (3×2 mL), dichloromethane (3×2 mL) and dimethylformamide (2 mL). Then 20% piperidine in dimethylformamide (5 mL) was added and the mixture was shaken for 20 min, filtered and washed with dimethylformamide (3×2 mL), dichloromethane (3×2 mL) and dimethylformamide (2 mL). Then (2E)-5-(N-tert-butoxycarbonylamino)-5-methylhex-2-enoic acid (88 mg, 0.36 mmol) in dimethylformamide (1 mL), O-(7-azabenzotriazol-1-yl)-1,1,3,3-tetramethyluronium hexafluorophosphate is (137 mg, 0.36 mmol) in dimethylformamide (1 mL), 1-hydroxy-7-azabenzotriazole (49 mg, 0.36 mmol) in dimethylformamide (1 mL) and diisopropylethylamine (123 mL, 0.72 mmol) in dimethylformamide (1 mL) were added and the mixture was shaken overnight. The resin was filtered and washed with dimethylformamide (3×2 mL), dichloromethane (3×2 mL) and dimethylformamide (2 mL). The resin was cooled to 0° C. and 50% trifluoroacetic acid in dichloromethane (4 mL) was added and the mixture was shaken for 10 min at 0° C. The resin was filtered and washed with 50% trifluoroacetic acid in dichloromethane (2×0.5 mL) and the combined filtrates were concentrated under a stream of nitrogen. The obtained product was dissolved in acetonitrile/water 1:20 (10 mL) and applied to a C-18 Sep-Pak Classic® cartridge (0.25 g, purchased from Waters™), which had been prewashed with acetonitrile (10 mL) and water (10 mL). Then water/trifluoroacetic acid 99.9:0.1 (5 mL), followed by water/acetonitrile/trifluoroacetic acid 89.9:10:0.1 (4 mL) was run through the Sep-Pak® and the filtrate was discarded. Then the Sep-Pak was washed with water/acetonitrile/trifluoroacetic acid 64.9:35:0.1 (4 mL) and the filtrate was diluted with water (11 mL) and lyophilized to 52 mg of the title product.

HPLC: (A1) $R_t$=35.03 min (B1) $R_t$=36.93 min

LC-MS: 579.0 $(m+1)^+$

Example 45

(2E)-5-Amino-5-methylhex-2-enoic acid N-methyl-N-((1R)-1-{N-[(1R)-2-(1-naphthyl)-1-(methylcarbamoyl)ethyl]-N-methylcarbamoyl}-2-(4-methoxyphenyl)ethyl)amide:

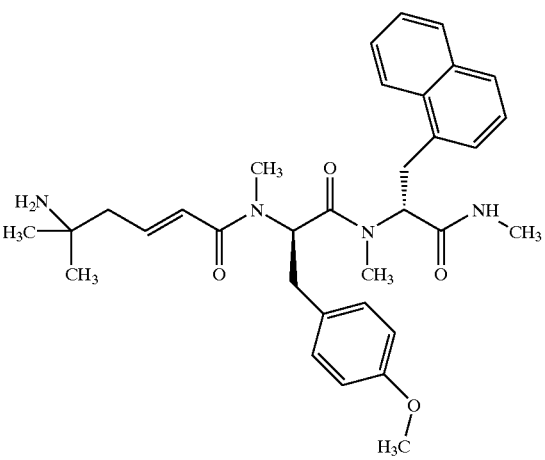

The title compound was prepared analogously to example 44 with (2R)-2-(N-((9H-fluoren-9-yl)methoxycarbonyl)-N-methylamino)-3-(4-methoxyphenyl)propionic acid instead of (2R)-2-(N-((9H-fluoren-9-yl)methoxycarbonyl)-N-methylamino)-3-(2-naphthyl)propionic acid.

Yield: 44 mg

HPLC: (A1) $R_t$=30.22 min (B1) $R_t$=32.10 min

LC-MS: 559.2 $(m+1)^+$

Example 46

(2E)-5-Amino-5-methylhex-2-enoic acid N-methyl-N-((1R)-1-{N-[(1R)-2-(1-naphthyl)-1-(methylcarbamoyl)ethyl]-N-methylcarbamoyl}-2-phenylethyl)amide:

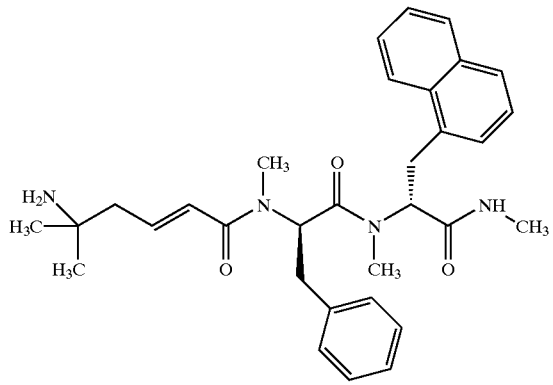

The title compound was prepared analogously to example 44 with (2R)-2-(N-((9H-fluoren-9-yl)methoxycarbonyl)-N-methylamino)-3-phenylpropionic acid instead of (2R)-2-(N-((9H-fluoren-9-yl)methoxycarbonyl)-N-methylamino)-3-(2-naphthyl)propionic acid.

Yield: 38 mg

HPLC: (A1) $R_t$=30.68 min (B1) $R_t$=32.33 min

LC-MS: 529.0 $(m+1)^+$

Example 47

(2E)-5-Amino-5-methylhex-2-enoic acid N-methyl-N-((1R)-1-{N-[(1R)-2-(2-naphthyl)-1-(methylcarbamoyl)ethyl]-N-methylcarbamoyl}-2-(1-naphthyl)ethyl)amide:

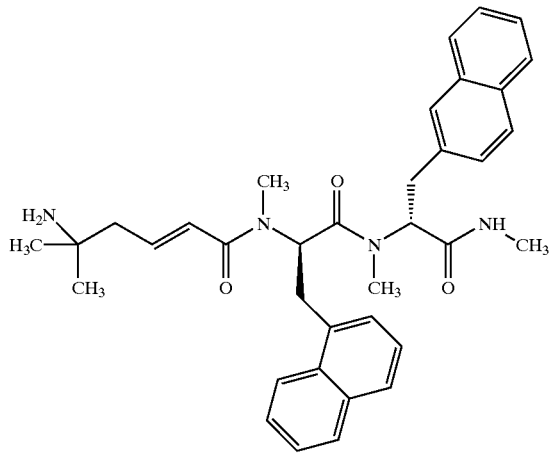

The title compound was prepared analogously to example 44 with (2R)-2-(N-((9H-fluoren-9yl)methoxycarbonyl)-N-methylamino)-3-(1-naphthyl)prop ionic acid instead of (2R)-2-(N-((9H-fluoren-9-yl)methoxycarbonyl)-N-methylamino)-3-(2-naphthyl)propionic acid and (2R)-2-(N-((9H-fluoren-9-yl)methyloxycarbonyl)-N-methylamino)-3-(2-naphthyl) propionic acid instead of (2R)-2-(N-((9H-fluoren-9yl)methoxycarbonyl)-N-methylamino)-3-(1-naphthyl)propionic acid. Yield: 70 mg HPLC: (A1) $R_t$=34.52 min (B1) $R_t$=36.38 min LC-MS: 579.0 $(m+1)^+$

Example 48

(2E)-5-Amino-5-methylhex-2-enoic acid N-methyl-N-((1R)-1-{N-[(1R)-2-(2-naphthyl)-1-(methylcarbamoyl)ethyl]-N-methylcarbamoyl}-2-phenylethyl)amide:

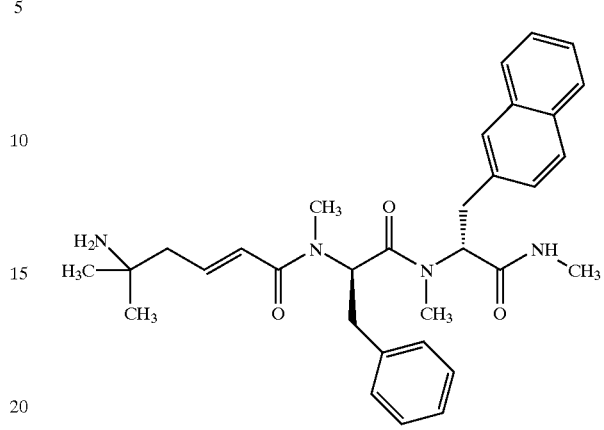

The title compound was prepared analogously to example 44 (2R)-2-(N-((9H-fluoren-9-yl)methoxycarbonyl)-N-methylamino)-3-phenylpropionic acid instead of (2R)-2-(N-((9H-fluoren-9-yl)methoxycarbonyl)-N-methylamino)-3-(2-naphthyl)propionic acid and (2R)-2-(N-((9H-fluoren-9-yl)methoxycarbonyl)-N-methylamino)-3-(2-naphthyl)propionic acid instead of (2R)-2-(N-((9H-fluoren-9-yl)methoxycarbonyl)-N-methylamino)-3-(1-naphthyl)propionic acid.

Yield: 49 mg

HPLC: (A1) $R_t$=30.52 min (B1) $R_t$=32.03 min

LC-MS: 529.0 $(m+1)^+$

Example 49

(2E)-5-Amino-5-methylhex-2-enoic acid N-methyl-N-((1R)-1-{N-[(1R)-2-(4-methoxyphenyl)-1-(methylcarbamoyl)ethyl]-N-methylcarbamoyl}-2-(1-naphthyl)ethyl)amide:

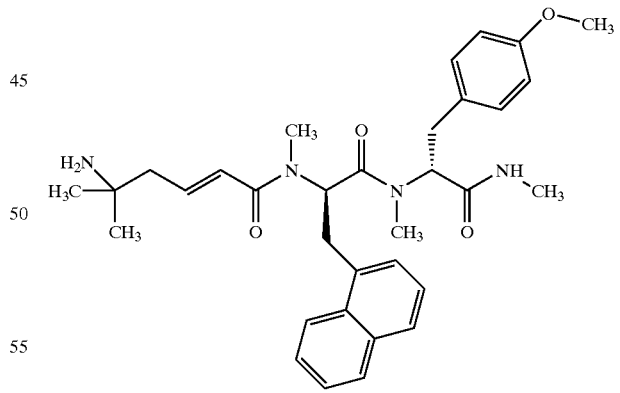

The title compound was prepared analogously to example 44 with (2R)-2-(N-((9H-fluoren-9-yl)methoxycarbonyl)-N-methylamino)-3-(I-naphthyl)propionic acid instead of (2R)-2-(N-((9H-fluoren-9-yl)methoxycarbonyl)-N-methylamino)-3-(2-naphthyl)propionic acid and (2R)-2-(N-((9H-fluoren-9-yl)methoxycarbonyl)-N-methylamino)-3-(4-methoxyphenyl)propionic acid instead of (2R)-2-(N-((9H-fluoren-9-yl)methoxycarbonyl)-N-methylamino)-3-(1-naphthyl)propionic acid.

Yield: 51 mg
HPLC: (A1) $R_t$=30.20 min (B1) $R_t$=31.70 min
LC-MS: 559.2 (m+1)$^+$ Example 50
(2E)-5-Amino-5-methylhex-2-enoic acid N-methyl-N-((1R)-1-{N-[(1R)-2-(4-methoxyphenyl)-1-(methylcarbamoyl)ethyl]-N-methylcarbamoyl}-2-(4-methoxyphenyl)ethyl)amide:

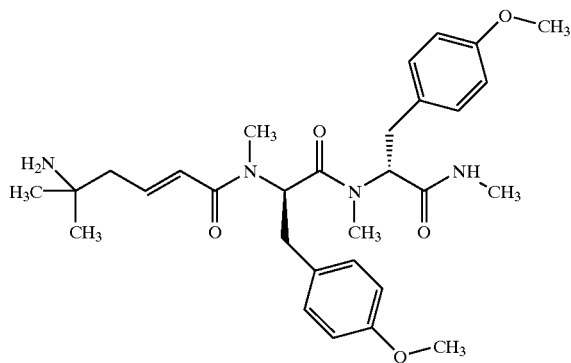

The title compound was prepared analogously to example 44 with (2R)-2-(N-((9H-fluoren-9-yl)methoxycarbonyl)-N-methylamino)-3-(4-methoxyphenyl)propionic acid instead of (2R)-2-(N-((9H-fluoren-9-yl)methoxycarbonyl)-N-methylamino)-3-(2-naphthyl)propionic acid and (2R)-2-(N-((9H-fluoren-9-yl)methoxycarbonyl)-N-methylamino)-3-(4-methoxyphenyl)propionic acid instead of (2R)-2-(N-((9H-fluoren-9-yl)methoxycarbonyl)-N-methylamino)-3-(1-naphthyl)propionic acid.
Yield: 26 mg
HPLC: (A1) $R_t$=25.75 min (B1) $R_t$=26.98 min
LC-MS: 539.2 (m+1)+

Example 51
(2E)-5-Amino-5-methylhex-2-enoic acid N-methyl-N-((1R)-1-{N-[(1R)-2-(4-methoxyphenyl)-1-(methylcarbamoyl)ethyl]-N-methylcarbamoyl}-2-(2,3,4,5,6-pentafluorophenyl)ethyl)amide:

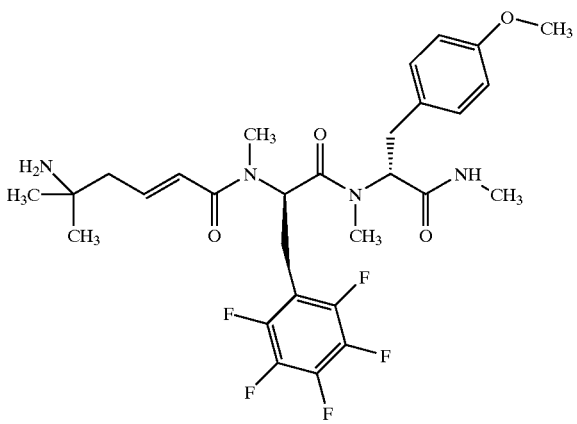

The title compound was prepared analogously to example 44 with (2R)-2-(N-((9H-fluoren-9-yl)methoxycarbonyl)-N-methylamino)-3-(2,3,4,5,6-pentafluorophenyl)propionic acid instead of (2R)-2-(N-((9H-fluoren-9-yl)methoxycarbonyl)-N-methylamino)-3-(2-naphthyl)propionic acid and (2R)-2-(N-((9H-fluoren-9yl)methoxycarbonyl)-N-methylamino)-3-(4-methoxyphenyl)propionic acid instead of (2R)-2-(N-((9H-fluoren-9-yl)methoxycarbonyl)-N-methylamino)-3-(1-naphthyl)propionic acid.
Yield: 42 mg
HPLC: (A1) $R_t$=31.05 min (B1) $R_t$=32.00 min
LC-MS: 599.0 (m+1)$^+$ Example 52
(2E)-5-Amino-5-methylhex-2-enoic acid N-methyl-N-((1R)-1-{N-[(1R)-2-(4-methoxyphenyl)-1-(methylcarbamoyl)ethyl]-N-methylcarbamoyl}-2-phenylethyl)amide:

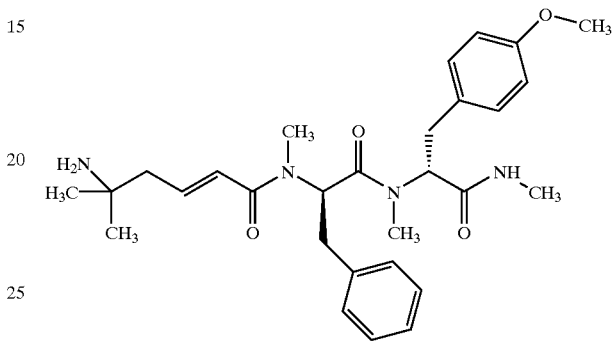

The title compound was prepared analogously to example 44 with (2R)-2-(N-((9H-fluoren-9-yl)methoxycarbonyl)-N-methylamino)-3-phenylpropionic acid instead of (2R)-2-(N-((9H-fluoren-9-yl)methoxycarbonyl)-N-methylamino)-(2-naphthyl)propionic acid and (2R)-2-(N-((9H-fluoren-9-yl)methoxycarbonyl)-N-methylamino)-3-(4-methoxyphenyl)propionic acid instead of (2R)-2-(N-((9H-fluoren-9-yl)methoxycarbonyl)-N-methylamino)-3-(1-naphthyl)propionic acid.
Yield: 31 mg
HPLC: (A1) $R_t$=25.68 min (B1) $R_t$=27.00 min
LC-MS: 509.2 (m+1)+

Example 53
(2E)-5-Amino-5-methylhex-2-enoic acid N-methyl-N-((1R)-1-{N-[(1R)-2-(2,3,4,5,6-pentafluorophenyl)-1-(methylcarbamoyl)ethyl]-N-methylcarbamoyl}2-(1-naphthyl)ethyl)amide:

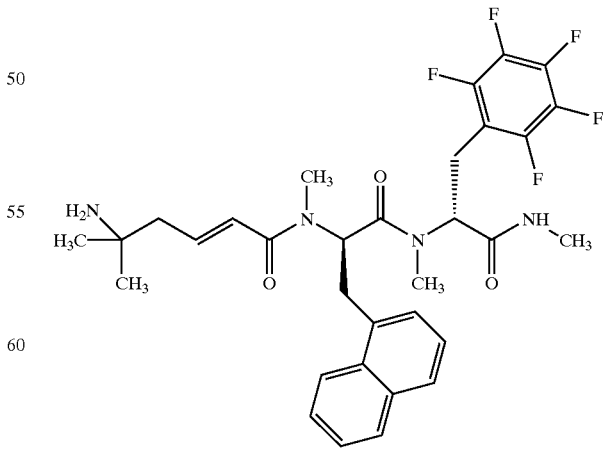

The title compound was prepared analogously to example 44 with (2R)-2-(N-((9H-fluoren-9-yl)methoxycarbonyl)-N- methylamino)-3-(1-naphthyl)propionic acid instead of (2R)-2-(N-((9H-fluoren-9-yl)methoxycarbonyl)-N-methylamino)-3-(2-naphthyl)propionic acid and (2R)-2-(N-((9H-fluoren-9-yl)methoxycarbonyl)-N-methylamino)-3-(2,3,4,5,6-pentafluorophenyl)propionic acid instead of (2R)-2-(N-((9H-fluoren-9-yl)methoxycarbonyl)-N-methylamino)-3-(1-naphthyl)propionic acid.

Yield: 38 mg

HPLC: (A1) $R_t$=34.88 min (B1) $R_t$=36.78 min

LC-MS: 619.0 $(m+1)^+$

Example 54

(2E)-5-Amino-5-methylhex-2-enoic acid N-methyl-N-((1R)-1-{N-[(1R)-2-(2,3,4,5,6-pentafluorophenyl)-1-(methylcarbamoyl)ethyl]-N-methylcarbamoyl}-2-(4-methoxyphenyl)ethyl)amide:

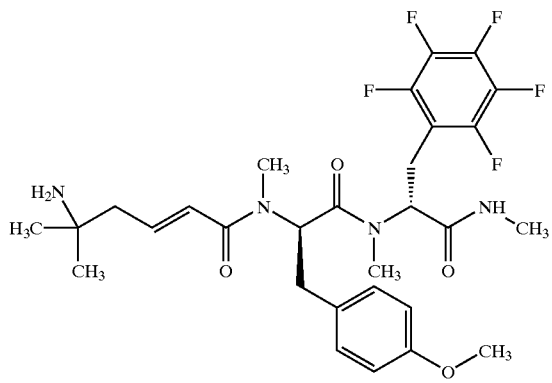

The title compound was prepared analogously to example 44 with (2R)-2-(N-((9H-fluoren-9-yl)methoxycarbonyl)-N-methylamino)-3-(4-methoxyphenyl)propionic acid instead of (2R)-2-(N-((9H-fluoren-9-yl)methoxycarbonyl)-N-methylamino)-3-(2-naphthyl)propionic acid and (2R)-2-(N-((9H-fluoren-9-yl)methoxycarbonyl)-N-methylamino)-3-(2,3,4,5,6-pentafluorophenyl)propionic acid instead of (2R)-2-(N-((9H-fluoren-9-yl)methoxycarbonyl)-N-methylamino)-3-(1-naphthyl)propionic acid.

Yield: 25 mg

HPLC:(A1) $R_t$=30.72 min (B1) $R_t$=32.32 min

LC-MS: 599.0 $(m+1)^1$

Example 55

(2E)-5-Amino-5-methylhex-2-enoic acid N-methyl-N-((1R)-1-{N-[(1R)-2-(2,3,4,5,6-pentafluorophenyl)-1-(methylcarbamoyl)ethyl]-N-methylcarbamoyl}2-phenylethyl)amide:

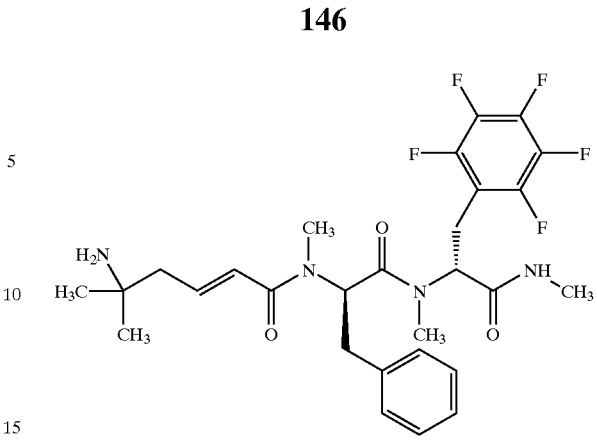

The title compound was prepared analogously to example 44 with (2R)-2-(N-((9H-fluoren-9-yl)methoxycarbonyl)-N-methylamino)-3-phenylpropionic acid instead of (2R)-2-(N-((9H-fluoren-9-yl)methoxycarbonyl)-N-methylamino)-3-(2-naphthyl)propionic acid and (2R)-2-(N-((9H-fluoren-9-yl)methoxycarbonyl)-N-methylamino)-3-(2,3,4,5,6-pentafluorophenyl)propionic acid instead of (2R)-2-(N-((9H-fluoren-9-yl)methoxycarbonyl)-N-methylamino)-3-(1-naphthyl)propionic acid.

Yield: 30 mg
HPLC: (A1) $R_t$=30.88 min (B1) $R_t$=32.55 min
LC-MS: 569.0 $(m+1)^+$ Example 56

(2E)-5-Amino-5-methylhex-2-enoic acid N-methyl-N-((1R)-1-{N-[(1R)-2-phenyl-1-(methylcarbamoyl)ethyl]-N-methylcarbamoyl}-2-(4-methoxyphenyl)ethyl)amide:

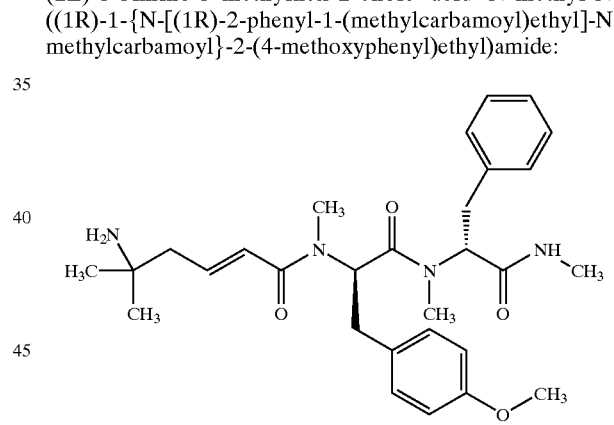

The title compound was prepared analogously to example 44 with (2R)-2-(N-((9H-fluoren-9-yl)methoxycarbonyl)-N-methylamino)-3-(4-methoxyphenyl)propionic acid instead of (2R)-2-(N-((9H-fluoren-9-yl)methoxycarbonyl)-N-methylamino)-3-(2-naphthyl)propionic acid and (2R)-2-(N-((9H-fluoren-9-yl)methoxycarbonyl)-N-methylamino)-3-phenylpropionic acid instead of (2R)-2-(N-((9H-fluoren-9-yl)methoxycarbonyl)-N-methylamino)-3-(1-naphthyl)propionic acid.

Yield: 25 mg
HPLC: (A1) $R_t$=25.95 min (B1) $R_t$=27.23 min
LC-MS: 509.4 $(m+1)^+$ Example 57
(2E)-5-Amino-5-methylhex-2-enoic acid N-methyl-N-((1R)-1-{N-[(1R)-2-phenyl-1-(methylcarbamoyl)ethyl]-N-methylcarbamoyl}-2-(2,3,4,5,6-pentafluorophenyl)ethyl)amide:

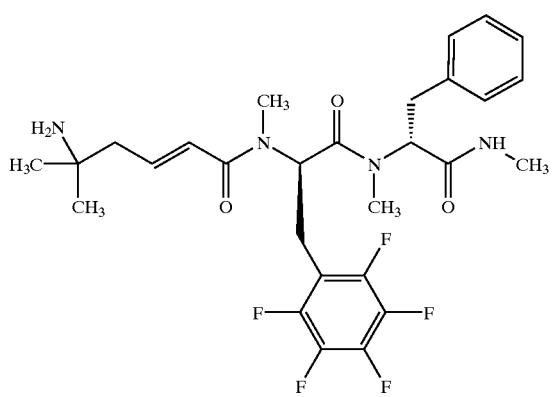

The title compound was prepared analogously to example 44 with (2R)-2-(N-((9H-fluoren-9-yl)methoxycarbonyl)-N-methylamino)-3-(2,3,4,5,6-pentafluorophenyl)propionic acid instead of (2R)-2-(N-((9H-fluoren-9-yl)methoxycarbonyl)-N-methylamino)-3-(2-naphthyl)propionic acid and (2R)-2-(N-((9H-fluoren-9-yl)methoxycarbonyl)-N-methylamino)-3-phenylpropionic acid instead of (2R)-2-(N-((9H-fluoren-9-yl)methoxycarbonyl)-N-methylamino)-3-(1-naphthyl)propionic acid.

Yield: 35 mg
HPLC: (A1) $R_t$=31.20 min (B1) $R_t$=32.47 min
LC-MS: 569.0 (m+1)[1]

Example 58
(2R)-2-(N-((2E)-5-Amino-5-methylhex-2-enoyl)-N-methylamino)-N-((1R)-1-benzyl-2-(3-cyclopropylthioureido)ethyl)-N-methyl-3-(2-naphthyl)propionamide

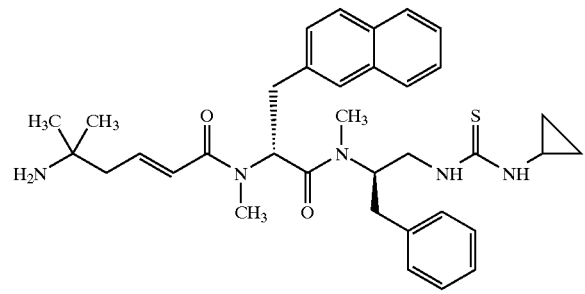

N-((1R)-1-Carbamoyl-2-phenylethyl)-N-methylcarbamic acid tert.-butylester.

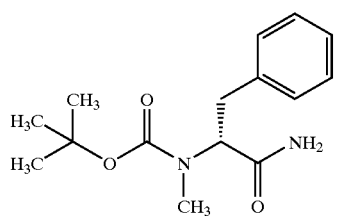

A solution of (2R)-2-(N-tert-butoxycarbonyl-N-methylamino)-3-phenylpropionic acid (4.00 g, 14.32 mmol) in N,N-dimethylformamide (1 0 ml) was cooled to 0° C. Ammonium hydrogen carbonate (5.66 g, 71.60 mmol) was added as a solid. 1-Hydroxybenzotriazole hydrate (1.94 g, 14.32 mmol) and successively N-(3-dimethylaminopropyl)-N'-ethylcarbodiimide hydrochloride (2.75 g, 14.32 mmol) were added. The suspension was stirred for 16 h, while warming up to room temperature. The reaction mixture was diluted with ethyl acetate (150 ml) and extracted with saturated sodium chloride solution/water (200 ml/300 ml). The aqueous phase was extracted with ethyl acetate (3×100 ml). The combined organic layers were washed with saturated sodium hydrogen carbonate solution and dried over magnesium sulfate. The solvent was removed in vacuo. The crude product was purified by flash-chromatography on silica (70 g), using ethyl acetate/heptane as eluent, to give 2.80 g of N-((1R)-1-carbamoyl-2-phenylethyl)-N-methylcarbamic acid tert.-butylester.

$^1$H-NMR (CDCl$_3$): d 1.29 and 1.40 (both s, together 9H); 2.74 (s, 3H); 2.95 (m, 1H); 3.37 (m, 1H); 4.75 and 4.96 (both m, together 1H); 5.55, 5.73, 5.95, and 6.17 (all br, together 2 H); 7.05–7.40 (m, 5H).

N-((1R)-1-Aminomethyl-2-phenylethyl)-N-methylcarbamic acid tert-butylester.

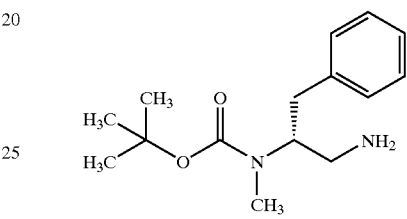

N-((1R)-1-Carbamoyl-2-phenylethyl)-N-methylcarbamic acid tert.-butylester (2.73 g, 9.81 mmol) was dissolved in tetrahydrofuran (10 ml). The solution was cooled to 5° C. A suspension of sodium borohydride (816 mg, 21.58 mmol) in tetrahydrofuran (10 ml) was added. A solution of iodine (1.24 g, 4.91 mmol) was added dropwise. After the addition was completed, the solution was heated to reflux for 16 h. It was cooled to 5° C. A 10% solution of ammonium chloride in water (60 ml) was added 15 dropwise. The solution was warmed to 50° C. for 1 h. It was cooled to room temperature. 1N sodium hydroxide solution was added until pH 14. It was extracted with tert-butyl methyl ether (4×100 ml). The combined organic layers were dried over magnesium sulfate. The solvent was removed in vacuo. The crude product was purified by flash chromatography on silica (150 g) using dichloromethane/methanol/25% aqueous ammonia 100:1:0:1 as eluent to give 453 mg of N-((1R)-1-aminomethyl-2-phenylethyl)-N-methylcarbamic acid tert-butylester.

$^1$H-NMR (CDCl$_3$): d 1.29 and 1.36 (both s, together 9 H); 2.60–2.90 (m, 7 H); 4.20 and 4. 38 (both br, together 1 H); 7.10–7.35 (m, 5 H).

N-((1R)-1-Benzyl-2-(3-cyclopropylthioureido)ethyl)-N-methylcarbamic acid tert-butylester.

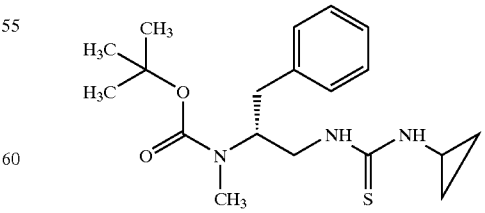

At 0° C., cyclopropylisothiocyanate (0.32 ml) was added to a solution of N-((1R)-1-aminomethyl-2-phenylethyl)-N-methylcarbamic acid tert-butylester (410 mg, 1.6 mmol) in dichloromethane (4 ml). The reaction mixture was first stirred at 0° C. for 10 min, and successively for 2.5 h at room temperature. The solvent were removed in vacuo. The crude product was purified by flash chromatography on silica (50 g) using ethyl acetate/heptane as eluent to give 492 mg of N-((1R) 1-benzyl-2-(3-cyclopropylthioureido)ethyl)-N-methylcarbamic acid tert-butylester.

$^1$H-NMR (CDCl$_3$): d 0.62 (br, 2 H); 1.26 and 1.36 (both s, together 9 H); 2.37 (br, 1 H); 2.60–3.00 (m, 5 H); 3.60 (m, 1 H); 3.98 (m, 1 H); 4.60 (m, 1 H); 6.30 and 6.85 (both m, together 2 H); 7.10–7.35 (m, 5 H).

N-Cyclopropyl-N'-((2R)-2-methylamino)-3-phenylpropyl) thiourea.

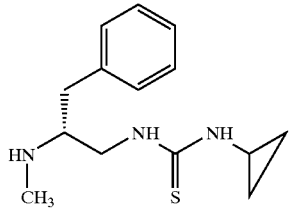

N-((1R)-1-Benzyl-2-(3-cyclopropylthioureido)ethyl)-N-methylcarbamic acid tert-butylester (404 mg, 1.1 mmol) was dissolved in dichloromethane (2 ml). The solution was cooled to 0° C. Trifluoroacetic acid (2 ml) was added. The reaction mixture was stirred for 7 min. The solvents were removed in vacuo. The residue was dissolved in dichloromethane and the solvent was removed in vacuo. This latter procedure was repeated two times. The crude product was purified by flash chromatography on silica (9 g), using dichloromethane/methanol/25% aqueous ammonia (100:10:1) as eluent, to give 255 mg of N-cyclopropyl-N'-((2R)-2-methylamino)-3-phenylpropyl)thiourea.

$^1$H-NMR (CDCl$_3$): d 0.64 (br, 2 H); 0.85 (m, 2 H); 2.38 (s, 3 H); 2.45 (m, 1 H); 2.77 (ABX, 2 H); 2.99 (m, 1 H); 3.58 (m, 1 H); 3.74 (m, 1 H); 6.25 (m, 1 H); 7.15 (m, 1 H); 7.15–7.35(m, 5 H).

N-((1R)-1-(N-((1R)-1-((3-Cyclopropylthioureido)methyl)-2-phenylethyl)-N-methylcarbamoyl)-2-(2-naphthyl)ethyl)-N-methylcarbamic Acid Tert-Butylester.

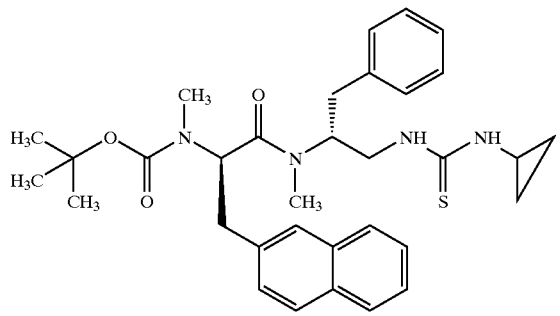

(2R)-2-(N-(tert-Butoxycarbonyl)-N-methylamino)-3-(2-naphthyl)propionic acid (290 mg, 0.88 mmol) was dissolved in dichloromethane (2 ml) and N,N-dimethylformamide (2 ml). 1-Hydroxy-7-azabenzotriazole (120 mg, 0.88 mmol) was added as a solid. The solution was cooled to 0° C. N-(3-dimethylaminopropyl)-N'-ethylcarbodiimide hydrochloride (202 mg, 1.06 mmol) was added. The solution was stirred for 20 min. N-Cyclopropyl-N'-((2R)-2-methylamino)-3-phenylpropyl)thiourea (231 mg, 0.88 mmol) was dissolved in dichloromethane (2 ml) and added. The reaction mixture was stirred for 16 h. It was diluted with ethyl acetate (100 ml) and extracted with 1 N hydrochloric acid (100 ml). The aqueous phase was extracted with ethyl acetate (2×10 ml). The combined organic layers were washed with saturated sodium hydrogen carbonate solution (100 ml) and dried over magnesium sulfate. The solvent was removed in vacuo. The crude product was purified by flash chromatography on silica (45 g) using ethyl acetate/heptane 1:1 as eluent to give 350 mg of N-((1R)-1-(N-((1R)-1-((3-Cyclopropylthioureido)methyl)-2-phenyl-ethyl)-N-methylcarbamoyl)-2-(2-naphthyl)ethyl)-N-methylcarbamic acid tert-butylester.

$^1$H-NMR (CDCl$_3$): d 0.06, 0.19, 0.30, 0.40, 0.55 (all m, together 4 H); 1.25 and 1.33 (both s, together 9 H); 1.41 and 1.60 (both m, together 1 H); 2.12 and 1.27 (both s, together 3 H); 2.70–3.00 (m, 6 H); 3.25 (m, 1 H); 3.55 (m, 1 H); 4.00 and 4.15 (both m, together 1 H); 5.02 and 5.37 (both t, together 1 H); 5.12 and 5.25 (both m, together 1 H); 5.90 and 5.99 (both br, together 1 H); 6.60 (m, 1 H); 7.10–7.85 (m, 12 H).

(2R)-N-((1R)-1-Benzyl-2-(3-cyclopropylthioureido)ethyl)-N-methyl-2-methylamino-3-(2-naphthy

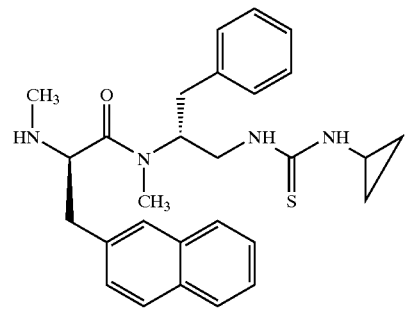

N-((1R)-1-(N-((1R)-1-((3-Cyclopropylthioureido) methyl)-2-phenylethyl)-N-methylcarbamoyl)-2-(2-naphthyl)ethyl)-N-methylcarbamic acid tert-butylester (579 mg, 1.01 mmol) was dissolved in dichloromethane (2 ml). The solution was cooled to 0° C. Trifluoroacetic acid (2 ml) was added. The solution was stirred for 5 min. The solvents were removed in vacuo without warming. The residue was dissolved in dichloromethane (100 ml) and the solvent was removed in vacuo. This latter procedure was repeated two times. The crude product was purified by flash chromatography on silica (45 g) using dichloromethanelmethanol/25% aqueous ammonia 100:10:1 as eluent to give 201 mg of (2R)-N-((1R)-1-benzyl-2-(3-cyclopropylthioureido)ethyl)-N-methyl-2-methylamino-3-(2-napthyl)propionamide.

$^1$H-NMR (CDCl$_3$): d 0.63 (m, 2H); 0.85 (m, 2 H); 1.90 (s, 3 H); 2.38 (br, 1H); 2.65 (s, 3 H); 2.70–3.05 (m, 5 H); 3.60 (m, 1 H); 4.05 (m, 1 H); 5.23 (m, 1 H), 6.30 (m, 1 H); 6.90–7.85 (m, 13 H).

(3E)-4-(N-((1R)-1-(N-((1R)-1-benzyl-2-(3-cyclopropylthioureido)ethyl)-N-methylcarbamoyl)-2-(2-naphthyl)ethyl)-N-methylcarbamoyl)-1,1-dimethylbut-3-enylcarbamic acid tert-butylester

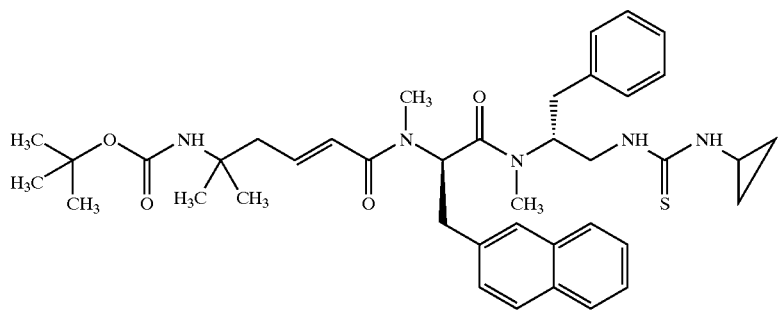

(2E)-5-tertButoxycarbonylamino-5-methylhex-2-enoic acid (1 82 mg, 0.75 mmol) 9 was dissolved in N,N-dimethylformamide (2 ml) and dichloromethane (2 ml). 1-Hydroxy-7-azabenzotriazole (102 mg, 0.75 mmol) was added. The solution was cooled to 0° C. N-(3-dimethylaminopropyl)-N'-ethylcarbodiimide hydrochloride (144 mg, 0.75 mmol) was added. The solution was stirred for 15 min at 0° C. (2R)-N-((1R)-1 Benzyl-2-(3-cyclopropylthioureido)ethyl)-N-methyl-2-methylamino-3-(2-naphthyl)propionamide (178 mg, 0.37 mmol) was dissolved in dichloromethane and added to the reaction mixture. Ethyldiisopropylamine (0.13 ml, 0.75 mmol) was added. The solution was stirred for 16 h, while it was warming up to room temperature. It was diluted with ethyl acetate (200 ml) and washed with 10% aqueous sodium hydrogen sulfate solution (100 ml). The aqueous solution was extracted with ethyl acetate (3×50 ml). The combined organic layers were washed with saturated sodium hydrogen carbonate solution (150 ml) and dried over magnesium sulfate. The solvent was removed in vacuo. The crude product was purified by flash chromatography on silica (45 g) to give 89 mg of (3E)-4-(N-((1R)-1-(N-((1R)-1 benzyl-2-(3-cyclopropylthioureido)ethyl)-N-methylcarbamoyl)-2-(2-naphthyl)ethyl)-N-methylcarbamoyl)-1,1-dimethylbut-3-enylcarbamic acid tert-butylester.

$^1$H-NMR (CDCl$_3$, selected values): d −0.08, 0.11, 0.20, 0.30, and 0.60 (all m, together 4 H); 3.34 (dd, 1 H); 4.00 (m, 1 H); 5.52 and 5.87 (dd, 1 H); 6.00 and 6.05 (both d, together 1 H); 6.65 and 6.80 (both m, together 1 H).

(3E)-4-(N-((1R)-1-(N-((1R)-1-Benzyl-2-(3-cyclopropylthioureido)ethyl)-N-methylcarbamoyl)-2-(2-naphthyl)ethyl)-N-methylcarbamoyl)-1,1-dimethylbut-3-enylcarbamic acid tert-butylester (63 mg, 0.09 mmol) was dissolved in dichloromethane (2 ml). The solution was cooled to 0° C. Trifluoracetic acid (2 ml) as added. The solution was stirred for 15 min at 0° C. The solvent was removed in vacuo at 20° C. The residue was dissolved in dichloromethane (50 ml), and the solvent was removed in vacuo. This latter procedure was repeated two times. The residue was dissolved in ethyl acetate (2 ml). Heptane (5 ml) was added. The precipitation was filtered off and was characterized to be 50 mg of the title compound as trifluoroacetic acid salt.

$^1$H-NMR (DMSO-d$_6$, selected values): d 0.25–0.75 (m, 4 H); 3.15 (dd, 1 H); 6.41 (m, 1 H).

HPLC:

The RP-HPLC analysis was performed using UV detection at 254 nm and a Lichrosorp RP-18 5 mM column, which was eluted at 1 ml/minute. Two solvent systems were used: Solvent system I: 0.1% Trifluoro acetic acid in acetonitrile.

Solvent system II: 0.1% Trifluoroacetic acid in water.

The column was equilibrated with a mixture composed of 20% of solvent system I and 80% of solvent system II. After injection of the sample a gradient of 20% to 80% of solvent system I in solvent system II was run over 30 minutes. The gradient was then extended to 100% of solvent system I over 5 minutes followed by isocratic elution with 100% of this system for 6 minutes.

R$_t$ 20.42 min.

MS: found 599.6 [M+H]$^+$, calc: 599.3.

m.p.: 138–145° C.

C$_{35}$H$_{45}$N$_5$O$_2$S.CF$_3$COOH.2H$_2$O calc.: C$_{59.26}$; H 6.72; N 9.34 found: C$_{59.23}$; H 6.64; N 8.83.

Example 59

(2R)-2-(N-[{2-Amino-2-methylpropoxy}acetyl]-N-methylamino)-N-((1R)-1-(dimethylcarbamoyl)-2-phenylethyl)-N-methyl-3-(2-naphthyl)propionamide:

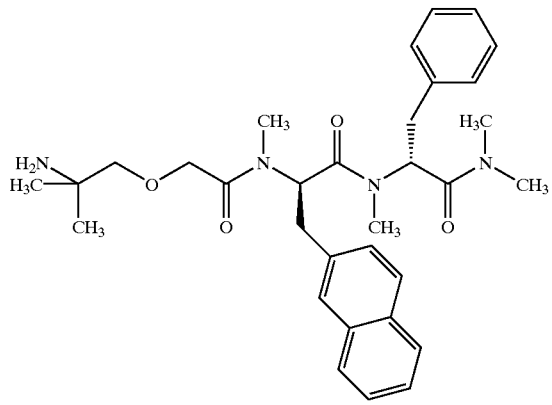

(2-tert-Butoxycarbonylamino-2-methylpropoxy)acetic acid:

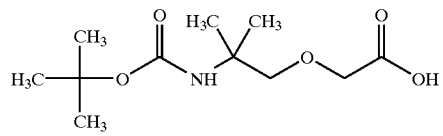

A solution of 2-tert-butoxycarbonylamino-2-methylpropanol (5.0 g, 26 mmol) and rhodium(II)acetate (90 mg) in 1,2-dichloroethane (500 ml) was heated to 80° C. Then ethyl diazoacetate (4.0 g, 35 mmol) was added over a period of 1 h, and the mixture was stirred at reflux for 3 h. Another portion of rhodium(II)acetate (90 mg) was added and the mixture was refluxed for another 5 h. The mixture was cooled overnight and saturated sodium bicarbonate (500 ml) was added, the phases were separated and the organic layer was washed with saturated sodium bicarbonate (2×200 ml), dried (magnesium sulfate) and concentrated in vacuo.

The obtained product was dissolved in 1 M lithium hydroxide in methanol/water 3:1 (200 ml) and stirred overnight. The solvent was removed in vacuo, water was added (pH>9) and the Mixture was washed with ether (200 ml). Then 1 M hydrochloric acid was added until pH<4 and the mixture was extracted with ethyl acetate (200 ml), dried (magnesium sulfate) and concentrated in vacuo to give 2.5 g of (2-tert-butoxycarbonylamino-2-methylpropoxy)acetic acid.

¹H-NMR (CDCl₃): d 1.3 (s, 6H) 1.45 (s, 9H) 3.5 (s, 2H) 4.15 (s, 2H) 9.9 (b, 1 H).

To a solution of 2-tert-butoxycarbonylamino-2-methylpropoxy)acetic acid (480 mg, 1.9 mmol) in dichloromethane (10 ml) were added 1-hydroxy-7-azabenzotriazole (264 mg, 1.9 mmol) and 1-ethyl-3-(3-dimethylaminopropyl)carbodiimide hydrochloride (409 mg, 2.1 mmol) and the mixture was stirred for 30 min. Then (2R)-N-((1R)-1-dimethylcarbamoyl-2-phenylethyl)-N-methyl-2-methylamino-3-(2-naphthyl)propionamide (434 mg, 0.97 mmol) in dichloromethane (5 ml) and diisopropylethylamine (0.22 ml, 1.3 mmol) were added and the mixture was stirred overnight at room temperature. The mixture was washed with water (20 ml), saturated aqueous sodium bicarbonate (20 ml), water (2×20 ml), brine (20 ml), dried over magnesium sulfate and concentrated in vacuo. The crude product was chromatographed on silica (400 g) with ethyl acetate/pentane 7:3 to give 432 mg of (2-[{N-((1R)-1-[N-{(1R)-1-(dimethylcarbamoyl)-2-phenylethyl}-N-methylcarbamoyl]-2-(2-naphthyl)ethyl)-N-methylcarbamoyl}methoxy]-1,1-dimethylethyl}carbamic acid tert-butylester. The obtained product was dissolved in 50% trifluoroacetic acid in dichloromethane (3 ml) and stirred for 10 min. Then saturated sodium bicarbonate was added until pH 8 and the phases were separated. The aqueous phase was extracted with dichloromethane (2×10 ml) and the combined organic phases were washed with brine (5 ml), dried (magnesium sulfate) and concentrated in vacuo. The product was redissolved in water (30 ml) and the mixture was lyophilized to give 300 mg of the title compound.

¹H-NMR (CDCl₃) (selected peaks): d 1.2 (d, 6H) 2.2 (s, 6H) 2.7 (s, 3H) 2.8 (s, 3H) 4.0 (q, 2H) 5.7 (m, 1H) 5.8 (m, 1H) 7.1–7.8 (m, 12H).

HPLC (A1): R$_t$=32.8 (B1): R$_t$=34.6
LC-MS: 547.0 (M+H)⁺

Example 60
5-methylamino-hex-2-enoic acid ((1R)-1-(((1R)-2-(3,4-difluorophenyl)-1-methylcarbamoylethyl)methylcarbamoyl)-2-(2-naphthyl)ethyl)methylamide

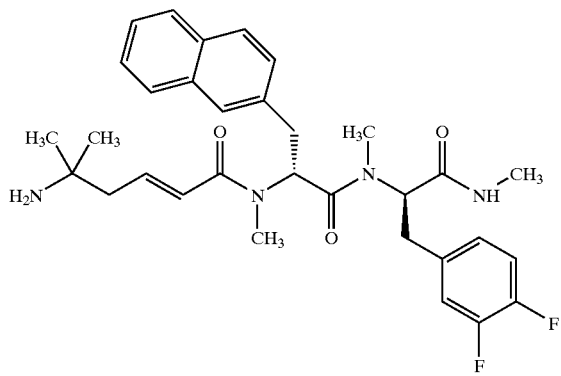

This compound was prepared analogously to example 1. 2-(3,4-difluorophenyl)-alanine was substituted for phenylalanine.

¹H-NMR (CDCl₃): (selected peaks for major rotamer) d 1.22 (s, 6H); 2.10 (d, 3H); 2.71 (s, 3H); 2.85 (s, 3H); 5.22 (dd, 1H); 5.86 (dd, 1H); 6.17 (d, 1H).
HPLC: r$_t$=33.18min. (A1)
PDMS: m/z 566.0 (M+H)⁺

Example 61
5-methylamino-hex-2-enoic Acid ((1R)-1-(((1R)-2-phenyl-1-ethylcarbamoylethyl)methylcarbamoyl)-2-(2-naphthyl)ethyl)methylamide

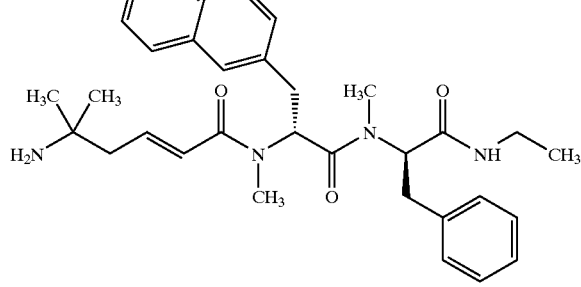

This compound was prepared analogously to example 1.
¹H-NMR (CDCl₃): (selected peaks for major rotamer) d 0.61 (t, 3H); 1.05 (s, 6H); 1.98 (s, 3H); 2.24 (s, 3H); 2.97 (d, 3H); 5.57 (dd, 1H); 5.85 (dd, 1H); 6.07 (d, 1H).
HPLC: r$_t$=33.0 min (A1)
PDMS : m/z 544.0 (M+H)⁺

Example 62
(2E)-5-Amino-5-methylhex-2-enoic acid N-methyl-N-((1R)-1-(N-methyl-N-((1R)-1-(methylcarbamoyl)-2-(thiophen-2-yl) ethyl)carbamoyl)-2-(2-naphthyl)ethyl) amide

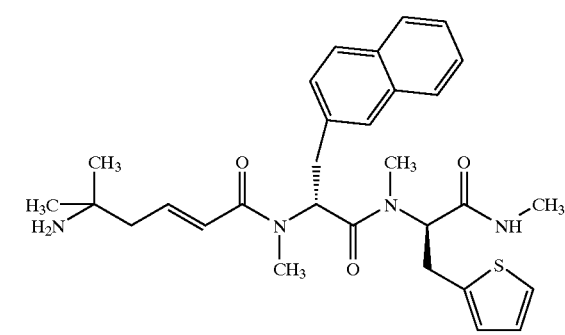

(2R)-2-(N-(tert-Butoxycarbonyl)-N-methylamino)-3-(thiophen-2-yl)propionic acid

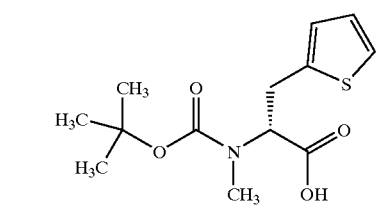

(2R)-2-(tert-Butoxycarbonylamino)-3(thiophen-2-yl) propionic acid (5.00 g; 18.4 mmol) was dissolved in tetrahydrofuran (60 ml). Methyliodide (9.2 ml; 147 mmol) was added and the solution was cooled to 0° C. Sodiumhydride (60% in oil; 1.90 g; 55.3 mmol) was added in portions and the reaction mixture was stirred at room temperature for two days. Ethyl acetate (50 ml) and water (20 ml) were added dropwise. The solvent was removed in vacuo and the residue was dissolved in ether (30 ml) and water (30 ml). The phases were separated and the organic phase was washed with saturated aqueous sodium hydrogencarbonate (3ml). The aqueous phase were mixed. Citric acid (5% (aq)) was added to pH 3 and the aqueous phase was extracted with ethyl acetate (4×30 ml). The combined organic phases were washed with water (2×30 ml), aqueous sodium thiosulfate (5%; 30 ml), water (30 ml) and dried over magnesium sulfate. The solvent was removed in vacuo. The residue was dissolved in ether (10 ml) and dicyclohexylamine (8.5 ml) was added and the mixture was left in a refrigerator overnight. The precipitate was filtered and washed with ether (2×15 ml) and then redissolved in methylene chloride and washed with a mixture of water (15 ml) and sodium hydrogensulfate (15 ml; 10%(aq)). The aqueous phase was washed with methylene chloride (3×15 ml). The combined organic phases were dried over magnesium sulfate and the solvent was removed in vacuo to give 5.10 g of (2R)-2-(N-(tert-Butoxycarbonyl)-N-methylamino)-3-(thiophen-2-yl)propionic acid.

$^1$H-NMR: (CDCl$_3$) (major rotamer) d 1.38 (s, 9 H); 2.85 (s, 3 H); 3.14 (dd, 1 H); 3.56 (dd, 1 H); 4.62 (dd, 1 H); 6.80–7.11 (3 arom. H).

N-Methyl-N-((1R)-1-(methylcarbamoyl)-2-(thiophen-2-yl)ethyl)carbamic Acid tert-butylester

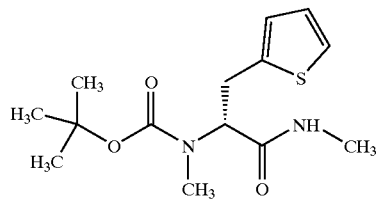

(2R)-2-(N-(tert-Butoxycarbonyl)-N-methylamino)-3-(thiophen-2-yl)propionic acid (2.00 g; 7.01 mmol ) was dissolved in methylene chloride (10 ml). 1-Hydroxybenzotriazole (0.95 g; 7.01 mmol) and 1-ethyl-3-(3-dimethylaminopropyl) carbodiimide hydrochloride (1.48 g ; 7.71 mmol) were added. The solution was stirred for 15 min. at roomtemperature. Methylamine (40% in methanol; 0.38 ml; 7.71 mmol) and diisopropylamine (1.2 ml; 7.01 mmol) were added and the reaction mixture was stirred at room temperature for two days. Water (10 ml) and methylene chloride (10 ml) were added to the solution. The phases were separated and the organic phase was washed with aqueous sodium hydrogensulfate (10%; 15 ml), saturated aqueous sodium hydrogencarbonate (15 ml), dried over magnesium sulfate and the solvent was removed in vacuo. The crude product was chromatographed on silica (4×40 cm) with ethyl acetate/methylene chloride (1:1) as eluent to give 1.18 g of N-Methyl-N-(1R)-1-(methylcarbamoyl)-2-(thiophen-2-yl)ethyl)carbamic acid tert-butylester.

$^1$H-NMR: (CDCl$_3$) (major rotamer) d 1.42 (s, 9H); 2.80 (s, 6H); 3.20 (m, 1H); 3.49 (dd, 1H); 4.92 (dd, 1H); 6.81–7.18 (arom.; 3H).

(2R)-N-Methyl-2-methylamino-3-(thiophen-2-yl)propionamide

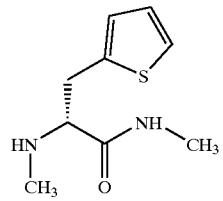

N-Methyl-N-((1R)-1-(methylcarbamoyl)-2-(thiophen-2-yl)ethyl)carbamic acid tert-butylester (1.17 g; 3.92 mmol) was dissolved in methylene chloride (4 ml). The reaction was cooled to 0° C. and triflouroacetic acid was added. The mixture was stirred at room temperature for 1.5 hour. Water (30 ml) and solid sodium hydrogencarbonate were added to pH 8. The phases were separated. The aqueous phase was extracted with methylene chloride (4×20 ml). The combined organic phases were dried over magnesium sulfate and the solvent was removed over vacuo to afford 0.70 g of (2R)-N-methyl-2-methylamino-3-(thiophen-2-yl)propionamide.

$^1$H-NMR: (CDCl$_3$)d 2.35 (s; 3H); 2.85 (d; 3H); 3.08 (dd; 1H); 3.25 (dd; 1H); 3.39 (dd; 1H); 6.88–7.29(arom.; 3H)

N-Methyl-N-((1R)-1-(N-methyl-N-((1R)-1-(methylcarbamoyl)-2-(thiophen-2-yl)ethyl)carbamoyl)-2-(2-naphthyl)ethyl) carbamic Acid Tert Butylester.

2-(tert Butoxycarbonylmethylamino)-3-(2-naphthyl) propionic acid (1.20 g ;3.55 mmol) was dissolved in methylene chloride (10 ml). 1-Hydroxy-7-azabenzotriazol (0.48 g; 3.55 mmol) and N-(3-dimethylaminopropyl)-N'-ethylcarbodiimide hydrochloride (0.75 g; 3.90 mmol) were added. The reaction mixture was stirred for 15 min at room temperature.

(2R)N-Methyl-2methylamino-3-(thiophen-2-yl) propionamide (0.70 g; 3.55 mmol) was dissolved in methylene chloride (10 ml) and added. Diisopropylamine (0.61 ml ; 3.55 mmol) was added. The reaction mixture was stirred at room temperature for 2 days. Methylene chloride (10 ml) and water (10 ml) were added to the reaction mixture. The phases were separated and the organic phase was washed with aqueous sodium hydrogensulfate (10%; 20 ml), saturated aqueous sodium hydrogencarbonate (20 ml). The organic phase was dried over magnesium sulfate and the solvent was removed in vacuo. The crude product was chromatographed on silica (2×20 cm) using ethylacetate/heptane (1:1) as eluent to afford 1.38 g of N-methyl-N-((1R)-1-(N-methyl-N-((1R)-1 (methylcarbamoyl)-2-(thiophen-2-yl)ethyl)carbamoyl)-2-(2-naphthyl) ethyl) carbamic acid tert butylester.

$^1$H-NMR: (CDCl$_3$)(selected peaks for major rotamer) d 1.33 (s, 9H); 2.27 (d, 3H); 2.81 (s, 3H); 2.95 (s, 3H); 5.02 (dd; 1H); 5.22 (dd, 1H).

(2R)-N-Methyl-2-methylamino-N-((1R)-1-(methylcarbamoyl)-2-(thiophen-2-yl)ethyl)-3-(2-naphthyl) propionamide

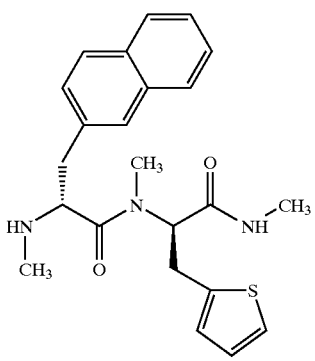

N-Methyl-N-((1R)-1-(N-methyl-N-((1R)-1-(methylcarbamoyl)-2-(thiophen-2-yl)ethyl)carbamoyl)-2-(2-naphthyl)ethyl) carbamic acid tert butylester (1.38 g; 2.71 mmol) was dissolved in methylene chloride (6 ml) and triflouroacetic acid (4 ml) was added. The reaction mixture was stirred for 1 hour at room temperature. Water (30 ml) and solid sodium hydrogencarbonate were added to pH 8. The is phases were separated and the aqueous phase was extracted with methylene chloride (4×20 ml). The organic phase was dried over magnesium sulfate and the solvent was removed over vacuo to afford 1.06 g of (2R)-N-methyl-2-methylamino-N-((1R)-1-(methylcarbamoyl)-2-(thiophen-2-yl)ethyl)-3-(2-naphthyl)propionamide.

$^1$H-NMR: (CDCl$_3$) (selected peaks for major rotamer) d 1.95 (s, 3H); 2.28 (d, 3H); 2.55 (s, 3H); 3.90 (dd, 1H); 5.42 (dd, 1H).

((3E)-1,1-Dimethyl-4-(N-methyl-N-((1R)-1-(N-methyl-N-((1R)-1-(methylcarbamoyl)-2-(thiophen-2-yl)ethyl)carbamoyl)-2-(2-naphthyl)ethyl)carbamoyl)but-3-enyl) carbamic acid tert butylester.

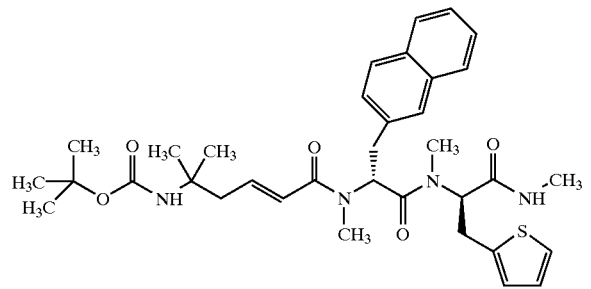

(2E)-5-(tert-Butyloxycarbonylamino)-5-methylhex-2-enoic acid (0.30 g; 1.22 mmol) was dissolved in methylene chloride (10 ml). 1-Hydroxy-7-azabenzotiazole (0.17 g; 1.22 mmol) and N-(3-dimethylaminopropyl)-N'-ethylcarbodiimide hydrochloride (0.26 g; 1.34 mmol) were added. The reaction mixture was stirred for 15 min at room temperature.

(2R)-N-Methyl-2-methylamino-N-((1R)-1-(methylcarbamoyl)-2-(thiophen-2-yl)ethyl)-3-(2-naphthyl) propionamide (0.50 g; 1.22 mmol) in methylene chloride (10 ml) was added to the reaction mixture. Diisopropylamine (0.21 ml; 1.22 mmol) was added. The reaction mixture was stirred 12 hours at room temperature. Water (10 ml) and methylene chloride (10 ml) were added. The phases were separated and the organic phase was washed with aqueous sodium hydrogensulfate (10%; 20 ml), saturated aqueous sodium hydrogencarbonate (20 ml), dried over magnesium sulfate and the solvent was removed in vacuo. The crude product was chromatographed on silica (2×20 cm) using ethyl acetate/methylene chloride (1:1) as eluent to afford 0.66 g of ((3E)-1,1-dimethyl-4-(N-methyl-N-((1R)-1-(N-methyl-N-((1R)-1-(methylcarbamoyl)-2-(thiophen-2-yl) ethyl)carbamoyl)-2-(2-naphthyl)ethyl)carbamoyl)but-3-enyl)carbamic acid tert butylester.

((3E)-1, 1-Dimethyl-4-(N-methyl-N-((1R)-1-(N-methyl-N-((1R)-1-(methylcarbamoyl)-2-(thiophen-2-yl)ethyl) carbamoyl)-2-(2-naphthyl)ethyl)carbamoyl)but-3-enyl) carbamic acid tert butylester (0.66g; 1.04 mmol) was dissolved in methylene chloride (3 ml) and triflouroacetic acid (2 ml) was added. The reaction mixture was stirred 5 min at room temperature. Water (2 ml) and solid sodium hydrogencarbonate was added to pH 8. The phases were seperated and the aqueous phase was extracted with methylene chloride (4×15 ml). The organic phase was dried over magnesium sulfate and the solvent was removed in vacuo to afford 0.53 g of the title compound.

$^1$H-NMR (CDCl$_3$) (selected peaks for major rotamer) d 2.31 (d, 3H); 2.63 (s, 3H); 2.91 (s, 3H); 5.18 (dd, 1H); 5.55 (dd, 1H); 6.19 (d, 1H).

HPLC: r$_t$=30.3 min (A1).
PDMS: m/z 534.8 (M+H)$^+$

Example 63
(2E)-5-Methyl-5-methylaminohex-2-enoic acid N-methyl-N-((1R)-1-(N-methyl-N-((1R)-1-(methylcarbamoyl)-2-phenyl ethyl)carbamoyl)-2-(2-naphthyl)ethyl)amide

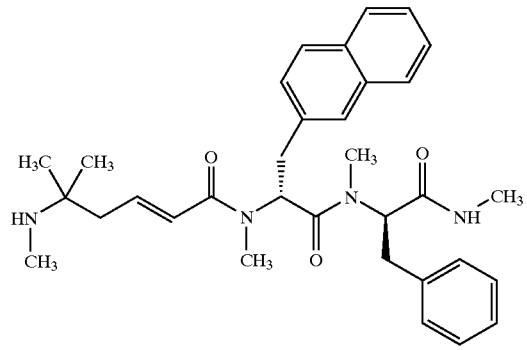

(2E)-5-(N-(tert Butoxycarbonyl)-N-methylamino)-5-methylhex-2-enoic acid.

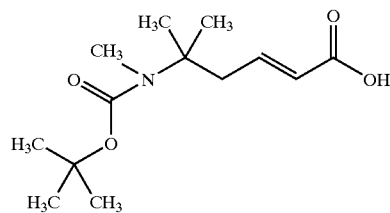

(2E)-5-(tert-Butyloxycarbonylamino)-5-methylhex-2-enoic acid (5.00 g; 20.6 mmol) was dissolved in tetrahydrofuran (70 ml). Methyliodide (10.3 ml; 164 mmol) was added and the solution was cooled to 0° C. Sodium hydride (60% in oil)(2.07 g; 61.6 mmol) was added in portions and the solution was stirred at roomtemperature for four days. Ethyl acetate (70 ml) and water (60 ml) was added dropwise and the solvent was removed in vacuo. The crude product was dissolved in water (40 ml) and ether (40 ml). The organic phase was washed with a saturated aqueous solution of sodium hydrogencarbonate (30 ml). The aqueous phases were mixed and 5% aqueous citric acid was added to pH 3. The aqueous phase was extracted with ethylacetate (4×50 ml). The organic phase was washed with water (2×40 ml), an aqueous solution of sodium thiosulfate (5%; 40 ml), water (40 ml), dried over MgSO$_4$ and the solvent was removed in vacuo. The residue was dissolved in ethylacetate (45 ml) and washed with an aqueous solution of sodium hydrogensulfate (10%; 3×30 ml), dried over MgSO$_4$ and and concentrated in vacuo to give 4.00 g of (2E)-5-(N-(tert Butoxycarbonyl)N-methylamino)-5-methylhex-2-enoic acid.

$^1$H-NMR (CDCl$_3$) d 1.38 (s, 6H), 1.45 (s, 9H ); 2.80 (d, 2H); 2.85 (s, 3H); 5.88 (d, 1H); 7.01 (q, 1H).

The title compound was prepared analogously to example 1. 5-Methylamino-5-methylhex-2-enoic acid was incorporated instead of 5-amino-5-methylhex-2-enoic acid.

$^1$H-NMR :(CDCl$_3$) (selected peaks for major rotamer) d 1.25 (s, 3H; 1.30 (s, 3H); 2.28 (d, 3H); 2.52 (s, 3H); 2.72 (s, 3H); 2.99 (d, 3H); 5.69 (dd, 1H); 5.81 (dd, 1H); 6.13 (d, 1H).

PDMS: m/z 544.4 (M+H)$^+$

HPLC: r$_t$=31.3 min (A1).

Example 64

(2E)-5Amino-3, 5-dimethylhex-2-enoic acid N-methyl-N-((1R)-1-(N-methyl-N-((1R)-1-(methylcarbamoyl)-2-(thiophen-2-yl)ethyl)carbamoyl)-2-(2-naphthyl)ethyl) amide.

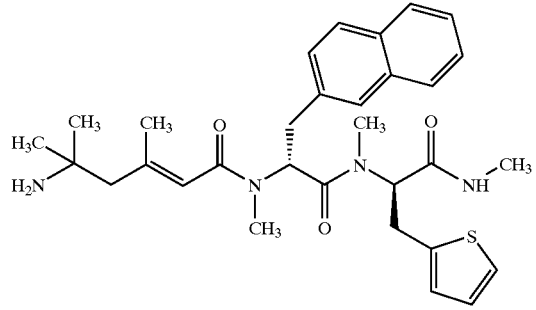

The title compound was prepared analogously to example 1. 2-thienylalanine was substituted for phenylalanine and 5-amino-3,5-dimethylhex-2-enoic acid was substituted for 5-amino-5-methylhex-2-enoic acid.

$^1$H-NMR: (CDCl$_3$) (selected peaks for major rotamer) d 1.24 (s, 3H); 1.25 (s, 3H); 1.76 (s, 2H); 2.32 (s, 3H); 2.76 (d, 3H); 2.99 (s, 3H); 5.65 (dd, 1H); 5.76 (s, 1H); 5.90 (dd, 1H)

HPLC: R$_t$=31.45 min.

PDMS: m/z 549.7 (M+H)$^+$

Example 65

5-Amino-5-methyl-hex-2-enoic acid ((1R)-1-(((1R)-1-((2S)-2-hydroxypropylcarbamoyl)-2-(3,4-difluorophenyl) ethyl)methylcarbamoyl)-2-(2-naphthyl)ethyl)methylamide.

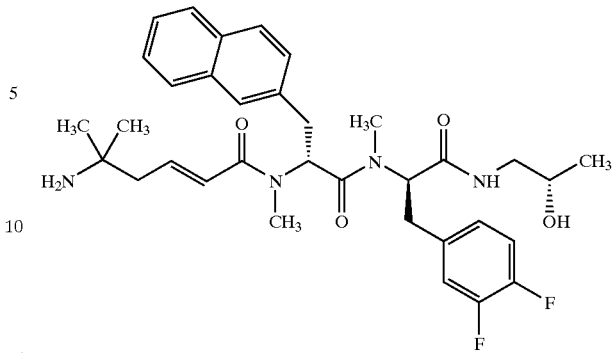

This compound was prepared analogously to example 1. 2-(3,4-difluorophenyl)-alanine was substituted for phenylalanine.

$^1$H-NMR (CDCl$_3$): (selected peaks for major rotamer) d 1.01 (t, 3H); 1.10 (s, 6H); 2.74 (s, 3H); 3.04 (s, 3H); 5.08 (dd, 1H); 5.56 (dd, 1H); 6.07 (d, 1H).

HPLC: r$_t$=32.9 min. (A1)

PDMS: m/z 610.3 (M+H)$^+$

Example 66

5-Amino-3,5-dimethylhex-2-enoic acid N-((1R)-2-(biphenyl-4-yl)-1-(N-methyl-N-((1R)-1-(methylcarbamoyl)-2-phenylethyl) carbamoyl)ethyl)-N-methylamide.

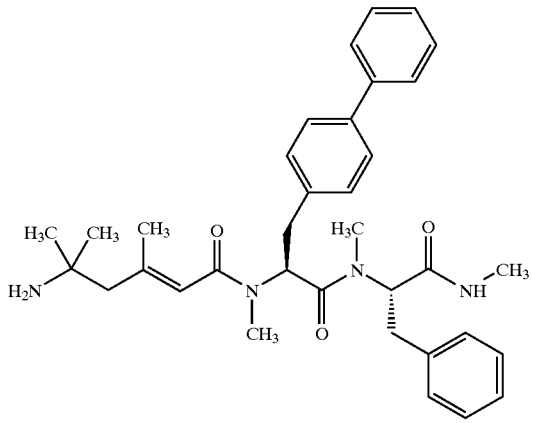

The title compound was prepared analogously to example 1. N-Tert-Butoxycarbonyl-N-methyl-D-biphenylalanin was substituted for N-tert-butoxycarbonyl-N-methyl-D-phenylalanin in step E.

(2E)-5-tert-Butoxycarbonylamino-3,5-dimethylhex-2-enoic acid was substituted for (2E)-5-(tert-Butyloxycarbonylamino)-5-methylhex-2-enoic acid in step I.

$^1$H-NMR (CDCl$_3$) (selected peaks for major rotamer) d 1.25 (s, 3H); 1.28 (s, 3H); 1.57 (s, 3H); 2.32 (s, 3H); 2.73 (d, 3H); 2.94 (s, 3H); 5.34 (dd, 1H); 5.45 (dd, 1H); 5.75 (s, 1H).

HPLC: r$_t$±35.37 min (Method A1)

PDMS: m/z =569.7 (M+H)$^+$

Example 67

(2E)-5-Amino-5-methylhex-2-enoic acid N-((1R)-1-(N-((1R)-2-(4-iodophenyl)-1-(methylcarbamoyl)ethyl)-N-methylcarbamoyl)-2-(2-naphthyl)ethyl)-N-methylamide

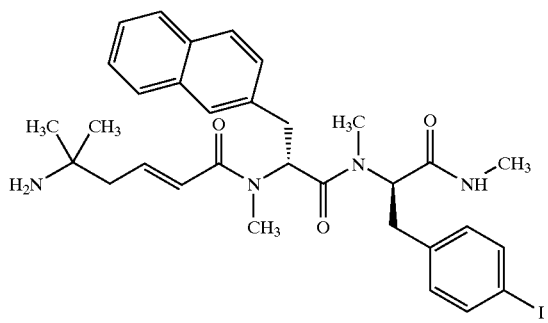

This compound was prepared analogously to example 1. N-tert-Butoxycarbonyl-N-methyl-D-4-iodophenylalanine was substituted for N-tert-butoxycarbonyl-N-methyl-D-phenylalanin in step E.

¹H-NMR (CDCl₃)(selected peaks for major rotamer) d 1.15 (s, 6H); 2.09 (d, 3H); 2.69 (s, 3H); 2.70 (s, 3H); 5.24 (dd, 1H); 5.90 (dd, 1H); 6.18 (d, 1H).

HPLC: r$_t$=35,25 min (Method A1)

PDMS: m/z =655.7 (M+H)⁺

Example 68

(2E)-5-Methyl-5-methylaminohex-2-enoic acid N-((1R)-1-(N-((1R)-2-(4-iodophenyl)-1-(methylcarbamoyl)ethyl)-N-methylcarbamoyl)-2-(2-naphthyl)ethyl)-N-methylamide

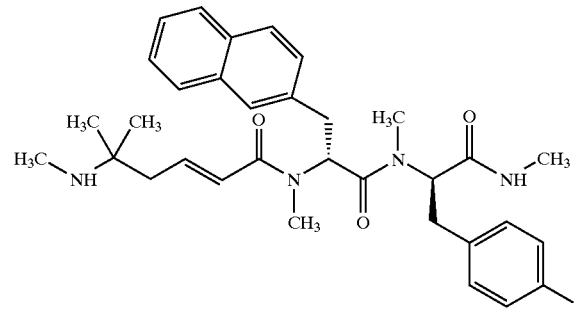

This compound was prepared analogously to example 1. N-Tert-butoxycarbonyl-N-methyl-D-4-iodophenylalanin was substituted for N-tert-butoxycarbonyl-N-methyl-D-phenylalanin in step E. (2E)-5-(N-(tert Butoxycarbonyl)-N-methylamino)-5-methylhex-2-enoic acid was substituted for (2E)-5-(tert-butyloxycarbonylamino)-5-methylhex-2-enoic acid in step I.

¹H-NMR: (CDCl₃)(selected peaks for major rotamer) d 1.17 (s, 6H); 2.07 (d, 3H); 2.39 (s, 3H); 2.71 (s, 6H); 2.92 (s, 3H); 5.25 (dd, 1H); 5.90 (dd, 1H); 6.20 (d, 1H).

HPLC: r$_t$=35.38 min (Method A1)

PDMS; m/z =668.9 (M+H)⁺

Example 69

(2E) 5-Methyl-5-amino-5-methylhex-2-enoic acid-N-methyl-N-((1R)-1-(N-methyl-N-((1R)-1-(methylcarbamoyl)-2-(thien-2-yl)ethyl)carbamoyl)-2-(2-naphthyl)ethyl)amide.

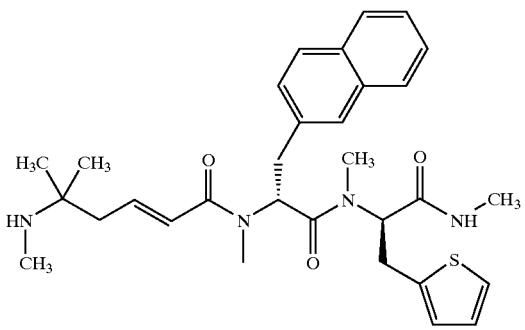

This compound was prepared analogously to example 1. 2-thienyl-alanine was substituted for phenylalanine and 5-methyl-5-methylaminohex-2-enoic acid was substituted for 5-amino-3,5-dimethylhex-2-enoic acid.

¹H-NMR (CDCl₃): (selected peaks for major rotamer) d 1.25 (s, 3H); 1.28 (s, 3H); 2.26 (d, 3H); 2.68 (s, 3H); 2.95 (s, 3H); 3.06 (s, 3H); 5.25 (dd, 1H); 5.89 (dd, 1H); 6.22 (d, 1H).

HPLC: r$_t$=30.4 min.

PDMS: m/z 549.2 (M+H)⁺

Example 70

(2E)-5-Amino-5-methyl-N-methyl-N-((1R)-1-(N-methyl-N-((1R)-1-((N-methyl-N-(methylsulfonyl)amino)methyl)-2-(2-thienyl)ethyl)carbamoyl)-2-(2-naphthyl)ethyl)hex-2-enamide

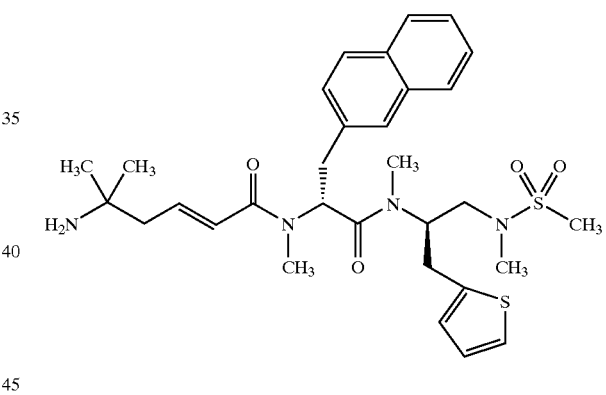

(2R)-2-(Formylamino)-3-(2thienyl)propionic acid

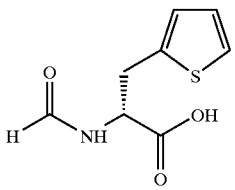

(2R)-2-Amino-3-(2-thienyl)propionic acid (5.00 g, 29.2 mmol) was dissolved in formic acid (50 ml). The solution was cooled to 0° C. Acetic acid anhydride (20 ml) was added dropwise. The reaction mixture was stirred for 16 h, while it was warming up to room temperature. It was cooled to 0° C. Water (20 ml) was added dropwise. The solution was warmed to room temperature. The solvent was is removed in vacuo. The resiude was suspended in ethyl acetate (20 ml). The precipitation was filtered off, collected, and dried in vacuo, to give 3.60 g of crude (2R)-2-(formylamino)-3-(2-thienyl)propionic acid, which was used for the following step.

¹H-NMR (DMSO d₆): d 3.05 and 3.15 (both ABX, together 1 H); 3.30 and 3.55 (m and ABX, together 1 H); 4.30 and 4.55 (both m, together 1 H); 6.90 (m, 1 H); 6.95 (m, 1 H); 7.35 (d, 1 H); 8.03 (s, 1 H); 8.40 (d, 1 H); 12.92 (br, 1 H).

(2R)-2-Methylamino-3-(2-thienyl)propan-1-ol

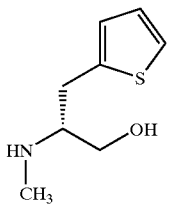

A solution of (2R)-2-(formylamino)-3-(2-thienyl) propionic acid (3.58 g, 18.0 mmol) in tetrahydrofuran (50 ml) was added dropwise to a suspension of sodium borohydride in tetrahydrofuran (50 ml), which was cooled to 7–12° C. (inside temperature). After the addition was finished, a solution of iodine (4.57 9, 18.0 mmol) in tetrahydrofuran (100 ml) was added dropwise. The reaction mixture was heated to reflux for 16 h. It was cooled to 0° C. Methanol (200 ml) was added dropwise. The solvent was removed in vacuo. The residue was dissolved in a freshly prepared 20% aqueous sodium hydroxide solution (200 ml). The aqueous phase was extracted with tert-butyl methyl ether (4×150 ml). The combined organic layers were dried over magnesium sulfate. The solvent was removed in vacuo to give 3.26 g of crude (2R)-2-methylamino-3-(2-thienyl) propan-1-ol, which was used for the following step.

¹H-NMR (DMSO d₆, selected values): d 2.32 (s, 3 H); 2.56 (m, 1 H); 2.84 (m, 2 H); 3,30 (m, 2 H); 6.85 (m, 1 H); 6.93 (m, 1 H); 7.28 (d, 1 H).

N-((1R)-1-(Hydroxymethyl)-2-(2-thienyl)ethyl)-N-methylcarbamic acid tert-butyl ester

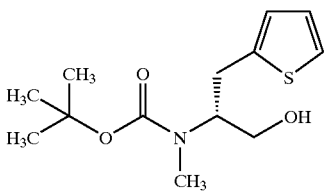

A solution of di-tert-butyldicarbonate (4.97 g, 22.8 mmol) in tetrahydrofuran (20 ml) was added dropwise to a solution of (2R)-2-methylamino-3-(2-thienyl)propan-1-ol in 1 N aqueous sodium hydroxide solution (19 ml) and tetrahydrofuran (20 ml). The reacion mixture was stirred at room temperature for 16 h. It was diluted with water (100 ml) and extracted with ethyl acetate (3×150 ml). The combined organic layers were washed with saturated sodium hydrogen carbonate solution (200 ml) and dried over magnesium sulfate. The solvent was removed in vacuo. The crude product was purified by flash chromatography on silica (220 g), using ethyl acetate/heptane 1:1 as eluent, to give 3.85 g of N-((1R)-1-(hydroxymethyl)-2-(2-thienyl)ethyl)-N-methylcarbamic acid tert-butyl ester.

¹H-NMR (CDCl₃, selected values) d 1.41 (br, 9 H); 2.75 (br, 3 H); 3.05–3.20 (both br, together 2 H); 3.75 (br, 2 H); 4.10 and 4.27 (both br, together 2 H); 6.82 (br, 1 H); 6.90 (m, 1 H); 7.14 (d, 1 H).

N-Methyl-N-((1R)-2-methylamino-1-((2-thienyl)methyl) ethyl)carbamic acid tert-butyl ester

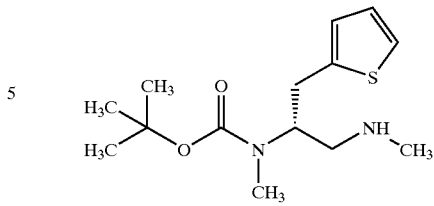

A solution of oxalyl chloride (1.81 ml, 20.8 mmol) in dichloromethane (180 ml) was cooled to −78° C. A solution of dimethylsulfoxide (2.15 ml, 27.8 mmol) in dichloromethane (2 ml) was added dropwise. The solution was stirred for 15 min at −78° C. A solution of N-((1R)-1-(hydroxymethyl)-2-(2-thienyl)ethyl)-N-methylcarbamic acid tert-butyl ester (3.78 g, 13.9 mmol) in dichloromethane (10 ml) was added dropwise. The solution was stirred for 20 min at −78° C. Triethylamine (7.71 ml, 55.6 mmol) was added. The solution was stirred for 5 min at −78° C. and warmed to −35° C. As soon as −35° C. was reached it was cooled to −78° C. Acetic acid (3.50 ml, 61.2 mmol) was added. The solution was warmed to room temperature and was washed with brine (200 ml). The organic phase was dried over magnesium sulfate. The solvent was removed in vacuo. The residue was dissolved in methanol (180 ml). 4 A mol (20 g) sieves was added. Acetic acid (5.5 ml, 97.3 mmol) was added. An 8.0 M solution of methylamine in ethanol (5.2 ml, 41.7 mmol) was added. Solid sodium cyano borohydride (0.57 g, 9.1 mmol) was added. The solution was stirred at room temperature for 1 h, before another portion of solid sodium cyano borohydride (0.57 g, 9.1 mmol) was added. The reaction mixture was stirred for 16 h at room temperature and filtered through a plug of celite. The celite was washed with methanol (150 ml). The solvent of the filtrate was removed in vacuo. The residue was dissolved in 1 N sodium hydroxide solution (200 ml). The solution was extracted with tert-butyl methyl ether (3×100 ml). The combined organic layers were dried over magnesium sulfate. The solvent was removed in vacuo. The crude product was purified by flash chromatography on silica (150 g), using dichloromethane/methanol/25% aqueous ammonia 100:10:1 as eluent, to give 1.72 g of N-methyl-N-((1R)-2-methylamino-1-((2-thienyl)methyl)ethyl)carbamic acid tert-butyl ester.

¹H-NMR (CDCl₃, selected values) d 1.32 and 1.42 (both br, together 9 H); 2.44 (s, 3 H); 2.63 (ABX, 1 H); 2.70–2.90 (m, 4 H); 2.95 and 3.03 (both br, together 2 H); 4.40 (br, 1 H); 6.82 (br, 1 H); 6.92 (m, 1 H); 7.15 (d, 1 H).

MS: 285 [M+1]⁺.

N-Methyl-N-((1R)-2-(N-methyl-N-(methylsulfonyl) amino)-1-((2-thienyl)methyl)ethyl)carbamic acid tert-butyl ester

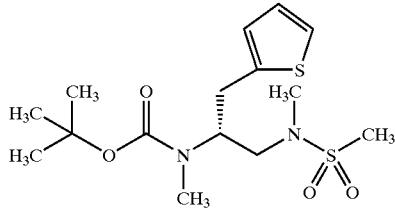

N-Methyl-N-((1R)-2-methylamino-1-((2-thienyl)methyl) ethyl)carbamic acid tert-butyl ester (1.72 g, 6.05 mmol) was dissolved in dichloromethane (30 ml). Triethylamine (0.84 ml, 6.05 mmol) was added. The solution was cooled to −78°

C. Methanesulfonyl chloride (0.47 ml, 6.05 mmol) was added dropwise. The reaction mixture was warmed to room temperature over a period of 3.5 h. It was stirred at room temperature for 16 h. The reaction mixture was diluted with dichloromethane (100 ml). It was washed with 10% aqueous sodium hydrogen sulfate solution (200 ml). The aqueous phase was extracted with dichloromethane (2×50 ml). The combined organic layers were washed with saturated sodium hydrogen carbonate solution (200 ml) and dried over magnesium sulfate. The solvent was removed in vacuo. The crude product was purified by flash chromatography on silica (180 g), using ethyl acetate/heptane 1:1 as eluent, to give 1.94 g of N-methyl-N-((1R)-2-(N-methyl-N-(methylsulfonyl)amino)-1-((2-thienyl)methyl)ethyl) carbamic acid tert-butyl ester.

¹H-NMR (CDCl₃) d 1.40 and 1.45 (both s, together 9 H); 2.74 and 2.80 (s and m, together 6 H); 2.91 (s, 3 H); 3.06 (m, 3 H); 3.57 (m, 1 H); 4.55 (br, 1 H); 6.85 (d, 1 H); 6.92 (m, 1 H); 7.16 (m, 1 H).

N-Methyl-N-((2R)-2-(methylamino)-3-(2-thienyl)propyl)methanesulfonamide

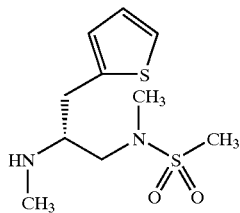

A solution of of N-methyl-N-((1R)-2-(N-methyl-N-(methylsulfonyl)amino)-1-((2-thienyl)methyl)ethyl) carbamic acid tert-butyl ester (1.87 g, 7.12 mmol) in dichloromethane (7 ml) was cooled to 0° C. Trifluoroacetic acid (7 ml) was added. The reaction mixture was stirred for 45 min at 0° C. Dichloromethane (10 ml) was added. A saturated aqueous solution of sodium hydrogen carbonate (10 ml) was added. Solid sodium hydrogen carbonate was added until pH 7. Water (100 ml) was added, until a clear solution was obtained. The phases were separated. The aqueous phase was extracted with dichloromethane (2×50 ml). The combined organic phases were dried over magnesium sulfate. The solvent was removed in vacuo. The crude product was purified by flash chromatography on silica (120 g), using dichloromethane/methanol/25% aqueous ammonia as eluent, to give 1.24 g of N-methyl-N-((2R)-2-(methylamino)-3-(2-thienyl)propyl)methanesulfonamide.

¹H-NMR (CDCl₃) d 2.47 (s, 3 H); 2.81 (s, 3 H); 2.88 (s, 3 H); 2.90–3.10 (m, 4 H); 3.22 (dd, 1 H); 6.86 (m, 1 H); 6.95 (m, 1 H); 7.19 (m, 1 H).

N-Methyl-N-((1R)-1-(N-methyl-N-((1R)-1-((N-methyl-N-(methylsufonyl)amino)methyl)-2-(2-thienyl)ethyl)carbamoyl)-2-(2-naphthyl)ethyl)carbamic acid tert-butyl ester

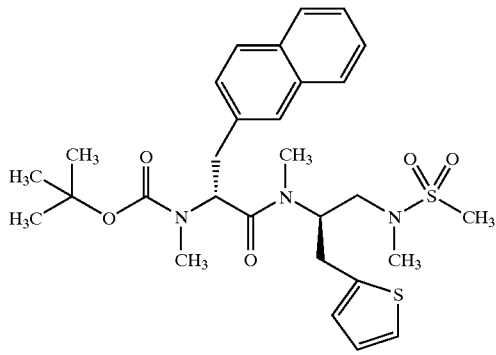

(2R)-2-(N-(tert-Butoxycarbonyl)-N-methylamino)-3-(2-naphthyl)propionic acid (1.46 g, 4.42 mmol) was dissolved in N,N-dimethylformamide (5 ml) and dichloromethane (5 ml). 1-Hydroxy-7-azabenzotridazole (0.60 g, 4.42 mmol) was added. The solution was cooled to 0° C. N-(3-Dimethylaminopropyl)-N'-ethylcarbodiimide hydrochloride (0.85 g, 4.42 mmol) was added. The reaction mixture was stirred for 20 min at 0° C. A solution of N-methyl-N-((2R)-2-(methylamino)-3-(2-thienyl)propyl)methanesulfonamide (1.16 g, 4.42 mmol) in dichloromethane (5 ml) and ethyldiisopropylamine (0.76 ml, 4.42 mmol) were added successively. The solution was stirred for 16 h, while it was warming up to room temperature. It was diluted with ethyl acetate (90 ml) and washed with 10% aqueous sodium hydrogen sulfate solution (100 ml). The aqueous phase was extracted with ethyl acetate (2×30 ml). The combined organic layers were washed with saturated sodium hydrogen carbonate solution (100 ml) and dried over magnesium sulfate. The solvent was removed in vacuo. The crude product was purified by flash chromatography on silica (240 g), using ethyl acetate/heptane 2:1 as eluent, to give 2.05 g of N-Methyl-N-((1R)-1-(N-methyl-N-((1R)-1-((N-methyl-N-(methylsufonyl)amino)methyl)-2-(2-thienyl)ethyl)carbamoyl)-2-(2-naphthyl)ethyl)carbamic acid tert-butyl ester.

¹H-NMR (CDCl₃, selected values) d 1.09 and 1.33 (both s, together 9 H); 5.05 and 5.37 (both dd, together 1 H).

(2R)-2-Methylamino-N-methyl-N-((1R)-1-((N-methyl-N-(methylsufonyl)amino)methyl)-2-(2-thienyl)ethyl)-3-(2-naphthyl)propionamide

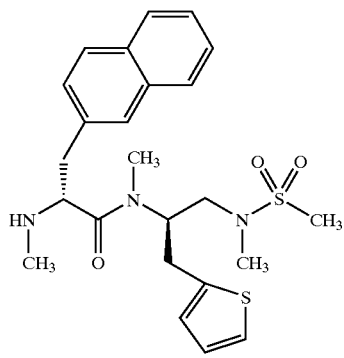

A solution of of N-Methyl-N-((1R)-1-(N-methyl-N-((1R)-1-((N-methyl-N-(methylsufonyl)amino)methyl)-2-(2-thienyl)ethyl)carbamoyl)-2-(2-naphthyl)ethyl)carbamic acid tert-butyl ester (1.94 g, 3.37 mmol) in dichloromethane (7 ml) was cooled to 0° C. Trifluoroacetic acid (7 ml) was added. The reaction mixture was stirred for 45 min at 0° C.

A saturated aqueous solution of sodium hydrogen carbonate (30 ml) was added. Solid sodium hydrogen carbonate was added until pH 7. Water (100 ml) was added, until a clear solution was obtained. The phases were separated. The aqueous solution was extracted with dichloromethane (2×50 ml). The combined organic layers were dried over magnesium sulfate. The solvent was removed in vacuo. The crude product was purified by flash chromatography on silica (200 g), using dichloromethanelmethanol/25% aqueous ammonia as eluent, to give 1.70 g of (2R)-2-Methylamino-N-methyl-N-((1R)-1-((N-methyl-N-(methylsulfonyl)amino)methyl)-2-(2-thienyl)ethyl)-3-(2-naphthyl)propionamide.

$^1$H-NMR (CDCl$_3$, selected values) d 2.04 and 2.32 (both s, together 3 H); 2.61 and 2.65 (both s, together 3 H); 2.71 and 2.73 (both s, together 3 H); 2.82 and 2.85 (both s, together 3 H); 3.68 and 3.75 (both t, together 1 H); 5.14 (br, 1 H).

((3E)-1,1-Dimethyl-4-(N-methyl-N-((1R)-1-(N-methyl-N-((1R)-1-((N-methyl-N-(methylsuflonyl)amino)methyl)-2-(2-thienyl)ethyl)carbamoyl)-2-(2-naphthyl)ethyl)carbamoyl)but-3-enyl)carbamic acid tert-butyl ester

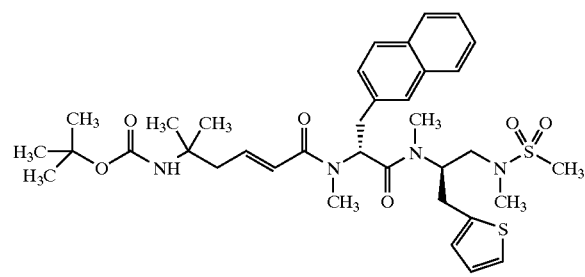

(2E)-5-(tert-Butoxycarbonylamino)-5-methylhex-2enoic acid (158 mg, 0.65 mmol) was dissolved in N,N-dimethylformamide (3 ml) and dichloromethane (3 ml). 1-Hydroxy-7-azabenzotriazole was added. The solution was cooled to 0° C. N-(3-Dimethylaminopropyl)-N'-ethylcarbodiimide hydrochloride (88 mg, 0.65 mmol) was added. The reaction mixture was stirred for 15 min at 0° C. A solution of (2R)-2-Methylamino-N-methyl-N-((1R)-1-((N-methyl-N-(methylsulfonyl)amino)methyl)-2-(2-thienyl)ethyl)-3-(2-naphthyl)propionamide in dichloromethane (3 ml) and ethyldiisopropylamine (0.12 ml, 0.65 mmol) were added successively. The reaction mixture was stirred for 16 h, while it was warming up to room temperature. It was diluted with ethyl acetate (50 ml) and washed with 10% aqueous sodium hydrogen sulfate solution (50 ml). The aqueous phase was extracted with ethyl acetate (2×50 ml). The organic layers were washed with a saturated aqueous solution of sodium hydrogen carbonate (100 ml) and dried over magnesium sulfate. The solvent was removed in vacuo. The crude product was purified on silica (120 g), using ethyl acetatelheptane 2:1 (250 ml) and successively ethyl acetate/heptane 3:1 as eluent, to give 282 mg of ((3E)-1,1-dimethyl-4-(N-methyl-N-((1R)-1-(N-methyl-N-((1R)-1-((N-methyl-N-(methylsuflonyl)amino)methyl)-2-(2-thienyl)ethyl)carbamoyl)-2-(2-naphthyl)ethyl)carbamoyl)but-3-enyl)carbamic acid tert-butyl ester.

$^1$H-NMR (CDCl$_3$, selected values) d 1.15–1.35 (m, 6H); 1.40 and 1.69 (m and br, together 9 H);5.69 and 5.85 (both m, together 1 H); 6.06, 6.13, and 6.27 (all d, together 1 H).

A solution of ((3E)-1,1-Dimethyl-4-(N-methyl-N-((1R)-1-(N-methyl-N-((1R)-1-((N-methyl-N-(methylsuflonyl)amino)methyl)-2-(2-thienyl)ethyl)carbamoyl)-2-(2-naphthyl)ethyl)carbamoyl)but-3-enyl)carbamic acid tert-butyl ester (251 mg, 0.36 mmol) in dichloromethane (3 ml) was cooled to 0° C. Trifluoroacetic acid (3 ml) was added. The solution was stirred for 50 min at 0° C. A saturated aqueous solution of sodium hydrogen carbonate (15 ml) was added. Solid sodium hydrogen carbonate was added until pH 7. Water (70 ml) was added, until a clear solution was obtained. The phases were separated. The aqueous phase was extracted with dichloromethane (3×30 ml). The combined organic layers were dried two times over magnesium sulfate. The solvent was removed in vacuo. The crude product was purified by flash chromatography on silica (120 g), using dichloromethane/methanol/25% aqueous ammonia as eluent, to give 159 mg of the title compound. The HPLC showed a 20% impurity, which is a diastereoisomere of the title compound.

$^1$H-NMR (CDCl$_3$, selected values) d 1.14 (br, 6H); 5.05 (br, 1H); 5.66, 5.77, and 5.85 (all dd, together 1 H); 6.08, 6.13 and 6.40 (all dd, together 1 H).

| | |
|---|---|
| MS | 598.8 [M + 1]$^+$; |
| | 599.0 [M + 1]$^+$, isomeric impurity. |
| HPLC | 31.22 min (A1); |
| | 32.75 min (A1, isomeric impurity); |
| | 33.18 min (B1); |
| | 34.88 min (B1, isomeric impurity). |

For biological testing, the title compound was transferred into its acetate salt, by liophilization from 0.5 M acetic acid (50 ml).

Example 71
(2E)-5-Amino-5-methyl-N-methyl-N-((1R)-1-(N-methyl-N-((1R)-2-phenyl-1-((2,2,2-trifluoroethyl)carbamoyl)ethyl)carbamoyl)-2-(2-naphthyl)ethyl)hex-2-enamide

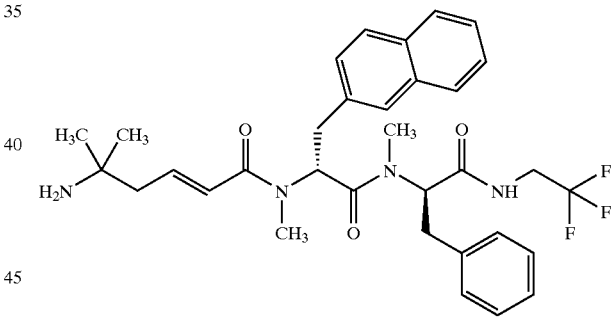

N-Methyl-N-((1R)-2-phenyl-1-((2,2, 2-trifluoroethyl) carbamoyl)ethyl)carbamic acid tert-butyl ester

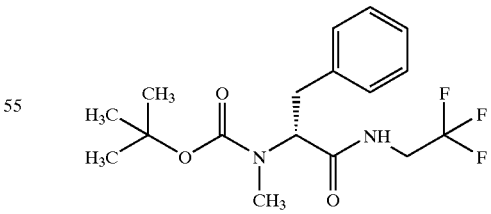

At 0° C., N-(3-dimethylaminopropyl)-N'-ethylcarbodiimide hydrochloride (2.18 g, 11.4 mmol) was added to a solution of (2R)-2-(N-(tert-butoxycarbonyl)-N-methylamino)-3-phenylpropionic acid (3.0 g, 11.4 mmol) and 1-hydroxybenzotriazole hydrate (1.54 g, 11.4 mmol) in N,N-dimethylformamide (2 ml) and dichloromethane (4 ml). The reaction mixture was stirred for 15 min at 0° C.

2,2,2-Trifluoroethylamine (0.91 ml, 11.4 mmol) and ethyldiisopropylamine (2.0 ml, 11.39 mmol) were added successively. The reaction mixture was stirred for 16 h, while it was warming up to room temperature. It was diluted with ethyl acetate (150 ml) and washed with 10% aqueous sodium hydrogen sulfate solution (200 ml). The aqueous phase was extracted with ethyl acetate (2×30 ml). The combined organic layers were washed with saturated sodium hydrogen carbonate solution (150 ml) and dried over magnesium sulfate. The solvent was removed in vacuo. The crude product was purified by flash chromatography on silica (240 g), using ethyl acetate/heptane 1:2 as eluent, to give 3.52 g of N-methyl-N-((1R)-2-phenyl-1-((2,2,2-trifluoroethyl)carbamoyl)ethyl)carbamic acid tert-butyl ester.

$^1$H-NMR (CDCl$_3$): d 1.30 and 1.42 (both br, together 9 H); 2.76 (s, 3 H); 3.04 (m, 1H); 3.35 and 3.48 (both m, together 1 H); 3.65 and 3.85 (both m, together 1 H); is 4.13 (m, 1 H); 4.74 and 4.92 (both br, together 1 H); 5.25 and 6.75 (both br, together 1 H); 7.10–7.40 (m, 5 H).

MS: 361.0 [M+1]$^+$; 261.0 [M+1−BOC]$^+$.

(2R)-2-Methylamino-3-phenyl-N-(2,2,2-trifluoroethyl)propionamide

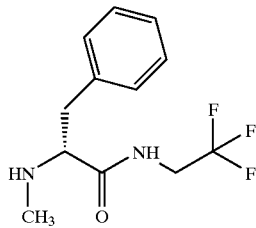

N-Methyl-N-((1R)-2-phenyl-1-((2,2,2-trifluoroethyl)carbamoyl)ethyl)carbamic acid tert-butyl ester (3.45 g, 9.57 mmol) was dissolved in dichloromethane (8 ml). The solution was cooled to 0° C. Trifluoroacetic acid (8 ml) was added. The reaction mixture was stirred for 45 min at 0° C. A saturated aqueous solution of sodium hydrogen carbonate (40 ml) was added. Solid sodium hydrogen carbonate was added until pH 7. Water (100 ml) was added, until a clear solution was obtained. The phases were separated. The aqueous phase was extracted with dichloromethane (3×30 ml). The combined organic layers were dried over magnesium sulfate. The solvent was removed in vacuo. The crude product was purified by flash chromatography on silica (180 g), using dichloromethane/methanol/25% aqueous ammonia as eluent to give 1.13 g of (2R)-2-methylamino-3-phenyl-N-(2,2,2-trifluoroethyl)propionamide.

$^1$H-NMR (CDCl$_3$): d 2.27 (s, 3H); 2.73 (dd, 1H); 3.15–3.35 (m, 2H); 3.95 (m, 2H); 7.15–7.40 (m, 5H); 7.70 (br, 1H).

N-Methyl-N-((1R)-1-(N-methyl-N-((1R)-2-phenyl-1-((2,2,2-trifluoroethyl)carbamoyl)ethyl)carbamoyl)-2-(2-naphthyl)ethyl)carbamic acid tert-butyl ester

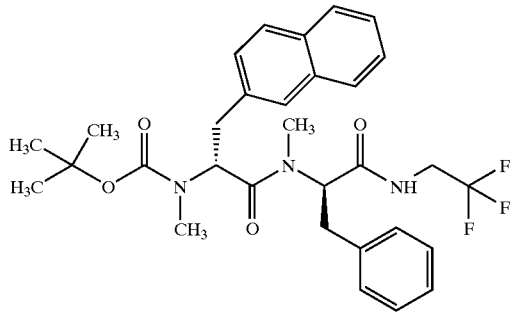

A solution of (2R)-2-(N-(tert-butoxycarbonyl)-N-methylamino)-3-(2-naphthyl)propionic acid (1.35 g, 4.1 mmol) and 1-hydroxy-7-azabenzotriazole (0.56 g, 4.1 mmol) in N,N-dimethylformamide (5 ml) and dichloromethane (5 ml) was cooled to 0° C. N-(3-Dimethylaminopropyl)-N'-ethylcarbodiimide hydrochloride (0.79 g, 4.1 mmol) was added. The reaction mixture was stirred for 15 min at 0° C. A solution of (2R)-2-methylamino-3-phenyl-N-(2,2,2-trifluoroethyl)propionamide (1.07 g, 4.1 mmol) in dichloromethane (5 ml) was added. Ethyldiisopropylamine (0.71 ml) was added. The reaction mixture was stirred for 16 h, while it was warming up to room temperature. It was diluted with ethyl acetate (100 ml) and washed with 10% aqueous sodium hydrogen sulfate solution (100 ml). The aqueous phase was extracted with with ethyl acetate (2×50 ml). The combined organic layers were washed with saturated sodium hydrogen carbonate solution (100 ml) and dried over magnesium sulfate. The solvent was removed in vacuo. The crude product was purified by flash chromatography on silica (170 g), using ethyl acetate/heptane 1:2 (300 ml), and then ethyl acetatelheptane/dichloromethane 1:1:1 as eluent to give 1.14 g of N-methyl-N-((1R)-1-(N-methyl-N-((1R)-2-phenyl-1-((2,2,2-trifluoroethyl)carbamoyl)ethyl)carbamoyl)-2-(2-naphthyl)ethyl)carbamic acid tert-butyl ester.

$^1$H-NMR (CDCl$_3$, selected values): d 1.09 and 1.31 (both s, together 9 H); 5.00–5.50 (m, together 2 H); 7.00–7.80 (m, 12 H).

(2R)-2-Methylamino-N-methyl-3-(2-naphthyl)-N-((1R)-2-phenyl-1-((2,2,2-trifluoroethyl)carbamoyl)ethyl)propionamide

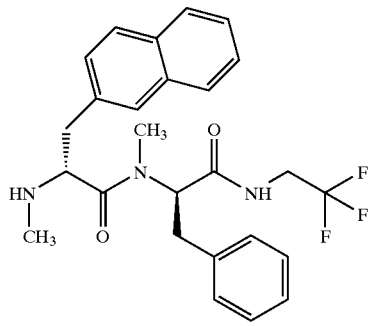

N-Methyl-N-((1R)-1-(N-methyl-N-((1R)-2-phenyl-1-((2,2,2-trifluoroethyl)carbamoyl)ethyl)carbamoyl)-2-(2-naphthyl)ethyl)carbamic acid tert-butyl ester (1.12 g, 1.97 mmol) was dissolved in dichloromethane (6 ml). The solution was cooled to 0° C. Trifluoroacetic acid (6 ml) was added. The reaction mixture was stirred for 45 min at 0° C. A saturated solution of aqueous sodium hydrogen carbonate (30 ml) was added. Solid sodium hydrogen carbonate was added until pH 7. Water (100 ml) was added until a clear solution was obtained. The phases were separated. The aqueous solution was extracted with dichloromethane (2×50 ml). The combined organic layers were dried over magnesium sulfate. The solvent was removed in vacuo. The crude product was purified by flash chromatography on silica (90 g), using dichloromethane/methanol/25% aqueous ammonia 100:10:1 as eluent, to give 946 mg of (2R)-2-methylamino-N-methyl-3-(2-naphthyl)-N-((1R)-2-phenyl-1-((2,2,2-trifluoroethyl)carbamoyl)ethyl)propionamide.

¹H-NMR (CDCl₃, selected values): d 1.77, 2.36, 2.65, and 2.91 (all s, together 6 H); 4.56 and 5.55 (both dd, together 1 H); 6.85–7.90 (m, together 12 H).

((3E)-4-(N-Methyl-N-((1R)-1-(N-methyl-N-((1R)-2-phenyl-1-((2,2,2-trifluoroethyl)carbamoyl)ethyl)carbamoyl)-2-(2-naphthyl)ethyl)carbamoyl)-1,1-dimethylbut-3-enyl)carbamic acid tert-butyl ester

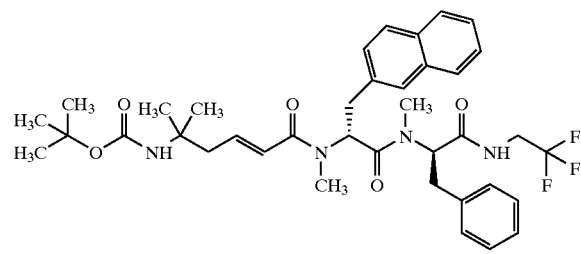

(2E)-5-(tert-Butoxycarbonylamino)-5-methylhex-2-enoic acid (168 mg, 0.69 mmol) and 1-hydroxy-7-azabenzotriazole (94 mg, 0.69 mmol) were dissolved in N,N-dimethylformamide (3 ml) and dichloromethane (3 ml). The solution was cooled to 0° C. N-(3-Dimethylaminopropyl)-N'-ethylcarbodiimide hydrochloride (132 mg, 0.69 mmol) was added. The reaction mixture was stirred for 15 min at 0° C. A solution of (2R)-2-methylamino-N-methyl-3-(2-naphthyl)-N-((1R)-2-phenyl-1-((2,2,2-trifluoroethyl)carbamoyl)ethyl)propionamide (327 mg, 0.69 mmol) in dichloromethane (3 ml) was added. Ethyldiisopropylamine (0.12 ml, 0.69 mmol) was added. The reaction mixture was stirred for 16 h, while it was warming up to room temperature. It was diluted with ethyl acetate (50 ml) and washed with 10% aqueous sodium hydrogen sulfate solution (50 ml). The aqueous phase was extracted with ethyl acetate (2×20 ml). The combined organic layers were washed with saturated sodium hydrogen carbonate solution (100 ml) and dried over magnesium sulfate. The solvent was removed in vacuo. The crude product was purified by flash chromatography on silica (160 g), using ethyl acetate/heptane 1:1 as eluent to give 447 mg of ((3E)-4-(N-methyl-N-((1R)-1-(N-methyl-N-((1R)-2-phenyl-1-((2,2,2-trifluoroethyl)carbamoyl)ethylcarbamoyl)-2-(2-naphthyl)ethyl)carbamoyl)-1,1-dimethylbut-3-enyl) carbamic acid tert-butyl ester.

¹H-NMR (CDCl₃, selected values): d 1.20, 1.23, 1.28, and 1.29 (all s, together 15 H); 2.55, 2.76, 2.95, and 3.02 (all s, together 6 H); 7.00–7.85 (m, 12 H).

((3E)-4-(N-Methyl-N-((1R)-1-(N-methyl-N-((1R)-2-phenyl-1-((2,2,2-trifluoroethyl)carbamoyl)ethyl)carbamoyl)-2-(2-naphthyl)ethyl)carbamoyl)-1,1-dimethylbut-3-enyl)carbamic acid tert-butyl ester (407 mg, 0.58 mmol) was dissolved in dichloromethane (4 ml). The solution was cooled to 0° C. Trifluoroacetic acid (4 ml) was added. The reaction mixture was stirred for 45 min at 0° C. A saturated aqueous solution of sodium hydrogen carbonate (5 ml) was added. Solid sodium hydrogen carbonate was added until pH 7. Water (100 ml) was added, until a clear solution was obtained. The phases were separated. The aqueous phase was extracted with dichloromethane (2×20 ml). The combined organic layers were dried over magnesium sulfate. The solvent was removed in vacuo. The crude product was purified on silica (90 g) using dichloromethane/methanol/25% aqueous ammonia as eluent, to give 251 mg of the title comopund.

¹H-NMR (CDCl₃, selected values): d 1.00 and 1.13 (both s, together 6 H); 2.57, 2.77, 2.98, and 3.06 (all s, together 6H); 5.30 (m, 1 H); 5.60 and 5.87 (both dd, together 1 H); 6.04 and 6.05 (both d, together 1 H) 6.86 (m, 1 H).

MS: 597.0 [M+1]⁺

HPLC: 35.55 min (A1) 37.87 min (B1).

For biological testing, the title compound was transferred into its acetate salt by liophilization from 0.5 M acetic acid (50 ml).

Example 72

(2E)-5-Amino-5-methylhex-2-enoic acid N-((1R)-1-(N-((1R)-1-(cyclopropylcarbamoyl)-2-phenylethyl)-N-methylcarbamoyl)-2-(2-naphthyl)ethyl)-N-methylamide

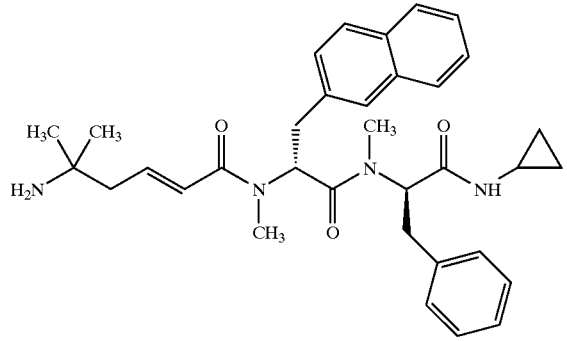

This compound was prepared analogously to example 1 using cyclopropylamine instead of methylamine.

¹H-NMR: (CDCl₃) (selected peaks for major rotamer) d 0.43 (m, 4H); 1.08 (s, 6H); 2.99 (s, 3H); 5.15 (dd, 1H); 5.57 (dd, 1H); 6.04 (d, 1H).

HPLC: r₁=33.2 min (A1)

PDMS: m/z 554 (M+H)⁺

Example 73

(2E)-4-(1-Aminocyclobutyl)but-2-enoic acid N-((1R)-1-(N-((1R)-2-(3,4-difluorophenyl)-1-(methylcarbamoyl)ethyl)-N-methylcarbamoyl)-2-(2-naphthyl)ethyl)-N-methylamide

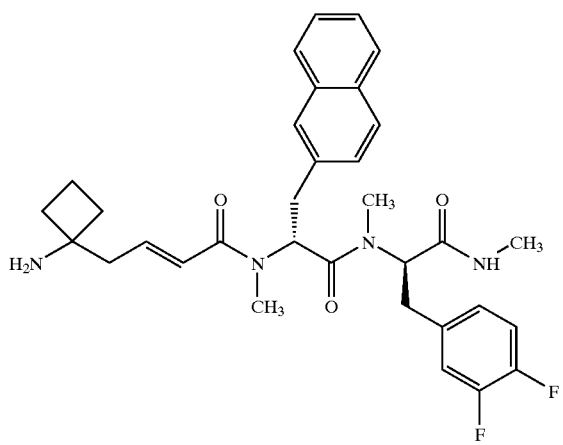

This compound was prepared analogously to example 1 using (3,4-difluorophenyl)alanine instead of phenylalanine and (2E)-4-(1-(tert-butoxycarbonylamino)cyclobutyl)but-2-enoic acid (prepared as in R. Graf, Org Synth. 46, 51 (1966)) instead of (2E)-5-(tert-butoxycarbonylamino)-5-methylhex-2-enoic acid.

$^1$H-NMR: (CDCl$_3$) (selected peaks for major rotamer) d 1.93 (s, 6H); 2.05 (s, 3H); 2.75 (s, 3H); 2.91 (s, 3H); 5.24 (dd, 1H); 5.92 (dd, 1H); 6.29 (d, 1H)

HPLC: r$_t$=33.9 min (A1)

PDMS: m/z 576 (M+H)$^+$

Example 74

(2E)-4-(1-Aminocyclobutyl)but-2-enoic acid N-((1R)-1-(N-((1R)-1-(cyclopropylcarbamoyl)-2-phenylethyl)-N-methylcarbamoyl)-2-(2-naphthyl)ethyl)-N-methylamide

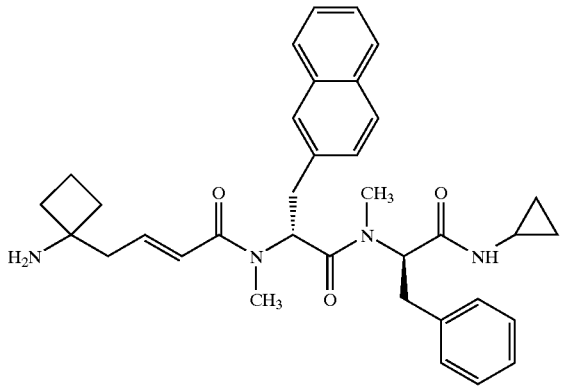

This compound was prepared analogously to example 1 using cyclopropylamine instead of methylamine and and (2E)A4-(1-(tert-butoxycarbonylamino)cyclobutyl)but-2-enoic acid (prepared as in R. Graf, Org Synth. 46, 51 (1966)) instead of (2E)-5-(tert-butoxycarbonylamino)-5-methylhex-2-enoic acid.

$^1$H-NMR: (CDCl$_3$) (selected peaks for major rotamer) d 0.45 (m, 4H); 2.49 (s, 3H); 2.95 (s, 3H); 5.18 (dd, 1H); 5.78 (dd, 3H); 6.33 (d, 1H)

HPLC: r$_t$=33.9 min (A1)

PDMS: m/z 567 (M+H)$^+$

Example 75

(2E) 4-(1-Aminocyclobutyl)-but-2-enoic acid N-((1R)-2-(biphenyl-4-yl)-1-(N-methyl-N-((1R)-1-(methylcarbamoyl)-2-phenylethyl)carbamoyl)ethyl)-N-methylamide

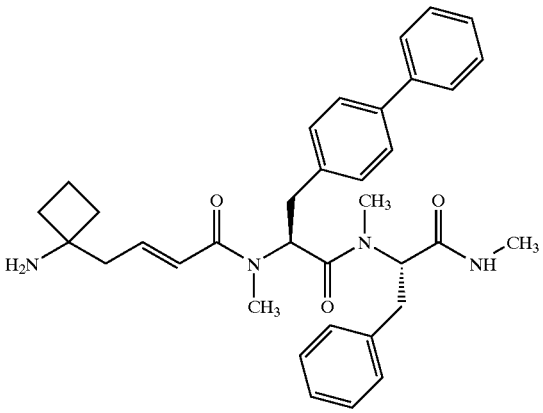

This compound was prepared analogously to example 1 using biphenylalanine instead of phenylalanine and and (2E)-4-(1-(tert-butoxycarbonylamino)cyclobutyl)but-2-enoic acid (prepared as in R. Graf, Org Synth. 46, 51 (1966)) instead of (2E)-5-(tert-butoxycarbonylamino)-5-methylhex-2-enoic acid.

$^1$H-NMR: (CDCl$_3$) (selected peaks for major rotamer) d 1.98 (m, 6H); 2.49 (s, 3H); 2.59 (d, 3H); 2.95 (s, 3H); 5.50 (dd, 1H); 5.78 (dd, 1H); 6.18 (d, 1H).

HPLC: r$_t$=34.9 min (A1)

PDMS: m/z (M+H)$^+$

LC-MS: 569.0 (m+1)$^+$

Example 76

3-(1-Aminoethyl)-N-methyl-N-((1R)-1-(N-methyl-N-((1R)-1-(methylcarbamoyl)-2-(2-thienyl)ethyl)-carbamoyl)-2-(2-naphthyl)ethyl)benzamide

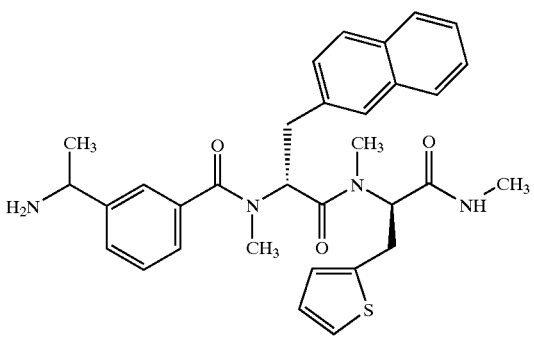

The N-Methyl-PAL-Resin (75 mg, 0.045 mmol, load: 0.60) was washed with 5% diisopropylethylamine in dichloromethane (2×2 mL), dichloromethane (3×2 mL) and dimethylformamide (3×2 mL) and then swelled in dimethylformamide (2 mL). Then 2-(N-((9H-fluoren-9-yl)

methoxycarbonyl)-N-methylamino)-3-(2thienyl)propionic acid (46 mg, 0.09 mmol) in dimethylformamide (1 mL), 0-(7-azabenzotriazol-1-yl)-1,1,3,3-tetramethyluronium hexafluorophosphate (34 mg, 0.09 mmol) in dimethylformamide (1 mL), 1-hydroxy-7-azabenzotriazole (15 mg, 0.09 mmol) in dimethylformamide (1 mL) and diisopropylethylamine (31 mL, 0.18 mmol) in dimethylformamide (I mL) were added and the mixture was shaken overnight. The resin was filtered and washed with dimethylformamide (3×2 mL), dichloromethane (3×2 mL) and dimethylformamide (2 mL). Then 20% piperidine in dimethylformamide (5 mL) was added and the mixture was shaken for 20 min, filtered and washed with dimethylformamide (3×2 mL), dichloromethane (3×2 mL) and dimethylformamide (2 mL). Then 2-(N-((9H-fluoren-9-yl)methoxycarbonyl)-N-methylamino) 3-(2-naphthyl)propionic acid (41 mg, 0.09 mmol) in dimethylformamide (1 mL), O-(7-azabenzotriazol-1-yl)-1,1,3,3-tetramethyluronium hexafluorophosphate (34 mg, 0.09 mmol) in dimethylformamide (1 mL), 1-hydroxy-7-azabenzotriazole (15 mg, 0.09 mmol) in dimethylformamide (1 mL) and diisopropylethylamine (31 ml, 0.18 mmol) in dimethylformamide (1 mL) were added and the mixture was shaken overnight. The resin was filtered and washed with dimethylformamide (3×2 mL), dichloromethane (3×2 mL) and dimethylformamide (2 mL). Then 20% piperidine in dimethylformamide (5 mL) was added and the mixture was shaken for 20 min, filtered and washed with dimethylformamide (3×2 mL), dichloromethane (3×2 mL) and dimethylformamide (2 mL). Then 3-(1-(tert-butoxycarbonylamino) ethyl)-benzoic acid(22 mg, 0.09 mmol) in dimethylformamide (1 mL), O-(7-azabenzotriazol-1-yl)-1,1,3,3-tetramethyluronium hexafluorophosphate (34 mg, 0.09 mmol) in dimethylformamide (1 mL), 1-hydroxy-7-azabenzotriazole (15 mg, 0.09 mmol) in dimethylformamide (1 mL) and diisopropylethylamine (31 mL, 0.18 mmol) in dimethylformamide (1 mL) were added and the mixture was shaken overnight. The resin was filtered and washed with dimethylformamide (3×2 mL), dichloromethane (3×2 mL) and dimethylformamide (2 mL). The resin was cooled to 0° C. and 50% trifluoroacetic acid in dichloromethane (4 mL) was added and the mixture was shaken for 10 min at 0° C. The resin was filtered and washed with 50% trifluoroacetic acid in dichloromethane (2×0.5 mL) and the combined filtrates were concentrated under a stream of nitrogen. The obtained product was dissolved in acetonitrile/water 1:20 (10 mL) and applied to a C-18 Sep-Pak Classic® cartridge (0.25 g, purchased from Waters™), which had been prewashed with acetonitrile (10 mL) and water (10 mL). Then water/trifluoroacetic acid 99.9:0.1 (5 mL), followed by water/acetonitrile/trifluoroacetic acid 89.9:20:0.1 (4 mL) was run through the Sep-Pak® and the filtrate was discarded. Then the Sep-Pak® was washed with water/acetonitrile/trifluoroacetic acid 64.9:35:0.1 (4 mL) and the filtrate was diluted with water (11 mL) and lyophilized to 4 mg of the title product.

HPLC: (A1) $R_t$=31.05 min (B1) $R_t$=33.00 min

LC-MS: 557.0 $(m+1)^+$

Example 77

3-Aminomethyl-N-methyl-N-((1R)-1-(N-methyl-N-((1R)-1-(methylcarbamoyl)-2-(2-thienyl)ethyl)carbamoyl)-2-(2-naphthyl)ethyl)benzamide:

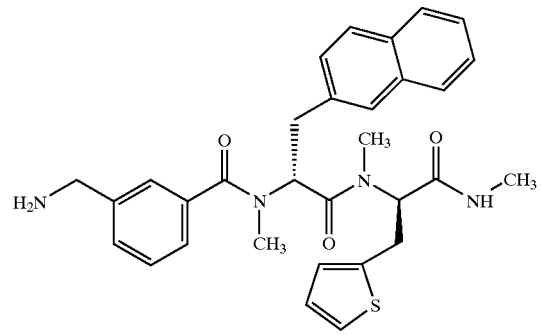

The title compound was prepared analogously to example 76 with 3-(1-(tert-butoxycarbonylamino)methyl)-benzoic acid instead of 3-(1-(tert-butoxy-carbonylamino)ethyl) benzoic acid.

Yield: 5.0 mg

HPLC: (A1) $R_t$=30.32 min (B1) $R_t$=32.22 min

LC-MS: 542.8 $(m+1)^+$

Example 78

(2R)-2-(N-((2-Aminobutoxy)acetyl)-N-methylamino)-N-methyl-N-((1R)-1-(methylcarbamoyl)-2-(2-thienyl)ethyl)-3-(2-naphthyl)propionamide:

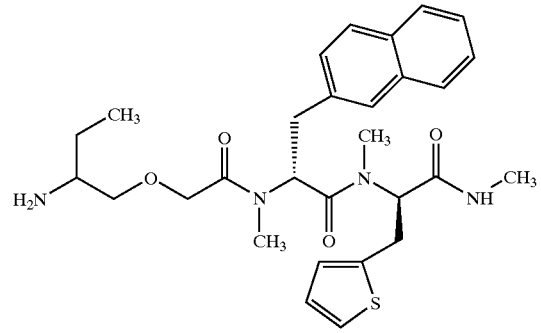

The title example 76 with (2-(tert-butoxycarbonylamino) butoxy)-acetic acid instead of 3-(t-(tert-butoxycarbonylamino)ethyl)benzoic acid.

Yield: 10.4 mg

HPLC: (A1) $R_t$=30.13 min (B1) $R_t$=31.98 min

LC-MS: $(m+1)^+$

Example 79

(2R)-2-(N-((((2S)-2-Pyrrolidinyl)methoxy)acetyl)-N-methylamino)-N-methyl-N-((1R)-1-(methylcarbamoyl)-2-(2-thienyl)ethyl)-3-(2-naphthyl)propionamide:

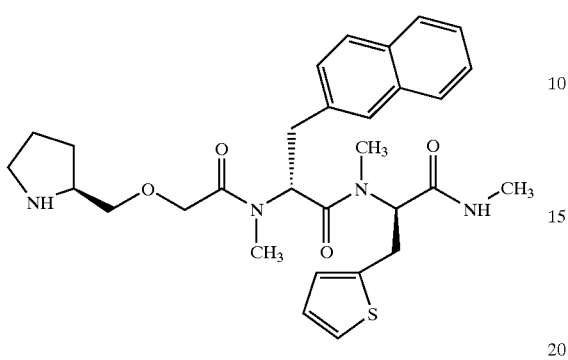

The title compound was prepared analogously to example 76 with (2S)-2-(((carboxy)methoxy)methyl)pyrro-lidin-1-carboxylic acid tert-butyl ester instead of 3-(1-(tert-butoxycarbonylamino)ethyl)benzoic acid.

Yield: 9.4 mg

HPLC: (A1) $R_t$=30.07 min (B1) $R_t$=31.88 min

LC-MS: (m+1)$^+$

Example 80

(2R)-2-(N-((2-Amino-2-methylpropoxy)acetyl)-N-methylamino)-N-methyl-N-((1R)-1-(methylcarbamoyl)-2-(2-thienyl)ethyl)-3-(2-naphthyl)propionamide:

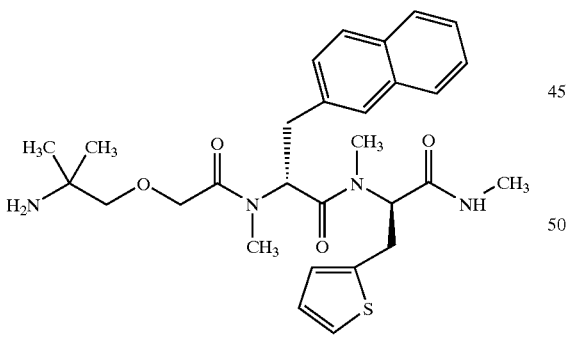

The title compound was prepared analogously to example 76 with (2-(tert-butoxycarbonylamino)-2-methylpropoxy) acetic acid instead of 3-(1-(tert-butoxycarbonylamino)ethyl) benzoic acid.

Yield: 10.5 mg

HPLC: (A1) $R_t$=29.77 min (B1) $R_t$=31.62 min

LC-MS: (m+1)$^+$

Example 81

3-(1-Aminoethyl)-N-methyl-N-((1R)-1-(N-methyl-N-((1R)-1-(methylcarbamoyl)-2-(2-thienyl)ethyl)-carbamoyl)-2-(benzo[b]thiophen-3-yl)ethyl)-benzamide:

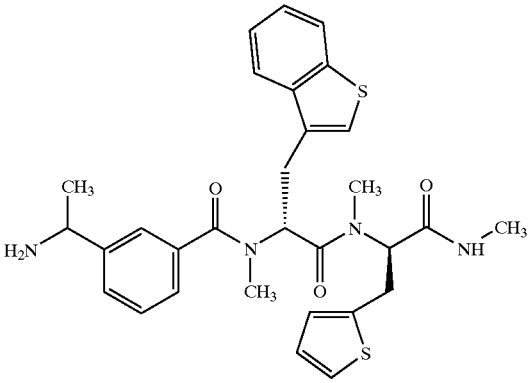

The title compound was prepared analogously to example 76 with (2R)-3-(benzo[b]thiophen-3-yl)-2-(N-(9H-fluoren-9-ylmethoxycarbonyl)-N-methylamino)-propionic acid instead of 2-(N-((9H-fluoren-9-yl)methoxycarbonyl)-N-methylamino)-3-(2-naphthyl)propionic acid.

Yield: 3.2 mg

HPLC: (A1) $R_t$=30.62 min (B1) $R_t$=32.57 min

LC-MS: 563.0 (m+1)$^+$

Example 82

3-(1-Aminomethyl)-N-methyl-N-((1R)-1-(N-methyl-N-((1R)-1-(methylcarbamoyl)-2-(2-thienyl)ethyl)-carbamoyl)-2-(benzo[b]thiophen-3-yl)ethyl)benzamide:

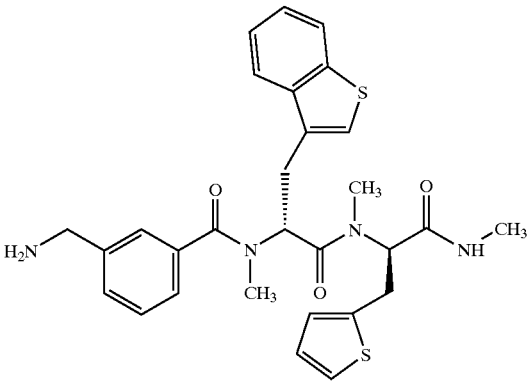

The title compound was prepared analogously to example 77 with (2R)-3-(benzo[b]thiophen-3-yl)-2-(N-(9H-fluoren-9-ylmethoxycarbonyl)-N-methylamino)-propionic acid instead of 2-(N-((9H-fluoren-9-yl)methoxycarbonyl)-N-methylamino)-3-(2-naphthyl)propionic acid.

Yield: 2.0 mg

HPLC: (A1) $R_t$=29.82 min (B1) $R_t$=31.73 min

LC-MS: 549.0 (m+1)$^+$

Example 83

(2R)-2-(N-((2-Aminobutoxy)acetyl)-N-methylamino)-N-methyl-N-((1R)-1-(methylcarbamoyl)-2-(2-thienyl)ethyl)-3-(benzo[b]thiophen-3-yl)propionamide:

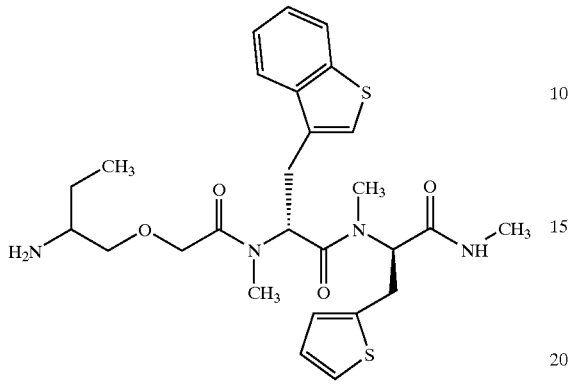

The title compound was prepared analogously to example 78 with (2R)-3-(benzo[b]thiophen-3-yl)-2-(N-(9H-fluoren-9-ylmethoxycarbonyl)-N-5 methylamino)-propionic acid instead of 2-(N-((9H-fluoren-9-yl)methoxycarbonyl)-N-methylamino)-3-(2-naphthyl)propionic acid.

Yield: mg

HPLC: (A1) $R_t$=min (B1) $R_t$=min

LC-MS: (m+1)$^+$

Example 84

(2R)-2-(N-((((2S)-2-Pyrrolidinyl)methoxy)acetyl)-N-methylamino)-N-methyl-N-((1R)-1-(methylcarbamoyl)-2-(2-thienyl)ethyl)-3-(benzo[b]thiophen-3-yl)propionamide:

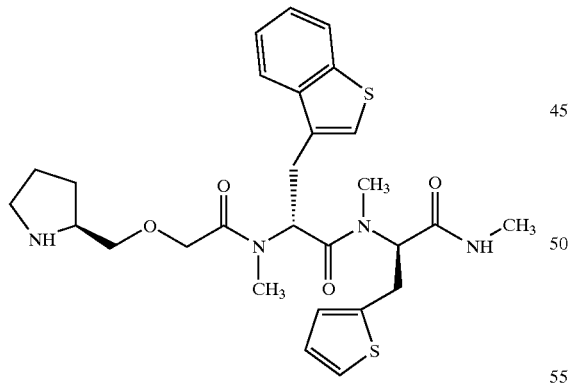

The title compound was prepared analogously to example 79 with (2R)-3-(be nzo[b]thiophen-3-yl)-2-(N-(9H-fluoren-9-ylmethoxycarbonyl)-N-methylamino)-propionic acid instead of 2-(N-((9H-fluoren-9-yl)methoxycarbonyl)-N-methylamino)-3-(2-naphthyl)propionic acid.

Yield: 7.6 mg

HPLC: (A1) $R_t$=29.42 min (B1) $R_t$=31.23 min

LC-MS: 557.0 (m+1)$^+$

Example 85

(2R) -2-(N-((2-Amino-2-methylpropoxy)acetyl)-N-methylamino)-N-methyl-N-((1R)-1-(methylcarbamoyl)-2-(2-thienyl)ethyl)-3-(benzo[b]thiophen-3-yl)propionamide:

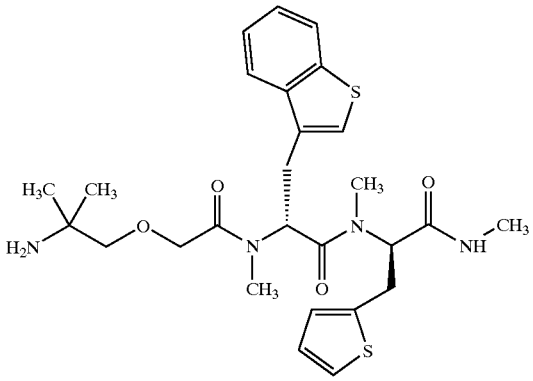

The title compound was prepared analogously to example 80 with (2R)-3-(benzo[b]thiophen-3-yl)-2-(N-(g H-fluoren-9-ylmethoxycarbonyl)-N-methylamino)-propionic acid instead of 2-(N-((9H-fluoren-9-yl)methoxycarbonyl)-N-methylamino)-3-(2-naphthyl)propionic acid.

Yield: 5.8 mg

HPLC: (A1) $R_t$=29.22 min (B1) $R_t$=31.00 min

LC-MS: 544.8 (m+1)$^+$

Example 86

(2E)-5-Amino-5-methylhex-2-enoic acid N-methyl-N-((1R)-1-(N-methyl-N-((1R)-1-(methylcarbamoyl)-2-(2-thienyl)ethyl)carbamoyl)-2-(benzo[b]thiophen-3-yl)ethyl)amide:

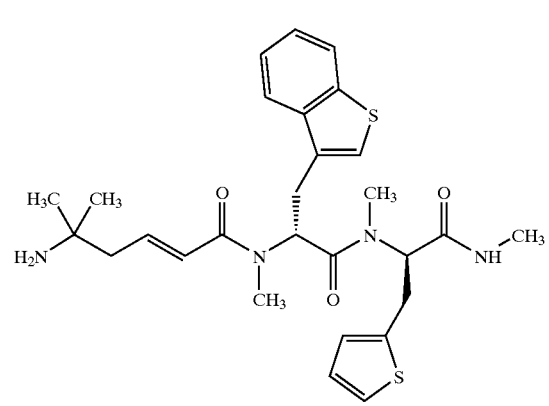

The title compound was prepared analogously to example 85 with (2E)-5-(tert-butoxycarbonylamino)-5-methylhex-2-enoic acid instead of (2-(tert-butoxycarbonylamino)2-methylpropoxy)acetic acid.

Yield: 2.0 mg

HPLC: (A1) $R_t$=29.62 min (B1) $R_t$=31.50 min.

LC-MS: 541.2 (m+1)$^+$

Example 87

3-(1-Aminoethyl)-N-methyl-N-((1R)-1-(N-methyl-N-((1R)-1-(methylcarbamoyl)-2-(2-thienyl)ethyl)-carbamoyl)-2-(benzyloxy)ethyl)benzamide:

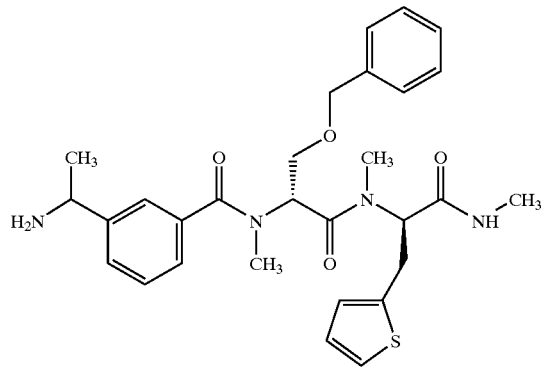

The title compound was prepared analogously to example 76 with (2R)-2-((9H-fluoren-9-ylmethoxy-carbamoyl)methylamino)-3-benzyloxypropionic acid instead of 2-(N-((9H-fluoren-9-yl)methoxycarbonyl)-N-methylamino)-3-(2-naphthyl)propionic acid.

Yield: 10.0 mg

HPLC: (A1) $R_t$=28.85 min (B1) $R_t$=30.67 ml

LC-MS: (m+1)$^+$

Example 88

3-Aminomethyl-N-methyl-N-((1R)-1-(N-methyl-N-((1R)-1-(methylcarbamoyl)-2-(2-thienyl)ethyl)carbamoyl)-2-(benzyloxy)ethyl)benzamide:

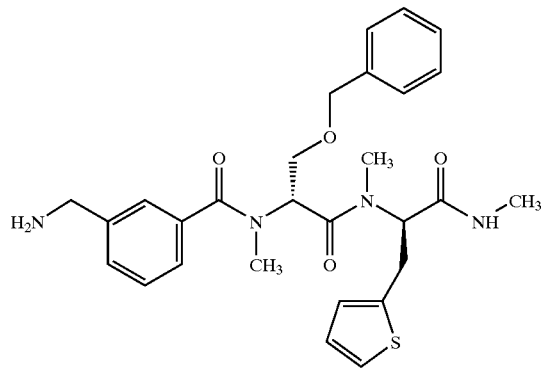

The title compound was prepared analogously to example 77 with (2R)-2-((9H-fluoren-9-ylmethoxy-carbamoyl)methylamino)-3-benzyloxypropionic acid instead of 2-(N-((9H-fluoren-9-yl)methoxycarbonyl)-N-methylamino)-3-(2-naphthyl)propionic acid.

Yield: 8.4 mg

HPLC: (A1) $R_t$=30.45 min (B1) $R_t$=30.43 min

LC-MS: 522.8 (m+1)$^+$

Example 89

(2R)-2-(N-((2-Aminobutoxy)acetyl)-N-methylamino)-N-methyl-N-((1R)-1-(methylcarbamoyl)-2-(2-thienyl)ethyl)-3-(benzyloxy)propionamide:

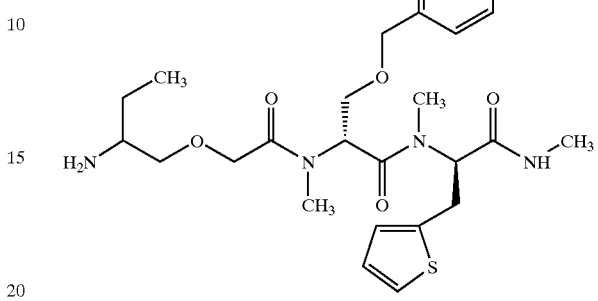

The title compound was prepared analogously to example 78 with (2R)-2-((9H-fluoren-9-ylmethoxy-carbamoyl)methylamino)-3-benzyloxypropionic acid instead of 2-(N-((9H-fluoren-9-yl)methoxycarbonyl)-N-methylamino)-3-(2-naphthyl)propionic acid.

Yield: 9.8 mg

HPLC: (A1) $R_t$=min (B1) $R_t$=min

LC-MS: 519.0 (m+1)$^+$

Example 90

(2R)-2-(N-((((2S)-2-Pyrrolidinyl)methoxy)acetyl)-N-methylamino)-N-methyl-N-((1R)-1-(methylcarbamoyl)-2-(2-thienyl)ethyl)-3-(benzyloxy)propionamide:

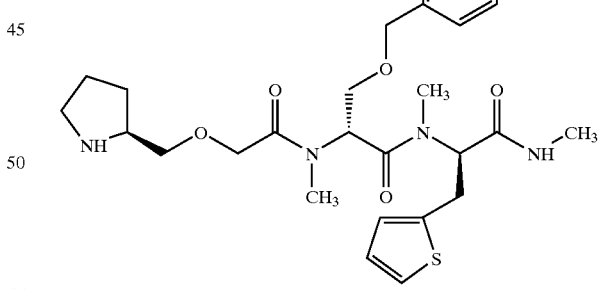

The title compound was prepared analogously to example 79 with (2R)-2-((9H-fluoren-9-ylmethoxy-carbamoyl)methylamino)-3-benzyloxypropionic acid instead of 2-(N-((9H-fluoren-9-yl)methoxycarbonyl)-N-methylamino)-3-(2-naphthyl)propionic acid.

Yield: 11.1 mg

HPLC: (A1) $R_t$=27.77 min (B1) $R_t$=29.40 min

LC-MS: (m+1)$^+$

Example 91

(2R)-2-(N-((2-Amino-2-methylpropoxy)acetyl)-N-methylamino)-N-methyl-N-((1R)-1-(methylcarbamoyl)-2-(2-thienyl)ethyl)-3-(benzyloxy)propionamide:

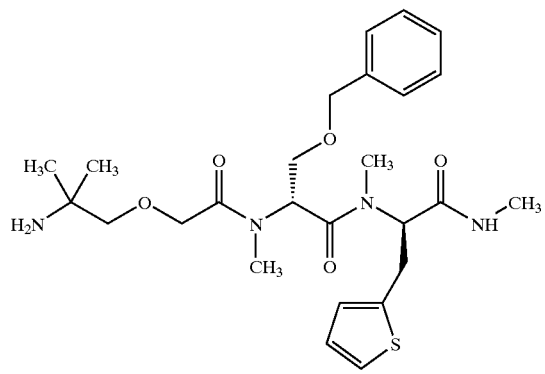

The title compound was prepared analogously to example 80 with (2R)-2-((9H-fluoren-9-ylmethoxy-carbamoyl)methylamino)-3-benzyloxypropionic acid instead of 2-(N-((9H-fluoren-9-yl)methoxycarbonyl)-N-methylamino)-3-(2-naphthyl)propionic acid.

Yield: 11.9 mg

HPLC: (A1) $R_t$=28.50 min (B1) $R_t$=29.23 min

LC-MS: 519.0 $(m+1)^+$

Example 92

(2E)-5-Amino-5-methylhex-2-enoic acid N-methyl-N-((1R)-1-(N-methyl-N-((1R)-1-(methylcarbamoyl)-2-(2-thienyl)ethyl)carbamoyl)-2-(benzyloxy)ethyl)amide:

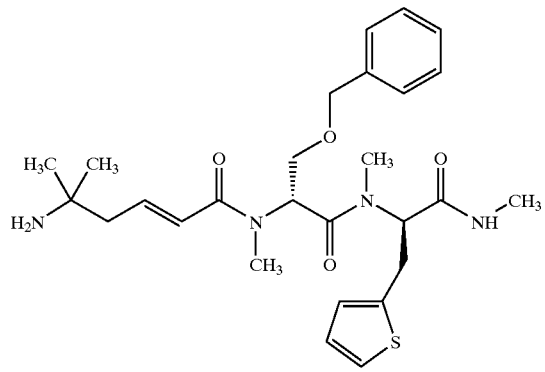

The title compound was prepared analogously to example 91 with (2E)-5-(tert-butoxycarbonylamino)-5-methylhex-2-enoic acid instead of (2-(tert-butoxycarbonylamino)-2-methylpropoxy)acetic acid.

Yield: 1.5 mg

HPLC: (A1) $R_t$=28.03 min (B1) $R_t$=29.77 min

LC-MS: $(m+1)^+$

Example 93

3-(1-Aminoethyl)-N-methyl-N-((1R)-1-(N-methyl-N-((1R)-1-(methylcarbamoyl)-2-(2-thienyl)ethyl)-carbamoyl)-2-(biphenyl-4-yl)ethyl)benzamide:

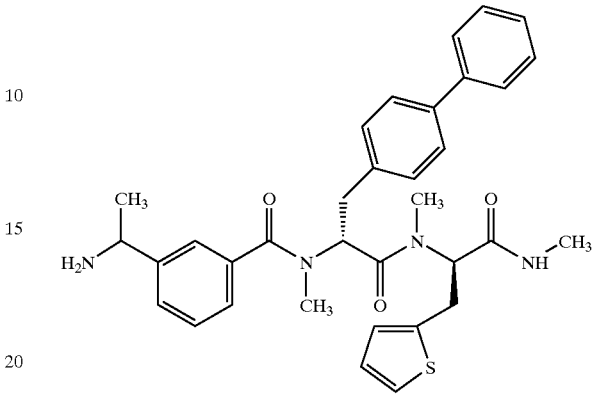

The title compound was prepared analogously to example 76 with (2R)-3-(biphenyl-4-yl)-2-(N-((9H-fluoren-9-yl)methoxycarbonyl)-N-methylamino)propionic acid instead of 2-(N-((9H-fluoren-9-yl)methoxycarbonyl)-N-methylamino)-3-(2-naphthyl)propionic acid.

Yield: 2.0 mg

HPLC: (A1) $R_t$=34.58 min (B1) $R_t$=36.67 min

LC-MS: $(m+1)^+$

Example 94

3-Aminomethyl-N-methyl-N-((1R)-1-(N-methyl-N-((1R)-1-(methylcarbamoyl)-2-(2-thienyl)ethyl)carbamoyl)-2-(biphenyl-4-yl)ethyl)benzamide:

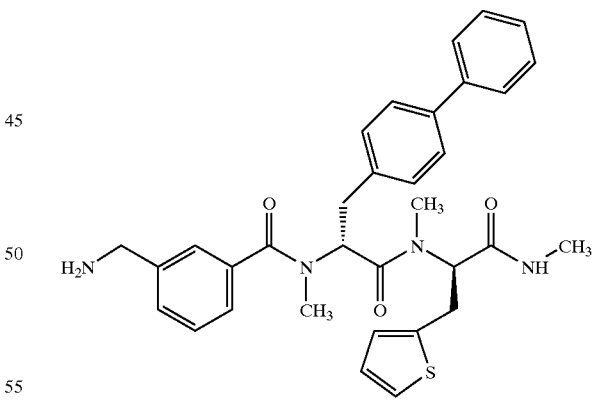

The title compound was prepared analogously to example 77 with (2R)-3-(biphenyl-4-yl)-2-(N-((9H-fluoren-9-yl)methoxycarbonyl)-N-methylamino)propionic acid instead of 2-(N-((9H-fluoren-9-yl)methoxycarbonyl)-N-methylamino)-3-(2-naphthyl)propionic acid.

Yield: 12.3 mg

HPLC: (A1) $R_t$=33.92 min (B1) $R_t$=35.97 min

LC-MS: $(m+1)^+$

Example 95

(2R)-2-(N-((2-Aminobutoxy)acetyl)-N-methylamino)-N-methyl-N-((1R)-1-(methylcarbamoyl)-2-(2-thienyl)ethyl)-3-(biphenyl-4-yl)propionamide:

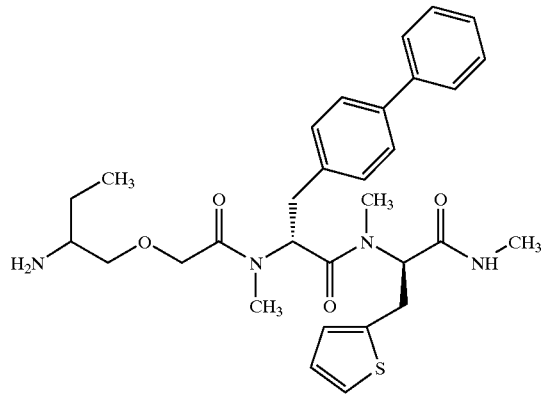

The title compound was prepared analogously to example 78 with (2R)-3-(biphenyl-4-yl)-2-(N-((9H-fluoren-9-yl)methoxycarbonyl)-N-methylamino)propionic acid instead of 2-(N-((9H-fluoren-9-yl)methoxycarbonyl)-N-methylamino)-3-(2-naphthyl)propionic acid.

Yield: 13.5 mg

HPLC: (A1) $R_t$=33.57 min (B1) $R_t$=34.47 min

LC-MS: $(m+1)^+$

Example 96

(2R) -2-(N-((((2S) -2-Pyrrolidinyl)methoxy)acetyl)-N-methylamino)-N-methyl-N-((1R)-1-(methylcarbamoyl)-2-(2-thienyl)ethyl)-3-(biphenyl-4-yl)propionamide:

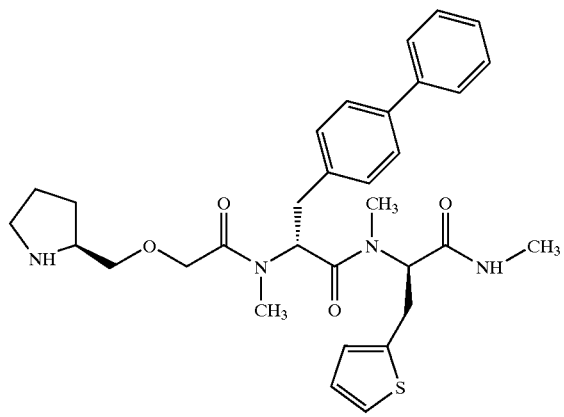

The title compound was prepared analogously to example 79 with (2R)-3-(biphenyl-4-yl)-2-(N-((9H-fluoren-9-yl)methoxycarbonyl)-N-methylamino)propionic acid instead of 2-(N-((9H-fluoren-9-yl)methoxycarbonyl)-N-methylamino)-3-(2-naphthyl)propionic acid.

Yield: 11.0 mg

HPLC: (A1) $R_t$=33.30 min (B1) $R_t$=35.24 min

LC-MS: $(m+1)^+$

Example 97

(2R)-2-(N-((2-Amino-2-methylpropoxy)acetyl)-N-methylamino)-N-methyl-N-((1R)-1-(methylcarbamoyl)-2-(2-thienyl)ethyl)-3-(biphenyl-4-yl)propionamide:

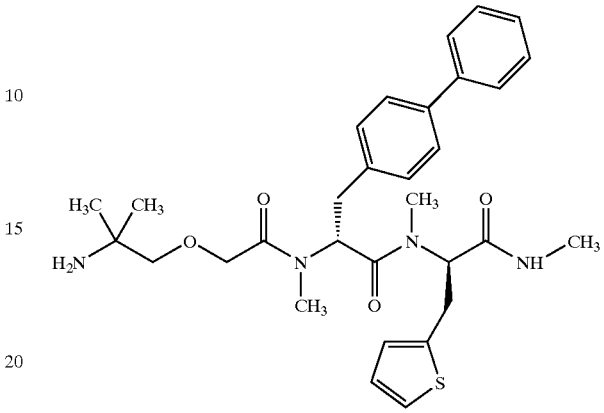

The title compound was prepared analogously to example 80 with (2R)-3-(biphenyl-4-yl)-2-(N-((9H-fluoren-9-yl)methoxycarbonyl)-N-methylamino)propionic acid instead of 2-(N-((9H-fluoren-9-yl)methoxycarbonyl)-N-methylamino)-3-(2-naphthyl)propionic acid.

Yield: 13.1 mg

HPLC: (A1) $R_t$=27.68 min (B1) $R_t$=30.22 min

LC-MS: $(m+1)^+$

Example 98

(2E)-5-Amino-5-methylhex-2-enoic acid N-methyl-N-((1R)-1-(N-methyl-N-((1R)-1-(methylcarbamoyl)-2-(2-thienyl)ethyl)carbamoyl)-2-(biphenyl-4-yl)ethyl)amide:

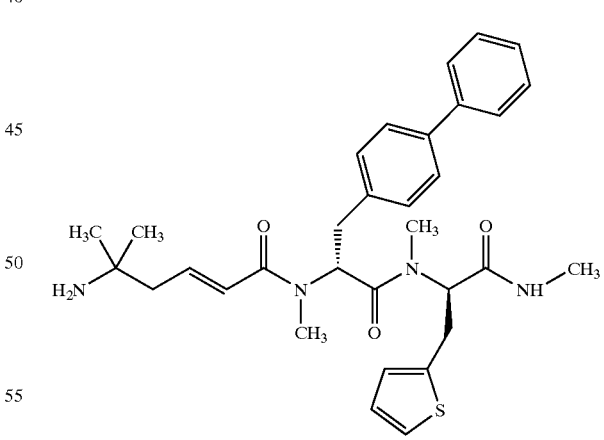

The title example 997 with (2E)-5-(tert-butoxycarbonylamino)-5-methylhex-2-enoic acid instead of (2-(tert-butoxycarbonylamino)-2-methylpropoxy)acetic acid.

Yield: 13.1 mg

HPLC: (A1) $R_t$=28.48 min (B1) $R_t$=30.03 min

LC-MS: $(m+1)^+$

Example 99

3-(1-Aminoethyl)-N-methyl-N-((1R)-1-(N-methyl-N-((1R)-1-(methylcarbamoyl)-2-(2-fluorophenyl)-ethyl)carbamoyl)-2-(2-naphthyl)ethyl)benzamide:

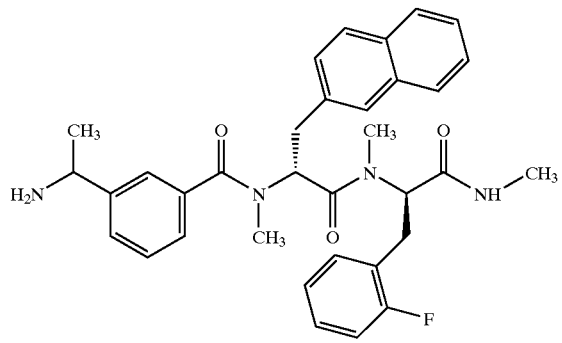

The title compound was prepared analogously to example 76 with (2R)-2-propionic acid instead of (2R)-2-(N-(9H-fluoren-9-ylmethoxycarbonyl)-N-methylamino)-3-(2-thienyl) propionic acid.

Yield: 5.0 mg

HPLC: (A1) $R_t$=32.00 min (B1) $R_t$=33.98 min

LC-MS: 568.8 (m+1)$^+$

Example 100

3-Aminomethyl-N-methyl-N-((1R)-1-(N-methyl-N-((1R)-1-(methylcarbamoyl)-2-(2-fluorophenyl)ethyl)-carbamoyl)-2-(2-naphthyl)ethyl)benzamide:

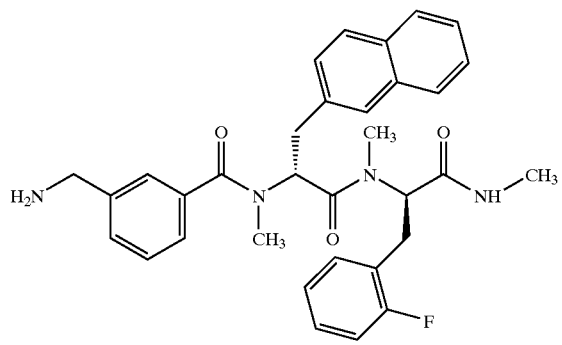

The title compound was prepared analogously to example 77 with (2R)-2-(N-((9H-fluoren-9-yl)methoxy-carbonyl)-N-methylamino)-3-(2-fluorophenyl)-propionic acid instead of (2R)-2-(N-(9H-fluoren-9-ylmethoxycarbonyl)-N-methylamino)-3-(2-thienyl)propionic acid.

Yield: 2.8 mg

HPLC: (A1) $R_t$=31.30 min (B1) $R_t$=33.23 min

LC-MS: 555.0 (m+1)$^+$

Example 101

(2R)-2-(N-((2-Aminobutoxy)acetyl)-N-methylamino)-N-methyl-N-((1R)-1-(methylcarbamoyl)-2-(2-fluorophenyl)ethyl)-3-(2-naphthyl)propionamide:

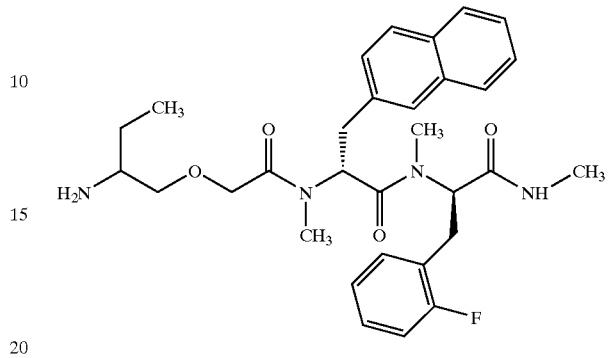

The title compound was prepared analogously to example 78 with (2R)-2-(N-((9H-fluoren-9-yl)methoxy-carbonyl)-N-methylamino)-3-(2-fluorophenyl)-propionic acid instead of (2R)-2-(N-(9H-fluoren-9-ylmethoxycarbonyl)-N-methylamino)-3-(2-thienyl)propionic acid.

Yield: 10.1 mg

HPLC: (A1) $R_t$=31.25 min (B1) $R_t$=33.03 min

LC-MS: (m+1)$^+$

Example 102

(2R)-2-(N-((((2S)-2-Pyrrolidinyl)methoxy)acetyl)-N-methylamino)-N-methyl-N-((1R)-1-(methylcarbamoyl)-2 (2fluorophenyl)ethyl)-3-(2-naphthyl)propionamide:

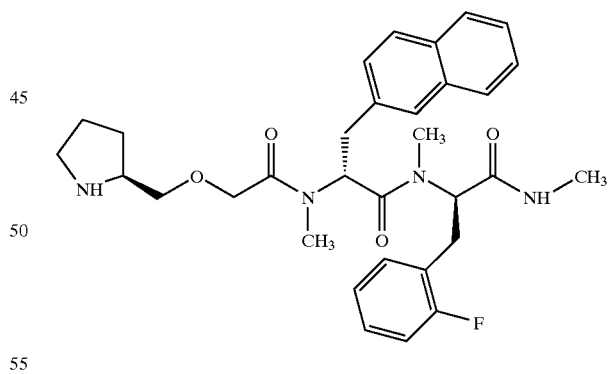

The title compound was prepared analogously to example 79 with (2R)-2-(N-((9H-fluoren-9-yl)methoxy-carbonyl)-N-methylamino)-3-(2-fluorophenyl)-propionic acid instead of (2R)-2-(N-(9H-fluoren-9-ylmethoxycarbonyl)-N-methylamino)-3-(2-thienyl)propionic acid.

Yield: 12.0mg

HPLC: (A1) $R_t$=31.90 min (B1) $R_t$=32.73 min

LC-MS: 563.0 (m+1)$^+$

Example 103

(2R)-2-(N-((2-Amino-2-methylpropoxy)acetyl)-N-methylamino)-N-methyl-N-((1R)-1-(methylcarbamoyl)-2-(2-fluorophenyl)ethyl)-3-(2-naphthyl)propion-amide:

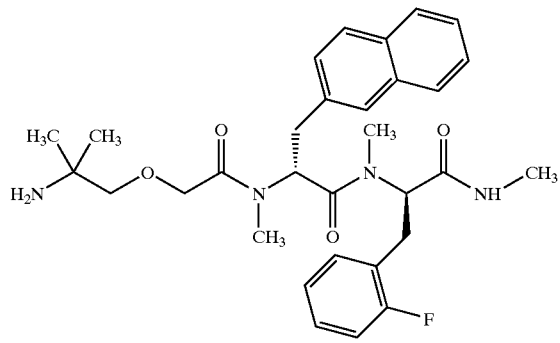

The title compound was prepared analogously to example 80 with (2R)-2-(N-((9H-fluoren-9-yl)methoxy-carbonyl)-N-methylamino)-3-(2-fluorophenyl)-propionic acid instead of (2R)-2-(N-(9H-fluoren-9-ylmethoxycarbonyl)-N-methylamino)-3-(2-thienyl)propionic acid.

Yield: 11.5 mg

HPLC: (A1) $R_t$=30.83 min (B1) $R_t$=32.63 min

LC-MS: 551.0 $(m+1)^+$

Example 104

3-(1-Aminoethyl)-N-methyl-N-((1R)-1-(N-methyl-N-((1R)-1-(methylcarbamoyl)-2-(2-fluorophenyl)-ethyl)carbamoyl)-2-(benzo[b]thiophen-3-yl)ethyl)-benzamide:

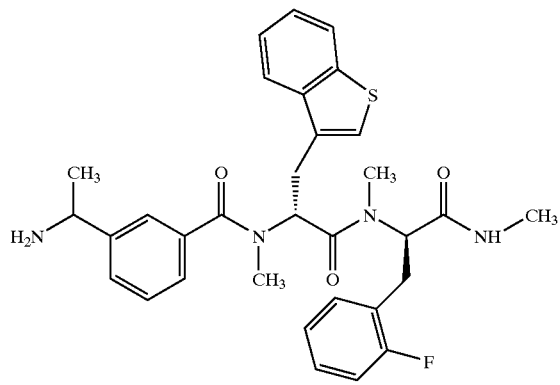

The title compound was prepared analogously to example 81 with (2R)-2-(N-((9H-fluoren-9-yl)methoxy-carbonyl)-N-methylamino)-3-(2-fluorophenyl)-propionic acid instead of (2R)-2-(N-(9H-fluoren-9-ylmethoxycarbonyl)-N-methylamino)-3-(2-thienyl)propionic acid.

Yield: 3.6 mg

HPLC: (A1) $R_t$=31.60 min (B1) $R_t$=33.57 min

LC-MS: 575.0 $(m+1)^+$

Example 105

3-Aminomethyl-N-methyl-N-((1R)-1-(N-methyl-N-((1R)-1-(methylcarbamoyl)-2-(2-fluorophenyl)ethyl)-carbamoyl)-2-(benzo[b]thiophen-3-yl)ethyl)benzamide:

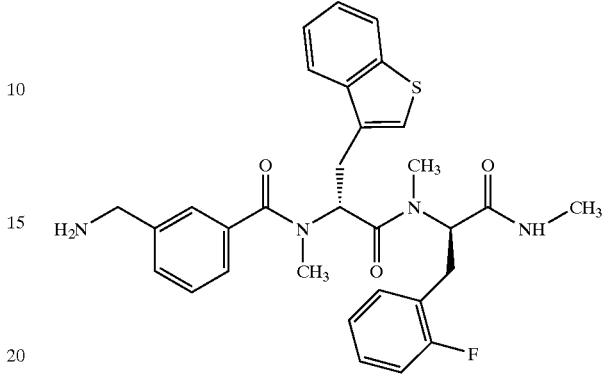

The title compound was prepared analogously to example 82 with (2R)-2-(N-((9H-fluoren-9-yl)methoxy-carbonyl)-N-methylamino)-3-(2-fluorophenyl)-propionic acid instead of (2R)-2-(N-(9H-fluoren-9-ylmethoxycarbonyl)-N-methylamino)-3-(2-thienyl)propionic acid.

Yield: 3.3 mg

HPLC: (A1) $R_t$=30.82 min (B1) R=32.77 min

LC-MS: 561.0 $(m+1)^+$

Example 106

(2R)-2-(N-((2-Aminobutoxy)acetyl)-N-methylamino)-N-methyl-N-((1R)-1-(methylcarbamoyl)-2-(2-fluorophenyl)ethyl)-3-(benzo[b]thiophen-3-yl)propionamide:

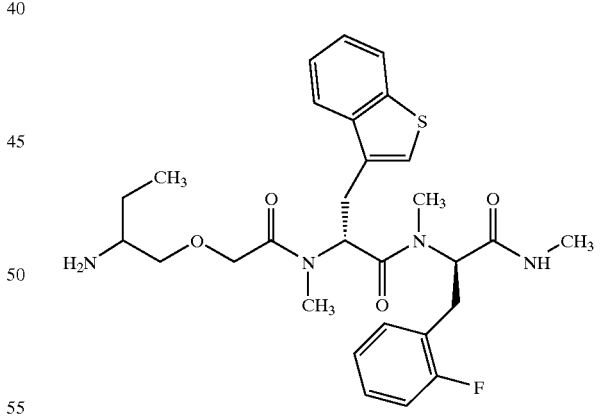

The title compound was prepared analogously to example 83 with (2R)-2-(N-((9H-fluoren-9-yl)methoxy-carbonyl)-N-methylamino)-3-(2-fluorophenyl)-propionic acid instead of (2R)-2-(N-(9H-fluoren-9-ylmethoxycarbonyl)-N-methylamino)-3-(2-thienyl)propionic acid.

Yield: 10.5 mg

HPLC: (A1) $R_t$=30.62 min (B1) $R_t$=32.45 min

LC-MS: 557.0 $(m+1)^+$

Example 107

(2R)-2-(N-((((2S)-2-Pyrrolidinyl)methoxy)acetyl)-N-methylamino)-N-methyl-N-((1R)-1 (methylcarbamoyl)-2-(2-fluorophenyl)ethyl)-3-(benzo[b]thiophen-3-yl) propionamide:

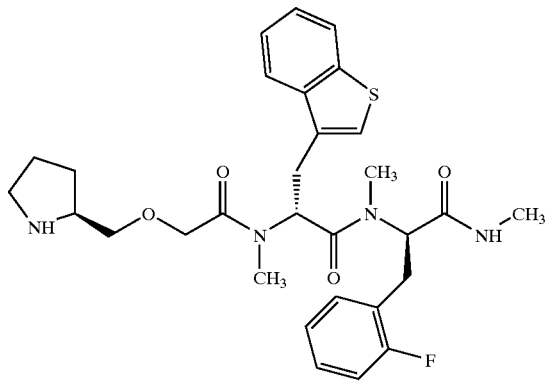

The title compound was prepared analogously to example 84 with (2R)-2-(N-((9H-fluoren-9-yl)methoxy-carbonyl)-N-methylamino)-3-(2-fluorophenyl)-propionic acid instead of (2R)-2-(N-(9H-fluoren-9-ylmethoxycarbonyl)-N-methylamino)-3-(2-thienyl)propionic acid.

Yield: 7.0 mg

HPLC: (A1) $R_t$=30.47 min (B1) $R_t$=32.30 min

LC-MS: 569.0 (m+1)$^+$

Example 108

(2R)-2-(N-((2-Amino-2-methylpropoxy)acetyl)-N-methylamino)-N-methyl-N-((1R)-1-(methylcarbamoyl)-2-(2-fluorophenyl)ethyl)-3-(benzo[b]thiophen-3-yl) propionamide.

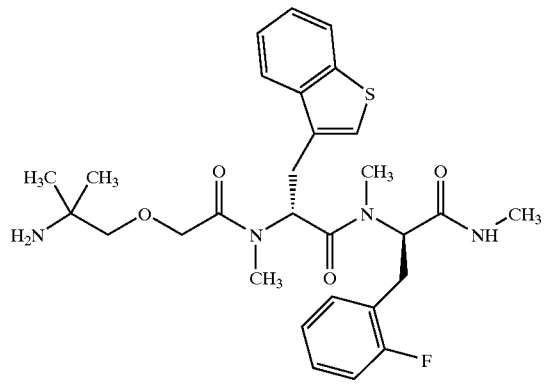

The title compound was prepared analogously to example 85 with (2R)-2-(N-((9H-fluoren-9-yl)methoxy-carbonyl)-N-methylamino)-3-(2-fluorophenyl)-propionic acid instead of (2R)-2-(N-(9H-fluoren-9-ylmethoxycarbonyl)-N-methylamino)-3-(2-thienyl)propionic acid.

Yield: 7.5 mg

HPLC: (A1) $R_t$=30.33 min (B1) $R_t$=32.1 0 min

LC-MS: 557.0 (m+1)$^+$

Example 109

3-(1-Aminoethyl)-N-methyl-N-((1R)-1-(N-methyl-N-((1R)-1-(methylcarbamoyl)-2-(2-fluorophenyl)ethyl) carbamoyl))-2-(benzyloxy)ethyl)benzamide:

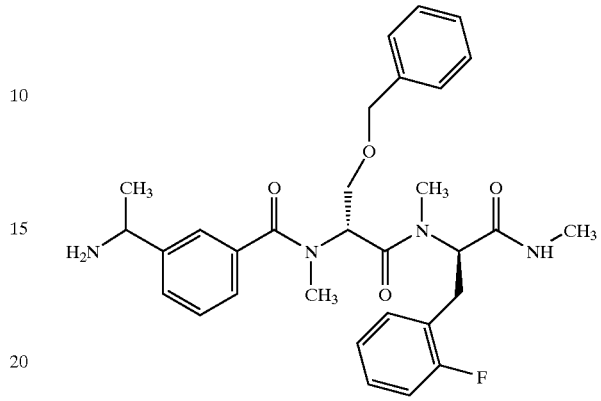

The title compound was prepared analogously to example 87 with (2R)-2-(N-((9H-fluoren-9-yl)methoxy-carbonyl)-N-methylamino)-3-(2-fluorophenyl)-propionic acid instead of (2R)-2-(N-(9H-fluoren-9-ylmethoxycarbonyl)-N-methylamino)-3-(2-thienyl)propionic acid.

Yield: 4.6 mg

HPLC: (A1) $R_t$=31.07 min (B1) $R_t$=32.97 min

LC-MS: 549.0 (m+1)$^+$

Example 110

3-Aminomethyl-N-methyl-N-((1R)-1-(N-methyl-N-((1R)-1 (methylcarbamoyl)-2-(2-fluorophenyl)-ethyl)carbamoyl)-2-(benzyloxy)ethyl)benzamide:

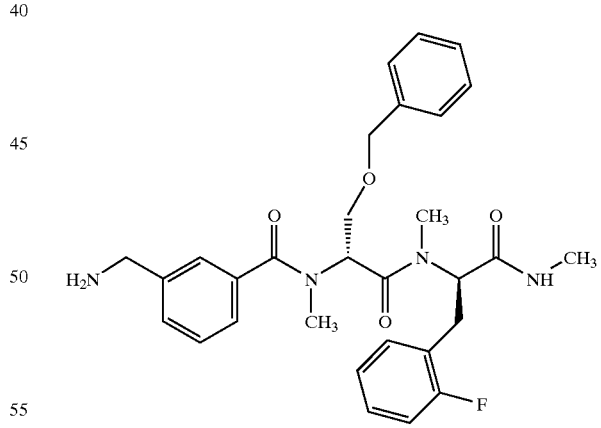

The title compound was prepared analogously to example 88 with (2R)-2-(N-((9H-fluoren-9-yl)methoxy-carbonyl)-N-methylamino)-3-(2-fluorophenyl)-propionic acid instead of (2R)-2-(N-(9H-fluoren-9-ylmethoxycarbonyl)-N-methylamino)-3-(2-thienyl)propionic acid.

Yield: 5.2 mg

HPLC: (A1) $R_t$=30.25 min (B1) $R_t$=32.10 min

LC-MS: 535.2 (m+1)$^+$

Example 111

(2R)-2-(N-((2-Aminobutoxy)acetyl)-N-methylamino)-N-methyl-N-((1R)-1-(methylcarbamoyl)-2-(2-fluorophenyl)ethyl)-3-(benzyloxy)propionamide:

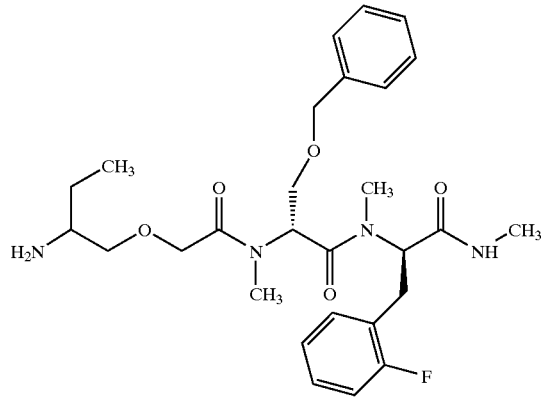

The title compound was prepared analogously to example 89 with (2R)-2-(N-((9H-fluoren-9-yl)methoxy-carbonyl)-N-methylamino)-3-(2-fluorophenyl)-propionic acid instead of (2R)-2-(N-(9H-fluoren-9-ylmethoxycarbonyl)-N-methylamino)-3-(2-thienyl)propionic acid.

Yield: 23.6 mg

HPLC: (A1) $R_t$=29.32 min (B1) $R_t$=30.97 min

LC-MS: (m+1)$^+$

Example 112

(2R)-2-(N-((((2S)-2-Pyrrolidinyl)methoxy)acetyl)-N-methylamino)-N-methyl-N-((1R)-1-(methylcarbamoyl)-2-(2-fluorophenyl)ethyl)-3(benzyloxy)propionamide:

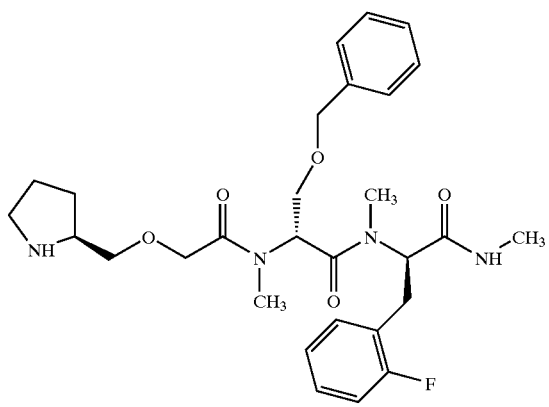

The title compound was prepared analogously to example 90 with (2R)-2-(N-((9H-fluoren-9-yl)methoxy-carbonyl)-N-methylamino)-3-(2-fluorophenyl)-propionic acid instead of (2R)-2-(N-(9H-fluoren-9-ylmethoxycarbonyl)-N-methylamino)-3-(2-thienyl)propionic acid.

Yield: 26.0 mg

HPLC: (A1) $R_t$=min (B1) $R_t$=min

LC-MS: 543.2 (m+1)$^+$

Example 113

(2R)-2-(N-((2-Amino-2-methylpropoxy)acetyl)-N-methylamino)-N-methyl-N-((1R)-1-(methylcarbamoyl)-2-(2-fluorophenyl)ethyl)-3-(benzyloxy)propionamide:

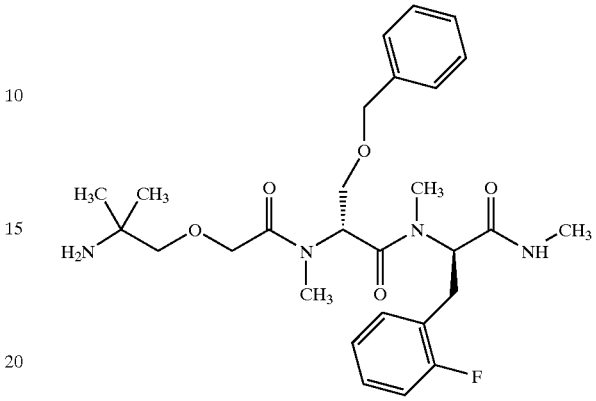

The title compound was prepared analogously to example 91 with (2R)-2-(N-((9H-fluoren-9-yl)methoxy-carbonyl)-N-methylamino)-3(2fluorophenyl)-propionic acid instead of (2R)-2-(N-(9H-fluoren-9-ylmethoxycarbonyl)-N-methylamino)-3-(2-thienyl)propionic acid.

Yield: 20.1 mg

HPLC: (A1) $R_t$=30.17 min (B1) $R_t$=30.77 min

LC-MS: 531.0 (m+1)$^+$

Example 114

3-(1-Aminoethyl)-N-methyl-N-((1R)-1-(N-methyl-N-((1R)-1-(methylcarbamoyl)-2-(2-fluorophenyl)ethyl)-carbamoyl)-2-(biphenyl-4-yl)ethyl)benzamide:

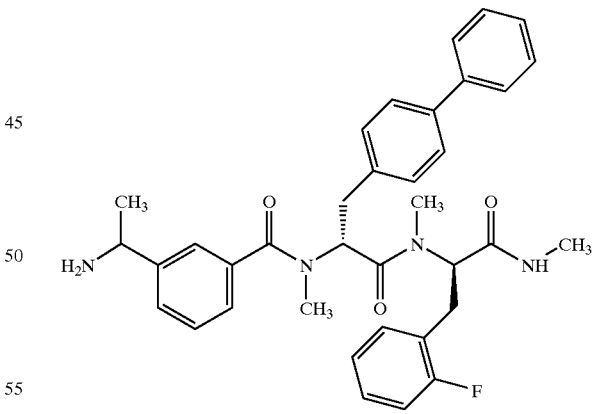

The title compound was prepared analogously to example 93 with (2R)-2-(N-((9H-fluoren-9-yl)methoxy-carbonyl)-N-methylamino)-3-(2-fluorophenyl)-propionic acid instead of (2R)-2-(N-(9H-fluoren-9-ylmethoxycarbonyl)-N-methylamino)-3-(2-thienyl)propionic acid.

Yield: 10.0 mg

HPLC: (A1) $R_t$=35.40 min (B1) $R_t$=37.58 min

LC-MS: 594.8 (m+1)$^+$

Example 115

3-Aminomethyl-N-methyl-N-((1R)-1-(N-methyl-N-((1R)-1-(methylcarbamoyl)-2-(2-fluorophenyl)ethyl)-carbamoyl)-2-(biphenyl-4-yl)ethyl)benzamide:

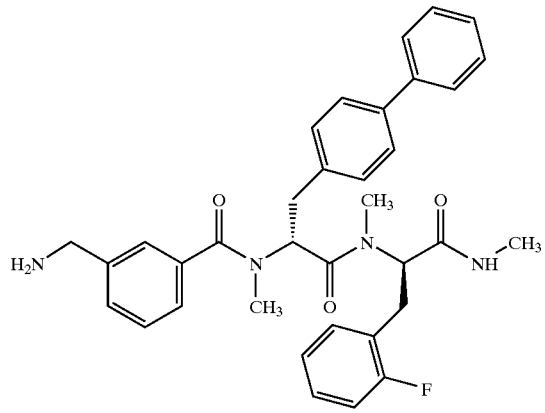

The title compound was prepared analogously to example 94 with (2R)-2-( ((9H-fluoren-9-yl)methoxy-carbonyl)-N-methylamino)-3-(2-fluorophenyl)-propionic acid instead of (2R)-2-(N-(9H-fluoren-9-ylmethoxycarbonyl)-N-methylamino)-3-(2-thienyl)propionic acid.

Yield: 6.6 mg

HPLC: (A1) $R_t$=34.70 min (B1) $R_t$=36.08 min

LC-MS: 581.0 (m+1)$^+$

Example 116

(2R)-2-(N-((2-Aminobutoxy)acetyl)-N-methylamino)-N-methyl-N-((1R)-1-(methylcarbamoyl)-2-(2-fluorophenyl)ethyl)-3-(biphenyl-4-yl)propionamide:

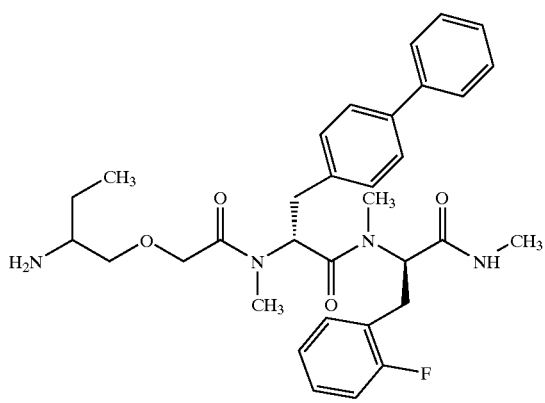

The title compound was prepared analogously to example 95 with (2R)-2-(N-((9H-fluoren-9-yl)methoxy-carbonyl)-N-methylamino)-3(2fluorophenyl)-propionic acid instead of (2R)-2-(N-(9H-fluoren-9-ylmethoxycarbonyl)-N-methylamino)-3-(2-thienyl)propionic acid.

Yield: 23.3 mg

HPLC: (A1) $R_t$=34.13 min (B1) $R_t$=36.08 min

LC-MS: (m+1)$^+$

Example 117

(2R)-2-N-((((2S)-2-Pyrrolidinyl)methoxy)acetyl)-N-methylamino)-N-methyl-N-((1R)-1-(methylcarbamoyl)-2-(2-fluorophenyl)ethyl)-3-(biphenyl-4-yl)propionamide:

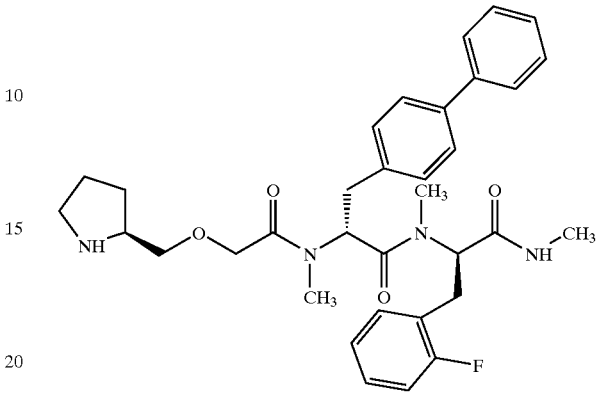

The title compound was prepared analogously to example 96 with (2R)-2-(N-((9H-fluoren-9-yl)methoxy-carbonyl)-N-methylamino)-3-(2-fluorophenyl)-propionic acid instead of (2R)-2-(N-(9H-fluoren-9-ylmethoxycarbonyl)-N-methylamino)-3-(2-thienyl)propionic acid.

Yield: 20.5 mg

HPLC: (A1) $R_t$=27.65 min (B1) $R_t$=30.18 min

LC-MS: (m+1)$^+$

Example 118

(2R)-2-(N-((2-Amino-2-methylpropoxy)acetyl)-N-methylamino)-N-methyl-N-((1R)-1-(methylcarbamoyl)-2-(2-fluorophenyl)ethyl)-3-(biphenyl-4-yl)propionamide:

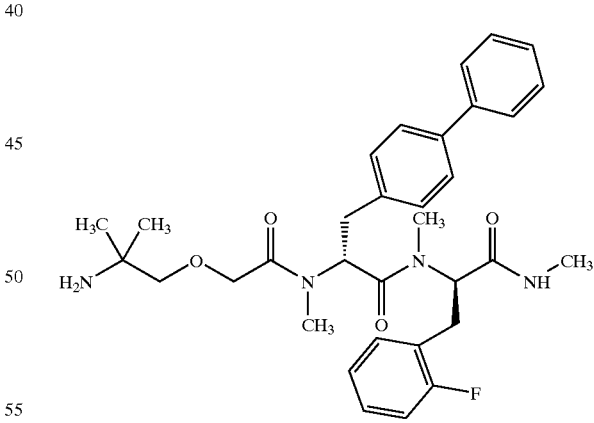

The title compound was prepared analogously to example 97 with (2R)-2-(N-((9H-fluoren-9-yl)methoxy-carbonyl)-N-methylamino)-3-(2-fluorophenyl)-propionic acid instead of (2R)-2-(N-(9H-fluoren-9-ylmethoxycarbonyl)-N-methylamino)-3-(2-thienyl)propionic acid.

Yield: 12.2 mg

HPLC: (A1) $R_t$=34.32 min (B1) $R_t$=36.13 min

LC-MS: 577.0 (m+1)$^+$

Example 119

(2E)-5-Amino-5-methylhex-2-enoic acid N-methyl-N-((1R)-1-(N-methyl-N-((1R)-1-(methylcarbamoyl)-2-(2-fluorophenyl)ethyl)carbamoyl)-2-(biphenyl-4-yl)ethyl) amide:

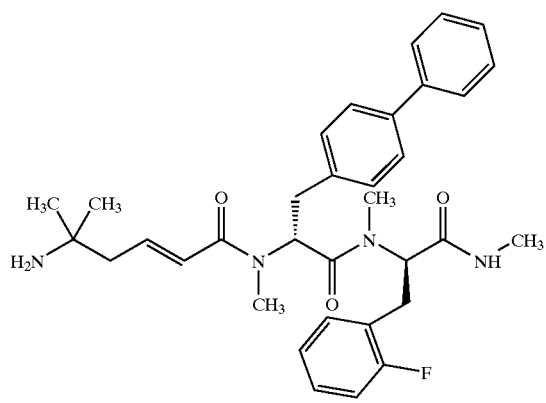

The title compound was prepared analogously to example 98 with (2R)-2-(N-((9H-fluoren-9-yl)methoxy-carbonyl)-N-methylamino)-3-(2-fluorophenyl)-propionic acid instead of (2R)-2-(N-(9H-fluoren-9-ylmethoxycarbonyl)-N-methylamino)-3-(2-thienyl)propionic acid.

Yield: 5.1 mg

HPLC: (A1) $R_t$=27.68 min (B1) $R_t$=30.20 min

LC-MS: $(m+1)^+$

Example 120

3-(1-Aminoethyl)-N-methyl-N-((1R)-1-(N-methyl-N-((1R)-1-(methylcarbamoyl)-2-phenylethyl)carbamoyl)-2-(benzo[b]thiophen-3-yl)ethyl)benzamide:

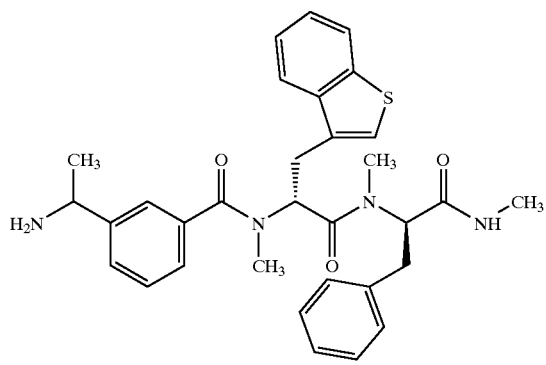

The title compound was prepared analogously to example 81 with (2R)-2-(N-((9H-fluoren-9-yl)methoxy-carbonyl)-N-methylamino)-3-phenylpropionic acid instead of (2R)-2-(N-(9H-fluoren-9-ylmethoxycarbonyl)-N-methylamino)-3-(2-thienyl)propionic acid.

Yield: 4.6 mg

HPLC: (A1) $R_t$=min (B1) $R_t$=min

LC-MS: 557.0 $(m+1)^+$

Example 121

3-Aminomethyl-N-methyl-N((1R)-1-(N-methyl-N-((1R)-1-(methylcarbamoyl)-2-phenylethyl)carbamoyl)-2-(benzo[b]thiophen-3-yl)ethyl)benzamide:

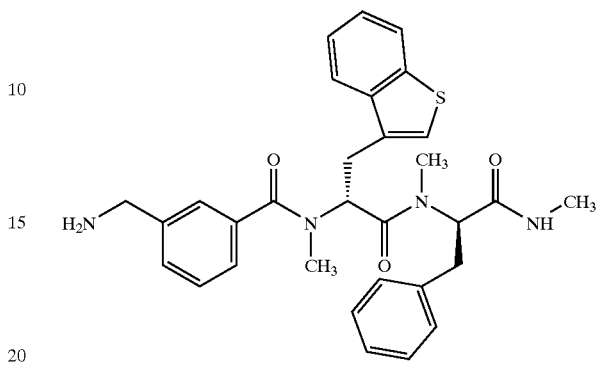

The title compound was prepared analogously to example 82 with (2R)-2-(N-((9H-fluoren-9-yl)methoxy-carbonyl)-N-methylamino)-3-phenylpropionic acid instead of (2R)-2-(N-(9H-fluoren-9-ylmethoxycarbonyl)-N-methylamino)-3-(2-thienyl)propionic acid.

Yield: 3.1 mg

HPLC: (A1) $R_t$=min (B1) $R_t$=min

LC-MS: 542.8 $(m+1)^+$

Example 122

(2R)-2-(N-((2-Aminobutoxy)acetyl)-N-methylamino)-N-methyl-N-((1R)-1-(methylcarbamoyl)-2-phenylethyl)-3-(benzo[b]thiophen-3-yl) propionamide:

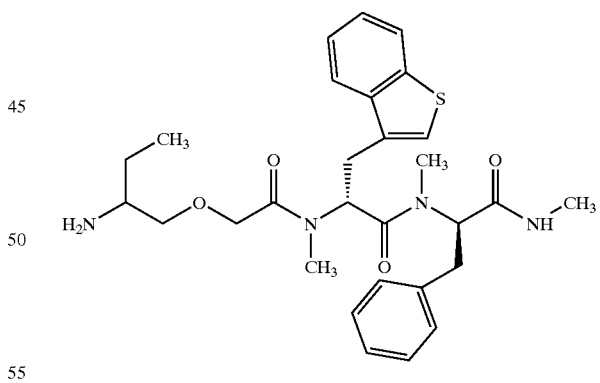

The title compound was prepared analogously to example 83 with (2R)-2-(N-((9H-fluoren-9-yl)methoxy-carbonyl)-N-methylamino)-3-phenylpropionic acid instead of (2R)-2-(N-(9H-fluoren-9-ylmethoxycarbonyl)-N-methylamino)-3-(2-thienyl)propionic acid.

Yield: 1.2 mg

HPLC: (A1) $R_t$=30.48 min (B1) $R_t$=min

LC-MS: 539.2 $(m+1)^+$

Example 123

(2R)-2-(N-((((2S)-2-Pyrrolidinyl)methoxy)acetyl)-N-methylamino)-N-methyl-N-((1R)-1-(methylcarbamoyl)-2-phenylethyl)-3-(benzo[b]thiophen-3-yl)propion-amide:

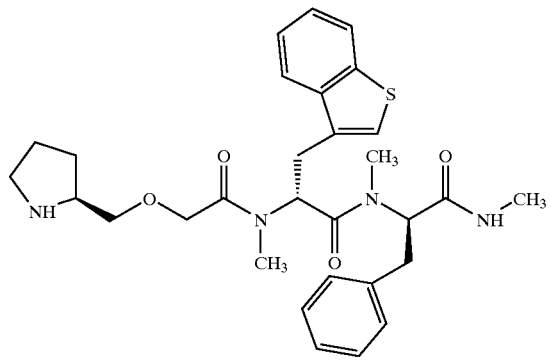

The title compound was prepared analogously to example 84 with (2R)-2-(N-((9H-fluoren-9-yl)methoxy-carbonyl)-N-methylamino)-3-phenylpropionic acid instead of (2R)-2-(N-(9H-fluoren-9-ylmethoxycarbonyl)-N-methylamino)-3-(2-thienyl)propionic acid.

Yield: 2.9 mg

HPLC: (A1) $R_t$=30.47 min (B1) $R_t$=min

LC-MS: 550.8 $(m+1)^+$

Example 124

(2R)-2-(N-((2-Amino-2-methylpropoxy)acetyl)-N-methylamino)-N-methyl-N-((1R)-1-(methylcarbamoyl)-2-phenylethyl)-3-(benzo[b]thiophen-3-yl)propionamide:

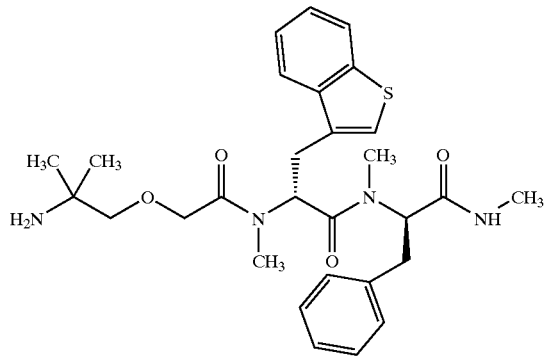

The title compound was prepared analogously to example 85 with (2R)-2-(N-((9H-fluoren-9-yl)methoxy-carbonyl)-N-methylamino)-3-phenylpropionic acid instead of (2R)-2-(N-(9H-fluoren-9-ylmethoxycarbonyl)-N-methylamino)-3-(2-thienyl)propionic acid.

Yield: 3.3 mg

HPLC: (A1) $R_t$=30.18 min (B1) $R_t$=min

LC-MS: 539.2 $(m+1)^+$

Example 125

(2E)-5-Amino-5-methylhex-2-enoic acid N-methyl-N-((1R)-1-(N-methyl-N-((1R)-1-(methylcarbamoyl)-2-phenylethyl)carbamoyl)-2-(benzob]thiophen-3-yl)ethyl)amide:

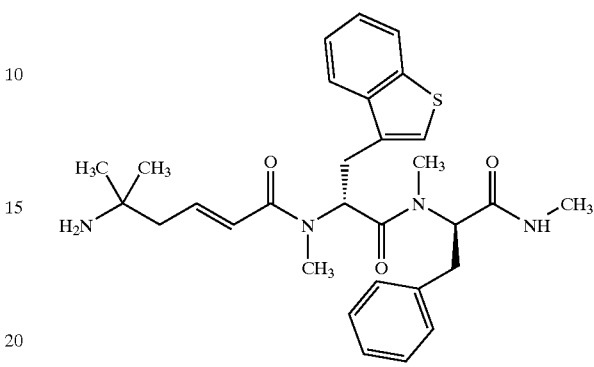

The title compound was prepared analogously to example 86 with (2R)-2-(N-((9H-fluoren-9-yl)methoxy-carbonyl)-N-methylamino)-3-phenylpropionic acid instead of (2R)-2-(N-(9H-fluoren-9-ylmethoxycarbonyl)-N-methylamino)-3-(2-thienyl)propionic acid.

Yield: 1.1 mg

HPLC: (A1) $R_t$=30.57 min (B1) $R_t$=min

LC-MS: 535.2 $(m+1)^+$

Example 126

3-(1-Aminoethyl)-N-methyl-N-((1R)-1-(N-methyl-N-((1R)-1-(methylcarbamoyl)-2-phenylethyl)carbamoyl)-2-(benzyloxy)ethyl)benzamide:

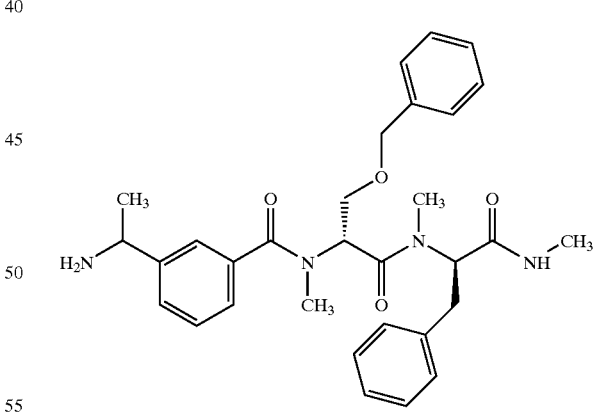

The title compound was prepared analogously to example 87 with (2R)-2-(N-((9H-fluoren-9-yl)methoxy-carbonyl)-N-methylamino)-3-phenylpropionic acid instead of (2R)-2-(N-(9H-fluoren-9-ylmethoxycarbonyl)-N-methylamino)-3-(2-thienyl)propionic acid.

Yield: 15.9 mg

HPLC: (A1) $R_t$=30.87 min (B1) $R_t$=32.50 min

LC-MS: 531.2 $(m+1)^+$

Example 127

3-Aminomethyl-N-methyl-N-((1R)-1-(N-methyl-N-((1R)-1-(methylcarbamoyl)-2-phenylethyl)carbamoyl)-2-(benzyloxy)ethyl)benzamide:

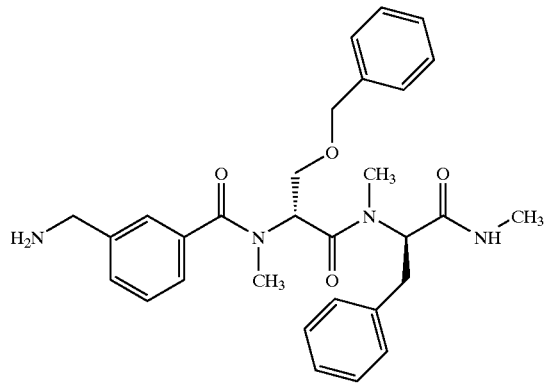

The title compound was prepared analogously to example 88 with (2R)-2-(N-((9H-fluoren-9-yl)methoxy-carbonyl)-N-methylamino)-3-phenylpropionic acid instead of (2R)-2-(N-(9H-fluoren-9-ylmethoxycarbonyl)-N-methylamino)-3-(2-thienyl)propionic acid.

Yield: 13.2 mg

HPLC: (A1) $R_t$=30.02 min (B1) $R_t$=31.65 min

LC-MS: 517.0 $(m+1)^+$

Example 128

(2R)-2-(N-((2-Aminobutoxy)acetyl)-N-methylamino)-N-methyl-N-((1R)-1-(methylcarbamoyl)-2-phenylethyl)-3-(benzyloxy)propionamide:

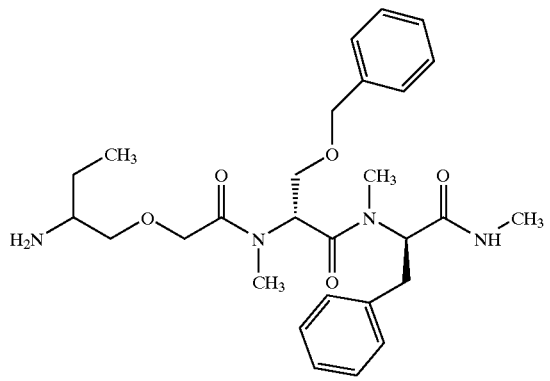

The title compound was prepared analogously to example 89 with (2R)-2-(N-((9H-fluoren-9-yl)methoxy-carbonyl)N-methylamino)-3phenylpropionic acid instead of (2R)-2-(N-(9H-fluoren-9-ylmethoxycarbonyl)N-methylamino)-3(2-thienyl)propionic acid.

Yield: 14.7 mg

HPLC: (A1) $R_t$=29.38 min (B1) $R_t$=30.85 min

LC-MS: 513.2 $(m+1)^+$

Example 129

(2R)-2-(N-((((2S)-2-Pyrrolidinyl)methoxy)acetyl)-N-methylamino-N-methyl-N-((1R)-1-(methylcarbamoyl)-2-phenylethyl)-3-(benzyloxy)propionamide:

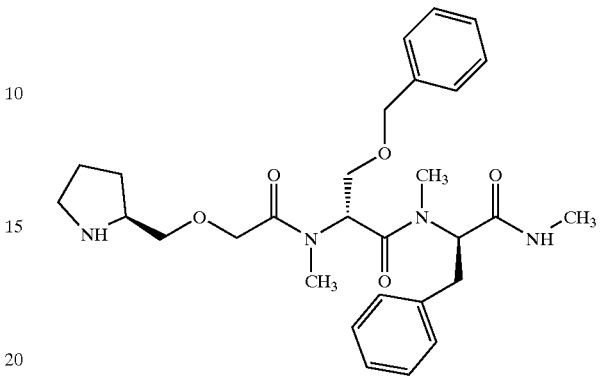

The title compound was prepared analogously to example 90 with (2R)-2-(N-((9H-fluoren-9-yl)methoxy-carbonyl)-N-methylamino)-3-phenylpropionic acid instead of (2R)-2-(N-(9H-fluoren-9-ylmethoxycarbonyl)-N-methylamino)-3-(2-thienyl)propionic acid.

Yield: 17.9 mg

HPLC: (A1) $R_t$=29.00 min (B1) $R_t$=30.45min

LC-MS: 525.0 $(m+1)^+$

Example 130

(2R)-2-(N((2Amino-2-methylpropoxy)acetyl)-N-methylamino)-N-methyl-N-((1R)-1-(methylcarbamoyl)-2-phenylethyl)-3-(benzyloxy)propionamide:

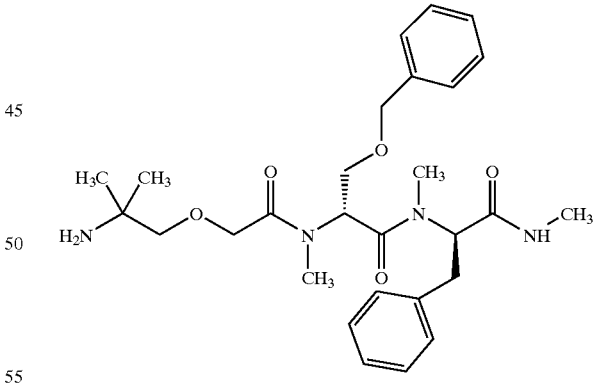

The title compound was prepared analogously to example 91 with (2R)-2-(N-((9H-fluoren-9-yl)methoxy-carbonyl)-N-methylamino)-3-phenylpropionic acid instead of (2R)-2-(N-(9H-fluoren-9-ylmethoxycarbonyl)-N-methylamino)-3-(2-thienyl)propionic acid.

Yield: 16.5 mg

HPLC: (A1) $R_t$=29.15 min (B1) $R_t$=30.57 min

LC-MS: 513.2 $(m+1)^+$

Example 131

3-(1-Aminoethyl)-N-methyl-N-((1R)-1-(N-methyl-N-((1R)-1-(methylcarbamoyl)-2-phenylethyl)carbamoyl)-2-(biphenyl-4-yl)ethyl)benzamide:

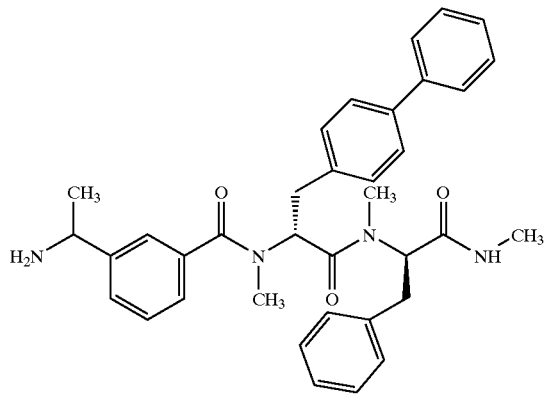

The title compound was prepared analogously to example 93 with (2R)-2-(N-((9H-fluoren-9-yl)methoxy-carbonyl)-N-methylamino)-3-phenylpropionic acid instead of (2R)-2-(N-(9H-fluoren-9-ylmethoxycarbonyl)-N-methylamino)-3-(2-thienyl)propionic acid.

Yield: 7.5 mg

HPLC: (A1) $R_t$=34.63 min (B1) $R_t$=min

LC-MS: $(m+1)^+$

Example 132

3-Aminomethyl-N-methyl-N-((1R)-1-(N-methyl-N-((1R)-1-(methylcarbamoyl)-2-phenylethyl)carbamoyl)-2-(biphenyl-4-yl)ethyl)benzamide:

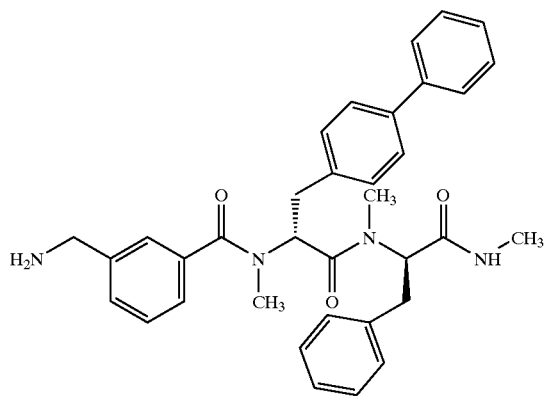

The title compound was prepared analogously to example 94 with (2R)-2-(N-((9H-fluoren-9-yl)methoxy-carbonyl)-N-methylamino)-3-phenylpropionic acid instead of (2R)-2-(N-(9H-fluoren-9-ylmethoxycarbonyl)-N-methylamino)-3-(2-thienyl)propionic acid.

Yield: 9.5 mg

HPLC: (A1) $R_t$=35.25 min (B1) $R_t$=36.93 min

LC-MS: $(m+1)^+$

Example 133

(2R)-2-(N-((2-Aminobutoxy)acetyl)-N-methylamino)-N-methyl-N-((1R)-1-(methylcarbamoyl)-2-phenylethyl)-3-(biphenyl-4-yl)propionamide:

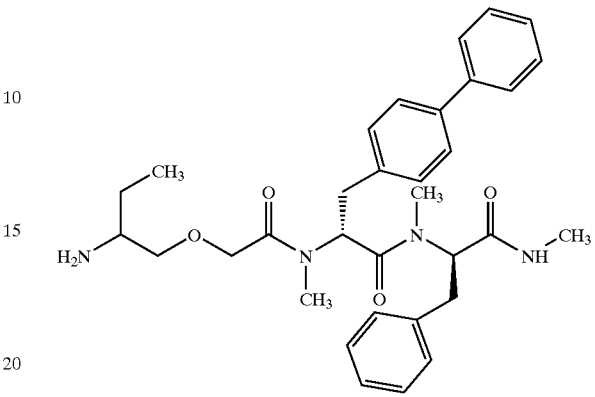

The title compound was prepared analogously to example 95 with (2R)-2-(N-((9H-fluoren-9-yl)methoxy-carbonyl)-N-methylamino)-3-phenylpropionic acid instead of (2R)-2-(N-(9H-fluoren-9-ylmethoxycarbonyl)-N-methylamino)-3-(2-thienyl)propionic acid.

Yield: 13.3 mg

HPLC: (A1) $R_t$=34.30 min (B1) $R_t$=36.1 0 min

LC-MS: 559.0 $(m+1)^+$

Example 134

(2R)-2-(N-((((2S)-2-Pyrrolidinyl)methoxy)acetyl)-N-methylamino-N-methyl-N-((1R)-1-(methylcarbamoyl)-2-phenylethyl)-3-(biphenyl-4-yl)propionamide:

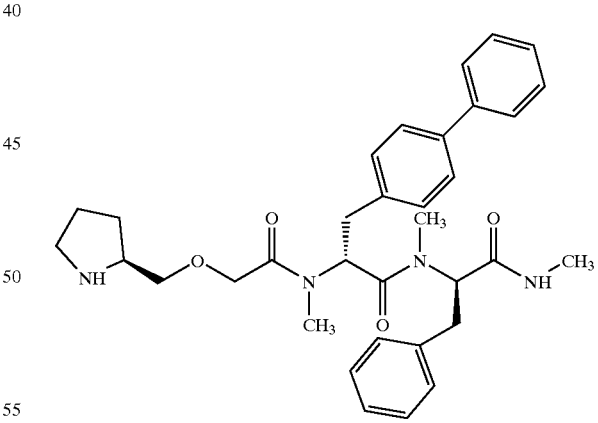

The title compound was prepared analogously to example 96 with (2R)-2-(N-((9H-fluoren-9-yl)methoxy-carbonyl)-N-methylamino)-3-phenylpropionic acid instead of (2R)-2-(N-(9H-fluoren-9-ylmethoxycarbonyl)-N-methylamino)-3-(2-thienyl)propionic acid.

Yield: 20.9 mg

HPLC: (A1) $R_t$=34.47 min (B1) $R_t$=36.17 min

LC-MS: 571.0 $(m+1)^+$

Example 135

(2R)-2-(N-((2-Amino-2-methylpropoxy)acetyl)-N-methylamino)-N-methyl-N-((1R)-1-(methylcarbamoyl)-2-phenylethyl)-3-(biphenyl-4-yl)propionamide:

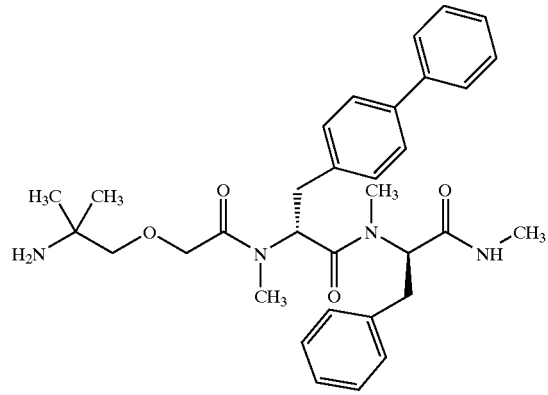

The title compound was prepared analogously to example 97 with (2R)-2-(N-((9H-fluoren-9-yl)methoxy-carbonyl)-N-methylamino)-3-phenylpropionic acid instead of (2R)-2-(N-(9H-fluoren-9-ylmethoxycarbonyl)-N-methylamino)-3-(2-thienyl)propionic acid.

Yield: 25.4 mg

HPLC: (A1) $R_t$=34.05 min (B1) $R_t$=35.78 min

LC-MS: 559.0 $(m+1)^+$

Example 136

3-(1-Aminoethyl)-N-methyl-N-((1R)-1-(N-methyl-N-((1R)-1-(methylcarbamoyl)-2-(4-methoxyphenyl)-ethyl)carbamoyl)-2-(2-naphthyl)ethyl)benzamide:

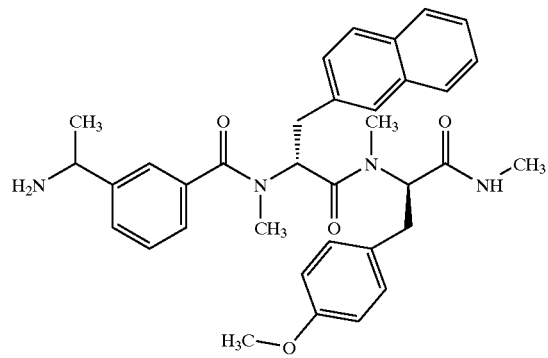

The title compound was prepared analogously to example 76 with (2R)-2-(N-((9H-fluoren-9-yl)methoxy-carbonyl)-N-methylamino)-3-(4-methoxyphenyl)-propionic acid instead of (2R)-2-(N-(9H-fluoren-9-ylmethoxycarbonyl)-N-methylamino)-3-(2-thienyl)-propionic acid.

Yield: 8.3 mg

HPLC: (A1) $R_t$=31.32 min (B1) $R_t$=32.92 min

LC-MS: 580.8 $(m+1)^+$

Example 137

3-Aminomethyl-N-methyl-N-((1R)-1-(N-methyl-N-((1R)-1-(methylcarbamoyl)-2-(4-methoxyphenyl)ethyl)-carbamoyl)-2-(2-naphthyl)ethyl)benzamide:

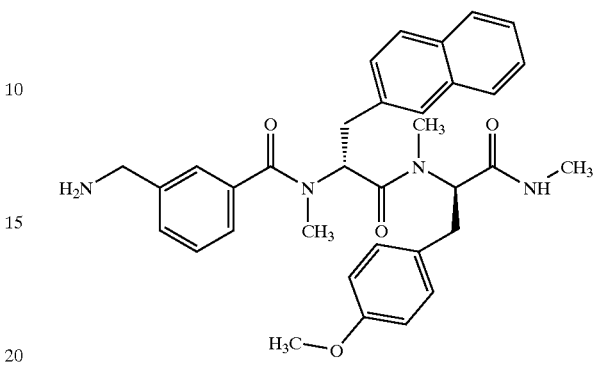

The title compound was prepared analogously to example 77 with (2R)-2-(N-((9H-fluoren-9-yl)methoxy-carbonyl)-N-methylamino)-3-(4-methoxyphenyl)-propionic acid instead of (2R)-2-(N-(9H-fluoren-9-ylmethoxycarbonyl)-N-methylamino)-3-(2-thienyl)-propionic acid.

Yield: 4.1 mg

HPLC: (A1) $R_t$=30.62 min (B1) $R_t$=min

LC-MS: 566.8 $(m+1)^+$

Example 138

(2R)-2-(N-((2-Aminobutoxy)acetyl)-N-methylamino)-N-methyl-N-((1R)-1-(methylcarbamoyl)-2-(4-methoxyphenyl)ethyl)-3-(2-naphthyl)propionamide:

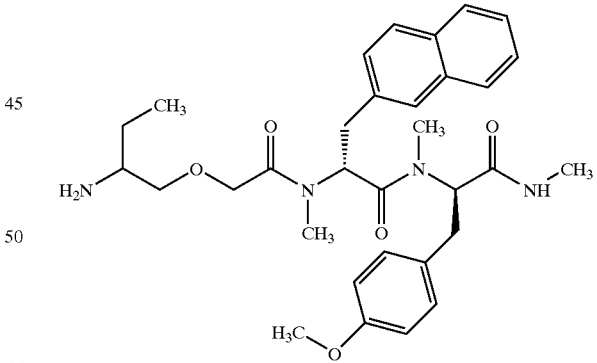

The title compound was prepared analogously to example 78 with (2R)-2-(N-((9H-fluoren-9-yl)methoxy-carbonyl)-N-methylamino)-3-(4-methoxyphenyl)-propionic acid instead of (2R)-2-(N-(9H-fluoren-9-ylmethoxycarbonyl)-N-methylamino)-3-(2-thienyl)-propionic acid.

Yield: 18.0 mg

HPLC: (A1) $R_t$=30.78 min (B1) $R_t$=32.27 m:

LC-MS: 563.2 $(m+1)^+$

Example 139

(2R)-2-(N-((((2S)-2-Pyrrolidinyl)methoxy)acetyl)-N-methylamino)-N-methyl-N-((1R)-1-(methylcarbamoyl)-2-(4-methoxyphenyl)ethyl)-3-(2-naphthyl)-propionamide:

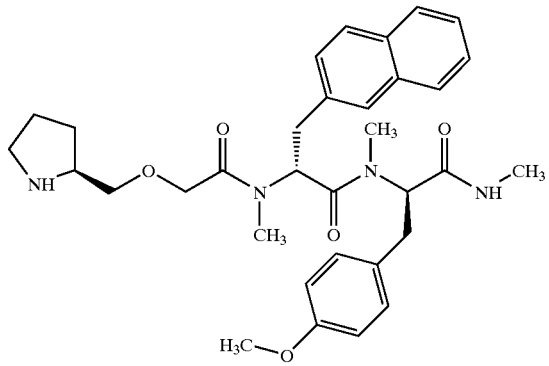

The title compound was prepared analogously to example 79 with (2R)-2-(N-((9H-fluoren-9-yl)methoxy-carbonyl)-N-methylamino)-3-(4-methoxyphenyl)-propionic acid instead of (2R)-2-(N-(9H-fluoren-9-ylmethoxycarbonyl)-N-methylamino)-3-(2-thienyl)-propionic acid.

Yield: 24.0 mg

HPLC: (A1) $R_t$=30.85 min (B1) $R_t$=32.40 min

LC-MS: 574.8 $(m+1)^+$

Example 140

(2R)-2-(N-((2-Amino-2-methylpropoxy)acetyl)-N-methylamino)-N-methyl-N-((1R)-1-(methylcarbamoyl)-2-(4-methoxyphenyl)ethyl)-3-(2-naphthyl)propionamide:

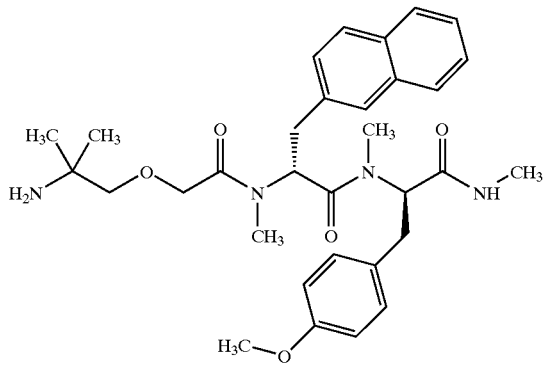

The title compound was prepared analogously to example 80 with (2R)-2-(N-((9H-fluoren-9-yl)methoxy-carbonyl)-N-methylamino)-3-(4-methoxyphenyl)-propionic acid instead of (2R)-2-(N-(9H-fluoren-9-ylmethoxycarbonyl)-N-methylamino)-3-(2-thienyl)-propionic acid.

Yield: 15.6 mg

HPLC: (A1) $R_t$=30.37 min (B1) $R_t$=31.90 min

LC-MS: 563.2 $(m+1)^+$

Example 141

(2E)-5-Amino-5-methylhex-2-enoic acid N-methyl-N-((1R)-1-(N-methyl-N-((1R)-1-(methylcarbamoyl)-2-(4-methoxyphenyl)ethyl)carbamoyl)-2-(2-naphthyl)-ethyl) amide:

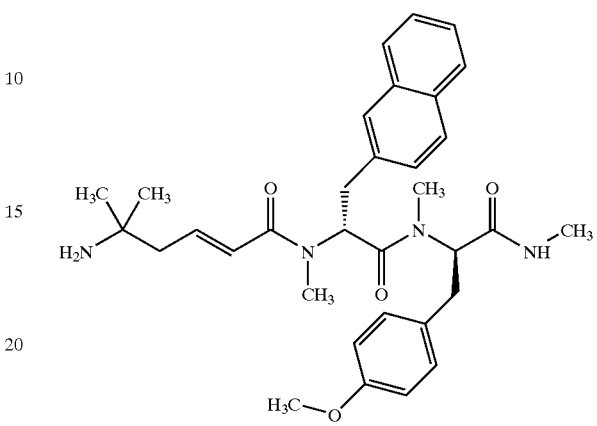

The title compound was prepared analogously to example 140 with (2E)-5-(tert-butoxycarbonylamino)-5-methylhex-2-enoic acid instead of (2-(tert-butoxycarbonylamino)-2-methylpropoxy)acetic acid.

Yield: 2.9 mg

HPLC: (A1) $R_t$=min (B1) $R_t$=min

LC-MS: 559.0 $(m+1)^+$

Example 142

3-(1-Aminoethyl)-N-methyl-N-((1R)-1-(N-methyl-N-((se R)-1-(methylcarbamoyl)-2-(4-methoxyphenyl)-ethyl)carbamoyl)-2-(benzo[b]thiophen-3-yl)ethyl)-benzamide:

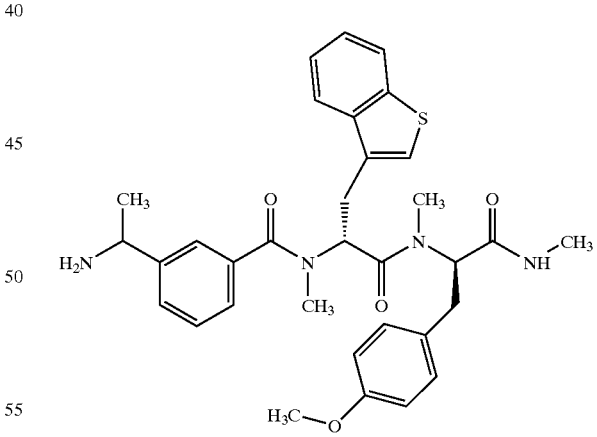

The title compound was prepared analogously to example 81 with (2R)-2-(N-((9H-fluoren-9-yl)methoxy-carbonyl)-N-methylamino)-3-(4-methoxyphenyl)-propionic acid instead of (2R)-2-(N-(9H-fluoren-9-ylmethoxycarbonyl)-N-methylamino)-3-(2-thienyl)-propionic acid.

Yield: 3.4 mg

HPLC: (A1) $R_t$=30.90 min (B1)$R_t$=min

LC-MS: 586.8 $(m+1)^+$

Example 143

3-Aminomethyl-N-methyl-N-((1R)-1-(N-methyl-N-((1R)-1-(methylcarbamoyl)-2-(4-methoxyphenyl)ethyl)-carbamoyl)-2-(benzo[b]thiophen-3-yl)ethyl)-benzamide:

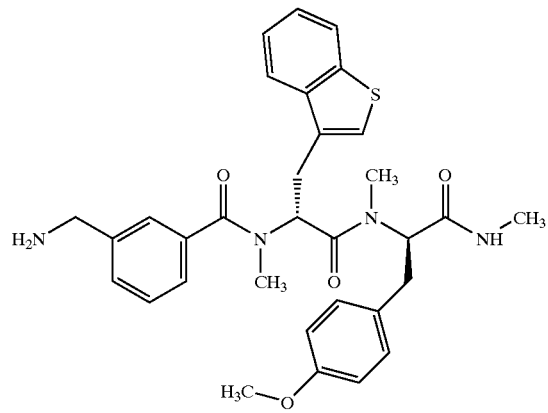

The title compound was prepared analogously to example 82 with (2R)-2-(N-((9H-fluoren-9-yl)methoxy-carbonyl)-N-methylamino)-3-(4-methoxyphenyl)-propionic acid instead of (2R)-2-(N-(9H-fluoren-9-ylmethoxycarbonyl)-N-methylamino)-3-(2-thienyl)-propionic acid.

Yield: 5.5 mg

HPLC: (A1) $R_t$=30.15 min (B1) $R_t$=min

LC-MS: 573.0 $(m+1)^+$

Example 144

(2R)-2-(N-((2-Aminobutoxy)acetyl)-N-methylamino)-N-methyl-N-((1R)-1-(methylcarbamoyl)-2-(4-methoxyphenyl)ethyl)-3-(benzo[b]thiophen-3-yl)propionamide:

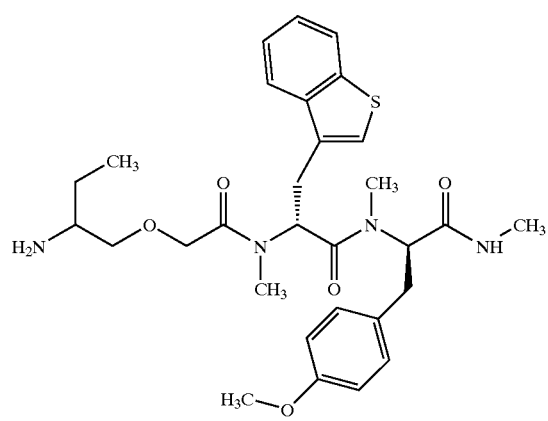

The title compound was prepared analogously to example 83 with (2R)-2-(N-((9H-fluoren-9-yl)methoxy-carbonyl)-N-methylamino)-3-(4-methoxyphenyl)-propionic acid instead of (2R)-2-(N-(9H-fluoren-9-ylmethoxycarbonyl)-N-methylamino)-3-(2-thienyl)-propionic acid.

Yield: 7.5 mg

HPLC: (A1) $R_t$=30.18 min (B1) $R_t$=min

LC-MS: 569.0 $(m+1)^+$

Example 145

(2R)-2-(N-((((2S)-2-Pyrrolidinyl) methoxy)acetyl)-N-methylamino)-N-methyl-N-((1R)-1-(methylcarbamoyl)-2-(4-methoxyphenyl)ethyl)-3-(benzo[b]thiophen-3-yl)propionamide:

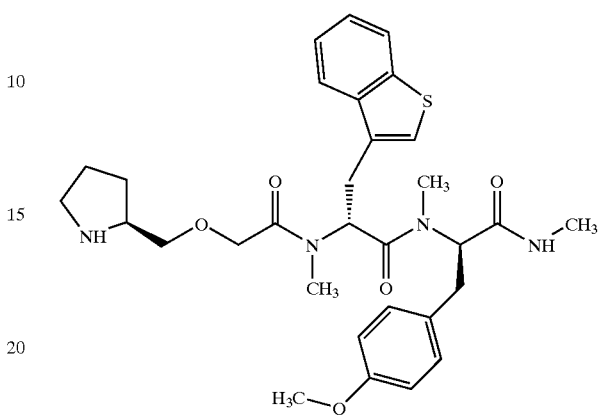

The title compound was prepared analogously to example 84 with (2R)-2-(N-((9H-fluoren-9-yl)methoxy-carbonyl)-N-methylamino)-3-(4-methoxyphenyl)-propionic acid instead of (2R)-2-(N-(9H-fluoren-9-ylmethoxycarbonyl)-N-methylamino)-3-(2-thienyl)-propionic acid.

Yield: 10.5 mg

HPLC: (A1) $R_t$=30.20 min (B1) $R_t$=min

LC-MS: 581.0 $(m+1)^+$

Example 146

(2R)-2-(N-((2Amino-2-methylpropoxy)acetyl)-N-methylamino)-N-methyl-N-((1R)-1-(methylcarbamoyl)-2-(4-methoxyphenyl)ethyl)-3-(benzo[b]thiophen-3-yl)propionamide:

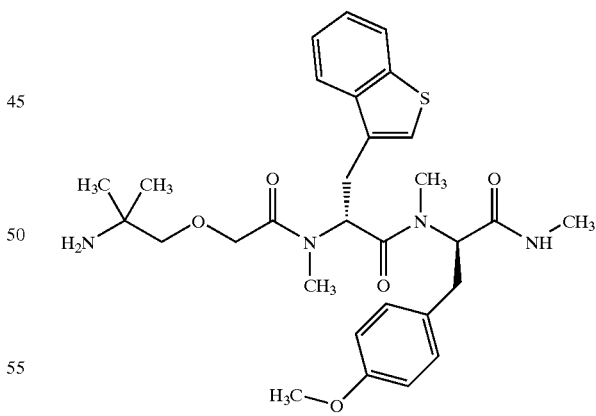

The title compound was prepared analogously to example 85 with (2R)-2-(N-((9H-fluoren-9-yl)methoxy-carbonyl)-N-methylamino)-3-(4-methoxyphenyl)-propionic acid instead of (2R)-2-(N-(9H-fluoren-9-ylmethoxycarbonyl)-N-methylamino)-3-(2-thienyl)-propionic acid.

Yield: 9.9 mg

HPLC: (A1) $R_t$=29.87 min (B1) $R_t$=min

LC-MS: 569.0 $(m+1)^+$

Example 147

(2E)-5-Amino-5-methylhex-2-enoic acid N-methyl-N-((1R)-1-(N-methyl-N-((1R)-1-(methylcarbamoyl)-2-(4-methoxyphenyl)ethyl)carbamoyl)-2-(benzo[b]thiophen-3-yl)ethyl)amide:

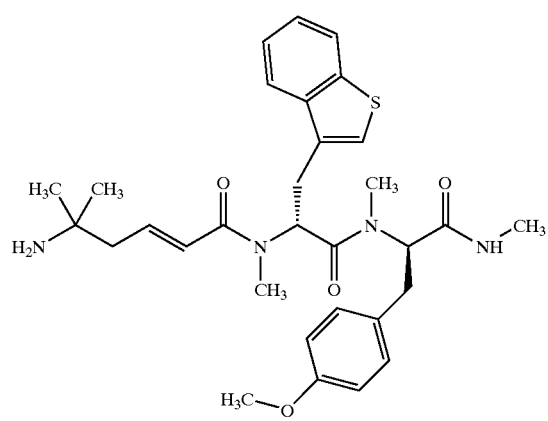

The title compound was prepared analogously to example 86 with (2R)-2-(N-((9H-fluoren-9-yl)methoxy-carbonyl)-N-methylamino)-3-(4-methoxyphenyl)-propionic acid instead of (2R)-2-(N-(9H-fluoren-9-ylmethoxycarbonyl)-N-methylamino)-3-(2-thienyl)-propionic acid.

Yield: 4.0 mg

HPLC: (A1) $R_t$=30.42 min (B1) $R_t$=min

LC-MS: (m+1)$^+$

Example 148

3-(1-Aminoethyl)-N-methyl-N-((1R)-1-(N-methyl-N-((1R)-1-(methylcarbamoyl)-2-(4-methoxyphenyl)-ethyl)carbamoyl)-2-(benzyloxy)ethyl)benzamide:

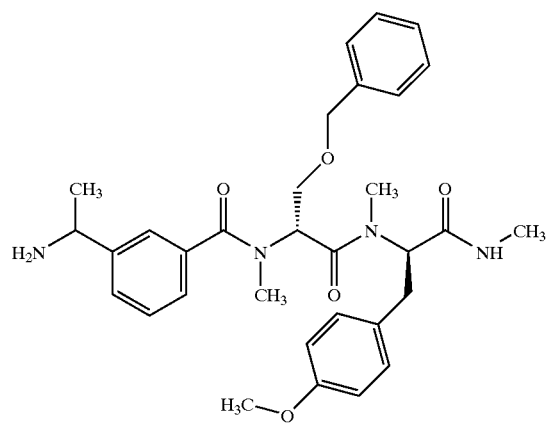

The title compound was prepared analogously to example 87 with (2R)-2-(N-((9H-fluoren-9-yl)methoxy-carbonyl)-N-methylamino)-3-(4-methoxyphenyl)-propionic acid instead of (2R)-2-(N-(9H-fluoren-9-ylmethoxycarbonyl)-N-methylamino)-3-(2-thienyl)-propionic acid.

Yield: 6.1 mg

HPLC: (A1) $R_t$=30.82 min (B1) $R_t$=min

LC-MS: 561.2 (m+1)$^+$

Example 149

3-Aminomethyl-N-methyl-N-((1R)-1-(N-methyl-N-((1R)-1-(methylcarbamoyl)-2-(4-methoxyphenyl)-ethyl)carbamoyl)-2-(benzyloxy)ethyl)benzamide:

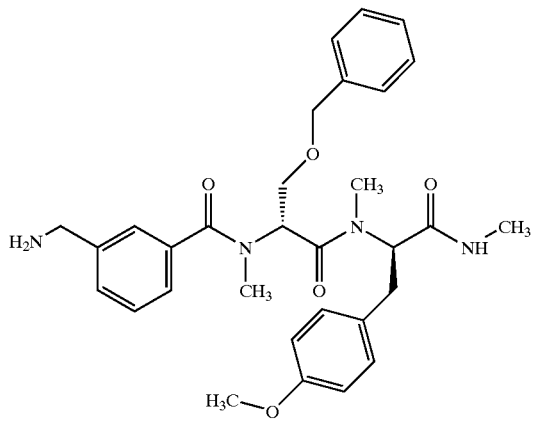

The title compound was prepared analogously to example 88 with (2R)-2-(N-((9H-fluoren-9-yl)methoxy-carbonyl)-N-methylamino)-3-(4-methoxyphenyl)-propionic acid instead of (2R)-2-(N-(9H-fluoren-9-ylmethoxycarbonyl)-N-methylamino)-3-(2-thienyl)-propionic acid.

Yield: 7.3 mg

HPLC: (A1) $R_t$=36.23 min (B1) $R_t$=min

LC-MS: 547.0 (m+1)$^+$

Example 150

(2R)-2-(N-((2-Aminobutoxy)acetyl)-N-methylamino)-N-methyl-N-((1R)-1-(methylcarbamoyl)-2-(4-methoxyphenyl)ethyl)-3-(benzyloxy)propionamide:

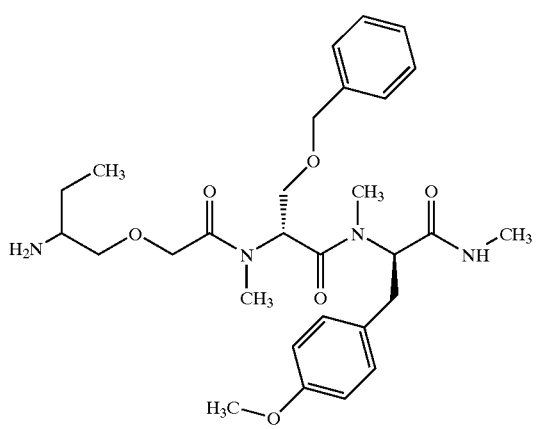

The title compound was prepared analogously to example 89 with (2R)-2-(N-((9H-fluoren-9-yl)methoxy-carbonyl)-N-methylamino)-3-(4-methoxyphenyl)-propionic acid instead of (2R)-2-(N-(9H-fluoren-9-ylmethoxycarbonyl)-N-methylamino)-3-(2thienyl)-prop ionic acid.

Yield: 2.4 mg

HPLC: (A1) $R_t$=min (B1) $R_t$=min

LC-MS: (m+1)$^+$

Example 151

(2R)-2-(N-((((2S)-2-Pyrrolidinyl)methoxy)acetyl)-N-methylamino)-N-methyl-N-((1R)-1-(methylcarbamoyl)-2-(4-methoxyphenyl)ethyl)-3-(benzyloxy)propionamide:

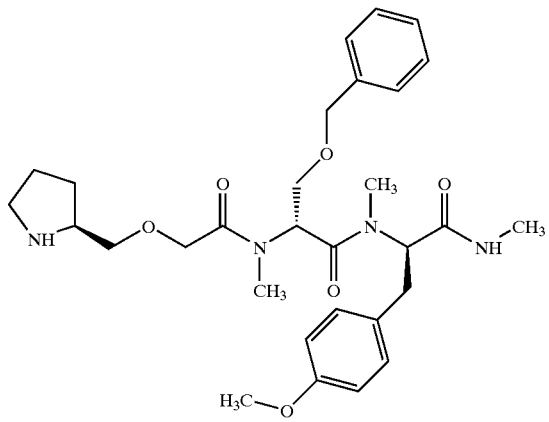

The title compound was prepared analogously to example 90 with (2R)-2-(N-((9H-fluoren-9-yl)methoxy-carbonyl)-N-methylamino)-3-(4-methoxyphenyl)-propionic acid instead of (2R)-2-(N-(9H-fluoren-9-ylmethoxycarbonyl)-N-methylamino)-3-(2thienyl)propionic acid.

Yield: 19.0 mg

HPLC: (A1) $R_t$=28.65 min (B1) $R_t$=30.02 min

LC-MS: 555.0 $(m+1)^+$

Example 152

(2R)-2-(N-((2-Amino-2-methylpropoxy)acetyl)-N-methylamino)-N-methyl-N-((1R)-1-(methylcarbamoyl)-2-(4-methoxyphenyl)ethyl)-3-(benzyloxy)propionamide:

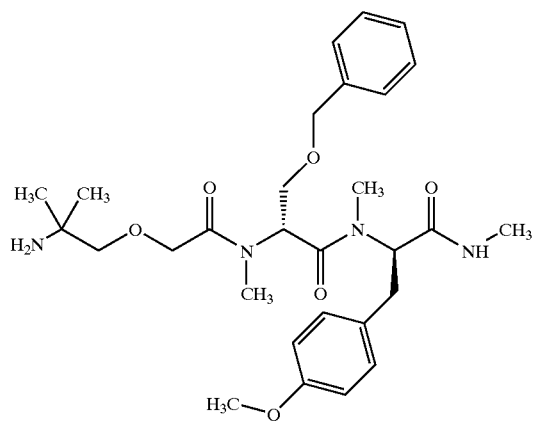

The title compound was prepared analogously to example 91 with (2R)-2-(N-((9H-fluoren-9-yl)methoxy-carbonyl)-N-methylamino)-3-(4-methoxyphenyl)-propionic acid instead of (2R)-2-(N-(9H-fluoren-9-ylmethoxycarbonyl)-N-methylamino)-3-(2-thienyl)-propionic acid.

Yield: 20.5 mg

HPLC: (A1) $R_t$=28.80 min (B1) $R_t$=30.17 min

LC-MS: 543.2 $(m+1)^+$

Example 153

(2E)-5-Amino-5-methylhex-2-enoic acid N-methyl-N-((1R)-1-(N-methyl-N-((1R)-1-(methylcarbamoyl)-2-(4-methoxyphenyl)ethyl)carbamoyl)-2-(benzyloxy)ethyl)amide:

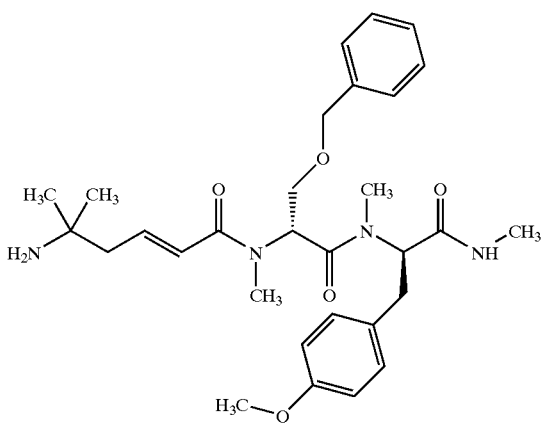

The title compound was prepared analogously to example 92 with (2R)-2-(N-((9H-fluoren-9-yl)methoxy-carbonyl)-N-methylamino)-3-(4-methoxyphenyl)-propionic acid instead of (2R)-2-(N-(9H-fluoren-9-ylmethoxycarbonyl)-N-methylamino)-3-(2-thienyl)-propionic acid.

Yield: 4.0 mg

HPLC: (A1) $R_t$=28.37 min (B1) $R_t$=min

LC-MS: 539.2 $(m+1)^+$

Example 154

3-(1-Aminoethyl)-N-methyl-N-((1R)-1-(N-methyl-N-((1R)-1-(methylcarbamoyl)-2-(4-methoxyphenyl)-ethyl)carbamoyl)-2-(biphen-4-yl)ethyl)benzamide:

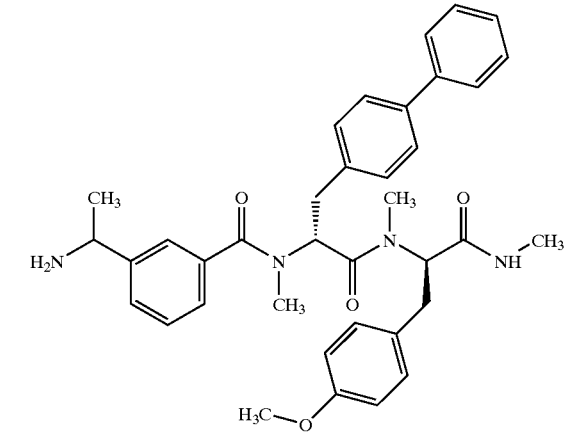

The title compound was prepared analogously to example 93 with (2R)-2-(N-((9H-fluoren-9-yl)methoxy-carbonyl)-N-methylamino)-3-(4-methoxyphenyl)-propionic acid instead of (2R)-2-(N-(9H-fluoren-9-ylmethoxycarbonyl)-N-methylamino)-3-(2-thienyl)-propionic acid.

Yield: 8.2 mg

HPLC: (A1) $R_t$=min (B1) $R_t$=min

LC-MS: 607.0 $(m+1)^+$

Example 155
3-Aminomethyl-N-methyl-N-((1R)-1-(N-methyl-N-((1R)-1-(methylcarbamoyl)-2-(4-methoxyphenyl)ethyl)-carbamoyl)-2-(biphenyl-4-yl)ethyl)benzamide:

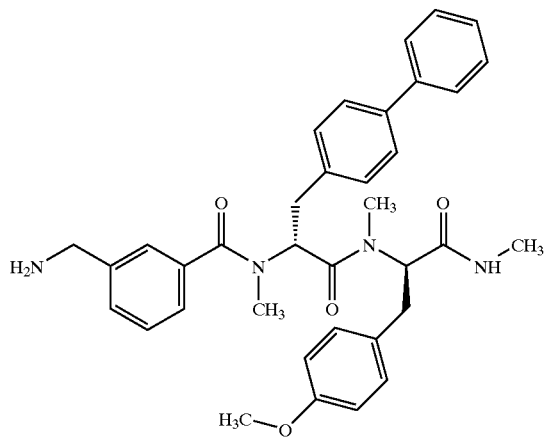

The title compound was prepared analogously to example 94 with (2R)-2-(N-((9H-fluoren-9-yl)methoxy-carbonyl)-N-methylamino)-3-(4-methoxyphenyl)-propionic acid instead of (2R)-2-(N-(9H-fluoren-9-ylmethoxycarbonyl)-N-methylamino)-3-(2-thienyl)-propionic acid.

Yield: 7.2 mg
HPLC: (A1) $R_t$=min (B1) $R_t$=min
LC-MS: 593.2 (m+1)$^+$

Example 156
(2R)-2-(N-((2-Aminobutoxy)acetyl)-N-methylamino)-N-methyl-N-((1R)-1-(methylcarbamoyl)-2-(4-methoxyphenyl)ethyl)-3-(biphenyl-4-yl)propionamide:

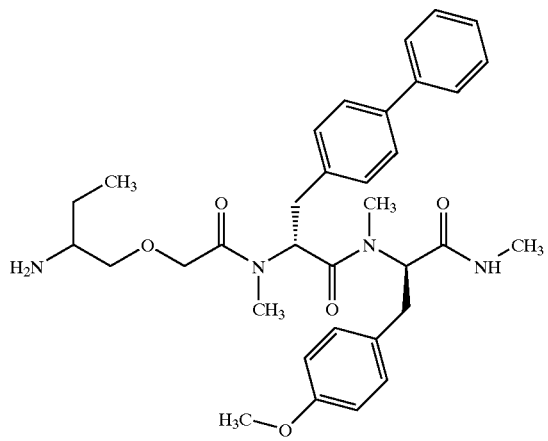

The title compound was prepared analogously to example 95 with (2R)-2-(N-((9H-fluoren-9-yl)methoxy-carbonyl)-N-methylamino)-3-(4-methoxyphenyl)-propionic acid instead of (2R)-2-(N-(9H-fluoren-9-ylmethoxycarbonyl)-N-methylamino)-3-(2-thienyl)-propionic acid.

Yield: 6.0 mg
HPLC: (A1) $R_t$=min (B1) $R_t$=min
LC-MS: 589.2 (m+1)$^+$

Example 157
(2R)-2-(N-((((2S)-2-Pyrrolidinyl)methoxy)acetyl)-N-methylamino)-N-methyl-N-((1R)-1-(methylcarbamoyl)-2-(4-methoxyphenyl)ethyl)-3-(biphenyl-4-yl)propionamide:

The title compound was prepared analogously to example 96 with (2R)-2-(N-((9H-fluoren-9-yl)methoxy-carbonyl)-N-methylamino)-3-(4-methoxyphenyl)-propionic acid instead of (2R)-2-(N-(9H-fluoren-9-ylmethoxycarbonyl)-N-methylamino)-3-(2-thienyl)-propionic acid.

Yield: 10.0 mg
HPLC: (A1) $R_t$=min (B1) $R_t$=min
LC-MS: 601.0 (m+1)$^+$

General Procedure for Example 158–533

The following 376 compounds were prepared as single entities by parallel synthesis on a solid support using an Fmoc strategy on an Advanced ChemTech Model 384 HTS employing HATU/HOAt (O-(7-azabenzotriazol-1-yl)-1,1,3,3-tetramethyluronium hexafluorophosphate/1-hydroxy-7-azabenzotriazole) mediated amidecoupling in dimethylformamide (DMF) according to a protocol known for those skilled in the art. The compounds were prepared sequentially according to the following equation Resin-[Building block 1]→Resin-[Building block 1]-[Building block 2]→Resin-[Building block 1]-[Building block 2]-[Building block 3]→Resin-[Building block 1]-[Building block 2]-[Building block 3]-[Building block 4]

and were simultaneously deprotected and cleaved from the resin with 50% trifluoroacetic acid (TFA) in dichloromethane (DCM) to give the desired compounds as individual entities according to the following formula

[Building block 4]-[Building block 3]-[Building block 2]-[Building block 1].

The starting resins were all prepared separately by reductive amination of [Building block 1] and a 5-(4-formyl-3,5-dimethoxyphenoxy)valerate resin as described in Example 44 for N-Me-PAL.

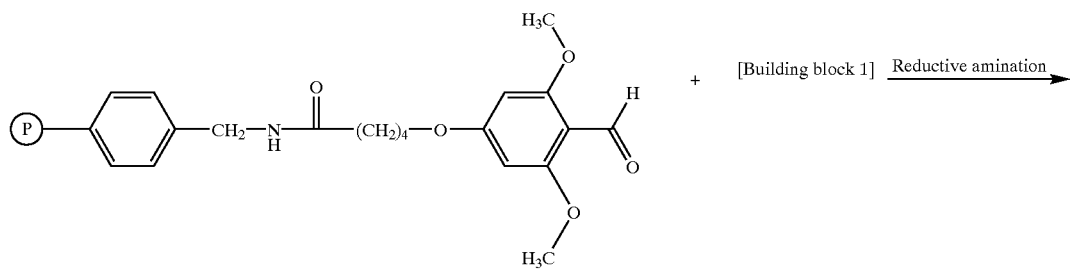

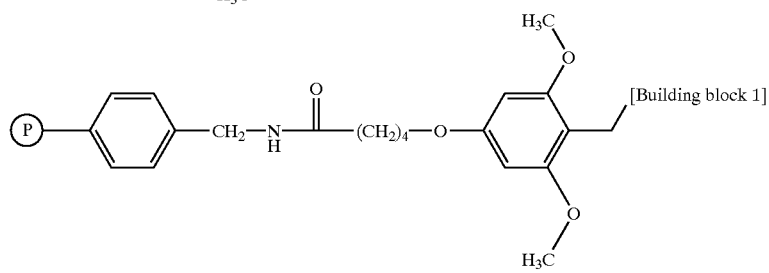

The substitution capacities of the resins were 0.5–0.7 mmol/g determined by UV monitoring of the deprotection of the Fmoc protection group.

All 376 compounds are based on a scaffold and four varying groups according to the following formula, which is included in general formula I:

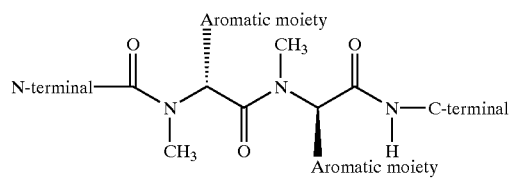

The 376 compounds were prepared as three separate libraries based on total combination of four selected building blocks (see example 158–253, example 254–353 and example 354–533) and prepared analogously to the procedure described in Example 158.

The following resins, here depicted as Resin-[Building block 1] were used:

Resins

Name: N-Me-PAL (described in Example 44)

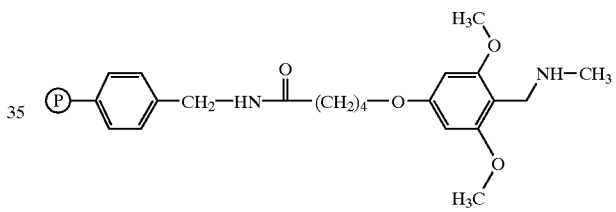

Name: N-PhenethylPAL (prepared analogously to N-Me-PAL)

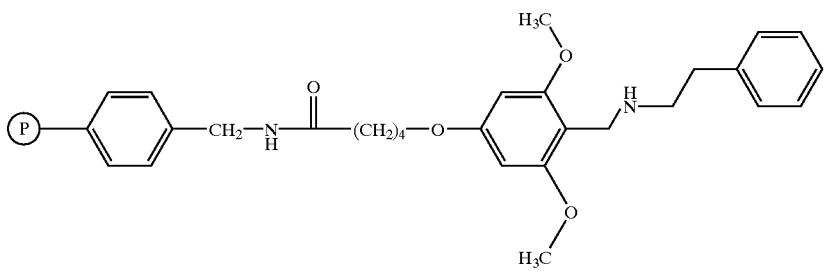

Name: N-(4-Pyridyl)ethyl-PAL (prepared analogously to N-Me-PAL)

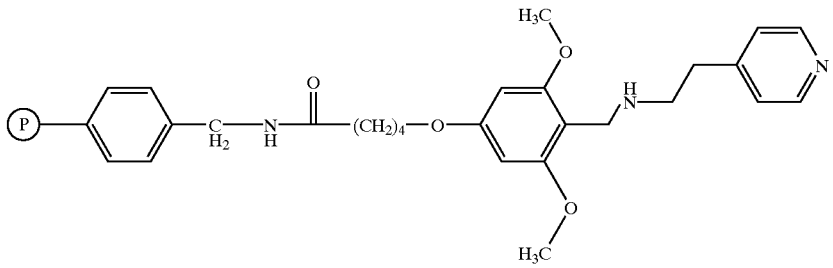

Name: N-((S)-2-Hydroxypropyl)PAL (prepared analogously to N-Me-PAL)
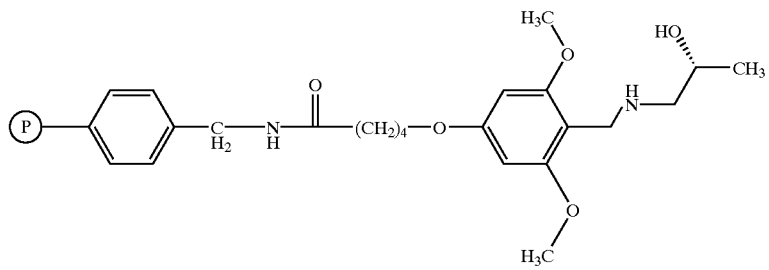
Name: N-(2,2-Dimethyl-3-hydroxypropyl)-PAL (prepared analogously to N-Me-PAL)
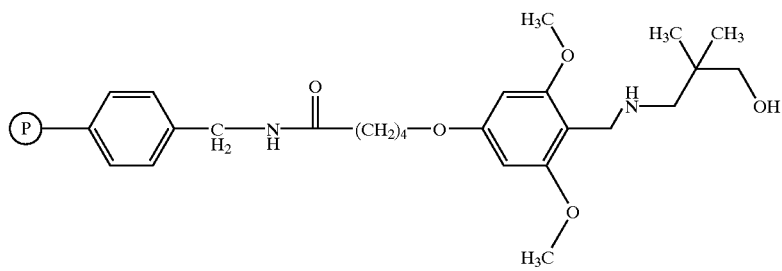
Name: N((1-Methylpyrrolidin-2-yl)ethyl)-PAL (prepared analogously to N-Me-PAL)
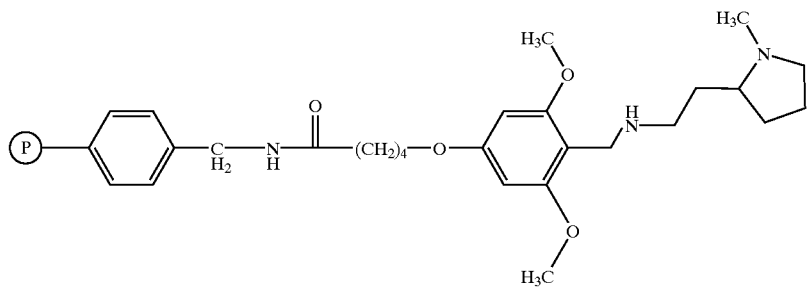
The following building blocks were used:
Building Block 1
Name: Methylamine
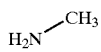
Name: Phenethylamine
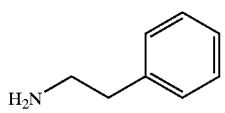
Name: 2-(4-pyridyl)ethylamine
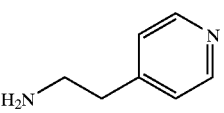
Name: (S)-2-Hydroxypropylamine
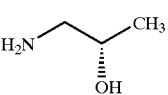

221

Name: 2,2-Dimethyl-3hydroxypropylamine

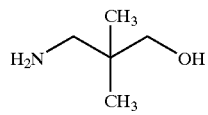

Name: 2-(1-Methylpyrrolidine-2-yl)ethylamine

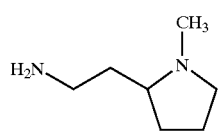

Building Block 2

Name: (2R)-2-[N-(9H-Fluoren-9-yl)methoxycarbonyl)-N-methylamino]-3-(3,4-difluorophenyl)propionic acid
Abbreviation: Fmoc-N-Me-D-Phe(3,4-F,F)-OH

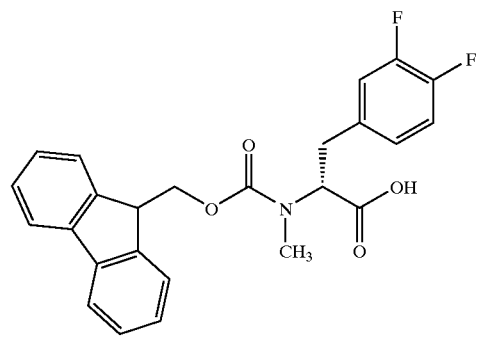

Name: (2R)-2-(N-(((9H-Fluoren-9-yl)methoxy)carbonyl)-N-methylamino)]-3-phenylpropionic acid
Abbreviation: Fmoc-N-Me-D-Phe-OH

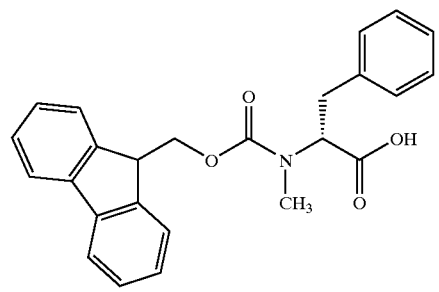

Name: (2R)-2-(N-(9H-Fluoren-9-ylmethoxycarbonyl)-N-methylamino)-3-(2-thienyl)propionic acid

222

Abbreviation: Fmoc-N-Me-D-ThiAla-OH

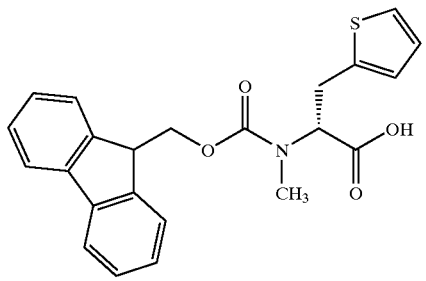

Name: (2R)-2-[N-(9H-Fluoren-9-yl)methoxycarbonyl)-N-methylamino]-3-(4-fluorophenyl)propionic acid
Abbreviation: Fmoc-N-Me-D-Phe(4-F)-OH

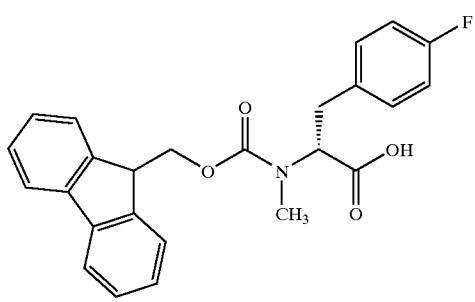

Building Block 3

Name: (2R)-2-(N-(((9H-Flouren-9-yl)meth oxy)carbonyl)-N-methylamino)-3-(2-naphtyl)propionic acid
Abbreviation: Fmoc-N-Me-D-2-Nal-OH

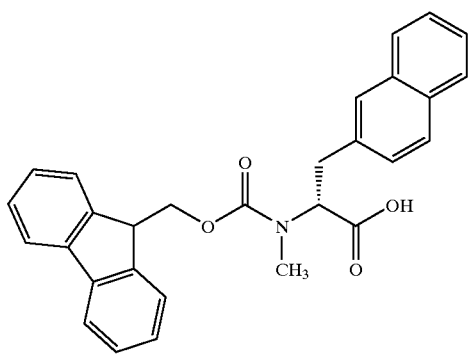

Name: (2R)-3-(Biphenyl-4-yl)-2-(N-((9H-fluoren-9-yl)methoxycarbonyl)-N-methylamino)propionic acid

223

Abbreviation: Fmoc-N-Me-D-Phe(4-Phe)-OH

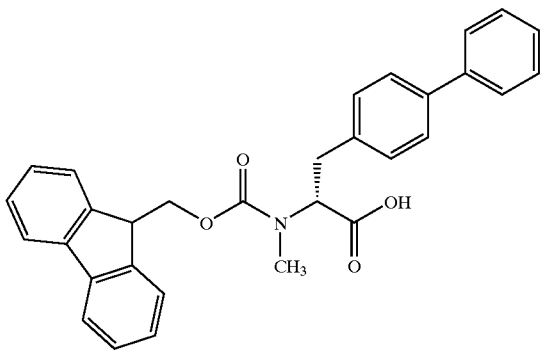

Building Block 4

Name: 3-(1-(tert-Butyloxycarbonylamino)ethyl)benzoic acid
Abbreviation: Boc-AEB-OH

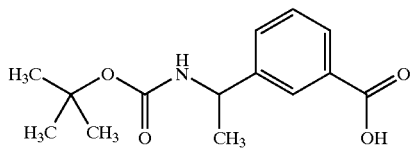

Name: 3-(t-Butyloxycarbonylaminomethyl)benzoic acid
Abbreviation: Boc-AMB-OH

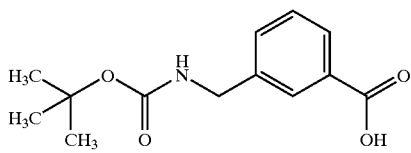

Name: (2E)-5-tert-Butoxycarbonylamino-3, 5-dimethylhex-2-enoic acid
Abbreviation: Boc-ADH-OH

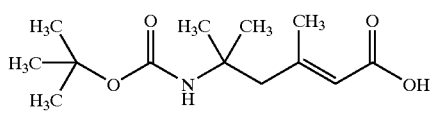

Name: (2E)-5-(N-(tert-Butoxycarbonyl)-N-methylamino)-5-methylhex-2-enoic acid.
Abbreviation: Boc-MAMH-OH

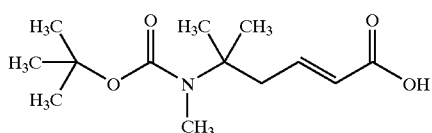

Name: (2S)-2-(((Carboxy)methoxy)methyl)pyrrolidin-1-carboxylic acid ten:-butyl ester

224

Abbreviation: Boc-SPMA-OH

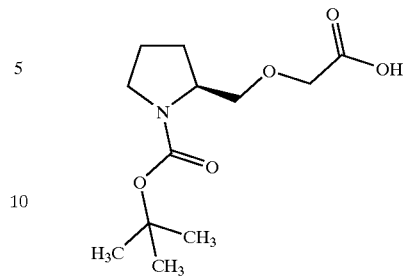

Name: (2R)-2-(((Carboxy)methoxy)methyl)pyrrolidin-1-carboxylic acid tert-butyl ester
Abbreviation: Boc-RPMA-OH

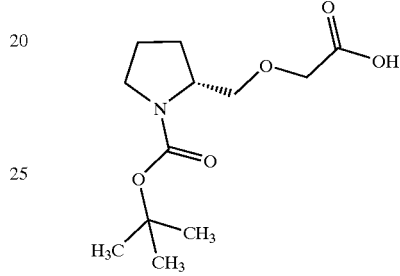

Name: (2E) 5-tert-Butoxycarbonylamino-5-ethylhept-2-enoic acid
Abbreviation: Boc-AEHA-OH

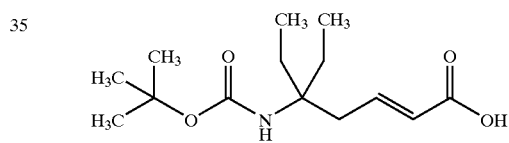

Name: (2E)A4-(1-(tert-Butoxycarbonylamino)cyclobutyl)but-2-enoic acid
Abbreviation: Boc-ACBB-OH

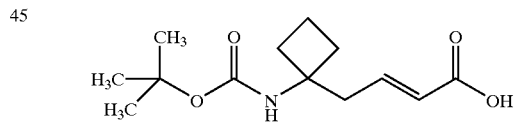

Name: (2E)-5-(tert-Butyloxycarbonylamino)-5-methylhex-2-enoic acid
Abbreviation: Boc-AM H-OH

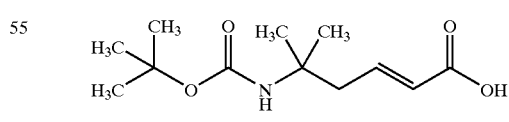

Example 158

The N-Me-PAL resin ([building block 1] attached to resin) (0.05 mmol) with a substitution capacity of 0.6 mmol/g was repeatedly (4 times) swelled in dichloromethane and dimethylformamide for 2 min and filtered.
1.0 Coupling: DIEA (0.025 mmol) in DCM (0.034 ml), HATU (0.0125 mmol) in DMF (0.5 ml), a solution of HOAt (0.0125 mmol) and Fmoc-N-Me-D-Phe(4-F)-OH [building block 2] (0.0125 mmol) in DMF (0.5 ml) and DMF (0.5 ml) were added. The mixture was allowed to shake for 16 hours. The resin was repeatedly (5 times) swelled in dimethylformamide for 90 sec and filtered.

1.5 Coupling: DIEA (0.00625 mmol) in DCM (0.0085 ml), HATU (0.003125 mmol) in DMF (0.125 ml), a solution of HOAt (0.003125 mmol) and Fmoc-N-Me-D-Phe(4-F)-OH [building block 2] (0.003125 mmol) in DMF (1.25 ml) were added. The mixture was allowed to shake for 4 hours. The resin was repeatedly (5 times) swelled in dimethylformamide for 90 sec and filtered.

Deprotection: A solution of 20% piperidine in DMF (1.5 ml) was added and the mixture was shaken for 20 min. The resin was repeatedly (7 times) swelled in dimethylformamide for 90 sec and filtered.

2.0 Coupling: DIEA (0.025 mmol) in DCM (0.034 ml), HATU (0.0125 mmol) in DMF (0.5 ml), a solution of HOAt (0.0125 mmol) and Fmoc-N-Me-D-2-Nal-OH [building block 3] (0.0125 mmol) in DMF (0.5 ml) and DMF (0.5 ml) were added. The mixture was allowed to shake for 16 hours. The resin was repeatedly (5 times) swelled in dimethylformamide for 90 sec and filtered.

2.5 Coupling: DIEA (0.00625 mmol) in DCM (0.0085 ml), HATU (0.003125 mmol) in DMF (0.125 ml), a solution of HOAt (0.003125 mmol) Fmoc-N-Me-D-2-Nal-OH [building block 3] (0.003125 mmol) in DMF (1.25 ml) were added. The mixture was allowed to shake for 4 hours. The resin was repeatedly (5 times) swelled in dimethylformamide for 90 sec and filtered.

Deprotection: A solution of 20% piperidine in DMF (1.5 ml) was added and the mixture was shaken for 20 min. The resin was repeatedly (7 times) swelled in dimethylformamide for 90 sec and filtered.

3.0 Coupling: DIEA (0.025 mmol) in DCM (0.034 ml), HATU (0.0125 mmol) in DMF (0.5 ml), a solution of HOAt (0.0125 mmol) and Boc-AMH-OH [building block 4] (0.0125 mmol) in DMF (0.5 ml) and DMF (0.5 ml) were added. The mixture was allowed to shake for 16 hours. The resin was repeatedly (5 times) swelled in dimethylformamide for 90 sec and filtered.

3.5 Coupling: DIEA (0.00625 mmol) in DCM (0.0085 ml), HATU (0.003125 mmol) in DMF (0.125 ml), a solution of HOAt (0.003125 mmol Boc-AMH-OH [building block 4] (0.003125 mmol) in DMF (1.25 ml) were added. The mixture was allowed to shake for 4 hours. The resin was repeatedly (5 times) swelled in dimethylformamide for 90 sec and filtered.

The resin was repeatedly (3 times) swelled in dichloromethane for 90 sec and filtered.

The compound was cleaved off the resin and deprotected by shaking for 10 min at −5° C. with a 50% solution of trifluoroacetic acid in dichloromethane (1.5 ml). Ethanol (1.5 ml) was added and the mixture was filtered and concentrated in vacuo to give the desired compound.

The final product obtained was characterized by analytical RP-HPLC (retention time) and by LC-MS (molecular mass).

The RP-HPLC analysis was performed on a Waters HPLC system consisting of Waters™ 600S Controller, Waters™ 996 Photodiode Array Detector, Waters™ 717 Autosampler, Waters™ 616 Pump, Waters™ 3 mm×150 mm 3.5m C-18 Symmetry and Millennium QuickSet Control Ver. 2.15 using UV detection at 214 nm. A gradient of 5% to 90% acetonitrile/0.1% trifluoroacetic acid/water during 15 min at 1 ml/min.

The LC-MS analysis was performed on a PE Sciex API 100 LC/MS System using a Water™ 3 mm×150 mm 3.5m C-18 Symmetry column and positive ionspray with a flow rate at 20 ml/min.

Examples 159–253

The following 95 compounds were synthesized in parallel as individual entities analogously to example 158 on an Advanced ChemTech Model 384 HTS using the following ChemFile to control the operation of the synthesizer (Advanced ChemTech Operator's Manual, version 1.2 July 1996, pp. 4–13):

ChemFile C:\ACT\CHEMFILE\2PETER.CHM Page 1
1 Flush Arm1 with DMF and NMP, Arm2 with DCM and DMF4
2 Empty RB1__1to96 for 3.000 minute(s)
3
4 Dispense System Fluid Dualarms__1+4*1000 µl to RB1__1to96[1–96]
5 "Mix RB1__1to96" for 2.00 minutes at 700 rpm(s)
6 Wait for 28.000 minute(s)
7 Empty RB1__1to96 for 3.000 minute(s)
8
9 REM Syntesestart her. Aminosyre 1
10 Dispense Sequence C:\ACT\displist\A1.DSP with 500 µl to RB1__1to96 rack using DMF
11 Dispense Sequence C:\ACT\displist\A2.DSP with 500 µl to RB1__1to96 rack using DMF
12 Mix "RB1__1to96" for 1.00 minutes at 600 rpm(s)
13 Transfer 500 µl from REAGENT__3[1] (HATU) to RB1__1to96 [1–96] using DMF
14 Transfer 68 µl from Monomer 1to36 [10] (DIEA) to RB1__1to96 [1–96] using DMF
15 Dispense System Fluid Dualarms__1+4*500 µl to RB1__1to96 [1–96]
16 Mix "RB11to96" for 5.00 minutes at 750 rpm(s)
17 Wait for 25.000 minute(s)
18 Repeat from step 16, 31 times
19 Pause
20 Empty RB1__1to96 for 3.000 minute(s)
21 Goto ChemFile WASH__DMF.CHM, line 1
22
23 REM Anden kobling 1 ste AA
24 Dispense Sequence C:\ACT\displist\A1.DSP with 125 µl to RB1__1to96 rack using DMF
25 Dispense Sequence C:\ACT\displist\A2.DSP with 125 µl to RB1__1to96 rack using DMF
26 Mix "RB1__1to96" for 1.00 minutes at 600 rpm(s)
27 Transfer 125 µl from REAGENT__3[1] (HATU) to RB1__1to96 [1–96] using DMF
28 Transfer 20 µl from Monomer 1to36 [10] (DIEA) to RB1__1to96 [1–96] using DMF
29 Dispense System Fluid Dualarms__1+4*1250 µl to RB1__1to96 [1–96]
30 Mix "RB1__1to96" for 5.00 minutes at 750 rpm(s)
31 Wait for 25.000 minute(s)
32 Repeat from step 30, 9 times
33 Empty RB1__1to96 for 3.000 minute(s)
34 Pause
35 Goto ChemFile COUPLING.CHM, line 1
36 Pause
37
38 Goto ChemFile WASH__DMF.CHM, line 1
39 Goto ChemFile DEPROTEC.CHM, line 1
50 Goto ChemFile WASH__DMF.CHM, line 1
41
42 REM Her starter anden aminosyre-kobling
43 Dispense Sequence C:\ACT\displist\B1.DSP with 500 µl to RB1__1to96 rack using DMF 44 Dispense Sequence C:\ACT\displist\B2.DSP with 500 μl to RB1__1to96 rack using DMF
45 Mix "RB1__1to96" for 1.00 minutes at 600 rpm(s)
46 Transfer 500 μl from REAGENT_3[1] (HATU) to RB1__1to96 [1–96] using DMF
47 Transfer 68 μl from Monomer 1to36 [10] (DIEA) to RB1__1to96 [1–96] using DMF
48 Dispense System Fluid Dualarms_1+4*500 μl to RB1__1to96 [1–96]
49 Mix "RB1__1to96" for 5.00 minutes at 750 rpm(s)
50 Wait for 25.000 minute(s)
51 Repeat from step 49, 31 times
52
53 Empty RB1 1to96 for 3.000 minute(s)
54 Goto ChemFile WASH_DMF.CHM, line 1
55
56 REM Anden AA. Anden kobling
57 Dispense Sequence C:\ACT\displist\B1.DSP with 125 μl to RB1__1to96 rack using DMF
58 Dispense Sequence C:\ACT\displist\B2.DSP with 125 μl to RB1__1to96 rack using DMF
59 Mix "RB1__1to96" for 1.00 minutes at 600 rpm(s)
60 Transfer 125 μl from REAGENT_3[1] (HATU) to RB1__1to96 [1–96] using DMF
61 Transfer 20 μl from Monomer1to36 [10] (DIEA) to RB1__1to96 [1–96] using DMF
62 Dispense System Fluid Dualarms_1+4*1250 μl to RB1__1to96 [1–96]
63 Mix "RB1__1to96" for 5.00 minutes at 750 rpm(s)
64 Wait for 25.000 minute(s)
65 Repeat from step 63, 9 times
66 Empty RB1 1to96 for 3.000 minute(s)
67 Goto ChemFile WASH_DMF.CHM, line 1
68 Goto ChemFile DEPROTEC.CHM, line 1
69 Goto ChemFile WASH_DMF.CHM, line 1
70
71 Pause
72
73 REM N-terminalkobling starter her
74 Dispense Sequence C:\ACT\displist\N1N2N3N4.DSP with 500 μl to RB1__1to96 rack using DMF
75 Mix "RB1__1to96" for 1.00 minutes at 600 rpm(s)
76 Transfer 500 μl from REAGENT_3[1] (HATU) to RB1__1to96 [1–96] using DMF
77 Transfer 68 μl from Monomer1to36 [10] (DIEA) to RB1__1to96 [1–96] using DMF
78 Dispense System Fluid Dualarms_1+4*500 μl to RB1__1to96 [1–96]
79 Mix "RB1__1to96" for 5.00 minutes at 750 rpm(s)
80 Wait for 25.000 minute(s)
81 Repeat from step 79, 20 times
82 Empty RB1 1to96 for 3.000 minute(s)
83 Goto ChemFile WASH_DMF.CHM, line 1
84
85 REM N-terminal. Anden kobling
86 Dispense Sequence C:\ACT\displist\N1N2N3N4.DSP with 125 μl to RB1__1to96 rack using DMF
87 Mix "RB1__1to96" for 1.00 minutes at 600 rpm(s)
88 Transfer 125 μl from REAGENT_3[1] (HATU) to RB1__1to96 [1–96] using DMF
89 Transfer 20 μl from Monomer1to36 [10] (DIEA) to RB1__1to96 [1–96] using DMF
90 Dispense System Fluid Dualarms_1+4*1250 μl to RB1__1to96 [1–96]
91 Mix "RB1__1to96" for 5.00 minutes at 750 rpm(s)
92 Wait for 25.000 minute(s)
93 Repeat from step 91, 9 times
94 Empty RB1 1to96 for 3.000 minute(s)
95 Goto ChemFile WASH_DMF.CHM, line 1
96 Goto ChemFile DEPROTEC.CHM, line 1
97 Goto ChemFile WASH_DMF.CHM, line 1
98

The building blocks were selected from the following groups:

[Building block 1]: N-Me-PAL, N-Phenethyl-PAL, N-(4-Pyridyl)ethyl-PAL, N-((S)-2-Hydroxypropyl)-PAL, N-(2,2-Dimethyl-3-hydroxypropyl)-PAL and N-((1-Methylpyrrolidin-2-yl)ethyl)-PAL.

[Building block 2]: Fmoc-N-Me-D-Phe(4-F)-OH and Fmoc-N-Me-D-Phe(3,4-F,F)-OH.

[Building block 3]: Fmoc-N-Me-D-Nal-OH and Fmoc-N-Me-D-Phe(4-Phe)-OH.

[Building block 4]: Boc-AMH-OH, Boc-ACBB-OH, Boc-SPMA-OH and Boc-AEB-OH.

See Table 1

Examples 254–353

The following 100 compounds were synthesized in parallel as individual entities analogously to example 158 on an Advanced ChemTech Model 384 HTS using the following ChemFiles to control the operation of the synthesizer (Advanced ChemTech Operator's Manual, version 1.2 July 1996, pp. 4–13):
ChemFile C:\ACT\CHEMFILE\3PETER.CHM Page 1
1 Flush Arm1 with DMF and NMP, Arm2 with DCM and DMF4
2 Empty RB2__1to96 for 3.000 minute(s)
3
4 Dispense System Fluid Dualarms_1 +4*1000 μl to RB2__1to96[1–96]
5 Mix "RB2__1to96" for 2.00 minutes at 700 rpm(s)
6 Wait for 28.000 minute(s)
7 Empty RB2__1to96 for 3.000 minute(s)
8
9 REM Syntesestart her. Aminosyre 1
10 Dispense Sequence C:\ACT\displist\A1.DSP with 500 μl to RB2__1to96 rack using DMF
11 Dispense Sequence C:\ACT\displist\A2.DSP with 500 μl to RB2__1to96 rack using DMF
12 Mix "RB2__1to96" for 1.00 minutes at 600 rpm(s)
13 Transfer 500 μl from REAGENT_3[1] (HATU) to RB2__1to96 [1–96] using DMF
14 Transfer 68 μl from Monomer1to36 [10] (DIEA) to RB2__1to96 [1–96] using DMF
15 Dispense System Fluid Dualarms_1+4*500 μl to RB2__1to96 [1–96]
16 Mix "RB2__1to96" for 5.00 minutes at 750 rpm(s)
17 Wait for 25.000 minute(s)
18 Repeat from step 16, 31 times
19 Pause
20 Empty RB2__1to96 for 3.000 minute(s)
21 Goto ChemFile WASH_DMF.CHM, line 1
23 REM Anden kobling 1ste M
24 Dispense Sequence C:\ACT\displist\A1.DSP with 125 μl to RB2__1to96 rack using DMF
25 Dispense Sequence C:\ACT\displist\A2.DSP with 125 μl to RB2__1to96 rack using DMF
26 Mix "RB2__1to96" for 1.00 minutes at 600 rpm(s)
27 Transfer 125 μl from REAGENT_3[1] (HATU) to RB2__1to96 [1–96] using DMF
28 Transfer 20 μl from Monomer1to36 [10] (DIEA) to RB2 1to96 [1–96] using DMF
29 Dispense System Fluid Dualarms_1+4*1250 μl to RB2__1to96 [1–96]

30 Mix "RB2_1to96" for 5.00 minutes at 750 rpm(s)
31 Wait for 25.000 minute(s)
32 Repeat from step 30, 7 times
33 Empty RB2_1to96 for 3.000 minute(s)
34 Goto ChemFile WASH_DMF.CHM, line 1
35 Pause
36
37 Goto ChemFile DEPROTEC.CHM, line 1
38 Goto ChemFile WASH_DMF.CHM, line 1
40 REM Her starter anden aminosyre-kobling
41 Dispense Sequence C:\ACT\displist\B1.DSP with 500 µl to RB2_1to96 rack using DMF
42 Dispense Sequence C:\ACT\displist\B2.DSP with 500 µl to RB2_1to96 rack using DMF
43 Mix "RB2_1to96" for 1.00 minutes at 600 rpm(s)
44 Transfer 500 µl from REAGENT_3[1] (HATU) to RB2_1to96 [1–96] using DMF
45 Transfer 68 µl from Monomer1to36 [10] (DIEA) to RB2_1to96 [1–96] using DMF
46 Dispense System Fluid Dualarms_1+4* 500 µl to RB2_1to96 [1–96]
47 Mix "RB2_1to96" for 5.00 minutes at 750 rpm(s)
48 Wait for 25.000 minute(s)
49 Repeat from step 47, 31 times
50
51 Empty RB2_1to96 for 3.000 minute(s)
52 Goto ChemFile WASH_DMF.CHM, line 1
54 REM Anden AA. Anden kobling
55 Dispense Sequence C:\ACT\displist\B1.DSP with 125 µl to RB2_1to96 rack using DMF
56 Dispense Sequence C:\ACT\displist\B2.DSP with 125 µl to RB2_1to96 rack using DMF
57 Mix "RB2_1to96" for 1.00 minutes at 600 rpm(s)
58 Transfer 125 µl from REAGENT_3[1] (HATU) to RB2_1to96 [1–96] using DMF
59 Transfer 20 µl from Monomer1to36 [10] (DIEA) to RB2_1to96 [1–96] using DMF
60 Dispense System Fluid Dualarms_1+4*1250 µl to RB2_1to96 [1–96]
61 Mix "RB2_1to96" for 5.00 minutes at 750 rpm(s)
62 Wait for 25.000 minute(s)
63 Repeat from step 61, 7 times
64 Empty RB2_1to96 for 3.000 minute(s)
65 Goto ChemFile WASH_DMF.CHM, line 1
66 Pause
67
68 Goto ChemFile DEPROTEC.CHM, line 1
69 Goto ChemFile WASH_DMF.CHM, line 1
70
71 Pause
72
73 REM N-terminalkobling starter her
74 Dispense Sequence C:\ACT\displist\N_56789.DSP with 500 µl to RB2_1to96 rack using DMF
75 Mix "RB2_1to96" for 1.00 minutes at 600 rpm(s)
76 Transfer 500 µl from REAGENT_3[1] (HATU) to RB2_1to96t[1–96] using DMF
77 Transfer 68 µl from Monomer1to36 [10] (DIEA) to RB2_1to96 [1–96] using DMF
78 Dispense System Fluid Dualarms_1+4*500 µl to RB2_1to96 [1–96]
79 Mix "RB2_1to96" for 5.00 minutes at 750 rpm(s)
80 Wait for 25.000 minute(s)
81 Repeat from step 79, 20 times
82 Empty RB2 1to96 for 3.000 minute(s)
83 Goto ChemFile WASH_DMF.CHM, line 1
84
85 REM N-terminal. Anden kobling
86 Dispense Sequence C:\ACT\displist\N_56789.DSP with 125 µl to RB2_1to96 rack using DMF
87 Mix "RB2_1to96" for 1.00 minutes at 600 rpm(s)
88 Transfer 125 µl from REAGENT_3[1] (HATU) to RB2_1to96 [1–96] using DMF
89 Transfer 20 µl from Monomer1to36 [10] (DIEA) to RB2_1to96 [1–96] using DMF
90 Dispense System Fluid Dualarms_1+4*1250 µl to RB2_1to96 [1–96]
91 Mix "RB2_1to96" for 5.00 minutes at 750 rpm(s)
92 Wait for 25.000 minute(s)
93 Repeat from step 91, 7 times
94 Empty RB2 1to96 for 3.000 minute(s)
95 Goto ChemFile WASH_DMF.CHM, line 1
96 Goto ChemFile WASH_DCM.CHM, line 1
97

The building blocks were selected from the following groups:

[Building block 1]: N-Phenethyl-PAL, N-(4-Pyridyl)ethyl-PAL, N-((S)-2-Hydroxypropyl)-PAL, N-(2,2-Dimethyl-3-hydroxypropyl)-PAL and N-((1-Methylpyrrolidin-2-yl)ethyl)-PAL.

[Building block 2]: Fmoc-N-Me-D-Phe(4-F)-OH and Fmoc-N-Me-D-Phe(3,4-F,F)-OH.

[Building block 3]: Fmoc-N-Me-D-Nal-OH and Fmoc-N-Me-D-Phe(4-Phe)-OH.

[Building block 4]: Boc-AMB-OH, Boc-ADH-OH, Boc-MAMH-OH, Boc-RPMA-OH and Boc-AEHA-OH.

See Table 2

Examples 354–533

The following 180 compounds were synthesized in parallel as individual entities analogously to example 158 on an Advanced ChemTech Model 384 HTS using the following ChemFiles to control the operation of the synthesizer (Advanced ChemTech Operator's Manual, version 1.2 July 1996, pp. 4–13):

ChemFile C:\ACT\CHEMFILE\4PETER.CHM Page 1
1 Flush Arm1 with DMF and THF, Arm2 with DCM and DMF4
2 Empty RB3_1to96 for 3.000 minute(s)
3 Empty RB4_1to96 for 3.000 minute(s)
4
5 Dispense System Fluid Dualarms_1+4*1500 µl to RB3_1to96[1–96]
6 Mix "RB3_1to96" for 30 seconds at 300 rpm(s)
7 Dispense System Fluid Dualarms_1+4*1500 µl to RB4_1to96[1–96]
8 Mix "RB4_1to96" for 30 seconds at 300 rpm(s)
9 Empty RB3_1to96 for 3.000 minute(s)
10 Empty RB3_1to96 for 3.000 minute(s)
11
12 REM!! SYNTESESTART HER!!
13
14 REM Aminosyre 1
15 Dispense Sequence C:\ACT\displist\A3_3.DSP with 500 µl to RB3_1to96 rack using DMF
16 Dispense Sequence C:\ACT\displist\A4_3.DSP with 500 µl to RB3_1to96 rack using DFM
17 Mix "RB3_1to96" for 30 seconds at 300 rpm(s)
18 Dispense Sequence C:\ACT\displist\A1A2_4.DSP with 500 µl to RB3_1to96 rack using DMF
19 Dispense Sequence C:\ACT\displist\A3_4.DSP with 500 µl to RB4_1to96 rack using DMF
20 Dispense Sequence C:\ACT\displist\A4_4.DSP with 500 µl to RB4_1to96 rack using DMF 21 Mix "RB4_1to96" for 30 seconds at 300 rpm(s)
22 Transfer 500 µl from REAGENT_3[1] (HATU) to RB3_1to96 [1–96] using DMF
23 Mix "RB3_1to96" for 30 seconds at 300 rpm(s)
24 Transfer 500 µl from REAGENT_3 [1] (HATU) to RB4_1to96 [1–96] using DMF4
25 Mix "RB4_1to96" for 30 seconds at 300 rpm(s)
26 Dispense System Fluid Dualarms 1+4*500 µl to RB3_1to96 [1–96]
27 Dispense System Fluid Dualarms_1+4*500 µl to RB4_1to96 [1–96]
28 Transfer 68 µl from Monomer1to36 [16] (DIEA) to RB3_1to96 [1–96] using DMF
29 Mix "RB3_1to96" for 1.00 minutes at 600 rpm(s)
30 Transfer 68 µl from Monomer1to36 [16] (DIEA) to RB4_1to96 [1–96] using DMF4
31 Start mixing "RB3_1to96" for 5.00 minutes at 600 rpm(s)
32 Mix "RB4_1to96" for 5.00 minutes at 600 rpm(s)
33 Wait for 25.000 minute(s)
34 Repeat from step 31, 31 times
35 Empty RB3_1to96 for 3.000 minute(s)
36 Empty RB4_1to96 for 3.000 minute(s)
37 Goto ChemFile WASH_DMF.CHM, line 1
38
39 REM Anden kobling 1ste AA
40 Dispense Sequence C:\ACT\displist\A3_3.DSP with 125 µl to RB3_1to96 rack using DMF
41 Dispense Sequence C:\ACT\displist\A43.DSP with 125 µl to RB3_1to96 rack using DMF
42 Mix "RB3_1to96" for 30 seconds at 300 rpm(s)
43 Dispense Sequence C:\ACT\displist\A1A2_4.DSP with 125 µl to RB3_1to96 rack using DMF
44 Dispense Sequence C:\ACT\Rdisplist\A3_4.DSP with 125 µl to RB3_1to96 rack using DMF
45 Dispense Sequence C:\ACT\displist\A4_4.DSP with 125 µl to RB4_1to96 rack using DMF
46 Mix "RB4_1to96" for 30 seconds at 300 rpm(s)
47 Transfer 125 µl from REAGENT_3[1] (HATU) to RB3_1to96 [1–96] using DMF
48 Mix "RB3_1to96" for 30 seconds at 300 rpm(s)
49 Transfer 125 µl from REAGENT_3[1] (HATU) to RB4_1to96 [1–96] using DMF4
50 Mix "RB3_1to96" for 30 seconds at 300 rpm(s)
51 Dispense System Fluid Dualarms_1+4*1250 µl to RB3_1to96 [1–96]
52 Dispense System Fluid Dualarms_1+4*1250 µl to RB4_1to96 [1–96]
53 Transfer 20 µl from Monomer1to36 [16] (DIEA) to RB3_1to96 [1–96] using DMF
54 Mix "RB3_1to96" for 1.00 minutes at 600 rpm(s)
55 Transfer 20 µl from Monomer1to36 [16] (DIEA) to RB4_1to96 [1–96] using DMF4
56 Start mixing "RB3_1to96" for 5.00 minutes at 600 rpm(s)
57 Mix "RB4_1to96" for 5.00 minutes at 600 rpm(s)
58 Wait for 25.000 minute(s)
59 Repeat from step 56, 7 times
60 Empty RB3_1to96 for 3.000 minute(s)
61 Empty RB4_1to96 for 3.000 minute(s)
62
63 Goto ChemFile WASH_DMF.CHM, line 1
64 Goto ChemFile DEPROTEC.CHM, line 1
65 Goto ChemFile WASH_DMF.CHM, line 1
66
67 Pause
68
69 REM Start anden M-kobling
70 Dispense Sequence C:\ACT\displist\B1_3.DSP with 500 µl to RB3_1to96 rack using DMF
71 Dispense Sequence C:\ACT\displist\B2_3.DSP with 500 µl to RB3_1to96 rack using DMF
72 Mix "RB3_1to96" for 30 seconds at 300 rpm(s)
73 Dispense Sequence C:\ACT\displist\B1_4.DSP with 500 µl to RB4_1to96 rack using DMF
74 Dispense Sequence C:\ACT\displist\B2_4.DSP with 500 µl to RB4_1to96 rack using DMF
75 Mix "RB4_1to96" for 30 seconds at 300 rpm(s)
76 Transfer 500 µl from REAGENT_3[1] (HATU) to RB3_1to96 [1–96] using DMF
77 Mix "RB3_1to96" for 30 seconds at 300 rpm(s)
78 Transfer 500 µl from REAGENT_3[1] (HATU) to RB4_1to96 [1–96] using DMF4
79 Mix "RB4_1to96" for 30 seconds at 300 rpm(s)
80 Dispense System Fluid Dualarms_1+4*500 µl to RB3_1to96 [1–96]
81 Dispense System Fluid Dualarms_1+4*500 µl to RB4_1to96 [1–96]
82 Transfer 68 µl from Monomer1to36 [16] (DIEA) to RB3_1to96 [1–96] using DMF
83 Mix "RB3_1to96" for 1.00 minutes at 600 rpm(s)
84 Transfer 68 µl from Monomer1to36 [16] (DIEA) to RB4_1to96 [1–96] using DMF4
85 Start mixing "RB3_1to96" for 5.00 minutes at 600 rpm(s)
86 Mix "RB4_1to96" for 5.00 minutes at 600 rpm(s)
87 Wait for 25.000 minute(s)
88 Repeat from step 85, 31 times
89 Empty RB3_1to96 for 3.000 minute(s)
90 Empty RB3_1to96 for 3.000 minute(s)
91 Goto ChemFile WASH_DMF.CHM, line 1
92
93 REM Anden kobling anden AA
94 Dispense Sequence C:\ACT\displist\B1_3.DSP with 125 µl to RB3_1to96 rack using DMF
95 Dispense Sequence C:\ACT\displiståB2_3.DSP with 125 µl to RB3_1to96 rack using DMF
96 Mix "RB3_1to96" for 30 seconds at 300 rpm(s)
97 Dispense Sequence C:\ACT\displist\B1_4.DSP with 125 µl to RB3_1to96 rack using DMF
98 Dispense Sequence C:\ACT\displist\B2_4.DSP with 125 µl to RB3_1to96 rack using DMF
99 Mix "RB4_1to96" for 30 seconds at 300 rpm(s)
100 Transfer 125 µl from REAGENT_3[1] (HATU) to RB3_1to96 [1–96] using DMF
101 Mix "RB3_1to96" for 30 seconds at 300 rpm(s)
102 Transfer 125 µl from REAGENT_3[1] (HATU) to RB4_1to96 [1–96] using DMF4
103 Mix "RB4_1to96" for 30 seconds at 300 rpm(s)
104 Dispense System Fluid Dualarms_1+4*1250 µl to RB3_1to96 [1–96]
105 Dispense System Fluid Dualarms_1+4*1250 µl to RB4_1to96 [1–96]
106 Transfer 20 µl from Monomer1to36 [16] (DIEA) to RB3_1to96 [1–96] using DMF
107 Mix "RB3_1to96" for 1.00 minutes at 600 rpm(s)
108 Transfer 20 µl from Monomer1to36 [16] (DIEA) to RB4_1to96 [1–96] using DMF
109 Start mixing "RB3_1to96" for 5.00 minutes at 600 rpm(s)
110 Mix "RB4_1to96" for 5.00 minutes at 600 rpm(s)
111 Wait for 25.000 minute(s)
112 Repeat from step 109, 7 times
113 Empty RB3_1to96 for 3.000 minute(s)

114 Empty RB4__1to96 for 3.000 minute(s)
115
116 Goto ChemFile WASH_DMF.CHM, line 1
117 Goto ChemFile DEPROTEC.CHM, line 1
118 Goto ChemFile WASH_DMF.CHM, line 1
119
120 Pause
121
122 REM N-terminal kobling start
123 Dispense Sequence C:\ACT\displist\N__3.DSP with 500 μl to RB3__1to96 rack using DMF
124 Mix "RB3__1to96" for 30 seconds at 300 rpm(s)
125 Dispense Sequence C:\ACT\displist\N__4.DSP with 500 μl to RB4__1to96 rack using DMF
126 Mix "RB4__1to96" for 30 seconds at 300 rpm(s)
127 Transfer 500 μl from REAGENT_3[1] (HATU) to RB3__1to96b[1–96] using DMF
128 Mix "RB3__1to96" for 30 seconds at 300 rpm(s)
129 Transfer 500 μl from REAGENT_3[1] (HATU) to RB4__1to96 [1–96] using DMF4
130 Mix "RB4__1to96" for 30 seconds at 300 rpm(s)
131 Dispense System Fluid Dualarms__1+4*500 μl to RB3__1to96 [1–96]
132 Dispense System Fluid Dualarms__1+4*500 μl to RB4__1to96 [1–96]
133 Transfer 68 μl from Monomer1to36 [16] (DIEA) to RB3__1to96 [1–96] using DMF
134 Mix "RB3__1to96" for 1.00 minutes at 600 rpm(s)
135 Transfer 68 μl from Monomer1to36 [16] (DIEA) to RB4__1to96 [1–96] using DMF4
136 Start mixing "RB3__1to96" for 5.00 minutes at 600 rpm(s)
137 Mix "RB4__1to96" for 5.00 minutes at 600 rpm(s)
138 Wait for 25.000 minute(s)
139 Repeat from step 136, 31 times
140 Empty RB3__1to96 for 3.000 minute(s)
141 Empty RB4__1to96 for 3.000 minute(s)
142 Goto ChemFile WASH_DMF.CHM, line 1
143
144 REM
145 Dispense Sequence C:\ACT\displist\N__3.DSP with 125 μl to RB_3__1to96 rack using DMF
146 Mix "RB3__1to96" for 30 seconds at 300 rpm(s)
147 Dispense Sequence C:\ACT\displist\N__4.DSP with 125 μl to RB4__1to96 rack using DMF
148 Mix "RB4__1to96" for 30 seconds at 300 rpm(s)
149 Transfer 125 μl from REAGENT_3[1] (HATU) to RB_3__1to96 [1–96] using DMF
150 Mix "RB3__1to96" for 30 seconds at 300 rpm(s)
151 Transfer 125 μl from REAGENT_3[1] (HATU) to RB4__1to96 [1–96] using DMF4
152 Mix "RB4__1to96" for 30 seconds at 300 rpm(s)
153 Dispense System Fluid Dualarms__1+4*1250 μl to RB3__1to96 [1–96]
154 Dispense System Fluid Dualarms__1+4*1250 μl to RB4__1to96 [1–96]
155 Transfer 20 μl from Monomer1to36 [16] (DIEA) to RB3__1to96 [1–96] using DMF
156 Mix "RB3__1to96" for 1.00 minutes at 600 rpm(s)
157 Transfer 20 μl from Monomer1to36 [16] (DIEA) to RB4__1to96 [1–96] using DMF4
158 Start mixing "RB3__1to96" for 5.00 minutes at 600 rpm(s)
159 Mix "RB4__1to96" for 5.00 minutes at 600 rpm(s)
160 Wait for 25.000 minute(s)
161 Repeat from step 158, 7 times
162 Empty RB3__1to96 for 3.000 minute(s)
163 Empty RB4__1to96 for 3.000 minute(s)
164 Goto ChemFile WASH_DMF.CHM, line 1
165

The building blocks were selected from the following groups:

[Building block 1]: N-Phenethyl-PAL, N-(4-Pyridyl)ethyl-PAL, N-((S)-2-Hydroxypropyl)-PAL, N-(2,2-Dimethyl-3-hydroxypropyl)-PAL and N-((1-Methylpyrrolidin-2-yl)ethyl)-PAL.

[Building block 2]: Fmoc-N-Me-D-Phe-OH and Fmoc-N-Me-D-ThiAla-OH.

[Building block 3]: Fmoc-N-Me-D-Nal-OH and Fmoc-N-Me-D-Phe(4-Phe)-OH.

[Building block 4]: Boc-AMH-OH, Boc-ACBMA-OH, Boc-RPMA-OH, Boc-AEB-OH, Boc-AMB-OH, Boc-ADH-OH, Boc-MAMH-OH, Boc-RPMA-OH and Boc-AEHA-OH.

See Table 3

TABLE 1

| Example | Structure | MW | HPLC | LCMS |
|---|---|---|---|---|
| 158 | 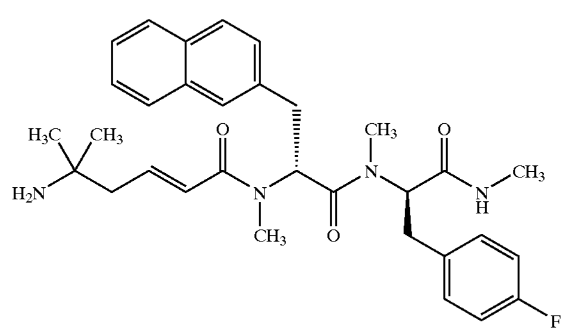 | 546.7 | 9.91 | 546.8 |

TABLE 1-continued

| Example | Structure | MW | HPLC | LCMS |
|---------|-----------|------|-------|-------|
| 159 | 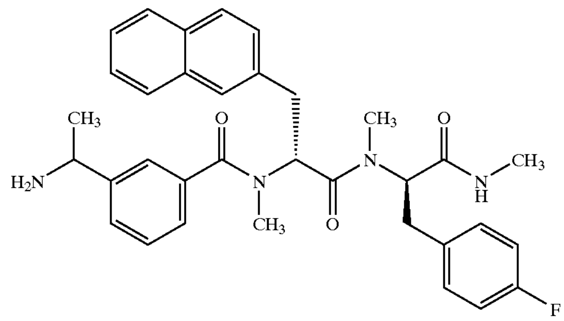 | 568.7 | 9.68 | 569.0 |
| 160 | 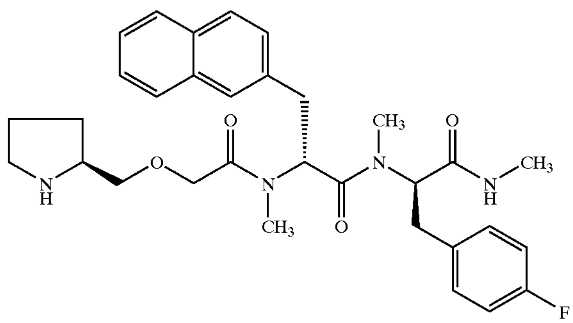 | 562.7 | 9.38 | 563.0 |
| 161 | 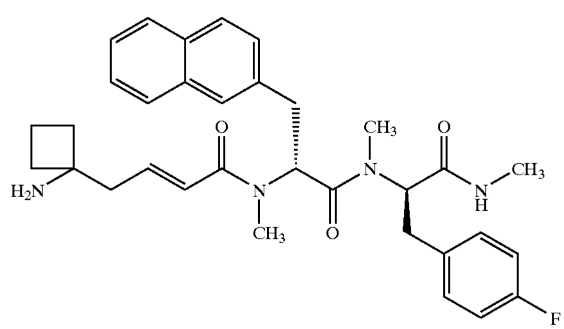 | 558.7 | 9.63 | 559.0 |
| 162 | 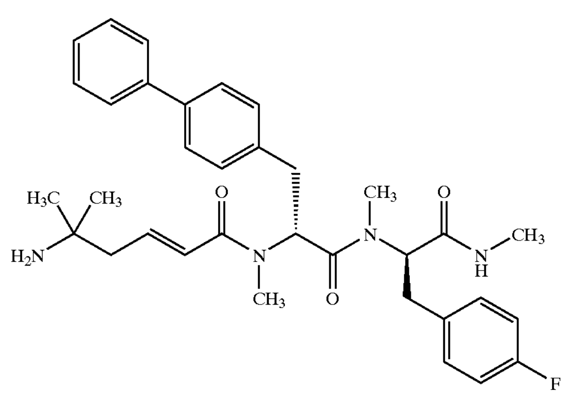 | 572.7 | 10.11 | 573.0 |

TABLE 1-continued

| Example | Structure | MW | HPLC | LCMS |
|---|---|---|---|---|
| 163 | 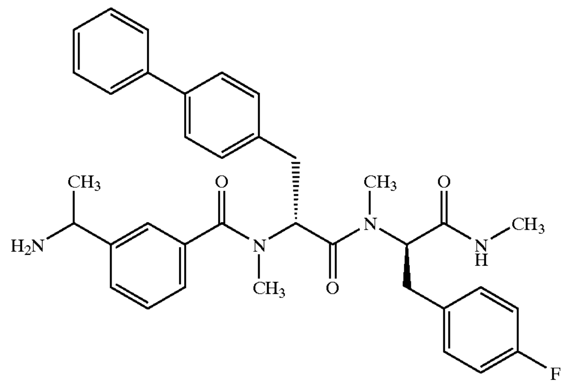 | 594.7 | | |
| 164 | 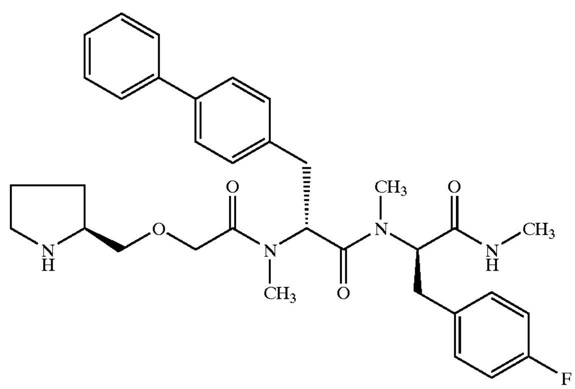 | 588.7 | 10.02 | 589.2 |
| 165 | 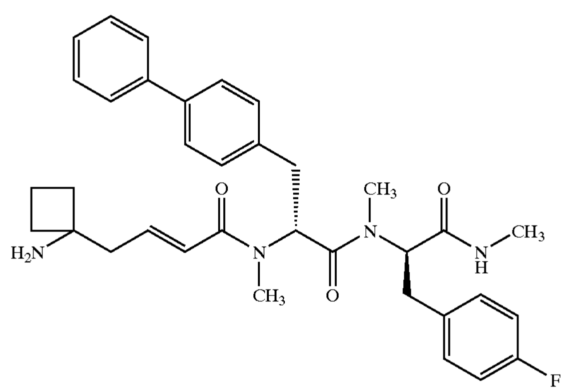 | 584.7 | | |
| 166 | 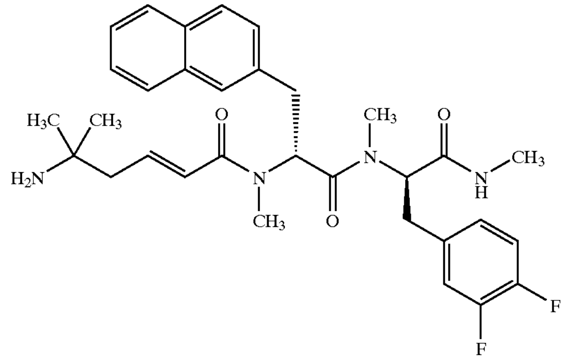 | 564.7 | 9.68 | 565.0 |

TABLE 1-continued
| Example | Structure | MW | HPLC | LCMS |
|---|---|---|---|---|
| 167 | 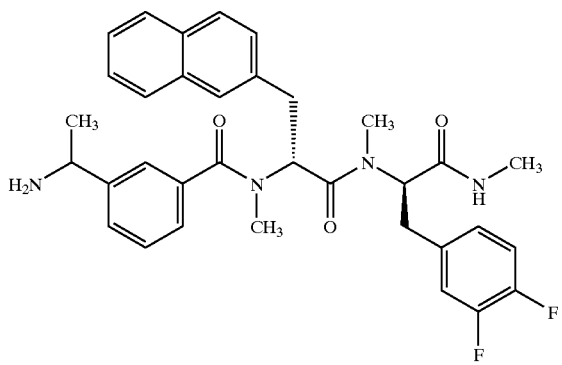 | 586.7 | 9.83 | 587.2 |
| 168 | 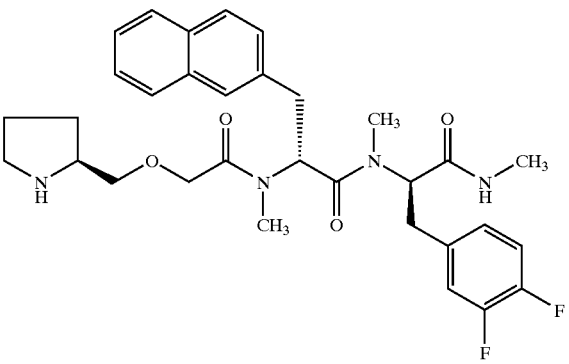 | 580.7 | 9.61 | 581.0 |
| 169 | 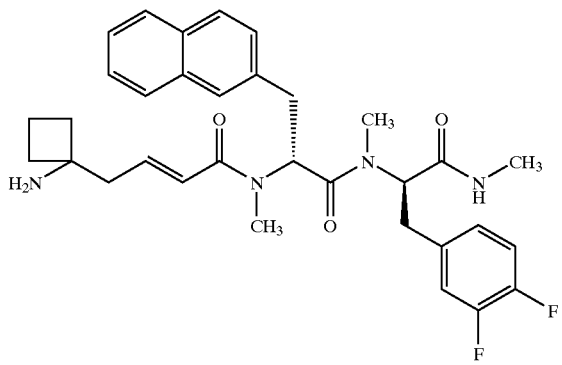 | 576.7 | | 576.8 |
| 170 | 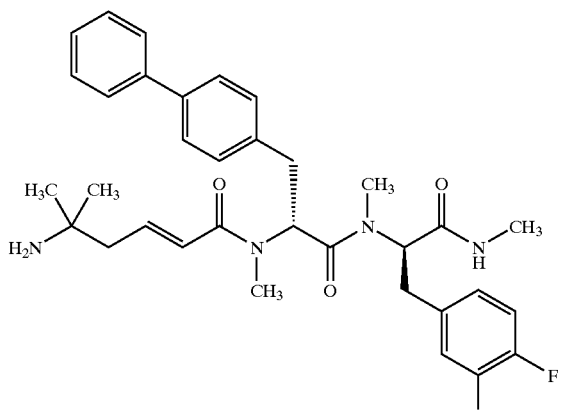 | 590.7 | | |

TABLE 1-continued
| Example | Structure | MW | HPLC | LCMS |
|---|---|---|---|---|
| 171 | 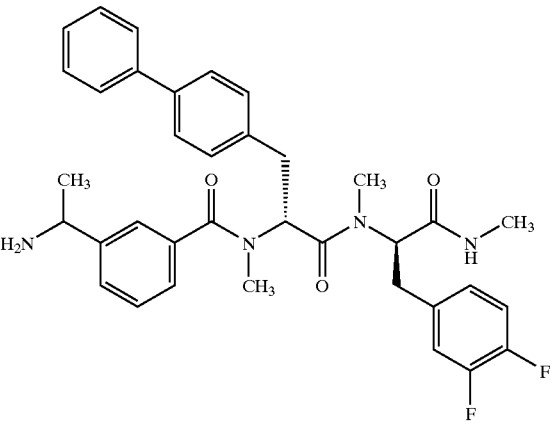 | 612.7 | 10.49 | 613.2 |
| 172 | 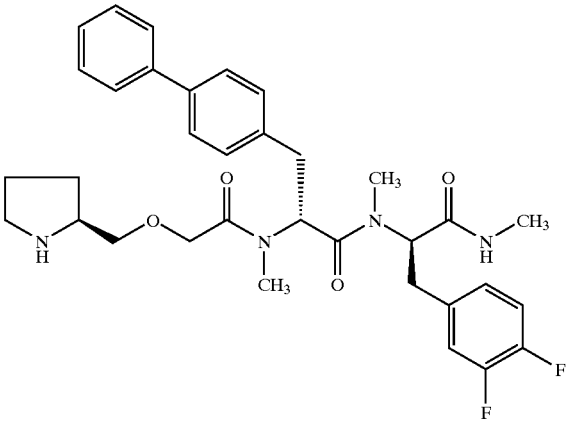 | 606.7 | 10.26 | 607.0 |
| 173 | 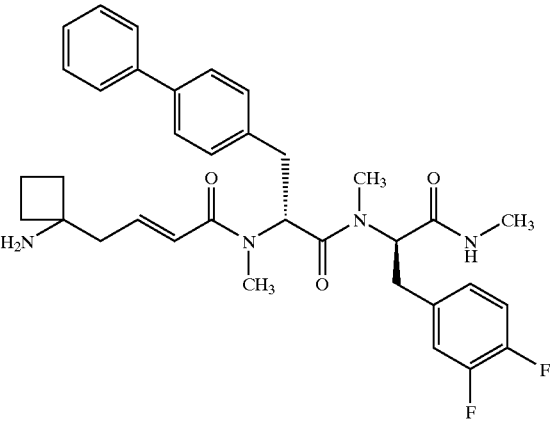 | 602.7 | 10.50 | 603.0 |

TABLE 1-continued
| Example | Structure | MW | HPLC | LCMS |
|---|---|---|---|---|
| 174 | 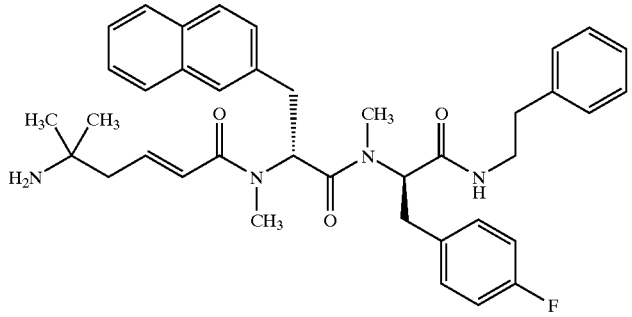 | 636.8 | 10.73 | 637.2 |
| 175 | 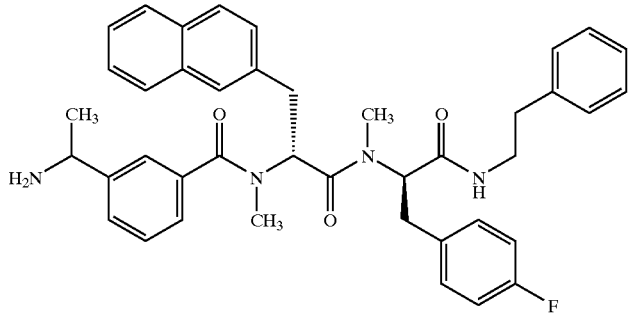 | 658.8 | 10.97 | 659.2 |
| 176 | 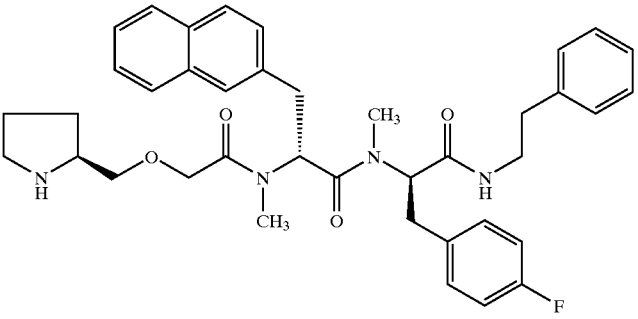 | 652.8 | 11.07 | 653.2 |
| 177 | 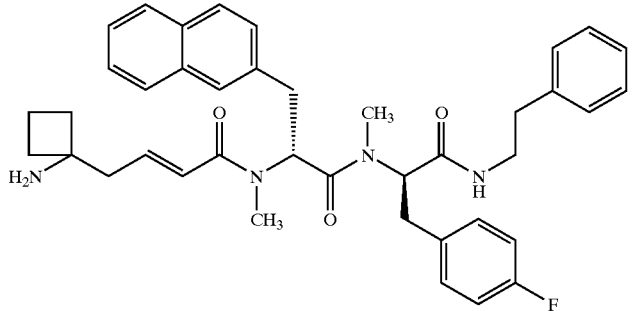 | 648.8 | | |

TABLE 1-continued

| Example | Structure | MW | HPLC | LCMS |
|---|---|---|---|---|
| 178 | 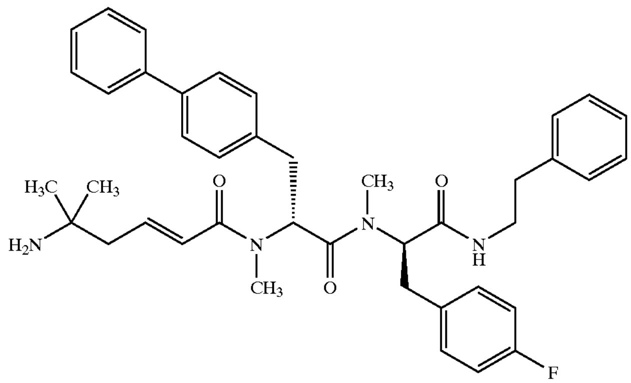 | 662.9 | 11.56 | 663.2 |
| 179 | 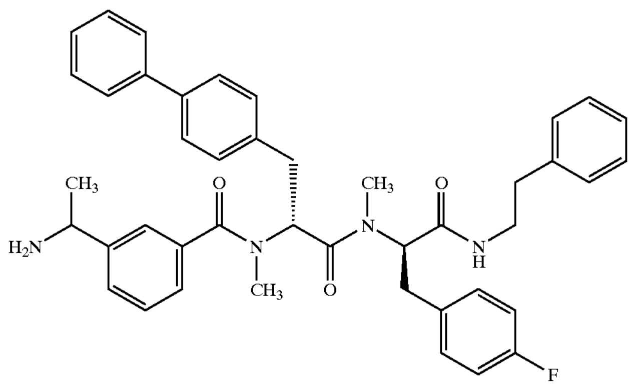 | 684.9 | 11.81 | 685.0 |
| 180 | 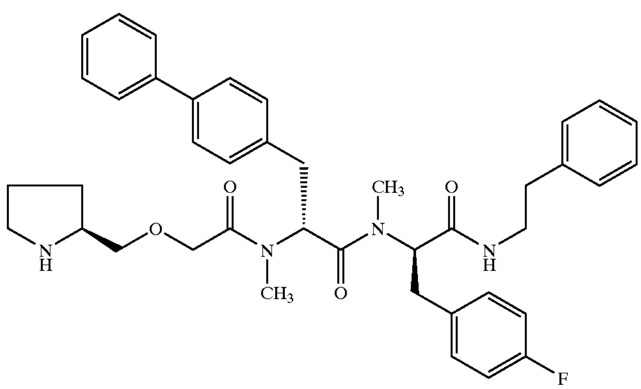 | 678.9 | 11.60 | 679.0 |
| 181 | 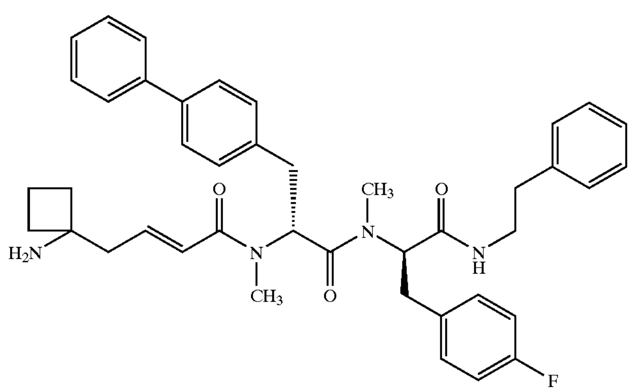 | 674.9 | 11.95 | 675.2 |

TABLE 1-continued
| Example | Structure | MW | HPLC | LCMS |
|---|---|---|---|---|
| 182 | 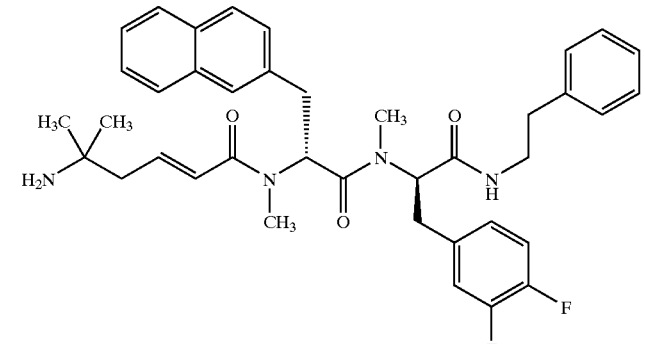 | 654.8 | 11.28 | 655.0 |
| 183 | 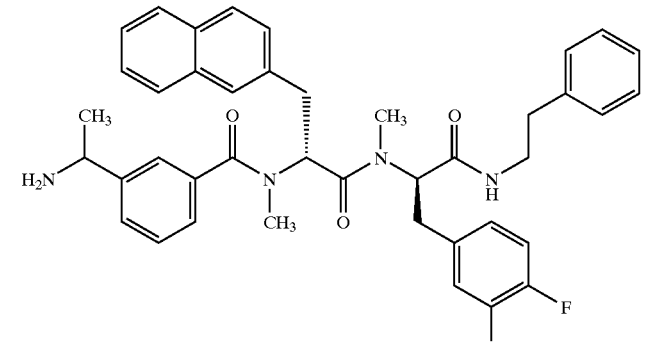 | 676.8 | 11.40 | 677.2 |
| 184 | 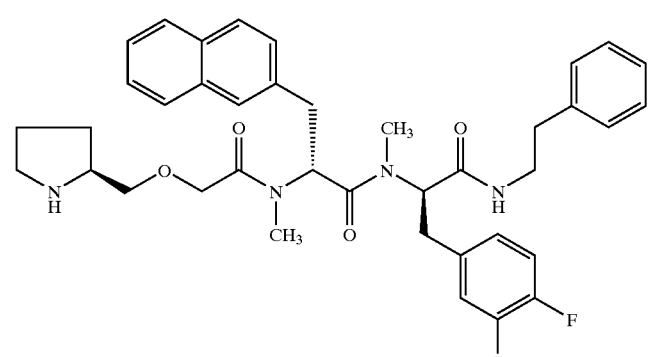 | 670.8 | 11.27 | 672.2 |
| 185 | 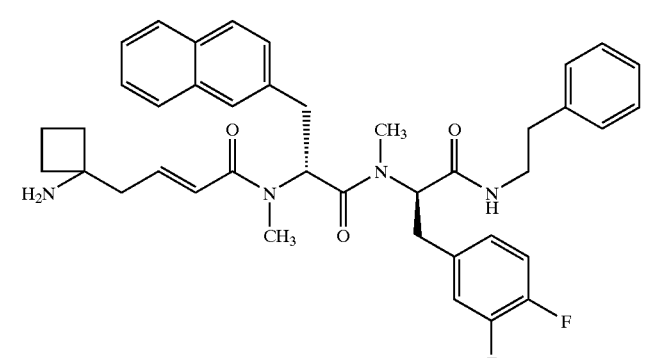 | 666.8 | 11.44 | 667.2 |

TABLE 1-continued

| Example | Structure | MW | HPLC | LCMS |
|---|---|---|---|---|
| 186 | 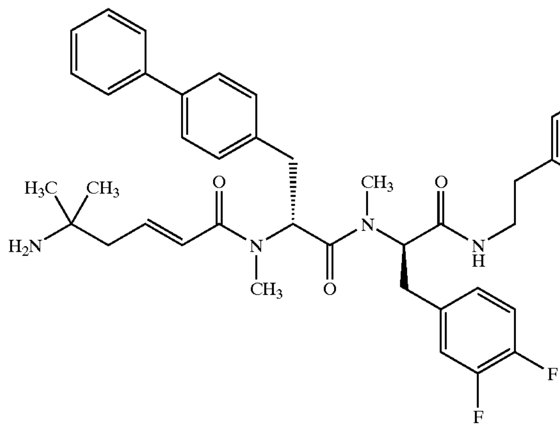 | 680.8 | 11.80 | 681.0 |
| 187 | 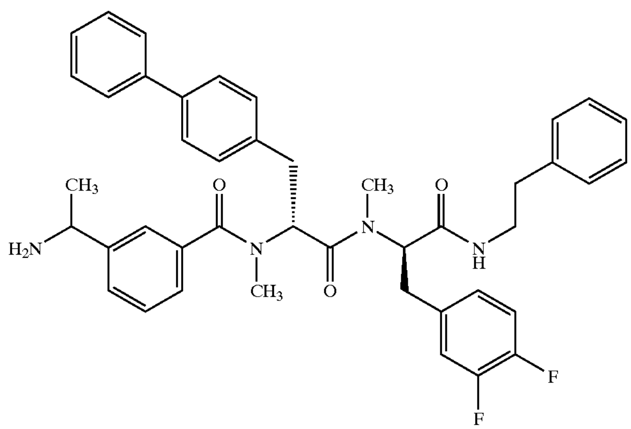 | 702.9 | 12.10 | 702.8 |
| 188 | 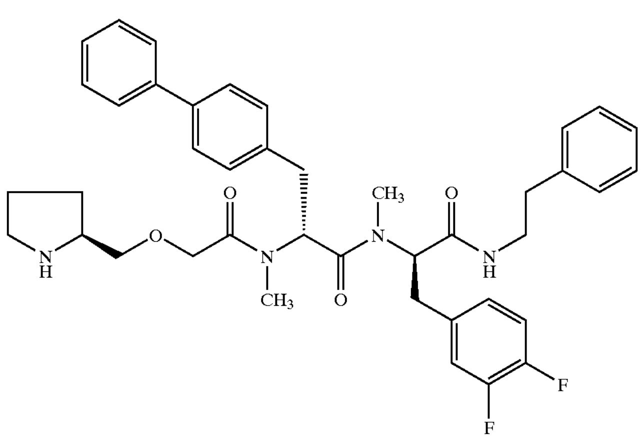 | 696.8 | 11.97 | 697.0 |

TABLE 1-continued
| Example | Structure | MW | HPLC | LCMS |
|---|---|---|---|---|
| 189 | 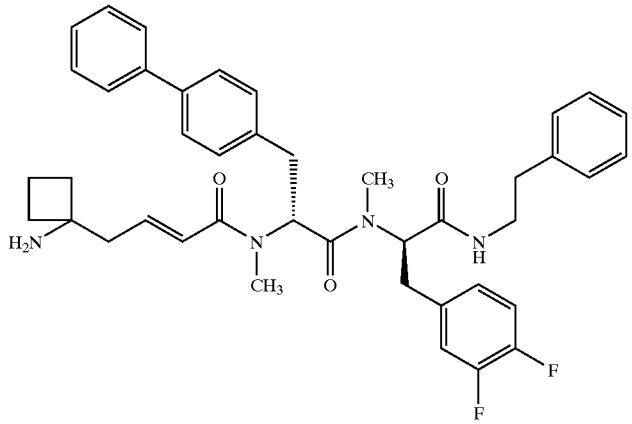 | 692.9 | | |
| 190 | 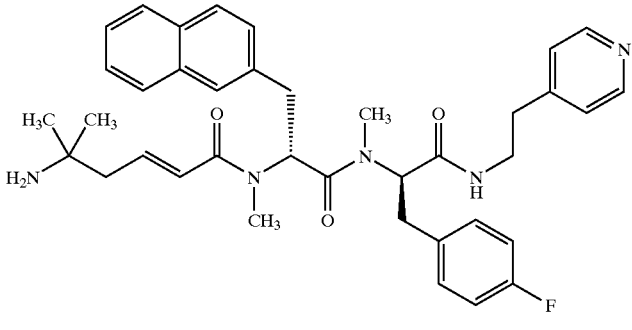 | 637.8 | 8.06 | 638.2 |
| 191 | 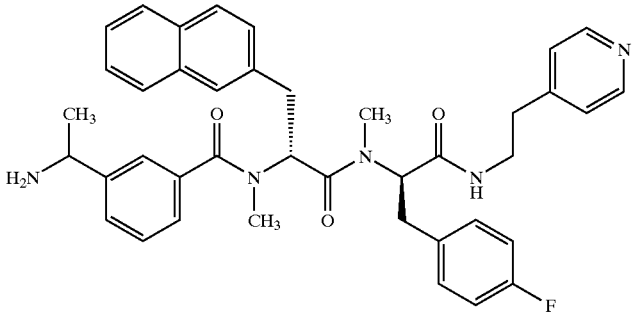 | 659.8 | 8.27 | 660.0 |
| 192 | 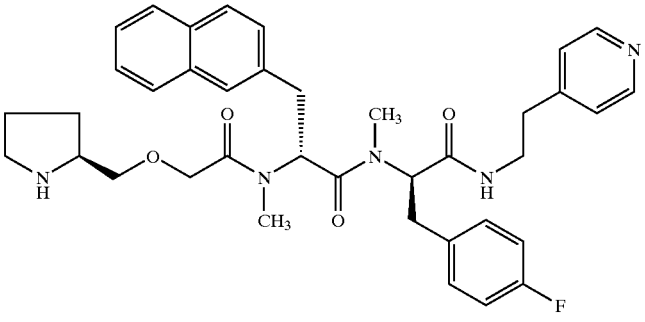 | 653.8 | 8.05 | 654.2 |

TABLE 1-continued
| Example | Structure | MW | HPLC | LCMS |
|---|---|---|---|---|
| 193 | 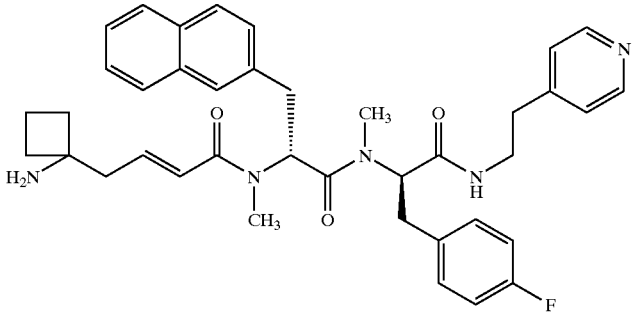 | 649.8 | 8.33 | 650.2 |
| 194 | 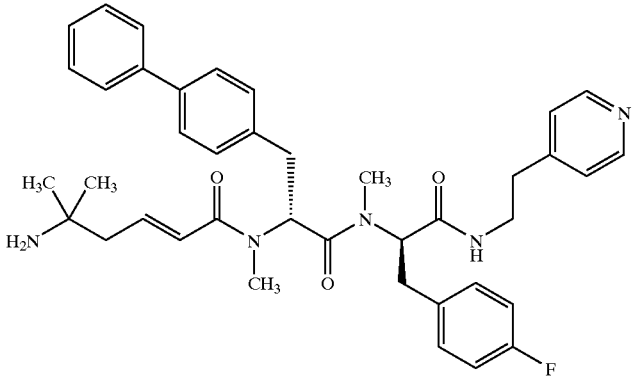 | 663.8 | 8.44 | 664.2 |
| 195 | 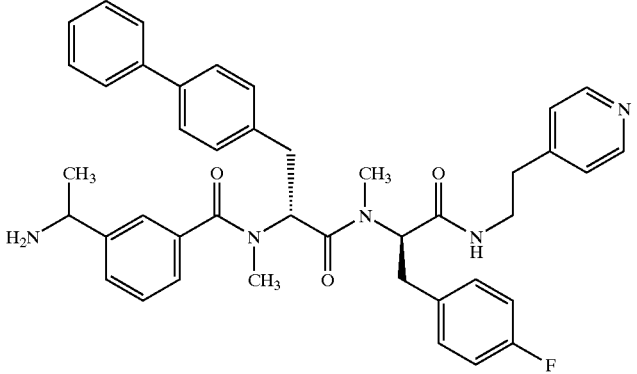 | 685.8 | 8.84 | 686.0 |
| 196 | 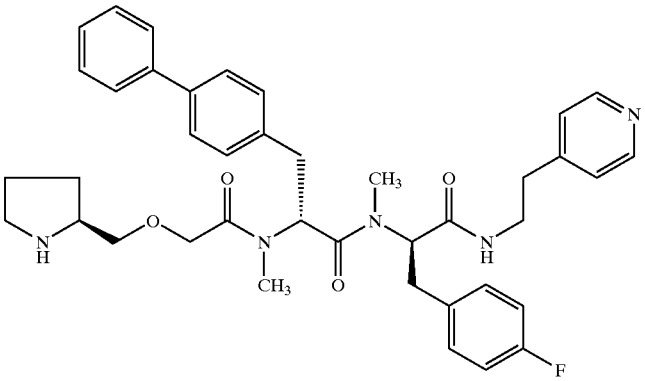 | 679.8 | 8.61 | 680.0 |

TABLE 1-continued

| Example | Structure | MW | HPLC | LCMS |
|---|---|---|---|---|
| 197 | 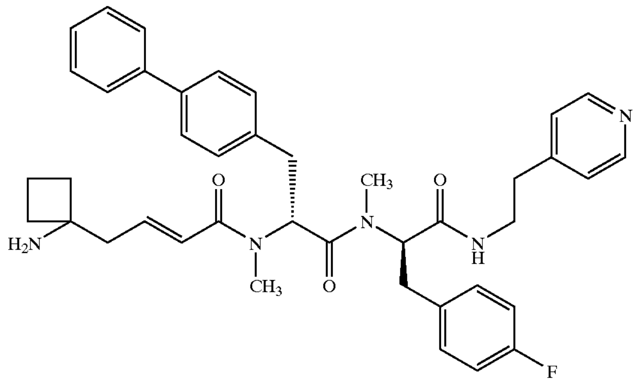 | 675.9 | | |
| 198 | 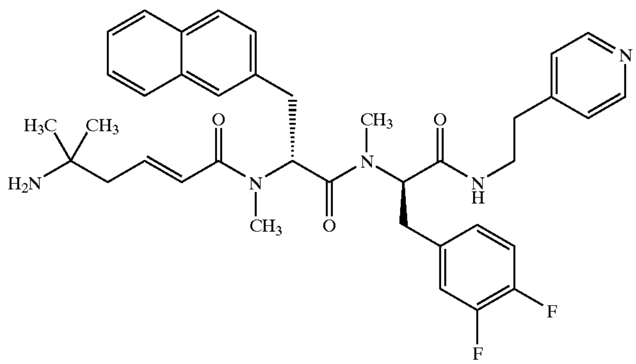 | 655.8 | 8.37 | 656.0 |
| 199 | 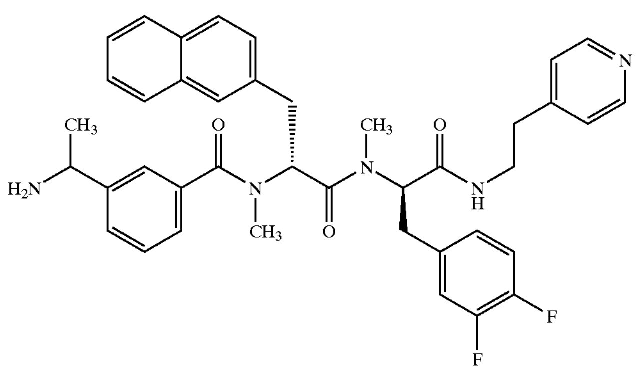 | 677.8 | 8.45 | 678.0 |
| 200 | 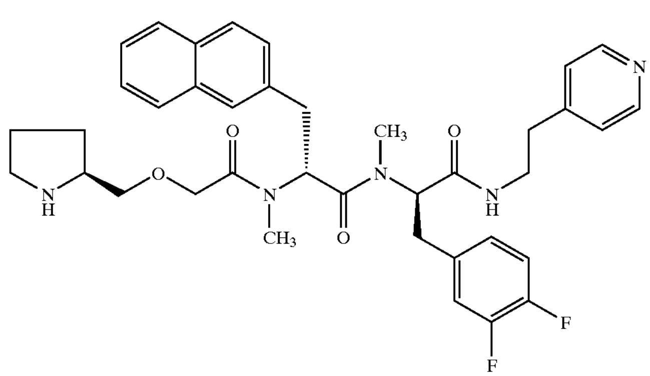 | 671.8 | 8.26 | 672.2 |

TABLE 1-continued

| Example | Structure | MW | HPLC | LCMS |
|---|---|---|---|---|
| 201 | 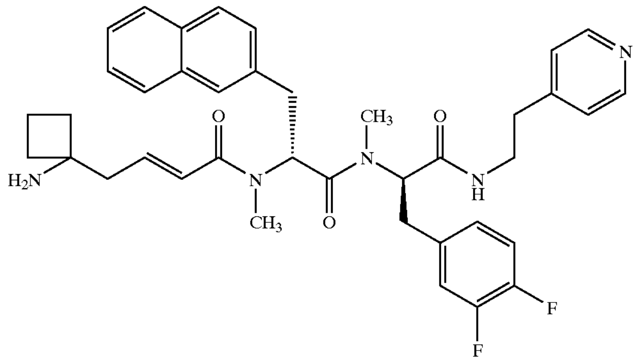 | 667.8 | 8.51 | 668.0 |
| 202 | 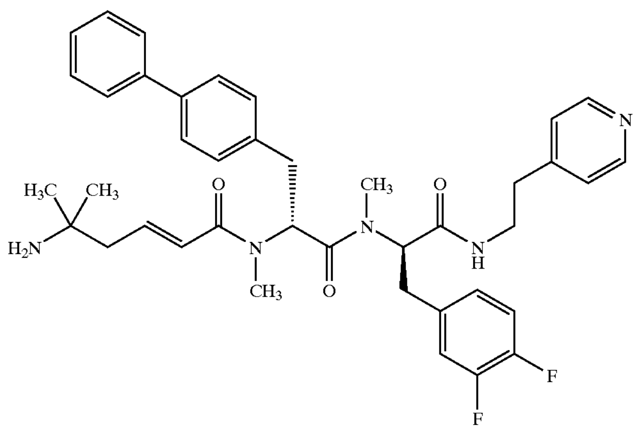 | 681.8 | 8.52 | 682.0 |
| 203 | 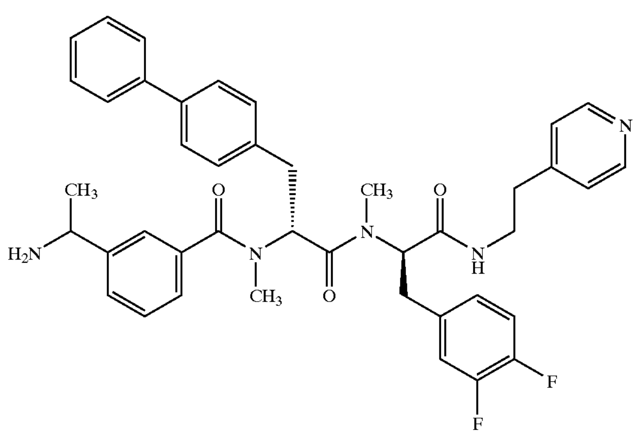 | 703.8 | 8.63 | 704.0 |

TABLE 1-continued

| Example | Structure | MW | HPLC | LCMS |
|---|---|---|---|---|
| 204 | 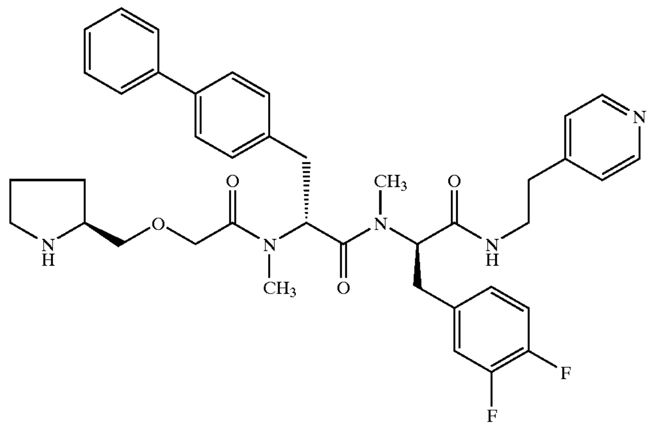 | 697.8 | 8.79 | 689.2 |
| 205 | 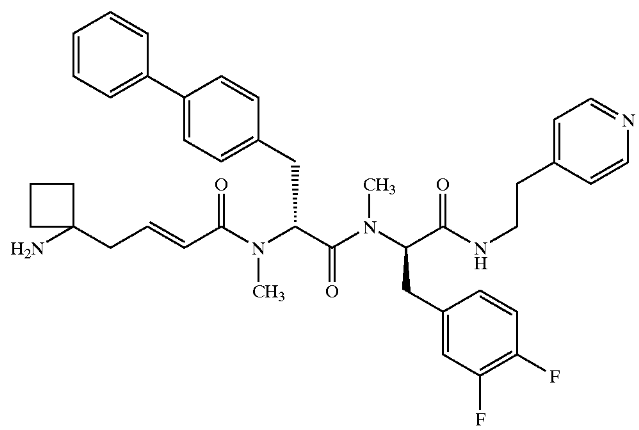 | 693.8 | 8.99 | |
| 206 | 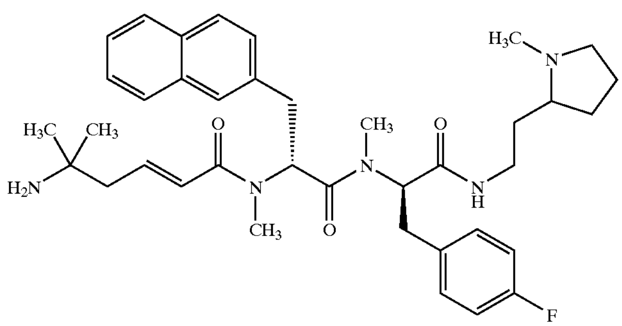 | 643.9 | 7.95 | 644.2 |
| 207 | 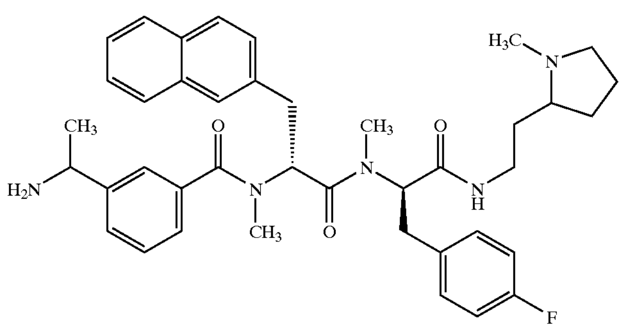 | 665.9 | 8.08 | 666.2 |

TABLE 1-continued

| Example | Structure | MW | HPLC | LCMS |
|---|---|---|---|---|
| 208 | 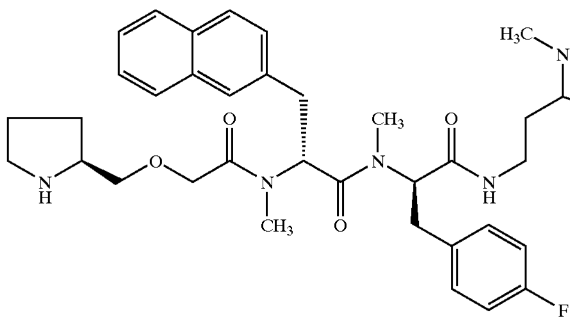 | 659.9 | 8.15 | 660.0 |
| 209 | 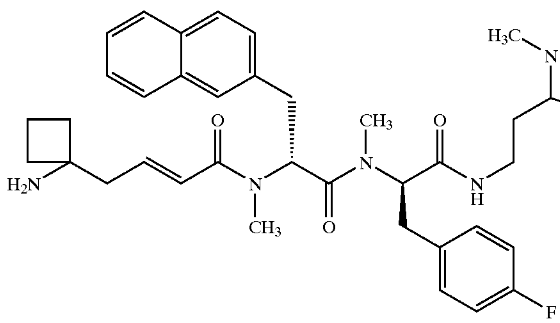 | 655.9 | 8.35 | 656.2 |
| 210 | 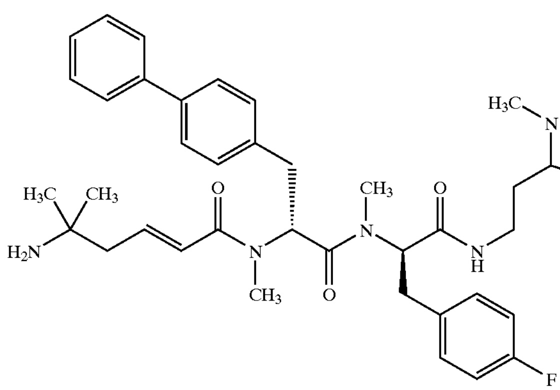 | 669.9 | 8.77 | 670.2 |
| 211 | 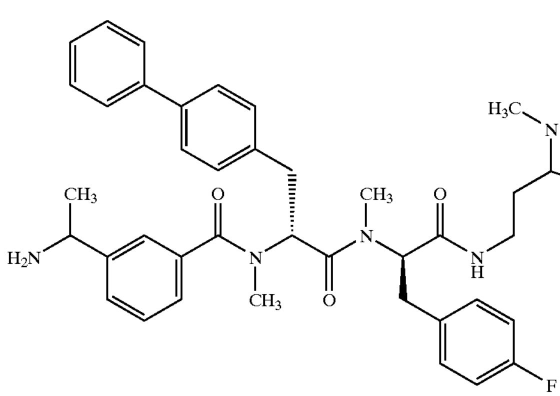 | 691.9 | 8.93 | 692.2 |

TABLE 1-continued
| Example | Structure | MW | HPLC | LCMS |
|---------|-----------|-----|------|------|
| 212 | 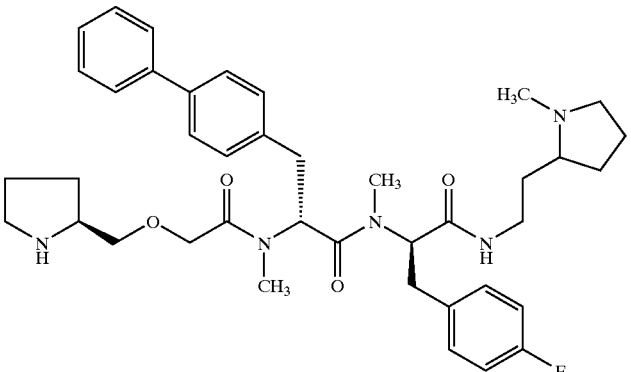 | 685.9 | 8.70 | 686.0 |
| 213 | 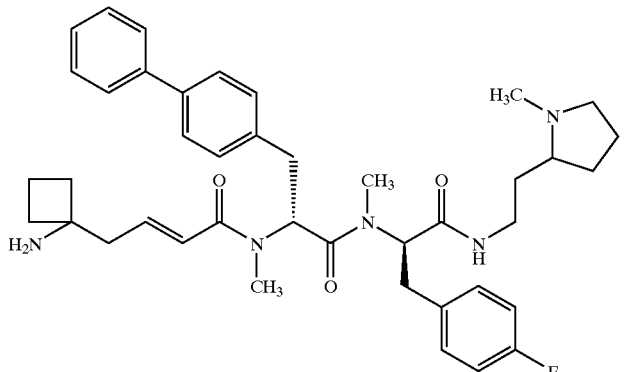 | 681.9 | | |
| 214 | 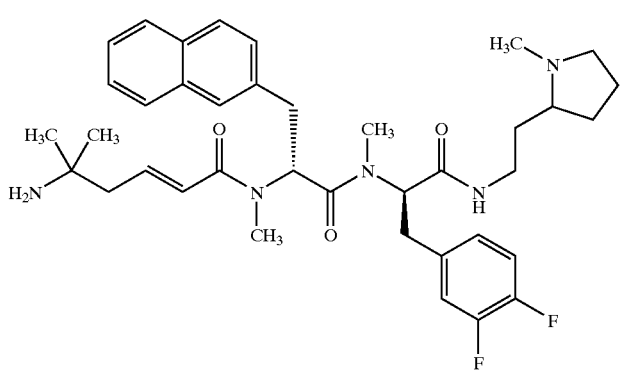 | 661.8 | 7.88 | 662.2 |
| 215 | 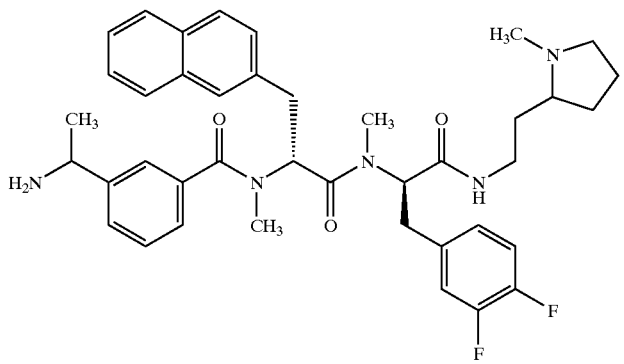 | 683.8 | 8.53 | 684.0 |

TABLE 1-continued

| Example | Structure | MW | HPLC | LCMS |
|---|---|---|---|---|
| 216 | 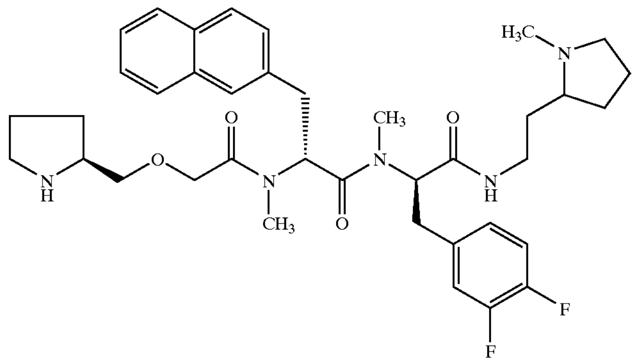 | 677.8 | 8.36 | 678.0 |
| 217 | 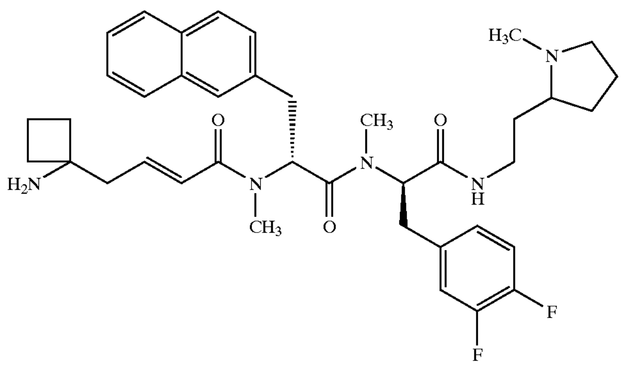 | 673.9 | | |
| 218 | 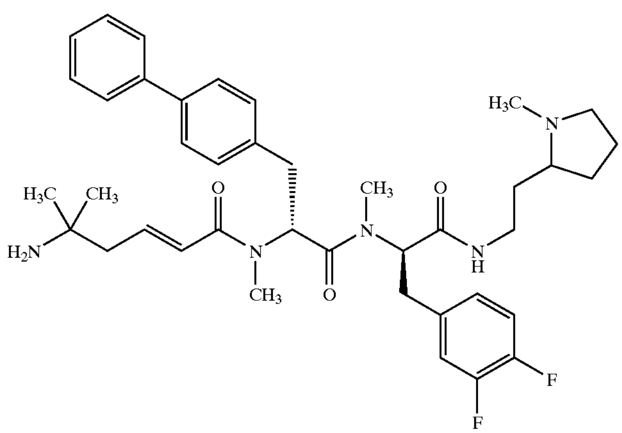 | 687.9 | | |
| 219 | 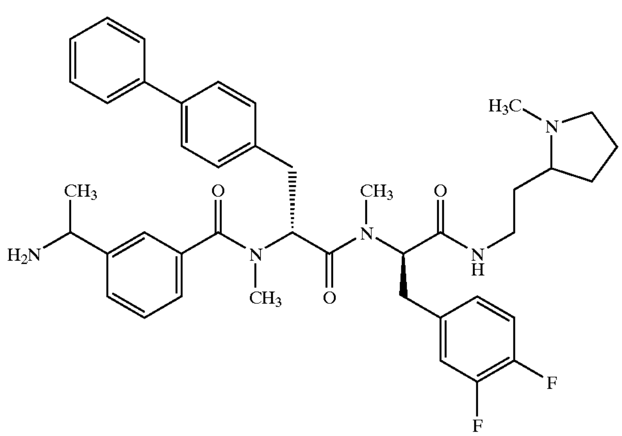 | 709.9 | 9.11 | 710.0 |

TABLE 1-continued
| Example | Structure | MW | HPLC | LCMS |
|---|---|---|---|---|
| 220 | 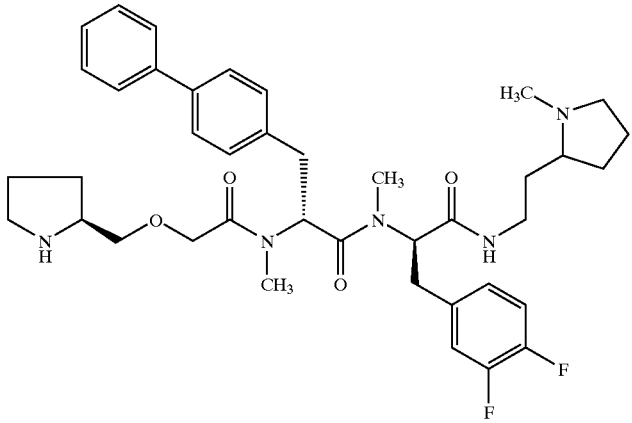 | 703.9 | 8.91 | 705.0 |
| 221 | 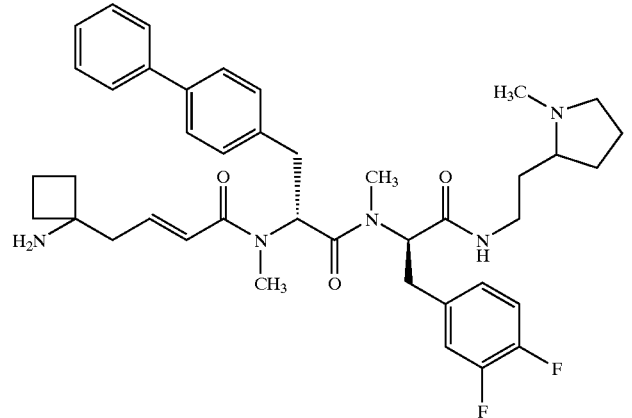 | 699.9 | | |
| 222 | 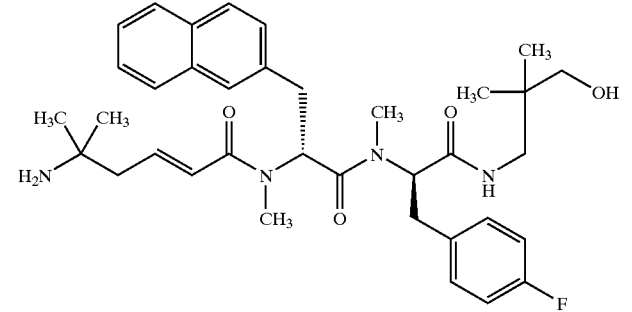 | 618.8 | 9.18 | 619.0 |
| 223 | 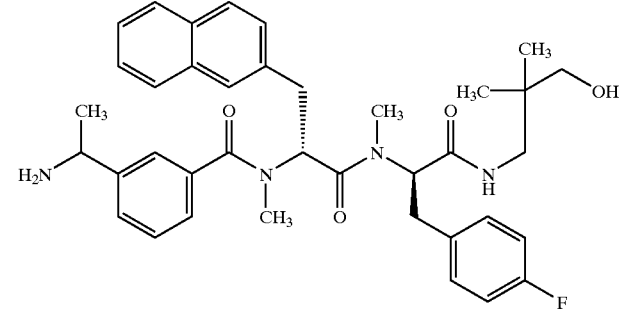 | 640.8 | | |

TABLE 1-continued

| Example | Structure | MW | HPLC | LCMS |
|---|---|---|---|---|
| 224 | 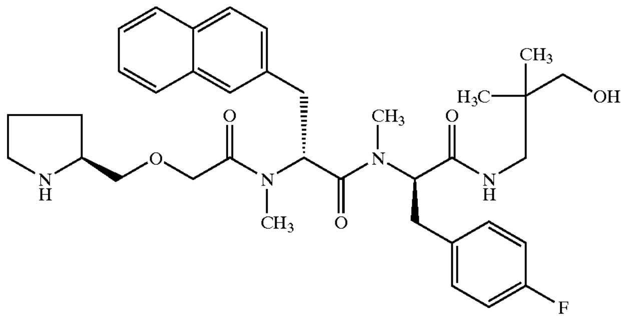 | 634.8 | 9.42 | 635.2 |
| 225 | 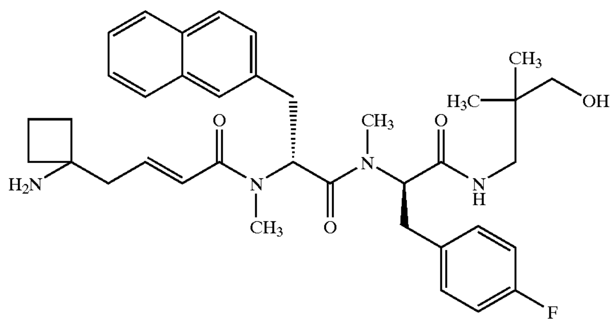 | 630.8 | 9.98 | 629.8 |
| 226 | 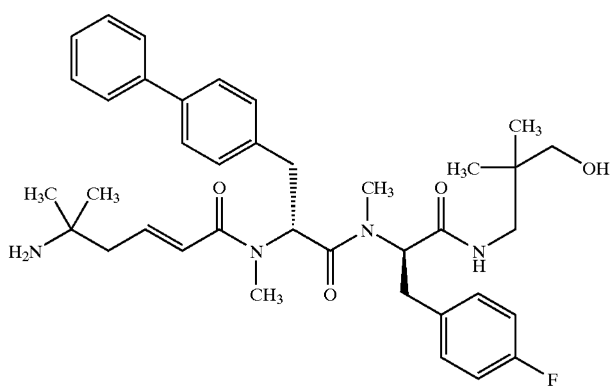 | 644.8 | | |
| 227 | 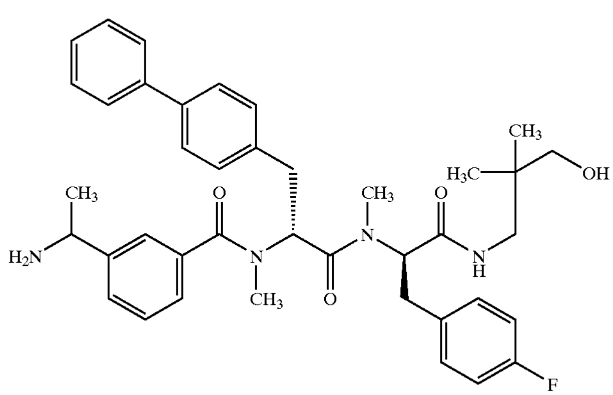 | 666.8 | 10.78 | 667.4 |

TABLE 1-continued
| Example | Structure | MW | HPLC | LCMS |
|---|---|---|---|---|
| 228 | 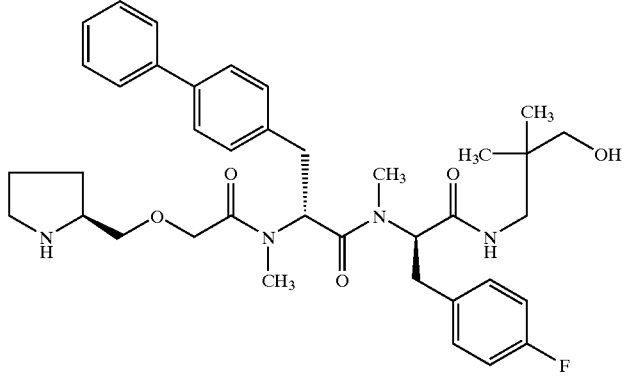 | 660.8 | | |
| 229 | 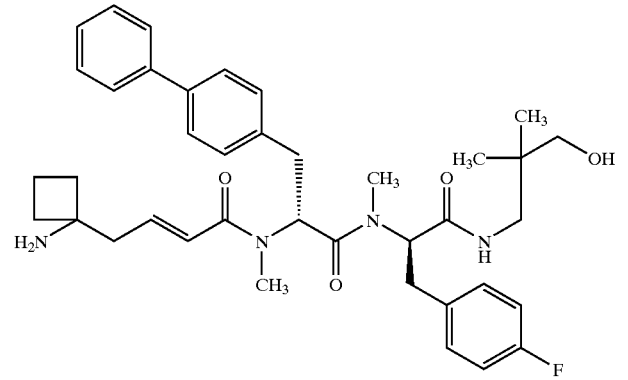 | 656.8 | | |
| 230 | 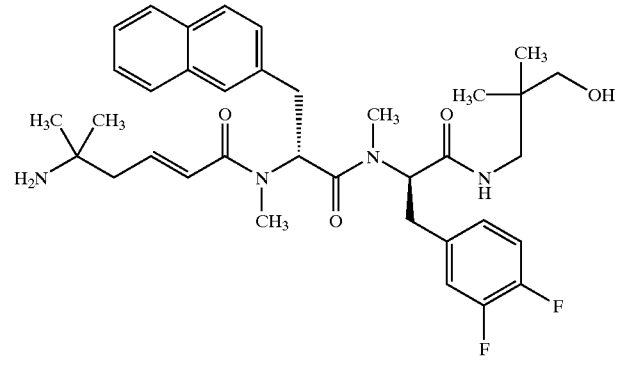 | 636.8 | | |
| 231 | 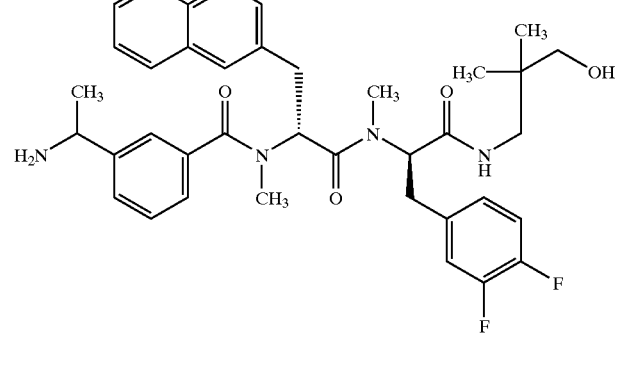 | 658.8 | 9.90 | 658.0 |

TABLE 1-continued

| Example | Structure | MW | HPLC | LCMS |
|---|---|---|---|---|
| 232 | 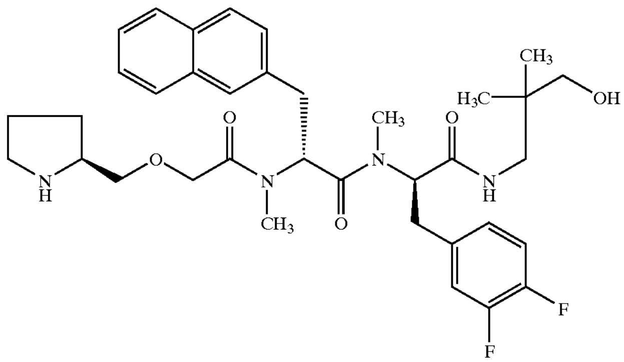 | 652.8 | 9.66 | 653.0 |
| 233 | 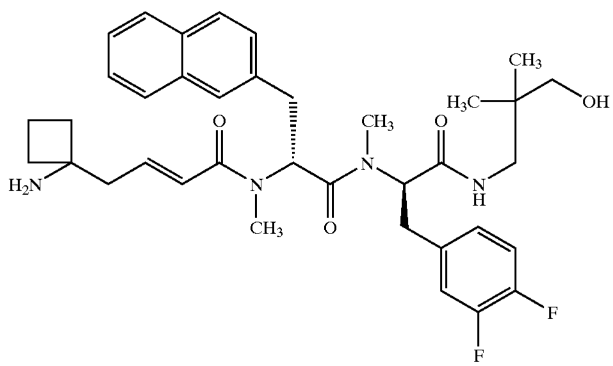 | 648.8 | | |
| 234 | 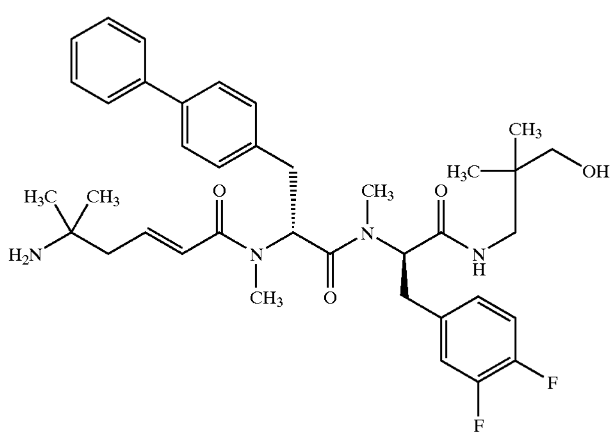 | 662.8 | 10.34 | 663.0 |
| 235 | 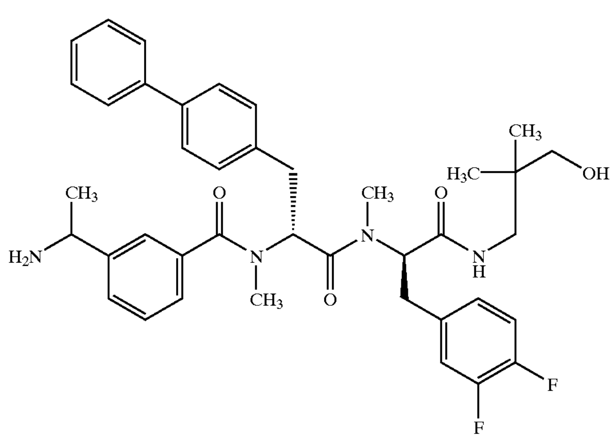 | 684.8 | | |

TABLE 1-continued
| Example | Structure | MW | HPLC | LCMS |
|---|---|---|---|---|
| 236 | 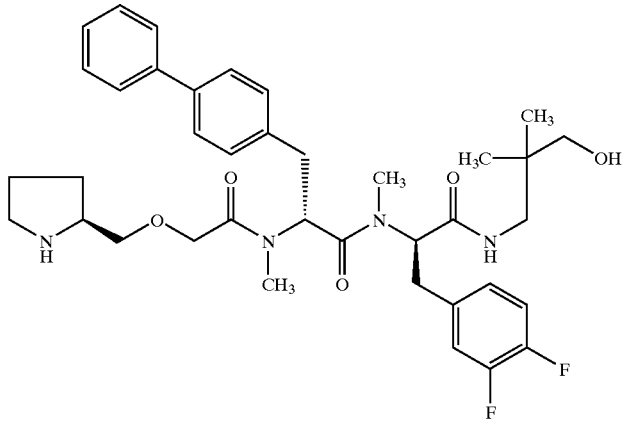 | 678.8 | 10.01 | 679.2 |
| 237 | 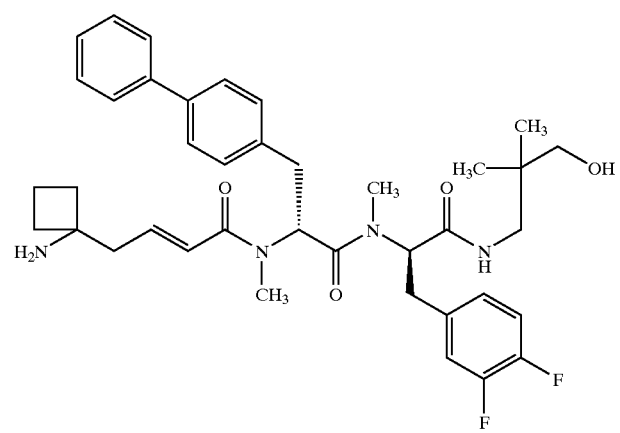 | 674.8 | | |
| 238 | 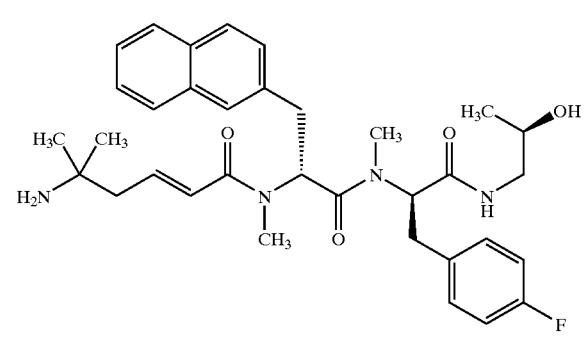 | 590.7 | 8.48 | 591.0 |
| 239 | 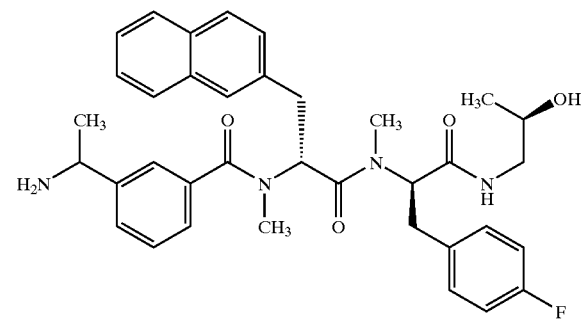 | 612.8 | 9.52 | 613.0 |

TABLE 1-continued
| Example | Structure | MW | HPLC | LCMS |
|---|---|---|---|---|
| 240 | 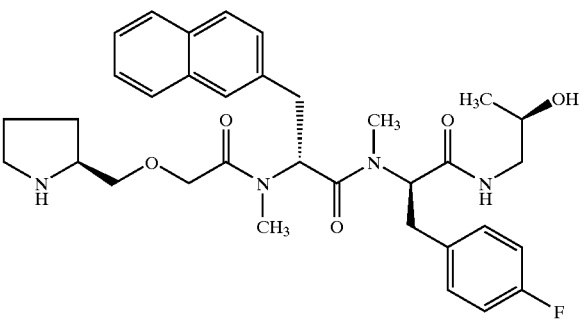 | 606.7 | 9.28 | 607.0 |
| 241 | 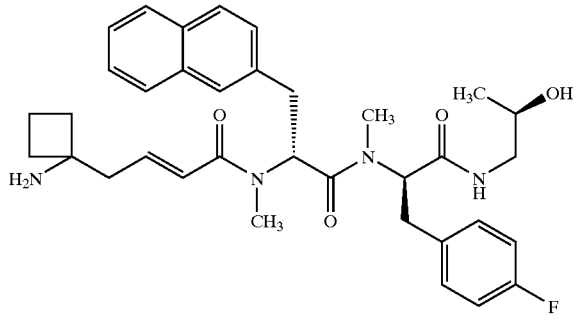 | 602.8 | 9.59 | 603.0 |
| 242 | 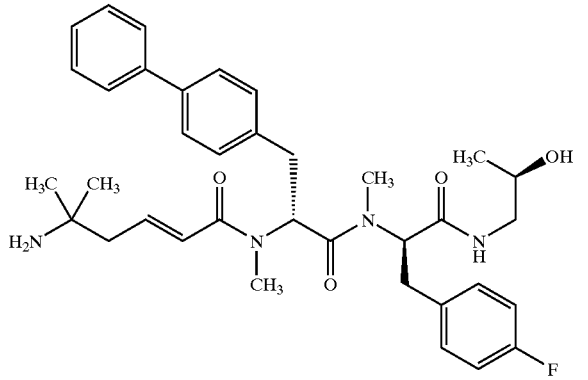 | 616.8 | 9.05 | 617.2 |
| 243 | 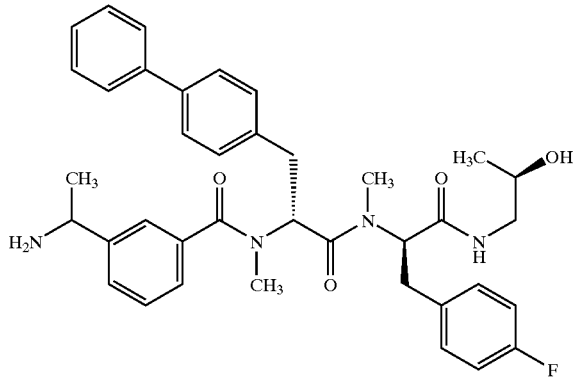 | 638.8 | 8.97 | 639.0 |

TABLE 1-continued
| Example | Structure | MW | HPLC | LCMS |
|---|---|---|---|---|
| 244 | 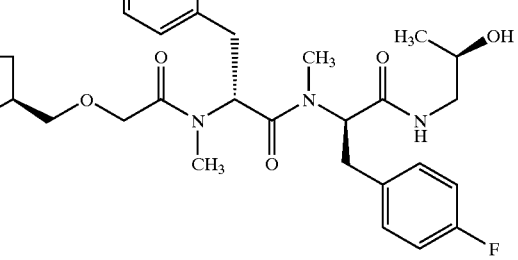 | 632.8 | | 633.0 |
| 245 | 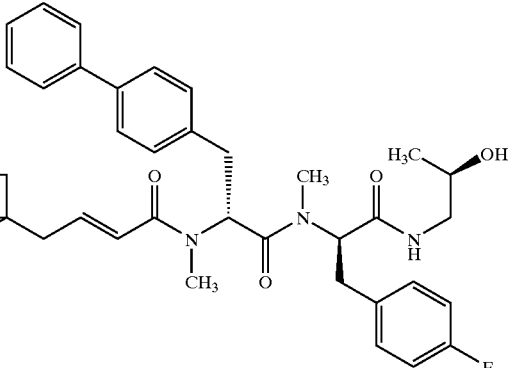 | 628.8 | | 629.0 |
| 246 | 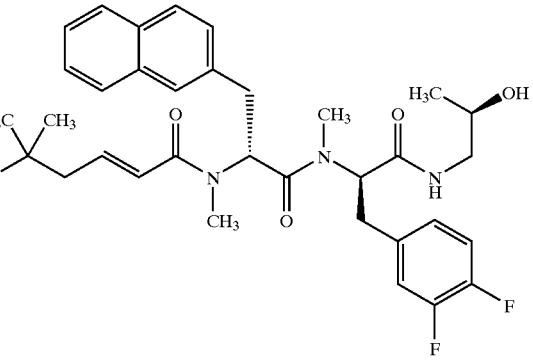 | 608.7 | 9.12 | 608.8 |
| 247 | 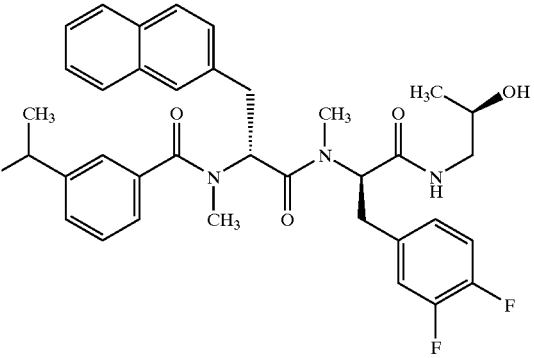 | 630.7 | 9.72 | 631.0 |

| Example | Structure | MW | HPLC | LCMS |
|---|---|---|---|---|
| 248 | 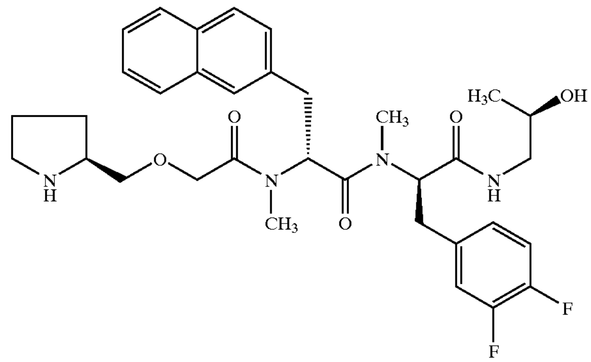 | 624.7 | 9.51 | 625.0 |
| 249 | 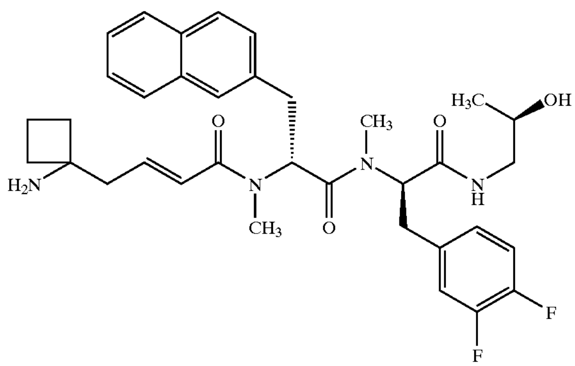 | 620.7 | 9.26 | 621.0 |
| 250 | 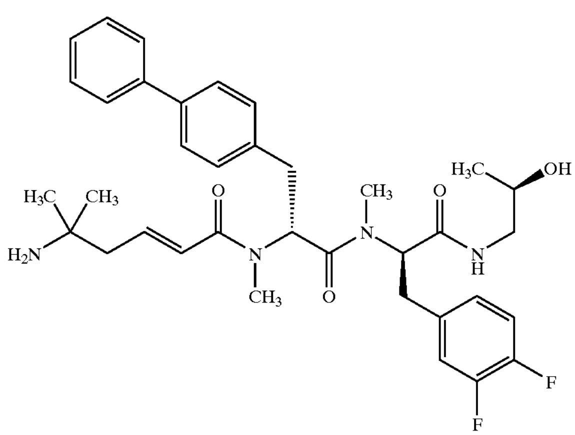 | 634.8 | | |
| 251 | 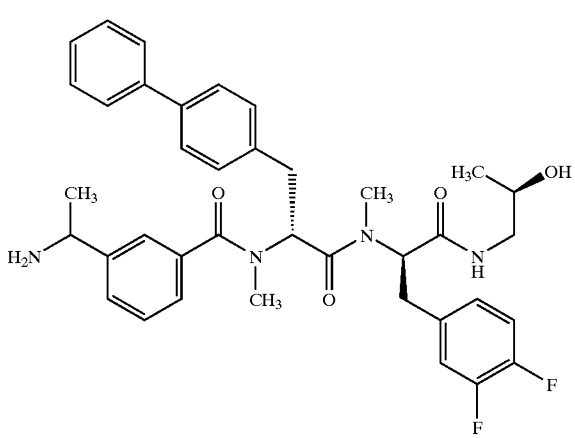 | 656.8 | 9.50 | 656.8 |

TABLE 1-continued
| Example | Structure | MW | HPLC | LCMS |
|---|---|---|---|---|
| 252 | 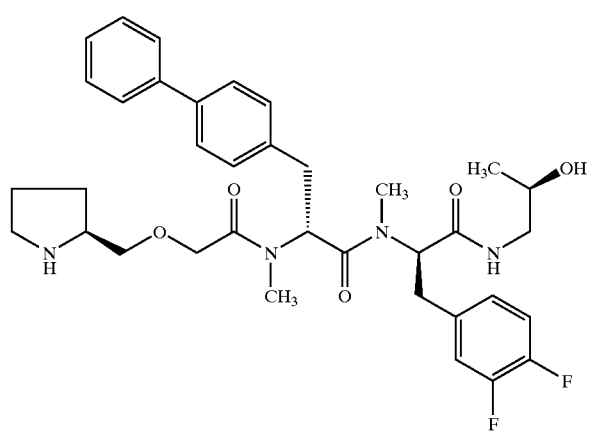 | 650.8 | 9.50 | 651.0 |
| 253 | 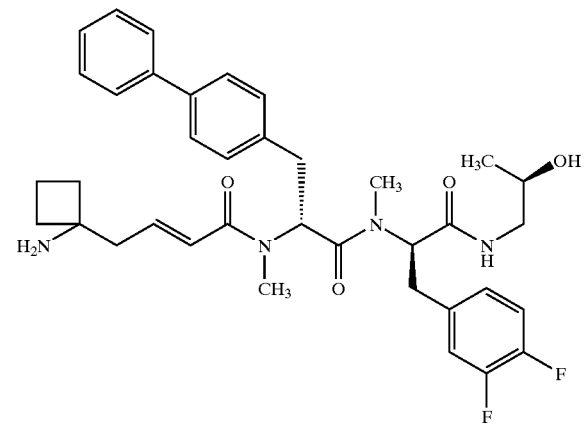 | 646.8 | 9.48 | |
TABLE 2
| Example | Structure | MW | HPLC | LC-MS |
|---|---|---|---|---|
| 254 | 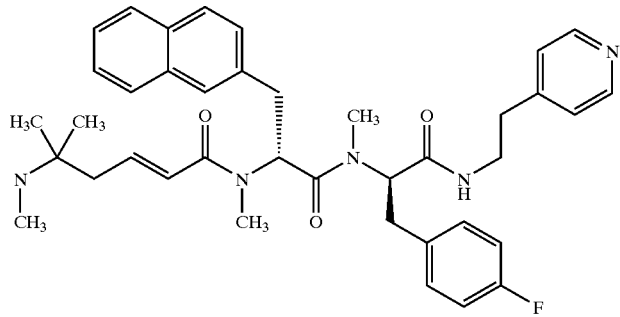 | 651.83 | | |

TABLE 2-continued
| Example | Structure | MW | HPLC | LC-MS |
|---|---|---|---|---|
| 255 | 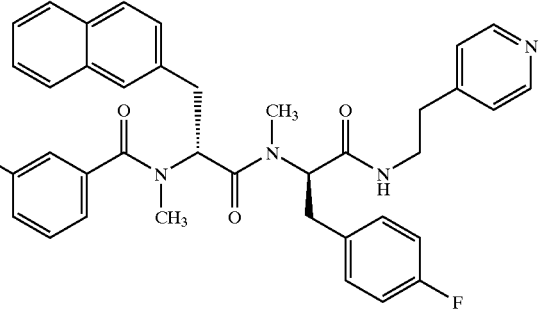 | 645.78 | | |
| 256 | 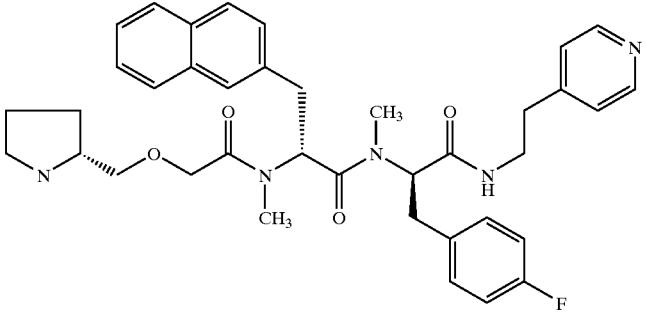 | 653.80 | | |
| 257 | 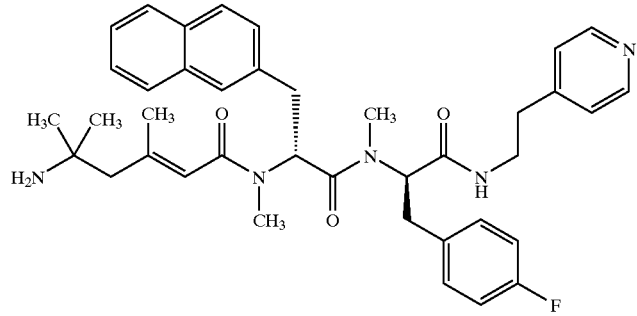 | 651.83 | | |
| 258 | 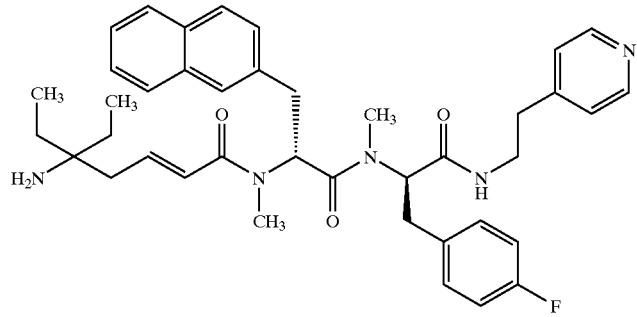 | 665.86 | | |

TABLE 2-continued

| Example | Structure | MW | HPLC | LC-MS |
|---|---|---|---|---|
| 259 | 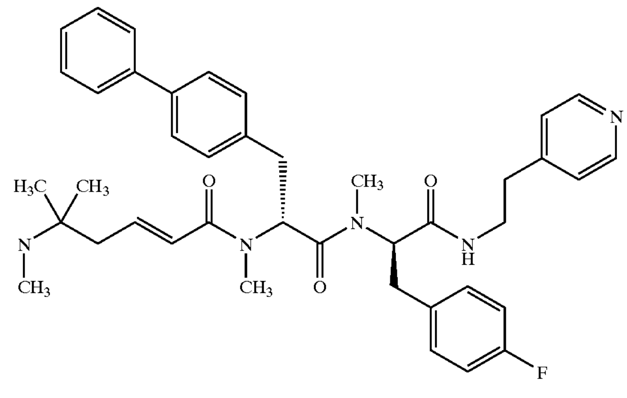 | 677.87 | | |
| 260 | 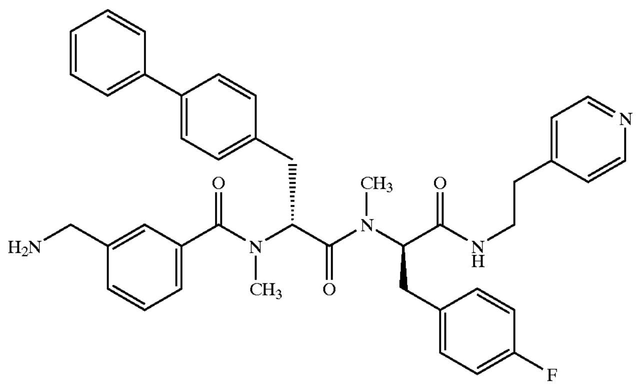 | 671.82 | | |
| 261 | 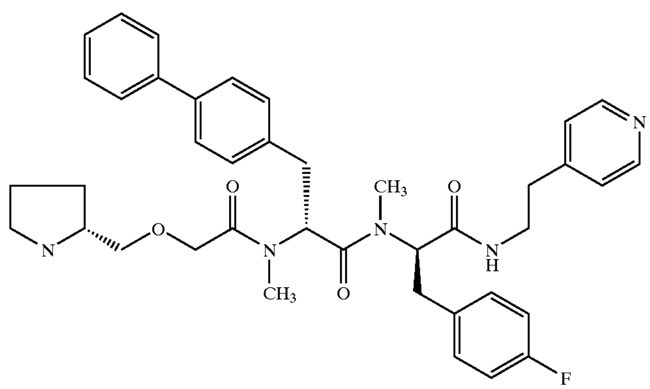 | 679.84 | | |
| 262 | 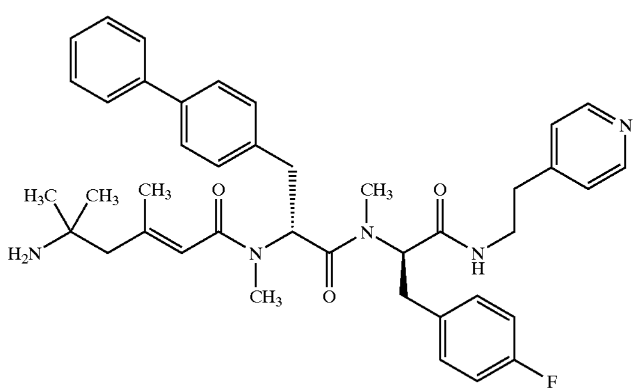 | 677.87 | | |

TABLE 2-continued

| Example | Structure | MW | HPLC | LC-MS |
|---|---|---|---|---|
| 263 | 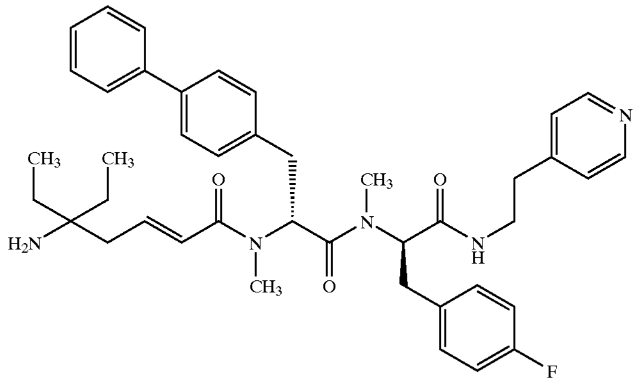 | 691.90 | | |
| 264 | 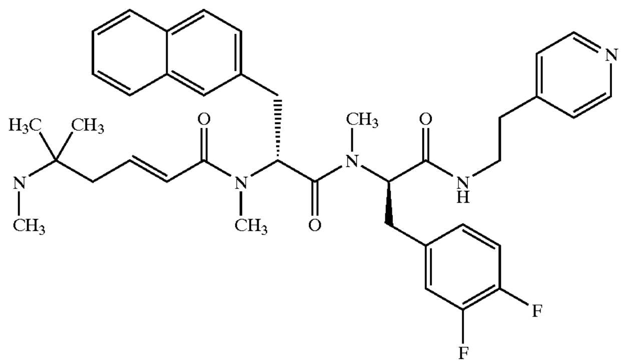 | 669.82 | | |
| 265 | 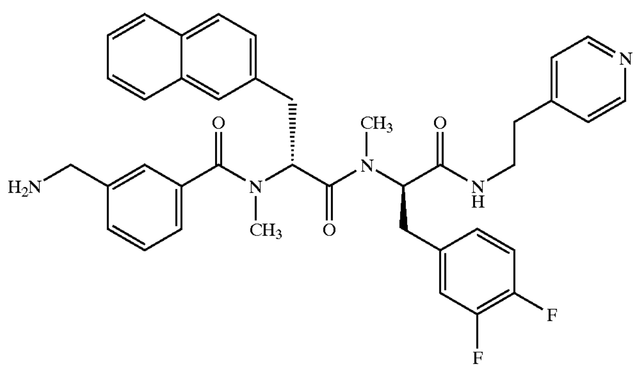 | 663.77 | | |
| 266 | 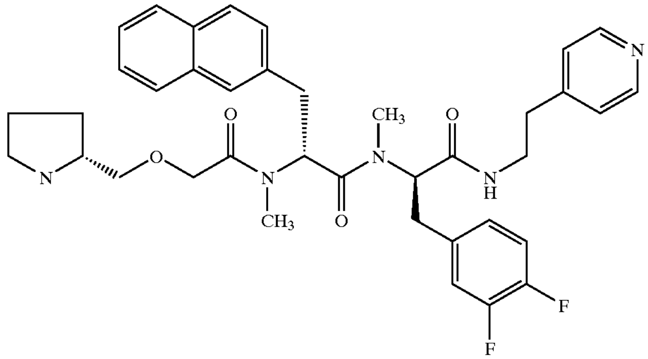 | 671.79 | | |

TABLE 2-continued

| Example | Structure | MW | HPLC | LC-MS |
|---|---|---|---|---|
| 267 | 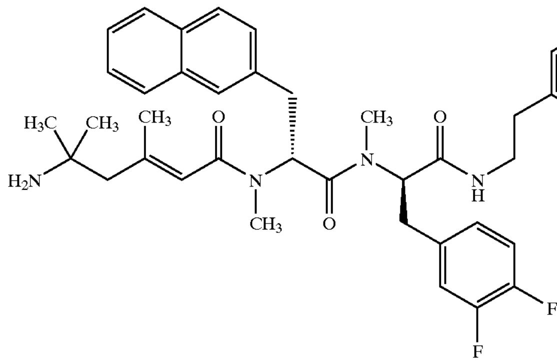 | 669.82 | | |
| 268 | 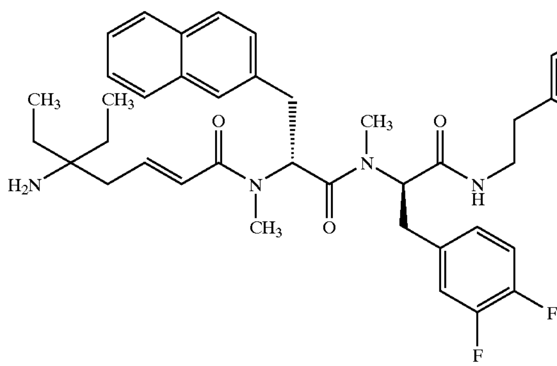 | 683.85 | | |
| 269 | 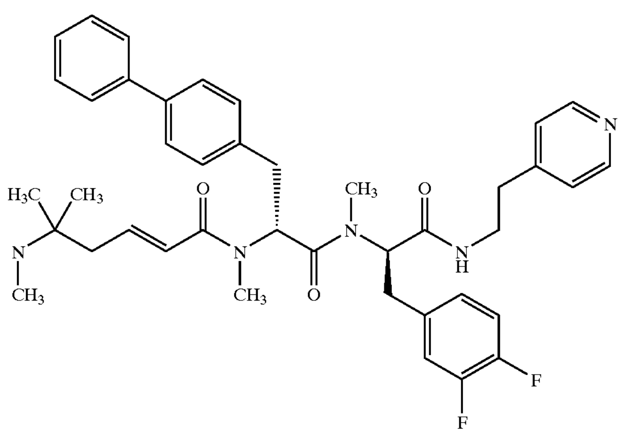 | 695.86 | | |
| 270 | 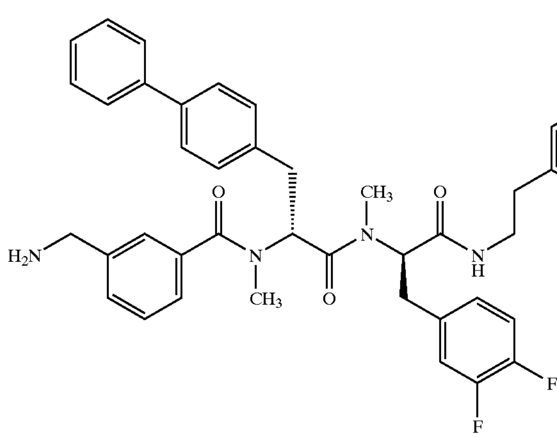 | 689.81 | | |

TABLE 2-continued
| Example | Structure | MW | HPLC | LC-MS |
|---|---|---|---|---|
| 271 | 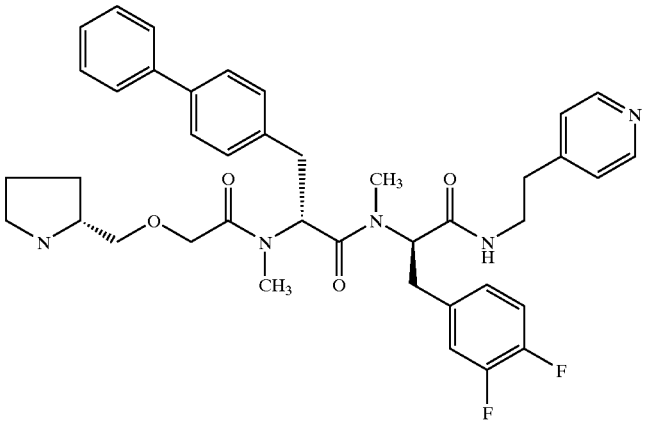 | 697.83 | | |
| 272 | 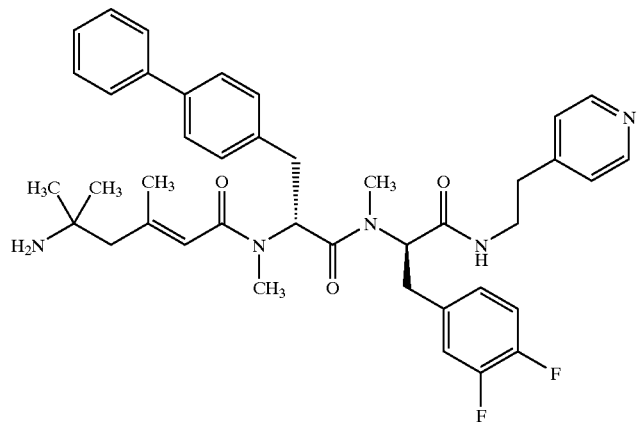 | 695.86 | | |
| 273 | 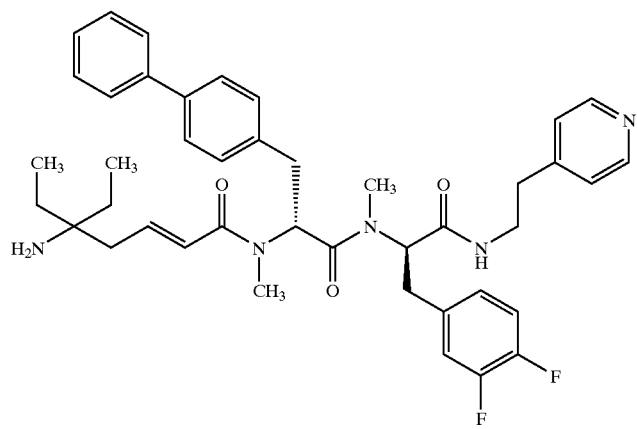 | 709.89 | | |

TABLE 2-continued
| Example | Structure | MW | HPLC | LC-MS |
|---|---|---|---|---|
| 274 | 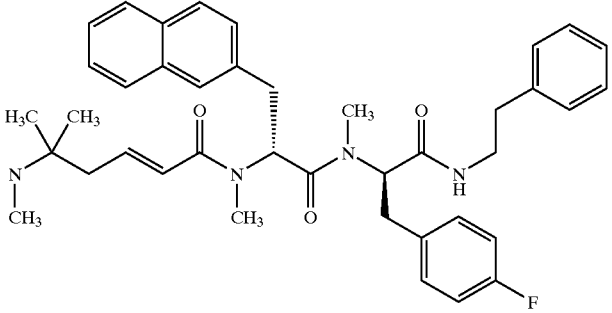 | 650.84 | | |
| 275 | 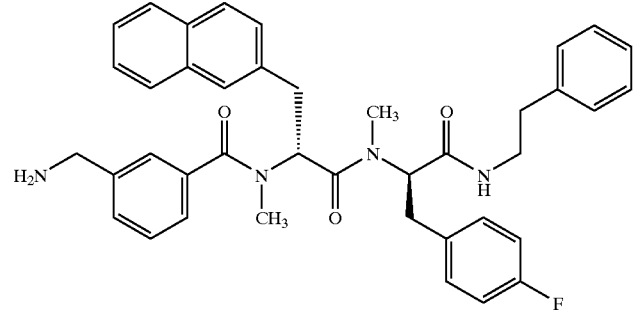 | 644.80 | | |
| 276 | 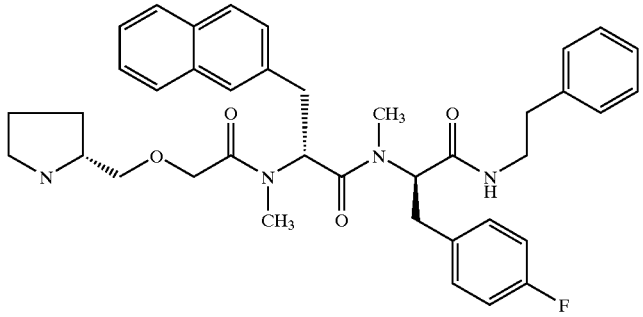 | 652.82 | | |
| 277 | 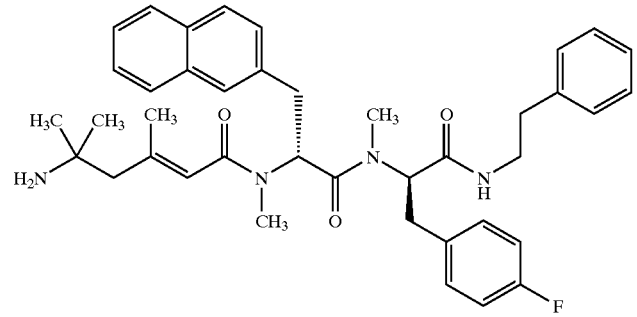 | 650.84 | | |

TABLE 2-continued

| Example | Structure | MW | HPLC | LC-MS |
|---|---|---|---|---|
| 278 | 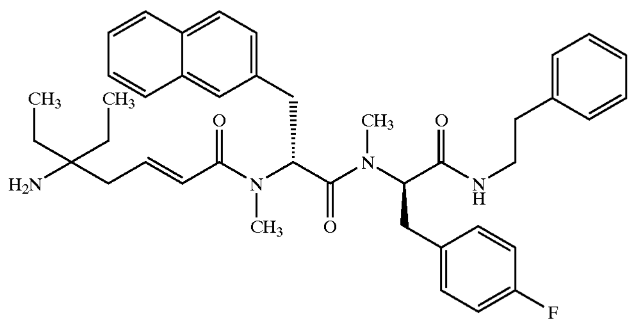 | 664.87 | | |
| 279 | 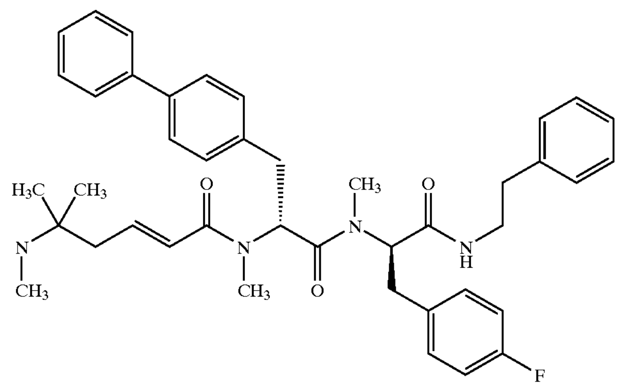 | 676.88 | | |
| 280 | 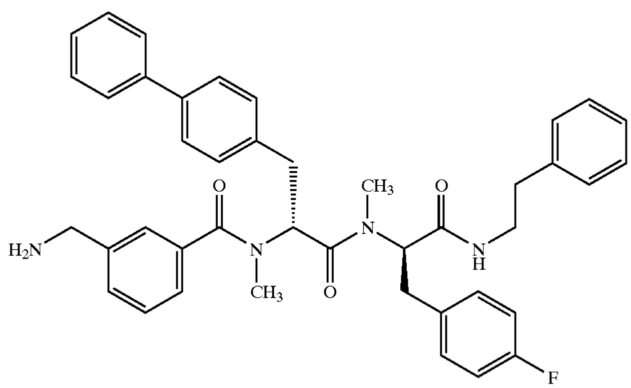 | 670.83 | | |
| 281 | 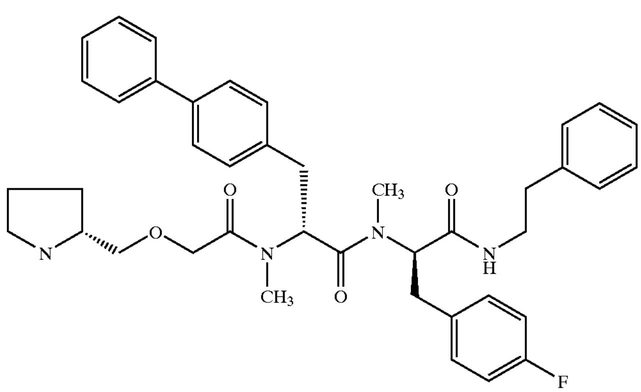 | 678.85 | | |

TABLE 2-continued

| Example | Structure | MW | HPLC | LC-MS |
|---|---|---|---|---|
| 282 | 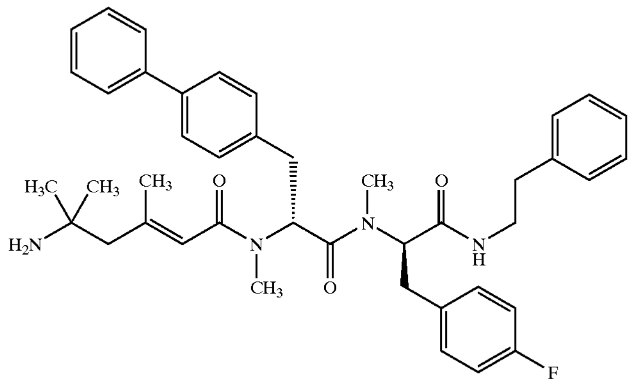 | 676.88 | | |
| 283 | 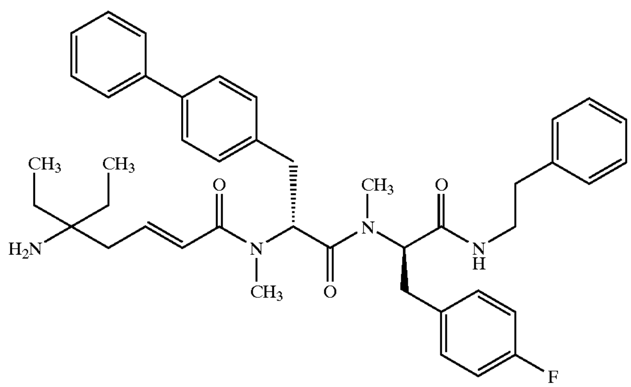 | 690.91 | | |
| 284 | 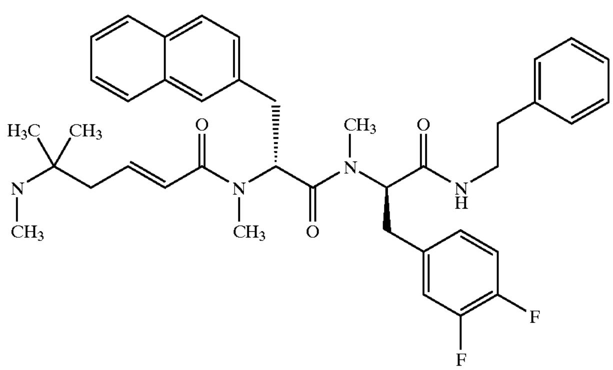 | 668.83 | | |
| 285 | 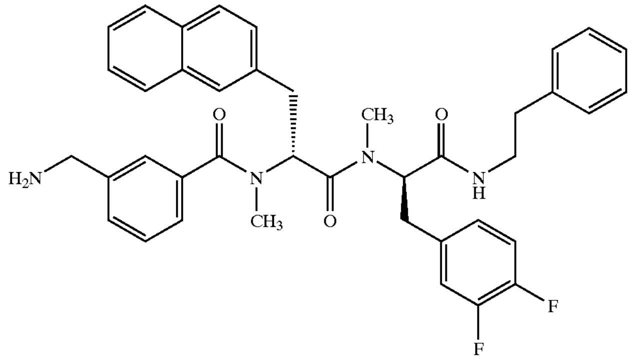 | 662.79 | | |

TABLE 2-continued

| Example | Structure | MW | HPLC | LC-MS |
|---|---|---|---|---|
| 286 | 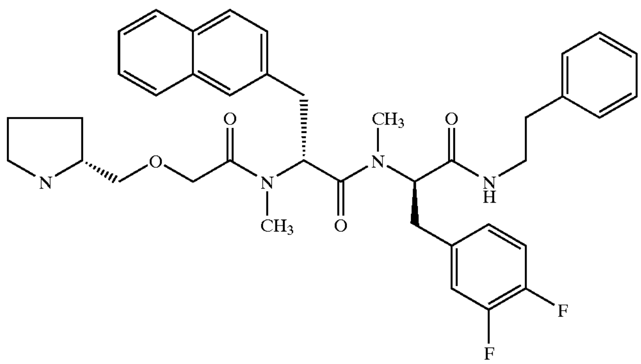 | 670.81 | | |
| 287 | 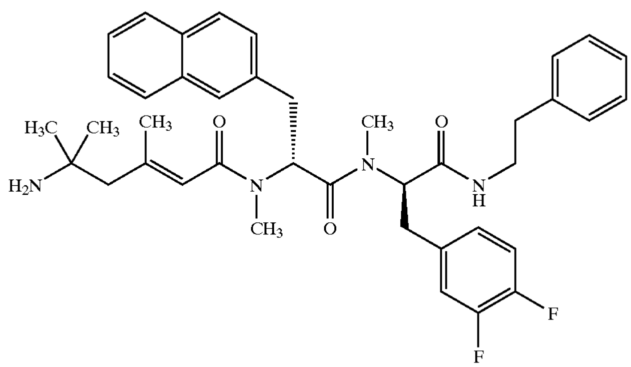 | 668.83 | | |
| 288 | 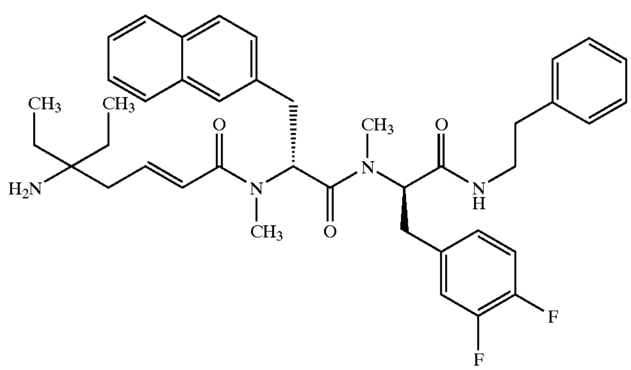 | 682.86 | | |
| 289 | 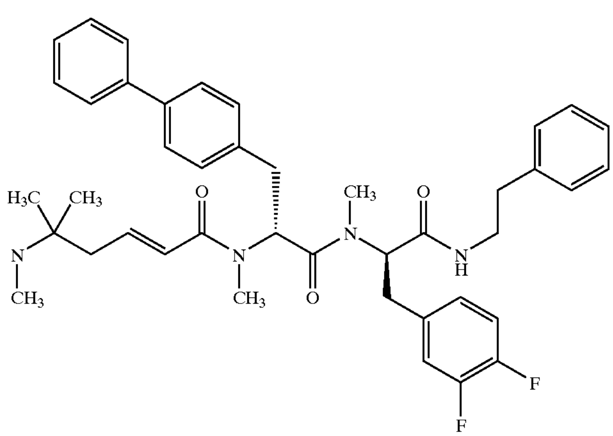 | 694.87 | | |

TABLE 2-continued

| Example | Structure | MW | HPLC | LC-MS |
|---|---|---|---|---|
| 290 | 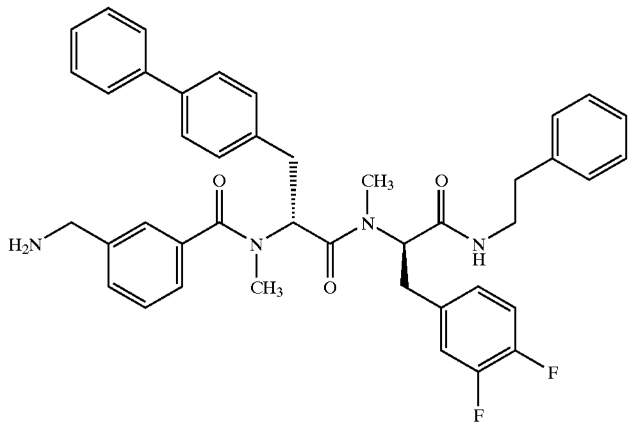 | 688.82 | | |
| 291 | 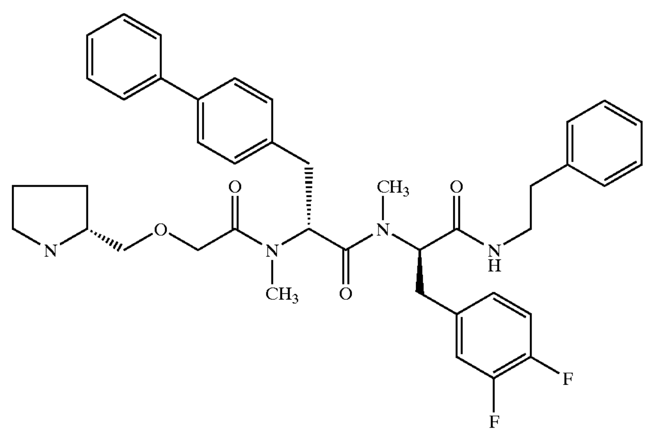 | 696.84 | | |
| 292 | 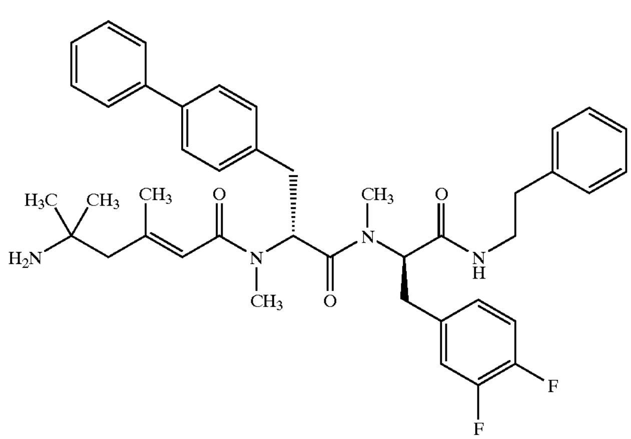 | 694.87 | | |

TABLE 2-continued

| Example | Structure | MW | HPLC | LC-MS |
|---------|-----------|-----|------|-------|
| 293 | 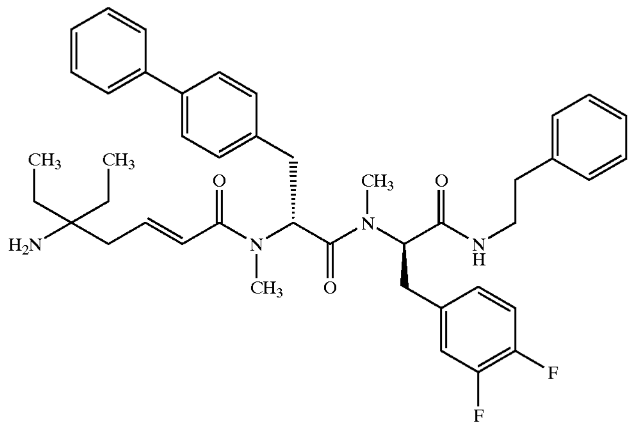 | 708.90 | | |
| 294 | 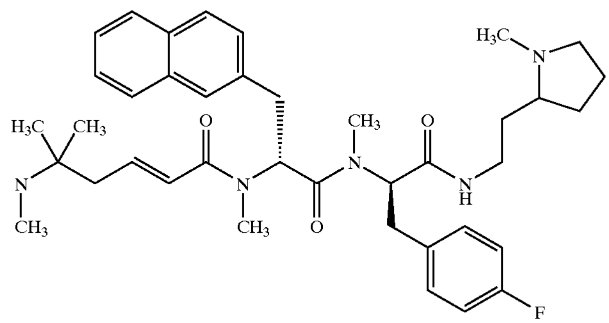 | 657.88 | | |
| 295 | 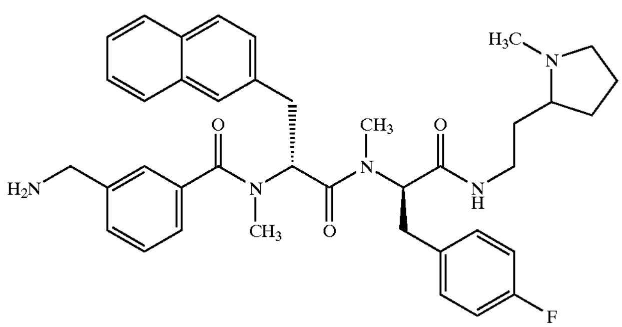 | 651.83 | | |
| 296 | 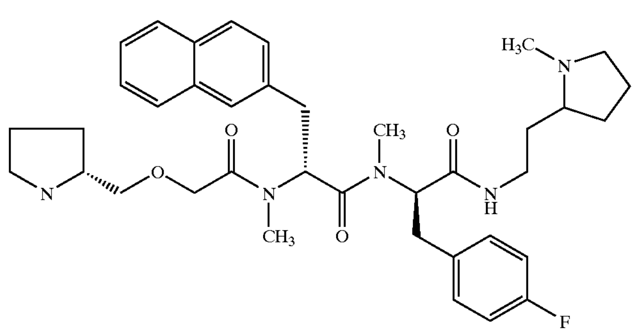 | 659.85 | | |

TABLE 2-continued
| Example | Structure | MW | HPLC | LC-MS |
|---|---|---|---|---|
| 297 | 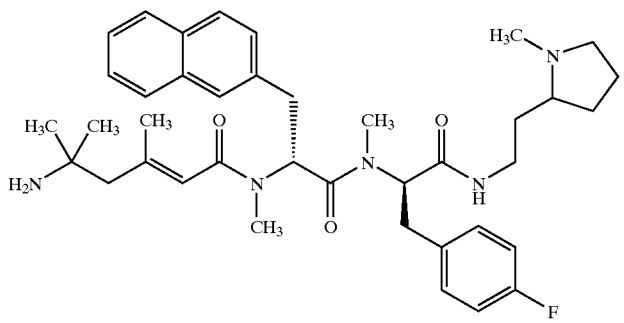 | 657.88 | | |
| 298 | 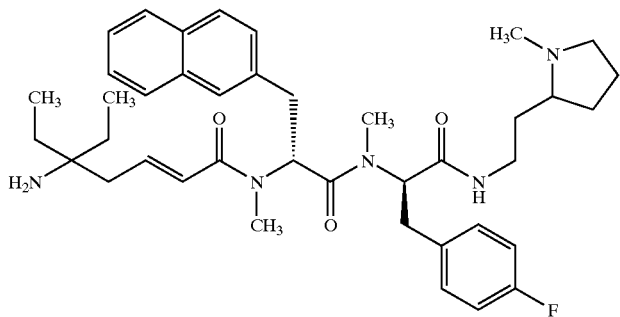 | 671.91 | | |
| 299 | 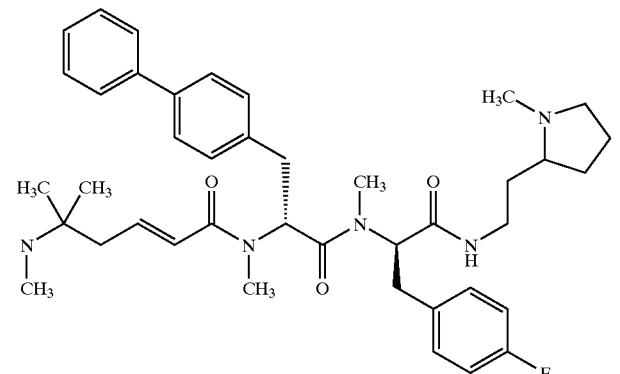 | 683.92 | | |
| 300 | 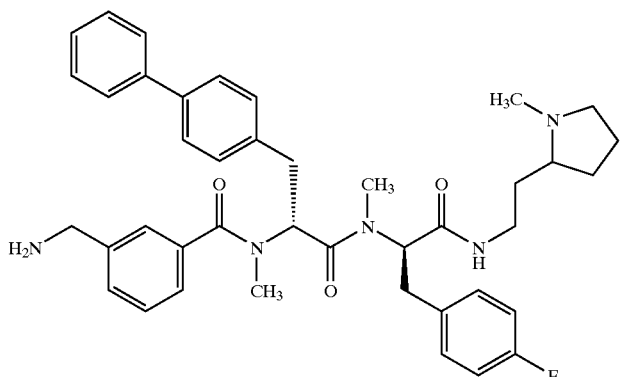 | 677.87 | | |

TABLE 2-continued
| Example | Structure | MW | HPLC | LC-MS |
|---|---|---|---|---|
| 301 | 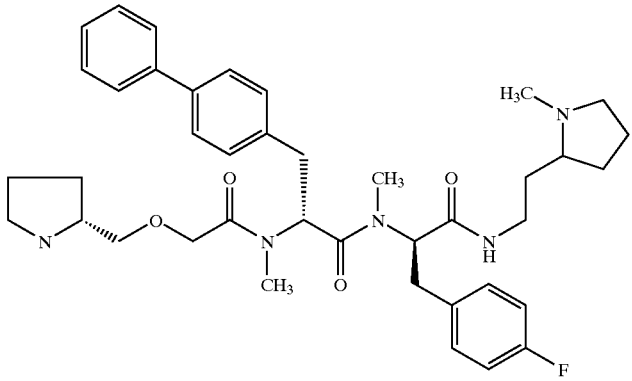 | 685.89 | | |
| 302 | 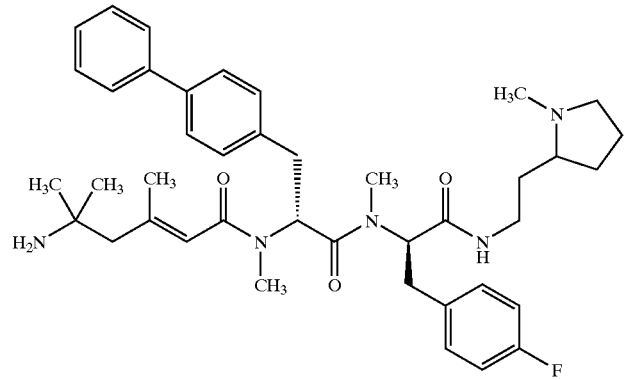 | 683.92 | | |
| 303 | 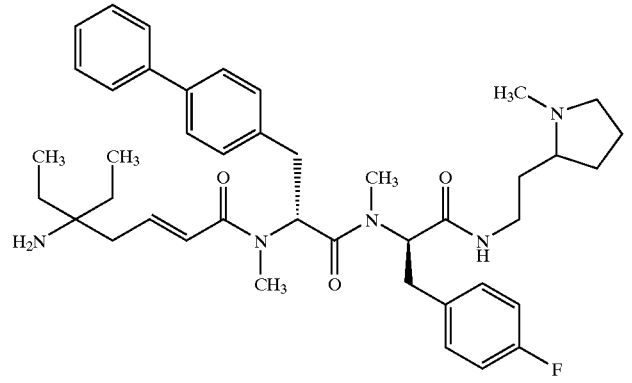 | 697.94 | | |
| 304 | 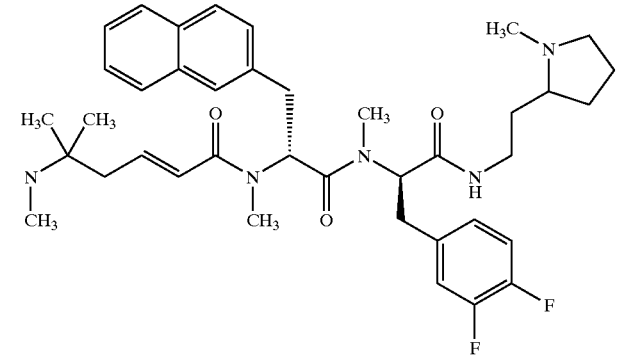 | 675.87 | | |

TABLE 2-continued

| Example | Structure | MW | HPLC | LC-MS |
|---------|-----------|-----|------|-------|
| 305 | 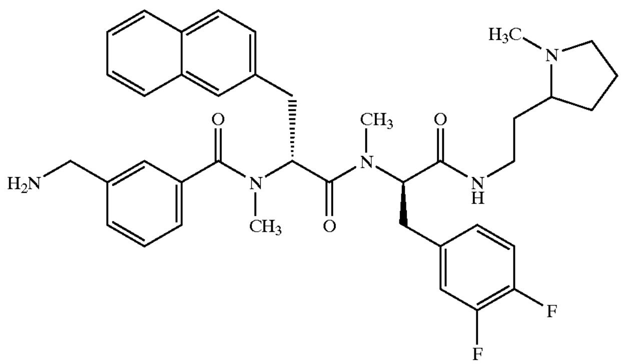 | 669.82 | | |
| 306 | 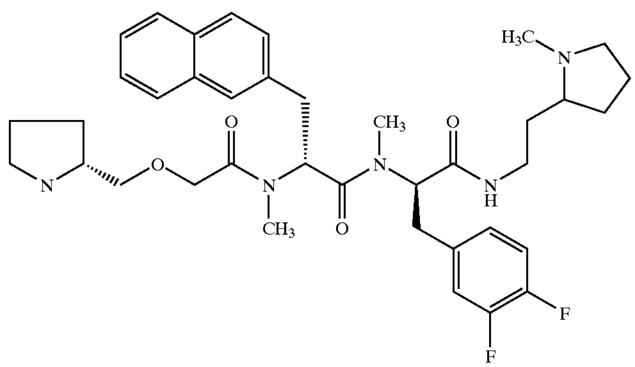 | 677.84 | | |
| 307 | 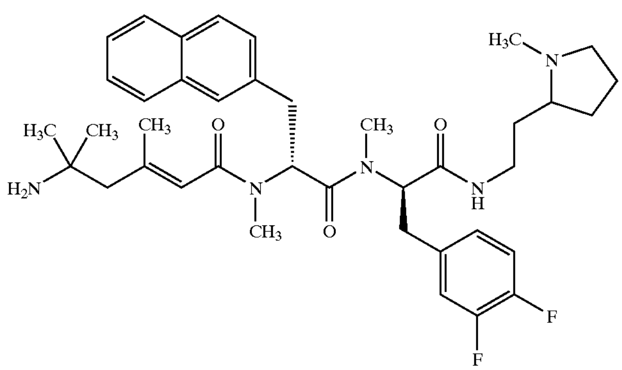 | 675.87 | | |
| 308 | 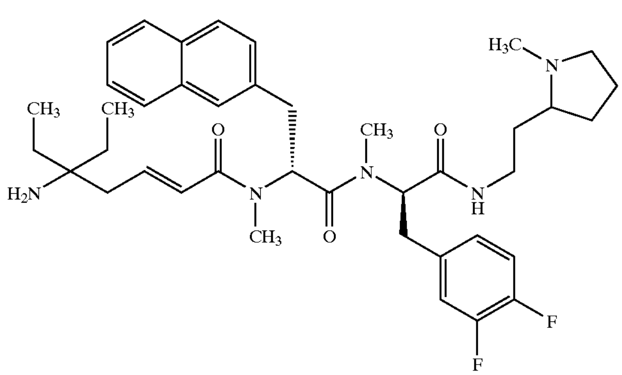 | 689.90 | | |

TABLE 2-continued

| Example | Structure | MW | HPLC | LC-MS |
|---|---|---|---|---|
| 309 | 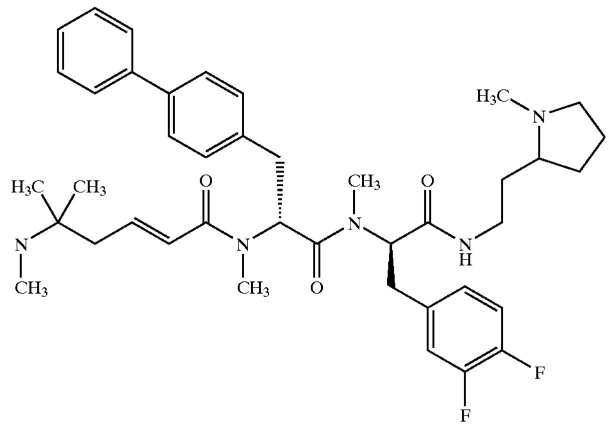 | 701.91 | | |
| 310 | 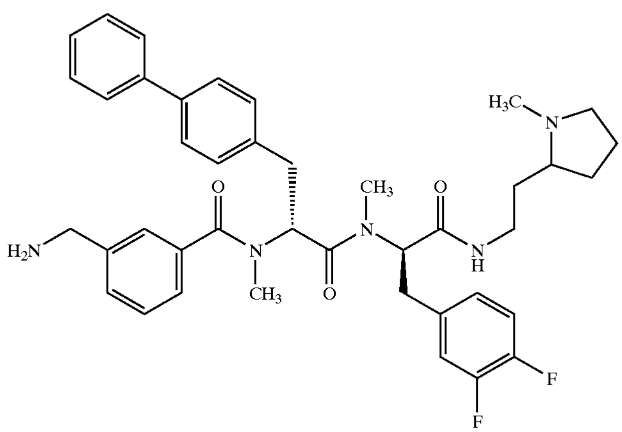 | 695.86 | | |
| 311 | 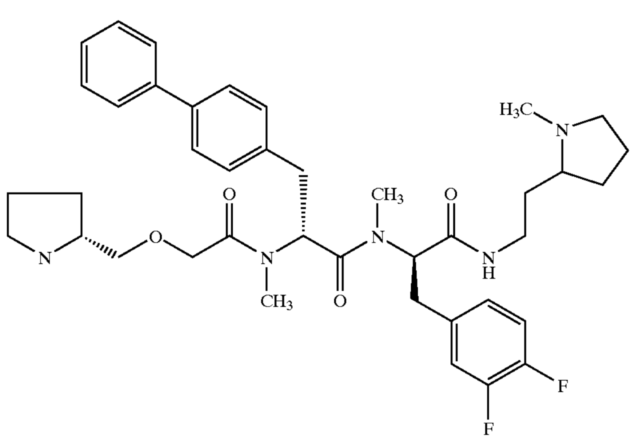 | 703.88 | | |

TABLE 2-continued

| Example | Structure | MW | HPLC | LC-MS |
|---|---|---|---|---|
| 312 | 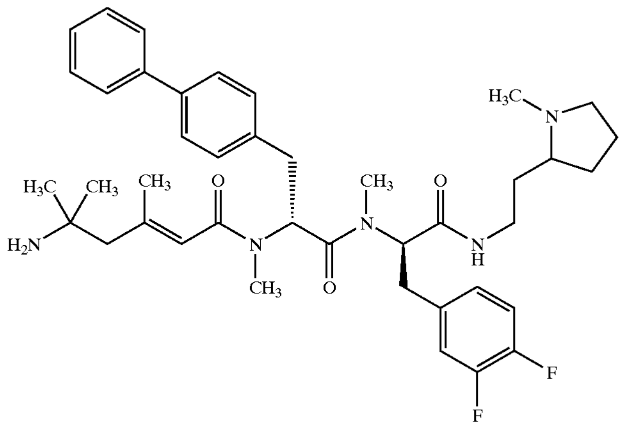 | 701.91 | | |
| 313 | 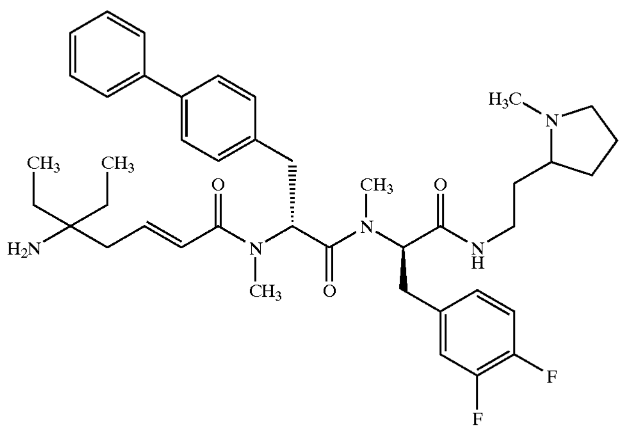 | 715.94 | | |
| 314 | 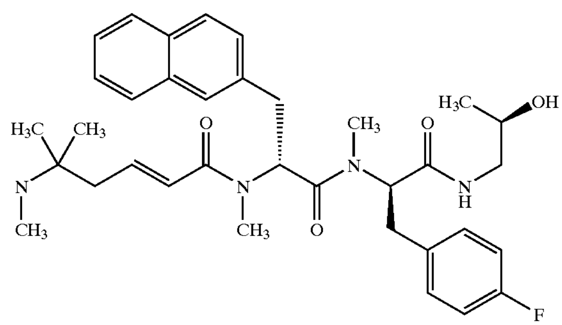 | 604.77 | | |
| 315 | 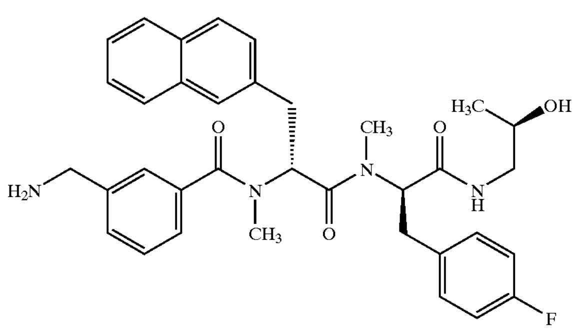 | 598.72 | | |

| Example | Structure | MW | HPLC | LC-MS |
|---------|-----------|-----|------|-------|
| 316 | 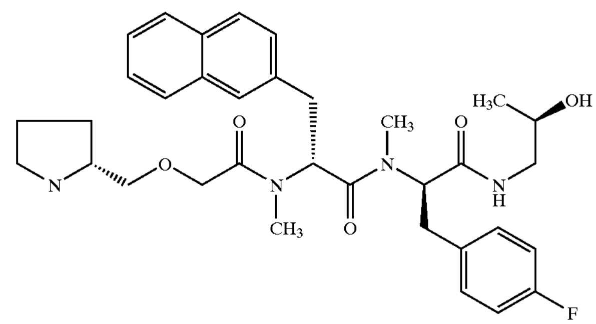 | 606.74 | | |
| 317 | 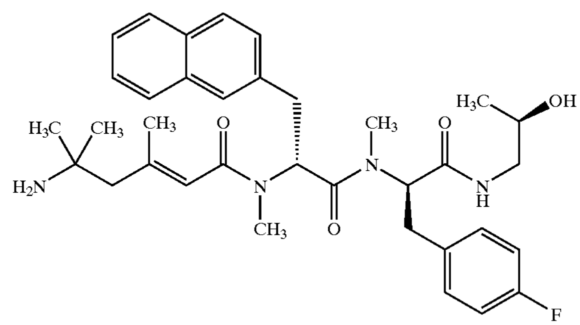 | 604.77 | | |
| 318 | 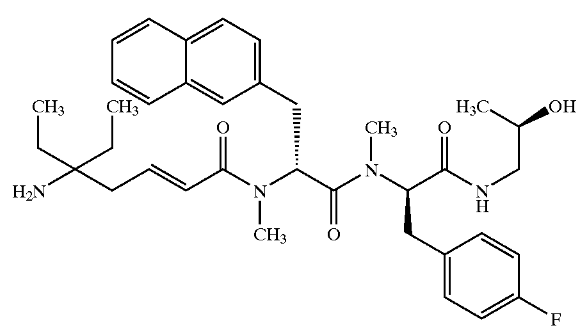 | 618.80 | | |
| 319 | 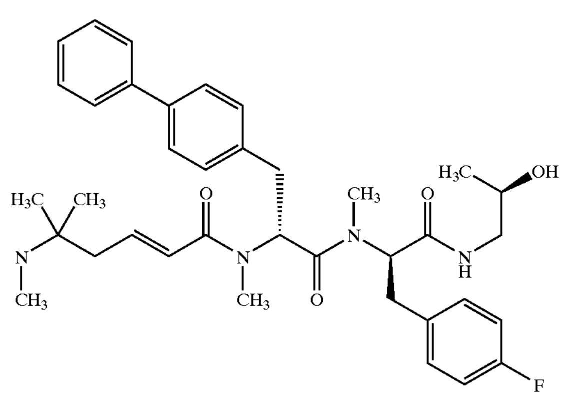 | 630.81 | | |

TABLE 2-continued

| Example | Structure | MW | HPLC | LC-MS |
|---|---|---|---|---|
| 320 | 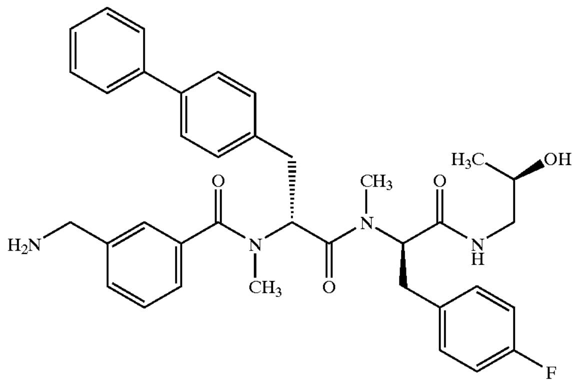 | 624.76 | | |
| 321 | 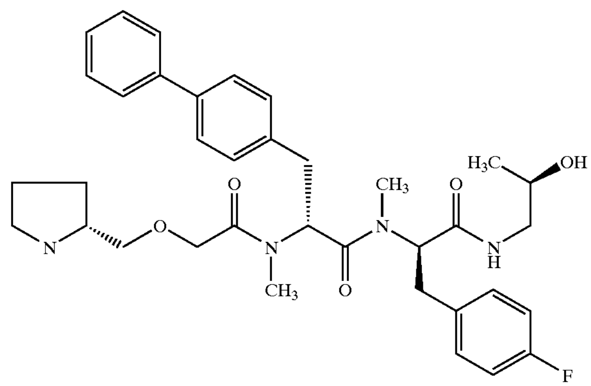 | 632.78 | | |
| 322 | 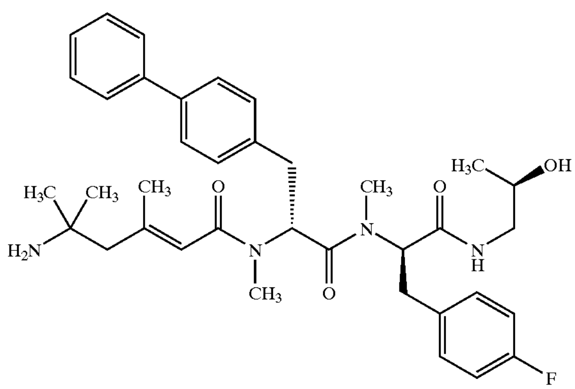 | 630.81 | | |
| 323 | 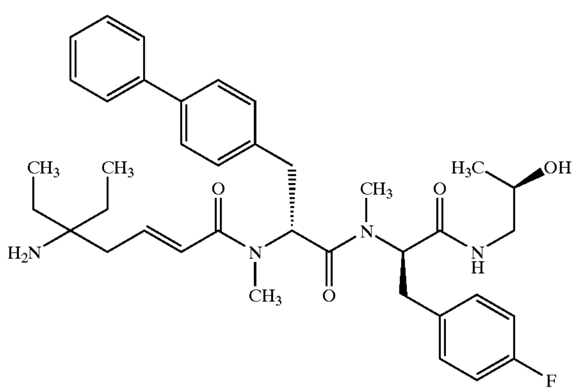 | 644.84 | | |

TABLE 2-continued

| Example | Structure | MW | HPLC | LC-MS |
|---|---|---|---|---|
| 324 | 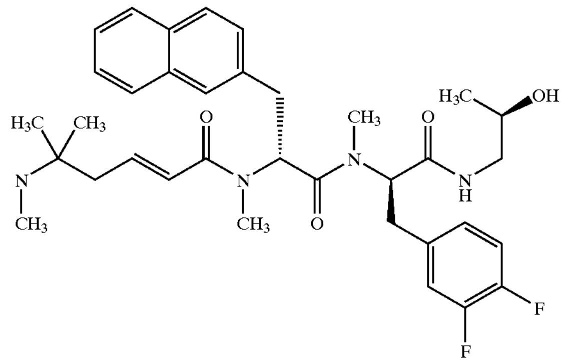 | 622.76 | | |
| 325 | 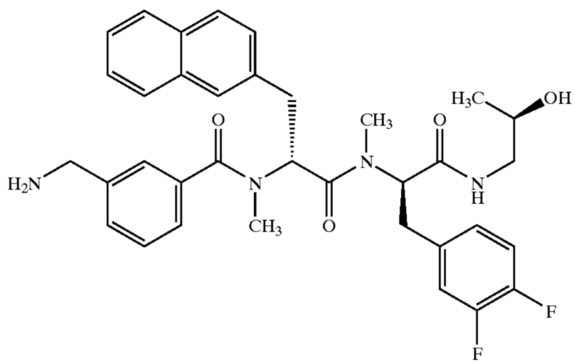 | 616.71 | | |
| 326 | 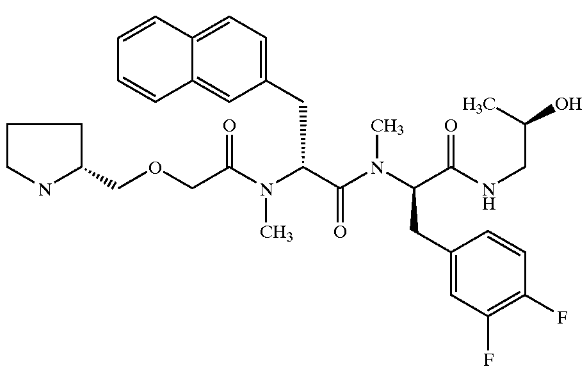 | 624.73 | | |
| 327 | 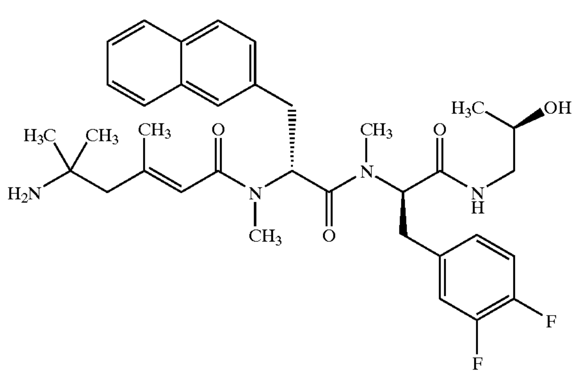 | 622.76 | | |

TABLE 2-continued

| Example | Structure | MW | HPLC | LC-MS |
| --- | --- | --- | --- | --- |
| 328 | 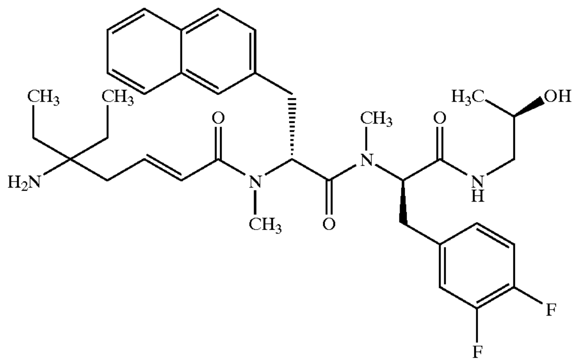 | 636.79 | | |
| 329 | 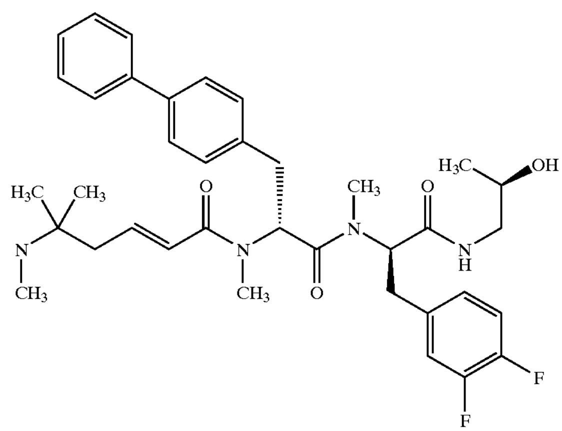 | 648.80 | | |
| 330 | 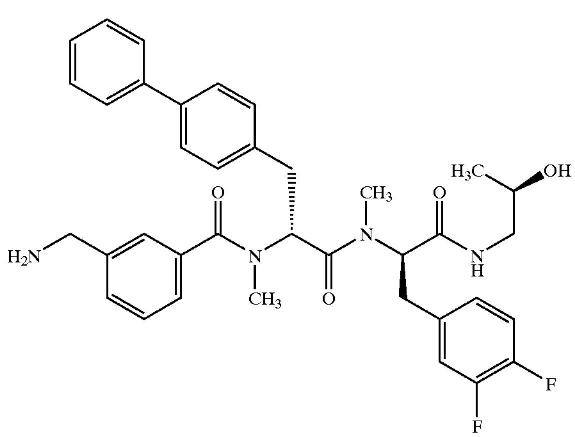 | 642.75 | | |

TABLE 2-continued

| Example | Structure | MW | HPLC | LC-MS |
|---|---|---|---|---|
| 331 | 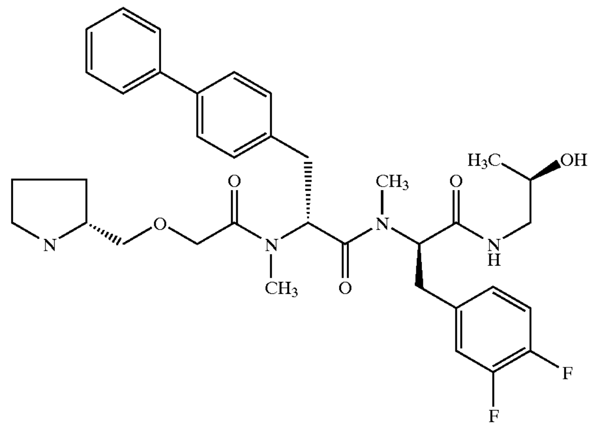 | 650.77 | | |
| 332 | 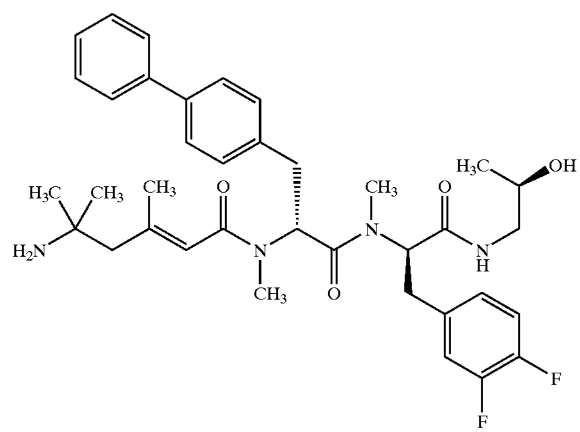 | 648.80 | | |
| 333 | 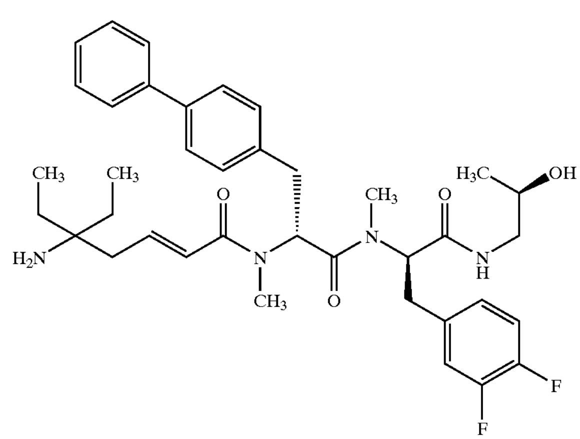 | 662.83 | | |

TABLE 2-continued

| Example | Structure | MW | HPLC | LC-MS |
|---------|-----------|----|----|----|
| 334 | 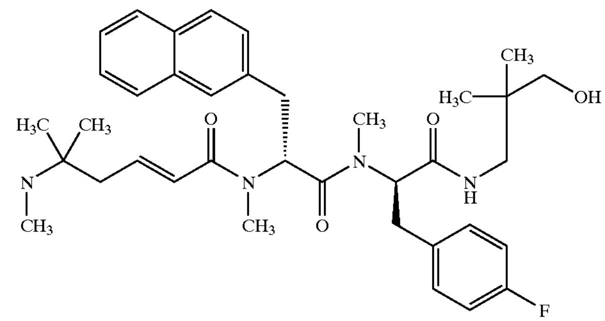 | 632.83 | | |
| 335 | 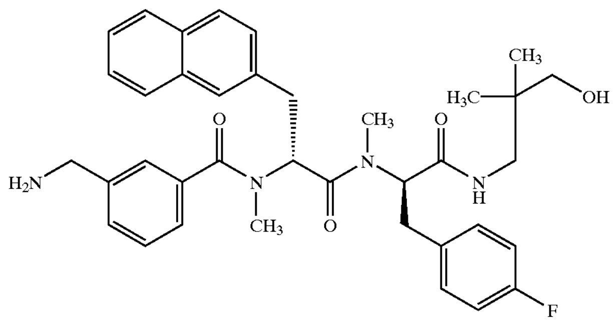 | 626.78 | | |
| 336 | 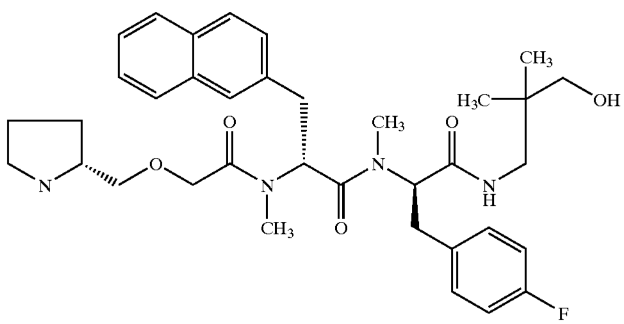 | 634.80 | | |
| 337 | 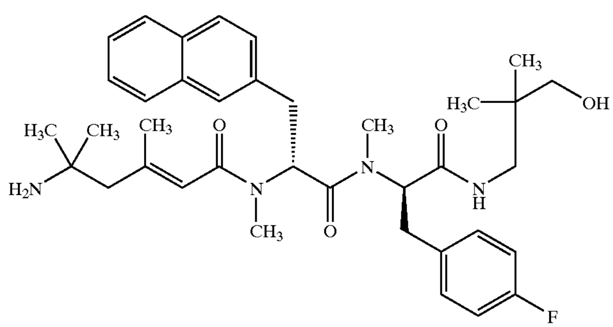 | 632.83 | | |

TABLE 2-continued
| Example | Structure | MW | HPLC | LC-MS |
|---|---|---|---|---|
| 338 | 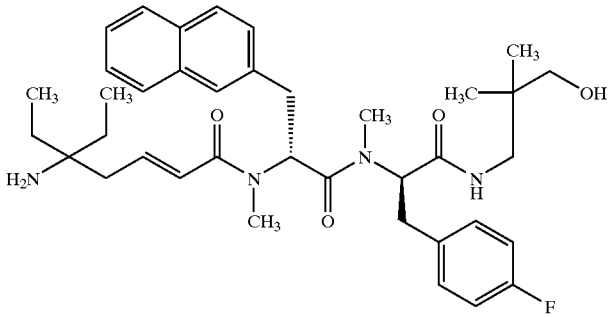 | 646.85 | | |
| 339 | 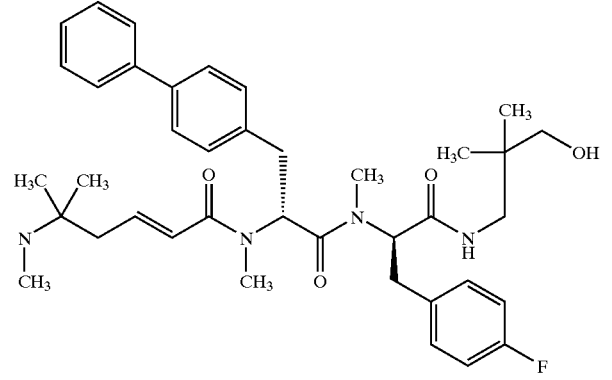 | 658.86 | | |
| 340 | 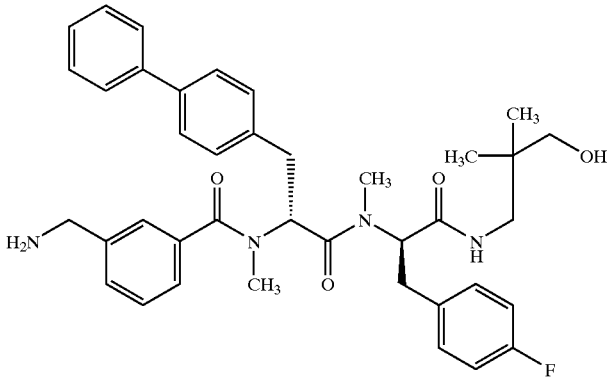 | 652.82 | | |
| 341 | 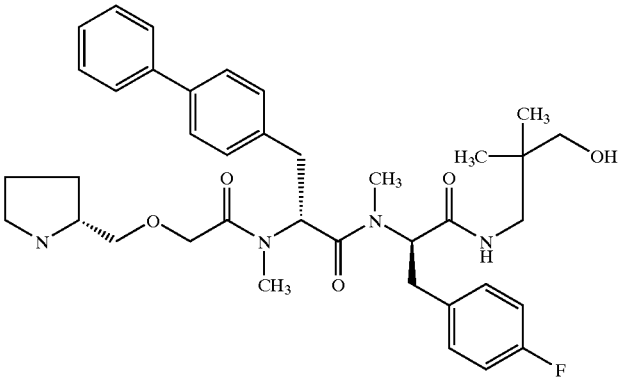 | 660.84 | | |

TABLE 2-continued

| Example | Structure | MW | HPLC | LC-MS |
|---|---|---|---|---|
| 342 | 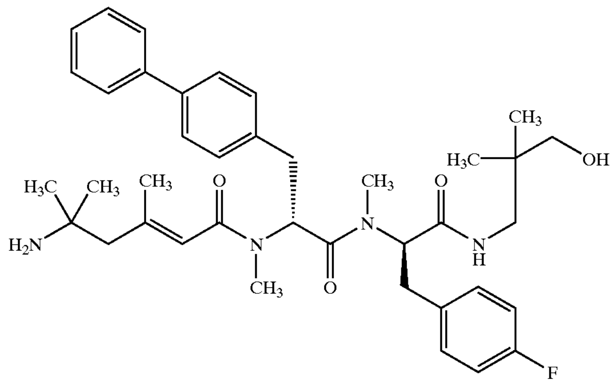 | 658.86 | | |
| 343 | 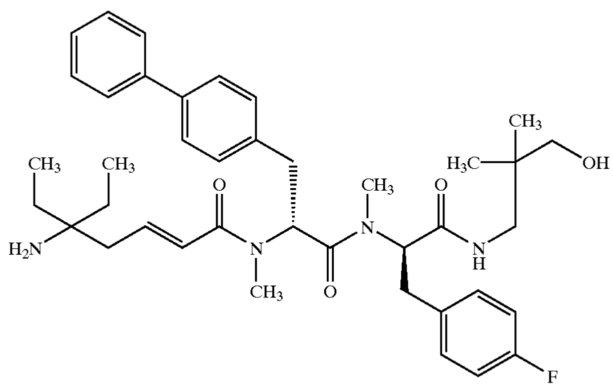 | 672.89 | | |
| 344 | 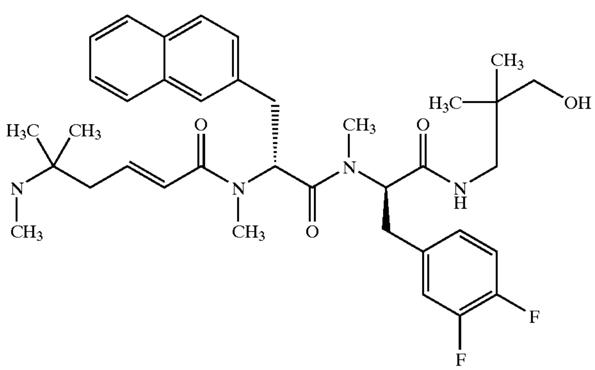 | 650.82 | | |
| 345 | 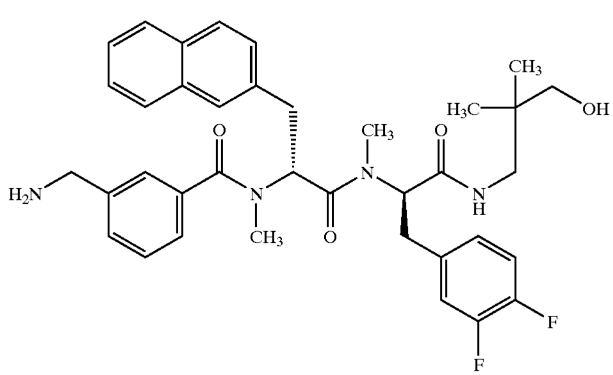 | 644.77 | | |

TABLE 2-continued

| Example | Structure | MW | HPLC | LC-MS |
|---|---|---|---|---|
| 346 | 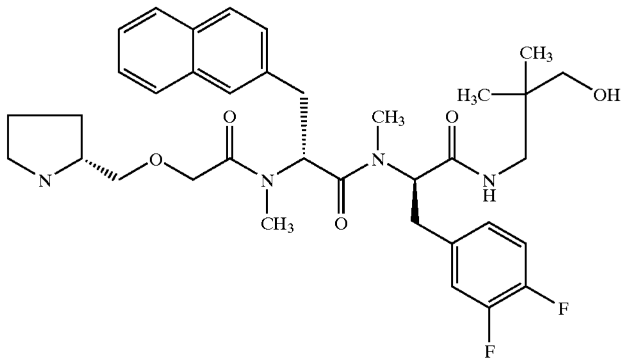 | 652.79 | | |
| 347 | 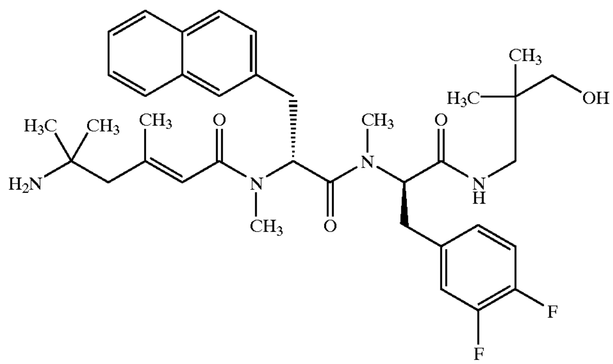 | 650.82 | | |
| 348 | 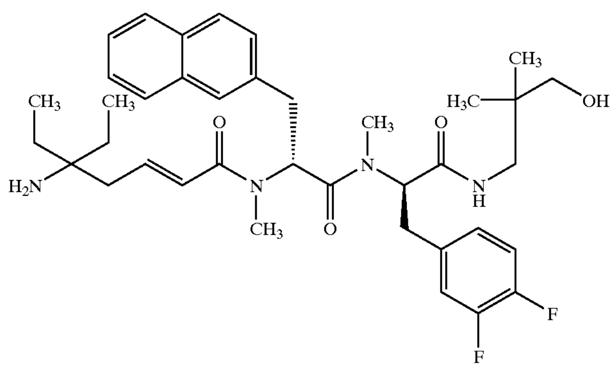 | 664.84 | | |
| 349 | 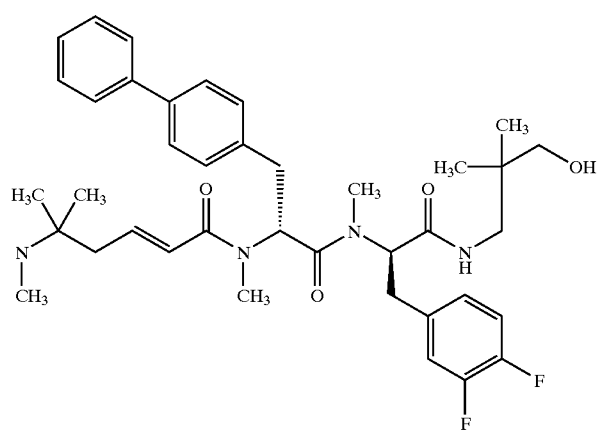 | 676.85 | | |

TABLE 2-continued

| Example | Structure | MW | HPLC | LC-MS |
|---|---|---|---|---|
| 350 | 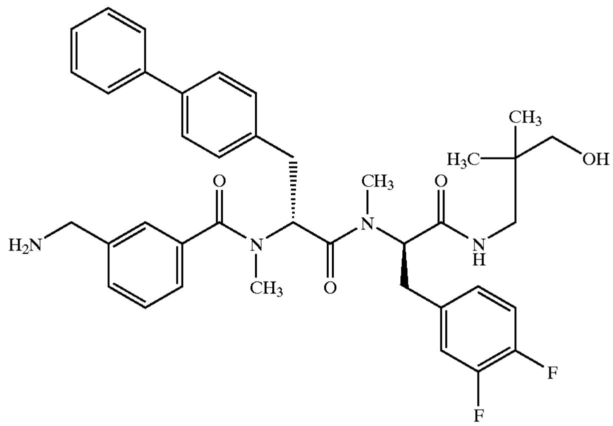 | 670.81 | | |
| 351 | 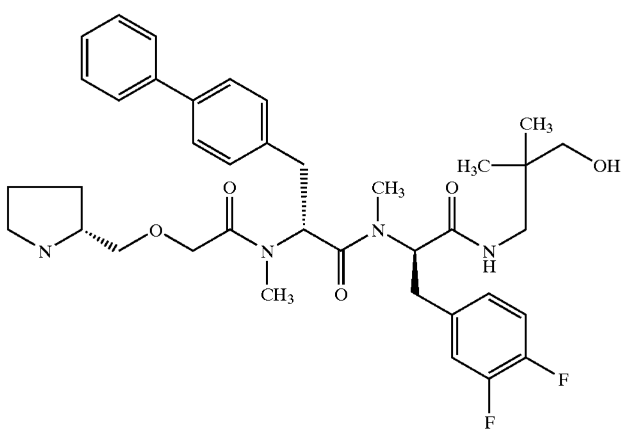 | 678.83 | | |
| 352 | 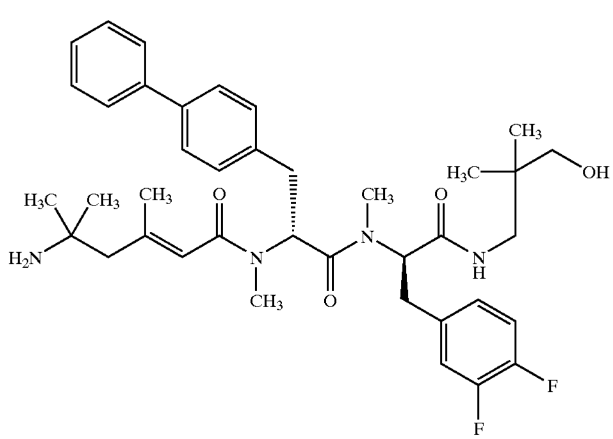 | 676.85 | | |

TABLE 2-continued

| Example | Structure | MW | HPLC | LC-MS |
|---|---|---|---|---|
| 353 | 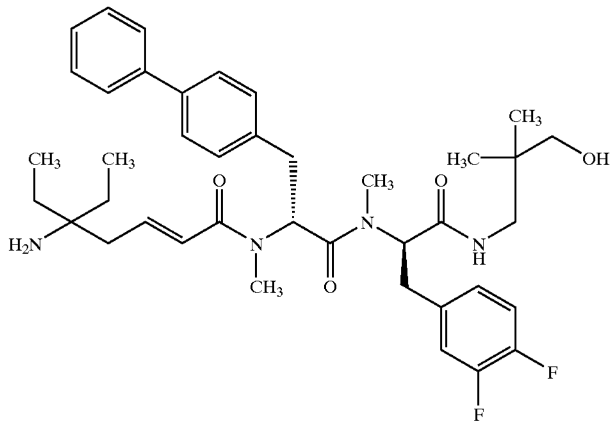 | 690.88 | | |

TABLE 3

| Example | Structure | MW | HPLC | LC-MS |
|---|---|---|---|---|
| 354 | 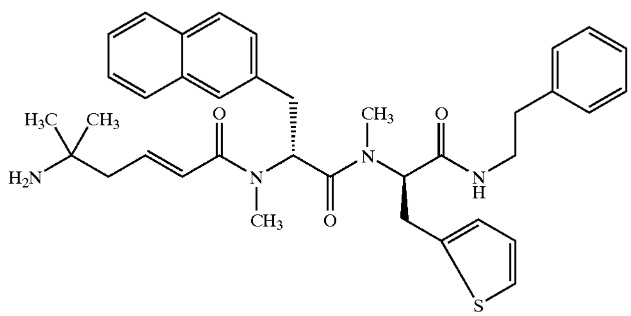 | 624.9 | | |
| 355 | 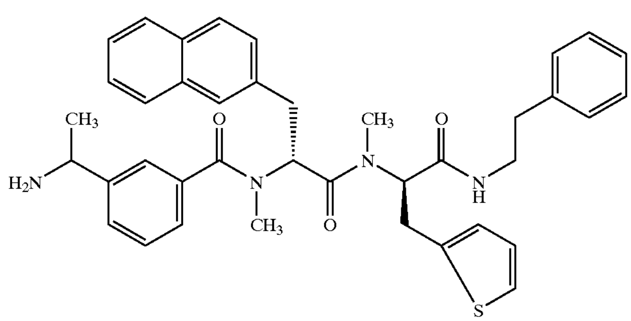 | 646.9 | | |
| 356 | 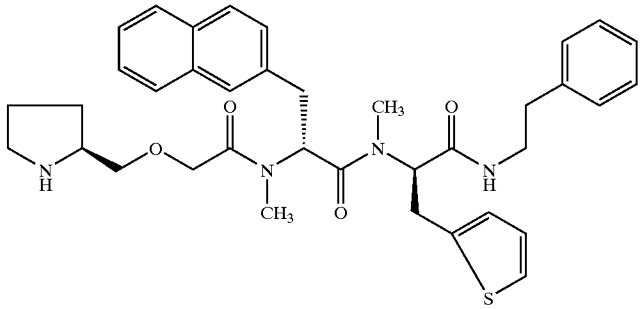 | 640.9 | | |

TABLE 3-continued

| Example | Structure | MW | HPLC | LC-MS |
|---|---|---|---|---|
| 357 | 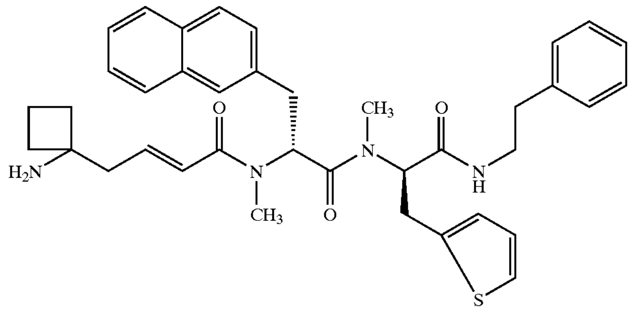 | 636.9 | | |
| 358 | 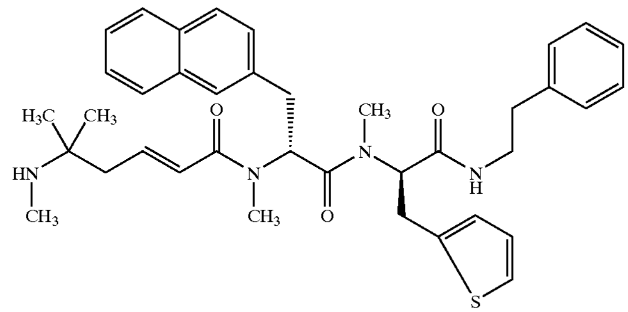 | 638.9 | | |
| 359 | 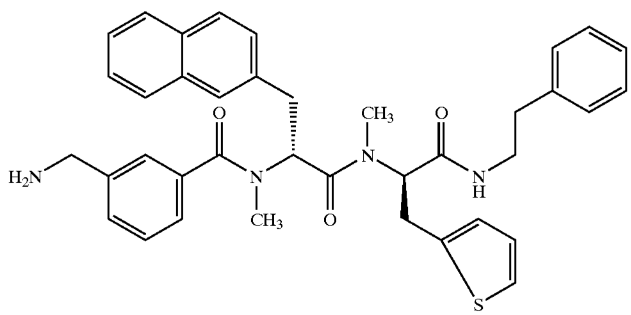 | 632.8 | | |
| 360 | 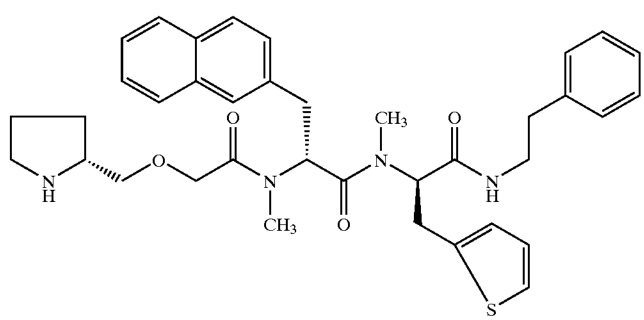 | 640.9 | | |
| 361 | 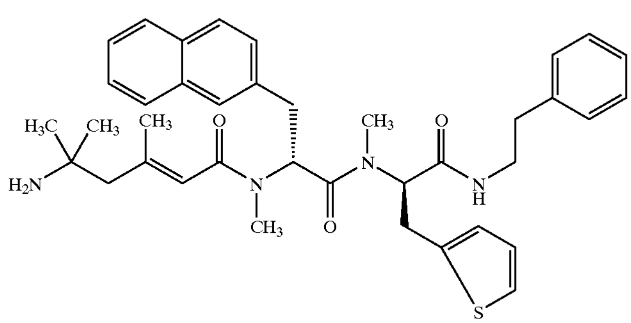 | 638.9 | | |

TABLE 3-continued
| Example | Structure | MW | HPLC | LC-MS |
|---|---|---|---|---|
| 362 | 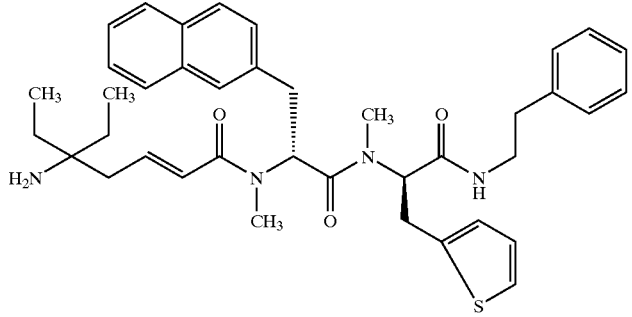 | 652.9 | | |
| 363 | 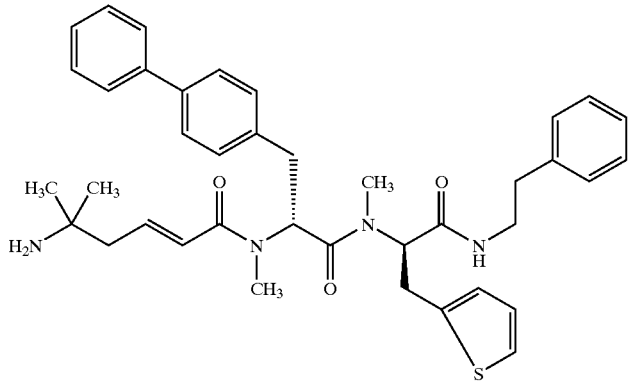 | 650.9 | | |
| 364 | 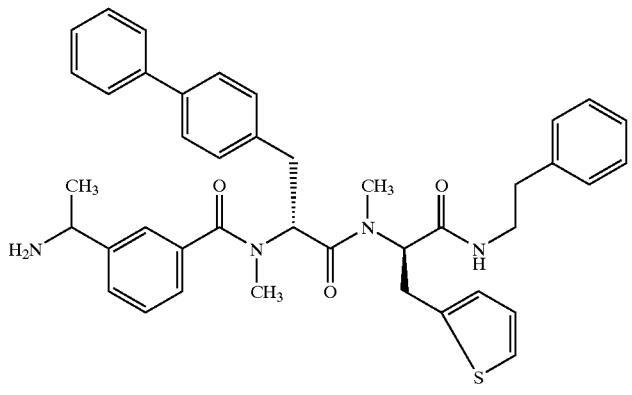 | 672.9 | | |
| 365 | 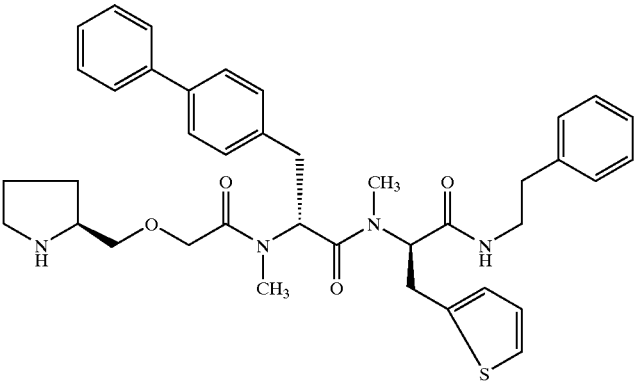 | 666.9 | | |

TABLE 3-continued

| Example | Structure | MW | HPLC | LC-MS |
|---|---|---|---|---|
| 366 | 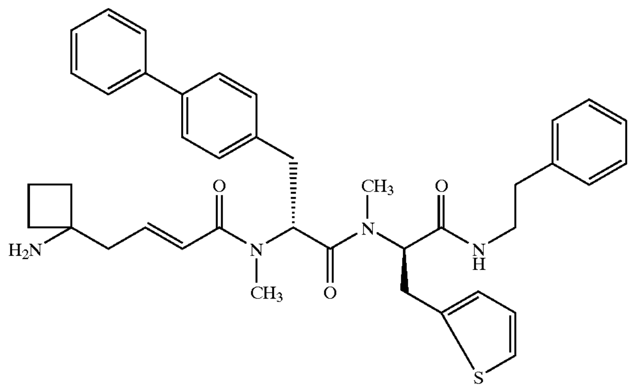 | 662.9 | | |
| 367 | 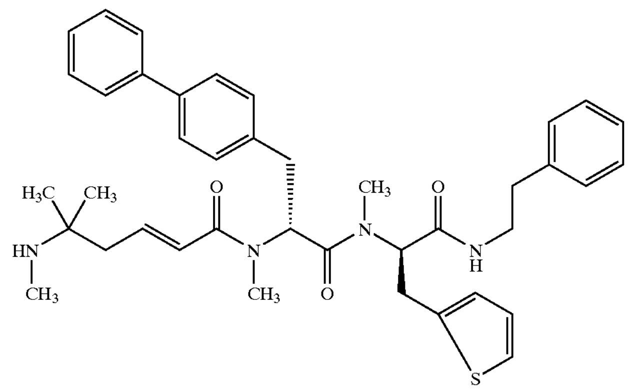 | 664.9 | | |
| 368 | 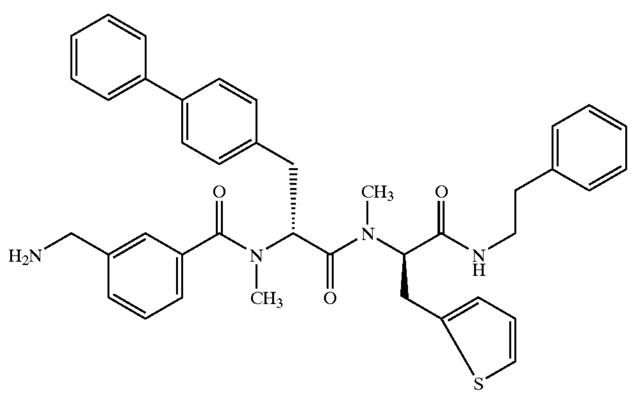 | 658.9 | | |
| 369 | 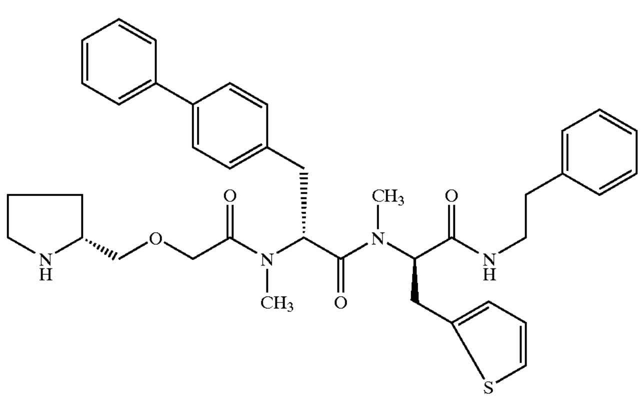 | 666.9 | | |

TABLE 3-continued
| Example | Structure | MW | HPLC | LC-MS |
|---|---|---|---|---|
| 370 | 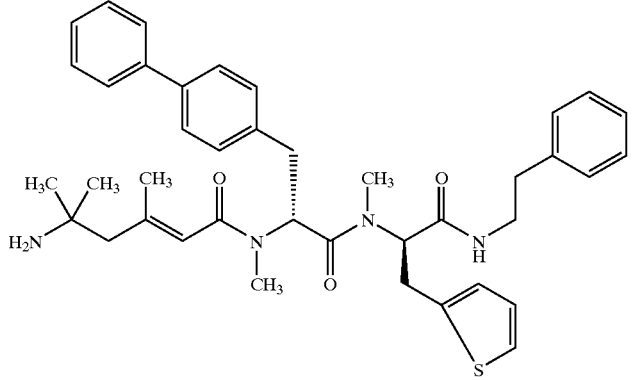 | 664.9 | | |
| 371 | 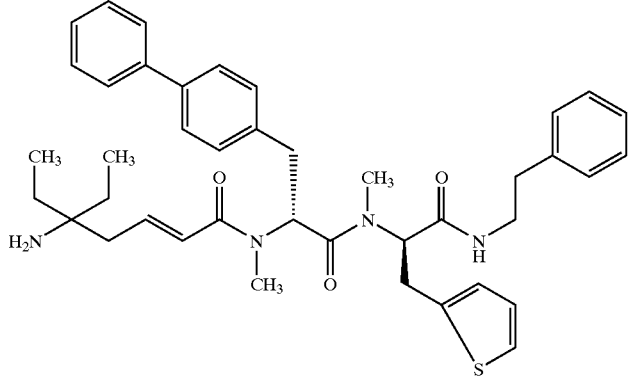 | 678.9 | | |
| 372 | 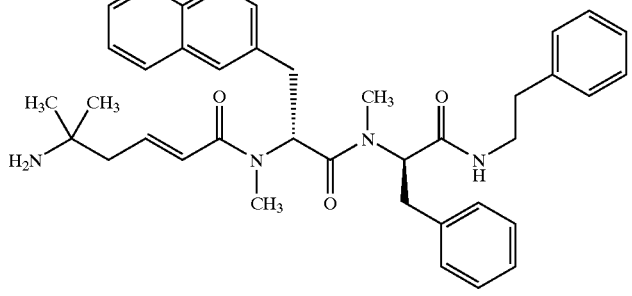 | 618.8 | | |
| 373 | 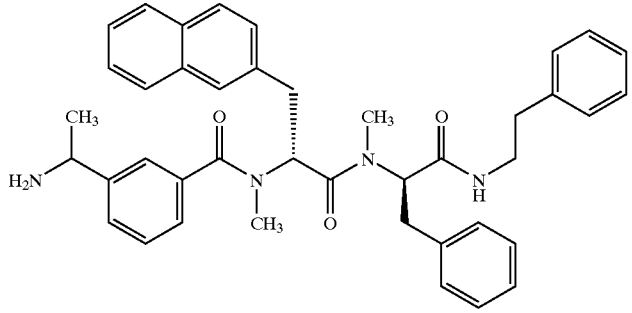 | 640.8 | | |

TABLE 3-continued

| Example | Structure | MW | HPLC | LC-MS |
|---|---|---|---|---|
| 374 | 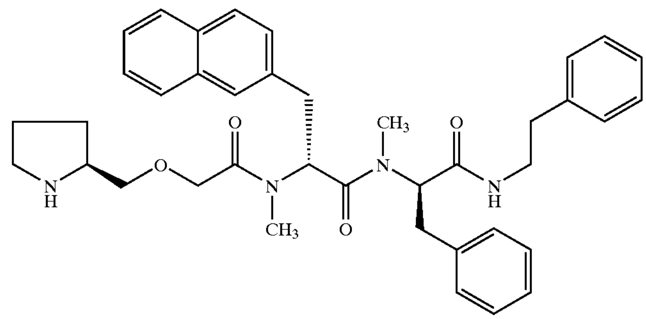 | 634.8 | | |
| 375 | 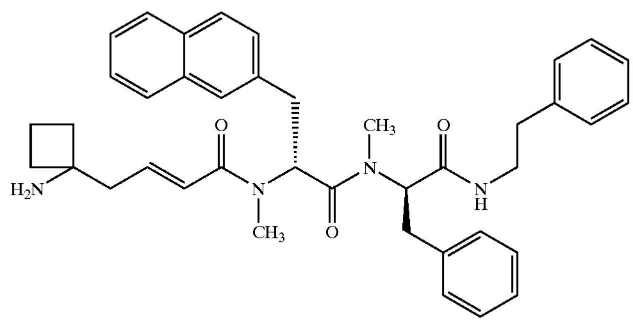 | 630.8 | | |
| 376 | 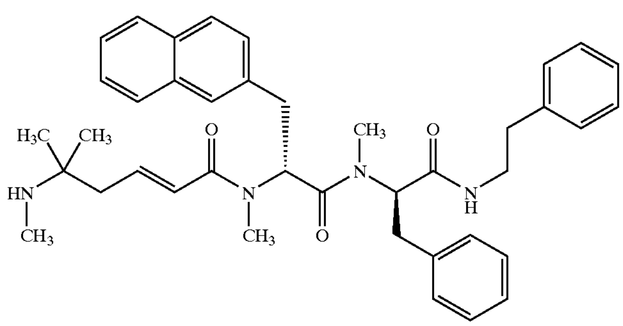 | 632.9 | | |
| 377 | 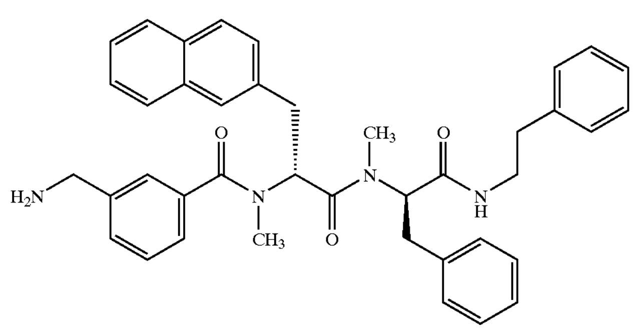 | 626.8 | | |

TABLE 3-continued
| Example | Structure | MW | HPLC | LC-MS |
|---|---|---|---|---|
| 378 | 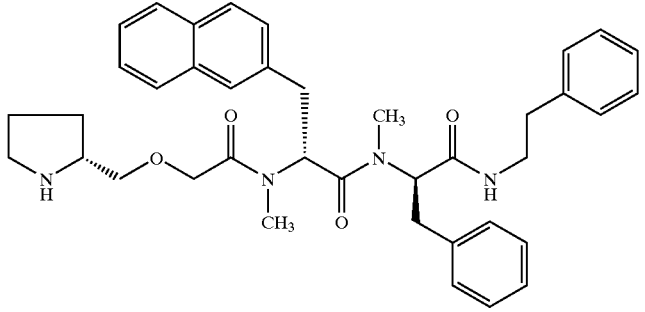 | 634.8 | | |
| 379 | 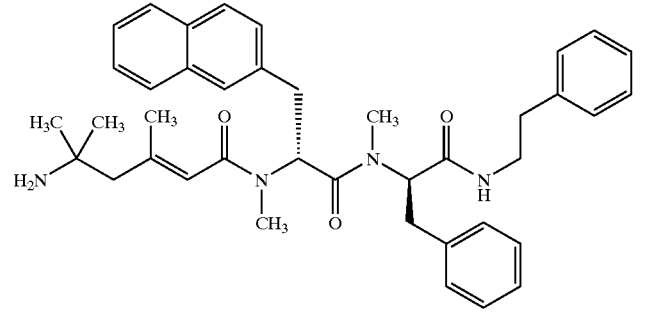 | 632.9 | | |
| 380 | 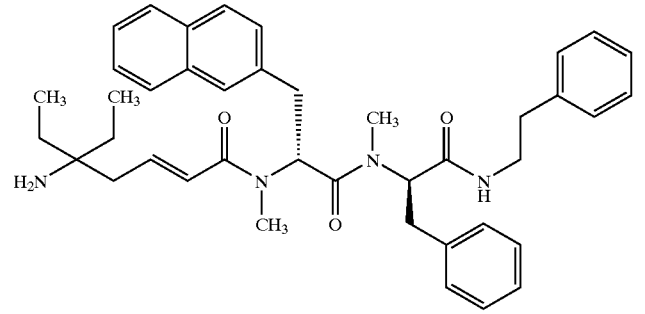 | 646.9 | | |
| 381 | 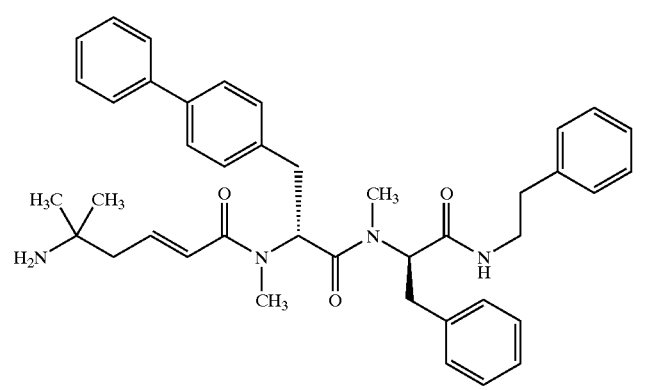 | 644.9 | | |

TABLE 3-continued

| Example | Structure | MW | HPLC | LC-MS |
|---|---|---|---|---|
| 382 | 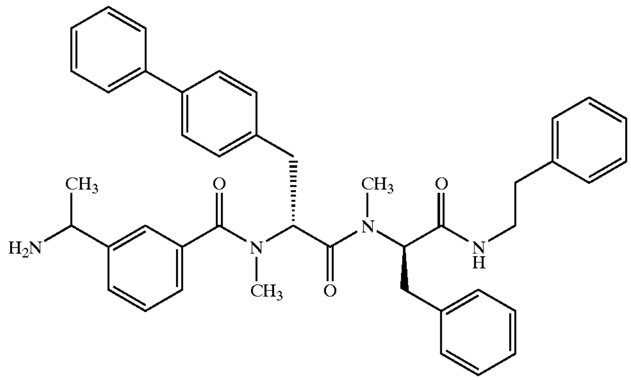 | 666.9 | | |
| 383 | 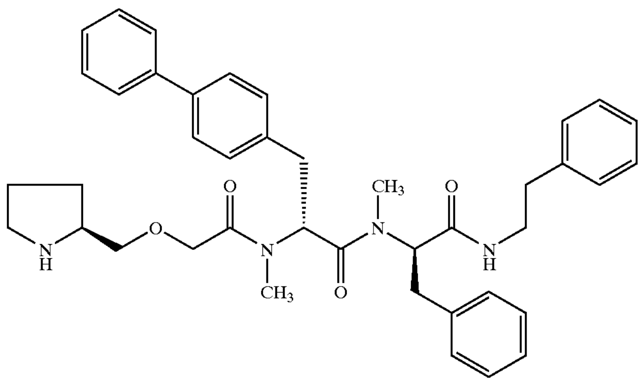 | 660.9 | | |
| 384 | 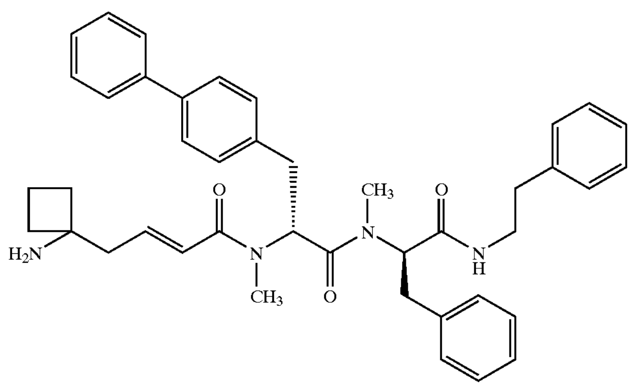 | 656.9 | | |
| 385 | 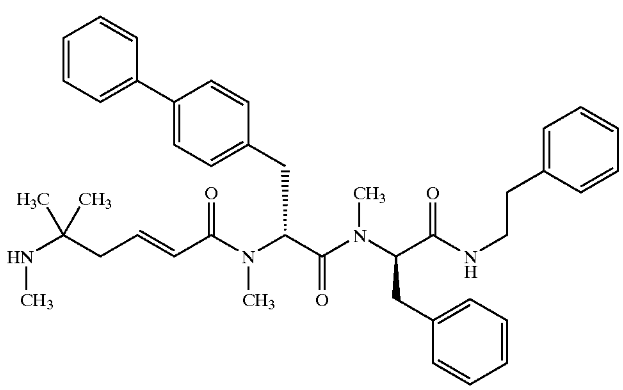 | 658.9 | | |

TABLE 3-continued

| Example | Structure | MW | HPLC | LC-MS |
|---|---|---|---|---|
| 386 | 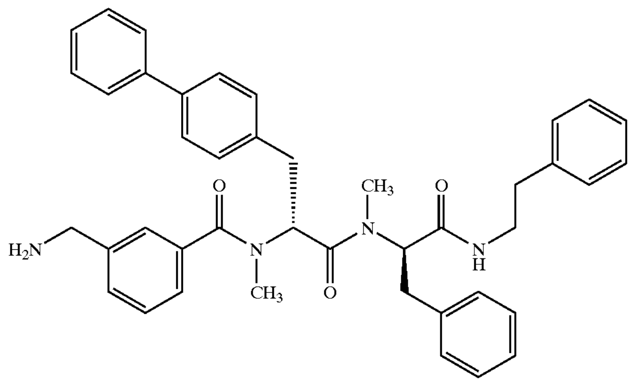 | 652.8 | | |
| 387 | 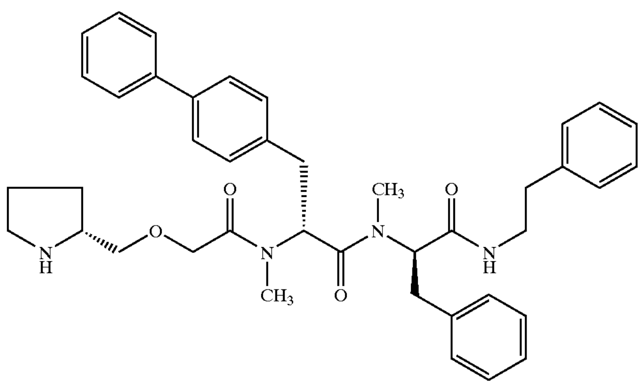 | 660.9 | | |
| 388 | 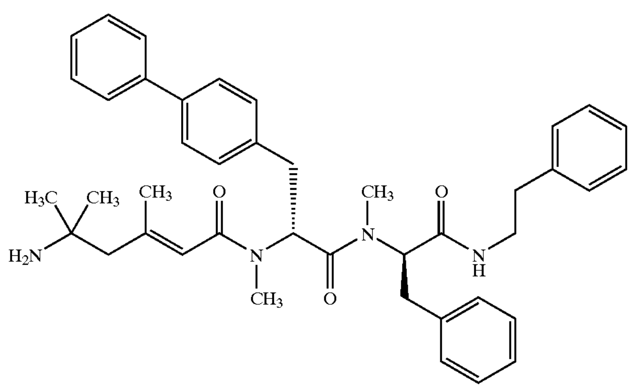 | 658.9 | | |
| 389 | 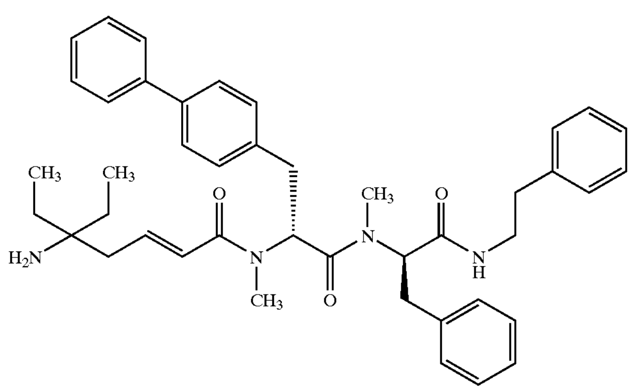 | 672.9 | | |

TABLE 3-continued
| Example | Structure | MW | HPLC | LC-MS |
|---|---|---|---|---|
| 390 | 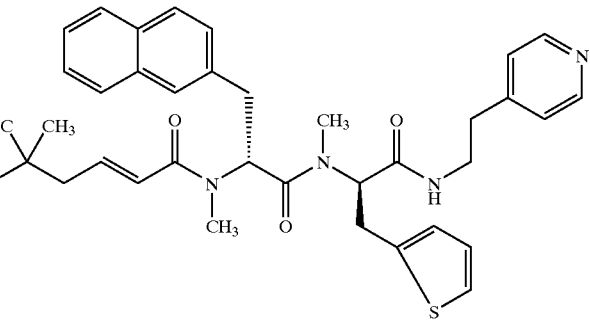 | 625.8 | | |
| 391 | 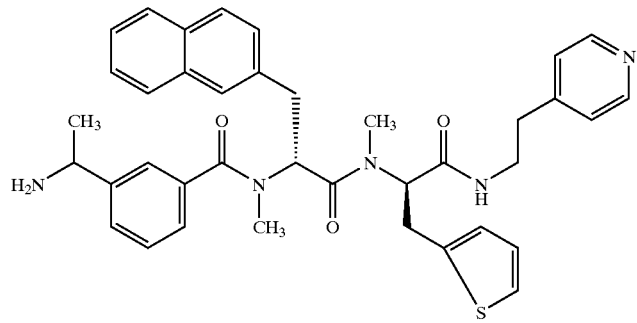 | 647.8 | | |
| 392 | 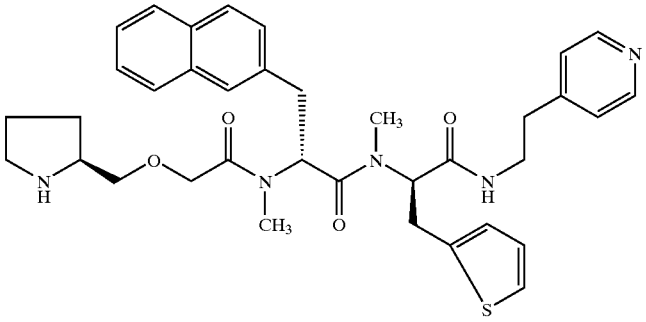 | 641.8 | | |
| 393 | 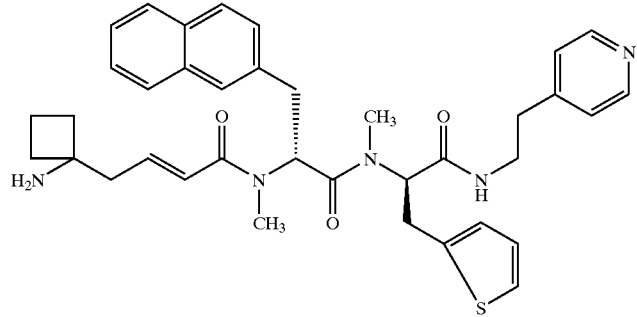 | 637.9 | | |

TABLE 3-continued
| Example | Structure | MW | HPLC | LC-MS |
|---|---|---|---|---|
| 394 | 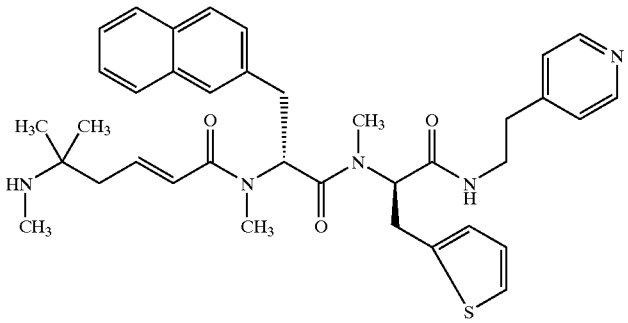 | 639.9 | | |
| 395 | 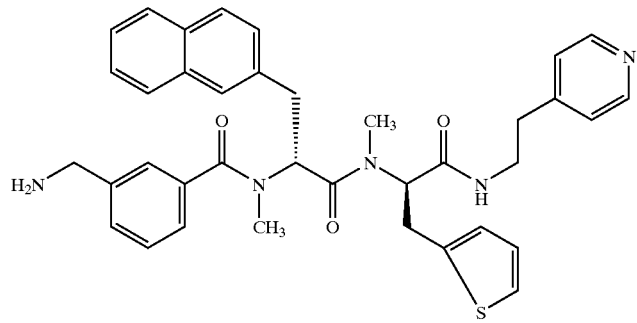 | 633.8 | | |
| 396 | 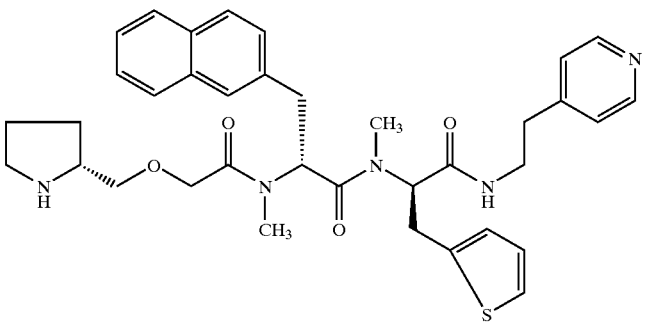 | 641.8 | | |
| 397 | 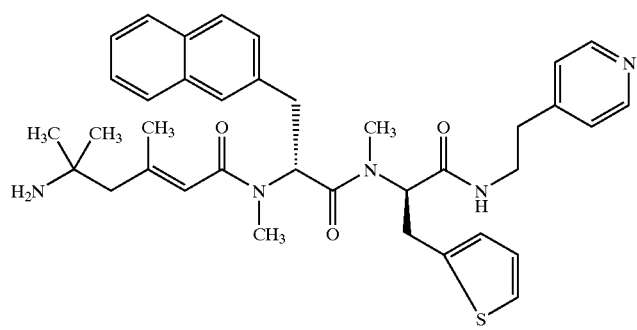 | 639.9 | | |

TABLE 3-continued

| Example | Structure | MW | HPLC | LC-MS |
|---|---|---|---|---|
| 398 | 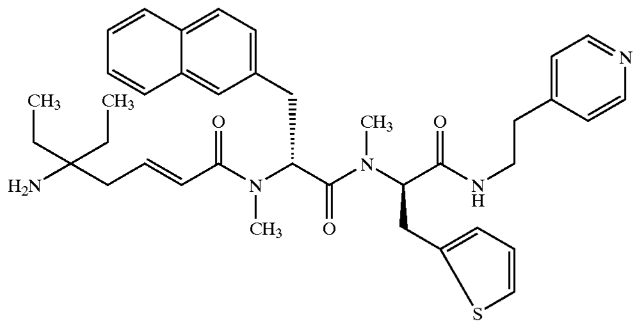 | 653.9 | | |
| 399 | 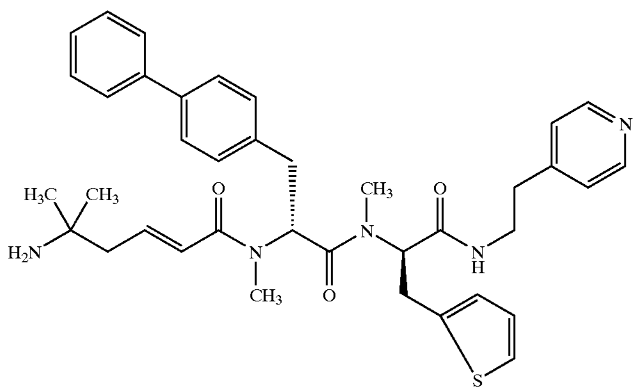 | 651.9 | | |
| 400 | 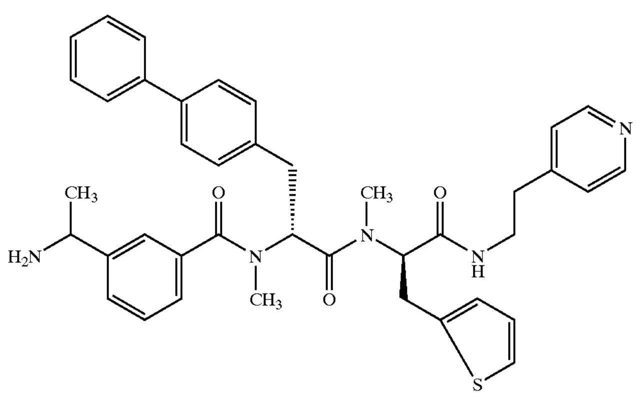 | 673.9 | | |
| 401 | 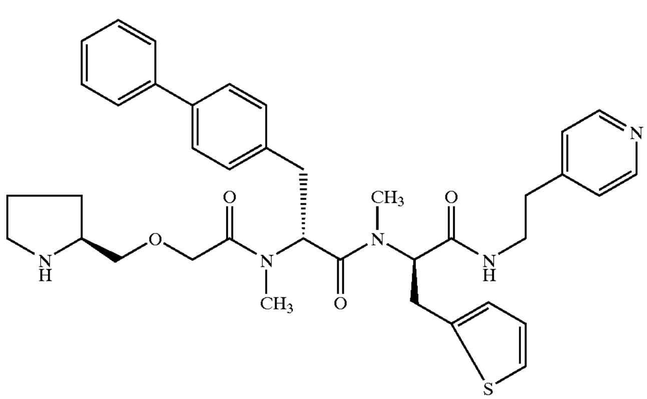 | 667.9 | | |

TABLE 3-continued

| Example | Structure | MW | HPLC | LC-MS |
|---|---|---|---|---|
| 402 | 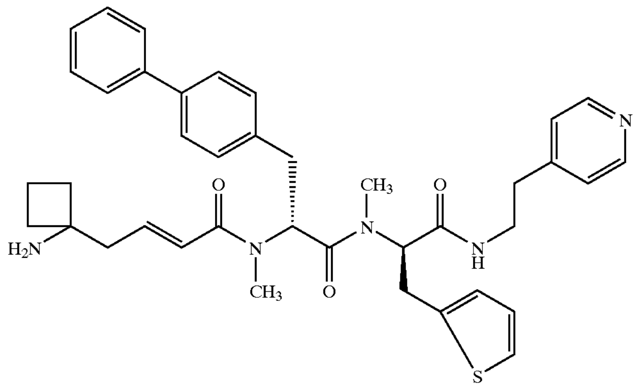 | 663.9 | | |
| 403 | 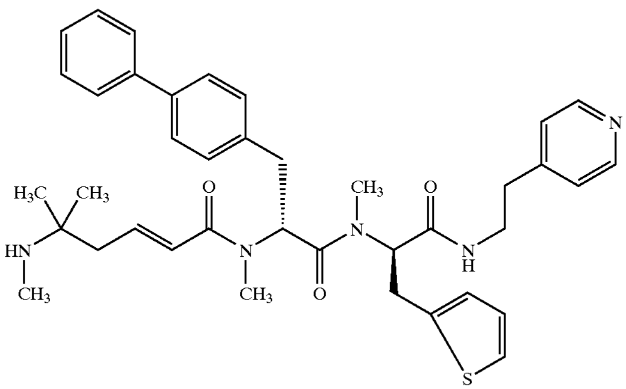 | 665.9 | | |
| 404 | 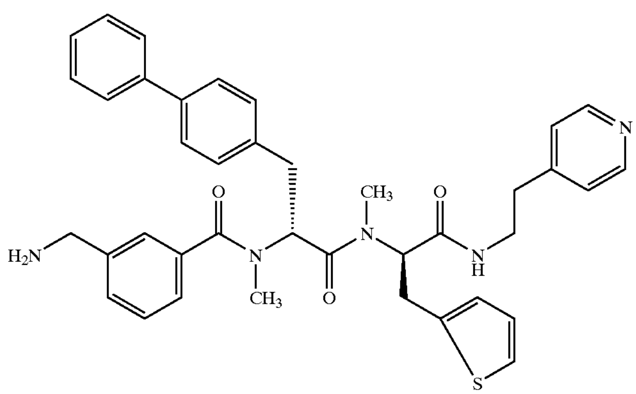 | 659.9 | | |
| 405 | 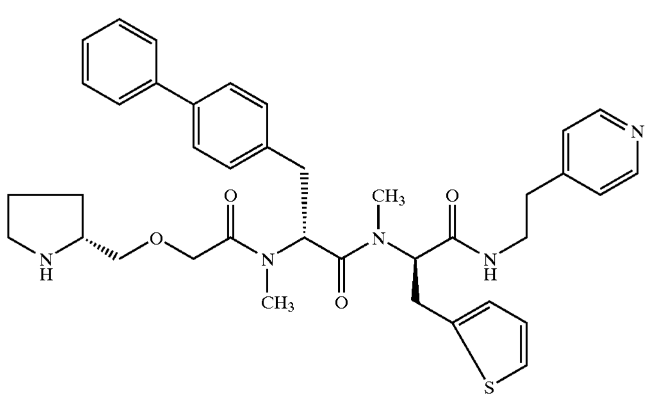 | 667.9 | | |

TABLE 3-continued

| Example | Structure | MW | HPLC | LC-MS |
|---|---|---|---|---|
| 406 | 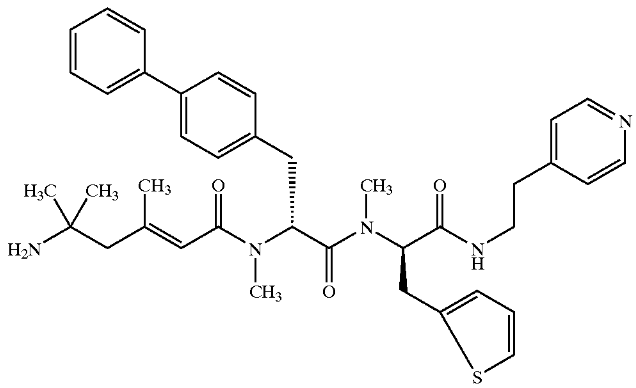 | 665.9 | | |
| 407 | 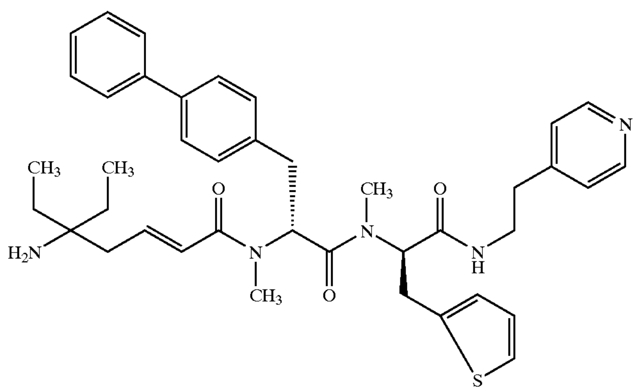 | 679.9 | | |
| 408 | 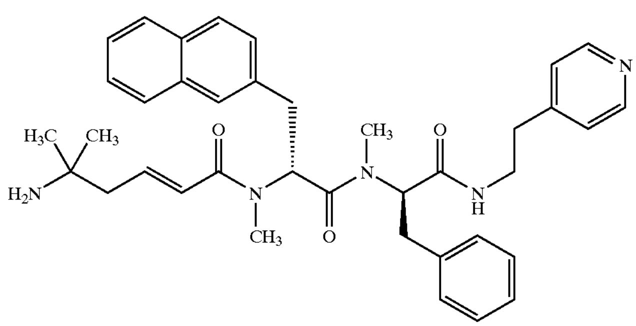 | 619.8 | | |
| 409 | 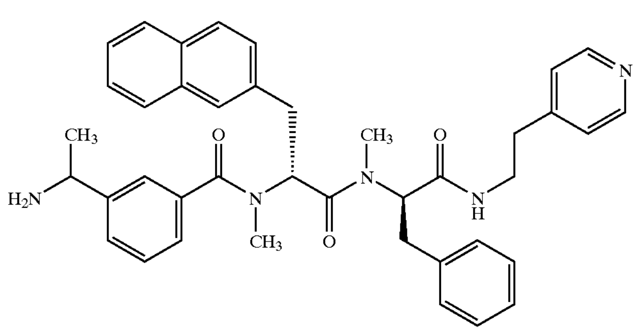 | 641.8 | | |

TABLE 3-continued

| Example | Structure | MW | HPLC | LC-MS |
|---|---|---|---|---|
| 410 | 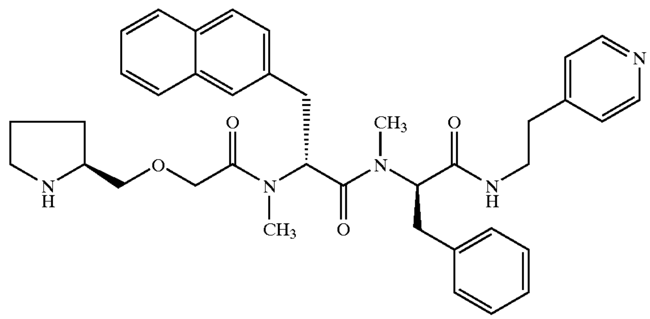 | 635.8 | | |
| 411 | 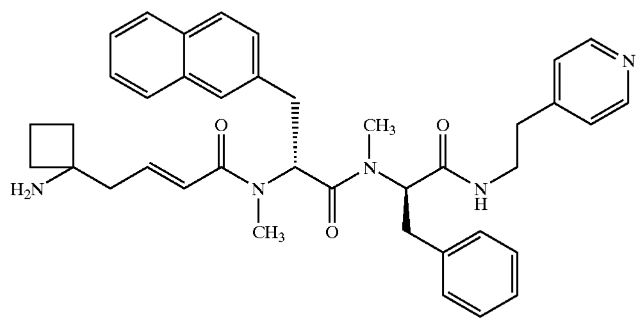 | 631.8 | | |
| 412 | 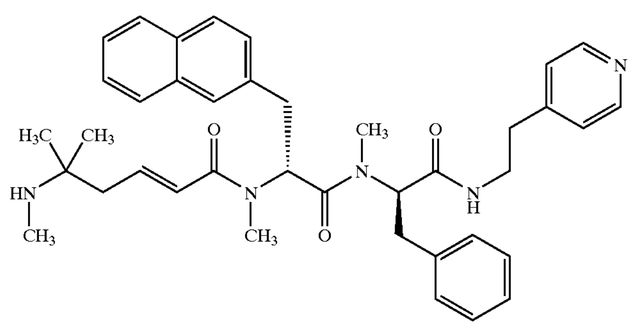 | 633.8 | | |
| 413 | 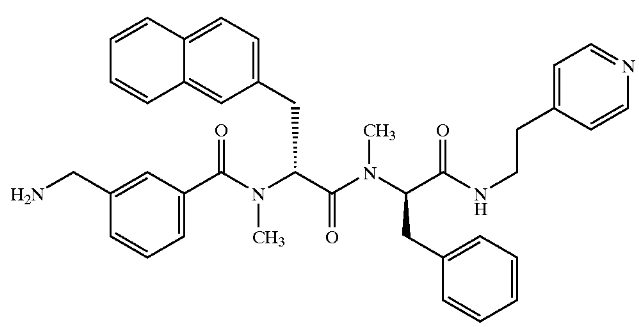 | 627.8 | | |

TABLE 3-continued

| Example | Structure | MW | HPLC | LC-MS |
|---|---|---|---|---|
| 414 | 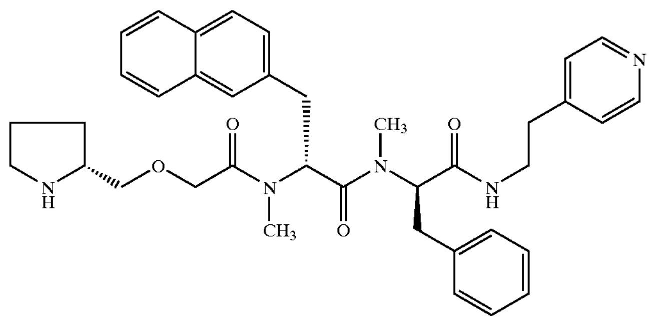 | 635.8 | | |
| 415 | 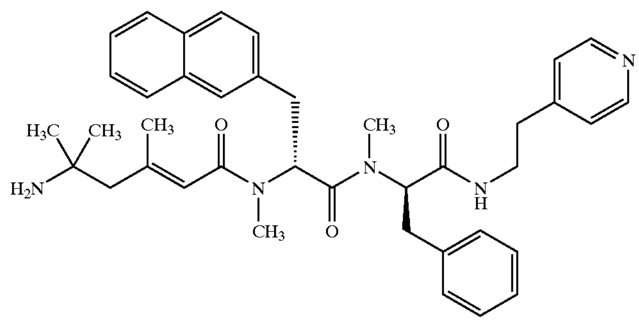 | 633.8 | | |
| 416 | 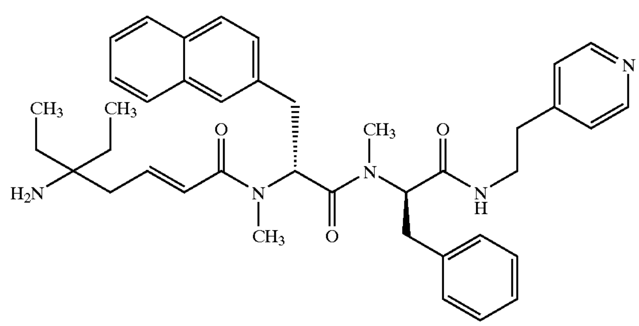 | 647.9 | | |
| 417 | 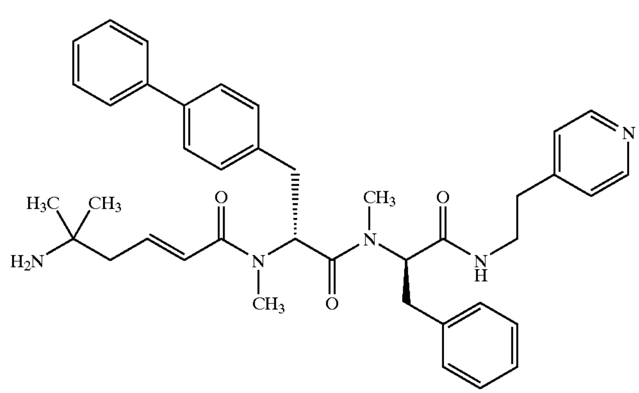 | 645.9 | | |

TABLE 3-continued

| Example | Structure | MW | HPLC | LC-MS |
|---|---|---|---|---|
| 418 | 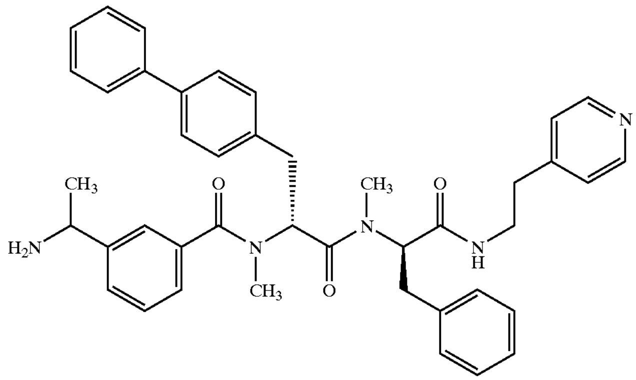 | 667.9 | | |
| 419 | 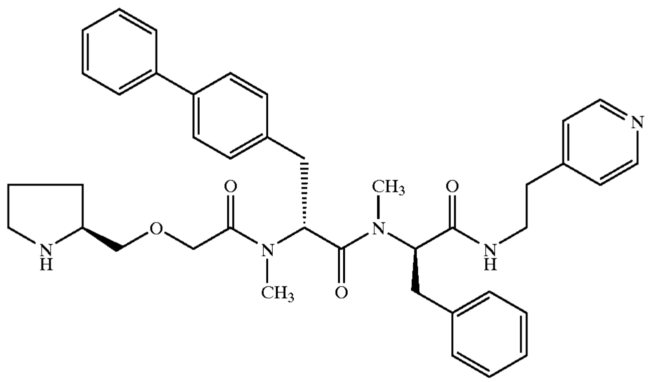 | 661.9 | | |
| 420 | 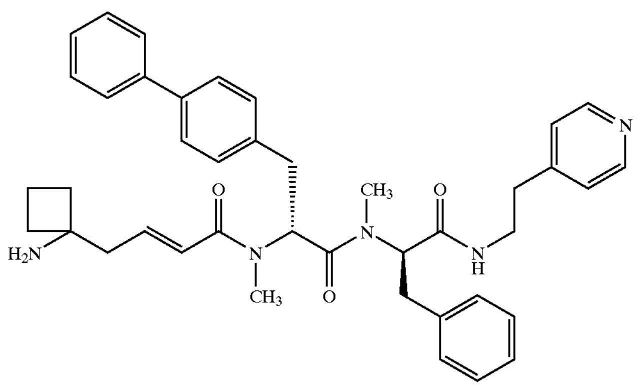 | 657.9 | | |
| 421 | 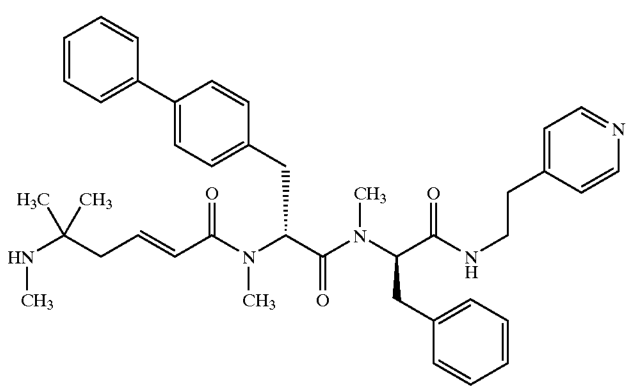 | 659.9 | | |

TABLE 3-continued

| Example | Structure | MW | HPLC | LC-MS |
|---|---|---|---|---|
| 422 | 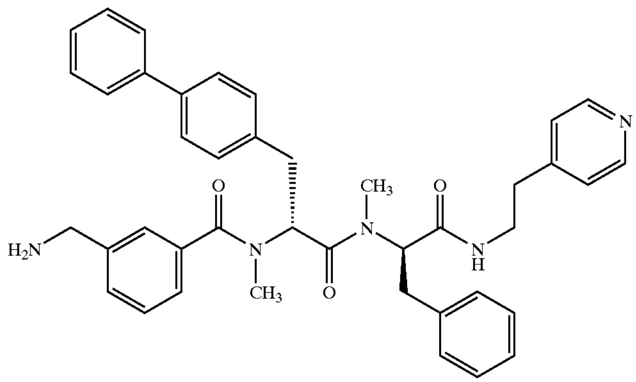 | 653.8 | | |
| 423 | 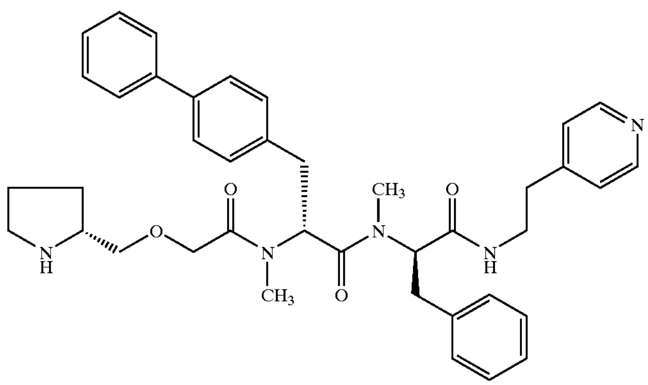 | 661.9 | | |
| 424 | 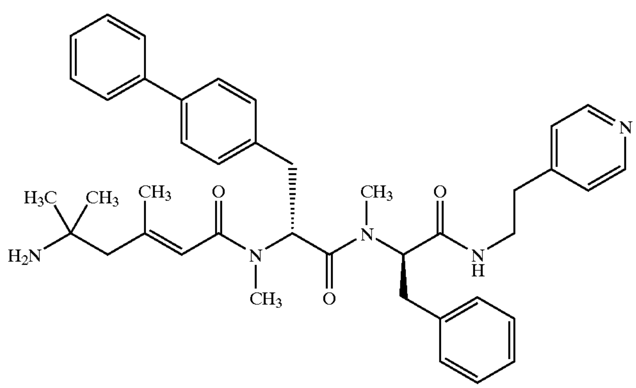 | 659.9 | | |
| 425 | 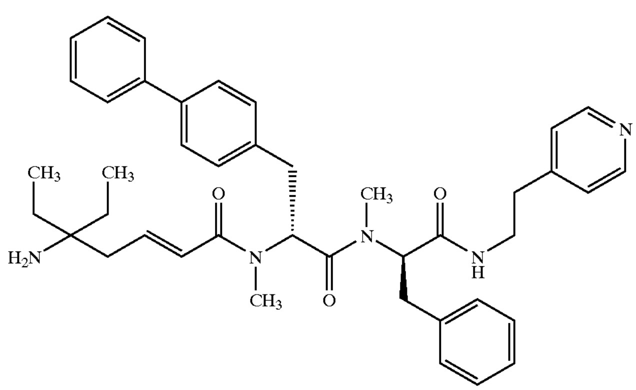 | 673.9 | | |

TABLE 3-continued

| Example | Structure | MW | HPLC | LC-MS |
|---------|-----------|----|----|----|
| 426 | 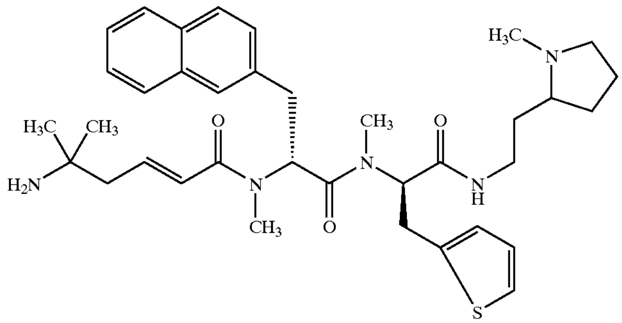 | 631.9 | | |
| 427 | 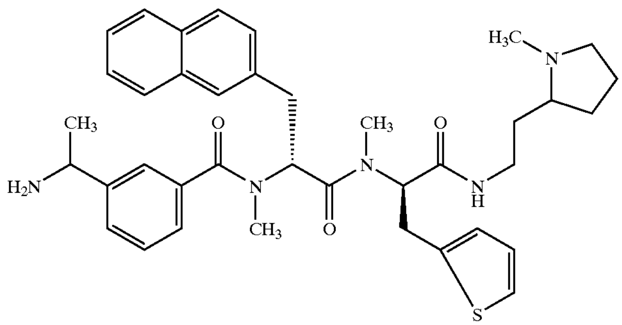 | 653.9 | | |
| 428 | 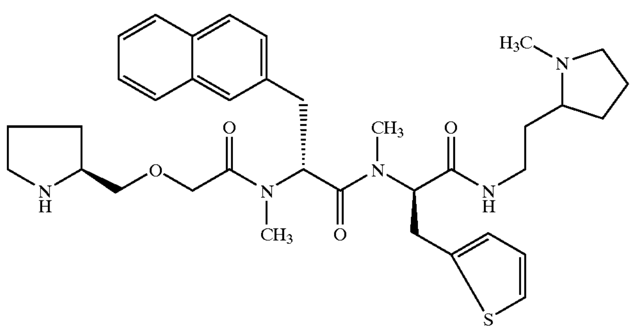 | 647.9 | | |
| 429 | 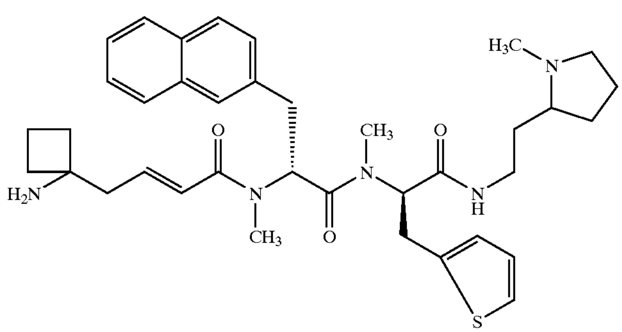 | 643.9 | | |

TABLE 3-continued

| Example | Structure | MW | HPLC | LC-MS |
|---|---|---|---|---|
| 430 | 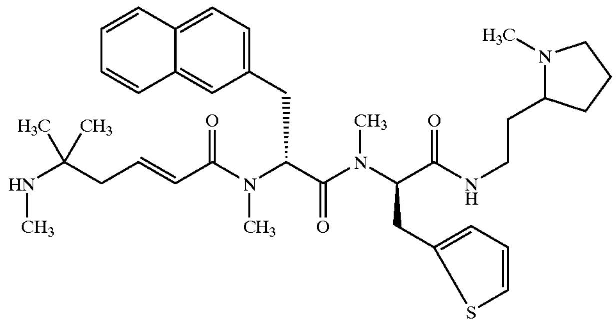 | 645.9 | | |
| 431 | 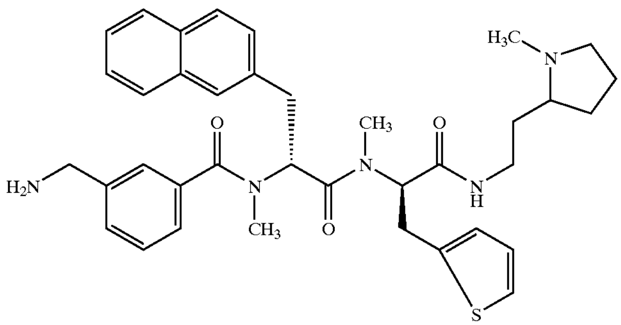 | 639.9 | | |
| 432 | 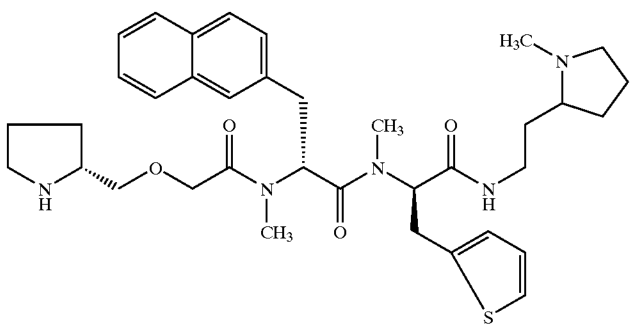 | 647.9 | | |
| 433 | 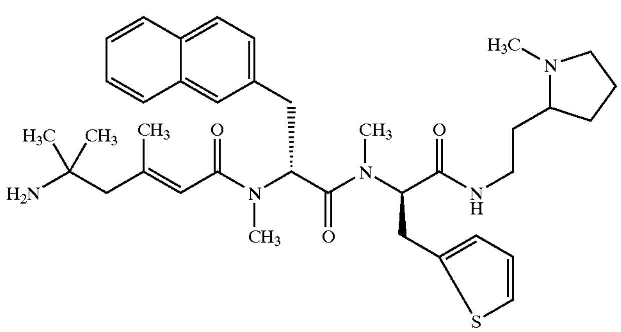 | 645.9 | | |

TABLE 3-continued
| Example | Structure | MW | HPLC | LC-MS |
|---|---|---|---|---|
| 434 | 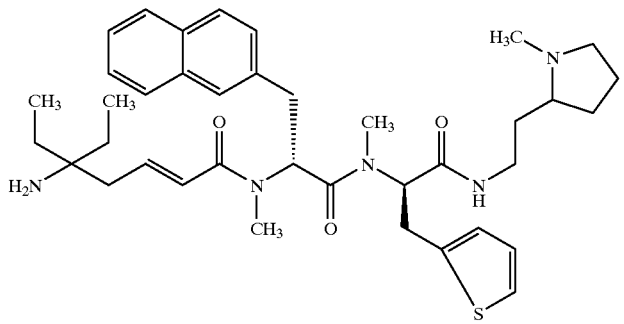 | 659.9 | | |
| 435 | 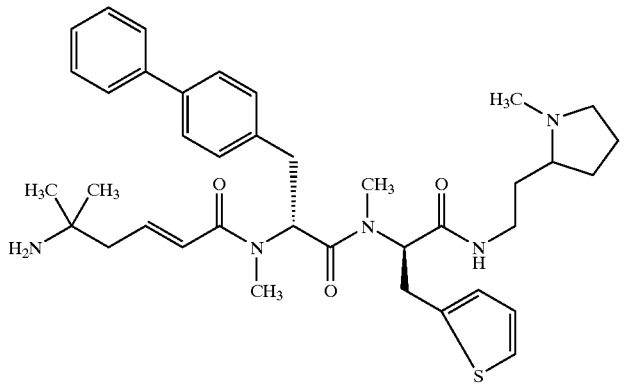 | 657.9 | | |
| 436 | 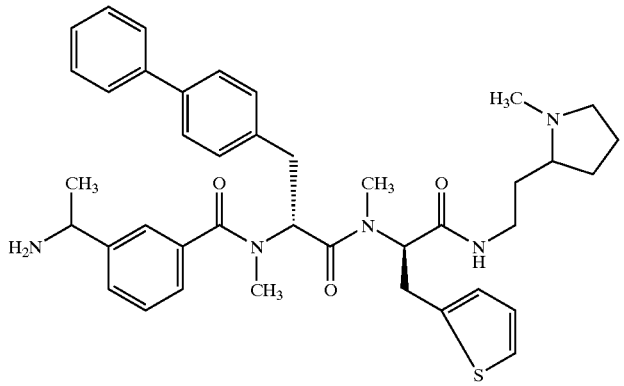 | 679.9 | | |
| 437 | 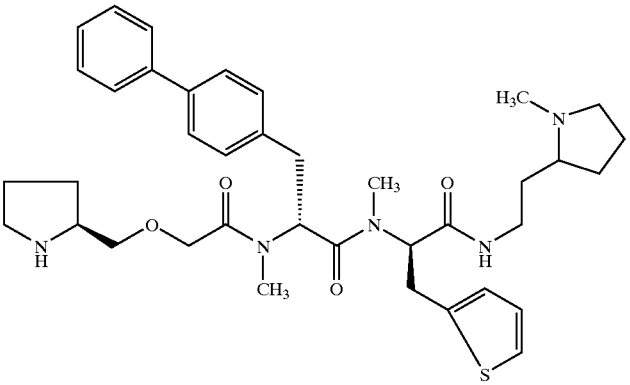 | 673.9 | | |

TABLE 3-continued

| Example | Structure | MW | HPLC | LC-MS |
|---|---|---|---|---|
| 438 | 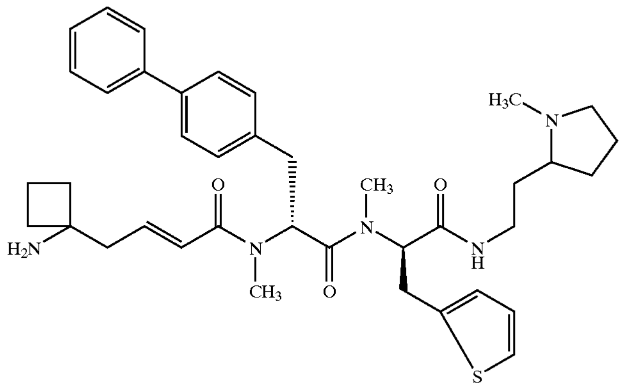 | 669.9 | | |
| 439 | 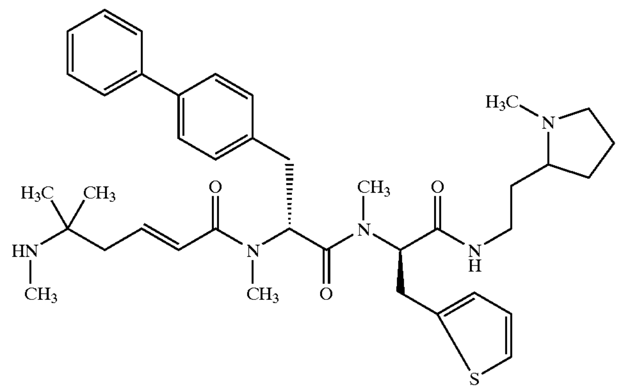 | 672.0 | | |
| 440 | 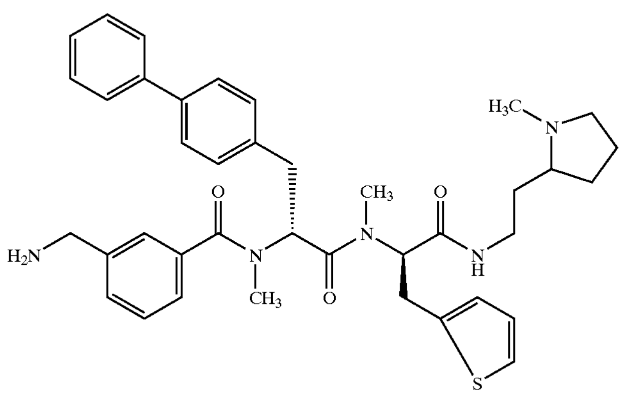 | 665.9 | | |
| 441 | 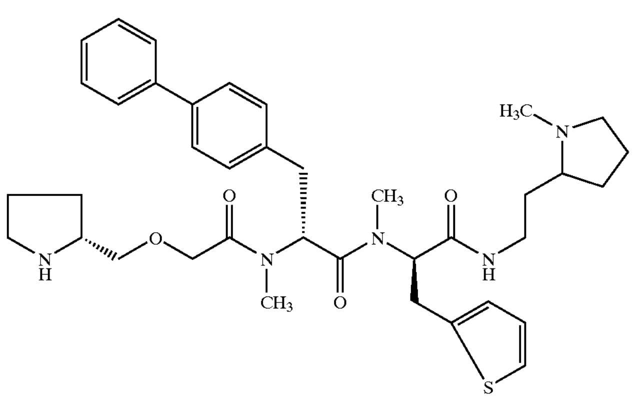 | 673.9 | | |

TABLE 3-continued

| Example | Structure | MW | HPLC | LC-MS |
|---|---|---|---|---|
| 442 | 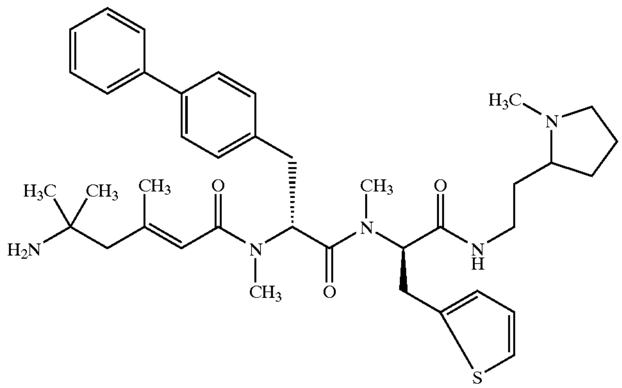 | 672.0 | | |
| 443 | 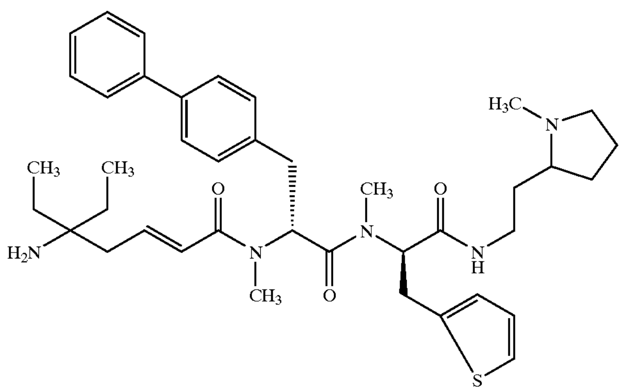 | 686.0 | | |
| 444 | 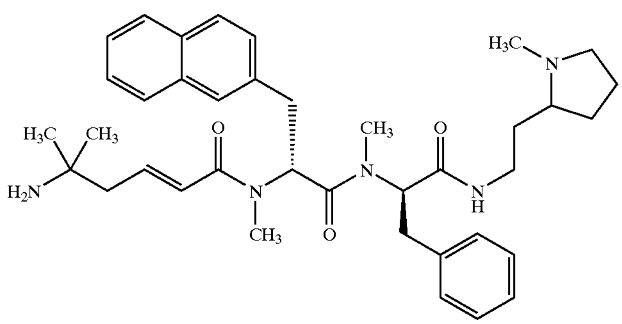 | 625.9 | | |
| 445 | 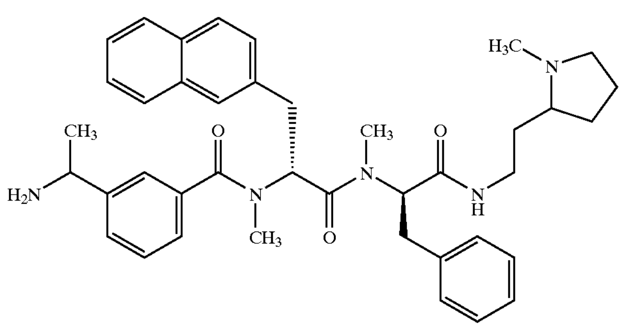 | 647.9 | | |

TABLE 3-continued

| Example | Structure | MW | HPLC | LC-MS |
|---------|-----------|-----|------|-------|
| 446 | 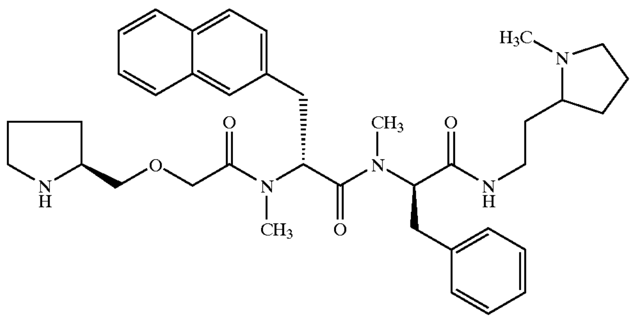 | 641.9 | | |
| 447 | 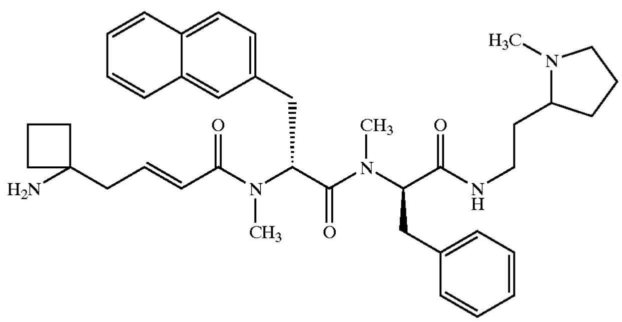 | 637.9 | | |
| 448 | 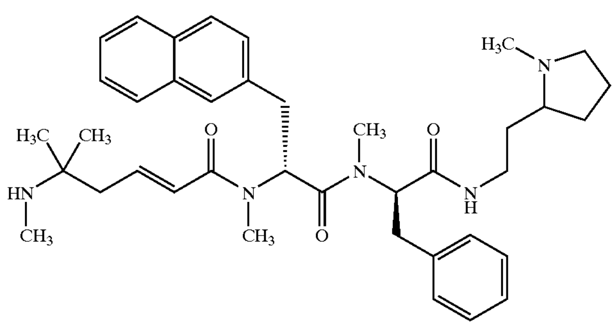 | 639.9 | | |
| 449 | 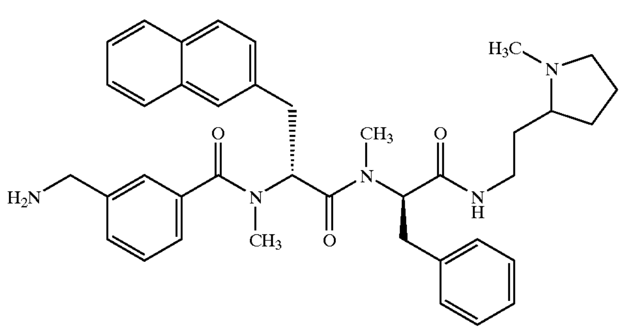 | 633.8 | | |

TABLE 3-continued

| Example | Structure | MW | HPLC | LC-MS |
|---|---|---|---|---|
| 450 | 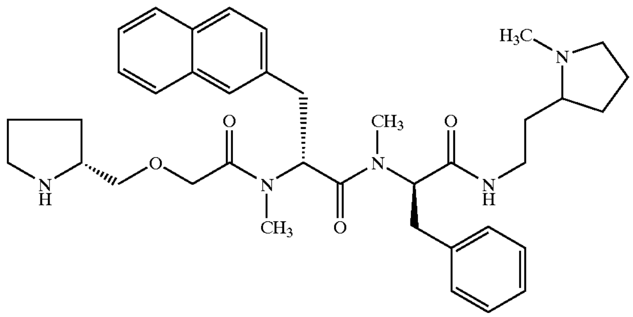 | 641.9 | | |
| 451 | 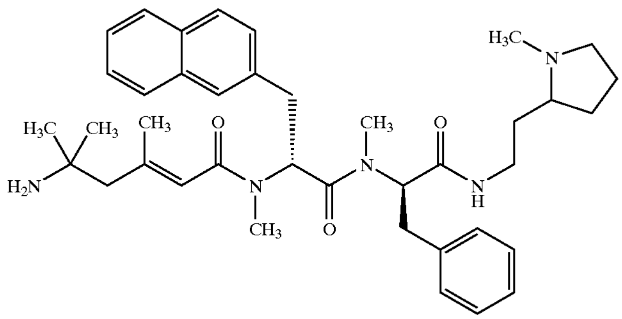 | 639.9 | | |
| 452 | 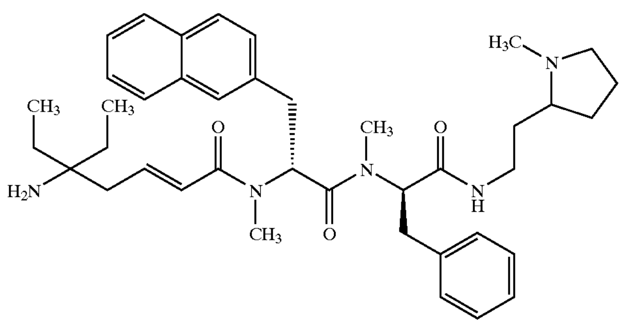 | 653.9 | | |
| 453 | 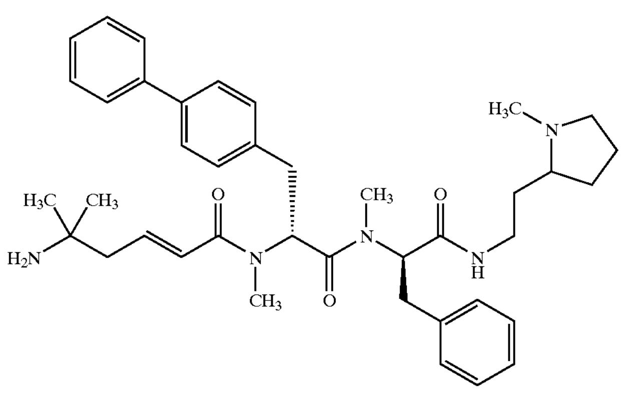 | 651.9 | | |

TABLE 3-continued

| Example | Structure | MW | HPLC | LC-MS |
|---|---|---|---|---|
| 454 | 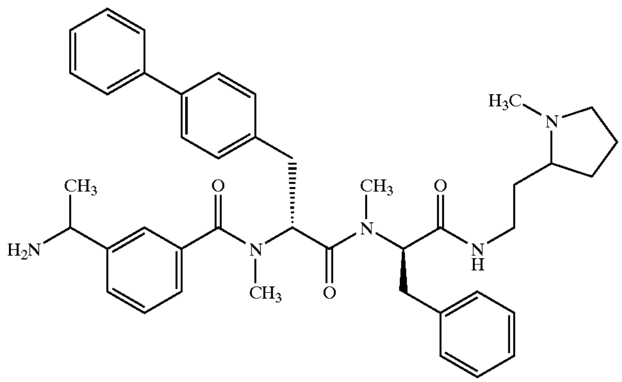 | 673.9 | | |
| 455 | 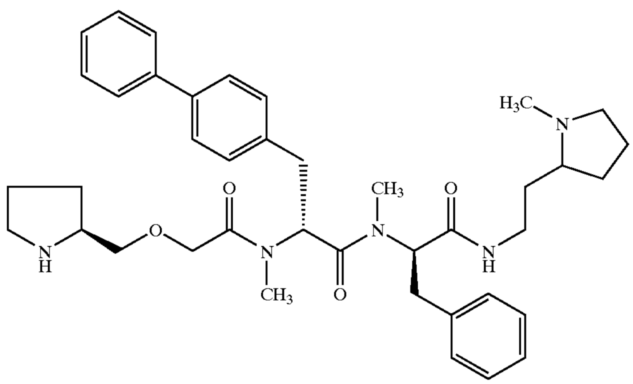 | 667.9 | | |
| 456 | 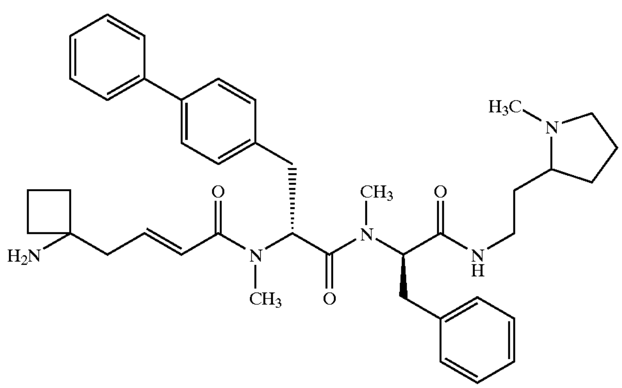 | 663.9 | | |
| 457 | 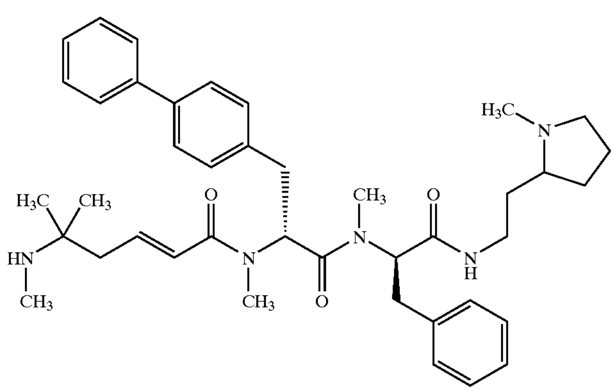 | 665.9 | | |

TABLE 3-continued
| Example | Structure | MW | HPLC | LC-MS |
|---|---|---|---|---|
| 458 | 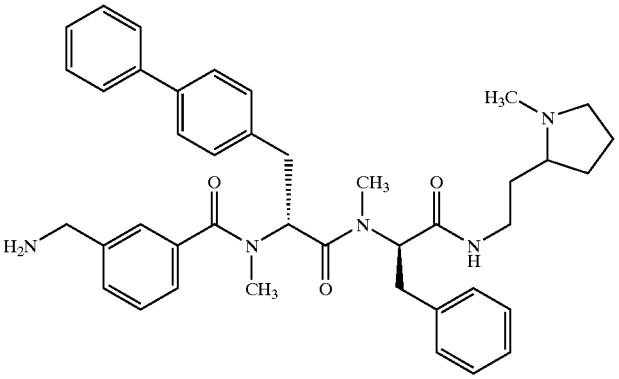 | 659.9 | | |
| 459 | 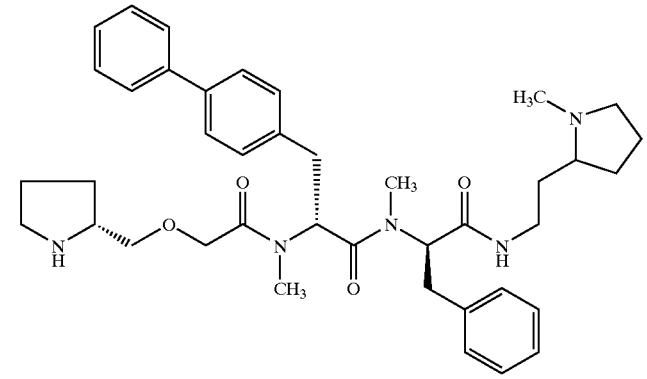 | 667.9 | | |
| 460 | 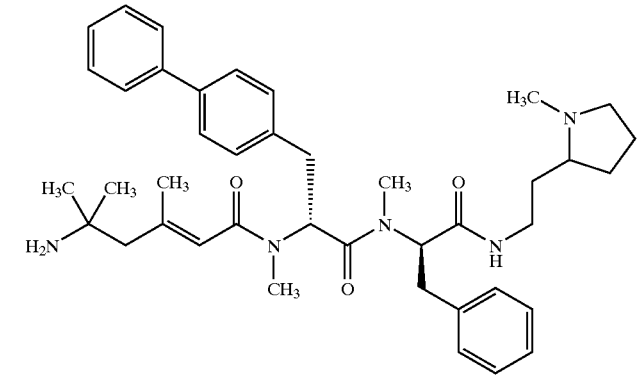 | 665.9 | | |
| 461 | 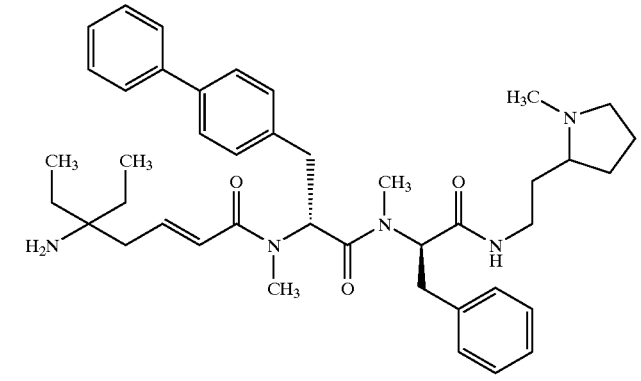 | 680.0 | | |

TABLE 3-continued
| Example | Structure | MW | HPLC | LC-MS |
|---|---|---|---|---|
| 462 | 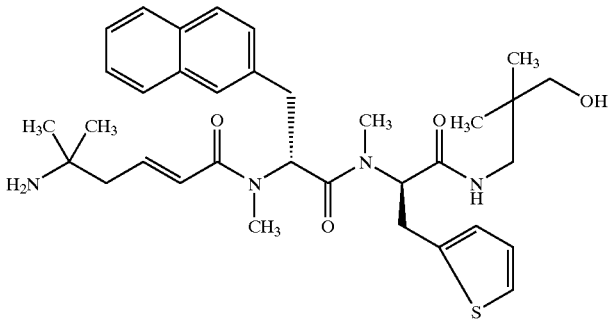 | 606.8 | | |
| 463 | 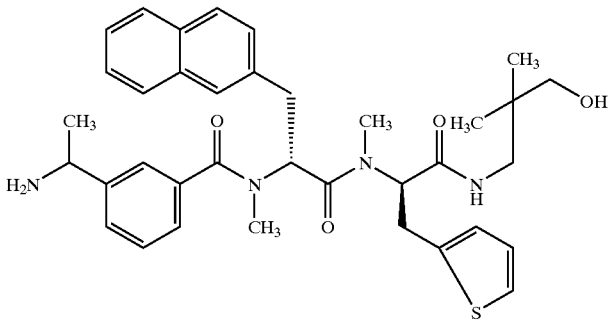 | 628.8 | | |
| 464 | 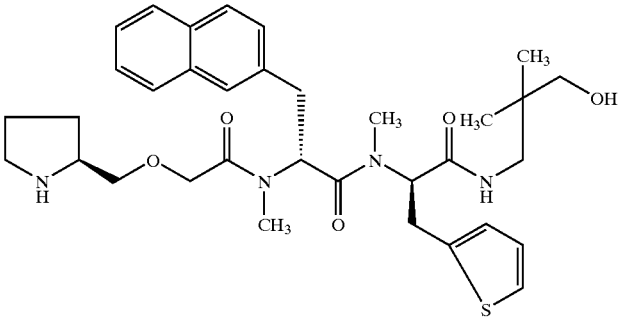 | 622.8 | | |
| 465 | 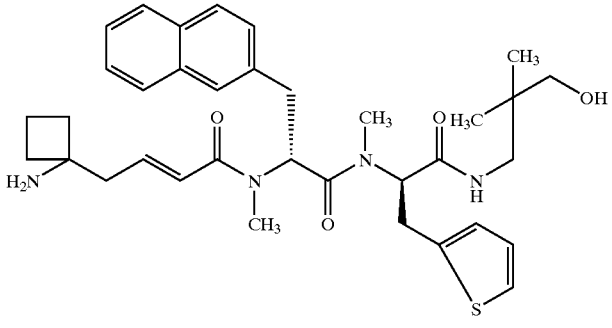 | 618.8 | | |

TABLE 3-continued

| Example | Structure | MW | HPLC | LC-MS |
|---------|-----------|-----|------|-------|
| 466 | 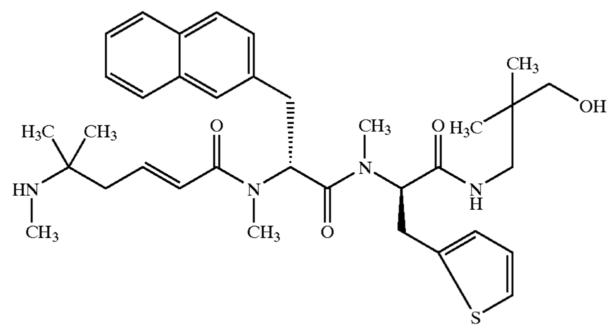 | 620.9 | | |
| 467 | 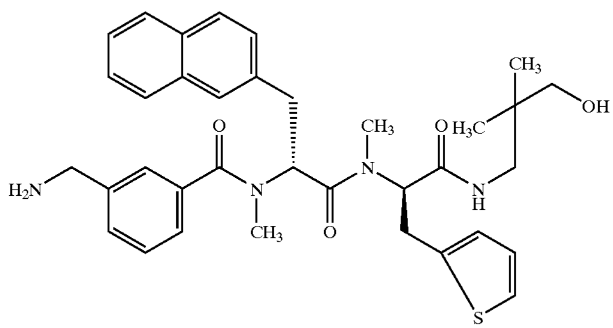 | 614.8 | | |
| 468 | 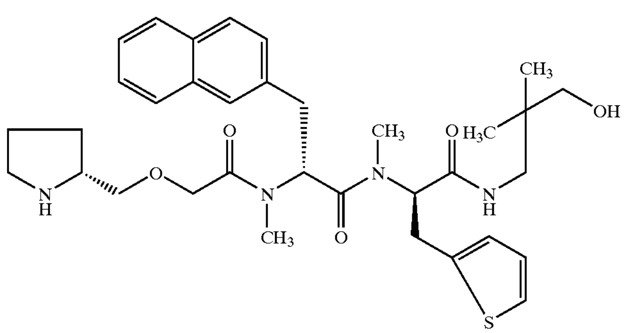 | 622.8 | | |
| 469 | 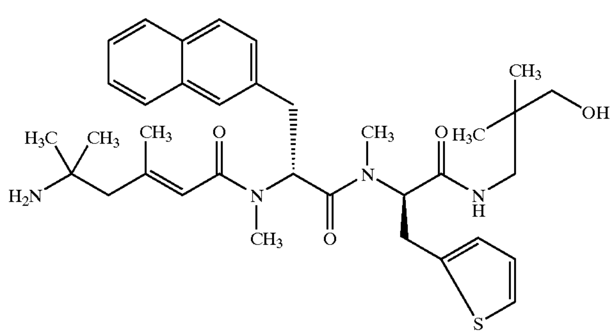 | 620.9 | | |

TABLE 3-continued

| Example | Structure | MW | HPLC | LC-MS |
|---------|-----------|-----|------|-------|
| 470 | 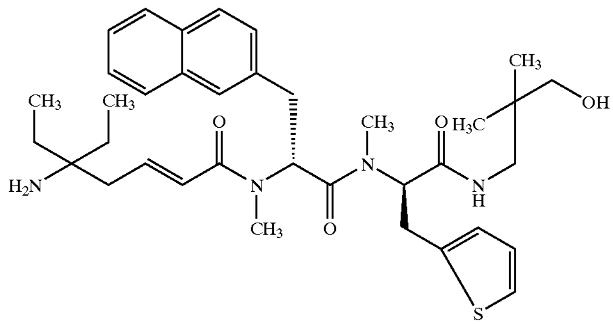 | 634.9 | | |
| 471 | 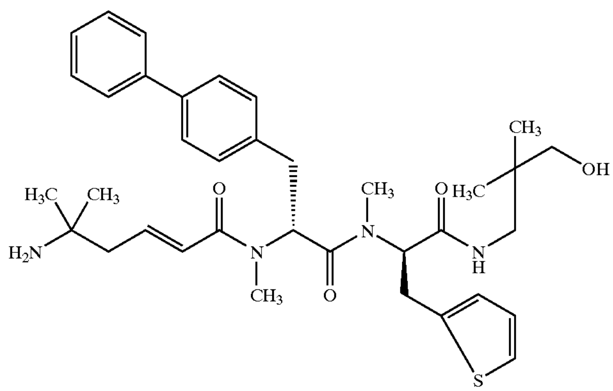 | 632.9 | | |
| 472 | 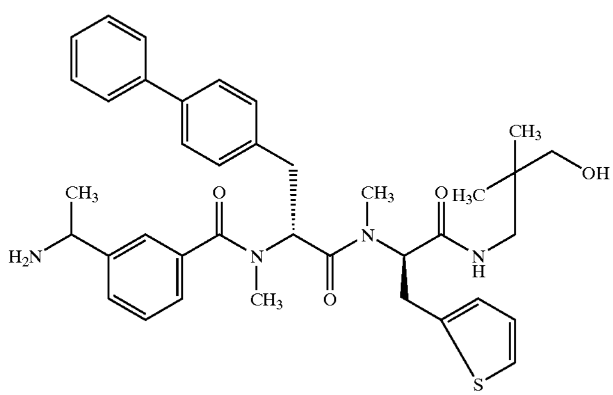 | 654.9 | | |
| 473 | 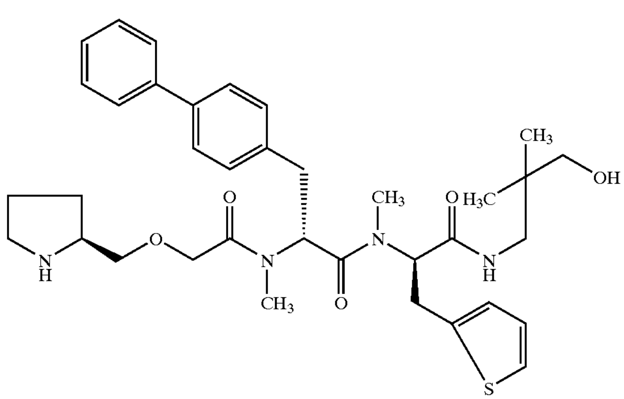 | 648.9 | | |

TABLE 3-continued

| Example | Structure | MW | HPLC | LC-MS |
|---|---|---|---|---|
| 474 | 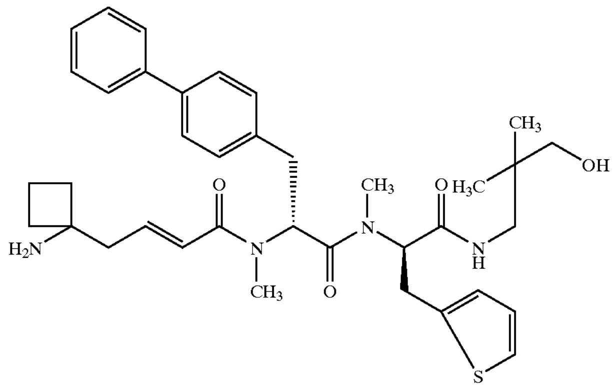 | 644.9 | | |
| 475 | 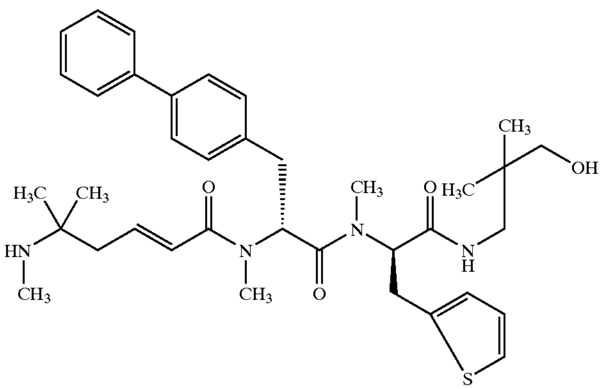 | 646.9 | | |
| 476 | 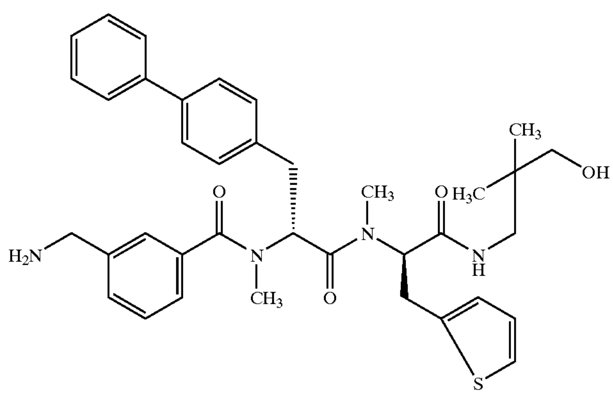 | 640.9 | | |
| 477 | 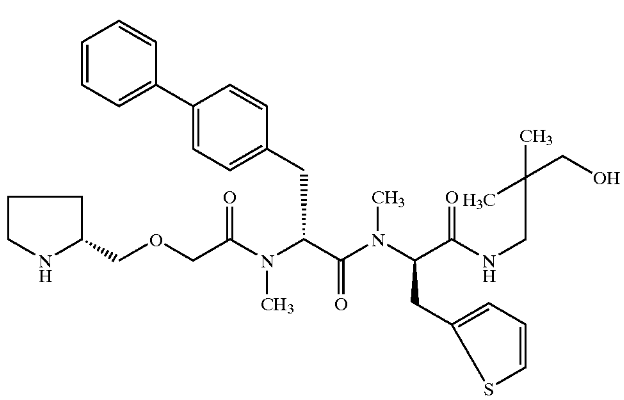 | 648.9 | | |

TABLE 3-continued
| Example | Structure | MW | HPLC | LC-MS |
|---|---|---|---|---|
| 478 | 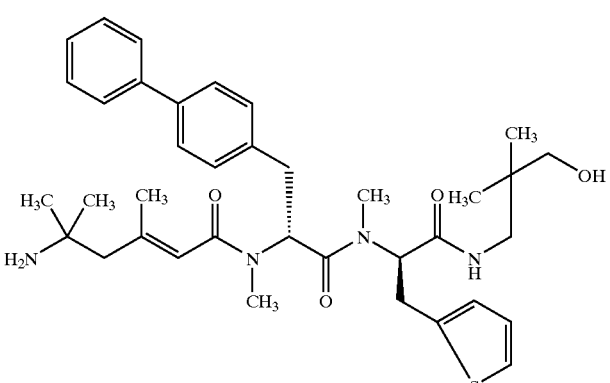 | 646.9 | | |
| 479 | 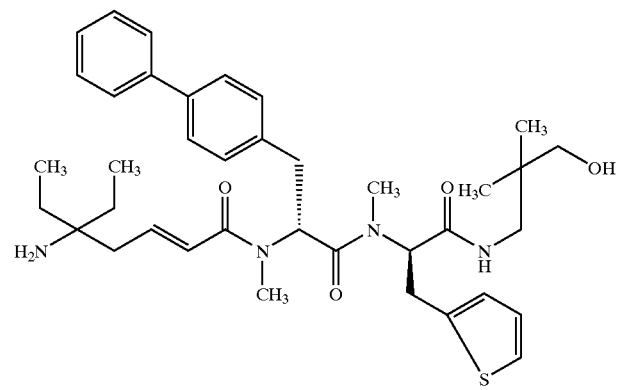 | 660.9 | | |
| 480 | 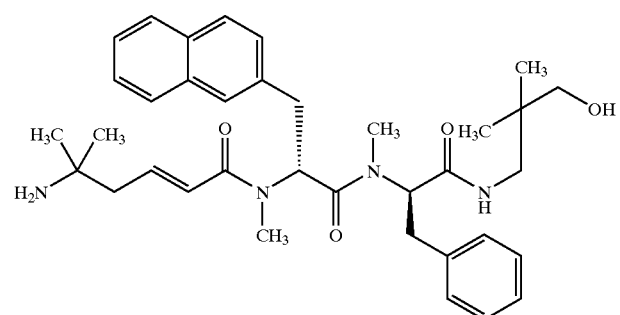 | 600.8 | | |
| 481 | 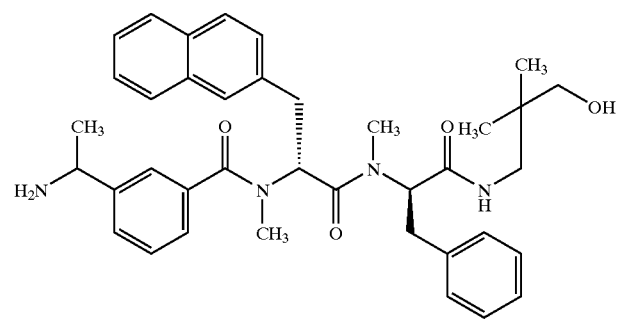 | 622.8 | | |

TABLE 3-continued
| Example | Structure | MW | HPLC | LC-MS |
|---|---|---|---|---|
| 482 | 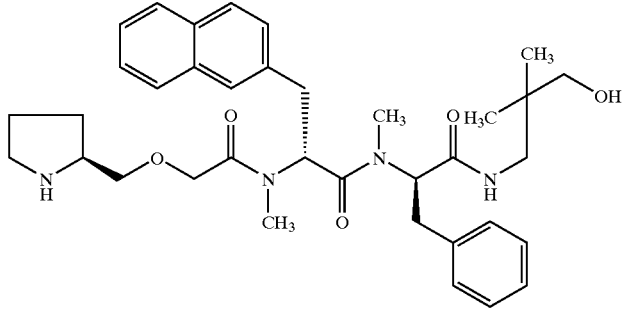 | 616.8 | | |
| 483 | 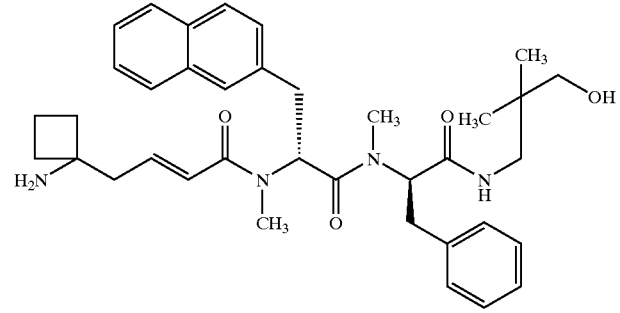 | 612.8 | | |
| 484 | 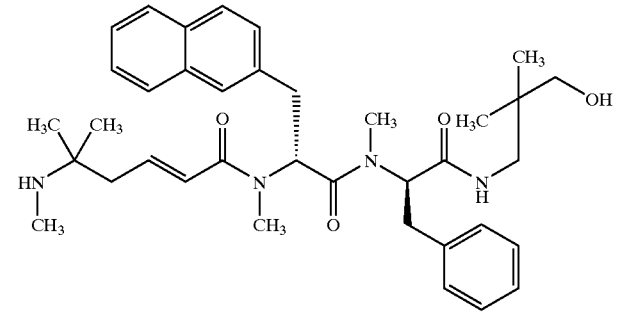 | 614.8 | | |
| 485 | 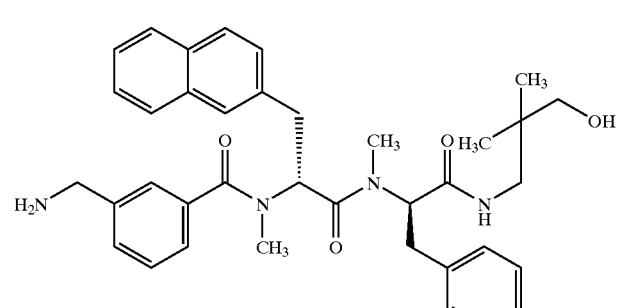 | 608.8 | | |

TABLE 3-continued

| Example | Structure | MW | HPLC | LC-MS |
|---------|-----------|-----|------|-------|
| 486 | 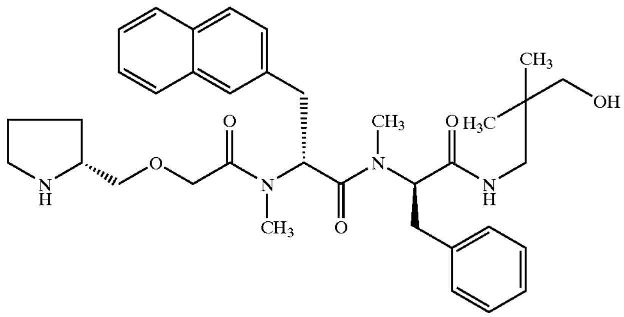 | 616.8 | | |
| 487 | 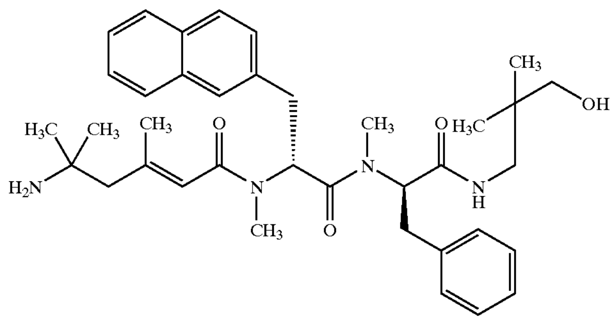 | 614.8 | | |
| 488 | 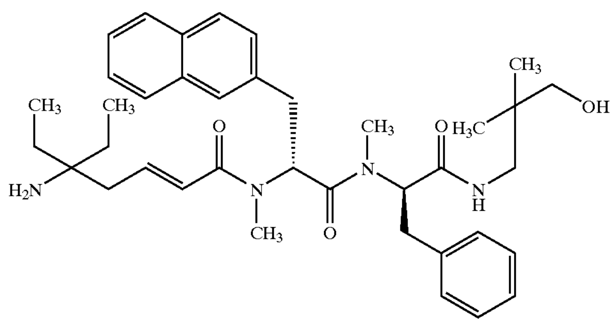 | 628.9 | | |
| 489 | 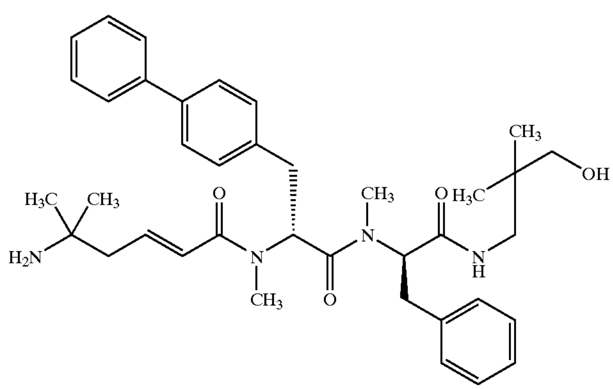 | 626.8 | | |

TABLE 3-continued

| Example | Structure | MW | HPLC | LC-MS |
|---|---|---|---|---|
| 490 | 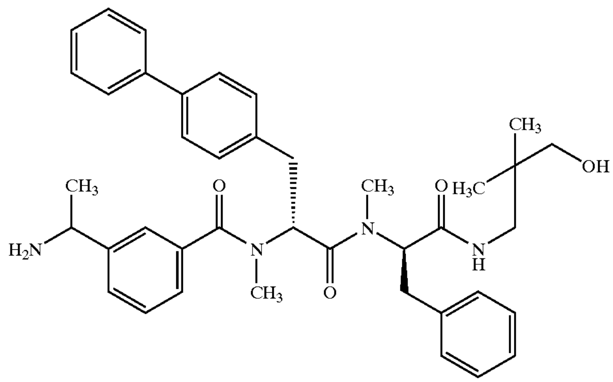 | 648.9 | | |
| 491 | 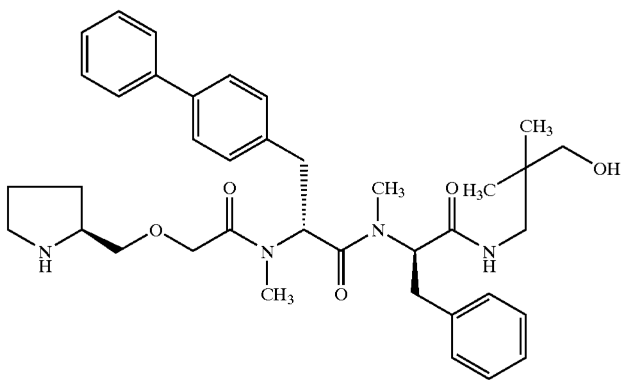 | 642.8 | | |
| 492 | 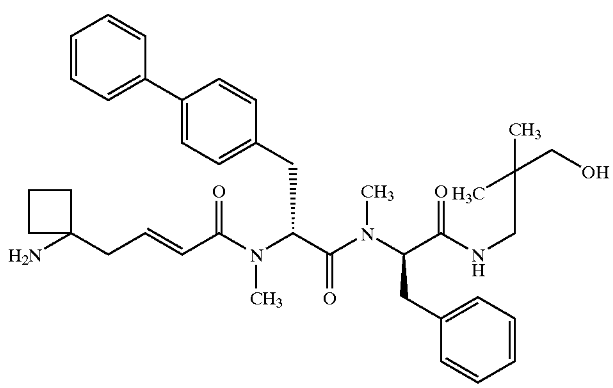 | 638.9 | | |
| 493 | 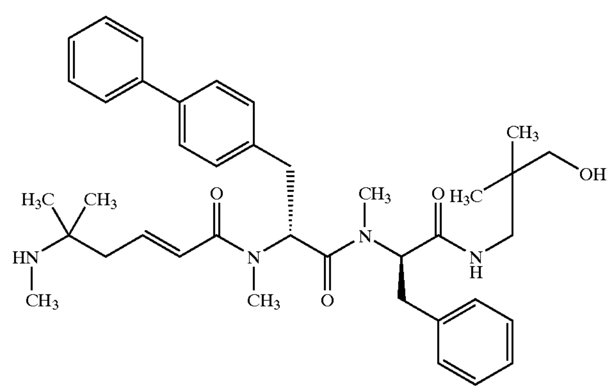 | 640.9 | | |

TABLE 3-continued

| Example | Structure | MW | HPLC | LC-MS |
|---------|-----------|-----|------|-------|
| 494 | 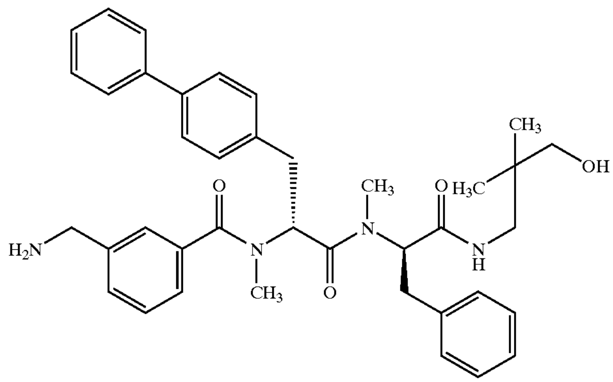 | 634.8 | | |
| 495 | 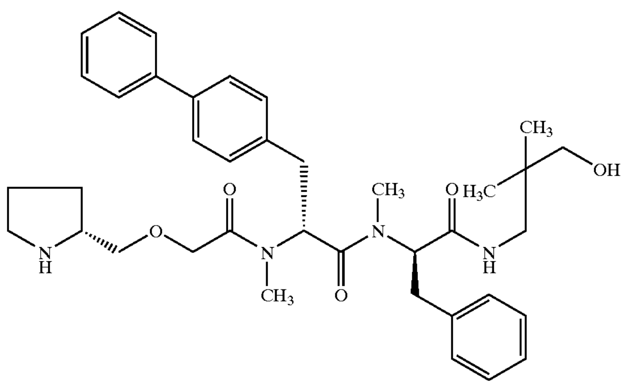 | 642.8 | | |
| 496 | 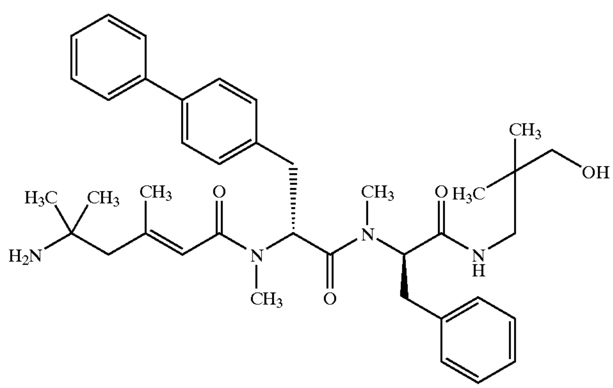 | 640.9 | | |
| 497 | 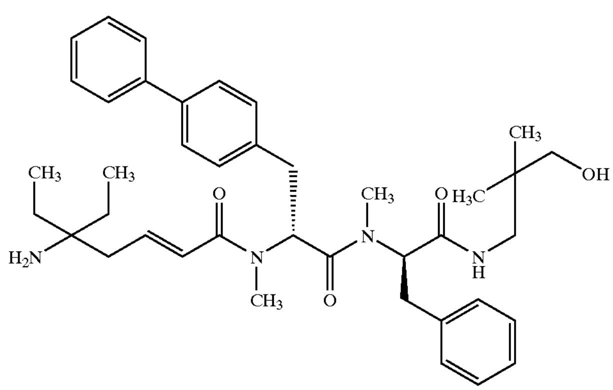 | 654.9 | | |

TABLE 3-continued
| Example | Structure | MW | HPLC | LC-MS |
|---|---|---|---|---|
| 498 | 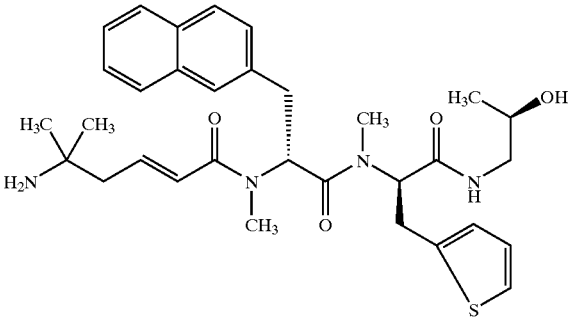 | 578.8 | | |
| 499 | 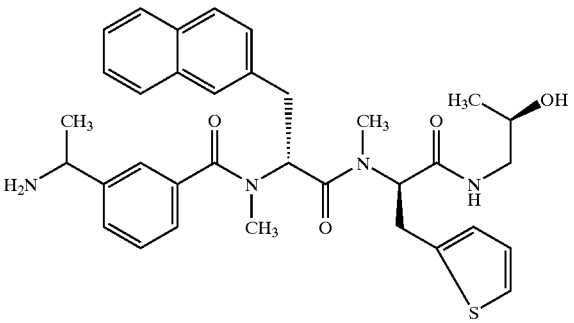 | 600.8 | | |
| 500 | 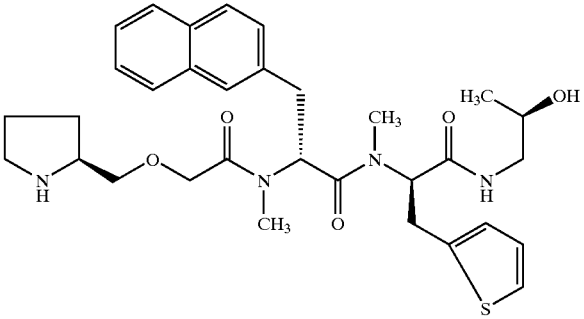 | 594.8 | | |
| 501 | 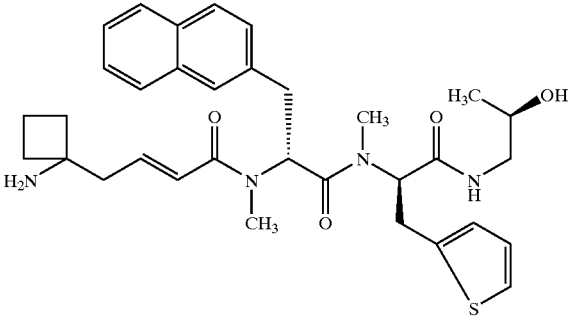 | 590.8 | | |

TABLE 3-continued

| Example | Structure | MW | HPLC | LC-MS |
|---|---|---|---|---|
| 502 | 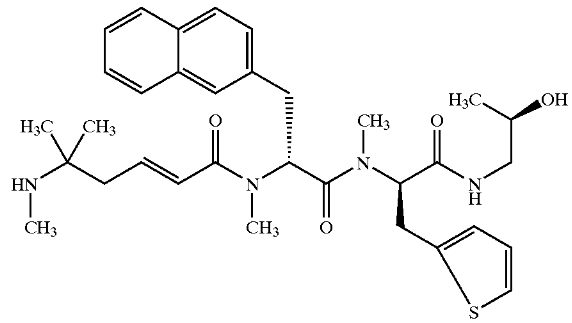 | 592.8 | | |
| 503 | 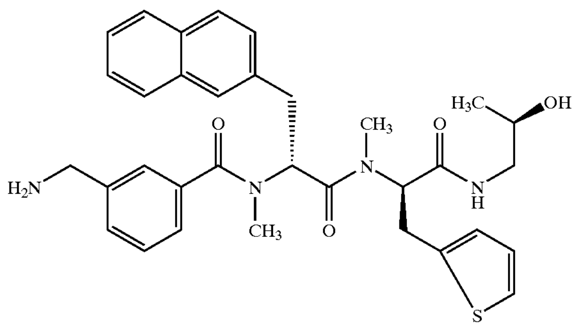 | 586.8 | | |
| 504 | 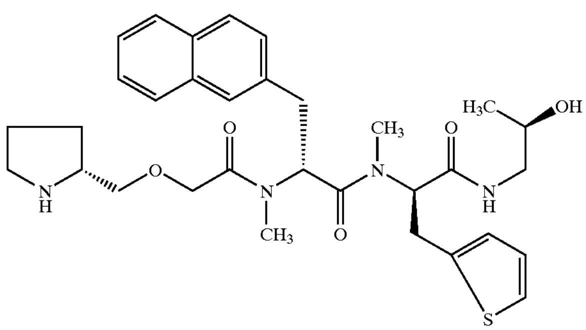 | 594.8 | | |
| 505 | 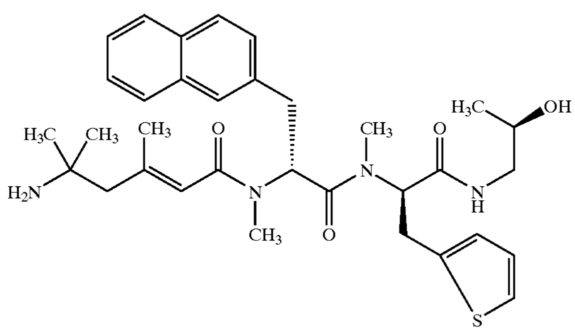 | 592.8 | | |

TABLE 3-continued

| Example | Structure | MW | HPLC | LC-MS |
|---|---|---|---|---|
| 506 | 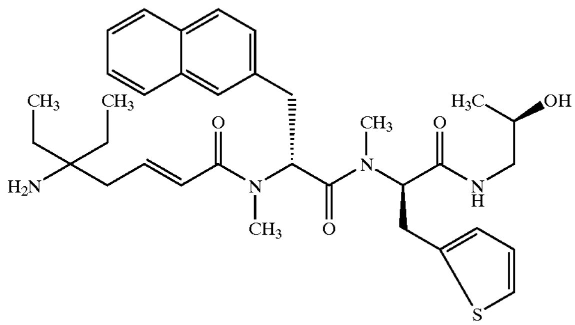 | 606.8 | | |
| 507 | 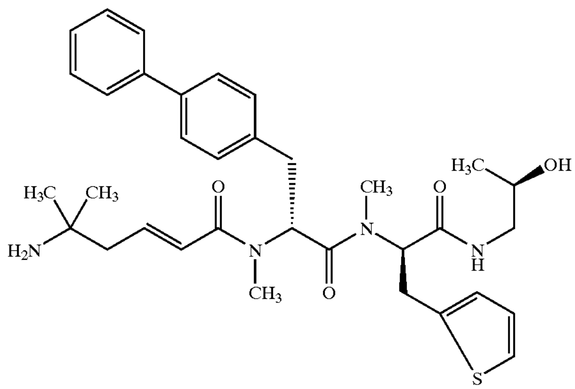 | 604.8 | | |
| 508 | 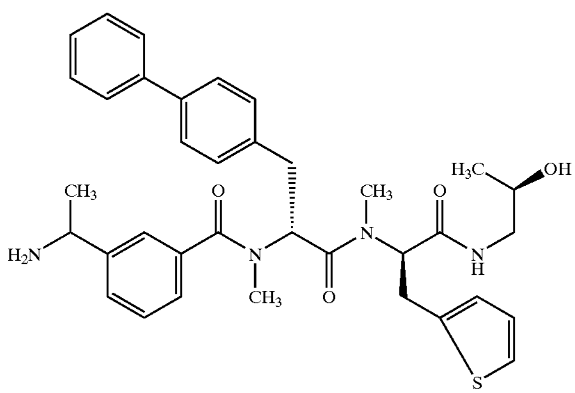 | 626.8 | | |
| 509 | 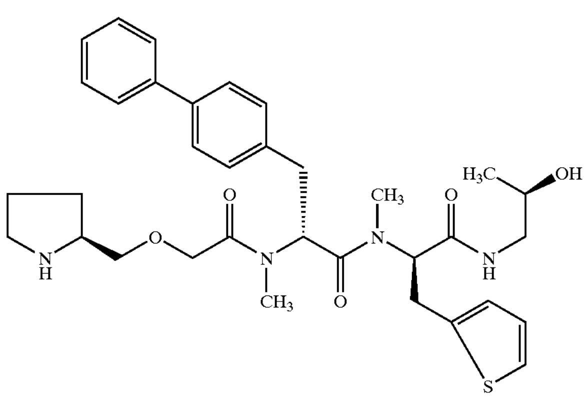 | 620.8 | | |

TABLE 3-continued
| Example | Structure | MW | HPLC | LC-MS |
|---|---|---|---|---|
| 510 | 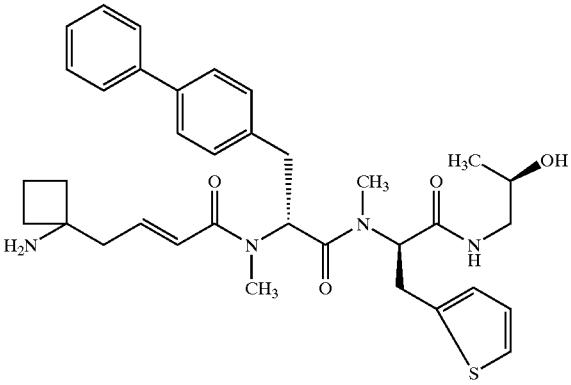 | 616.8 | | |
| 511 | 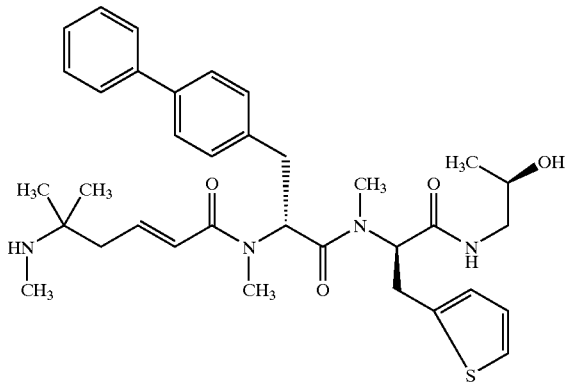 | 618.8 | | |
| 512 | 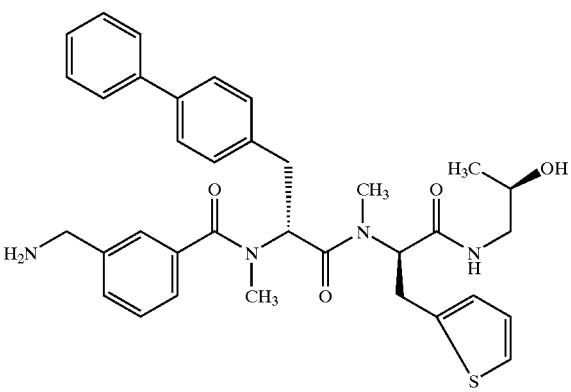 | 612.8 | | |
| 513 | 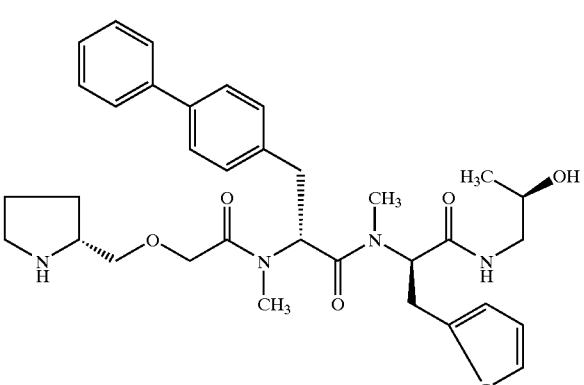 | 620.8 | | |

TABLE 3-continued
| Example | Structure | MW | HPLC | LC-MS |
|---|---|---|---|---|
| 514 | 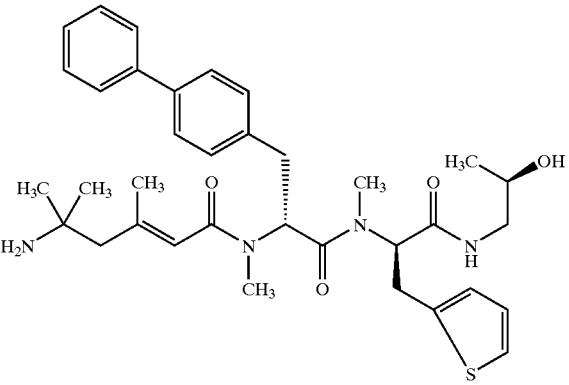 | 618.8 | | |
| 515 | 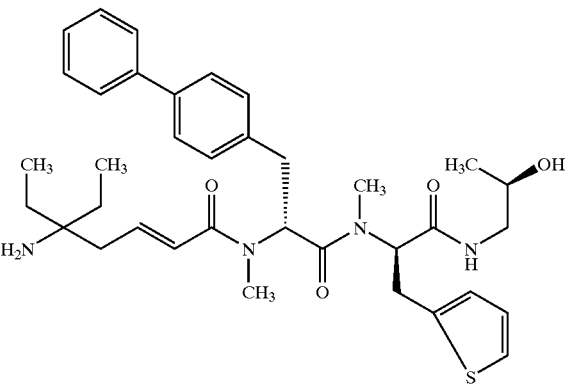 | 632.9 | | |
| 516 | 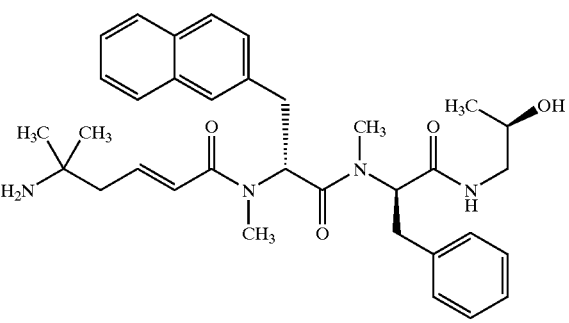 | 572.8 | | |
| 517 | 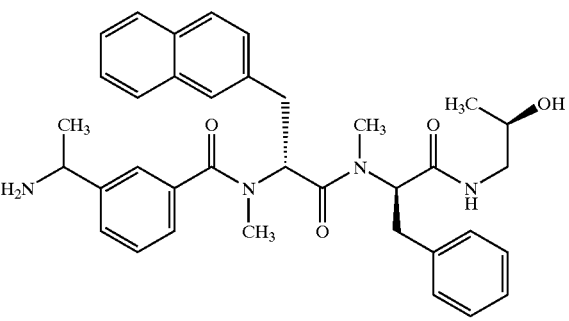 | 594.8 | | |

TABLE 3-continued

| Example | Structure | MW | HPLC | LC-MS |
|---|---|---|---|---|
| 518 | 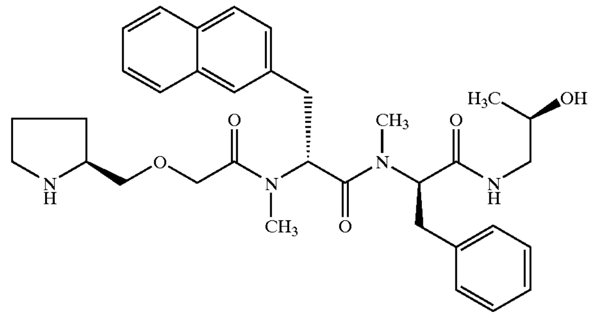 | 588.8 | | |
| 519 | 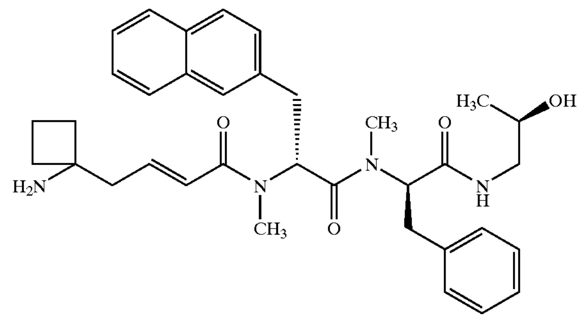 | 584.8 | | |
| 520 | 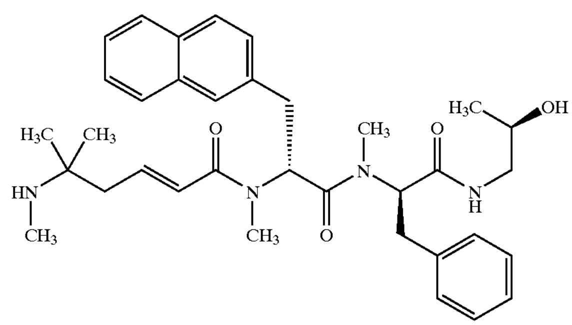 | 586.8 | | |
| 521 | 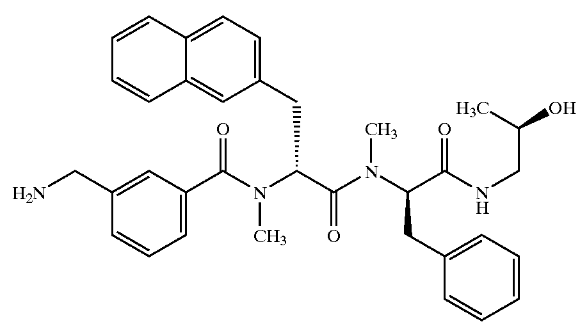 | 580.7 | | |

TABLE 3-continued

| Example | Structure | MW | HPLC | LC-MS |
|---|---|---|---|---|
| 522 | 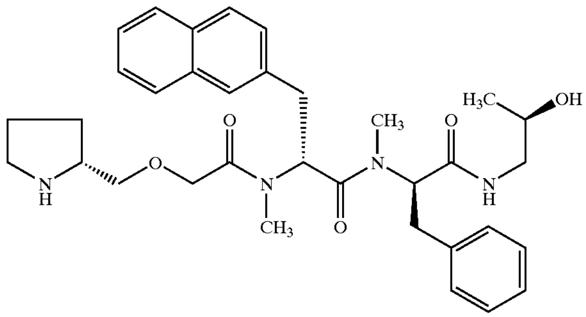 | 588.8 | | |
| 523 | 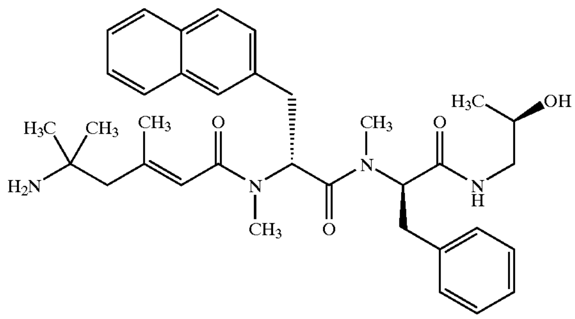 | 586.8 | | |
| 524 | 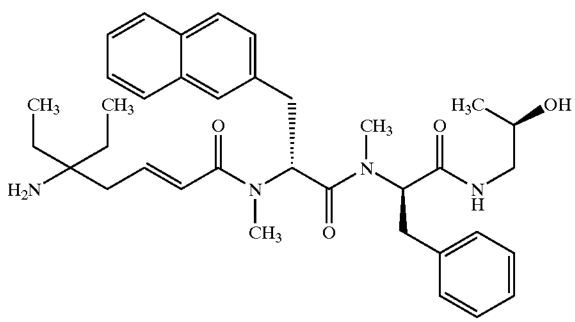 | 600.8 | | |
| 525 | 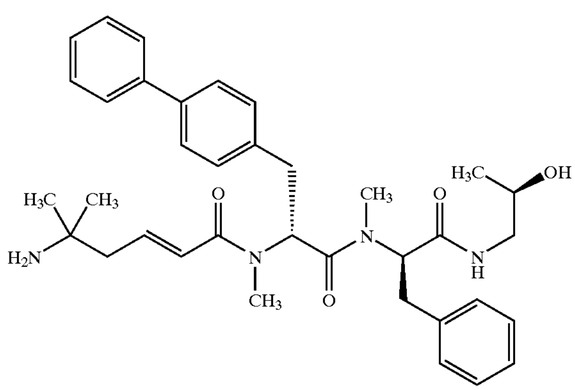 | 598.8 | | |

TABLE 3-continued

| Example | Structure | MW | HPLC | LC-MS |
|---|---|---|---|---|
| 526 | 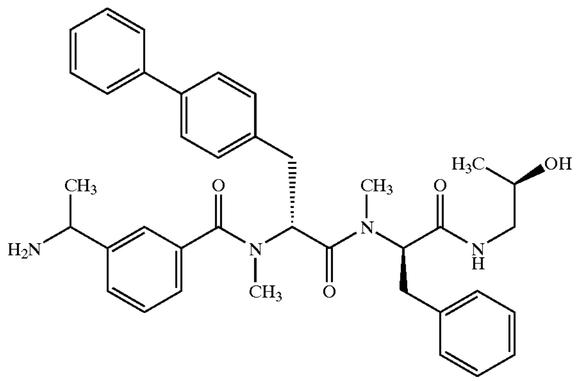 | 620.8 | | |
| 527 | 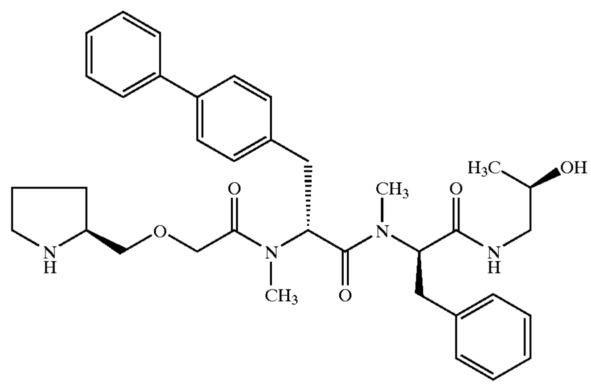 | 614.8 | | |
| 528 | 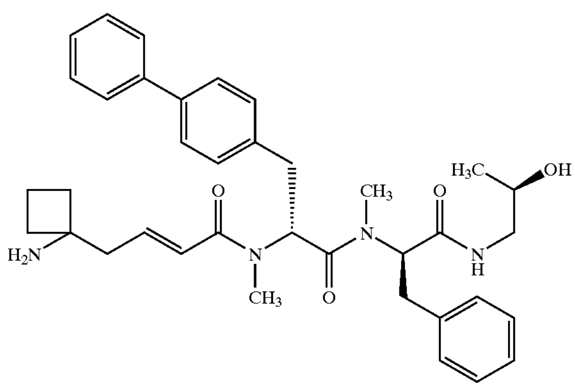 | 610.8 | | |
| 529 | 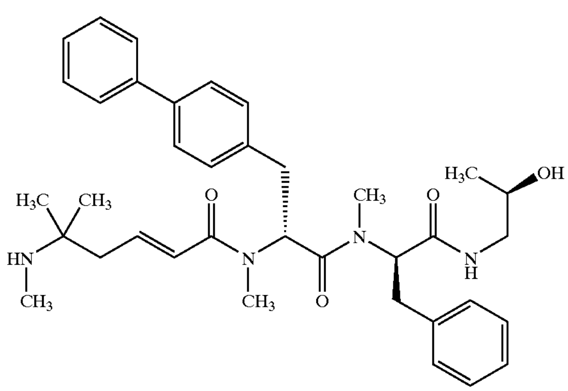 | 612.8 | | |

TABLE 3-continued

| Example | Structure | MW | HPLC | LC-MS |
|---|---|---|---|---|
| 530 | 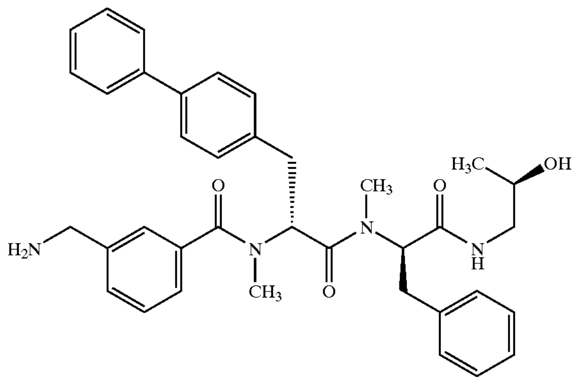 | 606.8 | | |
| 531 | 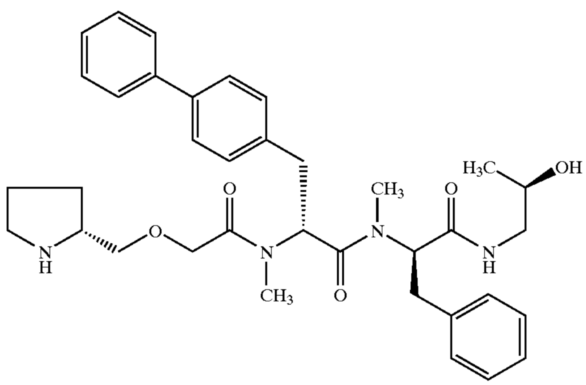 | 614.8 | | |
| 532 | 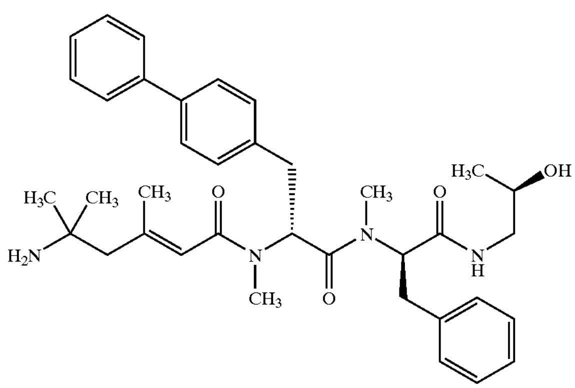 | 612.8 | | |
| 533 | 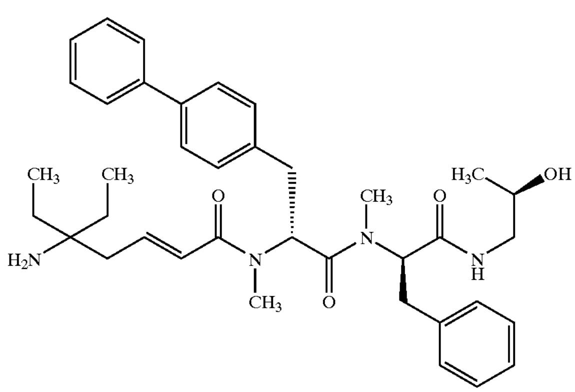 | 626.8 | | |

Example 534
(2E)-5-Amino-5-methylhex-2-enoic acid N-((1R)-1-(N-((1R)-1-(N-methyl-N-(3-dimethylaminopropyl)carbamoyl)-2-phenylethyl)-N-methylcarbamoyl)-2-(2-naphthyl)ethyl)-N-methylamide

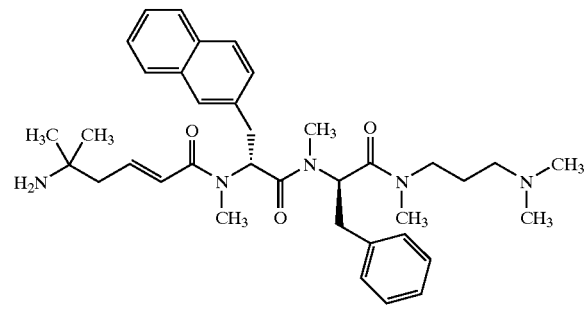

The title compound was prepared as in example 1 using N,N,N'-trimethylpropylenediamine instead of methylamine.

Example 535
(2E)-5-Amino-5-methylhex-2-enoic acid N-((1R)-1-(N-((1R)-1-(N-methylcarbamoyl)-2-phenylethyl)-N-ethylcarbamoyl)-2-(2-naphthyl)ethyl)-N-methylamide

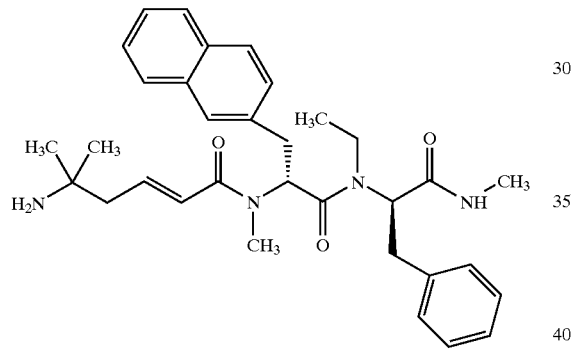

The title compound was prepared as in example 1. N-ethylation of D-Boc-phenylalanine was carried out by the use of ethyl iodide instead of methyl iodide.

Example 536
(2E)-5-Amino-5-methylhex-2-enoic acid-N-(1R)-1-(N-((1R)-1-(N-(N,N-dimethylcarbamoylmethyl)carbamoyl)-2-phenylethyl)-N-methylcarbamoyl)-2-(2-naphthyl)ethyl)-N-methylamide

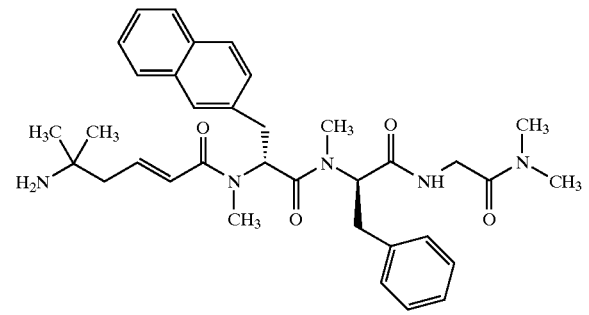

The title compound was prepared as in example 1 using glycine dimethylamide instead of methylamine.

Example 537
(2E)-5-Amino-5-methylhex-2-enoic acid-N-((1R)-1-(N-((1R)-1-(N-(carbamoylmethyl)carbamoyl)-2-phenylethyl)-N-methylcarbamoyl)-2-(2-naphthyl)ethyl)-N-methylamide

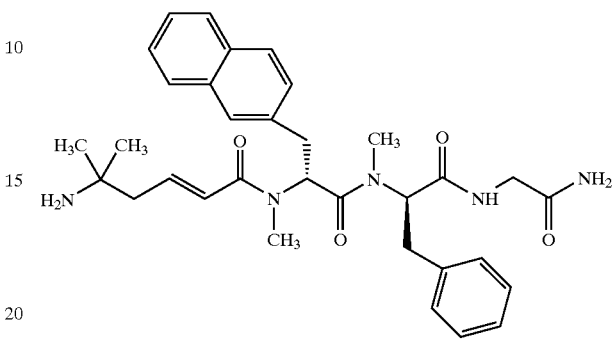

The title compound was prepared as in example 1 using glycine amide instead of methylamine.

What is claimed is:

1. A compound of Formula I

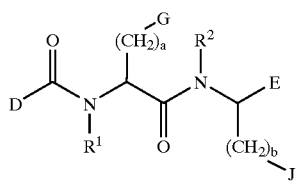

wherein $R^1$ and $R^2$ are independently hydrogen, or $C_{1-6}$-alkyl;

a and b are independently 1 or 2;

G is

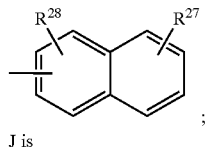

J is

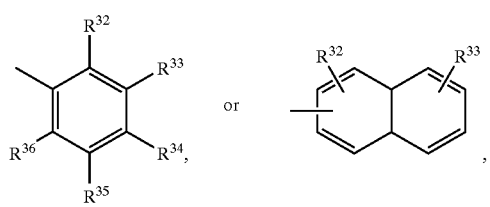

wherein $R^{27}$, $R^{28}$, $R^{32}$, $R^{33}$, $R^{34}$, $R^{35}$ and $R^{36}$ independently are hydrogen;

D is

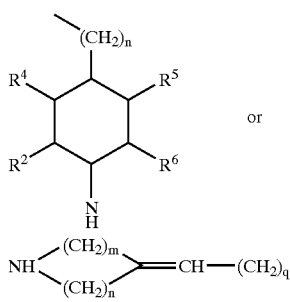

or

wherein $R^3$, $R^4$, $R^5$ and $R^6$ are independently hydrogen or $C_{1-6}$ alkyl, n, m, and q are independently 0, 1, 2, or 3;

when E is

—$CONR^{12}R^{13}$ wherein $R^{12}$ is hydrogen and $R^{13}$ $C_{1-6}$-alkyl, or

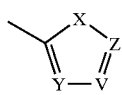

wherein

X is —O—,

Z is —N=,

V is —$C(R^{16})$=

Y is —N=, $R^{16}$ is —$(CH_2)_wR^{19}$;

wherein $R^{19}$ is $C_{1-6}$alkyl and w is independently, 0, 1, 2 or 3, or a pharmaceutically acceptable salt thereof.

2. The compound according to claim 1, wherein D is piperidin-4-ylidenyl or 2-methylpiperidin-4-yl.

3. The compound according to claim 1, wherein E is methycarbamoyl or 3-methyl-1,2,4-oxadiazol-5-yl.

4. The compound according to claim 1, wherein $R^1$ and $R^2$ independently are hydrogen, methyl or ethyl.

5. The compound according to claim 1, wherein a and b independently are 1.

6. The compound according to claim 1, wherein said compound is

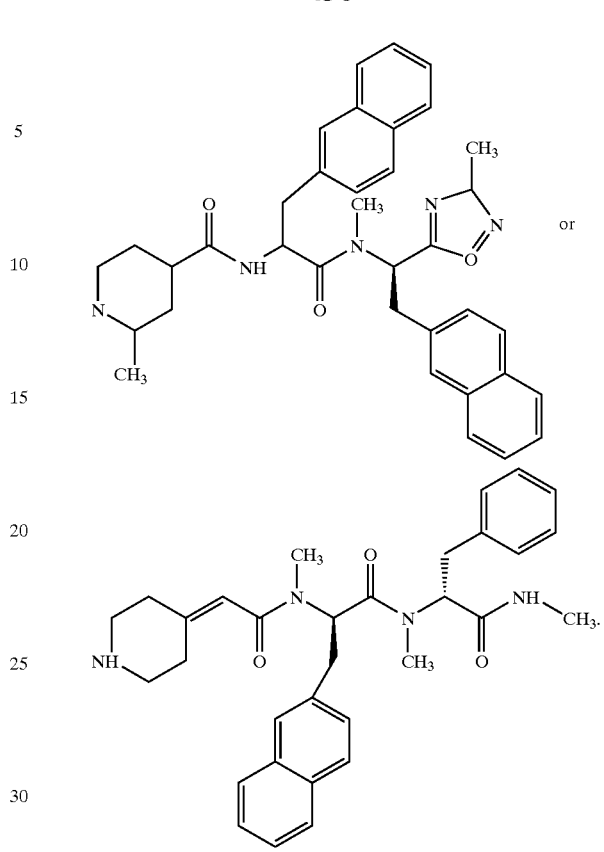

or

7. A method of increasing rate and extent of growth, improving milk and/or wool production and/or treating ailments in an animal resulting from a deficiency of growth hormone, the method comprising administering to said animal in need thereof an effective amount of the compound according to claim 1.

8. A composition comprising a compound according to claim 1 together with a pharmaceutically acceptable carrier or diluent.

9. The composition according to claim 8 in unit dosage form, comprising from about 10 to about 200 mg of said compound.

10. The composition according to claim 8 for oral, nasal, transdermal, pulmonary, or parenteral administration.

11. A method of stimulating the release of growth hormone from the pituitary, the method comprising administering to a subject in need thereof an effective amount of the compound according to claim 1.

12. The method according to claim 11, wherein the effective amount of said compound is in the range of from about 0.0001 to about 100 mg/kg body weight per day.

13. The method according to claim 11, wherein said administration is carried out by the oral, nasal, transdermal, pulmonary, or parenteral route.

14. The method according to claim 11, wherein the effective amount of said compound is in the range of from about 0.001 to about 50 mg/kg body weight per day.

* * * * *

UNITED STATES PATENT AND TRADEMARK OFFICE
CERTIFICATE OF CORRECTION

PATENT NO. : 6,939,880 B2  
APPLICATION NO. : 10/067895  
DATED : September 6, 2005  
INVENTOR(S) : Hansen et al.

It is certified that error appears in the above-identified patent and that said Letters Patent is hereby corrected as shown below:

Column 429, line 52, Claim 3 – change "methycarbamoyl" to --methylcarbamoyl--

Signed and Sealed this

Thirty-first Day of July, 2007

JON W. DUDAS  
*Director of the United States Patent and Trademark Office*